(12) United States Patent
Windisch et al.

(10) Patent No.: US 9,809,602 B2
(45) Date of Patent: Nov. 7, 2017

(54) COMPOUNDS FOR TREATING VIRAL INFECTIONS

(71) Applicant: INSTITUT PASTEUR KOREA, Gyeonggi-do (KR)

(72) Inventors: Marc P. Windisch, Datteln (DE); Hee-Young Kim, Gyeonggi-do (KR); Jaewon Yang, Gyeonggi-do (KR); Jong Yeon Hwang, Jeollabuk-do (KR); Suyeon Jo, Gyeonggi-do (KR); Jeongjin Kwon, Gyeonggi-do (KR); Dongsik Park, Gyeonggi-do (KR); Jihyun Choi, Seoul (KR); Jaeheon Lee, Seoul (KR)

(73) Assignee: Institut Pasteur Korea, Seongnam-si (KR)

( * ) Notice: Subject to any disclaimer, the term of this patent is extended or adjusted under 35 U.S.C. 154(b) by 0 days.

(21) Appl. No.: 15/304,612

(22) PCT Filed: Apr. 17, 2015

(86) PCT No.: PCT/EP2015/058421
§ 371 (c)(1),
(2) Date: Oct. 17, 2016

(87) PCT Pub. No.: WO2015/158908
PCT Pub. Date: Oct. 22, 2015

(65) Prior Publication Data
US 2017/0044181 A1 Feb. 16, 2017

Related U.S. Application Data

(60) Provisional application No. 61/980,940, filed on Apr. 17, 2014.

(51) Int. Cl.
| | |
|---|---|
| *C07D 495/04* | (2006.01) |
| *A61K 45/06* | (2006.01) |
| *A61K 31/4365* | (2006.01) |
| *C07D 333/68* | (2006.01) |
| *C07D 211/44* | (2006.01) |
| *C07D 295/12* | (2006.01) |
| *C07D 211/58* | (2006.01) |
| *C07D 409/14* | (2006.01) |
| *C07D 401/04* | (2006.01) |
| *C07D 407/12* | (2006.01) |
| *C07D 211/14* | (2006.01) |
| *C07D 487/04* | (2006.01) |
| *C07D 401/06* | (2006.01) |
| *C07D 401/12* | (2006.01) |
| *C07D 409/12* | (2006.01) |

(52) U.S. Cl.
CPC ........ *C07D 495/04* (2013.01); *A61K 31/4365* (2013.01); *A61K 45/06* (2013.01); *C07D 211/14* (2013.01); *C07D 211/44* (2013.01); *C07D 211/58* (2013.01); *C07D 295/12* (2013.01); *C07D 333/68* (2013.01); *C07D 401/04* (2013.01); *C07D 401/06* (2013.01); *C07D 401/12* (2013.01); *C07D 407/12* (2013.01); *C07D 409/12* (2013.01); *C07D 409/14* (2013.01); *C07D 487/04* (2013.01)

(58) Field of Classification Search
CPC .. C07D 495/04; C07D 333/68; C07D 211/44; C07D 295/12; C07D 211/58; C07D 409/14; C07D 401/04; C07D 401/06; C07D 401/12; C07D 407/12; C07D 409/12; C07D 211/14; C07D 487/04; A61K 45/06; A61K 31/4365
See application file for complete search history.

(56) References Cited

U.S. PATENT DOCUMENTS

| | | | |
|---|---|---|---|
| 5,422,335 A | 6/1995 | Hagen et al. | |
| 2005/0075385 A1 | 4/2005 | Lang et al. | |
| 2008/0064874 A1 | 3/2008 | Dunkel et al. | |

FOREIGN PATENT DOCUMENTS

| | | |
|---|---|---|
| WO | 98/52558 A1 | 11/1998 |
| WO | 98/52559 A1 | 11/1998 |
| WO | 2008/031888 A2 | 3/2008 |
| WO | 2010/108187 A2 | 9/2010 |

OTHER PUBLICATIONS

[No Author Listed] Database accession No. 931713-26-7; Compounds with Registry No. 931713-26-7, 931713-23-4, 931759-73-8; Database Registry [Online], Chemical Abstracts Service, Columbus, Ohio, US; Apr. 22, 2007 (Apr. 22, 2007).
[No Author Listed] Database Accession No. 937645-86-8, Chemical Abstracts Service, Jun. 17, 2007, XP002744197.
Aghemo, A., E. Degasperi, and M. Colombo, Directly acting antivirals for the treatment of chronic hepatitis C: Unresolved topics from registration trials. Dig Liver Dis, 2012.
Ali, S., et al., Hepatitis C virus subgenomic replicons in the human embryonic kidney 293 cell line. J Viral, 2004. 78(1): p. 491-501.
Amr, A. el-G., et al., Antiarrhythmic, serotonin antagonist and antianxiety activities of novel substituted thiophene derivatives synthesized from 2-amino-4,5,6,7-tetrahydro-N-phenylbenzo[b]thiophene-3-carboxamide, Eur J Med Chem. Dec. 2010;45(12):5935-42. doi: 10.1016/j.ejmech.2010.09.059. Epub Oct. 14, 2010.
Antonysamy, S. S., et al., "Fragment-based discovery of hepatitis c virus NS5b RNA polymerase inhibitors," Bioorganic & Medicinal Chemistry Letters, vol. 18, No. 9, May 1, 2008 (May 1, 2008), pp. 2990-2995.
Arhin, F., et al., "A new class of small molecule RNA polymerase inhibitors with activity against rifampicin-resistant *Staphylococcus aureus*," Bioorg Med Chem. Sep. 1, 2006;14(17):5812-32. Epub Jun. 8, 2006.

(Continued)

*Primary Examiner* — Matt Mauro
(74) *Attorney, Agent, or Firm* — Nutter McClennen & Fish LLP; John J. Penny, Jr.; Alex Nagorniy

(57) ABSTRACT

The present invention relates to small molecule compounds and their use in the treatment of diseases, in particular viral diseases, in particular hepatitis C virus (HCV).

17 Claims, No Drawings

(56) References Cited

OTHER PUBLICATIONS

Badran, M. M., et al., "Synthesis of certain fused pyrrolothieno[3,2-e] pyrazine derivatives with possible anxiolytic activity," Organic Chemistr (An Indian Journal), 2013, v. 9, No. 11, pp. 427-436.
Bartosch, B., J. Dubuisson, and F.L. Cosset, Infectious hepatitis C virus pseudo-particles containing functional E1-E2 envelope protein complexes. J Exp Med, 2003. 197(5): p. 633-42.
Beaulieu, P. L., et al., "N-Acetamideindolecarboxylic acid allosteric 'finger-loop' inhibitors of the hepatitis C virus NS5B polymerase: discovery and initial optimization studies," Bioorg Med Chem Lett. Feb. 1, 2010;20(3):857-61. doi: 10.1016/i.bmcl.2009.12.101. Epub Jan. 4, 2010.
Bung, C., et al., Influence of the hepatitis C virus 3'-untranslated region on IRES-dependent and cap-dependent translation initiation. FEBS Lett. 584(4): p. 837-42.
Chen, G. et al., "Discovery of N-(4'-(indol-2-yl)phenyl)sulfonamides as novel inhibitors of HCV replication," Bioorg Med Chem Lett. Jul. 1, 2013;23(13):3942-6. doi: 10.1016/j.bmcl.2013.04.050. Epub Apr. 30, 2013.
Chou TC, Theoretical basis, experimental design, and computerized simulation of synergism and antagonism in drug combination studies. Pharmacol. Rev., 2006. 58(3): p. 621-681.
Della Rosa, C., et al., "A new approach to the synthesis of beta-amino acids," Synthesis, 2006, No. 18, pp. 3092-3098.
Donner, P. et al., "High potency improvements to weak aryl uracil HCV polymerase inhibitor leads," Bioorg Med Chem Lett. Aug. 1, 2013;23(15):4367-9. doi: 10.1016/j.bmcl.2013.05.078. Epub Jun. 4, 2013.
Dorner, M., et al., A genetically humanized mouse model for hepatitis C virus infection. Nature. 474(7350): p. 208-11.
El Hefnawi, M.M., et al., Natural genetic engineering of hepatitis C virus NS5A for immune system counterattack. Ann N Y Acad Sci, 2009. 1178: p. 173-85.
El Hefnawi, M.M., et al., "Prediction of prognostic biomarkers for Interferon-based therapy to Hepatitis C Virus patients: a metaanalysis of the NS5A protein in subtypes 1a, 1b, and 3a," Virol J. 2010; 7: 130.
Friebe, P., et al., Sequences in the 5' nontranslated region of hepatitis C virus required for RNA replication. J Virol, 2001. 75(24): p. 12047-57.
Gaertner, R., "Rearrangements involving 2-Thenylmagnesium chloride," J. Amer. Chem. Soc., 1951, v. 73, pp. 3934-3937.
Gallego, J. and G. Varani, The hepatitis C virus internal ribosome-entry site: a new target for antiviral research. Biochem Soc Trans, 2002. 30(2): p. 140-5.
Gewald, K., et al., "Zur Reaktion von 2-Aminothiophen-3-carbonitrilen mit Heterocumulenen," Journ. Fuer Praktische Chemie, 1991, v. 333, No. 2, pp. 229-236 (w/English abstract).
Hofmann, W.P., et al., Impact of ribavirin on HCV replicon RNA decline during treatment with interferon-alpha and the protease inhibitors boceprevir or telaprevir. Antivir Ther, 2011. 16(5): p. 695-704.
Khalil, A. M., et al., "Synthesis and Antimicrobial Evaluation of Some New Thiophene Derivatives," Synthetic communications, 2010, v. 40, pp. 1658-1669.

Kim, N. D. et al., "Discovery of novel HCV polymerase inhibitors using pharmacophore-based virtual screening," Bioorg Med Chem Lett. Jun. 1, 2011;21(11):3329-34. doi: 10.1016/j.bmcl.2011.04.010. Epub Apr. 9, 2011.
Koch, U., et al., "2-(2-Thienyl)-5,6-dihydroxy-4-carboxypyrimidines as inhibitors of the hepatitis C virus NS5B polymerase: discovery, SAR, modeling, and mutagenesis," J Med Chem. Mar. 9, 2006;49(5):1693-705.
LaPorte, M. G., et al., "Tetrahydrobenzothiophene inhibitors of hepatitis C virus NS5B polymerase," Bioorg Med Chem Lett. Jan. 1, 2006;16(1):100-3. Epub Nov. 2, 2005.
Lavanchy, D., The global burden of hepatitis C. Liver Int, 2009. 29 Suppl 1: p. 74-81.
Lindenbach, B.D. and C.M. Rice, Unravelling hepatitis C virus replication from genome to function. Nature, 2005. 436 (7053): p. 933-8.
Lohmann, V., et al., Replication of subgenomic hepatitis C virus RNAs in a hepatoma cell line. Science, 1999. 285 (5424): p. 110-3.
Long, G., et al., Mouse hepatic cells support assembly of infectious hepatitis C virus particles. Gastroenterology, 2011. 141(3): p. 1057-66.
Muraro, G. et al., "Recherches en serie thiophenique. Synthese d'acides omega-(dichloro-2,5 thienyl-3) alcanoiques et omega-(ditertiobutyl-2,5 thienyl-3) alcanoiques," Bull. Soc. Chim. France, 1973, pp. 310-317.
Nilsson, M., et al., "Synthesis and SAR of potent inhibitors of the Hepatitis C virus NS3/4A protease: Exploration of P2 quinazoline substituents," Bioorg. Medicinal Chem. Lett., 2010, v. 20, pp. 4004-4011.
Patch, R. J. et al., "Identification of 2-acylaminothiophene-3-carboxamides as potent inhibitors of FLT3," Bioorg. Medicinal Chem. Lett., 2006, v. 16, pp. 3282-3286.
Paulsen, R.B., et al., Inhibitor-induced structural change in the HCE IRES domain IIa RNA. Proc Natl Acad Sci U S A, 2010. 107(16): p. 7263-8.
Rault, S., et al., "Synthesis of 4H-6-aminopyrrolo[1,2-a]thieno[3,2-f]-1,4-diazepine," Compte Rendus des Seances de L'Academie des Sciences, Serie C, Sciences Chimiques, v. 290, No. 9, Mar. 3, 1980, pp. 169-171.
Shimoike, T., et al., Down-regulation of the internal ribosome entry site (IRES)-mediated translation of the hepatitis C virus: critical role of binding of the stem-loop IIId domain of IRES and the viral core protein. Virology, 2006. 345(2): p. 434-45.
Simmonds, P., et al., Consensus proposals for a unified system of nomenclature of hepatitis C virus genotypes. Hepatology, 2005. 42(4): p. 962-73.
Van Regenmortel, M.H., Virus species and virus identification: past and current controversies. Infect Genet Evol, 2007. 7(1): p. 133-44.
Wakita, T., et al., Production of infectious hepatitis C virus in tissue culture from a cloned viral genome. Nat Med, 2005. 11(7): p. 791-6.
Wang, Y., et al., "Dipeptidyl aspartyl fluoromethylketones as potent caspase inhibitors: peptidomimetic replacement of the P(2) amino acid by 2-aminoaryl acids and other non-natural amino acids," Bioorg Med Chem Lett. Nov. 15, 2007;17 (22):6178-82. Epub Sep. 8, 2007.
Webster, D.P., et al., Development of novel treatments for hepatitis C. Lancet Infect Dis, 2009. 9(2): p. 108-17.
Windisch, M.P., et al., Dissecting the interferon-induced inhibition of hepatitis C virus replication by using a novel host cell line. J Virol, 2005. 79(21): p. 13778-93.
International Search Report and Written Opinion for Application No. PCT/EP2015/058421, dated Oct. 2, 2015.

COMPOUNDS FOR TREATING VIRAL INFECTIONS

The present application claims priority under 35 U.S.C. §120 to U.S. Provisional Patent Application No. 61/980,940 filed in the United States of America on Apr. 17, 2014, and under 35 U.S.C. §365 to PCT/EP2015/058421, filed on Apr. 17, 2015, the disclosures of which are incorporated herein by reference.

BACKGROUND OF THE INVENTION

Approximately 200 million people worldwide are chronically infected with HCV. This pathogen is the major cause of acute hepatitis and chronic liver disease, including cirrhosis and liver cancer and thereby HCV is the leading indication for liver transplantation [1]. HCV is an enveloped, positive-stranded RNA virus, member of the Flaviviridae family in the hepacivirus genus. HCV is closely related to the flavivirus genus, which includes a number of viruses implicated in human disease, such as dengue virus and yellow fever virus [2]. Seven major HCV genotypes and numerous subtypes have been described, which differ as much as ~30% in the nucleotide sequences [3, 4]. The single stranded 9.6 kb genome consists of a single open reading frame (ORF) which is flanked at the 5' and 3' ends by highly structured and conserved non-translated regions (NTRs) important for both viral translation and viral replication [5]. At the 5' end, the approximately 340 nucleotide long NTR sequence contains an internal ribosome entry site (IRES) that directs translation independent of a capstructure. The viral polyprotein is co- and posttranslationally processed into ten viral proteins (core, E1, E2, p7, NS2, NS3, NS4A, NS4B, NS5A, and NS5B). The HCV 5'NTR and its IRES are characterized by the formation of complexes with the host cell small ribosomal subunit (40 S) and eukaryotic initiation factor (eIF), resulting in the recognition of the viral start codon, thus starting the viral protein synthesis [6].

With the development of various cell culture models to study HCV, major progress has been made. Recently, it has become feasible to investigate all steps of the viral life cycle, entry, viral RNA replication, infectious viral particle formation (packaging, assembly and release) and in vivo infection using pseudoparticles (HCVpp) [11], subgenomic replicon cells [12], infectious cell culture system (HCVcc) [13] and transgenic mice [14], respectively. Among these, the development of the subgenomic replicon system was the most important advance, in that for the first time it was possible to utilize a cell-based assay to evaluate potential antiviral therapies. HCV subgenomic replicons consist of a HCV RNA in which the HCV structural region is replaced by the neomycin phosphotransferase gene and translation of the viral proteins NS3 to NS5 is directed by the encephalomyocarditis virus (EMCV) IRES element flanked by the 5' and 3' NTRs. Stable HCV RNA replication has been established in various liver and non-liver, human and non-human cell lines which are excellent tools to study the HCV life cycle and to validate novel antivirals [12, 15-17].

Despite increasing efforts to develop novel drugs effective against HCV, patients are being mainly treated with a virus-unspecific combination therapy of pegylated interferon alpha (PEG-IFN) and ribavirin (RBV). This treatment is expensive, associated with severe side effects and is effective in only 50-60% of patients infected with HCV genotype 1 [18]. Since early 2011, two direct acting antivirals (DAAs) targeting the viral NS3 protease are FDA approved. Unfortunately both drugs induce severe side effects, have a low resistance barrier and the administration regime is inconvenient to patients [19]. Furthermore, at one point, viral resistance may become an issue, and due to potential HCV genotype specificity, it is unclear whether all seven HCV genotypes and their subtypes are covered [20]. Therefore, it is a primary goal to identify targets with a significant higher genetic barrier of resistance covering all HCV genotypes. Other challenges include the appearance of escape mutants, the high costs of current therapy regimens, and their side effects. The mechanisms of resistance to IFN-based therapy through immune-system interception [21], and to DAAs like telaprevir and boceprevir through resistance conferring mutations could be avoided by combinatorial treatment. Although drugs targeting the virus are in clinical trials, there is a medical need for new HCV therapeutic agents. In particular, there is a need for HCV therapeutic agents that have broad activity against the majority of HCV genotypes and their subtypes (e.g. 1a/b, 2a/b, 3a/b, 4a/b, etc.). There is also a particular need for agents that are less susceptible to viral drug resistance.

Formula I compounds and Formula II compounds in accordance with the present invention, have been found to possess useful activity against all major HCV genotypes. Additionally, compounds in accordance with the present invention have been shown to have significant antiviral activity against drug resistant viruses (protease, NS5A and polymerase).

Drug combination experiments with compounds according to the present invention and selected HCV-specific FDA- and not yet FDA approved DAAs revealed beneficial properties that make them well suited to fulfill the current needs for HCV agents.

It was an object of the present invention to identify compounds with an anti-viral activity.

It was also an object of the present invention to identify compounds effective against viral disease, in particular HCV.

DETAILED DESCRIPTION OF THE INVENTION

In describing the invention, chemical elements are identified in accordance with the Periodic Table of Elements. Abbreviations and symbols utilized herein are in accordance with the common usage of such abbreviations and symbols by those skilled in the chemical and biological arts. Specifically, the following abbreviations may be used in the examples and throughout the specification.

g (grams); mg (milligrams);
kg (kilograms); μg (micrograms);
L (liters); mL (milliliters);
μL (microliters); psi (pounds per square inch);
M (molar); mM (millimolar);
μM (micromolar); nM (nanomolar);
pM (picomolar); nm (nanometers);
mm (millimeters); wt (weight);
N (Normal); CFU (colony forming units);
i.v. (intravenous); Hz (Hertz);
MHz (megahertz); mol (moles);
mmol (millimoles); RT (room temperature);
mn (minutes); h (hours);
b.p. (boiling point); TLC (thin layer chromatography);
Tr (retention time); RP (reverse phase);
MeOH (methanol); i-PrOH (isopropanol);
TEA (triethlamine); TFA (trifluoroacetic acid);
TFAA (trifluoroacetic anhydride); THF (tetrahydrofuran);
DMSO (dimethylsulfoxide); EtOAc (ethyl acetate);

DME (1,2-dimethoxyethane); DCM (dichloromethane); DCE (dichloroethane); DMF (N,N-dimethylformamide); DMPU (N,N'-dimethylpropyleneurea); CDI (1,1-carbonyldiimidazole);

IBCF (isobutyl chloroformate); AcOH (acetic acid);

THP (tetrahydropyran); NMM (N-methylmorpholine);

Pd/C (Palladium on Carbon); MTBE (tert-butyl methyl ether);

HOBT (1-hydroxybenzotriazole); mCPBA (meta-chloroperbenzoic acid);

EDC (1-[3-dimethylamino]propyl)-3-ethylcarbodiimide hydrochloride);

DCC (dicyclohexylcarbodiimide); CBZ (benzyloxycarbonyl);

Ac (acetyl); atm (atmosphere);

TMSE (2-(trimethylsilyl)ethyl); TMS (trimethylsilyl);

TIPS (triisopropylsilyl); TBS (t-butyldimethylsilyl);

DMAP (4-dimethylaminopyridine); BSA (bovine serum albumin);

NAD (nicotinamide adenine dinucleotide); HPLC (high pressure liquid chromatography);

LC/MS (liquid chromatography/mass spectrometry);

BOP (bis(2-oxo-3-oxazolidinyl)phosphinic chloride); TBAF (tetra-n-butylammonium fluoride);

HBTU (O-benzotriazole-1-yl-N,N,N',N'-tetramethyluroniumhexafluoro phosphate);

HEPES (4-(2-hydroxyethyl)-1-piperazine ethane sulfonic acid);

DPPA (diphenylphosphoryl azide); LAH (Lithium aluminum hydride);

NaOMe (sodium methoxide); EDTA (ethylenediaminetetraacetic acid);

TMEDA (N,N,N',N'-tetramethyl-1,2-ethanediamine);

NBS (N-bromosuccinimide); DIPEA (diisopropylethylamine);

Dppf (1,1'-bis(diphenylphosphino)ferrocene); and NIS (N-iodosuccinimide).

All references to ether are to diethyl ether and brine refers to a saturated aqueous solution of NaCl.

TERMS AND DEFINITIONS

"Alkyl" refers to a monovalent saturated hydrocarbon chain having the specified number of member carbon atoms. For example, C1-C7 alkyl refers to an alkyl group having from 1 to 7 member carbon atoms. Alkyl groups may be optionally substituted with one or more substituents with one or more substituents as defined herein. Alkyl groups may be straight or branched. Representative branched alkyl groups have one, two, or three branches. In one embodiment, "alkyl" refers to $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$ $C_{17}$, $C_{18}$, $C_{19}$, $C_{20}$, $C_{21}$, $C_{22}$, $C_{23}$ and/or $C_{24}$, alkyl, and combinations of any of the foregoing including the ranges $C_1$ to $C_4$, alkyl, $C_2$-$C_4$ alkyl, $C_2$-$C_{12}$ alkyl, $C_3$-$C_6$ alkyl, $C_3$-$C_{12}$ alkyl, $C_4$-$C_6$ alkyl, $C_4$-$C_8$ alkyl, $C_4$-$C_{10}$ alkyl, $C_4$-$C_{12}$ alkyl, $C_5$-$C_8$ alkyl, $C_5$-$C_{10}$ alkyl, $C_5$-$C_{12}$ alkyl, $C_5$-$C_{14}$ alkyl, $C_6$-$C_8$ alkyl, $C_6$-$C_{10}$ alkyl, $C_6$-$C_{12}$ alkyl.

"Alkenyl" refers to an unsaturated hydrocarbon chain having the specified number of member carbon atoms and having one or more carbon-carbon double bonds within the chain. For example, C2-C6 alkenyl refers to an alkenyl group having from 2 to 6 member carbon atoms. In certain embodiments, alkenyl groups have one carbon-carbon double bond within the chain. In other embodiments, alkenyl groups have more than one carbon-carbon double bond within the chain. Alkenyl groups may be optionally substituted with one or more substituents as defined herein. Alkenyl groups may be straight or branched. Examples of alkenyl useful in accordance with the present invention are $C_2$-$C_{10}$, $C_2$-$C_9$, $C_2$-$C_8$, $C_2$-$C_7$, $C_2$-$C_6$, $C_2$-$C_5$ and $C_2$-$C_4$ alkenyl.

"Alkoxy" refers to an alkyl moiety attached through an oxygen bridge (i.e. a —O—C1-C6 alkyl group wherein C1-C6 is defined herein). Examples of such groups include methoxy, ethoxy, propoxy, butoxy, pentoxy and hexoxy.

"Alkynyl" refers to an unsaturated hydrocarbon chain having the specified number of member carbon atoms and having one or more carbon-carbon ripple bonds within the chain. For example, C2-C6 alkynyl refers to an alkynyl group having from 2 to 6 member atoms. Alkynyl groups may be optionally substituted with one or more substituents. Examples of alkynyls useful in accordance with the present invention are $C_2$-$C_{10}$, $C_2$-$C_9$, $C_2$-$C_8$, $C_2$-$C_7$, $C_2$-$C_6$, $C_2$-$C_5$ and $C_2$-$C_4$ alkynyl.

"Aryl" refers to an aromatic hydrocarbon ring system. Aryl groups are monocyclic ring systems or bicyclic ring systems. Monocyclic aryl ring refers to phenyl. Bicyclic aryl rings refer to naphthyl and to rings wherein phenyl is fused to a cycloalkyl or cycloalkenyl ring having 5, 6, or 7 member carbon atoms. Aryl groups may be optionally substituted with one or more substituents as defined herein. Examples of substituents that are suitable include but are not limited to hydroxyl, halogen, cyano, sulfonyl, further aryl(s), $C_1$-$C_5$ alkyl, $C_1$-$C_4$ alkoxy, oxo, $C_3$-$C_6$ cycloalkyl, heteroaryl, heterocycloalkyl, $C_1$-$C_3$ sulfanyl.

'Cycloalkyl" refers to a saturated hydrocarbon ring having the specified number of member carbon atoms. Cycloalkyl groups are monocyclic ring systems. For example, C3-C7 cycloalkyl refers to a cycloalkyl group having from 3 to 6 member atoms. Cycloalkyl groups may be optionally substituted with one or more substituents as defined herein. Cycloalkyl includes cyclopropyl, cyclobutyl, cyclopentyl, cyclohexyl, and cycloheptyl. Examples of substituents that are suitable include but are not limited to hydroxyl, halogen, cyano, sulfonyl, further aryl(s), $C_1$-$C_5$ alkyl, $C_1$-$C_4$ alkoxy, oxo, $C_3$-$C_6$ cycloalkyl, heteroaryl, heterocycloalkyl, $C_1$-$C_3$ sulfanyl.

"Boc" refers to tert-butyloxycarbonyl.

"Cycloalkenyl" refers to an unsaturated carbon ring having the specified number of member carbon atoms and having a carbon-carbon double bond within the ring. For example, C3-C6 cycloalkenyl refers to a cycloalkenyl group having from 3 to 6 member carbon atoms. Cycloalkenyl rings are not aromatic. Cycloalkenyl groups are monocyclic ring systems. Cycloalkenyl groups may be optionally substituted with one or more substituents as defined herein.

"Halo" refers to the halogen radicals fluoro, chloro, bromo, and iodo.

"Haloalkyl" refers to an alkyl group wherein at least one hydrogen atom attached to a member atom within the alkyl group is replaced with halo. The number of halo substituents include but are not limited to 1, 2, 3, 4, 5, or 6 substituents. Haloalkyl includes monofluoromethyl, difluoroethyl, and trifluoromethyl.

"Heteroaryl" refers to an aromatic ring containing from 1 to 5, suitably 1 to 4, more suitably 1 or 2 heteroatoms as member atoms in the ring. Heteroaryl groups containing more than one heteroatom may contain different heteroatoms. Heteroaryl groups may be optionally substituted with one or more substituents as defined herein. Heteroaryl groups are monocyclic ring systems, or fused bicyclic ring systems. Monocyclic heteroaryl rings have from 5 to 6 member atoms. Bicyclic heteroaryl rings have from 8 to 10 member atoms. Bicylic heteroaryl rings include those rings wherein the primary heteroaryl and the secondary monocyclic cycloalkyl, cycloalkenyl, heterocycloalkyl, aryl or heteroaryl ring are attached, forming a fused bicyclic ring system. Heteroaryl includes, among others, pyrrolyl, pyrazolyl, imidazolyl, oxazolyl, isoxazolyl, oxadiazolyl, thiazolyl, isothiazolyl, thiadiazolyl, furanyl, furazanyl, thienyl, triazolyl, pyridinyl, pyrimidinyl, pyridazinyl, pyrazinyl, triazinyl, tetrazinyl, tetrazolyl, indolyl, isoindolyl, indolizinyl, indazolyl, purinyl, quinolinyl, isoquinolinyl, quinoxalinyl, quinazolinyl, pteridinyl, cinnolinyl, benzimidazolyl, benzopyranyl, benzoxazolyl, benzisoazolyl, benzofuranyl, isobenzofuranyl, benzothiazoyl, benzisothiazolyl, benzothienyl, furopyridinyl, naphthyridinyl, pyrazolopyridyl, pyrazolopyrimidinyl, 3H-[1,2,3]triazolo[4,5-d]pyrimidinyl, and 3H-[1,2,3]triazolo[4,5-b]pyridinyl.

"Heteroatom" refers to a nitrogen, sulfur, or oxygen atom.

"Heterocycloalkyl" refers to a saturated or unsaturated ring containing from 1 to 4 heteroatoms as member atoms in the ring. Heterocycloalkyl rings are not aromatic. Heterocycloalkyl groups containing more than one heteroatom may contain different heteroatoms. Heterocycloalkyl groups may be optionally substituted with one or more substituents as defined herein. Heterocycloalkyl groups are monocyclic ring systems or are fused, spiro, or bridged bicyclic ring systems. Monocyclic heterocycloalkyl rings have from 4 to 7 member atoms. Bicyclic heterocycloalkyl rings have from 7 to 11 member atoms. Heterocycloalkyl includes, among others, pyrrolidinyl, tetrahydrofuranyl, dihydrofuranyl, pyranyl, tetrahydropyranyl, dihydropyranyl, tetrahydrothienyl, pyrazolidinyl, oxazolidinyl, thiazolidinyl, piperidinyl, homopiperidinyl, piperazinyl, morpholinyl, thiamorpholinyl, 1-pyrazolidinyl, azepinyl, 1,3-dioxanyl, 1,4-dioxanyl, 1,3-oxathiolanyl, 1,3-dithianyl, azetidinyl, is oxazolidinyl, 3-azabicyclo[3.1.0]hexyl, azabicyclo[3.2.1]octyl, azabicyclo[3.3.1]nonyl, azabicyclo[4.3.0]nonyl, 2,5-diazabicyclo[2.2.1]heptanyl, octahydropyrrolo[1,2-a]pyrazinyl, octahydropyrazino[2,1-c][1,4]oxazinyl, oxabicyclo[2.2.1]heptyl, hexahydro-1H-azepinyl-2,3,4,7-tetrahydro-1H-azepinyl, oxabicyclo[2.2.1]heptyl, tetrahydro-5H-[1,3]dioxolo[4,5-c]pyrrolyl, tetrahydro-1H-furo[3,4-c]pyrrol-93H)-yl, hexahydropyrrolo[1,2-a]pyrazin-(1H)-yl, octahydropyrazino[1,2-a]azepin-(1H)-yl, hexahydropyrazino[2,1-c][1,4]oxazin-(1H0-yl, hexahydropyrrolo[3,4-c]pyrrol-(1H)-yl, 10-oxa-4-azatricyclo[5.2.1.02.6]decyl, octahydro-1(2H)-quinoxalinyl, octahydro-1H-cyclopenta[b]pyrazinyl, hexahydrofuro[3,4-b]pyrazin-(2H)-yl, octahydro-6H-pyrrolo[3,4-b]pyridinyl, 4,7-diazaspiro[2.5]octyl, and 5-azaspiro[2.4]heptyl.

"Member atoms" refers to the atom or atoms that form a chain or ring. Where more than one member atom is present in a chain and within a ring, each member atom is covalently bound to an adjacent member atom in the chain or ring. Atoms that make up a substituent group on a chain or ring are no member atoms in the chain or ring.

"Optionally substituted" indicates that a group, such as alkyl, alkenyl, alkynyl, aryl, cycloalkyl, cycloalkenyl, heterocycloalkyl, or heteroaryl, may be unsubstituted, or the group may be substituted with one or more substituents as defined herein.

"Pharmaceutically acceptable" refers to those compounds, materials, compositions, and dosage forms which are, within the scope of sound medical judgment, suitable for use in contact with the tissues of human beings or animals without excessive toxicity, irritation, or other problem or complication, commensurate with a reasonable benefit/risk ratio.

"Substituted" in reference to a group indicates that one or more hydrogen atoms attached to a member atom within the group is replaced with a substituent selected from the group of defined or suitable substituents. It should be understood that the term "substituted" includes the implicit provision that such substitution be in accordance with the permitted valence of the substituted atom and the substituent, and that the substitution results in a stable compound. When it is stated that a group may contain one or more substituents, one or more member atom within the group may be substituted. In addition, a single member atom within the group may be substituted with more than one substituent as long as such substitution is in accordance with the permitted valence of the atom.

Compounds

In one aspect, the present invention is directed to compounds according to Formula I:

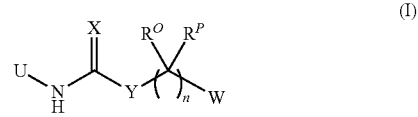

U is an aryl or heteroaryl; preferably a thiophene or phenyl; W is an aryl or heteroaryl; preferably a thiophene or phenyl. $R^O$ and $R^P$ are each independently at each occurrence selected from the group consisting of H, C1-C5 alkyl, C1-C5 alkenyl, C1-C5 alkynyl, C3-C6 cycloalkyl; heterocycloalkyl; heteroaryl; phenyl; with either the proviso that, when one of $R^O$ or $R^P$ is H, then the other one of $R^O$ or $R^P$ is not methyl; or with the proviso that the compound is not compound 1 as shown in table 1;

Or $R^O$ and $R^P$ are joined together, forming a cycloalkyl group, cycloalkenyl group, or heterocycloalkyl group optionally substituted with one to four $R^I$ groups; wherein $R^I$ is selected from the group consisting of H; halo; cyano; C1-C5 alkyl, preferably C1-C3 alkyl; C1-C3 sulfanyl; C1-C4 alkoxy, preferably C1-C3 alkoxy; C1-C3 haloalkyl; hydroxyl; oxo; —NRaRb; —C(O)NRaRb; —C(O)Rc; —C(O)ORc; sulfonyl; sulfoxide; $(CH_2)_pOH$; $(CH_2)_pORa$; $(CH_2)_pNR^GR^H$; $(CH_2)_pOC(O)NRaRb$; $(CH_2)_pC(O)NRaRb$; C3-C6 cycloalkyl; heterocycloalkyl; aryl; heteroaryl; phenyl;

Ra and Rb are each independently at each occurrence selected from the group consisting of hydrogen, C1-C6 alkyl, substituted C1-C6 alkyl, C1-C6 alkoxyC1-C6 alkyl, C6-C14 alkyl chain containing one or several of —O—, —C(O)NH—, —NHC(O)—, —N—, or —NHC(O)O— optionally with a terminal —NH$_2$ or —NH-Boc; C1-C6 alkenyl, substituted C1-C6 alkenyl, C1-C6 alkynyl, substituted C1-C6 alkynyl, C3-C7 cycloalkyl, substituted C3-C7 cycloalkyl, aryl, substituted aryl, heteroaryl, substituted heteroaryl, heterocycloalkyl, substituted heterocycloalkyl; or Ra and Rb, together with the nitrogen atom to which they are bonded, form a 4- to 10-membered saturated or unsaturated heterocyclic ring which is optionally substituted with one or more C1-C3 alkyl, benzyl, phenyl, C1-C3 alkoxy or halogen;

Rc is selected from the group consisting of hydrogen, C1-C10 alkyl, preferably C1-C6 alkyl, C1-C10 alkenyl, preferably C1-C6 alkenyl, C1-C10 alkynyl, preferably C1-C6 alkynyl, C3-C10 cycloalkyl, preferably C3-C7 cycloalkyl, C1-C3 haloalkyl, aryl, heteroaryl, heterocycloalkyl, wherein each of the aforementioned alkyl, alkenyl, alkynyl, cycloalkyl, aryl, heteroaryl and heterocycloalkyl may be substituted with one or more of hydroxyl, halo, alkoxy, oxo, sulfonyl, sulfoxide, aryl, heteroaryl or —NRaRb;

$R^G$ is selected from the group consisting of H; C1-C6 alkyl; C1-C6 alkoxy; C3-C6 cycloalkyl; heterocycloalkyl; heteroaryl; phenyl;

$R^H$ is selected from the group consisting of H; C1-C6 alkyl; C1-C6 alkoxy; C3-C6 cycloalkyl; heterocycloalkyl; heteroaryl; phenyl; or $R^G$ and $R^H$, together with the nitrogen atom to which they are bonded, form a 4- to 10-membered saturated or unsaturated heterocyclic ring which is optionally substituted with one or more $C_1$-$C_3$ alkyl, benzyl, phenyl, $C_1$-$C_3$ alkoxy or halogen;

X is O, S or N—CN;
Y is NH, O, —C(O)NH— or a bond;
n is an integer from 0 to 3, preferably 0, 1, 2 or 3;
and p is an integer from 0 to 5, preferably 0, 1, 2, 3, 4 or 5.

It should be noted that the invention also relates to pharmaceutically acceptable salts of these compounds and of the compounds shown and described further below.

One embodiment relates to compounds according to Formula (Ia):

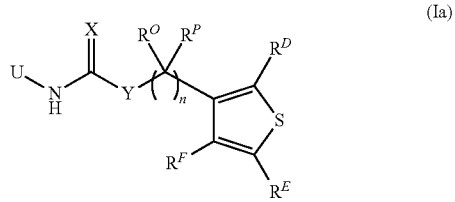

(Ia)

wherein
U is selected from

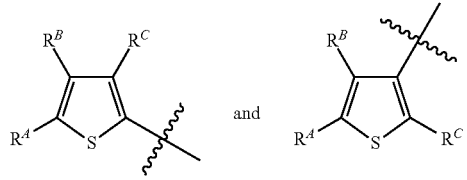

and $R^A$ is selected from the group consisting of H; halo; cyano; C1-C5 alkyl; C3-C6 cycloalkyl; C1-C3 alkoxy; C1-C3 haloalkyl; —C(O)NRaRb; —C(O)Rc; —C(O)ORc; C1-C3 sulfanyl; phenyl; heteroaryl; —$NR^GR^H$;

$R^B$ is selected from the group consisting of H; halo; cyano; C1-C5 alkyl; C3-C6 cycloalkyl; C1-C3 alkoxy; —C(O)NRaRb; —C(O)Rc; —C(O)ORc; C1-C3 haloalkyl; C1-C3 sulfanyl; phenyl; heteroaryl; —$NR^GR^H$;

Or $R^A$ and $R^B$ are joined together forming a cycloalkyl group, aryl, heteroaryl, or heterocycloalkyl group optionally substituted with one to four $R^I$ groups;

$R^C$ is selected from the group consisting of H; halo; cyano; —C(O)NRaRb; —C(O)Rc; —C(O)ORc; C1-C3 sulfanyl; sulfonyl; sulfoxide; phenyl; aryl; heteroaryl; C1-C5 alkyl; C1-C5 alkenyl; C1-C5 alkynyl; C1-C5 alkyl, alkenyl, or alkynyl substituted with hydroxyl, alkoxy, or —NRaRb; C3-C6 cycloalkyl; C1-C3 alkoxy; C1-C3 haloalkyl; —$NR^GR^H$;

$R^D$ is selected from the group consisting of halo; cyano; C1-C5 alkyl; C3-C6 cycloalkyl; C1-C3 alkoxy; C1-C3 haloalkyl; C1-C3 sulfanyl; phenyl; aryl; heteroaryl; —$NR^GR^H$; —C(O)NRaRb; —C(O)Rc; —C(O)ORc; sulfonyl; sulfoxide;

$R^E$ is selected from the group consisting of H; halo; cyano; C1-C5 alkyl; C3-C6 cycloalkyl; C1-C3 alkoxy; C1-C3 haloalkyl; C1-C3 sulfanyl; phenyl; heteroaryl; —$NR^GR^H$; —$CH_2NR^MR^N$;

$R^F$ is selected from the group consisting of H; halo; cyano; C1-C5 alkyl; C3-C6 cycloalkyl; C1-C3 alkoxy; C1-C3 haloalkyl; C1-C3 sulfanyl; phenyl; heteroaryl; —$NR^GR^H$;

Or $R^E$ and $R^F$ are joined together forming a cycloalkyl group, heteroaryl, or heterocycloalkyl group optionally substituted with one to four $R^I$ groups.

$R^G$ is selected from the group consisting of H; C1-C6 alkyl; C1-C6 alkoxy; C3-C6 cycloalkyl; heterocycloalkyl; heteroaryl; phenyl;

$R^H$ is selected from the group consisting of H; C1-C6 alkyl; C1-C6 alkoxy; C3-C6 cycloalkyl; heterocycloalkyl; heteroaryl; phenyl; or $R^G$ and $R^H$, together with the nitrogen atom to which they are bonded, form a 4- to 10-membered saturated or unsaturated heterocyclic ring which is optionally substituted with one or more C1-C3 alkyl, benzyl, phenyl, C1-C3 alkoxy or halogen;

$R^I$ is selected from the group consisting of H; halo; cyano; C1-C5 alkyl, preferably C1-C3 alkyl; C1-C3 sulfanyl; C1-C4 alkoxy, preferably C1-C3 alkoxy; C1-C3 haloalkyl; hydroxyl; oxo; —NRaRb; —C(O)NRaRb; —C(O)Rc; —C(O)ORc; sulfonyl; sulfoxide; $(CH_2)_pOH$; $(CH_2)_pORa$; $(CH_2)_pNR^GR^H$; $(CH_2)_pOC(O)NRaRb$; $(CH_2)_pC(O)NRaRb$; C3-C6 cycloalkyl; heterocycloalkyl; aryl; heteroaryl; phenyl;

$R^O$ and $R^P$ are each independently at each occurrence selected from the group consisting of H, C1-C5 alkyl, C1-C5 alkenyl, C1-C5 alkynyl, C3-C6 cycloalkyl; heterocycloalkyl; heteroaryl; phenyl; with either the proviso that, when one of $R^O$ or $R^P$ is H, then the other one of $R^O$ or $R^P$ is not methyl; or with the proviso that the compound is not compound 1 as shown in table 1;

Or $R^O$ and $R^P$ are joined together, forming a cycloalkyl group, cycloalkenyl group, or heterocycloalkyl group optionally substituted with one to four $R^I$ groups as defined above;

$R^M$ and $R^N$ are each independently at each occurrence selected from the group consisting of H; C1-C6 alkyl, C3-C6 cycloalkyl, C1-C3 haloalkyl, phenyl; aryl; heteroaryl; —$NR^GR^H$; —C(O)NRaRb; —C(O)Rc; —C(O)ORc; sulfonyl; sulfoxide; C1-C6 alkyl substituted with hydroxyl, alkoxy, or —NRaRb, phenyl; —$NR^GR^H$; —C(O)NRaRb; —C(O)Rc; —C(O)ORc; sulfonyl; sulfoxide;

or $R^M$ and $R^N$ are joined together with the N-atom to which they are attached, forming a heterocycloalkyl group;

Ra and Rb are each independently at each occurrence selected from the group consisting of hydrogen, C1-C6 alkyl, substituted C1-C6 alkyl, C1-C6 alkoxyC1-C6 alkyl, C6-C14 alkyl chain containing one or several of —O—, —C(O)NH—, —NHC(O)—, —N—, or —NHC(O)O—, optionally with a terminal $NH_2$, or —NH-Boc; C1-C6 alkenyl, substituted C1-C6 alkenyl, C1-C6 alkynyl, substituted C1-C6 alkynyl, C3-C7 cycloalkyl, substituted C3-C7 cycloalkyl, aryl, substituted aryl, heteroaryl, substituted heteroaryl, heterocycloalkyl, substituted heterocycloalkyl; or Ra and Rb, together with the nitrogen atom to which they are bonded, form a 4- to 10-membered saturated or unsaturated heterocyclic ring which is optionally substituted with one or more C1-C3 alkyl, benzyl, phenyl, C1-C3 alkoxy or halogen;

Rc is selected from the group consisting of hydrogen, C1-C10 alkyl, preferably C1-C6 alkyl, C1-C10 alkenyl, preferably C1-C6 alkenyl, C1-C10 alkynyl, preferably C1-C6 alkynyl, C3-C10 cycloalkyl, preferably C3-C7 cycloalkyl, C1-C3 haloalkyl, aryl, heteroaryl, heterocycloalkyl, wherein each of the aforementioned alkyl, alkenyl, alkynyl, cycloalkyl, aryl, heteroaryl and heterocycloalkyl may be substituted with one or more of hydroxyl, halo, alkoxy, oxo, sulfonyl, sulfoxide, aryl, heteroaryl or —NRaRb;

X is O, S or N—CN;
Y is NH, O, —C(O)NH— or a bond;
n is an integer from 0 to 3, preferably 0, 1, 2 or 3;
p is an integer from 0 to 5, preferably 0, 1, 2, 3, 4 or 5.

In one embodiment Y is NH.

One embodiment relates to compounds according to Formula (Ib):

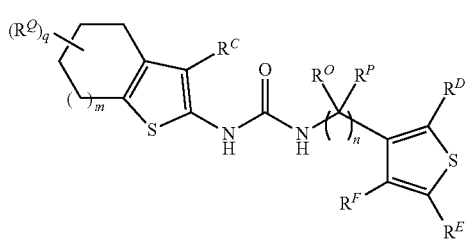

(Ib)

wherein $R^C$, $R^D$, $R^E$, $R^F$, $R^O$, $R^P$, and n are as defined above, and wherein $R^Q$ represents a-substituent which is independently at each occurrence selected from the group consisting of H; halo; cyano; C1-C5 alkyl; C3-C6 cycloalkyl; C1-C3 alkoxy; C1-C3 haloalkyl; C1-C3 sulfanyl; phenyl; aryl; heteroaryl; —NR$^G$R$^H$; —C(O)NRaRb; —C(O)Rc; —C(O)ORc; sulfonyl; sulfoxide; $(CH_2)_p$OH; $(CH_2)_p$ORa; $(CH_2)_p$NR$^G$R$^H$; $(CH_2)_p$OC(O)NRaRb; $(CH_2)_p$C(O)NRaRb;

$R^G$, $R^H$, Ra, Rb, and Rc have the same meanings defined above;
m is an integer from 0 to 2; preferably 0, 1 or 2;
n is an integer from 0 to 3 preferably 0, 1, 2 or 3;
p is an integer from 0 to 5; preferably 0, 1, 2, 3, 4 or 5;
q is an integer from 1 to 3; preferably 1, 2 or 3.

One embodiment relates to compounds according to Formula (Ic):

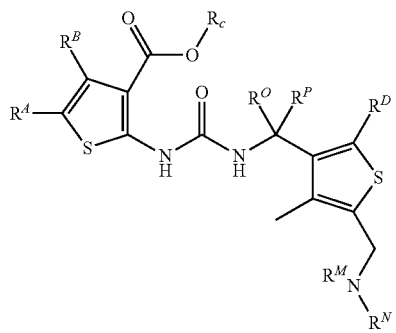

(Ic)

Wherein Rc is selected from C1-C10 alkyl, C1-C10 alkenyl, C1-C10 alkynyl, C3-C10 cycloalkyl, C1-C3 haloalkyl, aryl, heteroaryl, heterocycloalkyl, wherein each of the aforementioned alkyl, alkenyl, alkynyl, cycloalkyl, aryl, heteroaryl and heterocycloalkyl may be substituted with one or more of hydroxyl, halo, alkoxy, oxo, sulfonyl, sulfoxide, aryl, heteroaryl or —NRaRb;

$R^M$ and $R^N$ are each independently selected from the group consisting of H; C1-C6 alkyl, C3-C6 cycloalkyl, C1-C3 haloalkyl, phenyl; aryl; heteroaryl; —NR$^G$R$^H$; —C(O)NRaRb; —C(O)Rc; —C(O)ORc; sulfonyl; sulfoxide; C1-C6 alkyl substituted with hydroxyl, alkoxy, —NRaRb, phenyl, —NR$^G$R$^H$, —C(O)NRaRb, —C(O)Rc, —C(O)ORc, sulfonyl, or sulfoxide;

or $R^M$ and $R^N$ are joined together with the N-atom to which they are attached, forming a heterocycloalkyl group;

with $R^A$, $R^B$, $R^D$, $R^O$, $R^P$, $R^G$, $R^H$, Ra, Rb, and Rc having the same meanings defined above One embodiment relates to compounds according to Formula (Id):

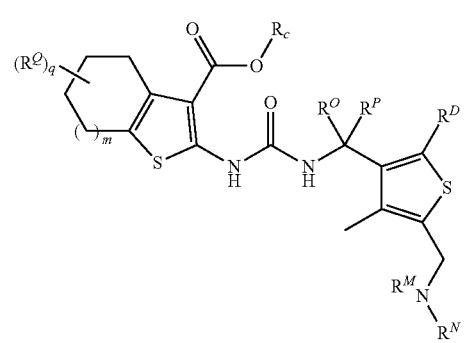

(Id)

Rc is selected from C1-C10 alkyl, C1-C10 alkenyl, C1-C10 alkynyl, C3-C10 cycloalkyl, C1-C3 haloalkyl, -aryl, heteroaryl, heterocycloalkyl, wherein each of the aforementioned alkyl, alkenyl, alkynyl, cycloalkyl, aryl, heteroaryl and heterocycloalkyl may be substituted with one or more of hydroxyl, halo, alkoxy, oxo, sulfonyl sulfoxide, aryl, heteroaryl or
—NRaRb;

$R^M$ and $R^N$ are each independently selected from the group consisting of H; C1-C6 alkyl, C3-C6 cycloalkyl, C1-C3 haloalkyl, phenyl; aryl; heteroaryl; —NR$^G$R$^H$; —C(O)NRaRb; —C(O)Rc; —C(O)ORc; sulfonyl; sulfoxide; C1-C6 alkyl substituted with hydroxyl, alkoxy, —NRaRb, phenyl, —NR$^G$R$^H$, —C(O)NRaRb, —C(O)Rc, —C(O)ORc, sulfonyl or sulfoxide;

or $R^M$ and $R^N$ are joined together with the N-atom to which they are attached, forming a heterocycloalkyl group;

$R^Q$ represents a substituent which is at each occurrence independently selected from the group consisting of H; halo; cyano; C1-C5 alkyl; C3-C6 cycloalkyl; C1-C3 alkoxy; C1-C3 haloalkyl; C1-C3 sulfanyl; phenyl; aryl; heteroaryl; —NR$^G$R$^H$; —C(O)NRaRb; —C(O)Rc; —C(O)ORc; sulfonyl; sulfoxide; $(CH_2)_p$OH; $(CH_2)_p$ORa; $(CH_2)_p$NR$^G$R$^H$; $(CH_2)_p$OC(O)NRaRb; $(CH_2)_p$C(O)NRaRb;

with $R^A$, $R^B$, $R^D$, $R^G$, $R^H$, $R^O$, $R^P$, Ra, Rb, and Rc having the same meanings defined above;
m is an integer from 0 to 2, preferably 0, 1 or 2;
p is an integer from 0 to 5, preferably 0, 1, 2, 3, 4 or 5;
q is an integer from 1 to 3, preferably 1, 2 or 3.

One embodiment relates to compounds according to Formula (Ie):

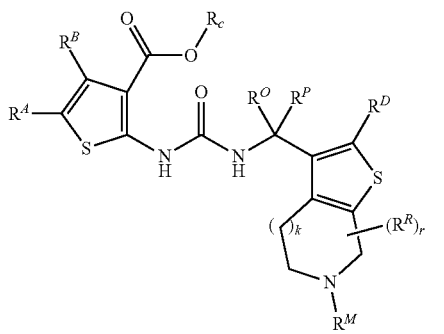

(Ie)

Rc is selected from C1-C10 alkyl, C1-C10 alkenyl, C1-C10 alkynyl, C3-C10 cycloalkyl, C1-C3 haloalkyl, aryl, heteroaryl, heterocycloalkyl, wherein each of the aforementioned alkyl, alkenyl, alkynyl, cycloalkyl, aryl, heteroaryl and heterocycloalkyl may be substituted with one or more of hydroxyl, halo, alkoxy, oxo, sulfonyl, sulfoxide, aryl, heteroaryl or —NRaRb;

$R^M$ is selected from the group consisting of H; C1-C6 alkyl, C3-C6 cycloalkyl, C1-C3 haloalkyl, phenyl; aryl; heteroaryl; —NR$^G$R$^H$; —C(O)NRaRb; —C(O)Rc; —C(O)ORc; sulfonyl; sulfoxide; C1-C6 alkyl substituted with hydroxyl, alkoxy, —NRaRb, phenyl, —NR$^G$R$^H$, —C(O)NRaRb, —C(O)Rc, —C(O)ORc, sulfonyl or sulfoxide;

$R^R$ represents a-substituent which is independently at each occurrence selected from the group consisting of H; halo; cyano; C1-C5 alkyl; C3-C6 cycloalkyl; C1-C3 alkoxy; C1-C3 haloalkyl; C1-C3 sulfanyl; phenyl; aryl; heteroaryl; —NR$^G$R$^H$; —C(O)NRaRb; —C(O)Rc; —C(O)ORc; sulfonyl; sulfoxide; $(CH_2)_pOH$; $(CH_2)_pORa$; $(CH_2)_pNR^GR^H$; $(CH_2)_pOC(O)NRaRb$; $(CH_2)_pC(O)NRaRb$;

with $R^A$, $R^B$, $R^D$, $R^G$, $R^H$, $R^O$, $R^P$, Ra, Rb, and Rc having the same meanings defined above;

k is an integer from 0 to 2, preferably 0, 1 or 2;
p is an integer from 0 to 5, preferably 0, 1, 2, 3, 4 or 5;
r is an integer from 1 to 3, preferably 1, 2 or 3.

One embodiment relates to compounds according to Formula (If):

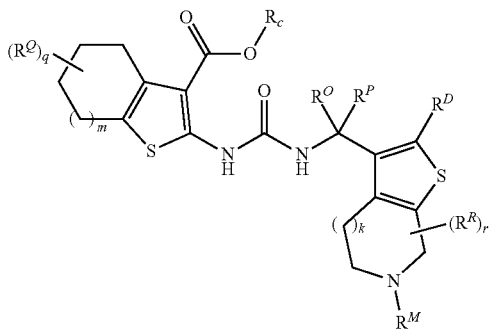

(If)

Rc is selected from C1-C10 alkyl, C1-C10 alkenyl, C1-C10 alkynyl, C3-C10 cycloalkyl, C1-C3 haloalkyl, -aryl, heteroaryl, heterocycloalkyl, wherein each of the aforementioned alkyl, alkenyl, alkynyl, cycloalkyl, aryl, heteroaryl and heterocycloalkyl may be substituted with one or more of hydroxyl, halo, alkoxy, oxo, sulfonyl, sulfoxide, aryl, heteroaryl or —NRaRb;

$R^M$ is selected from the group consisting of H; C1-C6 alkyl, C3-C6 cycloalkyl, C1-C3 haloalkyl, phenyl; aryl; heteroaryl; —NR$^G$R$^H$; —C(O)NRaRb; —C(O)Rc; —C(O)ORc; sulfonyl; sulfoxide; C1-C6 alkyl substituted with hydroxyl, alkoxy, —NRaRb, phenyl, —NR$^G$R$^H$, —C(O)NRaRb, —C(O)Rc, —C(O)ORc; sulfonyl, or sulfoxide;

$R^Q$ and $R^R$ represents a substituent which is at each occurrence independently selected from the group consisting of H; halo; cyano; C1-C5 alkyl; C3-C6 cycloalkyl; C1-C3 alkoxy; C1-C3 haloalkyl; C1-C3 sulfanyl; phenyl; aryl; heteroaryl; —NR$^G$R$^H$; —C(O)NRaRb; —C(O)Rc; —C(O)ORc; sulfonyl; sulfoxide; $(CH_2)_pOH$; $(CH_2)_pORa$; $(CH_2)_pNR^GR^H$; $(CH_2)_pOC(O)NRaRb$; $(CH_2)_pC(O)NRaRb$;

with $R^D$, $R^G$, $R^H$, $R^O$, $R^P$, Ra, Rb, and Rc having the same meanings defined above;

m is an integer from 0 to 2, preferably 0, 1 or 2;
k is an integer from 0 to 2, preferably 0, 1 or 2;
p is an integer from 0 to 5, preferably 0, 1, 2, 3, 4 or 5;
q is an integer from 1 to 3, preferably 1, 2, or 3; and
r is an integer from 1 to 3, preferably 1, 2 or 3.

One embodiment relates to compounds according to Formula (Ig):

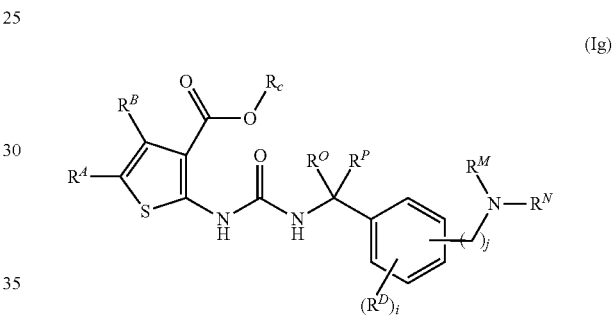

(Ig)

wherein $R^A$ is selected from the group consisting of H; halo; cyano; C1-C5 alkyl; C3-C6 cycloalkyl; C1-C3 alkoxy; C1-C3 haloalkyl; —C(O)NRaRb; —C(O)Rc; —C(O)ORc; C1-C3 sulfanyl; phenyl; heteroaryl; —NR$^G$R$^H$;

$R^B$ is selected from the group consisting of H; halo; cyano; C1-C5 alkyl; C3-C6 cycloalkyl; C1-C3 alkoxy; —C(O)NRaRb; —C(O)Rc; —C(O)ORc; C1-C3 haloalkyl; C1-C3 sulfanyl; phenyl; heteroaryl; —NR$^G$R$^H$;

Or $R^A$ and $R^B$ are joined together forming a cycloalkyl group, aryl, heteroaryl, or heterocycloalkyl group optionally substituted with one to four $R^I$ groups;

$R^D$ is a substituent which is independently at each occurrence selected from the group consisting of halo; cyano; C1-C5 alkyl; C3-C6 cycloalkyl; C1-C3 alkoxy; C1-C3 haloalkyl; C1-C3 sulfanyl; phenyl; aryl; heteroaryl; NR$^G$R$^H$; —C(O)NRaRb; —C(O)Rc; —C(O)ORc; sulfonyl; sulfoxide;

$R^G$ is selected from the group consisting of H; C1-C6 alkyl; C1-C6 alkoxy; C3-C6 cycloalkyl; heterocycloalkyl; heteroaryl; phenyl;

$R^H$ is selected from the group consisting of H; C1-C6 alkyl; C1-C6 alkoxy; C3-C6 cycloalkyl; heterocycloalkyl; heteroaryl; phenyl; or $R^G$ and $R^H$, together with the nitrogen atom to which they are bonded, form a 4- to 10-membered saturated or unsaturated heterocyclic ring which is optionally substituted with one or more C1-C3 alkyl, benzyl, phenyl, $C_1$-$C_3$ alkoxy or halogen;

$R^I$ is selected from the group consisting of H; halo; cyano; C1-C5 alkyl, preferably C1-C3 alkyl; C1-C3 sulfanyl; C1-C4 alkoxy, preferably C1-C3 alkoxy; C1-C3 haloalkyl; hydroxyl; oxo; —NRaRb; —C(O)NRaRb; —C(O)Rc; —C(O)ORc; sulfonyl; sulfoxide; $(CH_2)_pOH$; $(CH_2)_pORa$; $(CH_2)_pNR^GR^H$; $(CH_2)_pOC(O)NRaRb$; $(CH_2)_pC(O)NRaRb$; C3-C6 cycloalkyl; heterocycloalkyl; aryl; heteroaryl; phenyl;

$R^O$ and $R^P$ are each independently at each occurrence selected from the group consisting of H, C1-C5 alkyl, C1-C5 alkenyl, C1-C5 alkynyl, C3-C6 cycloalkyl; heterocycloalkyl; heteroaryl; phenyl; with the proviso that, when one of $R^O$ or $R^P$ is H, then the other one of $R^O$ or $R^P$ is not methyl;

Or $R^O$ and $R^P$ are joined together, forming a cycloalkyl group, cycloalkenyl group, or heterocycloalkyl group optionally substituted with one to four $R^I$ groups as defined above;

$R^M$ and $R^N$ are each independently at each occurrence selected from the group consisting of H; C1-C6 alkyl, C3-C6 cycloalkyl, C1-C3 haloalkyl, phenyl; aryl; heteroaryl; —$NR^GR^H$; —C(O)NRaRb; —C(O)Rc; —C(O)ORc; sulfonyl; sulfoxide; C1-C6 alkyl substituted with hydroxyl, alkoxy, or —NRaRb, phenyl; —$NR^GR^H$; —C(O)NRaRb; —C(O)Rc; —C(O)ORc; sulfonyl; sulfoxide;

or $R^M$ and $R^N$ are joined together with the N-atom to which they are attached, forming a heterocycloalkyl group;

Ra and Rb are each independently at each occurrence selected from the group consisting of hydrogen, C1-C6 alkyl, substituted C1-C6 alkyl, $C_1$-$C_6$ alkoxyC1-C6 alkyl, C6-C14 alkyl chain containing one or several of —O—, —C(O)NH—, —NHC(O)—, —N—, or —NHC(O)O—, optionally with a terminal $NH_2$, or —NH-Boc; C1-C6 alkenyl, substituted C1-C6 alkenyl, C1-C6 alkynyl, substituted C1-C6 alkynyl, C3-C7 cycloalkyl, substituted C3-C7 cycloalkyl, aryl, substituted aryl, heteroaryl, substituted heteroaryl, heterocycloalkyl, substituted heterocycloalkyl; or Ra and Rb, together with the nitrogen atom to which they are bonded, form a 4- to 10-membered saturated or unsaturated heterocyclic ring which is optionally substituted with one or more C1-C3 alkyl, benzyl, phenyl, C1-C3 alkoxy or halogen;

Rc is selected from the group consisting of hydrogen, C1-C10 alkyl, preferably C1-C6 alkyl, C1-C10 alkenyl, preferably C1-C6 alkenyl, C1-C10 alkynyl, preferably C1-C6 alkynyl, C3-C0 cycloalkyl, preferably C3-C7 cycloalkyl, C1-C3 haloalkyl, aryl, heteroaryl, heterocycloalkyl, wherein each of the aforementioned alkyl, alkenyl, alkynyl, cycloalkyl, aryl, heteroaryl and heterocycloalkyl may be substituted with one or more of hydroxyl, halo, alkoxy, oxo, sulfonyl, sulfoxide, aryl, heteroaryl or —NraRb;

i is an integer from 0 to 3, preferably 0, 1, 2 or 3;

j is an integer from 0 to 2, preferably 0, 1 or 2; and p is an integer from 0 to 5, preferably 0, 1, 2, 3, 4 or 5.

One embodiment relates to compounds according to Formula (Ih):

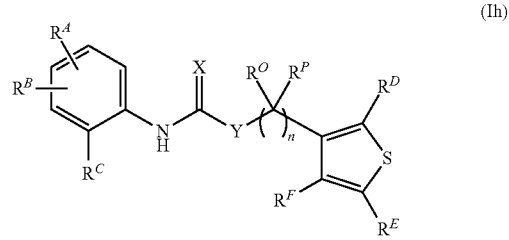

(Ih)

$R^A$ is selected from the group consisting of H; halo; cyano; C1-C5 alkyl; C3-C6 cycloalkyl; C1-C3 alkoxy; C1-C3 haloalkyl; —C(O)NRaRb; —C(O)Rc; —C(O)ORc; C1-C3 sulfanyl; phenyl; heteroaryl; —$NR^GR^H$;

$R^B$ is selected from the group consisting of H; halo; cyano; C1-C5 alkyl; C3-C6 cycloalkyl; C1-C3 alkoxy; —C(O)NRaRb; —C(O)Rc; —C(O)ORc; C1-C3 haloalkyl; C1-C3 sulfanyl; phenyl; heteroaryl; —$NR^GR^H$;

Or $R^A$ and $R^B$ are joined together forming a cycloalkyl group, aryl, heteroaryl, or heterocycloalkyl group optionally substituted with one to four $R^I$ groups;

$R^C$ is selected from the group consisting of H; halo; cyano; —C(O)NRaRb; —C(O)Rc; —C(O)ORc; C1-C3 sulfanyl; sulfonyl; sulfoxide; phenyl; aryl; heteroaryl; C1-C5 alkyl; C1-C5 alkenyl; C1-C5 alkynyl; C1-C5 alkyl, alkenyl, or alkynyl substituted with hydroxyl, alkoxy, or —NRaRb; C3-C6 cycloalkyl; C1-C3 alkoxy; C1-C3 haloalkyl; —$NR^GR^H$;

$R^D$ is selected from the group consisting of halo; cyano; C1-C5 alkyl; C3-C6 cycloalkyl; C1-C3 alkoxy; C1-C3 haloalkyl; C1-C3 sulfanyl; phenyl; aryl; heteroaryl; —$NR^GR^H$; —C(O)NRaRb; —C(O)Rc; —C(O)ORc; sulfonyl; sulfoxide;

$R^E$ is selected from the group consisting of H; halo; cyano; C1-C5 alkyl; C3-C6 cycloalkyl; C1-C3 alkoxy; C1-C3 haloalkyl; C1-C3 sulfanyl; phenyl; heteroaryl; —$NR^GR^H$; —$CH_2NR^MR^N$;

$R^F$ is selected from the group consisting of H; halo; cyano; C1-C5 alkyl; C3-C6 cycloalkyl; C1-C3 alkoxy; C1-C3 haloalkyl; C1-C3 sulfanyl; phenyl; heteroaryl; —$NR^GR^H$;

Or $R^E$ and $R^F$ are joined together forming a cycloalkyl group, heteroaryl, or heterocycloalkyl group optionally substituted with one to four $R^I$ groups.

$R^G$ is selected from the group consisting of H; C1-C6 alkyl; C1-C6 alkoxy; C3-C6 cycloalkyl; heterocycloalkyl; heteroaryl; phenyl;

$R^H$ is selected from the group consisting of H; C1-C6 alkyl; C1-C6 alkoxy; C3-C6 cycloalkyl; heterocycloalkyl; heteroaryl; phenyl; or $R^G$ and $R^H$, together with the nitrogen atom to which they are bonded, form a 4- to 10-membered saturated or unsaturated heterocyclic ring which is optionally substituted with one or more $C_1$-$C_3$ alkyl, benzyl, phenyl, $C_1$-$C_3$ alkoxy or halogen; $R^I$ is selected from the group consisting of H; halo; cyano; C1-C5 alkyl, preferably C1-C3 alkyl; C1-C3 sulfanyl; C1-C4 alkoxy, preferably C1-C3 alkoxy; C1-C3 haloalkyl; hydroxyl; oxo; —NRaRb; —C(O)NRaRb; —C(O)Rc; —C(O)ORc; sulfonyl; sulfoxide; $(CH_2)_pOH$; $(CH_2)_pORa$; $(CH_2)_pNR^GR^H$; $(CH_2)_pOC(O)NRaRb$; $(CH_2)_pC(O)NRaRb$; C3-C6 cycloalkyl; heterocycloalkyl; aryl; heteroaryl; phenyl;

$R^O$ and $R^P$ are each independently at each occurrence selected from the group consisting of H, C1-C5 alkyl, C1-C5 alkenyl, C1-C5 alkynyl, C3-C6 cycloalkyl; heterocycloalkyl; heteroaryl; phenyl; with the proviso that, when one of $R^O$ or $R^P$ is H, then the other one of $R^O$ or $R^P$ is not methyl;

Or $R^O$ and $R^P$ are joined together, forming a cycloalkyl group, cycloalkenyl group, or heterocycloalkyl group optionally substituted with one to four $R^1$ groups;

$R^M$ and $R^N$ are each independently selected from the group consisting of H; C1-C6 alkyl, C3-C6 cycloalkyl, C1-C3 haloalkyl, phenyl; aryl; heteroaryl; —$NR^GR^H$; —C(O)NRaRb; —C(O)Rc; —C(O)ORc; sulfonyl; sulfoxide; C1-C6 alkyl substituted with hydroxyl, alkoxy, or —NRaRb, phenyl; —$NR^GR^H$; —C(O)NRaRb; —C(O)Rc; —C(O)ORc; sulfonyl; sulfoxide;

or $R^M$ and $R^N$ are joined together with the N-atom to which they are attached, forming a heterocycloalkyl group;

$R^I$ is selected from the group consisting of H; halo; cyano; C1-C5 alkyl, preferably C1-C3 alkyl; C1-C3 sulfanyl; C1-C4 alkoxy, preferably C1-C3 alkoxy; C1-C3 haloalkyl; hydroxyl; oxo; —NRaRb; —C(O)NRaRb; —C(O)Rc; —C(O)ORc; sulfonyl; sulfoxide; $(CH_2)_pOH$; $(CH_2)_pORa$; $(CH_2)_pNR^GR^H$; $(CH_2)_pOC(O)NRaRb$; $(CH_2)_pC(O)NRaRb$; C3-C6 cycloalkyl; heterocycloalkyl; aryl; heteroaryl; phenyl;

Ra and Rb are each independently at each occurrence selected from the group consisting of hydrogen, C1-C6 alkyl, substituted C1-C6 alkyl; C1-C6 alkoxyC1-C6 alkyl, C6-C14 alkyl chain containing one or several of —O—, —C(O)NH—, —NHC(O)—, —N—, or —NHC(O)O— optionally with a terminal $NH_2$ or —NH-Boc; C1-C6 alkenyl, substituted C1-C6 alkenyl, C1-C6 alkynyl, substituted C1-C6 alkynyl, C3-C7 cycloalkyl, substituted C3-C7 cycloalkyl, aryl, substituted aryl, heteroaryl, substituted heteroaryl, heterocycloalkyl, substituted heterocycloalkyl; or Ra and Rb, together with the nitrogen atom to which they are bonded, form a 4- to 10-membered saturated or unsaturated heterocyclic ring which is optionally substituted with one or more C1-C3 alkyl, benzyl, phenyl, C1-C3 alkoxy or halogen;

Rc is selected from the group consisting of hydrogen, C1-C10 alkyl, preferably C1-C6 alkyl, C1-C10 alkenyl, preferably C1-C6 alkenyl, C1-C10 alkynyl, preferably C1-C6 alkynyl, C3-C10 cycloalkyl, preferably C3-C7 cycloalkyl, C1-C3 haloalkyl, aryl, heteroaryl, heterocycloalkyl, wherein each of the aforementioned alkyl, alkenyl, alkynyl, cycloalkyl, aryl, heteroaryl and heterocycloalkyl may be substituted with one or more of hydroxyl, halo, alkoxy, oxo, sulfonyl, sulfoxide, aryl, heteroaryl or —NRaRb;

X is O, S or N—CN;
Y is NH, O, —C(O)NH— or a bond;
n is an integer from 0 to 3, preferably 0, 1, 2 or 3;
p is an integer from 0 to 5, preferably 0, 1, 2, 3, 4 or 5.

In one embodiment Y is NH.

The invention also relates to pharmaceutically acceptable salts of the aforementioned compounds of formulae I, Ia-Ih.

In one aspect, the present invention is also directed to compounds according to Formula II:

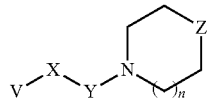

(II)

V is an aryl or heteroaryl selected from the group consisting of

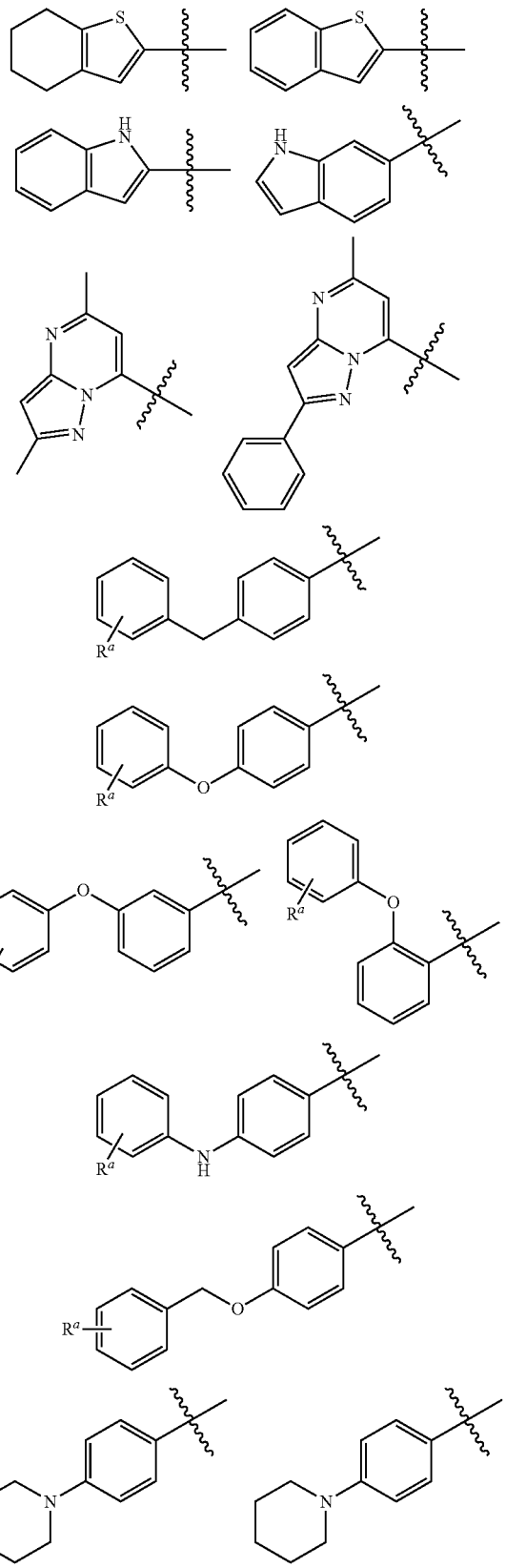

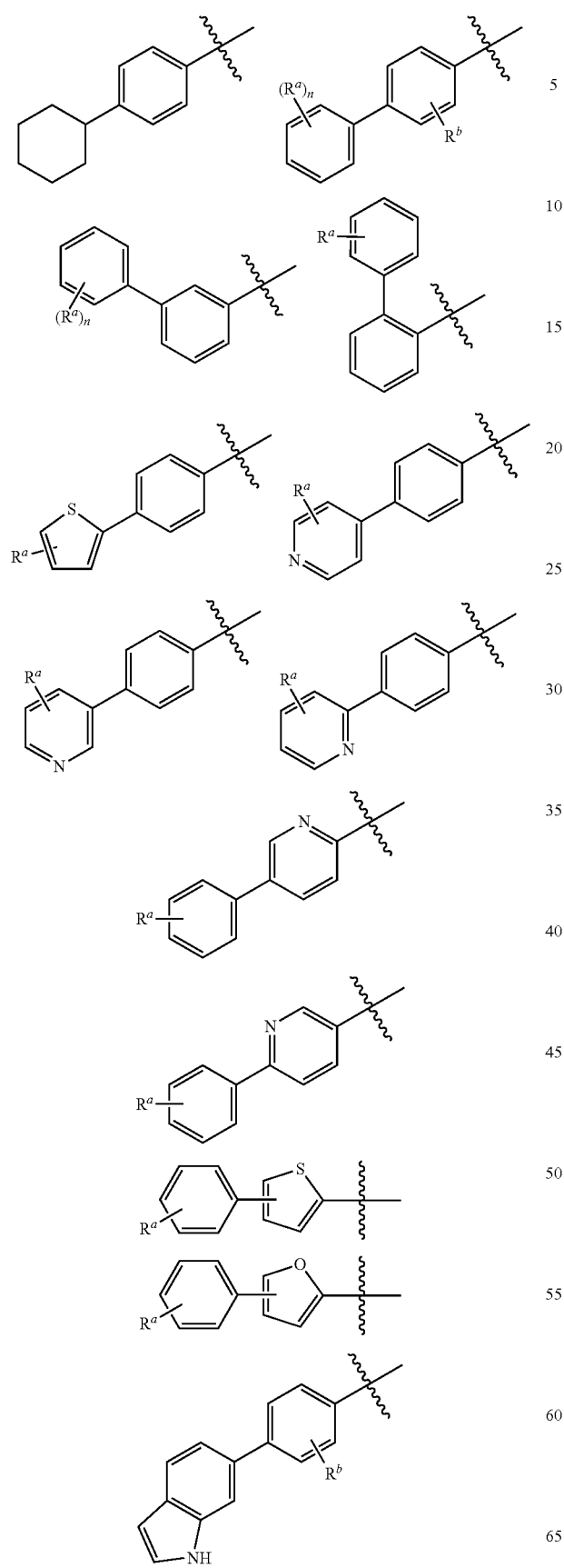
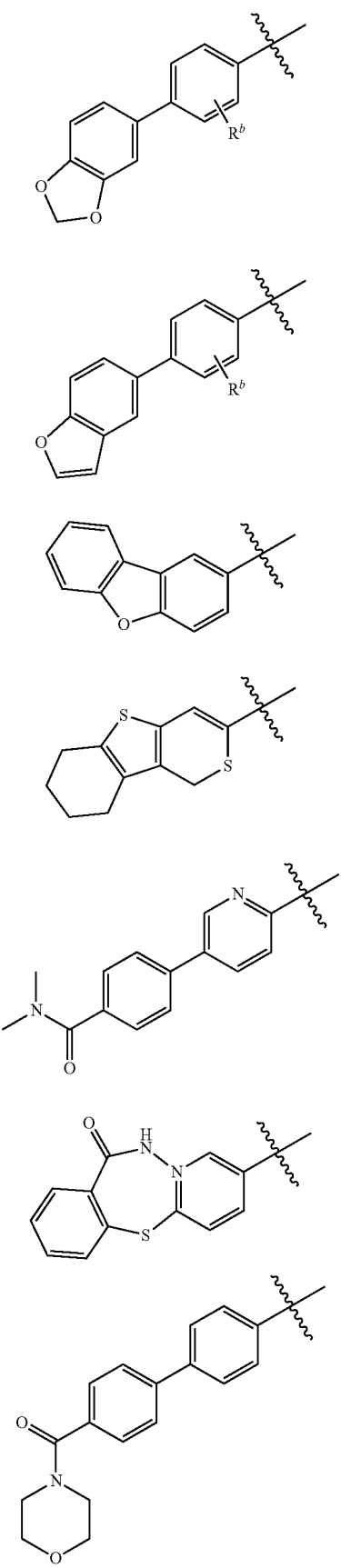

-continued

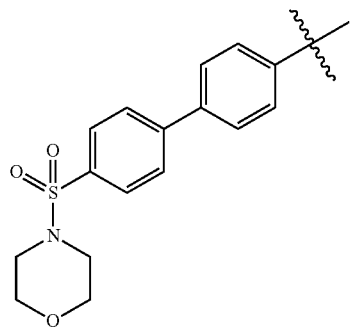

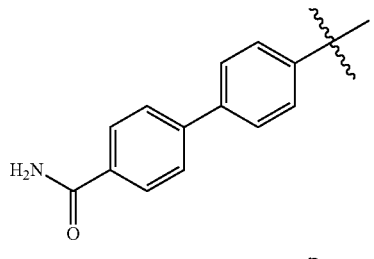

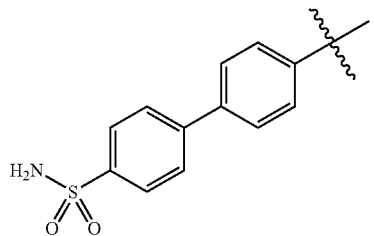

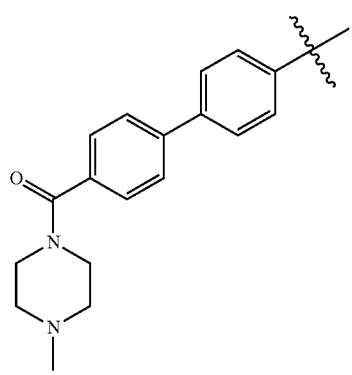

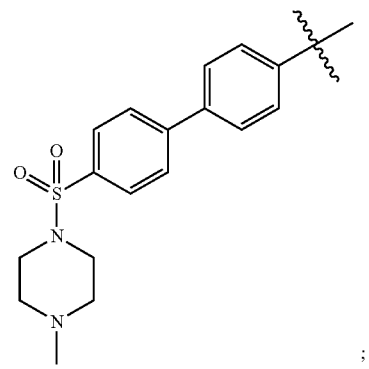

;

R$^a$ is, independently at each occurrence, selected from the group consisting of H, C1-C4 alkyl, C1-C3 alkoxy, halo, such as Cl or F, cyano, —C(O)NRR, CF$_3$, OCF$_3$, hydroxyl, N(CH$_3$)$_2$, NO$_2$, morpholinyl, —NHC(O) C1-C3 alkyl, C(O)(O) C1-C4 alkyl, NH$_2$C(O)—, NH$_2$S(O)$_2$—, CH$_2$OH, CH$_2$-morpholinyl; with R being independently at each occurrence selected from the group consisting of H, C1-C4 alkyl, C3-C7 cycloalkyl and CF$_3$;

R$^b$ is selected from the group consisting of H, C1-C4 alkyl, C1-C3 alkoxy, halo, CF$_3$, OCF$_3$, cyano;

X is selected from the group consisting of —C(O)NR—, —NR—C(O)—, —NRC(O)NR—, —C(O)NCH$_3$—, NCH$_3$—C(O)—, —NR—, —RNHR—, —RNHC(O)NR—, —S(O)$_2$NH—; —C(O)—; with R being independently at each occurrence selected from the group consisting of H, C1-C4 alkyl, C3-C7 cycloalkyl and CF$_3$;

Y is selected from groups consisting of

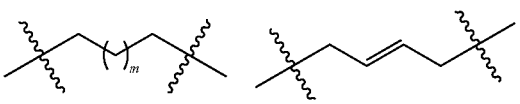

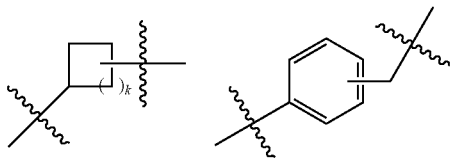

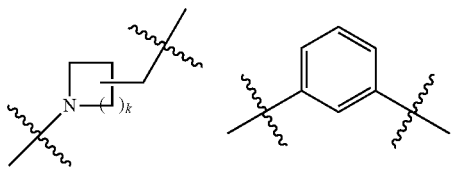

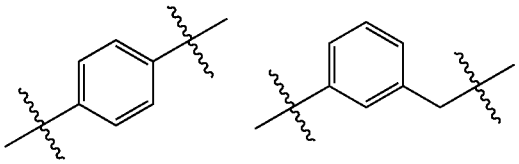

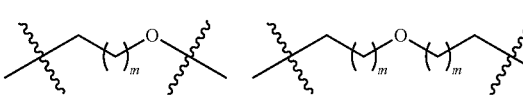

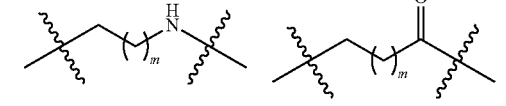

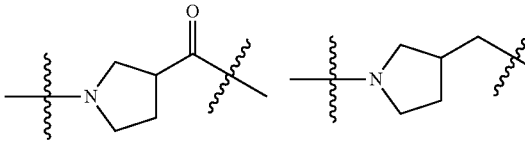

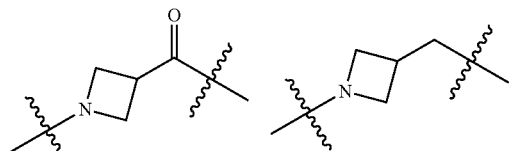

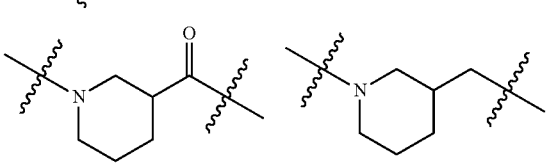

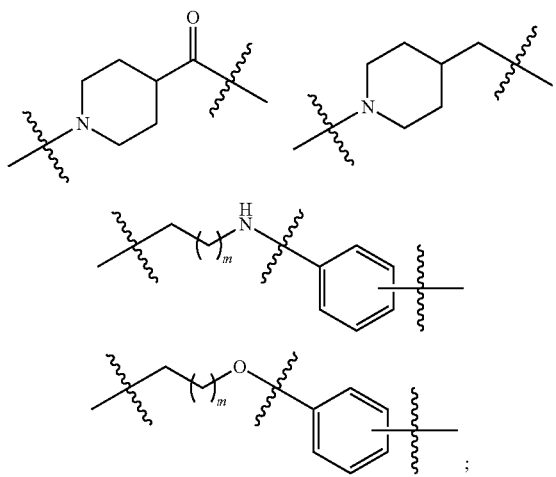

m is independently at each occurrence an integer from 0 to 4, preferably 0, 1, 2, 3 or 4;

k is an integer from 1 to 3, preferably 0, 1, 2 or 3;

n is an integer from 0 to 3, preferably 0, 1, 2 or 3;

Z is selected from the group consisting of $CH_2$,

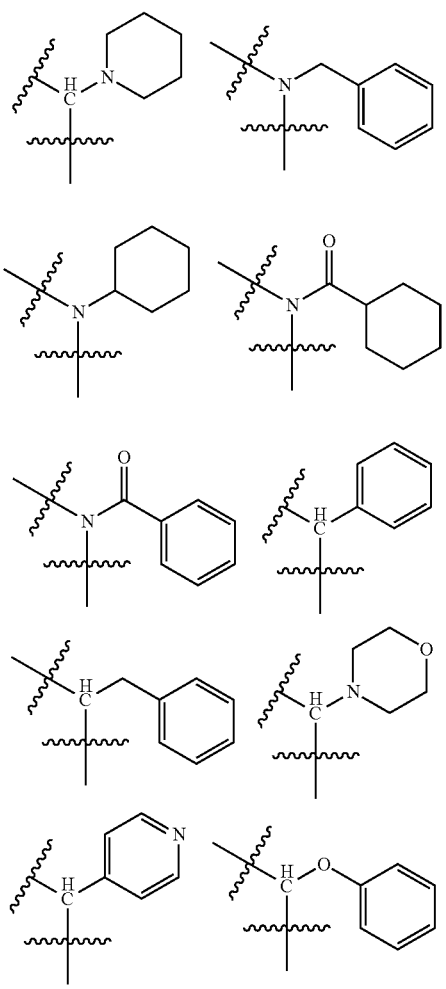

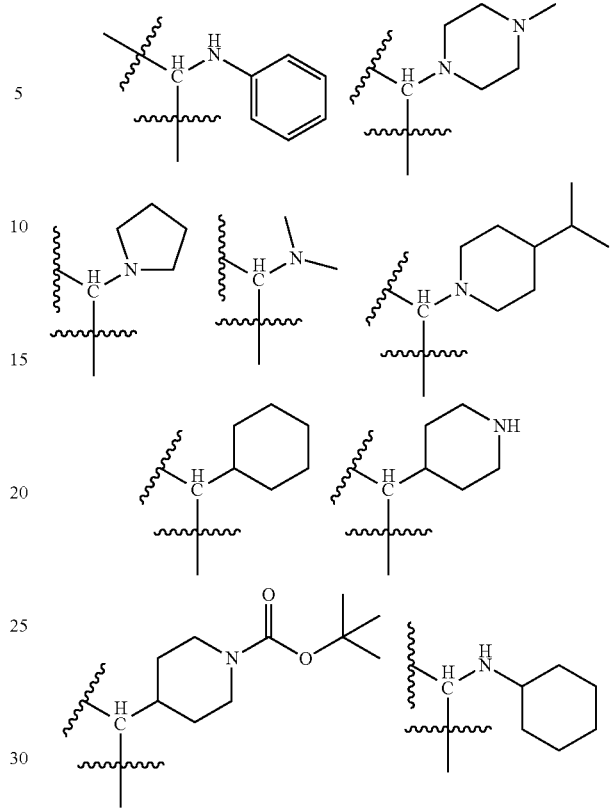

The invention also relates to pharmaceutically acceptable salts of these compounds according to formula II. It should be noted that, as far as product protection is concerned the present invention does not encompass the compound designated "1001" in table 2 as shown further below.

One embodiment relates to compounds according to Formula II, wherein

X is —C(O)NR—, with R being selected from the group consisting of H, C1-C4 alkyl, C3-C7 cycloalkyl and CF3; and Y is —$(CH_2)_m$—, m being 0 to 4, preferably 0, 1, 2, 3 or 4.

One embodiment relates to compounds according to Formula II wherein X is —NR—C(O)—, with R being selected from the group consisting of H, C1-C4 alkyl, C3-C7 cycloalkyl and CF3; and Y is —$(CH_2)_m$—, m being 0 to 4, preferably 0, 1, 2, 3 or 4.

One embodiment relates to compounds according to Formula II
wherein X is —C(O)NR—, with R being selected from the group consisting of H, C1-C4 alkyl, C3-C7 cycloalkyl, $CF_3$; Y is —$(CH_2)_m$—, m being 0 to 4; n is 1 and Z is

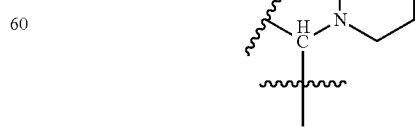

One embodiment relates to compounds according to Formula II wherein X is —NR—C(O)—, with R being selected from the group consisting of H, C1-C4 alkyl, C3-C7 cycloalkyl, CF$_3$; Y is —(CH$_2$)$_m$—, with m being 0 to 4; n being 1; Z being

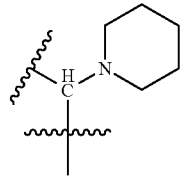 [SMILES: *C(*)N1CCCCC1]

In one embodiment, the compound according to the present invention is for use in the treatment of a viral disease, preferably HCV. In one embodiment, said HCV is HCV genotype 1, 2, 3, 4, 5, 6, 7, including subtypes, preferably genotypes and subtypes 1a, 1b, 2a, 2b, 3a, 4a, 5a, 6a and/or 7a, more preferably 1a, 1b, 2a, 2b and/or 3a.

In one embodiment, the compound according to the present invention has one of the formulae 2-374, as shown in Table 1 and/or Example 1, as shown further below, or a pharmaceutically acceptable salts thereof, preferably having one of the formulae 2-4, 7, 12, 14, 18-22, 24-44, 46-48, 51-54, 56-57, 59-63, 65-76, 78-82, 87, 91, 93-94, 96-99, 101-103, 106-108, 110-119, 121-200, 203-222, 224-229, 231-245, 247-256, 258-320, 322-351, 354-361, 363-373, as indicated in Table 1 more preferably having one of the formulae 14, 19, 21, 27, 110-119, 121, 167, 316 as indicated in Tables 1, 3, 4 or 5; or a pharmaceutically acceptable salt thereof.

In one embodiment, the compound according to the present invention has one of the formulae 1002-1159, as shown in Table 2 and/or Example 1, as shown further below, or a pharmaceutically acceptable salt thereof, preferably having one of the formulae 1003, 1005, 1012-1013, 1015-1016, 1018-1023, 1027-1028, 1032, 1045-1046, 1049, 1052, 1060, 1065, 1067-1069, 1073, 1075-1076, 1078-1083, 1085-1088, 1090-1102, 1104-1108, 1110-1119, 1121-1126, 1130-1137, 1139, 1141, 1145-1147, 1149-1150, 1152-1159 as indicated in Table 2 more preferably having one of the formulae 1013, 1019, 1022, 1152 as indicated in Tables 2-3; or a pharmaceutically acceptable salt thereof.

In one aspect the present invention relates to a composition comprising a compound as defined above and a pharmaceutically acceptable carrier, excipient or diluent.

In one embodiment, the composition according to the present invention is for use in the treatment of a viral disease, preferably HCV. In one embodiment, said HCV is HCV genotype 1, 2, 3, 4, 5, 6 or 7, including subtypes, preferably genotypes and subtypes 1a, 1b, 2a, 2b, 3a, 4a, 5a, 6a and/or 7a, more preferably 1a, 1b, 2a, 2b and/or 3a.

In one embodiment, said treatment comprises administering a suitable amount of a compound as defined above or of a composition as defined above to a patient in need thereof suffering from a viral disease, preferably HCV.

In a further aspect, the present invention relates to a method of treatment of a viral disease, said disease preferably being HCV. Said method comprising the administration of a suitable amount of a compound as defined above or of a composition as defined above to a patient in need thereof, suffering from a viral disease, said viral disease preferably being HCV.

In one embodiment, said HCV is HCV genotype 1, 2, 3, 4, 5, 6 or 7, including subtypes, preferably genotype 1a, 1b, 2a, 2b, 3a, 4a, 5a, 6a and/or 7a, more preferably 1a, 1b, 2a, 2b and/or 3a.

In one embodiment, said suitable amount is an amount in the range of 0.01 mg/kg body weight to 1 g/kg body weight of said patient.

In one embodiment, said patient is a patient suffering from a viral disease, preferably HCV.

In one embodiment, the present invention also relates to pharmaceutically acceptable salts of the compounds according to the present invention, for use in the treatment of a viral disease, preferably HCV.

In one embodiment, said compound has an inhibitory activity on viral infection, preferably HCV, at a concentration of said compound between 0.0001-50 uM, particularly preferably having an EC$_{50}$ of less than 1 uM.

In one aspect, the present invention relates to compounds for use in the treatment of a viral disease, e.g. HCV, according to the present invention, said compound preferably having one of the formulae 1-374 and/or 1001-1159, as shown in Tables 1 and 2 and Example 1, preferably having one of the formulae 1-4, 7, 12, 14, 18-22, 24-44, 46-48, 51-54, 56-57, 59-63, 65-76, 78-82, 87, 91, 93-94, 96-99, 101-103, 106-108, 110-119, 121-200, 203-222, -224-229, 231-245, 247-256, 258-320, 322-351, 354-361, 363-373, 1001, 1003, 1005, 1012-1013, 1015-1016, 1018-1023, 1027-1028, 1032, 1045-1046, 1049, 1052, 1060, 1065, 1067-1069, 1073, 1075-1076, 1078-1083, 1085-1088, 1090-1102, 1104-1108, 1110-1119, 1121-1126, 1130-1137, 1139, 1141, 1145-1147, 1149-1150, 1152-1159 as indicated in Table 1, more preferably having one of the formulae 14, 19, 21, 27, 110-119, 113-119, 121, 167, 316, 1013, 1019, 1022, 1152 as indicated in Tables 1-5; or a pharmaceutically acceptable salt thereof.

Preferably, the compounds as defined above have an inhibitory activity on viral infection, preferably an HCV infection at a concentration of said compound between 0.0001-50 uM, particularly preferably having an EC$_{50}$ of less than 1 uM.

In one aspect the present invention relates to a composition comprising a compound according to the present invention and a pharmaceutically acceptable carrier, excipient or diluent, for use in the treatment of a viral disease, preferably HCV, HCV being as defined above.

In one embodiment, said treatment comprises administering a suitable amount of a compound or of a composition as defined above to a patient in need thereof, suffering from a viral disease, preferably HCV, HCV being as defined above.

In a further aspect, the present invention relates to a compound that competitively inhibits the specific binding of a compound according to the present invention as defined above.

In yet a further aspect, the present invention relates to method of treatment of a viral disease, e.g. HCV, said method comprising the administration of a suitable amount of a compound as just defined, i.e. a compound that competitively inhibits the specific binding of a compound according to the present invention to a patient in need thereof.

Such compound that competitively inhibits the specific binding of a compound according to the present invention is herein also sometimes referred to as a "competitively inhibitory compound".

In one embodiment, such patient is a patient suffering from a viral disease, preferably HCV.

In one aspect, the present invention also relates to a composition, preferably a pharmaceutical composition, comprising a compound according to the present invention, as defined above, further comprising at least one antiviral compound and, optionally, a pharmaceutically acceptable carrier, excipient or diluent. This composition is also sometimes herein referred to as a "combination composition". In one embodiment, said at least one antiviral compound is selected from interferon-alpha, ribavirin, direct acting antivirals, such as telaprevir, boceprevir, sofosbuvir, daclatasvir, NS5A-inhibitors, non-nucleoside inhibitors of HCV-RNA-dependent RNA polymerase (RdRp).

In one embodiment, such combination composition is for use in the treatment of a viral disease, preferably, HCV, more preferably, HCV genotype 1, 2, 3, 4, 5, 6 or 7, including subtypes, preferably genotype 1a, 1b, 2a, 2b, 3a, 4a, 5a, 6a and/or 7a, more preferably 1a, 1b, 2a, 2b and/or 3a.

In one embodiment of such composition, the compound according to the present invention has one of the formulae 1-374, as shown in Table 1 and/or Example 1, as shown further below, or pharmaceutically acceptable salts thereof, preferably having one of the formulae 1-4, 7, 12, 14, 18-22, 24-44, 46-48, 51-54, 56-57, 59-63, 65-76, 78-82, 87, 91, 93-94, 96-99, 101-103, 106-108, 110-119, 121-200, 203-222, 224-229, 231-245, 247-256, 258-320, 322-351, 354-361, 363-373, as indicated in Table 1 more preferably having one of the formulae 14, 19, 21, 27, 110-119, 121, 167, 316 as indicated in Tables 1, 3, 4 or 5; or a pharmaceutically acceptable salt thereof.

In one embodiment of such composition, the compound according to the present invention has one of the formulae 1001-1163, as shown in Table 2 and/or Example 1, as shown further below, or a pharmaceutically acceptable salt thereof, preferably having one of the formula 1001, 1003, 1005, 1012-1013, 1015-1016, 1018-1023, 1027-1028, 1032, 1045-1046, 1049, 1052, 1060, 1065, 1067-1069, 1073, 1075-1076, 1078-1083, 1085-1088, 1090-1102, 1104-1108, 1110-1119, 1121-1126, 1130-1137, 1139, 1141, 1145-1147, 1149-1150, 1152-1159 as indicated in Table 2 more preferably having one of the formulae 1013, 1019, 1022, 1152 as indicated in Tables 2-3; or pharmaceutically acceptable salt thereof.

In one aspect, the present invention relates to a method of treatment of a viral disease, preferably HCV, said method preferably comprising the administration of a suitable amount of a composition, as defined above, comprising a compound according to the present invention and at least one antiviral compound, (="combination composition"), to a patient in need thereof, suffering from a viral disease, preferably HCV, more preferably HCV genotype 1, 2, 3, 4, 5, 6 or 7, including subtypes, preferably genotype 1a, 1b, 2a, 2b, 3a, 4a, 5a, 6a and/or 7a, more preferably 1a, 1b, 2a, 2b and/or 3a.

The term "$EC_{50}$" refer to the half-maximal effective concentration of a compound with respect to a given activity, for example, an inhibition of infection of a cell with a pathogen, e.g. a virus. The EC50 of a graded dose response curve therefore represents the concentration of a compound where 50% of its maximal effect is observed. One example of an $EC_{50}$ is the half-maximal inhibitory concentration of a compound for the infection of cell with HCV.

Pharmaceutical Compositions
Pharmaceutical Acceptable Salts

Examples of pharmaceutically acceptable addition salts include, without limitation, the non-toxic inorganic and organic acid addition salts such as the acetate derived from acetic acid, the aconate derived from aconitic acid, the ascorbate derived from ascorbic acid, the benzenesulfonate derived from benzenesulfonic acid, the benzoate derived from benzoic acid, the cinnamate derived from cinnamic acid, the citrate derived from citric acid, the embonate derived from embonic acid, the enanthate derived from enanthic acid, the formate derived from formic acid, the fumarate derived from fumaric acid, the glutamate derived from glutamic acid, the glycolate derived from glycolic acid, the hydrochloride derived from hydrochloric acid, the hydrobromide derived from hydrobromic acid, the lactate derived from lactic acid, the maleate derived from maleic acid, the malonate derived from malonic acid, the mandelate derived from mandelic acid, the methanesulfonate derived from methane sulphonic acid, the naphthalene-2-sulphonate derived from naphthalene-2-sulphonic acid, the nitrate derived from nitric acid, the perchlorate derived from perchloric acid, the phosphate derived from phosphoric acid, the phthalate derived from phthalic acid, the salicylate derived from salicylic acid, the sorbate derived from sorbic acid, the stearate derived from stearic acid, the succinate derived from succinic acid, the sulphate derived from sulphuric acid, the tartrate derived from tartaric acid, the toluene-p-sulphonate derived from p-toluene sulphonic acid, and the like. Such salts may be formed by procedures well known and described in the art.

Other acids such as oxalic acid, which may not be considered pharmaceutically acceptable, may be useful in the preparation of salts useful as intermediates in obtaining a chemical compound of the invention and its pharmaceutically acceptable acid addition salt, for use in the treatment of an inflammatory disease.

In another embodiment, the compounds of the invention are used in their respective free base form, for use in the treatment of an inflammatory disease, according to the present invention.

Metal salts of a chemical compound of the invention include alkali metal salts, such as the sodium salt of a chemical compound of the invention containing a carboxy group.

The chemical compounds of the invention may be provided in unsolvated or solvated forms together with a pharmaceutically acceptable solvent(s) such as water, ethanol, and the like. Solvated forms may also include hydrated forms such as the monohydrate, the dihydrate, the hemihydrate, the trihydrate, the tetrahydrate, and the like. In general, solvated forms are considered equivalent to unsolvated forms for the purposes of this invention.

Administration and Formulation

The production of medicaments containing the compounds of the invention, its active metabolites or isomers and salts according to the invention and their application can be performed according to well-known pharmaceutical methods.

While the compounds of the invention, useable according to the invention for use in therapy, may be administered in the form of the raw chemical compound, it is preferred to introduce the active ingredient, optionally in the form of a physiologically acceptable salt in a pharmaceutical composition together with one or more adjuvants, excipients, carriers, buffers, diluents, and/or other customary pharmaceutical auxiliaries. Such salts of the compounds of the invention may be anhydrous or solvated.

In a preferred embodiment, the invention provides medicaments comprising a compound useable according to the invention, or a pharmaceutically acceptable salt or derivative thereof, together with one or more pharmaceutically acceptable carriers therefor, and, optionally, other therapeutic and/or prophylactic ingredients. The carrier(s) must be "acceptable" in the sense of being compatible with the other ingredients of the formulation and not harmful to the recipient thereof.

A medicament of the invention may be those suitable for oral, rectal, bronchial, nasal, topical, buccal, sub-lingual, transdermal, vaginal or parenteral (including cutaneous, subcutaneous, intramuscular, intraperitoneal, intravenous, intraarterial, intracerebral, intraocular injection or infusion) administration, or those in a form suitable for administration by inhalation or insufflation, including powders and liquid aerosol administration, or by sustained release systems. Suitable examples of sustained release systems include semipermeable matrices of solid hydrophobic polymers containing the compound of the invention, which matrices may be in form of shaped articles, e.g. films or microcapsules.

The compounds useable according to the invention, together with a conventional adjuvant, carrier, or diluent, may thus be placed into the form of medicament and unit dosages thereof. Such forms include solids, and in particular tablets, filled capsules, powder and pellet forms, and liquids, in particular aqueous or non-aqueous solutions, suspensions, emulsions, elixirs, and capsules filled with the same, all for oral use, suppositories for rectal administration, and sterile injectable solutions for parenteral use. Such medicament and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

The compounds useable according to the invention can be administered in a wide variety of oral and parenteral dosage forms. It will be obvious to those skilled in the art that the following dosage forms may comprise, as the active component, either a compound(s) useable according to the invention or a pharmaceutically acceptable salt of a compound(s) useable according to the invention.

For preparing a medicament from a compound useable according to the invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid which is in a mixture with the finely divided active component. In tablets, the active component is mixed with the carrier having the necessary binding capacity in suitable proportions and compacted in the shape and size desired. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as a mixture of fatty acid glyceride or cocoa butter, is first melted and the active component is dispersed homogeneously therein, as by stirring. The molten homogenous mixture is then poured into convenient sized moulds, allowed to cool, and thereby to solidify. Compositions suitable for vaginal administration may be presented as pessaries, tampons, creams, gels, pastes, foams or sprays containing in addition to the active ingredient such carriers as are known in the art to be appropriate. Liquid preparations include solutions, suspensions, and emulsions, for example, water or water-propylene glycol solutions. For example, parenteral injection liquid preparations can be formulated as solutions in aqueous polyethylene glycol solution.

The chemical compounds according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulation agents such as suspending, stabilising and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous solutions suitable for oral use can be prepared by dissolving the active component in water and adding suitable colorants, flavours, stabilising and thickening agents, as desired. Aqueous suspensions suitable for oral use can be made by dispersing the finely divided active component in water with viscous material, such as natural or synthetic gums, resins, methylcellulose, sodium carboxymethylcellulose, or other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavours, stabilisers, buffers, artificial and natural sweeteners, dispersants, thickeners, solubilizing agents, and the like.

In one embodiment of the present invention, the medicament is applied topically or systemically or via a combination of the two routes.

For administration, the compounds of the present invention may, in one embodiment, be administered in a formulation containing 0.001% to 70% per weight of the compound, preferably between 0.01% to 70% per weight of the compound, even more preferred between 0.1% and 70% per weight of the compound. In one embodiment, a suitable amount of compound administered is in the range of 0.01 mg/kg body weight to 1 g/kg body weight.

Compositions suitable for administration also include lozenges comprising the active agent in a flavoured base, usually sucrose and acacia or tragacanth; pastilles comprising the active ingredient in an inert base such as gelatin and glycerol or sucrose and acacia; and mouthwashes comprising the active ingredient in a suitable liquid carrier.

Solutions or suspensions are applied directly to the nasal cavity by conventional means, for example with a dropper, pipette or spray. The compositions may be provided in single or multi-dose form. In the latter case of a dropper or pipette, this may be achieved by the patient administering an appropriate, predetermined volume of the solution or suspension. In the case of a spray, this may be achieved for example by means of a metering atomising spray pump.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

In compositions intended for administration to the respiratory tract, including intranasal compositions, the compound will generally have a small particle size for example of the order of 5 microns or less. Such a particle size may be obtained by means known in the art, for example by micronization.

When desired, compositions adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packaged tablets, capsules, and powders in vials or ampoules. Also, the unit dosage form can be a capsule, tablet, cachet, or lozenge itself, or it can be the appropriate number of any of these in packaged form. Tablets or capsules for oral administration and liquids for intravenous administration and continuous infusion are preferred compositions.

Further details on techniques for formulation and administration may be found in the latest edition of Remington's Pharmaceutical Sciences (Maack Publishing Co. Easton, Pa.) and Remington: The science and practice of pharmacy", Lippincott Williams and Wilkins.

Appropriate formulations and ways of manufacturing them are, for example also disclosed in "Arzneiformenlehre, Paul Heinz List, EinLehrbuchfürPharmazeuten, WissenschaftlicheVerlagsgesellschaft Stuttgart, 4. Auflage, 1985", or "The theory and practice of industrial pharmacy" by Lachman et al., Varghese Publishing House, 1987", or "Modern Pharmaceutics", edited by James Swarbrick, 2. Edition".

FIGURES AND TABLES

Table 1 summarizes anti-HCVcc genotype 1/2 activity for Formula I Series.

Table 2 summarizes anti-HCVcc genotype 1/2 activity for Formula II Series.

Table 3 summarizes anti-HCV cross-genotypic activity for a representative of Formula I and II Series.

Table 4 summarizes the drug combination evaluation for a representative of Formula I Series in the HCV genotype 2 infectious system.

Table 5 summarizes the drug combination evaluation for a representative of Formula I Series in the HCV genotype 1/2 chimeric infectious system.

EXAMPLES

The invention is now further described by reference to the following examples which are intended to illustrate, not to limit the scope of the invention.

Example 1: Compound Preparation

The compounds according to Formula I are prepared using conventional organic syntheses. Suitable synthetic routes are depicted below in the following general reaction schemes. In the following, sometimes reference is made to compounds according to the present invention as "TU-" followed by a letter, such as "A", "B" etc. "TU" is meant to abbreviate "thiophene urea" from which these compounds are derived. "A", "B" etc. is just a numbering. However, it should be noted that the designation "TU" or "thiophene urea" when used in conjunction with the designation of the compounds according to the present invention is not meant to be construed in a limiting manner. The compounds according to the present invention are intended to be limited only by the various claims appended hereto, and in particular by the structures and formulae indicated therein.

Synthesis of Formula (I) Inventive Compounds

<General Procedure 1>

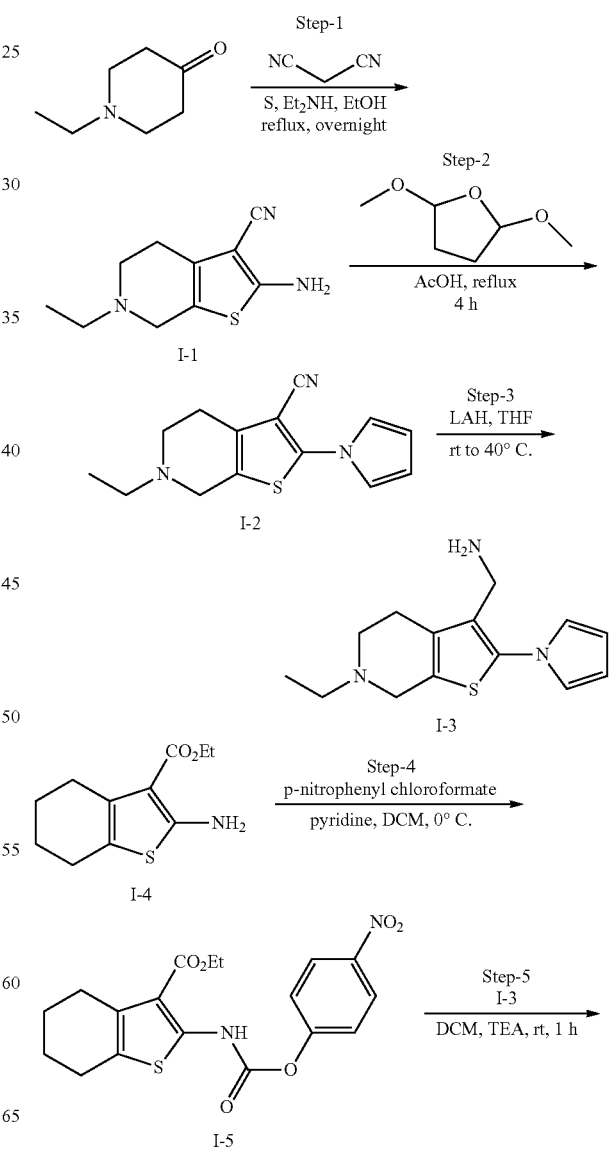

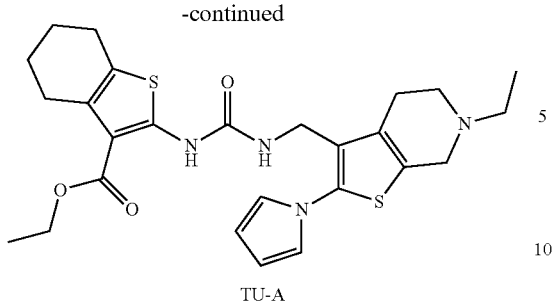

TU-A

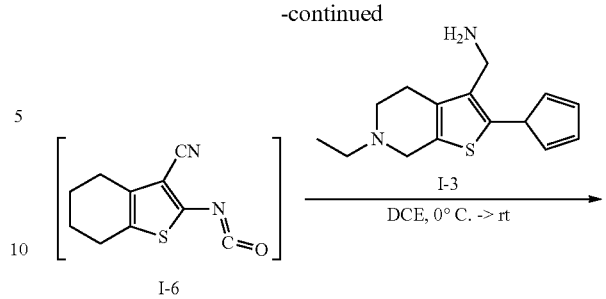

<Step-1>

A solution of 1-ethylpiperidin-4-one (2.0 ml, 15.73 mmol), sulfur (606 mg, 18.88 mmol), malonitrile (1.3 g, 18.88 mmol), and diethylamine (2.0 ml, 18.88 mmol) in EtOH were heated at 70° C. for 18 h. The mixture were concentrated in vacuo, diluted with ethyl acetate, and washed with water. The organic layer was dried over $MgSO_4$ and concentrated in vacuo to give I-1 as brown solid. (60%).

<Step-2>

A solution of I-1 (605 mg, 3.39 mmol), 2,5-dimethoxytetrahydrofuran (0.5 ml, 3.73 mmol) in AcOH (7 mL) was refluxed at 120° C. for 4 h. After reaction was completed, the mixture was concentrated under reduced pressure, diluted with EA, washed subsequently with $NaHCO_3$, and brine. The organic layer was dried over $MgSO_4$ and concentrated in vacuo to give I-2 as white solid. (80%).

<Step-3>

To a solution of I-2 (560 mg, 2.18 mmol) in anhydrous THF (6.0 mL) was carefully added LAH (165 mg, 4.35 mmol) at 0° C. The reaction mixture was stirred at rt overnight. The reaction was quenched by adding iced water and extracted with EA, washed with brine and dried over $MgSO_4$. The organic layer was concentrated in vacuo and purified by column chromatography to give I-3 as brown solid. (76%).

<Step-4>

To a solution of I-4 (500 mg, 2.22 mmol) and pyridine (0.36 ml, 4.44 mmol) in DCM (15 mL) was added dropwise p-nitrophenyl chloroformate (490 mg, 2.44 mmol) in DCM (3 mL) at 0° C. The mixture was stirred at 0° C. for 1 h and diluted with DCM. The organic layer was washed with water and concentrated under reduced pressure. The solid product was washed with ether to give pure compound I-5 as pale yellow solid. (70%).

<Step-5>

A solution of I-5 (50 mg, 0.13 mmol), I-3 (33 mg, 0.13 mmol), and TEA (0.020 ml, 0.14 mmol) in DCM was stirred at rt overnight. The mixture was washed with water, dried over $MgSO_4$, concentrated in vacuo, and purified by column chromatography to give TU-A as white solid. (74%).

<General Procedure 1-a>

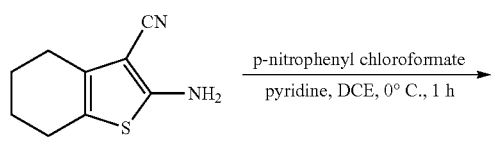

To a solution of 2-amino-4,5,6,7-tetrahydrobenzo[b]thiophene-3-carbonitrile (500 mg, 2.81 mmol) and pyridine (0.453 ml, 5.62 mmol) in DCE (15 mL) was added dropwise p-nitrophenyl chloroformate (623 mg, 3.09 mmol) in DCE (3 mL) at 0° C. The mixture was stirred at 0° C. for 1 h. The mixture was concentrated in vacuo. The solid was washed with ether to give the crude mixture I-6 as white solid. A solution of I-6 (50 mg, 0.25 mmol) and I-3 (64 mg, 0.25 mmol) in DCE was stirred at rt for 0.5 h. The mixture was concentrated and purified by column chromatography to give TU-B (25 mg) as yellow gel. (22%).

<General Procedure 2>

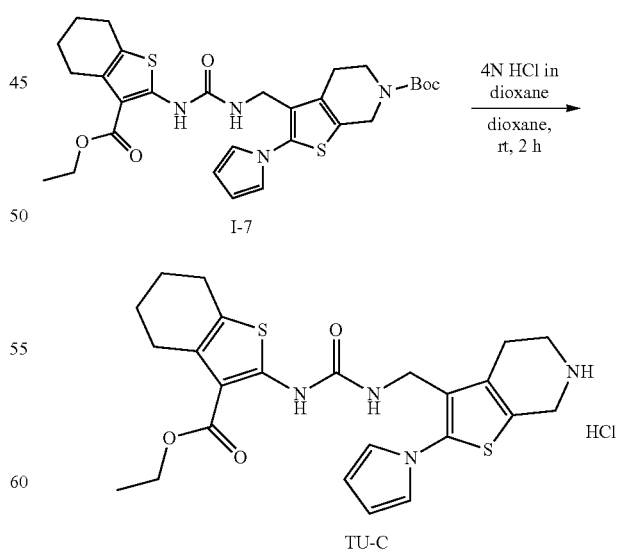

A solution of I-7 in 4 N HCl in dioxane was stirred at rt for 2 h. The mixture was concentrated and washed with ether to give TU-C as white solid.

\<General Procedure 3\>

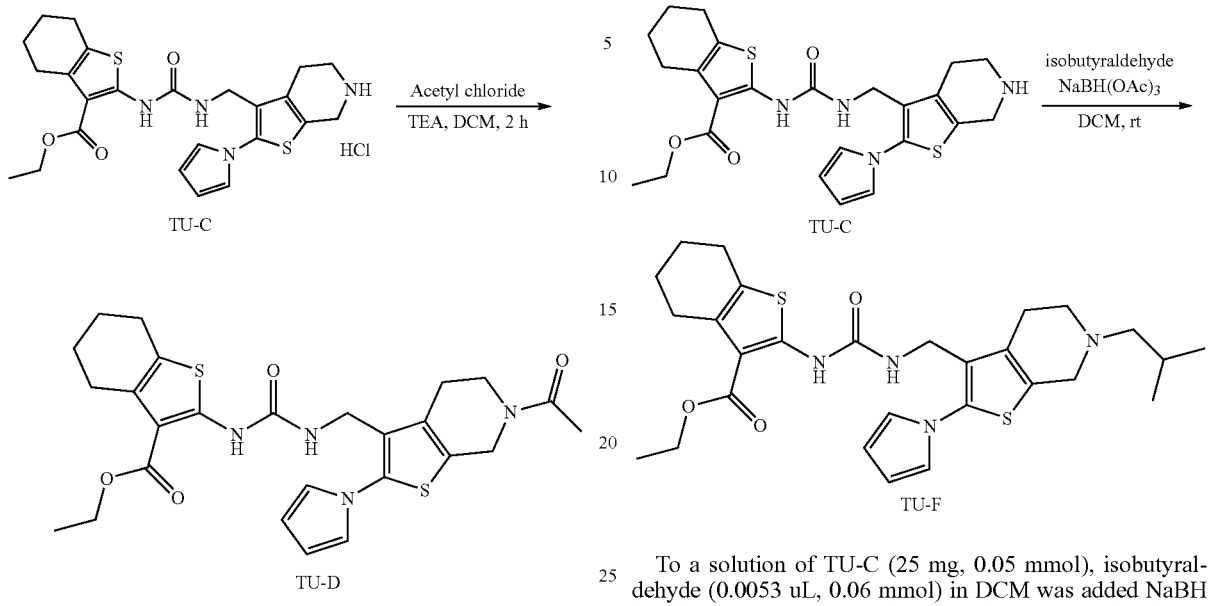

To a solution of TU-C (25 mg, 0.05 mmol) and acetyl chloride (3.75 uL, 0.05 mmol) in DCM was added TEA (14.7 uL, 0.11 mmol). The mixture was stirred at rt for 2 h and washed with water. The organic layer was dried over MgSO₄, concentrated in vacuo, and purified by column chromatography to give TU-D (yield=71%).

\<General Procedure 4\>

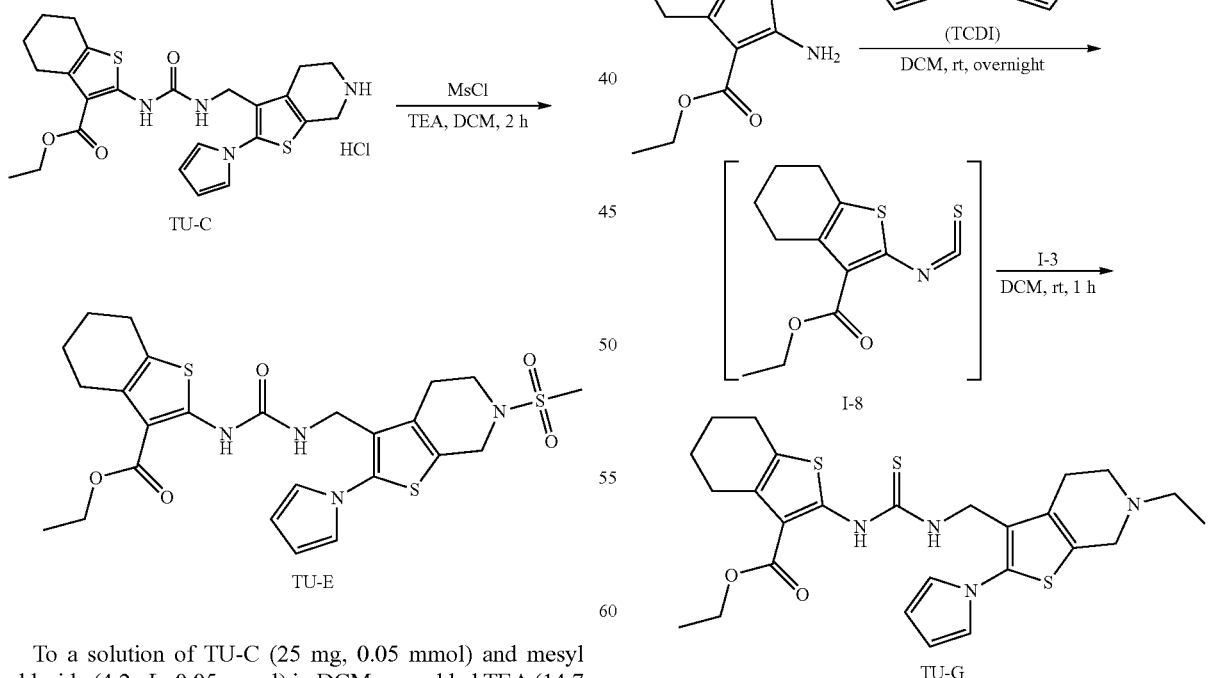

To a solution of TU-C (25 mg, 0.05 mmol) and mesyl chloride (4.2 uL, 0.05 mmol) in DCM was added TEA (14.7 uL, 0.11 mmol). The mixture was stirred at rt for 2 h and washed with water. The organic layer was dried over MgSO₄, concentrated in vacuo, and purified by column chromatography to give TU-E (78%)

\<General Procedure 5\>

To a solution of TU-C (25 mg, 0.05 mmol), isobutyraldehyde (0.0053 uL, 0.06 mmol) in DCM was added NaBH(OAc)₃ (8 mg, 0.07 mmol). The mixture was stirred at rt overnight and diluted with DCM. The mixture was sequentially washed with water and sat. NaHCO₃, dried over MgSO₄, concentrated in vacuo, and purified by column chromatography to give TU-F (15 mg, 58%) as ivory solid.

\<General Procedure 6\>

To a solution of ethyl 2-amino-4,5,6,7-tetrahydrobenzo[b]thiophene-3-carboxylate (50 mg, 0.22 mmol) in DCM (10 mL) was added thiocarbonyldiimidazole (40 mg, 0.22 mmol), and stirred overnight at room temperature. I-8 (70 mg, 0.29 mmol) was added to the reaction mixture and stirred at room temperature for 2 h. The mixture was diluted with DCM and washed with water and concentrated under reduced pressure. The residue was purified by column chromatography to give TU-G as brown gel.

<General Procedure 7>

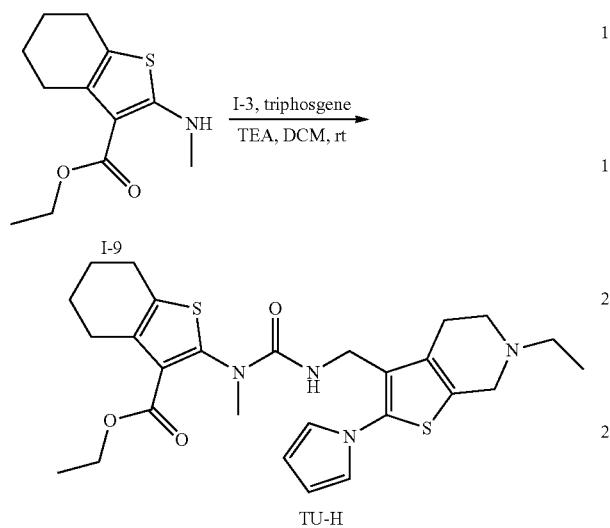

To a solution of I-9 (0.03 mg, 0.13 mmol) in acetone (2 mL) was added triphosgene (0.023 mL, 0.19 mmol) at 0° C. The mixture was stirred for 1 h at room temperature. A solution of the amine (33 mg, 0.13 mmol) and TEA (26.2 uL, 0.13 mmol) in DCM (2 mL) was added to the reaction mixture and stirred for 2 h at room temperature. The mixture was diluted with DCM, washed with water, dried over MgSO$_4$, and concentrated in vacuo. The residue was purified by column chromatography to give TU-H (28 mg, 42%) as brown gel.

<General Procedure 8>

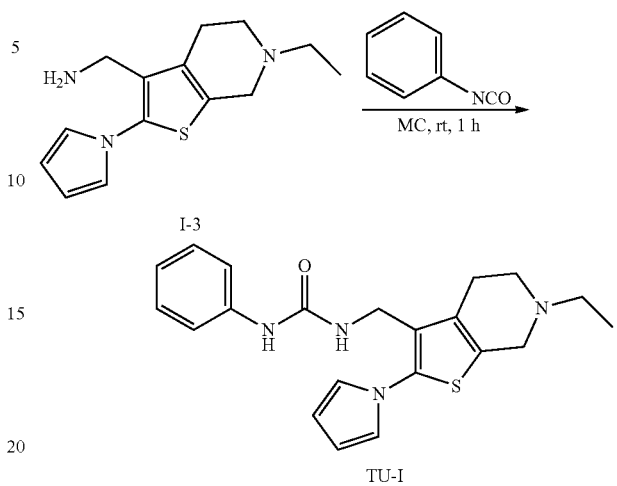

To a stirred solution of I-3 (40 mg, 0.15 mmol) in DCM (1.0 mL) was added isocyanate (0.033 ml, 0.31 mmol). The reaction mixture was stirred at room temperature for 1 h. After reaction was completed, the reaction mixture was diluted with DCM and washed with brine. The organic layer was dried over anhydrous MgSO$_4$ and concentrated in vacuo. The crude product was purified by flash column chromatography to give TU-I. (8.2 mg, yield=14%).

<General Procedure 9>

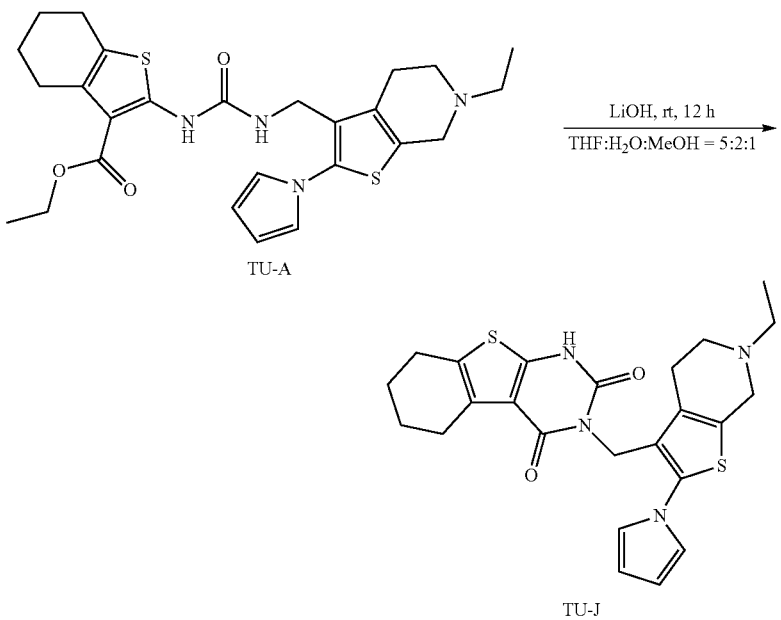

To a stirred solution of TU-A (45 mg, 0.09 mmol) in THF (0.5 mL) and MeOH (0.1 mL) and H$_2$O (0.2 mL) was added lithium hydroxide (11 mg, 0.44 mmol). The reaction mixture was stirred at room temperature for overnight. After reaction was completed, the mixture was evaporated and 1 N HCl (10.0 mL) was added until pH was 6. The residual pale solid was collected by filtration and washed with H₂O to give TU-J. (28 mg, 68%).

<General Procedure 10>

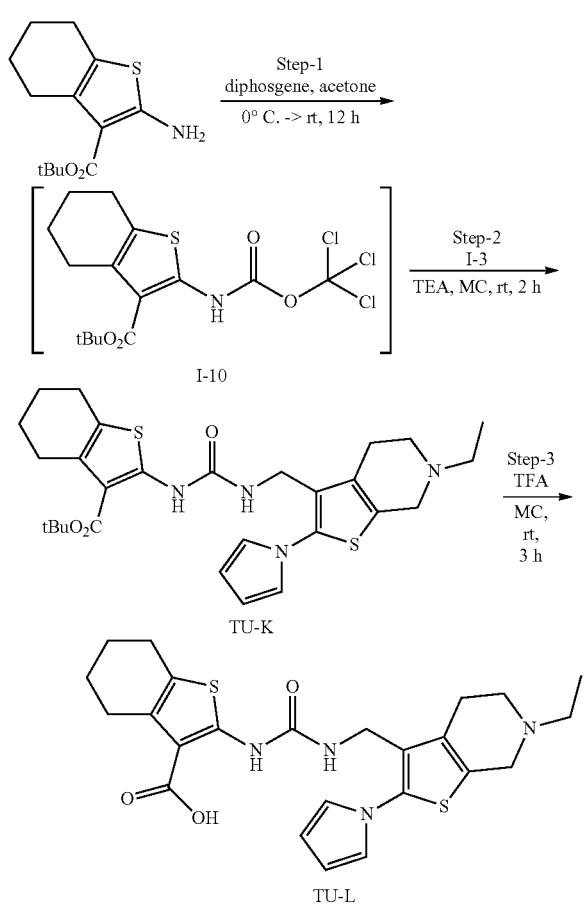

TU-K

TU-L

<Step-1>
To a stirred solution of t-butyl 2-amino-4,5,6,7-tetrahydrobenzo[b]thiophene-3-carboxylate (20 mg, 0.08 mmol) in acetone (0.3 mL) was added diphosgene (0.014 mL, 0.12 mmol) and then stirred at room temperature for 12 h. After reaction was completed, the reaction mixture was diluted with DCM and washed with brine. The organic layer was dried over anhydrous MgSO₄ and concentrated to give I-10.

<Step-2>
To a stirred solution of I-10 in DCM (0.5 mL) was added TEA (0.012 mL, 0.09 mmol), I-3 (20 mg, 0.08 mmol) and then stirred at room temperature for 1 h. After reaction was completed, the reaction mixture was diluted with DCM and washed with brine. The organic layer was dried over anhydrous MgSO₄ and concentrated in vacuo. The crude product was purified by flash column chromatography to give TU-K. (13 mg, two-step yield=30%).

<Step-3>
To a stirred solution of TU-K (10 mg, 0.02 mmol) in DCM (1.0 mL) was added TFA (0.5 mL). The reaction mixture was stirred at room temperature for 3 h. After reaction was completed, the reaction mixture was evaporated and 1 N NaOH (1.0 mL) was added until pH 6. The mixture was diluted with DCM and washed with brine. The organic layer was dried over anhydrous MgSO₄ and concentrated to give TU-L. (2.8 mg, 31%).

<General Procedure 11>

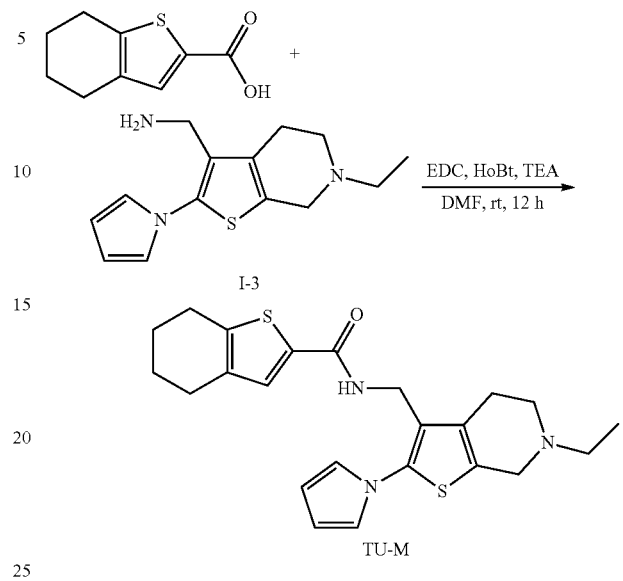

TU-M

To a stirred solution of 4,5,6,7-tetrahydrobenzo[b]thiophene-2-carboxylic acid (50 mg, 0.27 mmol) in DMF (2.0 mL) was added I-3 (86 mg, 0.33 mmol), EDC (79 mg, 0.41 mmol), HoBt (44 mg, 0.33 mmol) and TEA (0.076 mL, 0.55 mmol). The reaction mixture was stirred at room temperature for 12 h. After reaction was completed, the reaction mixture was diluted with EtOAc and washed with brine. The organic layer was dried over anhydrous MgSO₄ and concentrated in vacuo. The crude product was purified by flash column chromatography to give TU-M. (53 mg, 45%).

<General Procedure 12>

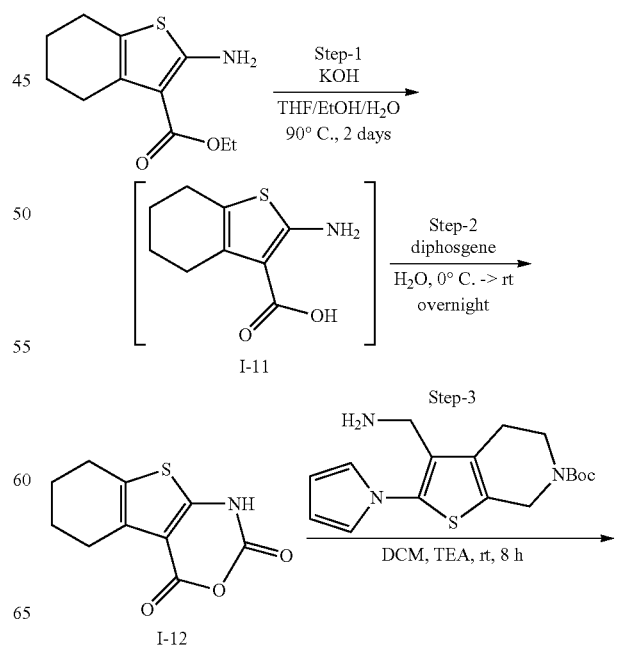


I-13

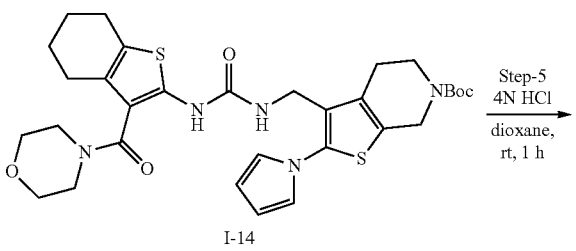

I-14

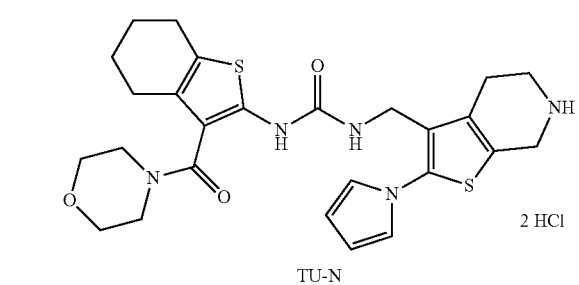

TU-N

<Step-1>

To a stirred solution of ethyl 2-amino-4,5,6,7-tetrahydrobenzo[b]thiophene-3-carboxylate (300 mg, 1.33 mmol) in $H_2O$ (4.0 mL) and EtOH (1.0 mL) was added KOH (746 mg, 10.0 mmol). The reaction mixture was stirred at 90° C. for 12 h and treated with KOH (10.0 mmol) again. The reaction mixture was further stirred overnight at 90° C. and needed additional KOH (10.0 mmol). After reaction was completed, solvents were removed under reduced pressure. No further purification was performed.

<Step-2>

Crude intermediate I-11 was dissolved in $H_2O$ (4.0 mL) and treated with diphosgene (0.24 mL, 2.00 mmol) slowly with an ice cooling bath. The mixture was allowed to stand overnight at room temperature, diluted with excess water and sonicated. Solid was filtered and washed with water enough. Dried solid was purified by column chromatography to give I-12. (144 mg, two step yield=48%).

<Step-3>

To a stirred solution of I-12 (16.0 mg, 0.07 mmol) in DCM (1.0 mL) was added tert-butyl 3-(aminomethyl)-2-(1H-pyrrol-1-yl)-4,7-dihydrothieno[2,3-c]pyridine-6(5H)-carboxylate (24 mg, 0.07 mmol). The reaction mixture was stirred at room temperature for 3 h. After reaction was completed, the reaction mixture was diluted with DCM and washed with brine. The organic layer was dried over anhydrous $MgSO_4$ and concentrated in vacuo. The crude product was purified by flash column chromatography to give I-13. (10.4 mg, yield=26%).

<Step-4>

To a stirred solution of I-13 (10.4 mg, 0.02 mmol) in DMF (2.0 mL) was added morpholine (0.004 mL, 0.04 mmol), EDC (5.5 mg, 0.03 mmol), HoBt (3.1 mg, 0.024 mmol) and TEA (0.005 mL, 0.04 mmol). The reaction mixture was stirred at room temperature for 12 h. After reaction was completed, the reaction mixture was diluted with EtOAc and washed with brine. The organic layer was dried over anhydrous $MgSO_4$ and concentrated in vacuo. The crude product was purified by flash column chromatography to give I-14. (5.0 mg, yield=44.6%).

<Step-5>

To a stirred solution of I-14 (5.0 mg, 0.008 mmol) in dioxane (0.05 mL) was added 4N HCl in dioxane (0.1 mL) and then stirred at room temperature for 2 h. After reaction was completed, the reaction mixture was concentrate in vacuo to give TU-N. (3.8 mg, 84%).

<General Procedure 3

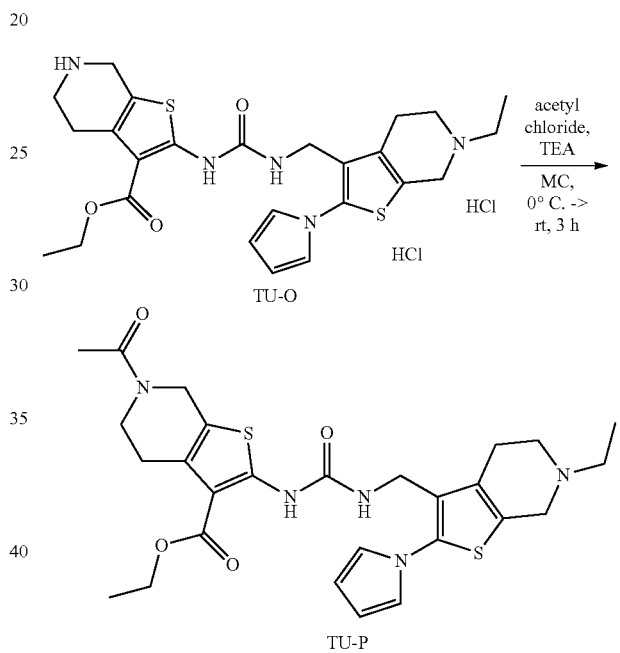

To a stirred solution of TU-0 (38 mg, 0.07 mmol), TEA (0.07 mL, 0.10 mmol) in DCM (0.5 mL) was added acetyl chloride (0.05 mg, 0.33 mmol) at 0° C. The reaction mixture was stirred at room temperature for 3 h. After reaction was completed, the reaction mixture was diluted with DCM and washed with brine. The organic layer was dried over anhydrous $MgSO_4$ and concentrated in vacuo. The crude product was purified by flash column chromatography to give TU-P. (15.6 mg, yield=43.3%).

<General Procedure 13>

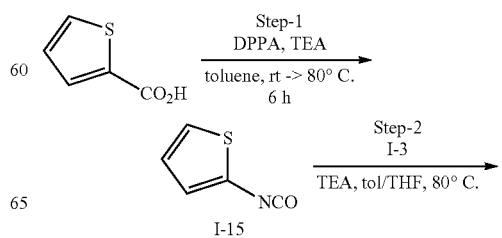

I-15

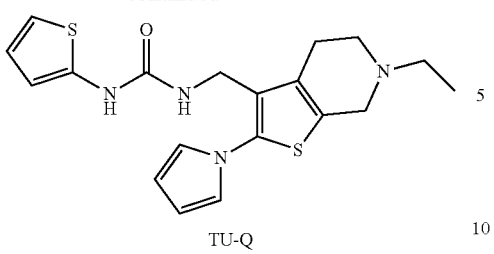

TU-Q

<Step-1>

A mixture of thiophene-2-carboxylic acid (64 mg, 0.50 mmol) and toluene (2.5 mL) was treated with diphenyl phosphoryl azide (0.13 ml, 0.60 mmol) and triethylamine (0.09 mL, 0.65 mmol). Reaction mixture was stirred for 30 min at room temperature and heated to 80° C. for 5 h.

<Step-2>

A quarter aliquot of I-15 (0.13 mmol) in toluene was treated with a solution of I-3 (30 mg, 0.11 mmol), triethylamine (0.02 mL, 0.11 mmol) in THF (1.5 mL). The mixture was heated to 80° C. for 1 h and allowed to stand at room temperature overnight. Concentrated residue was dissolved in DCM and washed with 1N HCl and sat'd NaHCO₃ solution successively. Organic layer was dried over MgSO₄, concentrated under reduced pressure and purified by column chromatography (DCM:MeOH=20:1) to give TU-Q.

<General Procedure 14>

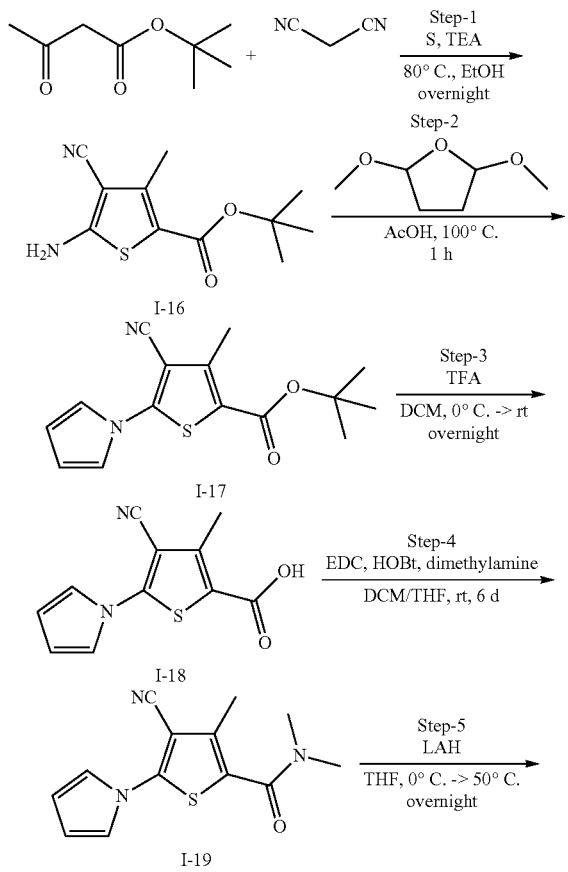

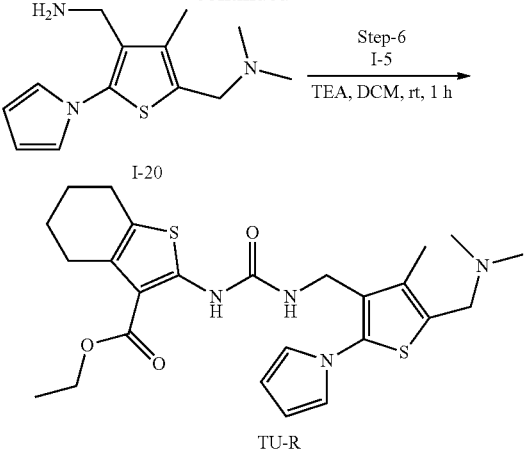

TU-R

<Step-1>

To a solution of t-butylacetoacetate (1.5 mL, 9.20 mmol) in EtOH (18.5 mL) were added malononitrile (608 mg, 9.20 mmol), sulfur (295 mg, 9.20 mmol) and triethylamine (1.28 mL, 9.20 mmol). The reaction mixture was heated overnight at 80° C., concentrated and purified by column chromatography (n-hexane:EtOAc:DCM=7:1:2) to give I-16 as a brown solid (65%).

<Step-2>

To a solution of I-16 (715 mg, 3.00 mmol) in acetic acid (6 mL) was added 2,5-dimethoxytetrahydrofuran (0.43 mL, 3.30 mmol) and stirred for 1 h at 100° C. Acetic acid was removed under reduced pressure, the residue was basified with sat'd NaHCO₃ and dissolved in ethyl acetate. Phases were separated and organic phase was dried over MgSO₄, concentrated and purified by column chromatography (n-hexane:EtOAc:DCM=10:1:2) to obtain I-17 as a light yellow solid (92%).

<Step-3>

To a solution of I-17 (395 mg, 1.37 mmol) in dry dichloromethane (7 mL) was added TFA (10 mL) at 0° C. After 30 min, reaction mixture was warmed to rt and stirred overnight. TFA was removed under reduced pressure, the residue was diluted with DCM and washed with water. Organic phase was dried over MgSO₄, concentrated to give pure compound I-18 as a pale yellow solid (93%).

<Step-4>

A solution of I-18 (209 mg, 0.90 mmol), EDC (207 mg, 1.08 mmol), HOBt (146 mg, 1.08 mmol) in DCM (4.5 mL) was treated with dimethylamine (2M in THF, 0.7 mL, 1.78 mmol) and TEA (0.25 mL, 1.80 mmol). After 6 days, the mixture was washed with water and brine successively. Organic phases was dried over MgSO₄, concentrated under reduced pressure and purified by column chromatography (n-hexane:EtOAc:DCM=3:1:2) to afford I-19 as a white solid (62%).

<Step-5>

To a solution of I-19 (143 mg, 0.55 mmol) in dry THF (3 mL) was added LAH (104 mg, 2.76 mmol) in several portions at 0° C. The mixture was stirred overnight at ambient temperature and heated overnight at 80° C. Excess LAH was quenched by adding water at 0° C. carefully and mixture was dried over MgSO₄. Slurry was filtered through celite pad and concentrated. Crude residue was purified by column chromatography (DCM:MeOH=20:1) to give I-20 as a yellow oil.

<Step-6>

A solution of I-20 (26 mg, 0.10 mmol) in DCM (1.0 mL) was treated with I-5 (41 mg, 0.10 mmol) and triethylamine (0.02 mL, 0.16 mmol). When the reaction was complete, the mixture was diluted in additional DCM and washed with excess water and brine, then dried over MgSO₄ Concentrated residue was purified by column chromatography (n-hexane:EtOAc:DCM=3:1:2) to give TU-R.

<General Procedure 15>

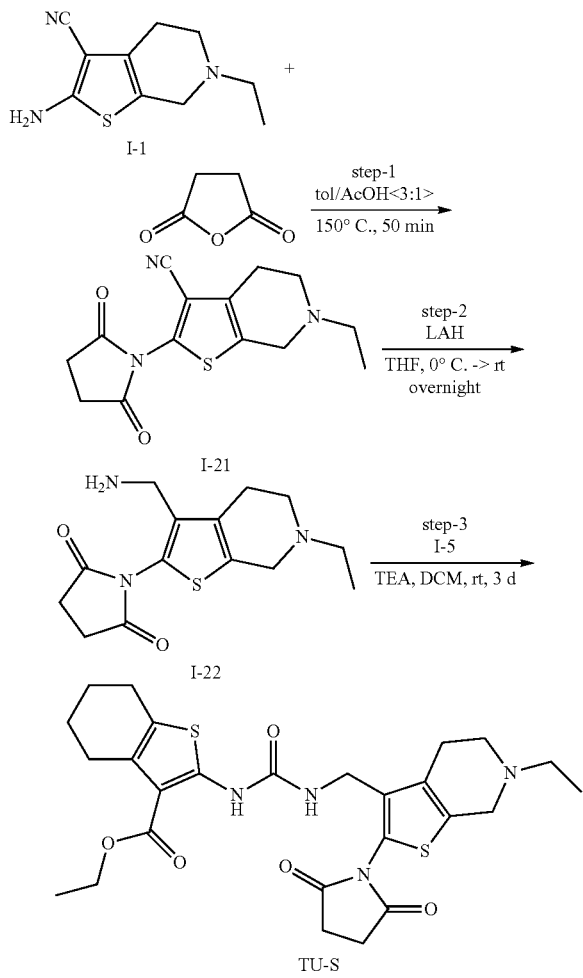

<Step-1>

I-1 (518 mg, 2.5 mmol) and succinic anhydride (318 mg, 3.13 mmol) were dissolved in toluene/acetic acid solution (3:1, 5 mL) and heated to 150° C. by microwave irradiation for 50 min. The resulting mixture was basified with sat'd NaHCO₃ and extracted with ethyl acetate twice. Combined solution was washed with brine, dried over MgSO₄, filtered and concentrated. Crude product was purified by column chromatography (n-hexane:EtOAc:DCM=1:1:2 to EtOAc) to obtain I-21 as a white solid (50%).

<Step-2>

To a solution of I-21 (180 mg, 0.62 mmol) in dry THF (3 mL) was added LAH (24 mg, 0.62 mmol) portionwise at 0° C. The mixture was stirred overnight in an ice-water bath and quenched by water at 0° C. Excess dichloromethane was poured into the reaction mixture and product was extracted 5 times from aqueous phase. Organic phase was dried over MgSO₄, filtered, concentrated and purified by column chromatography (DCM:MeOH=30:1 to 5:1) to I-22 as a yellow solid (8%).

<Step-3>

The procedure TU-S was followed by procedure of General procedure 1 (Step-5) (36%).

<General Procedure 16>

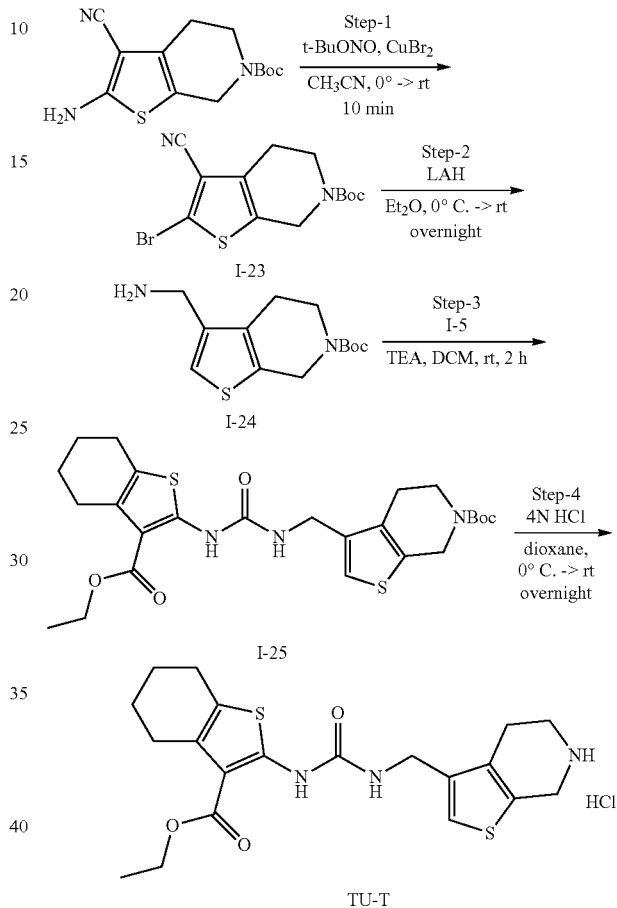

<Step-1>

To a solution of copper (II) bromide (1.92 g, 8.59 mmol) in anhydrous acetonitrile (36 mL) was added t-butyl nitrite (90%, 0.95 mL 7.16 mmol) under nitrogen at 0° C. After 10 min, tert-butyl 2-amino-3-cyano-4,7-dihydrothieno[2,3-c]pyridine-6(5H)-carboxylate (1.993 g, 7.16 mmol) was added portionwise to a stirred reaction mixture over 10 min at room temperature. When the conversion was complete, reaction mixture was concentrated under reduced pressure, dissolved in ethyl acetate and washed with water and brine successively. Aqueous layers were extracted with ethyl acetate one more time and combined organic phase was dried over MgSO₄, filtered and concentrated in vacuo. Crude product was purified by column chromatography (n-hexane:EtOAc:DCM=20:1:2) to afford I-23 as a white solid (50%).

<Step-2>

To a solution of I-23 (100 mg, 0.36 mmol) in anhydrous diethyl ether (2 mL) was added LAH (14 mg, 0.36 mmol) at 0° C. The mixture was stirred overnight at room temperature, quenched by adding water carefully at 0° C., dried over MgSO₄ and filtered through celite pad. Filtrate was concentrated under reduced pressure and purified by column chromatography (DCM:MeOH=30:1 to 5:1) to give I-24 as a colorless oil (22%).

<Step-3>
The procedure I-25 was followed by procedure of General procedure 1 (Step-5) (36%, yellow oil).
<Step-4>
I-25 (10 mg, 0.02 mmol) was treated with 4N HCl dioxane solution (1.8 mL) under nitrogen at 0° C. The solution was stirred overnight at ambient temperature and concentrated to give desired product TU-T.
<General Procedure 17>

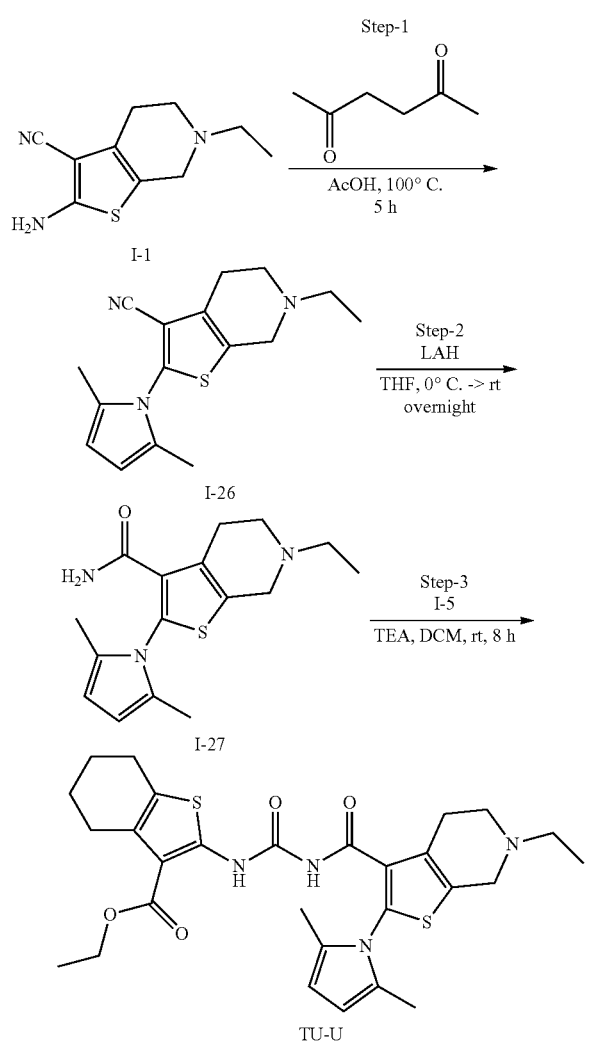

<Step-1>
The procedure I-26 was followed by procedure of General procedure 14 (Step-2) (61%, ivory solid).
<Step-2>
A solution of I-26 (87 mg, 0.30 mmol) in dry THF (2 mL) was treated with LAH (11 mg, 0.30 mmol) at 0° C. and stirred for 2.5 h in an ice-water bath and warmed to rt. After 2 h, LAH (11 mg, 0.30 mmol) was added again at 0° C. and stirred overnight at rt. LAH (11 mg, 0.30 mmol) was added to reaction mixture at 0° C. and reaction was quenched by adding water and dried over MgSO$_4$. Slurry was filtered through celite pad, washed with dichloromethane and the filtrate was concentrated. Crude residue was purified by column chromatography (DCM:MeOH=30:1) to give I-27 (12%, yellow oil).

<Step-3>
The procedure TU-U was followed by procedure of General procedure 1 (Step-5) (9%)
<General Procedure 18>

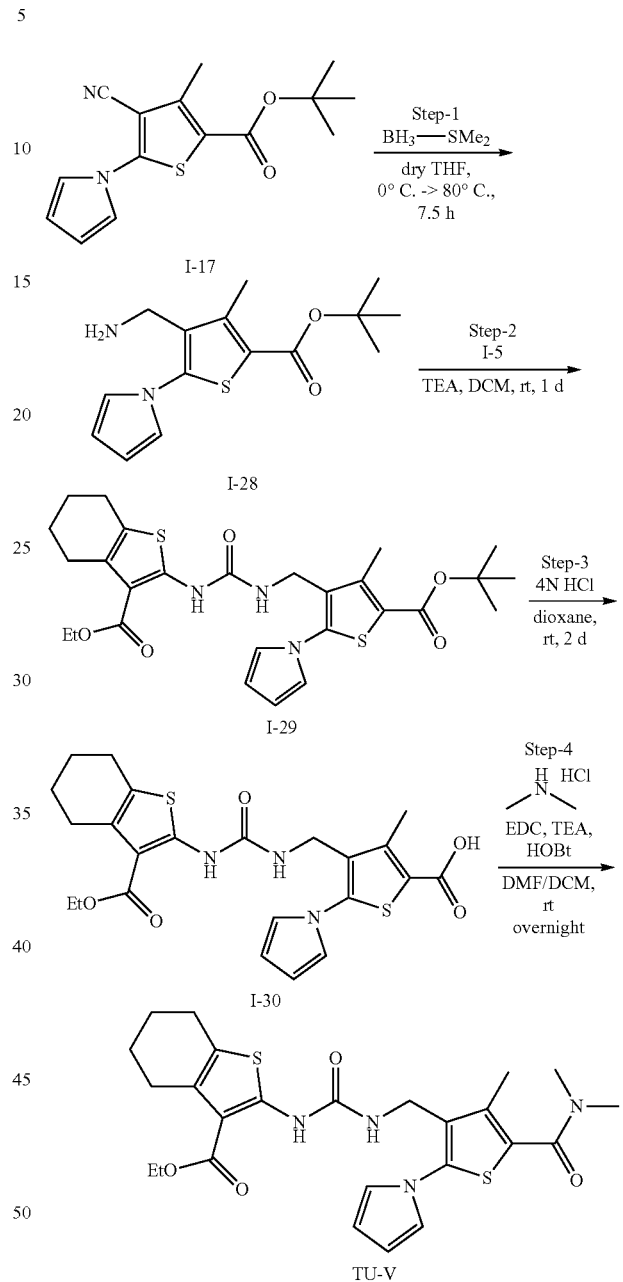

<Step-1>
To a solution of I-17 (115 mg, 0.40 mmol) in dry THF (4 mL) was added borane-dimethyl sulfide complex (94%, 0.09 ml, 0.80 mmol) at 0° C. under a nitrogen atmosphere and heated overnight at 50° C. Reaction mixture was heated to 80° C. for 7.5 h and cooled to rt. Methanol was added slowly and the solution was stirred for a while. Crude residue was concentrated under reduced pressure and purified by column chromatography (dichloromethane:MeOH=20:1) to obtain I-28 (17%, yellow oil).
<Step-2>
The procedure I-29 was followed by procedure of General procedure 1 (Step-5) (46%)

<Step-3>

I-29 (15 mg, 0.03 mmol) was dissolved in dry dioxane (0.5 mL) and treated with 4N HCl (1 mL). After the reaction was complete, concentrated crude residue was purified by column chromatography (DCM:MeOH=20:1) to give I-30 as a white solid (59%).

<Step-4>

A mixture of I-30 (5 mg, 0.01 mmol), dimethylamine hydrogen chloride (1 mg, 0.012 mmol), EDC (2 mg, 0.012 mmol), TEA (0.01 ml, 0.25 mol), HOBt (1 mg, 0.012 mmol) and dry DMF (0.5 mL)/dichloromethane (1 mL) was stirred overnight. The mixture was diluted excess ethyl acetate and water. Two phases were separated and organic phase was dried over $MgSO_4$, filtered and concentrated. Crude residue was purified by column chromatography (DCM:MeOH=30:1) to give TU-V (28%).

<General Procedure 19>

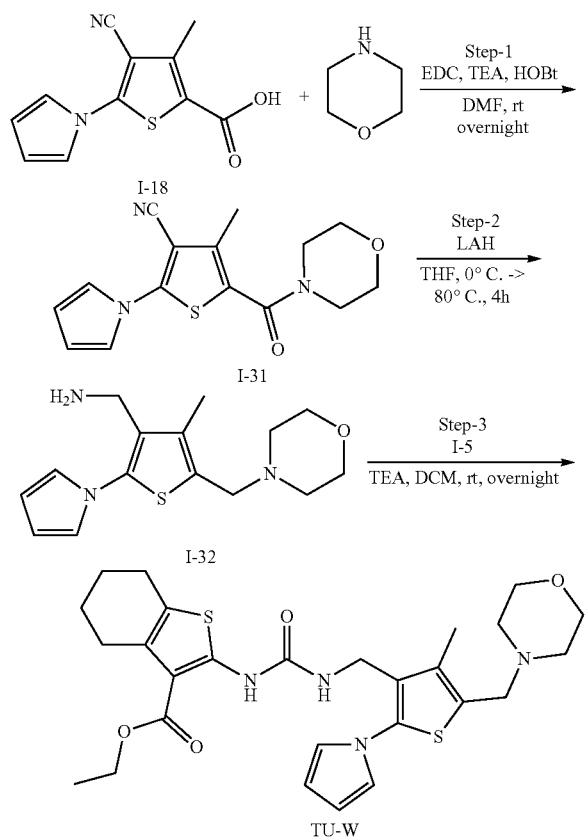

<Step-1>

A mixture of I-18 (130 mg, 0.56 mmol), morpholine (0.06 ml, 0.67 mmol), EDC (128 mg, 0.67 mmol), TEA (0.09 ml, 0.67 mol), HOBt (91 mg, 0.67 mmol) and dry DMF (2.8 mL) was stirred overnight. Reaction mixture was diluted excess ethyl acetate and water. Two phases were separated and organic phase was dried over $MgSO_4$, filtered and concentrated under reduced pressure. The crude product was purified by column chromatography (n-hexane:EtOAc:DCM=3:1:2) to obtain I-31 as an ivory solid (50%).

<Step-2>

To a solution of I-31 (66 mg, 0.22 mmol) in dry THF (4.4 mL) was added LAH (25 mg, 0.66 mmol) in several portions at 0° C. and the mixture was heated to 80° C. for 4 hr. The mixture was diluted with diethyl ether, excess LAH was quenched by adding water at 0° C. carefully, and dried over $MgSO_4$. Slurry was filtered through celite pad, washed with dichloromethane and the filtrate was concentrated under reduced pressure. Crude residue was purified by column chromatography (DCM:MeOH=10:1 to 6:1) to obtain I-32 as a yellow oil (11%).

<Step-3>

The procedure TU-W was followed by procedure of General procedure 1 (Step-5) (18%).

<General Procedure 20>

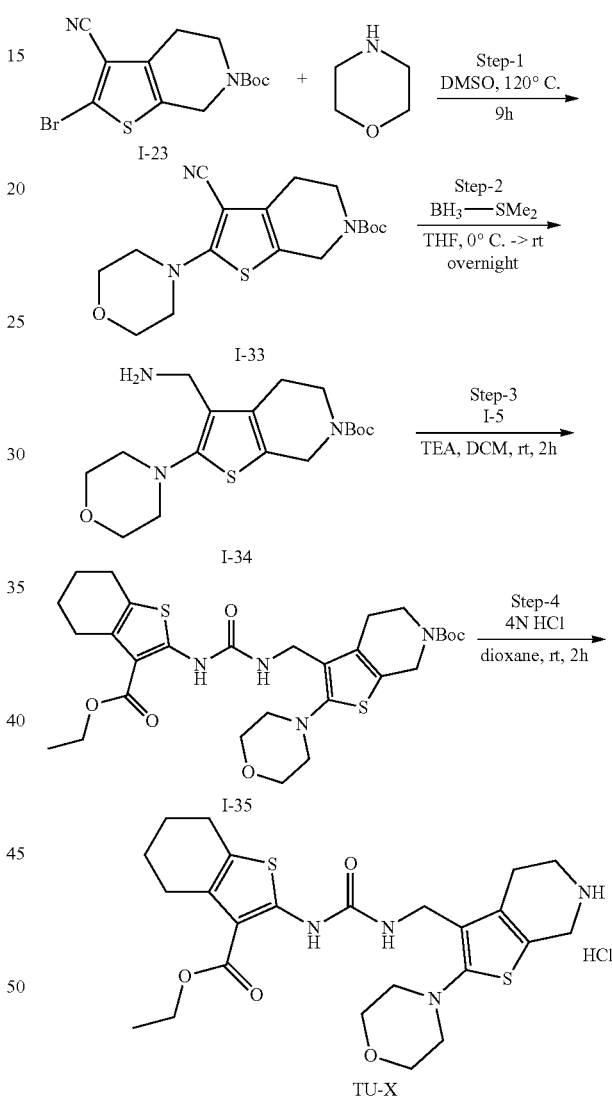

<Step-1>

I-23 (210 mg, 0.75 mmol) was placed in a sealed tube and dissolved in dry DMSO (1.5 mL). The solution was treated with morpholine (1.1 mL, 6.8 mmol) and heated to 120° C. When the conversion of starting material was complete, the mixture was diluted excess ethyl acetate and water. Two phases were separated and organic layer was dried over $MgSO_4$, filtered and concentrated under reduced pressure. The crude product was purified by column chromatography (n-hexane:EtOAc:DCM=8:1:2) to obtain I-33 as a white solid (72%).

<Step-2>

To a solution of I-33 (42 mg, 0.12 mmol) in anhydrous THF (1.2 mL) was added borane-dimethyl sulfide complex (94%, 0.03 mL, 0.24 mmol) at 0° C. under a nitrogen atmosphere. The mixture was stirred overnight, quenched with MeOH and concentrated under reduced pressure. The residue was dissolved in ethyl acetate and washed with water. Organic layer was dried over $MgSO_4$. Concentrate crude product was used without no further purification.

<Step-3>

The procedure I-35 was followed by procedure of General procedure 1 (Step-5) (two-step yield=59%, colorless oil).

<Step-4>

I-35 (25 mg, 0.04 mmol) was treated with 4N HCl (1.5 mL) and stirred for 2 h. When the conversion of starting material was complete, mixture was concentrate in vacuo to give TU-X (86%).

<General Procedure 21>

<Step-1>

A mixture of I-23 (54 mg, 0.20 mmol), phenyl boronic acid (37 mg, 0.30 mmol), tetrakis(triphenylphosphine) palladium(0) (12 mg, 5 mol %) and sodium carbonate solution (2M, 0.20 mL) in toluene/ethanol (2/1, 1 mL) was heated to 120° C. by microwave irradiation. After the reaction was complete, excess ethyl acetate was poured and washed with water twice. Organic phase was dried over $MgSO_4$, filtered and concentrated under reduced pressure. Crude residue was purified by column chromatography (n-hexane:EtOAc:DCM=10:1:2) to give I-36 as a colorless oil (82%).

<Step-2>

To a solution of I-36 (56 mg, 0.16 mmol) in dry THF (1 mL) was added borane-dimethyl sulfide complex (94%, 0.08 mL, 0.80 mmol) at 0° C. under a nitrogen atmosphere and stirred overnight. Methanol was added slowly, crude mixture was concentrated under reduced pressure and dissolved in ethyl acetate. Organic phase was washed with water, dried over $MgSO_4$, filtered and concentrated under reduced pressure. The extracts was purified by column chromatography (DCM:MeOH=10:1) to give I-37 as a colorless oil (60%).

<Step-3>

The procedure I-38 was followed by procedure of General procedure 1 (Step-5) (47%, colorless oil).

<Step-4>

A solution of I-38 (18 mg, 0.03 mmol) in anhydrous dioxane (1 mL) was treated with 4N HCl (1 mL) and stirred at room temperature. After the reaction was complete, concentrated residue was dissolved in diethyl ether and solid formed was filtered, washed with diethyl ether enough (44%).

<General Procedure 22>

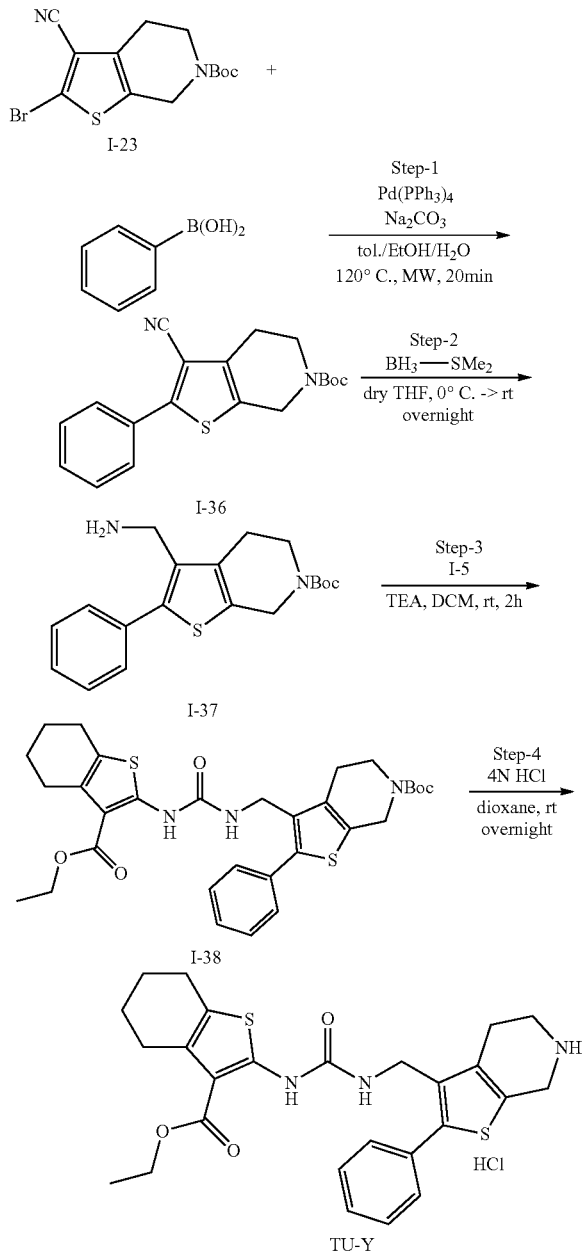

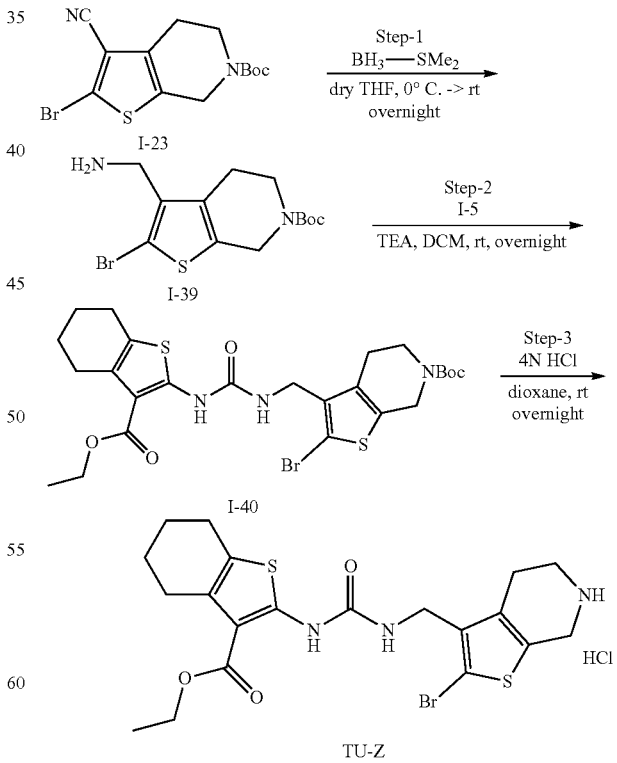

<Step-1>

The procedure I-39 was followed by procedure of General procedure 21 (Step-2) (55%, colorless oil).

<Step-2>
The procedure I-40 was followed by procedure of General procedure 1 (Step-5) (41%).
<Step-3>
The procedure TU-Z was followed by procedure of General procedure 2 (86%).
<General Procedure 23>

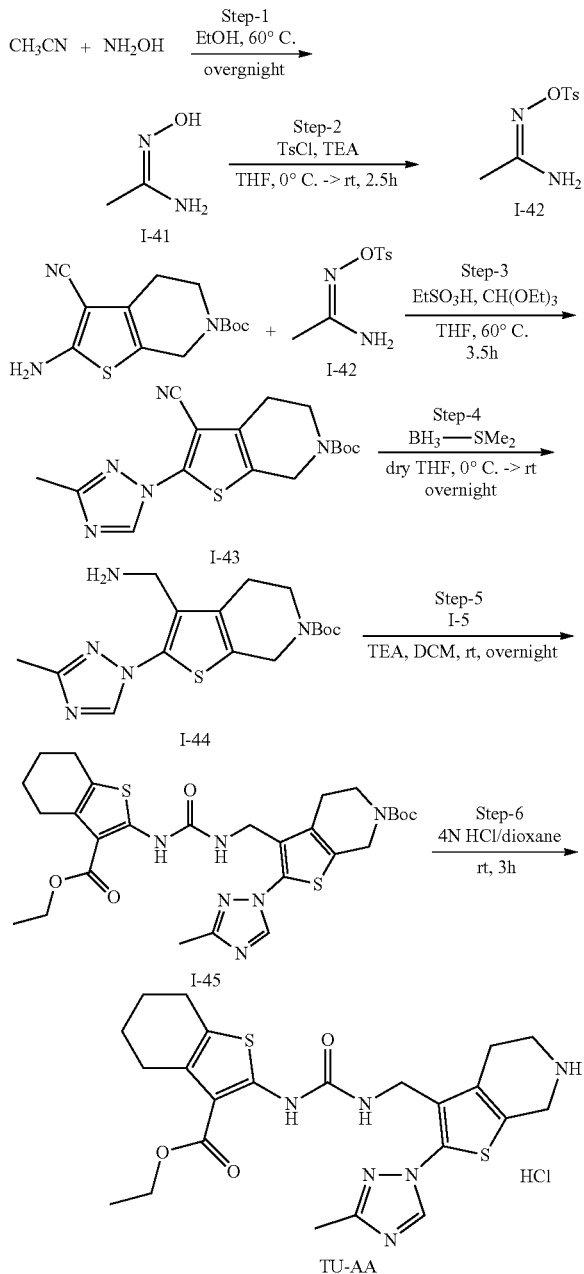

<Step-1>
A mixture of acetonitrile (1.0 mL, 19.15 mmol) and EtOH (5.0 mL) in a sealed tube was treated with hydroxylamine (50 wt. % in water, 1.76 mL, 28.73 mmol) and allowed to stand overnight at 60° C. Reaction mixture was heated to 90° C. for 2 h, cooled to rt and concentrated under reduced pressure Minimum EtOH was added, slurry was washed with EtOH and then n-hexane to obtain I-41 as a white solid (63%).

<Step-2>
To a solution of I-41 (893 mg, 12.05 mmol) in THF (24.0 mL) was added triethylamine (2.2 mL, 15.67 mmol). The mixture was stirred at room temperature until the solution became clear. p-Toluenesulfonyl chloride (2.53 g, 13.26 mmol) was added portionwise at 0° C. and an ice-water bath was removed immediately. The reaction mixture was stirred for 2.5 h, white precipitate was filtered off and washed with THF. The filtrate was concentrated under reduced pressure, dissolved in ethyl acetate, washed with water and brine. Organic layer was dried over $MgSO_4$, filtered and concentrated under reduced pressure to give I-42 as a light yellow solid.
<Step-3>
To a solution of amine (279 mg, 1.0 mmol) in THF (5.0 mL) was added I-42 (228 mg, 1.2 mmol). Triethyl orthoformate (0.33 mL, 2.0 mmol) and ethanesulfonic acid (0.82 mmol) were added successively and the reaction mixture was heated for 3.5 h at 60° C. After concentration, the crude residue was basified by adding sat'd $NaHCO_3$ solution and extracted with ethyl acetate twice. The organic layer was dried over $MgSO_4$, filtered, concentrated under reduced pressure and purified by column chromatography (n-hexane: EtOAc:DCM=3:1:2) to obtain a mixture of target compound and tosylamidoxime.
<Step-4>
The procedure I-44 was followed by procedure of General procedure 21 (Step-2) (two-step yield=6%, yellow oil).
<Step-5>
The procedure I-45 was followed by procedure of General procedure 1 (Step-5) (25%, colorless oil)
<Step-6>
The procedure TU-AA was followed by procedure of General procedure 2 (26%).
<General Procedure 24>

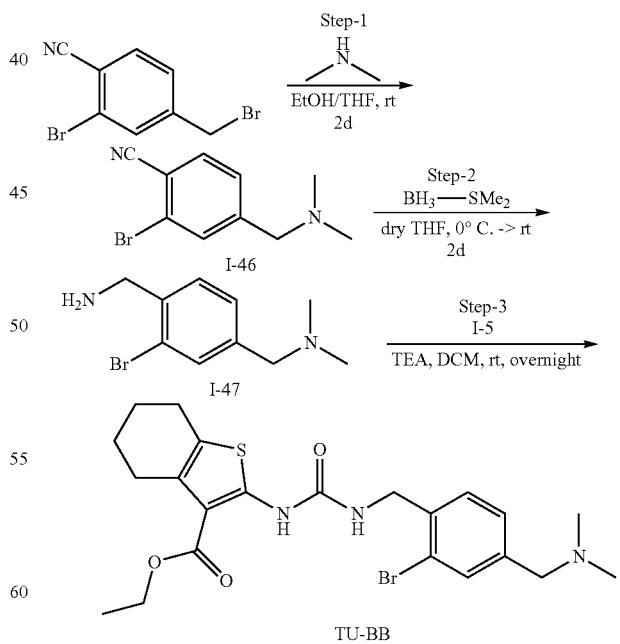

<Step-1>
To a solution of 2-bromo-4-(bromomethyl)benzonitrile (330 mg, 1.24 mmol) in EtOH (2.5 mL) was added Dimethylamine (2.0 M in THF, 3.1 mL, 6.18 mmol). The reaction mixture was stirred and removed volatiles under reduced pressure. The crude residue was diluted with EtOAc and washed with sat'd NaHCO₃ and brine. The organic layer was dried over MgSO₄, filtered, concentrated under reduced pressure and purified by column chromatography (DCM: MeOH=40:1) to afford pure compound I-46 as an ivory oil (85%).

<Step-2>

The procedure I-47 was followed by procedure of General procedure 21 (Step-2) (38%, yellow oil).

<Step-3>

The procedure TU-BB was followed by procedure of General procedure 1 (Step-5) (33%).

<General Procedure 25>

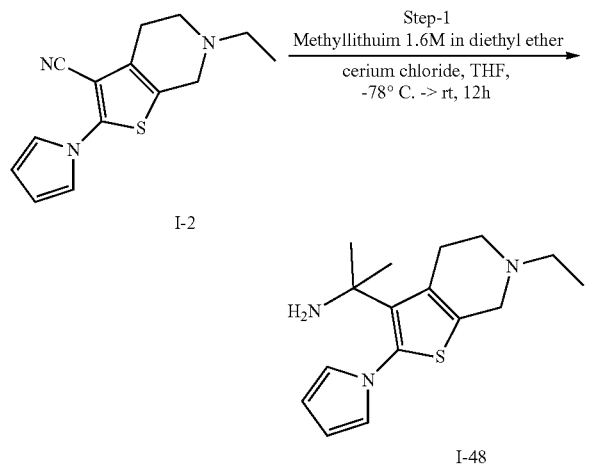

<Step-1>

Anhydrous cerium chloride (0.9 g, 3.67 mmol) was suspended in tetrahydrofuran (8 mL) and stirred overnight at room temperature. While cooling with dry ice and acetone, methyllithium (1.2 M in diethyl ether, 1.17 mL) was slowly added dropwise to the suspension, followed by stirring for 30 minutes. To this reaction system, a solution of I-2 (0.3 g) in tetrahydrofuran (0.2 mL) was added dropwise at the same temperature. The reaction mixture was further stirred while gradually warming to room temperature over 5 hours. While stirring the reaction mixture under ice cooling, 25 percent aqueous ammonia (12.5 mL) was added dropwise. The suspension was filtered through celite and the resulting filtrate was extracted with diethyl ether (25 mL). The extracted solution was washed with saturated aqueous sodium chloride (20 mL), dried over anhydrous magnesium sulfate, filtered to remove the desiccant and then concentrated under reduced pressure to give I-48 as a black liquid (0.13 g, 39%).

<General Procedure 26>

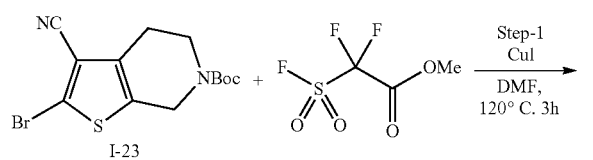

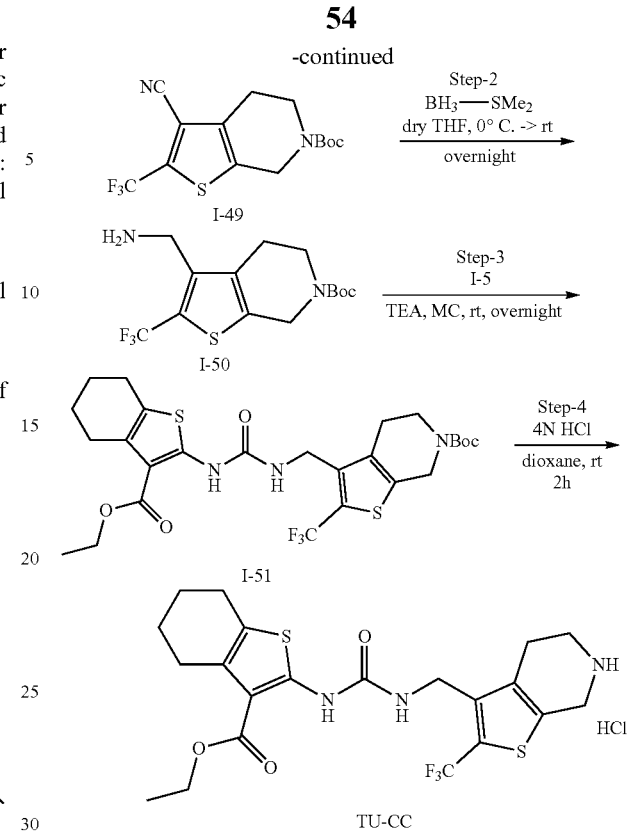

<Step-1>

To a solution of I-23 (343 mg, 1.0 mmol) and CuI (38 mg, 50 mol %) in anhydrous DMF (4 mL) was added Methyl fluorosulphonyldifluoroacetate (0.38 mL, 3.0 mmol) under a nitrogen atmosphere. Reaction mixture was heated at 120° C. for 3 hr. After cooling, resulting mixture was basified with sat'd NaHCO₃ and extracted with EtOAc twice. Organic phase was dried over MgSO₄, filtered, concentrated under reduced pressure and purified by column chromatography (n-hexane:EtOAc=95:5) to give I-49 as a light yellow solid (70%).

<Step-2>

The procedure I-50 was followed by procedure of General procedure 21 (Step-2) (38%, yellow oil).

<Step-3>

The procedure I-51 was followed by procedure of General procedure 1 (Step-5) (91%, yellow solid).

<Step-4>

The procedure TU-CC was followed by procedure of General procedure 2 (93%).

<General Procedure 27>

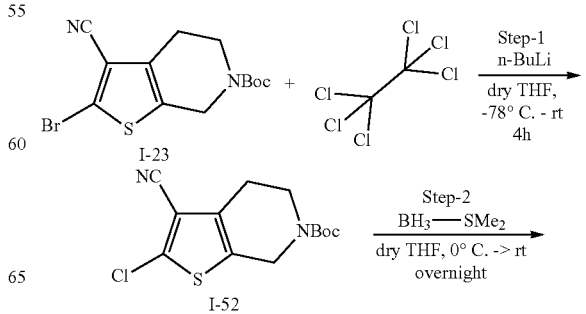

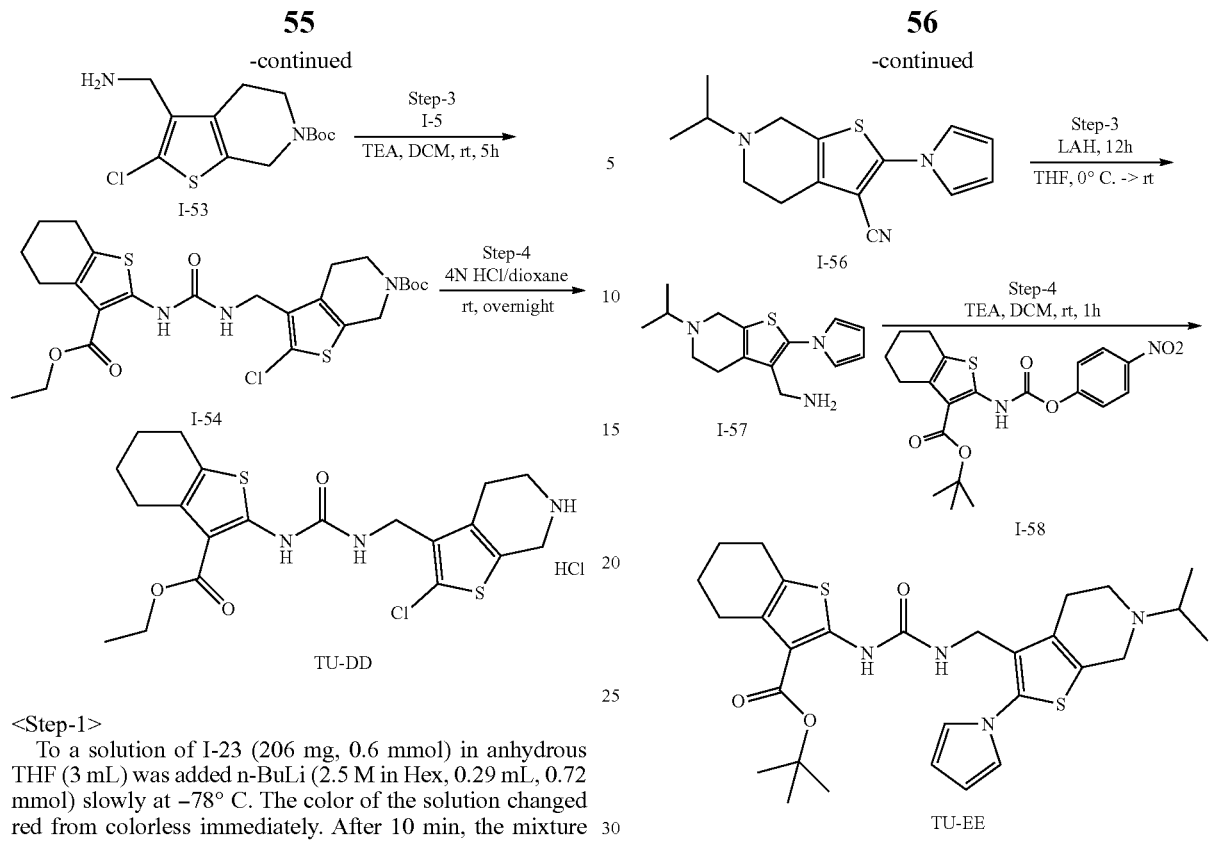

<Step-1>

To a solution of I-23 (206 mg, 0.6 mmol) in anhydrous THF (3 mL) was added n-BuLi (2.5 M in Hex, 0.29 mL, 0.72 mmol) slowly at −78° C. The color of the solution changed red from colorless immediately. After 10 min, the mixture was treated with hexachloroethane solution (170 mg, 0.72 mmol, 3 mL THF). The color changed purple. After 20 min, reaction mixture was warmed to rt and stirred for 4 h. The reaction was quenched by adding sat'd NH$_4$Cl solution at 78° C., extracted with EtOAc, dried over MgSO$_4$, filtered, concentrated under reduced pressure. The residue was purified by column chromatography (n-hexane:EtOAc: DCM=20:1:2) to give a white solid (100%).

<Step-2>

The procedure I-53 was followed by procedure of General procedure 21 (Step-2) (51%, colorless oil).

<Step-3>

The procedure I-54 was followed by procedure of General procedure 1 (Step-5) (68%, ivory solid).

<Step-4>

The procedure TU-DD was followed by procedure of General procedure 2 (51%).

<General Procedure 1-b>

<Step-1>

The procedure I-55 was followed by procedure of General procedure 1 (Step-1) (167 mg, 21%).

<Step-2>

The procedure I-56 was followed by procedure of General procedure 1 (Step-2) (131 mg, 63%).

<Step-3>

The procedure I-57 was followed by procedure of General procedure 1 (Step-3) (90 mg, 68%).

<Step-4>

The procedure TU-EE was followed by procedure of General procedure 1 (Step-5) (8 mg, 34%).

<General Procedure 1-c>

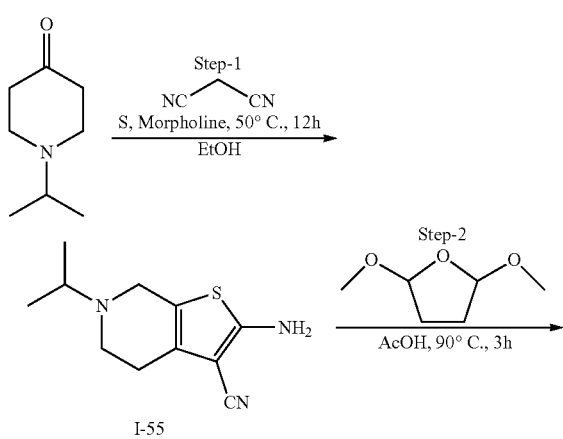

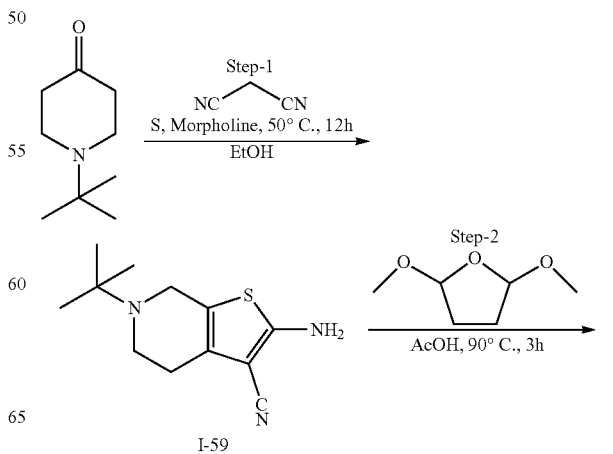

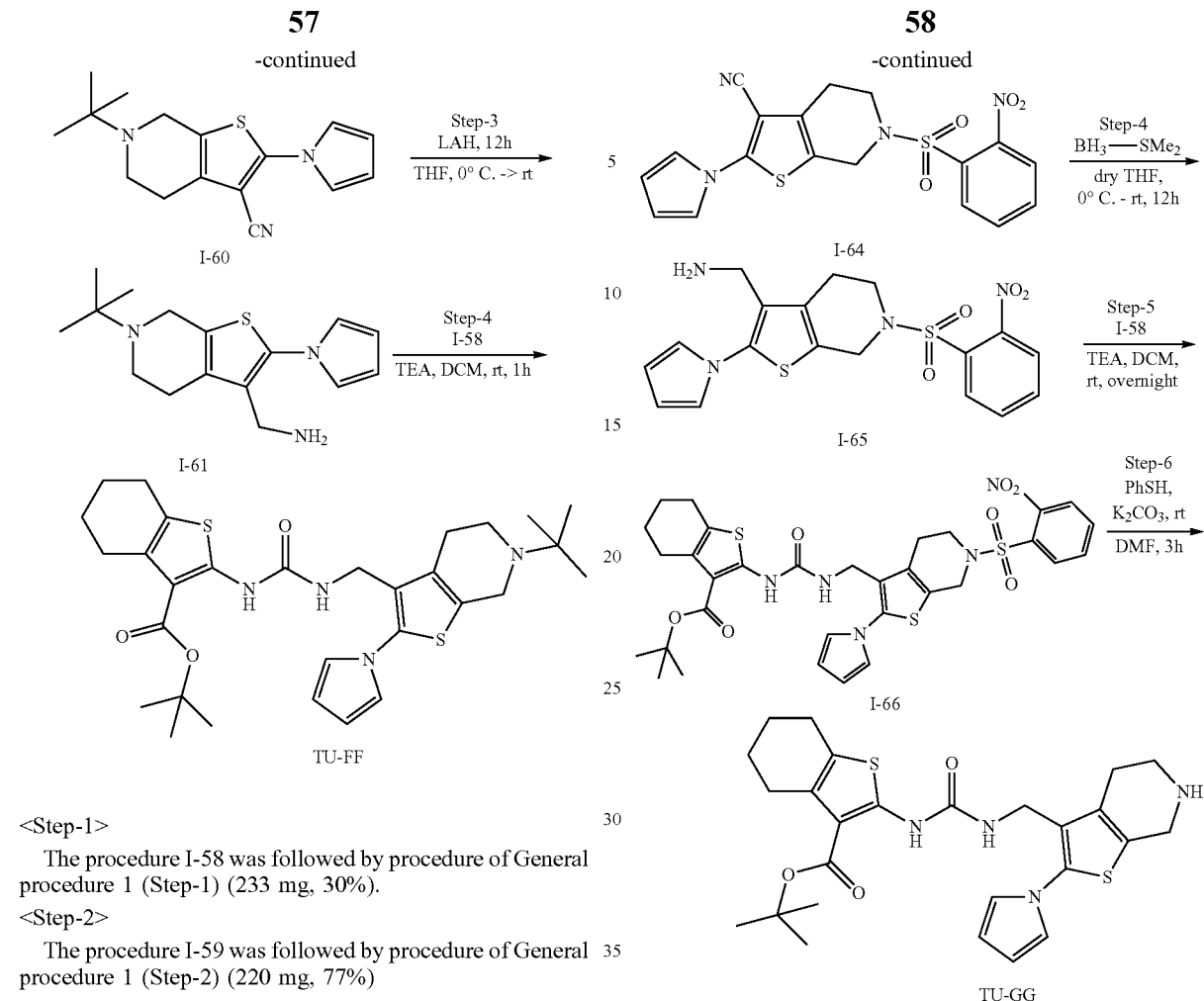

<Step-1>

The procedure I-58 was followed by procedure of General procedure 1 (Step-1) (233 mg, 30%).

<Step-2>

The procedure I-59 was followed by procedure of General procedure 1 (Step-2) (220 mg, 77%)

<Step-3>

The procedure I-60 was followed by procedure of General procedure 1 (Step-3) (151 mg, 68%).

<Step-4>

The procedure TU-FF was followed by procedure of General procedure 1 (Step-5) (8 mg, 34%).

<General Procedure 28>

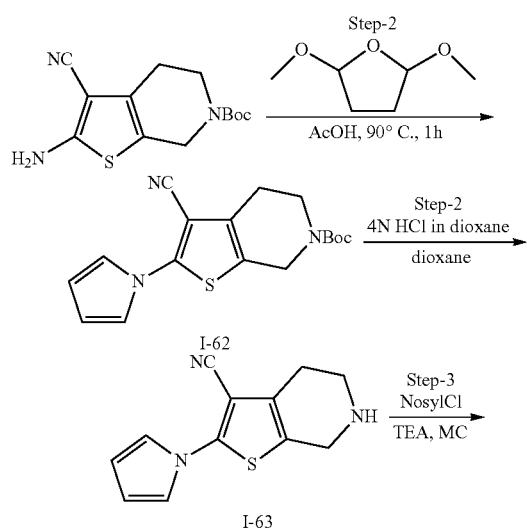

<Step-1>

The procedure I-62 was followed by procedure of General procedure 1 (Step-2) (1 g, 85%).

<Step-2>

The procedure I-63 was followed by procedure of General procedure 2 (383 mg, 100%).

<Step-3>

To a stirred solution of I-63 (330 mg, 1.44 mmol), triethylamine (160 mg, 1.58 mmol) in CH$_2$Cl$_2$ (14 mL) was added 2-nitrobenzenesulfonyl chloride (25 mg, 0.12 mmol) at 0° C. The reaction mixture was stirred at room temperature for 2 h. After reaction was completed, the reaction mixture was diluted with CH$_2$Cl$_2$ and washed with brine. The organic layer was dried over anhydrous MgSO$_4$ and concentrated in vacuo. The crude product was purified by flash column chromatography to give I-64. (380 mg, 67%).

<Step-4>

The procedure I-65 was followed by procedure of General procedure 21 (Step-2) (260 mg, 67%).

<Step-5>

The procedure I-66 was followed by procedure of General procedure 1 (Step-5) (115 mg, 94%).

<Step-6>

To a stirred solution of I-66 (40 mg, 0.03 mmol), K$_2$CO$_3$ (14 mg, 0.1 mmol) in DMF (1 mL) was added benzenethiol (4 mg, 0.04 mmol). The reaction mixture was stirred at room temperature for 3 h. After reaction was completed, the reaction mixture was diluted with CH$_2$Cl$_2$ and washed with brine. The organic layer was dried over anhydrous MgSO₄ and concentrated in vacuo. The crude product was purified by flash column chromatography to give TU-GG (14 mg, 80%).

<General Procedure 29>

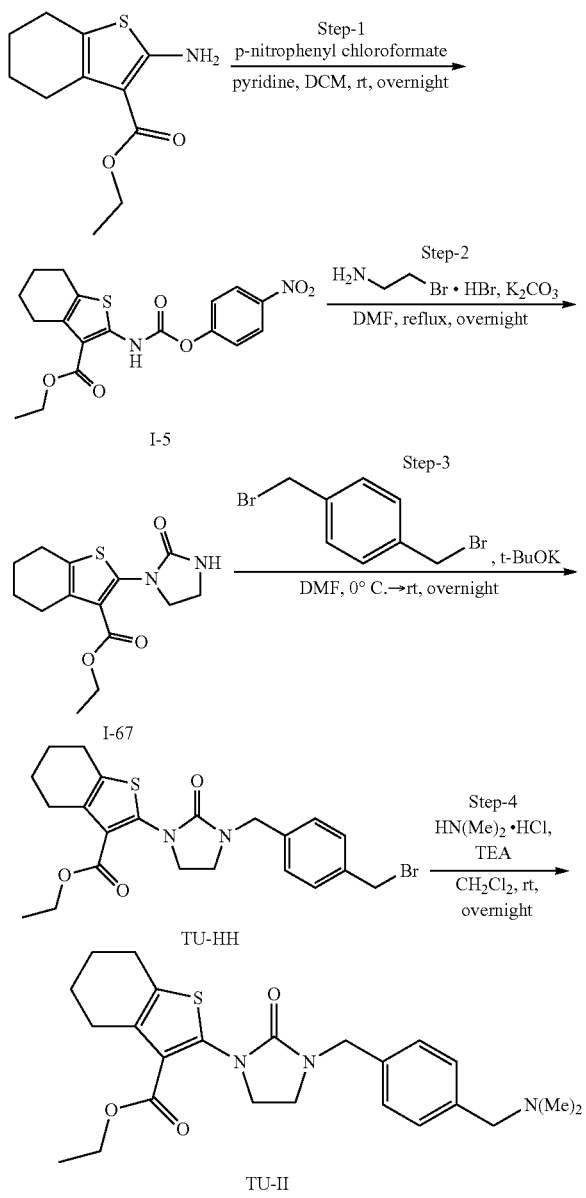

<Step-1>

A mixture of pyridine (0.70 g, 8.877 mmol) and ethyl 2-amino-4,5,6,7-tetrahydrobenzo[b]thiophene-3-carboxylate (1.00 g, 4.438 mmol) in 50 mL of dry CH₂Cl₂ was stirred at room temperature for 30 min. To the reaction mixture, a solution of p-nitrophenyl chloroformate (1.34 g, 6.657 mmol), in 5 mL of dry CH₂Cl₂, was added drop wise over a period of 15 min. The reaction was stirred at room temperature for 12 h and then evaporated in vacuo to yield the crude product which was purified by column chromatography (silica gel, gradient 0-15 percent, ethyl acetate in hexane) to afford I-5 (1.25 g, yield=72%) as a pale-yellow solid.

<Step-2>

A solution of 2-bromoethan-1-amine hydrobromide (0.06 g, 0.282 mmol) in dry DMF (3 mL) was treated sequentially with I-5 (0.1 g, 0.256 mmol) and potassium carbonate (0.11 g, 0.768 mmol). The mixture was refluxed overnight and evaporated in vacuo to yield the crude product which was purified by column chromatography (silica gel, gradient 0-50 percent, ethyl acetate in hexane) to afford I-67 (0.05 g, 59%) as a pale-yellow oil.

<Step-3>

To a stirred solution of I-67 (0.04 g, 0.136 mmol) and 1,4-bis(bromomethyl)benzene (0.05 g, 0.204 mmol) in DMF (3 mL) was added potassium tert-butoxide (0.02 g, 0.163 mmol) at 0° C. under nitrogen atmosphere. After being stirred for 12 h at room temperature, the reaction was quenched with saturated aqueous NH₄Cl. The reaction mixture was extracted with EtOAc (50 mL×3). The combined organic layers were washed with H₂O (25 mL×2), brine, dried over MgSO₄ and evaporated. The resulting residue was purified by column chromatography (silica gel, gradient 0-30 percent, ethyl acetate in hexane) to afford TU-HH (0.02 g, 23%) as a pale-yellow oil.

<Step-4>

To a solution of the compound (0.02 g, 0.031 mmol) obtained in step TU-HH, and triethylamine (0.02 mL, 0.157 mmol) in dry CH₂Cl₂ (2 mL) was added dimethylamine hydrochloride (0.015 g, 0.188 mmol) and the resulting mixture was stirred overnight at room temperature. The mixture was washed with H₂O (25 mL×2), brine, dried over MgSO₄ and filtered, and then concentrated. The resulting residue was purified by column chromatography (silica gel, gradient 0-7 percent, methanol in methylene chloride) to afford TU-II (0.01 g, 43%) as a pale-yellow oil.

<General Procedure 30>

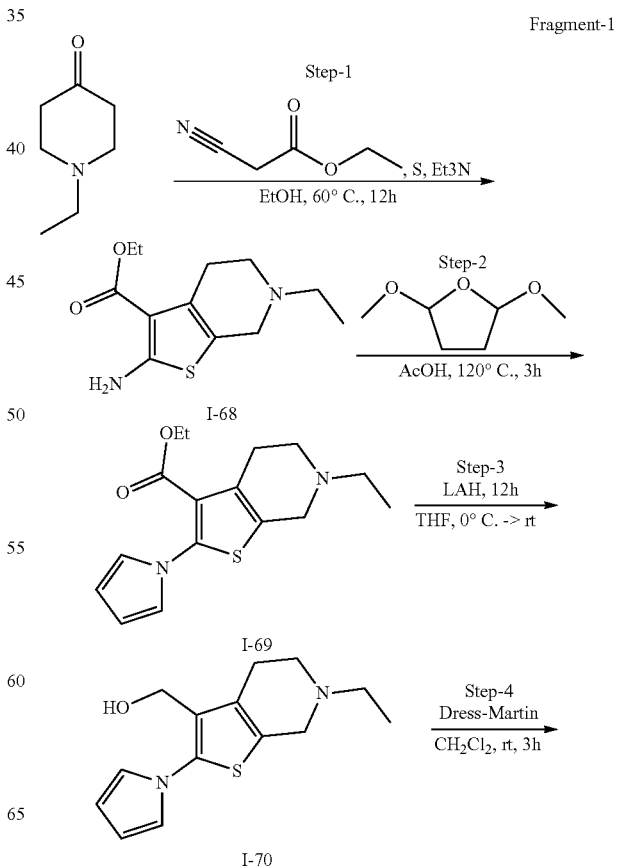

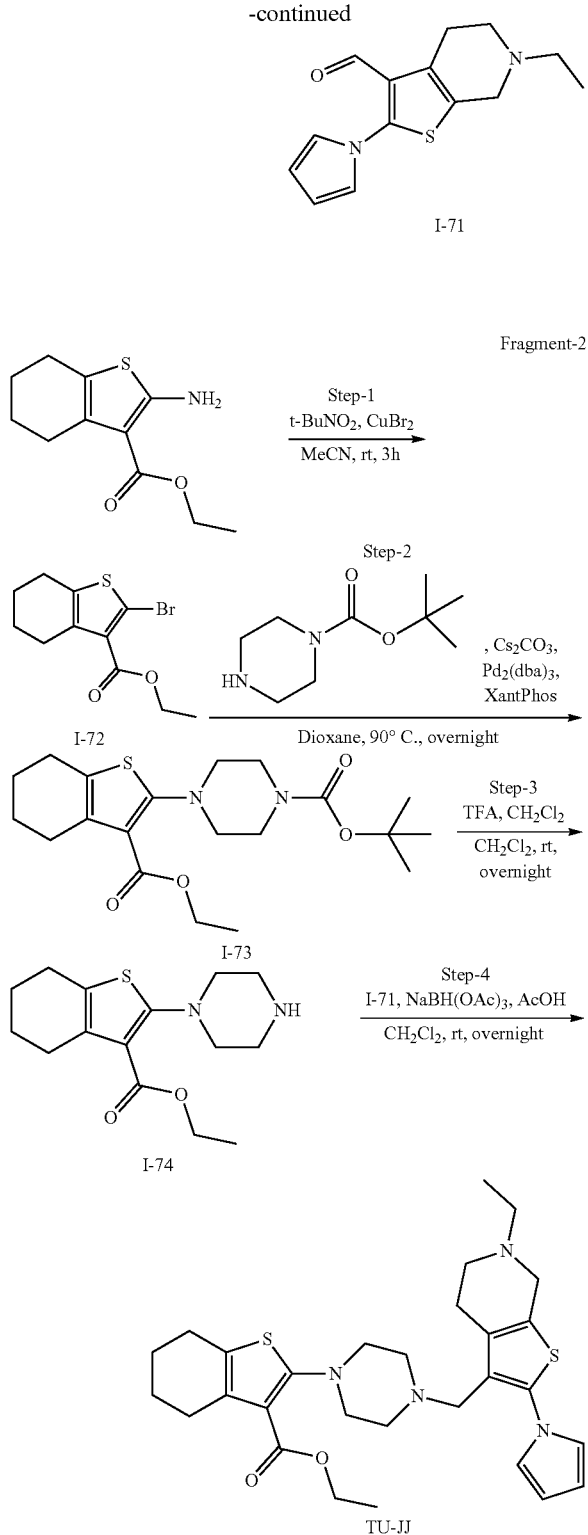

solvent was removed under vacuum. The reaction mixture was diluted with water and the precipitate was collected by filtration and recrystallized from ethanol to afford I-68 (2.10 g, 45%) as a yellow solid <Step-2>

A solution of I-68 (1.7 g, 6.684 mmol) and 2,5-dimethoxytetrahydrofuran (1.06 g, 8.021 mmol) in acetic acid (15 mL) was heated under reflux for 4 h. After completion of reaction, the mixture was cooled to room temperature and iced-water (30 mL) was added. And the crude mixture was extracted with $CH_2Cl_2$ (50 mL×3) and the combined organic layers were washed with $H_2O$ (25 mL×2)), brine, dried over $MgSO_4$, and dried in vacuo to afford I-69 (1.80 g, 88%) as a brown oil.

<Step-3>

To a suspension of lithium aluminum hydride (0.25 g, 6.568 mmol) in THF (10 mL) was added dropwise a solution of I-69 (0.5 g, 1.643 mmol) in THF (5 mL) at 0° C. The reaction mixture was stirred at the same temperature for 1 h, the temperature was gradually raised to room temperature and the mixture was further stirred for 12 h. Water and 15 percent aqueous sodium hydroxide solution were added, and anhydrous $MgSO_4$ was added to the mixture. The mixture was filtered, and the filtrate was concentrated under reduced pressure. The residue was subjected to column chromatography (silica gel, gradient 0-7 percent, methanol in methylene chloride) to afford I-70 (0.29 g, 68%) as a pale-yellow oil.

<Step-4>

Solid Dess-Martin periodinane (0.63 g, 1.482 mmol) was added to a solution of alcohol, I-70 (0.30 g, 1.12 mmol) dissolved in $CH_2Cl_2$ (6 mL). After stirring for 20 min, the mixture was quenched with 20 mL of saturated aqueous $NaHCO_3$ solution and this mixture was then stirred for approximately 15 min. The mixture was extracted with EtOAc (2×50 mL) and the organic layers were dried over $Na_2SO_4$ and concentrated to afford I-71 (0.27 g, 92%) as a pale-yellow oil.

Fragment-2

<Step-1>

Under ice-cooling, to a suspension of $CuBr_2$ (1.19 g, 5.326 mmol) in MeCN (40 mL) was added tert-butyl nitrate (0.69 g, 6.657 mmol). And ethyl 2-amino-4,5,6,7-tetrahydrobenzo[b]thiophene-3-carboxylate (1.0 g, 4.438 mmol) was added portion wise thereto, followed by stirring under ice-cooling for 2 h and then at room temperature for 3 h. To the reaction mixture was poured 50 mL of 10 percent aqueous HCl solution, and the aqueous layer was extracted with EtOAc (2×50 mL). The organic layer was washed with water and brine in this order, dried over $MgSO_4$, and concentrated under reduced pressure. The residue was purified by column chromatography (silica gel, gradient 0-25 percent, ethyl acetate in hexane) to afford I-72 (1.05 g, 81%) as a brown oil.

<Step-2>

To a mixture of I-72 (0.2 g, 1.074 mmol), tert-butyl piperazine-1-carboxylate (0.34 g, 1.181 mmol), $Cs_2CO_3$ (0.53 g, 1.611 mmol) and 9,9-dimethyl-4,5-bis(diphenylphosphino)xanthene (XANTPHOS; 0.05 g, 0.086 mmol) in 1,4-dioxane (2 mL) was added tris(dibenzylideneacetone)dipalladium (0) ($Pd_2(dba)_3$; 0.04 g, 0.043 mmol) and heated at 90° C. overnight. The reaction mixture was cooled to room temperature, treated with 1M HCl (20 mL) and extracted with EtOAc (3×30 mL). The crude product was purified by column chromatography (silica gel, gradient 0-10 percent, ethyl acetate in hexane) to afford I-73 (0.13 g, 30%) as a yellow oil.

Fragment-1

<Step-1>

A mixture of cyclohexanone (2.0 g, 20.379 mmol) and ethyl 2-cyanoacetate (1.31 g, 20.379 mmol), triethylamine (2.84 mL, 20.379 mmol) and sulfur (0.65 g, 20.379 mmol) in EtOH (20 mL) was refluxed for 12 h. After completion of reaction, the mixture was cooled to room temperature, the <Step-3>

To a solution of I-73 (0.13 g, 0.322 mmol) in CH$_2$Cl$_2$ (5 mL) was added trifluoroacetic acid (0.5 mL). The mixture was stirred at room temperature overnight. The solvent was evaporated under vacuum and the residue was dissolved in chloroform. The organic phase was washed by saturated solution of NaHCO$_3$, dried over Na$_2$SO$_4$ and evaporated to afford I-74 (0.09 g, 97%) as a brown oil.

<Step-4>

To a solution of I-74 (0.09 g, 0.312 mmol) in DCM (3 mL) was added I-71 (0.08 g, 0.312 mmol). After 45 min, sodium triacetoxyborohydride (0.09 g, 0.468 mmol) was added and the reaction mixture was stirred at room temperature for 18 h. More sodium triacetoxyborohydride (0.09 g, 0.468 mmol) was added and the mixture was stirred for an additional 2 h. The reaction mixture was quenched with saturated aqueous NaHCO$_3$ and the phases were separated. Organic phase was collected and the aqueous layer was extracted with CH$_2$Cl$_2$ (3×50 mL). The combined organic layers were concentrated and the residue was purified by column chromatography (silica gel, gradient 0-10 percent, methanol in methylene chloride) to afford TU-JJ (0.07 g, 41%) as a yellow oil.

<General Procedure 31>

<Step-2>

Tert-butyl 4-(pyridin-3-ylmethyl)piperazine-1-carboxylate I-75 (200 mg, 0.72 mmol) was dissolved in a 4N HCl solution in dioxane (3 mL). The resulting solution was stirred for 4 hours at room temperature. Dioxane was removed under reduced pressure to provide a salt of I-76 as a white solid (110 mg, 85%).

<Step-3>

A solution of I-76 (20 mg, 0.11 mmol) in dichloromethane (1 ml) was treated with carbamate (44 mg, 0.11 mmol) and triethylamine (0.03 ml, 0.23 mmol). When the reaction was complete, the mixture was diluted in additional dichloromethane and washed with excess water and brine, then dried over MgSO$_4$. Concentrated residue was purified by column chromatography (n-hexane:EtOAc=3:1) to give TU-KK.

<General Procedure 32>

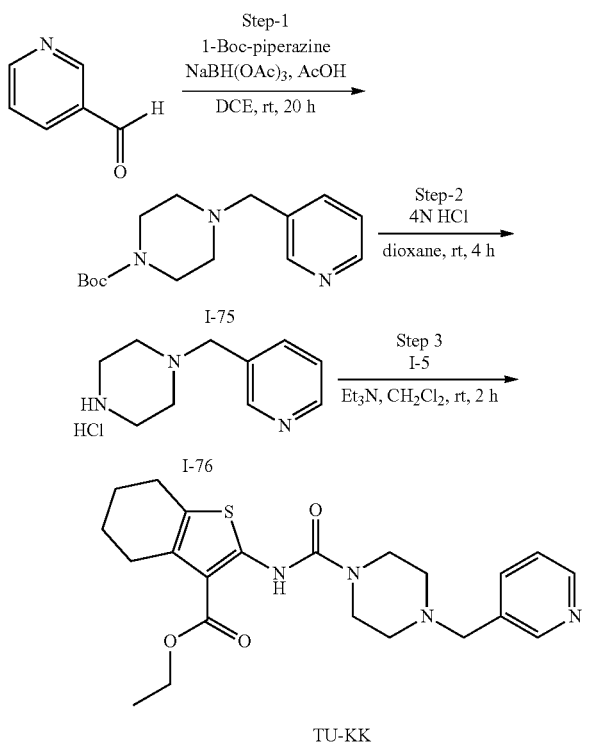

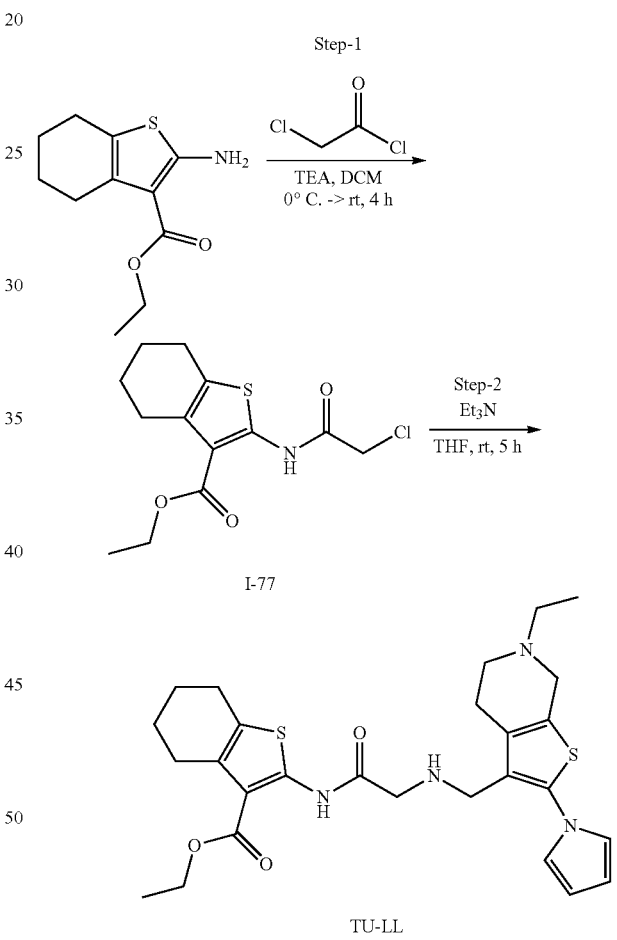

<Step-1>

To a mixture of nicotinaldehyde (500 mg, 4.67 mmol) in dichloromethane (10 mL) was added 1-Boc-piperazine (1.00 g, 5.60 mmol) under N$_2$. The mixture was stirred at room temperature for 1 h. Sodium triacetoxyborohydride (2.00 g, 9.34 mmol) were added. The reaction mixture was stirred at room temperature under N$_2$ for 20 h. The reaction was quenched with water and then partitioned between dichloromethane and water. The organic extract was washed with brine, dried over magnesium sulfate and evaporated. The residue was purified by silica column chromatography, eluting with a gradient of 50 percent EtOAc in Hexane to give I-75 as a pale yellow solid (800 mg, 61%).

<Step-1>

To a stirred solution of ethyl 2-amino-4,5,6,7-tetrahydrobenzo[b]thiophene-3-carboxylate (100 mg, 0.444 mmol), TEA (0.12 ml, 0.888 mmol) in DCM (3 ml) was added chloracetyl chloride (0.04 ml, 0.488 mmol) at 0° C. The reaction mixture was stirred at room temperature for 4 h. After reaction was completed, the reaction mixture was diluted with DCM and washed with brine. The organic layer was dried over anhydrous MgSO$_4$ and concentrated in vacuo. The crude product was purified by flash column chromatography to give I-77. (120 mg, 89%).

Step-2

To a stirred solution of I-77 (50 mg, 0.166 mmol), TEA (0.02 ml, 0.166 mmol) in THF (3 ml) was added amine (65 mg, 0.249 mmol). The reaction mixture was stirred at room temperature for 4 h. After reaction was completed, the reaction mixture was diluted with DCM and washed with brine. The organic layer was dried over anhydrous MgSO$_4$ and concentrated in vacuo. The crude product was purified by flash column chromatography to give TU-LL.

General Procedure 33

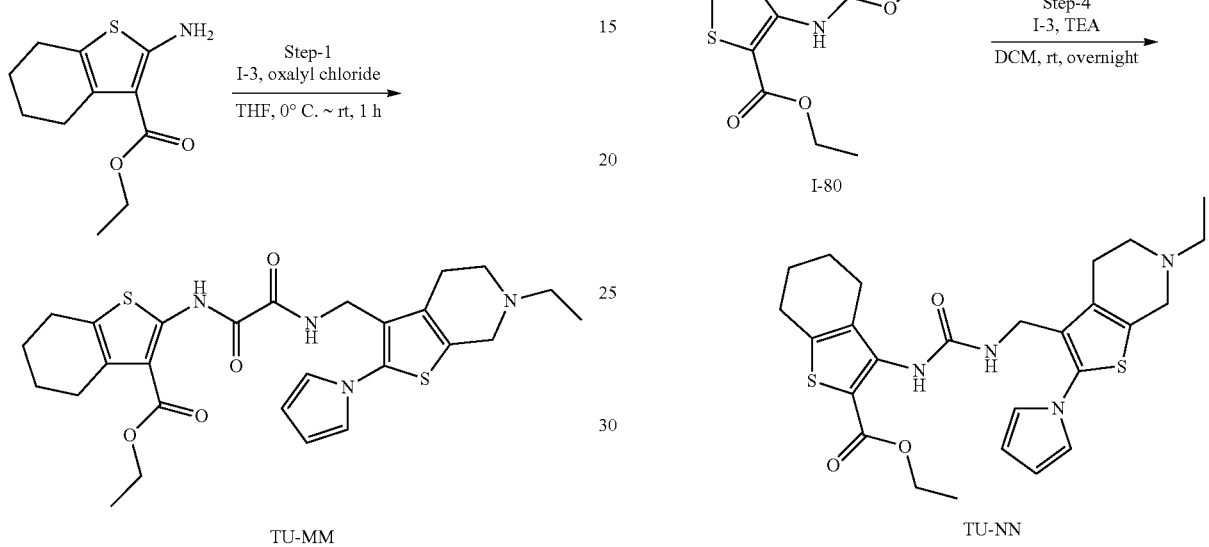

Step-1

To a solution of oxalyl dichloride (37 ul, 0.443 mmol) in THF was added ethyl 2-amino-4,5,6,7-tetrahydrobenzo[b]thiophene-3-carboxylate (100 mg, 0.443 mmol) and sequentially I-3 (116 mg, 0.443 mmol). The reaction was stirred at room temperature for 1 h. The solvents were removed under reduced pressure and MC was added. The MC extracts were washed with brine and dried over sodium sulfate. The mixture was filtered and purified by silica gel column chromatography (n-hexane:EtOAc=1:1) to give TU-MM (65 mg, 0.120 mmol, 27%) as a solid.

General Procedure 34

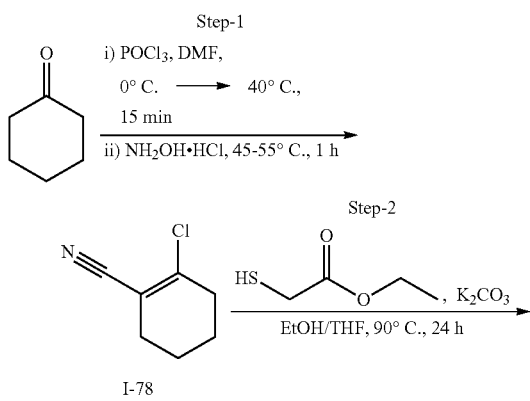

Step-1

Phosphorus oxychloride (1.53 mL, 16.410 mmol) was cooled in an ice-bath and DMF (1.33 mL, 17.204 mmol) was added over a period of 20 min (a sticky white solid was formed). Cyclohexanone (1.06 mL, 10.190 mmol) was added over 15 min (the sticky solid turned into a bright yellow solution). The mixture was heated at 50° C. and hydroxylamine hydrochloride (3.97 g, 57.170 mmol) was added in 5 portions at 5 min intervals maintaining the temperature between 45 and 55° C. via cooling if needed. The reaction mixture was poured into ice-water (100 mL) and the aqueous mixture was stirred for 1 h. The brown solid was filtered, washed with water and dried under reduced pressure to afford I-78 (0.77 g, 53%) as a brown solid.

Step-2

A solution of I-78 (0.77 g, 5.438 mmol) in EtOH/THF (6 mL/1 mL) was treated sequentially with ethyl 2-mercaptoacetate (0.98 g, 8.286 mmol) and potassium carbonate (0.80 g, 5.770 mmol). The mixture was heated at 90° C. for 24 h and evaporated in vacuo to yield the crude product which was purified by column chromatography (silica gel, gradient 0-15 percent, ethyl acetate in hexane) to afford I-79 (0.53 g, 43%) as a pale-yellow oil.

Step-3

A solution of I-79 (0.1 g, 0.432 mmol) in acetone (20 mL) was stirred, and trichloromethyl carbonochloridate (0.05 mL, 0.432 mmol) in 5 mL of acetone was added dropwise and then the mixture was stirred overnight at room temperature. Upon completion of reaction, the mixture was concentrated under reduced pressure and the product was used immediately in the next reaction without further purification (0.09 g, 53%, pale-yellow oil).

<Step-4>

A mixture of I-3 (0.04 g, 0.155 mmol) and triethylamine (0.03 mL, 0.194 mmol) in 5 mL of dry CH$_2$Cl$_2$ was stirred at room temperature for 30 min. To the reaction mixture, a solution of I-80 (0.05 g, 0.129 mmol) in 5 mL of dry CH$_2$Cl$_2$, was added dropwise over a period of 15 min. The mixture was stirred at room temperature for 12 h and then evaporated in vacuo to yield the crude product which was purified by column chromatography (silica gel, gradient 0-10 percent, methanol in methylene chloride) to afford TU-NN (0.05 g, 72%) as a pale-yellow solid.

<General Procedure 35>

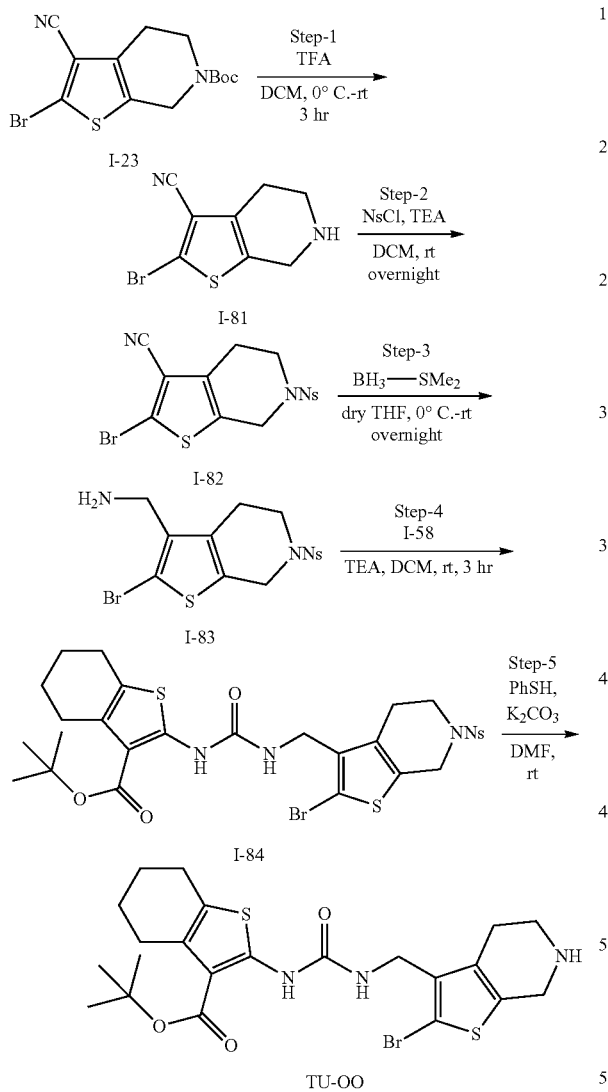

<Step-1>

To a solution of I-23 (343 mg, 1.0 mmol) in dichloromethane (10 ml) was added trifluoroacetic acid (3 ml) at 0° C. Reaction mixture was stirred for 3 hr at room temperature.

<Step-2>

To a solution of I-81 (240 mg, 1.0 mmol) in dichloromethane (5 ml) was added triethylamine (0.15 ml, 1.1 mmol) and o-Nitrobenzenesulfonyl chloride (222 mg, 1.0 mmol) at 0° C. After reaction completion, the mixture was washed with saturated NaHCO$_3$ solution, dried over MgSO$_4$ and concentrated under reduced pressure. Resulted yellow solid was dissolved in dichloromethane, filtered and washed with excess hexanes to obtain I-82 as an ivory solid (86%).

<Step-3>

To a solution of I-82 (120 mg, 0.28 mmol) was dissolved in anhydrous THF (2.8 ml) under a nitrogen atmosphere and added borane-dimethylsulfide complex (0.14 ml, 1.4 mmol) at 0° C. Reaction mixture was stirred overnight and quenched by adding MeOH and 2N HCl solution (2 ml) successively. After 10 min, the acidic media was neutralized with 2N NaOH (2 ml) and diluted in dichloromethane. Organic phase was washed with saturated NaHCO$_3$ solution twice and then brine. Combined organic phases were dried over MgSO$_4$, concentrated under reduced pressure and purified by column chromatography (DCM:MeOH=50:1-20:1) to give I-83 as an ivory solid (37%).

<Step-4>

The procedure I-84 was followed by procedure of General procedure 1 (Step-5) (ivory solid, 61%).

<Step-5>

I-84 (43 mg, 0.06 mmol) was dissolved in anhydrous DMF (1.2 ml) under a nitrogen atmosphere and treated with potassium carbonate (25 mg, 0.18 mmol) and thiophenol (7.4 ul, 0.07 mmol) successively. The reaction mixture was stirred for 3 hr and DMF was removed under reduced pressure. The crude residue was dissolved in dichloromethane, filtered and washed with acetone to obtain TU-OO (31%).

<General Procedure 36>

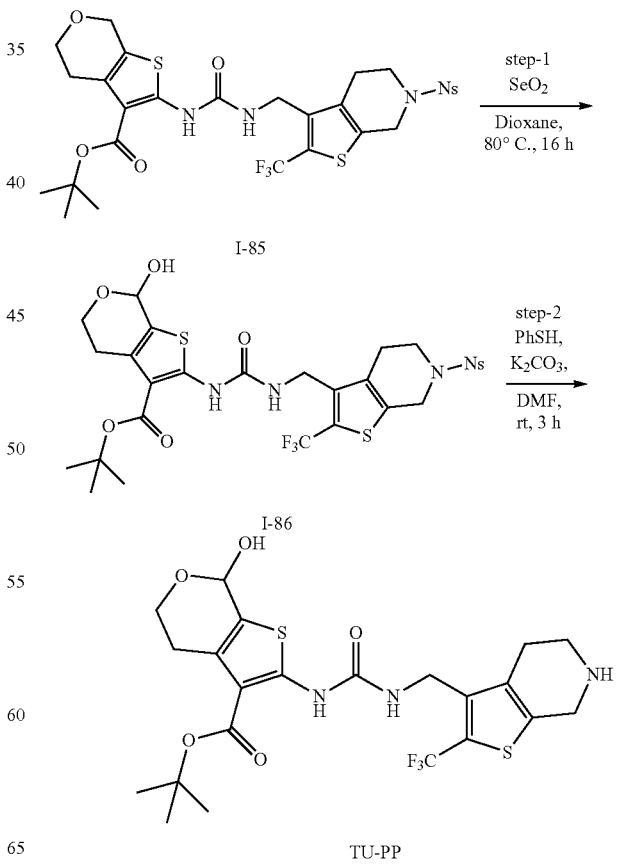

<Step-1>

To a stirred solution of 4-(3-((3-(3-(tert-butoxycarbonyl)-4,7-dihydro-5H-thieno[2,3-c]pyran-2-yl)ureido)methyl)-2-(trifluoromethyl)-4,7-dihydrothieno[2,3-c]pyridin-6(5H)-yl)-3-nitrobenzenesulfonic acid (100 mg, 0.140 mmol) in dioxane was added SeO$_2$ (31 mg, 0.280 mmol). The reaction mixture was stirred at 80° C. for 16 h. After reaction was completed, the reaction mixture was cooled to rt. SeO$_2$ was filtered, then dioxane was evaporated under reduced pressure. The mixture was diluted with DCM, then washed with H2O and brine. The organic layer was dried over MgSO$_4$. The organic layer was concentrated in vacuo and purified by column chromatography to give I-86 as white solid. (51%)

<Step-2>

To a stirred solution of 4-(3-((3-(3-(tert-butoxycarbonyl)-7-hydroxy-4,7-dihydro-5H-thieno[2,3-c]pyran-2-yl)ureido)methyl)-2-(trifluoromethyl)-4,7-dihydrothieno[2,3-c]pyridin-6(5H)-yl)-3-nitrobenzenesulfonic acid (60 mg, 0.083 mmol) in DMF were added K$_2$CO$_3$ (35 mg, 0.250 mmol) and benzenethiol (17 μl 0.167 mmol). The reaction mixture was stirred at rt for 3 h. After reaction was completed, the reaction mixture was diluted with DCM and washed with H2O and brine. The organic layer was dried over MgSO$_4$. The organic layer was concentrated in vacuo, then purified by column chromatography to give TU-PP as white solid. (34%)

<General Procedure 37>

<Step-1>

To a stirred solution of 4-(3-((3-(3-(tert-butoxycarbonyl)-7-hydroxy-4,7-dihydro-5H-thieno[2,3-c]pyran-2-yl)ureido)methyl)-2-(trifluoromethyl)-4,7-dihydrothieno[2,3-c]pyridin-6(5H)-yl)-3-nitrobenzenesulfonic acid (100 mg, 0.139 mmol) in DCM was added slowly Deoxo-fluor (28 μl mg, 0.153 mmol). The reaction mixture was stirred at rt for 1 h. After reaction was completed, the reaction mixture was diluted with DCM, then washed with H2O and brine. The organic layer was dried over MgSO$_4$. The organic layer was concentrated in vacuo, then purified by column chromatography to give I-87 as white solid. (89%)

<Step-2>

To a stirred solution of I-87 (88 mg, 0.122 mmol) in DMF were added K$_2$CO$_3$ (51 mg, 0.366 mmol) and benzenethiol (25 μl 0.244 mmol). The reaction mixture was stirred at rt for 3 h. After reaction was completed, the reaction mixture was diluted with DCM and washed with H$_2$O and brine. The organic layer was dried over MgSO$_4$. The organic layer was concentrated in vacuo, then purified by column chromatography to give TU-QQ as white solid. (43%)

<General Procedure 38>

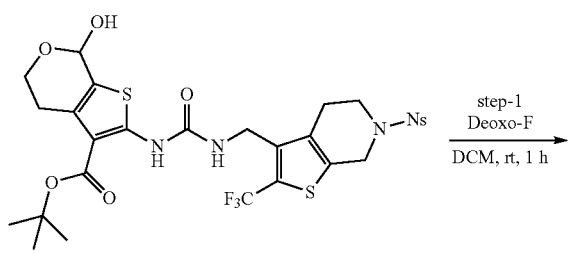

I-86

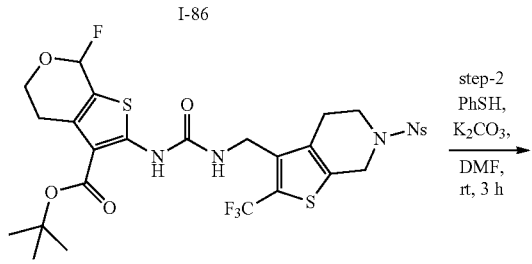

I-87

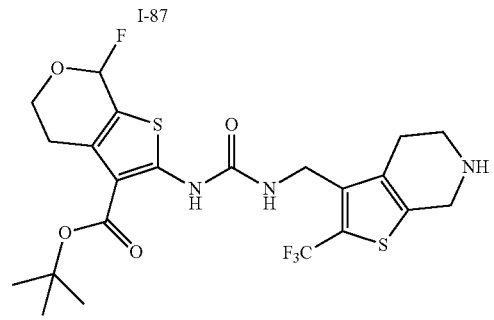

TU-QQ

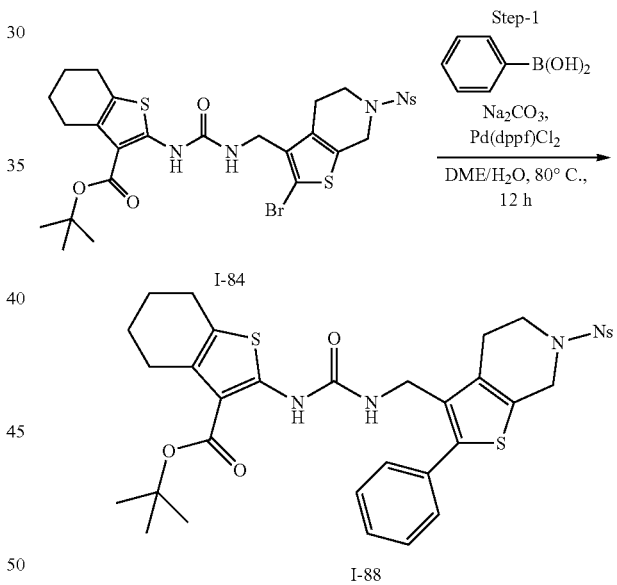

<Step-1> tert-butyl 2-(3-((2-bromo-6-((2-nitrophenyl)sulfonyl)-4,5,6,7-tetrahydrothieno[2,3-c]pyridin-3-yl)methyl)ureido)-4,5,6,7-tetrahydrobenzo[b]thiophene-3-carboxylate I-84 (0.07 g, 0.1 mmol), phenylboronic acid (0.023 g, 0.2 mmol), Pd(dppf)Cl$_2$ (0.0043 g, 0.006 mmol), Na$_2$CO$_3$ (0.02 g, 0.2 mmol), DME/H$_2$O (3 mL) were combined in a 50 ml of round bottom flask and the mixture was heated at 80° C. for 12 h. After the reaction was complete, excess CH$_2$Cl$_2$ was poured and washed with water twice. Organic phase was dried over MgSO$_4$, filtered and concentrated under reduced pressure. Crude residue was purified by column chromatography (n-hexane:EtOAc=4:1) to give I-88 as a yellow solid (0.056 g, 80%).

<General Procedure 39>

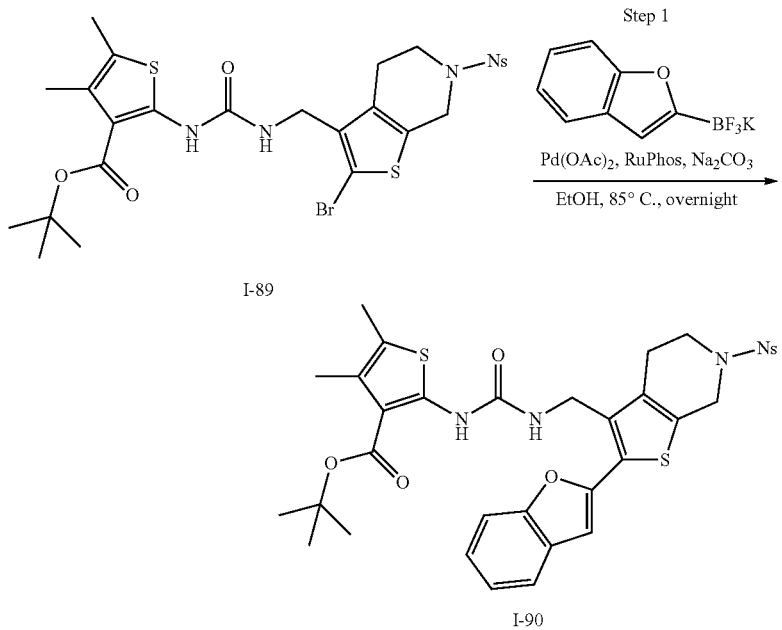

<Step-1>

I-89 (0.4 g, 0.58 mmol), Potassium benzofuran-2-trifluoroborate (0.26 g, 1.17 mmol), Pd(OAC)$_2$ (0.0079 g, 0.035 mmol), RuPhos (0.033 g, 0.12 mmol), Na$_2$CO$_3$ (0.123 g, 1.17 mmol), EtOH (6 mL) were combined in a 50 ml of round bottom flask and the mixture was heated at 85° C. for 12 h. After the reaction was completed, excess CH$_2$Cl$_2$ was poured and washed with water twice. Organic phase was dried over MgSO$_4$, filtered and concentrated under reduced pressure. Crude residue was purified by column chromatography (n-hexane:EtOAc=4:1) to give I-90 as a yellow solid (0.147 g, 34%).

<General Procedure 40>

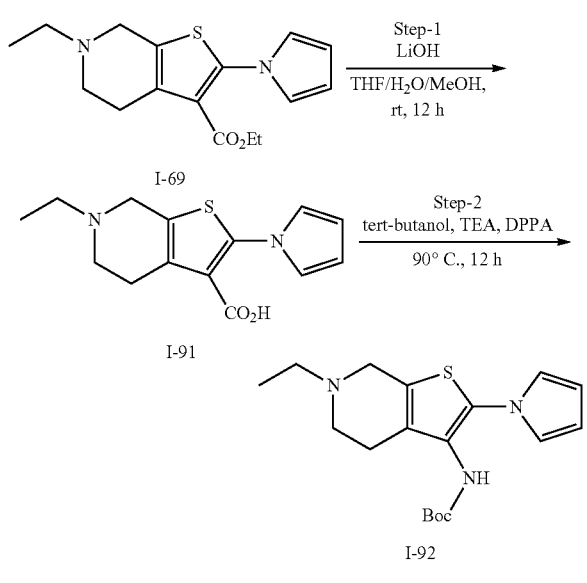

<Step-1>

To a stirred solution of I-69 (0.6 g, 1.97 mmol) in THF (9 mL) and MeOH (4 mL) and H$_2$O (2 ml) was added lithium hydroxide (236 mg, 9.86 mmol). The reaction mixture was stirred at room temperature for overnight. After reaction was completed, the mixture was evaporated and 1 N HCl (10.0 ml) was added until pH 7. The residual pale solid was collected by filtration and washed with H$_2$O to give I-91 (460 mg, yield=84%).

<Step-2>

To a solution of I-91 (340 mg, 1.23 mmol) in tert-butanol (10 ml) was added triethylamine (136 mg, 1.35 mmol) and diphenylphosphorylazide (406 mg, 1.48 mmol). The reaction was held at reflux for 12 h, cooled and the solvent removed under reduced pressure. The residue was dissolved in 100 ml ethyl acetate and washed with water, brine, dried (MgSO$_4$) and concentrated. The crude product was purified by flash column chromatography to give I-92. (62 mg, yield=14%)

The compounds according to Formula II are prepared using conventional organic syntheses. Suitable synthetic routes are depicted below in the following general reaction schemes.

Synthesis of Formula (II) Inventive Compounds.

General Procedure D-1

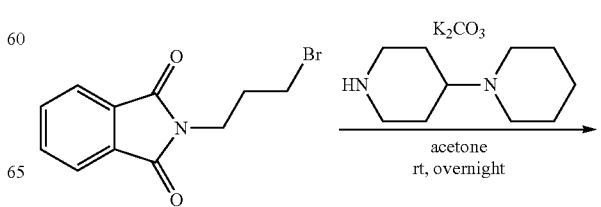

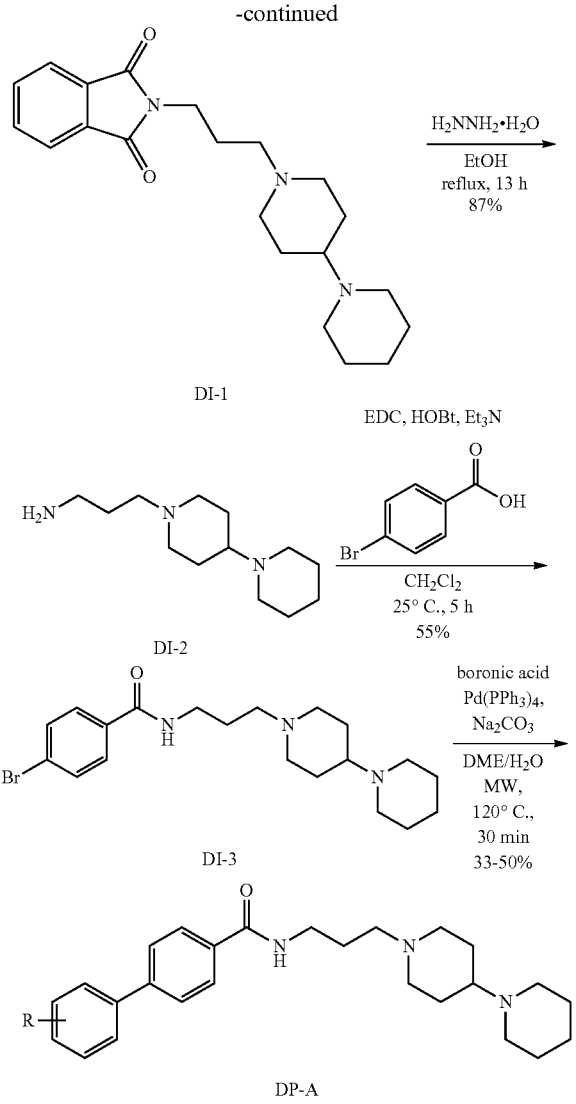

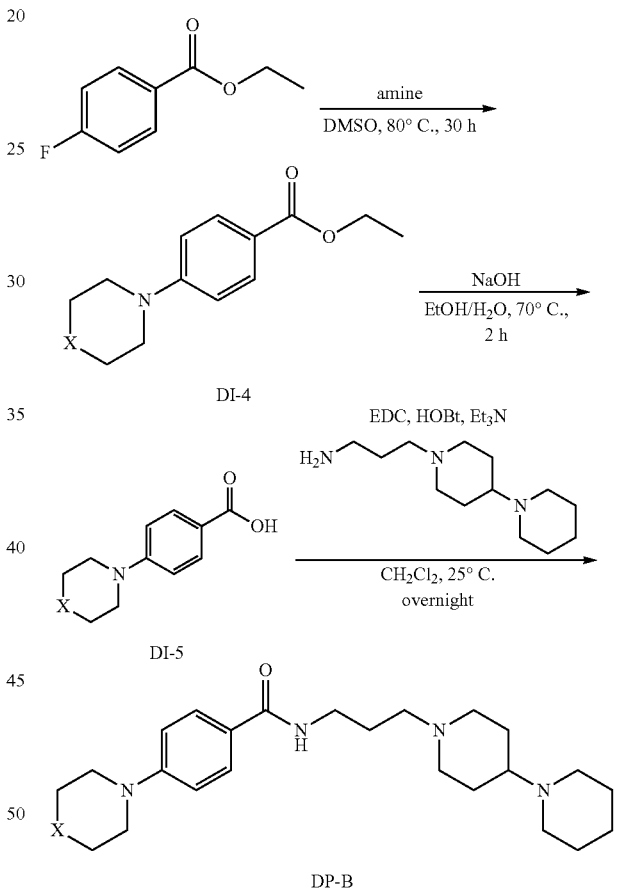

(1.1 g, 5.96 mmol), Et₃N (1.4 mL, 9.94 mmol) and HOBt (0.8 g, 5.96 mmol). After stirring at room temperature for 5 h, the mixture was partitioned between CH₂Cl₂ (10 mL) and water (10 mL). The organic layer was collected and concentrated in vacuo. Purification by column chromatography (30% MeOH in CH₂Cl₂) to give DI-3 (1.1 g, 55%) as an ivory solid.

Step 4) the Synthesis of DP-A

DI-3 (0.03 g, 0.073 mmol), boronic acid (0.088 mmol), Pd(PPh₃)₄ (0.002 g, 0.002 mmol), Na₂CO₃ (0.015 g, 0.146 mmol), DME/H₂O (2 mL) were combined in a 10 mL microwave tube and the mixture was subject to microwave irradiation at 120° C. for 30 min. The reaction mixture was then filtered and concentrated. The residue was purified by column chromatography (50% MeOH in CH₂Cl₂) to give DP-A (33-50%) as a white solid.

General Procedure D-2

Step 1) the Synthesis of DI-1

A mixture of piperidinopiperidine (2.5 g, 14.92 mmol), N-(3-bromopropyl)phthalimide (2.0 g, 7.46 mmol) and K₂CO₃ (1.2 g, 8.95 mmol) in acetone (20 mL) was stirred at room temperature for overnight. The solid was filtered and the filtrate was concentrated to provide DI-1, used without purification.

Step 2) the Synthesis of DI-2

A solution of DI-1 (crude 2 g, 5.63 mmol) and N₂H₄H₂O (0.6 g, 11.26 mmol) in EtOH (50 mL) was stirred at reflux for overnight. The solution was cooled to 5° C. for 2 h, the precipitate filtered, washed with EtOH (5 mL) and the filtrate evaporated to half volume. The solution was cooled 5° C. for a further 2 h, the precipitate filtered, washed with EtOH (5 mL) and the filtrate evaporated. The residue was dissolved in 1M HCl (50 mL), washed with Et₂O (2×50 mL) and the pH of the aqueous fraction adjected to 10 with dilute aqueous NH₃ solution. The mixture was extracted with CH₂Cl₂ (3×50 mL), the combined organic fraction dried and the solvent evaporated to give DI-2 (1.1 g, 87%) as a yellow oil.

Step 3) the Synthesis of DI-3

A solution of 4-bromobenzoic acid (1.0 g, 4.97 mmol) in CH₂Cl₂ (20 mL) was added DI-2 (1.1 g, 4.97 mmol), EDC Step 1) the Synthesis of DI-4

Cycloamine (1.19 mmol) is added to a suspension of 0.1 g (0.59 mmol) of ethyl 4-fluoro-benzoate in 2 mL DMSO. The reaction mixture is stirred overnight at 80° C. for 30 h. After water is added, the mixture is extracted with CH₂Cl₂ (10 mL×3), the organic phase is separated off and the solvent eliminated using the rotary evaporator. Purification by column chromatography (10% EtOAc in Hex) to give DI-4 (35-65%) as a ivory solid.

Step 2) the Synthesis of DI-5

DI-4 and NaOH (10 eq) were added to EtOH/H₂O (10:1) solution. The mixture was heated to reflux for 3 h. The mixture was cooled to room temperature and evaporated.

The mixture was dissolved in water and slowly acidified with 10% aq. HCl and extracted with CH$_2$Cl$_2$. The extract was dried over MgSO$_4$, filtered, and concentrated to afford DI-5 (90-92%) as ivory solid.

Step 3) the Synthesis of DP-B

A solution of 3-([1,4'-bipiperidin]-1'-yl)propan-1-amine (0.02 g, 0.09 mmol) in CH$_2$Cl$_2$ (2 mL) was added DI-5 (0.11 mmol), EDC (0.02 g, 0.11 mmol), Et$_3$N (0.02 mL, 0.18 mmol) and HOBt (0.014 g, 0.11 mmol). After stirring at room temperature for overnight, the mixture was partitioned between CH$_2$Cl$_2$ (10 mL) and water (10 mL). The organic layer was collected and concentrated in vacuo. Purification by column chromatography (30% MeOH in CH$_2$Cl$_2$) to give DP-B (15-22%).

General Procedure D-3 water and slowly acidified with 10% aq. HCl and extracted with CH$_2$Cl$_2$. The extract was dried over MgSO$_4$, filtered, and concentrated to afford DI-7 (0.08 g, 94%) as white solid.

Step 3) the Synthesis of DP-C

A solution of DI-7 (0.05 g, 0.21 mmol), EDC (0.05 g, 0.25 mmol), Et$_3$N (0.06 mL, 0.41 mmol) and HOBt (0.03 g, 0.25 mmol). After stirring at room temperature for 5 h, the mixture was partitioned between CH$_2$Cl$_2$ (10 mL) and water (10 mL). The organic layer was collected and concentrated in vacuo. Purification by column chromatography (30% MeOH in CH$_2$Cl$_2$) to give DP-C (12-35%).

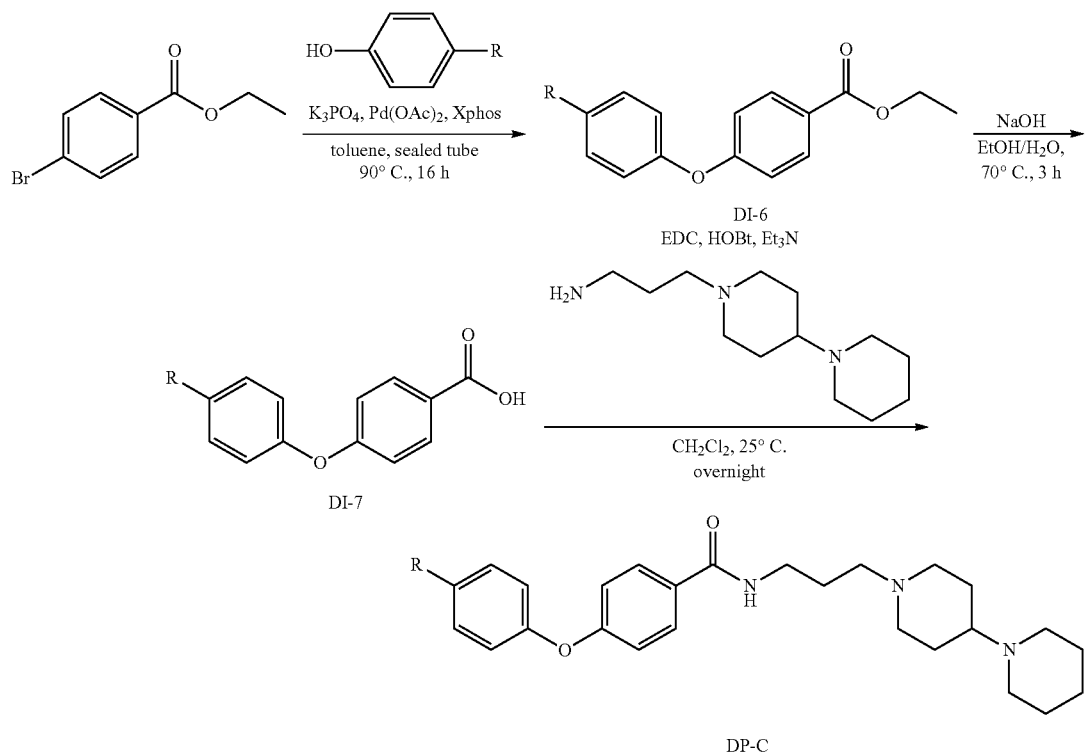

Step 1) the Synthesis of DI-6

Ethyl 4-bromobenzoate (0.10 g, 0.44 mmol), 4-methoxyphenol (0.27 g, 2.18 mmol), Pd(OAc)$_2$ (0.006 g, 0.03 mmol), X-phos (0.02 g, 0.04 mmol) and K$_3$PO$_4$ (0.23 g, 1.09 mmol) in toluene in sealed tube was purged with N$_2$ gas for 5 minutes, and the reaction mixture heated at 90° C. for 16 h. The reaction mixture was cooled to r.t., and the inorganic was removed by filtration. The filtrate was diluted with water and extracted with EtOAc. The organic was washed with a saturated brine solution, dried over Na$_2$SO$_4$ and concentrated. The crude product was purified by column chromatography using 0-20 percent EtOAc in Hexane as eluent.

Step 2) the Synthesis of DI-7

DI-6 (0.09 g, 0.33 mmol) was added NaOH (0.13 g, 3.30 mmol) in EtOH/H$_2$O (10:1) solution. The mixture was heated to reflux for 3 h. The mixture was cooled to room temperature and evaporated. The mixture was dissolved in General Procedure D-4

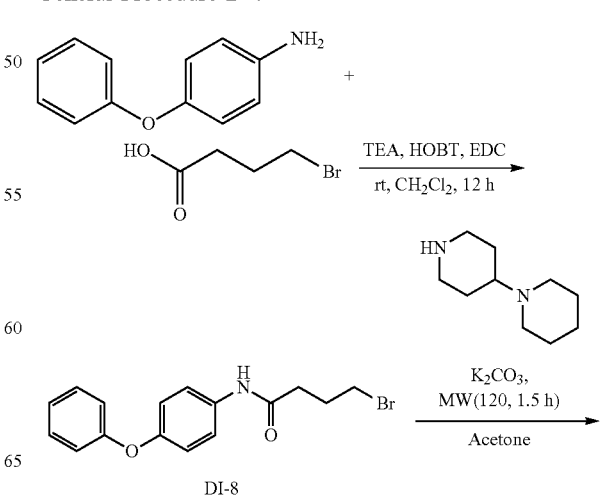

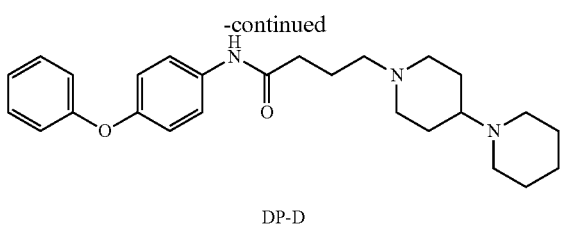

DP-D

Step 1) the Synthesis of DI-8

To a stirred solution of 4-bromobutanoic acid (2 g, 11.98 mmol) in $CH_2Cl_2$ (60.0 ml) was added 4-phenoxyaniline (2.2 g, 11.98 mmol), EDC (3.44 g, 17.96 mmol), HoBt (0.81 g, 5.99 mmol) and TEA (2.5 ml, 17.96 mmol). The reaction mixture was stirred at room temperature for 12 h. After reaction was completed, the reaction mixture was diluted with $CH_2Cl_2$ and washed with brine. The organic layer was dried over anhydrous $MgSO_4$ and concentrated in vacuo. The crude product was purified by flash column chromatography to give DI-8. (500 mg, yield=12%)

Step 2) the Synthesis of DP-D

To a stirred solution of DI-8 (97 mg, 0.29 mmol) in Acetone (1.0 ml) was added 1,4'-bipiperidine (97 mg, 0.58 mmol), $K_2CO_3$ (3.44 g, 17.96 mmol). The crude product was purified by flash column chromatography to give DP-D. (8 mg, yield=6%)

General Procedure D-5 concentrated in vacuo. The crude product was purified by flash column chromatography to give DI-9. (21 mg, yield=24%)

Step 2) the Synthesis of DP-E

To a solution of DI-9 (40 mg, 0.09 mmol) in 1,2-dimethoxyethane (1 ml) and $H_2O$ (0.5 ml), Boronic acid (16 mg, 0.12 mmol), $Pd(dppf)Cl_2$ (1.98 mg, 0.003 mmol) and $Na_2CO_3$ (19 mg, 0.18 mmol) were added. The reaction mixture was heated at 100° C. for 10 min under microwave irradiation. After reaction was completed, the reaction mixture was diluted with $CH_2Cl_2$ and washed with brine. The organic layer was dried over anhydrous $MgSO_4$ and concentrated in vacuo. The crude product was purified by flash column chromatography to give DP-E. (8 mg, yield=19%)

Example 2: Biological Activity

Genotype 1/2 Chimeric HCVcc Assay

Naïve Huh-7.5 target cells were plated at 2400 cells/well in 25 μL of culture media in 384-well plates (Greiner bio-one, μ clear black). After overnight incubation, compounds serially diluted in 10 μL of cell culture media were added. After 2 h compound treatment, cells were inoculated with 40 μL of genotype 1/2 chimeric cell culture derived HCV (HCVcc) which express structural proteins of an HCV

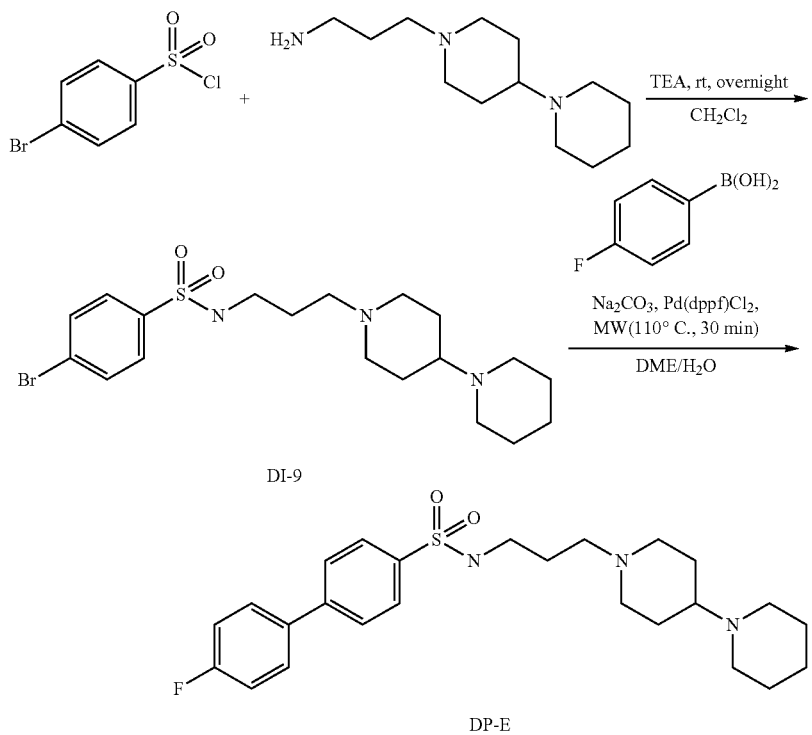

DI-9

DP-E

Step 1) the Synthesis of DI-9

To a solution of 4-bromobenzenesulfonyl chloride (50 mg, 0.20 mmol) was added 3-([1,4'-bipiperidin]-1'-yl)propan-1-amine (53 mg, 0.24 mmol) and Triethylamine (0.06 ml, 0.40 mmol) in $CH_2Cl_2$ (4 mL) at 0° C. The mixture was stirred for 2 h. After reaction was completed, the reaction mixture was diluted with $CH_2Cl_2$ and washed with brine. The organic layer was dried over anhydrous $MgSO_4$ and genotype 1a isolate (TN accession number EF621489) and non-structural proteins of HCV genotype 2a (JFH-1) with nano-luciferase reporter. At 72 h post infection, nano-luciferase activity (Nano-Glo™, Promega) and cellular ATP (Cell titer-Glo™, Promega) were measured as a marker for HCV replication and cytotoxicity, respectively. $EC_{50}$ and $CC_{50}$ were calculated by non-linear regression analyzing using GraphPad Prism (GraphPad Software).

Pan-Genotypic Activity Test Using Chimeric HCVcc Assay

In order to evaluate cross-genotypic antiviral activity against various HCV genotypes, Formulas I and II were tested using chimeric HCVcc as described above. HCV chimeras expressing the structural proteins of HCV genotype 1b (J4), 2a (J6), 2b (J8), 3a (S52), 4a (ED43), 5a (SA13), 6a (HK6a) or 7a (QC69), followed by HCV genotype 2a (JFH-1) derived non-structural proteins responsible for viral RNA replication and Renilla luciferase reporter gene were used to monitor viral replication. Formulas I and II efficiently inhibit all tested HCV subtypes and genotypes (Table 3).

Drug Combination Assay

Drug combination studies may be increasingly valuable for pre-clinical pharmaceutical research. In the clinics, chronically HCV infected patients may be treated with a combination of viral inhibitors to reduce treatment period, increase sustained viral response rates, prevent viral drug resistance, etc. If a combination is synergistic or additive, lower drug doses can be used to achieve the same or even better efficacy with lower toxicity can be evaluated in vitro by combining multiple inhibitors at various concentrations. Furthermore, drug combination studies are also being instrumentalized to rule out that new clinical compounds will not decrease the effectiveness of standard therapy, thereby avoiding potentially harmful consequences for patients. Groundbreaking work was published by Ting-Chao Chou (Theoretical Basis, Experimental Design, and Computerized Simulation of Synergism and Antagonism in Drug Combination Studies) and his work may be used to evaluate drug combinations in vitro (Chou, 2006) [22]. This work lead to the definition of the combination index (CI) of drugs with CI<1, =1 or >1 indicating synergism, an additive effect or antagonism, respectively.

According to Chou's work, we combined Formula I with selected antivirals (Telaprevir, Sofosbuvir, Daclatasvir or IFN-•) in seven different concentrations for each compound (49 data points for each combination in total) and determined the CI. Experiments were repeated three times and reproducibly we observed with genotype 2 (Table 4) and genotype 1/2 chimeric HCV (Table 5) strong synergistic effects with Telaprevir, Daclatasvir and IFN-• and synergistic effects with Sofosbuvir by calculating weighted CI values. Our calculated weighted CI values demonstrate that Formula I is extremely well suited for combinatorial therapy and as such beneficial to patients.

REFERENCES

1. Lavanchy, D., *The global burden of hepatitis C*. Liver Int, 2009. 29 Suppl 1: p. 74-81.
2. Lindenbach, B. D. and C. M. Rice, *Unravelling hepatitis C virus replication from genome to function*. Nature, 2005. 436(7053): p. 933-8.
3. Van Regenmortel, M. H., *Virus species and virus identification: past and current controversies*. Infect Genet Evol, 2007. 7(1): p. 133-44.
4. Simmonds, P., et al., *Consensus proposals for a unified system of nomenclature of hepatitis C virus genotypes*. Hepatology, 2005. 42(4): p. 962-73.
5. Friebe, P., et al., *Sequences in the 5' nontranslated region of hepatitis C virus required for RNA replication*. J Virol, 2001. 75(24): p. 12047-57.
6. Gallego, J. and G. Varani, *The hepatitis C virus internal ribosome-entry site: a new target for antiviral research*. Biochem Soc Trans, 2002. 30(2): p. 140-5.
7. Paulsen, R. B., et al., *Inhibitor-induced structural change in the HCV IRES domain IIa RNA*. Proc Natl Acad Sci USA, 2010. 107(16): p. 7263-8.
8. Webster, D. P., et al., *Development of novel treatments for hepatitis C*. Lancet Infect Dis, 2009. 9(2): p. 108-17.
9. Shimoike, T., et al., *Down-regulation of the internal ribosome entry site (IRES)-mediated translation of the hepatitis C virus: critical role of binding of the stem-loop IIId domain of IRES and the viral core protein*. Virology, 2006. 345(2): p. 434-45.
10. Bung, C., et al., *Influence of the hepatitis C virus 3'-untranslated region on IRES-dependent and cap-dependent translation initiation*. FEBS Lett. 584(4): p. 837-42.
11. Bartosch, B., J. Dubuisson, and F. L. Cosset, *Infectious hepatitis C virus pseudo-particles containing functional E1-E2 envelope protein complexes*. J Exp Med, 2003. 197(5): p. 633-42.
12. Lohmann, V., et al., *Replication of subgenomic hepatitis C virus RNAs in a hepatoma cell line*. Science, 1999. 285(5424): p. 110-3.
13. Wakita, T., et al., *Production of infectious hepatitis C virus in tissue culture from a cloned viral genome*. Nat Med, 2005. 11(7): p. 791-6.
14. Dorner, M., et al., *A genetically humanized mouse model for hepatitis C virus infection*. Nature. 474(7350): p. 208-11.
15. Windisch, M. P., et al., *Dissecting the interferon-induced inhibition of hepatitis C virus replication by using a novel host cell line*. J Virol, 2005. 79(21): p. 13778-93.
16. Ali, S., et al., *Hepatitis C virus subgenomic replicons in the human embryonic kidney 293 cell line*. J Virol, 2004. 78(1): p. 491-501.
17. Long, G., et al., *Mouse hepatic cells support assembly of infectious hepatitis C virus particles*. Gastroenterology, 2011. 141(3): p. 1057-66.
18. El Hefnawi, M. M., S. Zada, and I. A. El-Azab, *Research Prediction of prognostic biomarkers for Interferon-based therapy to Hepatitis C Virus patients: a metaanalysis of the NS5A protein in subtypes 1a, 1b, and 3a*. 2010.
19. Aghemo, A., E. Degasperi, and M. Colombo, *Directly acting antivirals for the treatment of chronic hepatitis C: Unresolved topics from registration trials*. Dig Liver Dis, 2012.
20. Hofmann, W. P., et al., *Impact of ribavirin on HCV replicon RNA decline during treatment with interferon-alpha and the protease inhibitors boceprevir or telaprevir*. Antivir Ther, 2011. 16(5): p. 695-704.
21. El Hefnawi, M. M., et al., *Natural genetic engineering of hepatitis C virus NS5A for immune system counterattack*. Ann N Y Acad Sci, 2009. 1178: p. 173-85.
22. Chou T C, *Theoretical basis, experimental design, and computerized simulation of synergism and antagonism in drug combination studies*. Pharmacological reviews, 2006. 58(3): p. 621-681

TABLE 1

Anti-HCVcc genotype ½ activity for Formula I Series

| No. | Structure | Data | EC$_{50}$ | General Procedure (GP) |
|---|---|---|---|---|
| 1 | 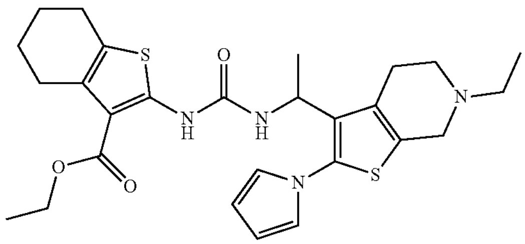 [SMILES: CCOC(=O)c1c(NC(=O)NC(C)c2c(-n3cccc3)sc3c2CCN(CC)C3)sc2c1CCCC2] | Commercial available compound | +++ | |
| 2 | 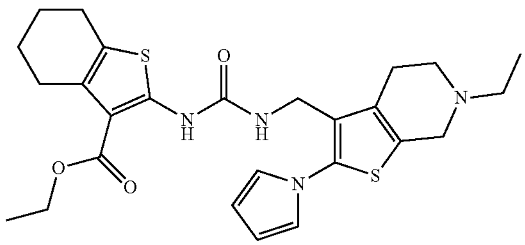 [SMILES: CCOC(=O)c1c(NC(=O)NCc2c(-n3cccc3)sc3c2CCN(CC)C3)sc2c1CCCC2] | White solid; $^1$H NMR (400 MHz, dmso) δ 10.29 (s, 1H), 8.03 (t, J = 4.8 Hz, 1 H), 6.99 (t, J = 2.0 Hz, 2H), 6.25 (t, J = 2.0 Hz, 2H), 4.24 (q, J = 7.1 Hz, 2H), 4.02 (d, J = 4.8 Hz, 2H), 3.54 (s, 2H), 2.76-2.63 (m, 4H), 2.60-2.50 (m, 6H), 1.70 (brs, 4H), 1.28 (t, J = 7.1 Hz, 3H), 1.07 (t, J = 7.1 Hz, 3H); LCMS (electrospray) m/z (M + H)$^+$ 513.17 | ++++ | GP 1 |
| 3 | 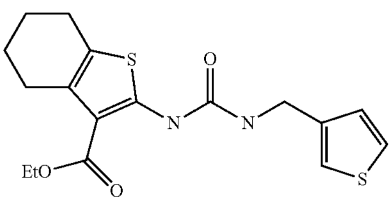 [SMILES: CCOC(=O)c1c(NC(=O)NCc2ccsc2)sc2c1CCCC2] | Yellow oil: $^1$H NMR (400 MHz, acetone) δ 10.43 (s, 1H), 7.47 (brs, 1H), 7.43-7.40 (m, 1H), 7.33 (brs, 1H), 7.12 (d, J = 4.9 Hz, 1H), 4.46 (d, J = 5.8 Hz, 2H), 4.26 (q, J = 7.2 Hz, 2H), 2.73-2.70 (m, 2H), 2.60-2.55 (m, 2H), 1.81-1.68 (m, 4H), 1.32 (t, J = 7.1 Hz, 3H); LCMS (electrospray) m/z (M + H)$^+$ 364.85 | ++++ | GP 1 |
| 4 | 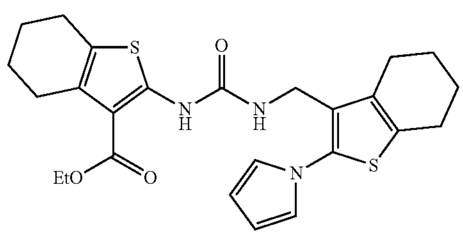 [SMILES: CCOC(=O)c1c(NC(=O)NCc2c(-n3cccc3)sc3c2CCCC3)sc2c1CCCC2] | White solid; $^1$H NMR (400 MHz, cdcl$_3$) δ 10.48 (s, 1H), 6.79 (s, 2H), 6.29 (s, 2H), 4.66 (brs, 1H), 4.35-4.20 (m, 4H), 2.73-2.70 (m, 4H), 2.68-2.51 (m, 4H), 1.91-1.68 (m, 8H), 1.34 (t, J = 7.1 Hz, 3H), 1.26 (t, J = 7.1 Hz, 3H); LCMS (electrospray) m/z (M + H)$^+$ 483.86. | ++++ | GP 1 |
| 5 | 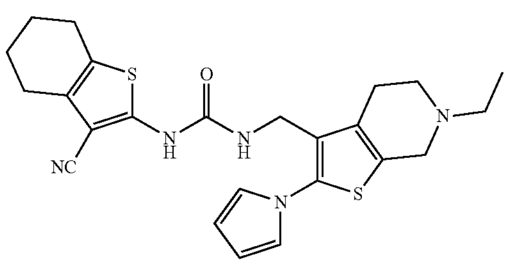 [SMILES: CCN1CCc2c(sc(-n3cccc3)c2CNC(=O)Nc2sc3c(c2C#N)CCCC3)C1] | Yellow gel; $^1$H NMR (400 MHz, cdcl$_3$) δ 8.67 (brs, 1H), 6.82 (t, J = 2.0 Hz, 2H), 6.28 (t, J = 2.0 Hz, 2H), 5.83 (s, 1H), 4.22 (d, J = 5.3 Hz, 2H), 3.64 (s, 2H), 2.82 (t, J = 5.6 Hz, 2H), 2.74 (d, J = 5.2 Hz, 2H), 2.65 (q, J = 7.2 Hz, 2H), 2.57 (d, J = 5.3 Hz, 2H), 2.47 (d, J = 5.4 Hz, 2H), 1.86-1.75 (m, 4H), 1.18 (t, J = 7.2 Hz, 3H); LCMS (electrospray) m/z (M + H)$^+$ 465.91. | + | GP 1-a (TU-B) |
| 6 | 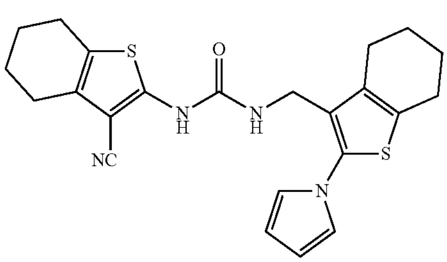 [SMILES: N#Cc1c(NC(=O)NCc2c(-n3cccc3)sc3c2CCCC3)sc2c1CCCC2] | White solid; $^1$H NMR (400 MHz, cdcl$_3$) δ 8.34 (s, 1H), 7.26 (s, 1H), 6.82 (t, J = 2.0 Hz, 2H), 6.28 (s, 2H), 5.42 (s, 1H), 4.21 (d, J = 5.2 Hz, 2H), 2.70 (t, J = 5.0 Hz, 2H), 2.57 (s, 4H), 2.44 (d, J = 5.3 Hz, 2H), 1.90-1.74 (m, 8H); LCMS (electrospray) m/z (M + H)$^+$ 436.87. | ++ | GP 1-a |

TABLE 1-continued

Anti-HCVcc genotype ½ activity for Formula I Series

| No. | Structure | Data | EC$_{50}$ | General Procedure (GP) |
|---|---|---|---|---|
| 7 | 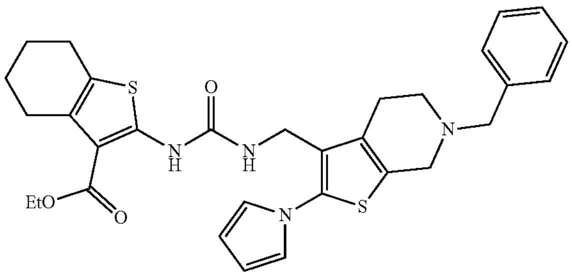 [SMILES: CCOC(=O)c1c(NC(=O)NCc2c(-n3cccc3)sc3c2CCN(Cc2ccccc2)C3)sc2c1CCCC2] | Yellow solid; $^1$H NMR (400 MHz, cdcl$_3$) δ 10.49 (s, 1H), 7.42-7.23 (m, 4H), 6.78 (t, J = 2.0 Hz, 2H), 6.29 (t, J = 2.0 Hz, 2H), 4.73 (s, 1H), 4.31-4.21 (m, 4H), 3.72 (s, 2H), 3.59 (s, 2H), 2.83 (t, J = 5.6 Hz, 2H), 2.73-2.70 (m, 4H), 2.58 (d, J = 5.0 Hz, 2H), 1.76 (brs, 4H), 1.34 (t, J = 7.1 Hz, 3H) LCMS (electrospray) m/z (M + H)$^+$ 575.02. | ++++ | GP 1 |
| 8 | 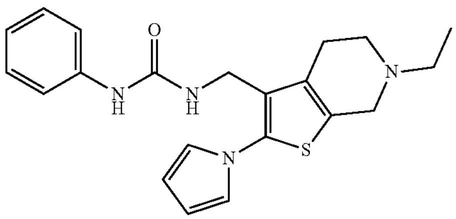 [SMILES: CCN1CCc2c(sc(-n3cccc3)c2CNC(=O)Nc2ccccc2)C1] | Brown solid; $^1$H NMR (400 MHz, acetone) δ 7.95 (s, 1H), 7.47 (d, J = 7.9 Hz, 2H), 7.21 (t, J = 7.9 Hz, 2H), 6.96 (s, 2H), 6.90 (t, J = 7.3 Hz, 1H), 6.24 (s, 2H), 5.96 (brs, 1H), 4.18 (d, J = 5.2 Hz, 2H), 3.62 (s, 2H), 2.83-2.71 (m, 4H), 2.62 (q, J = 7.2 Hz, 2H), 1.14 (t, J = 7.2 Hz, 3H); LCMS (electrospray) m/z (M + H)$^+$ 381.05 | + | GP 8 (TU-I) |
| 9 | 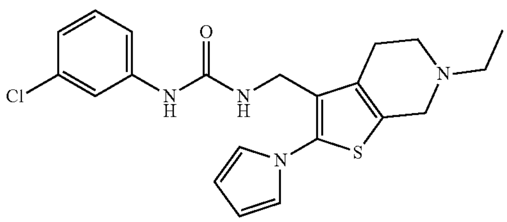 [SMILES: CCN1CCc2c(sc(-n3cccc3)c2CNC(=O)Nc2cccc(Cl)c2)C1] | Brown solid; $^1$H NMR (400 MHz, acetone) δ 8.06 (s, 1H), 7.76 (s, 1H), 7.28-7.17 (m, 2H), 6.95 (s, 2H), 6.92 (s, 1H) 6..24 (s, 2H), 5.99 (s, 1H), 4.18 (d, J = 4.9 Hz, 2H), 3.57 (s, 2H), 2.77-2.67 (m, 4H), 2.57 (q, J = 7.0 Hz, 2H), 1.12 (t, J = 7.1 Hz, 3H); LCMS (electrospray) m/z (M + H)$^+$ 415.00 | + | GP 8 |
| 10 | 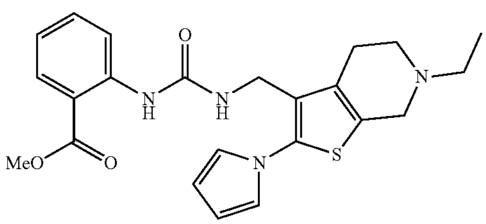 [SMILES: CCN1CCc2c(sc(-n3cccc3)c2CNC(=O)Nc2ccccc2C(=O)OC)C1] | Yellow solid; $^1$H NMR (400 MHz, acetone) δ 10.01 (s, 1H), 8.55 (d, J = 8.6 Hz, 1H), 7.92 (d, J = 8.0 Hz, 1H), 7.49 (t, J = 7.9 Hz, 1H), 7.20 (s, 1H), 7.01 (s, 2H), 6.97 (t, J = 7.6 Hz, 1H), 6.25 (s, 2H), 4.22 (d, J = 4.9 Hz, 2H), 4.06 (s, 2H), 3.86 (s, 3H), 3.20 (t, J = 5.3 Hz, 2H), 3.10-2.94 (m, 4H), 1.32 (t, J = 7.2 Hz, 3H); LCMS (electrospray) m/z (M + H)$^+$ 439.29 | + | GP 1 |
| 11 | 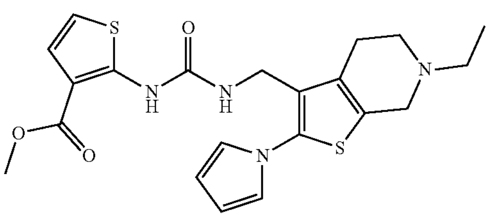 [SMILES: CCN1CCc2c(sc(-n3cccc3)c2CNC(=O)Nc2sccc2C(=O)OC)C1] | Light brown solid; mp = 201.8° C.; $^1$H NMR (400 MHz, CDCl$_3$); δ 10.10 (br s, 1H), 7.10 (d, J = 6.0 Hz, 1H), 6.81-6.79 (m, 2H), 6.59 (d, J = 6.4 Hz, 1H), 6.32-6.31 (m, 2H), 4.89 (br s, 1H), 4.28 (d, J = 5.2 Hz, 2H), 3.83 (s, 3H), 3.65 (s, 2H), 2.85-2.82 (m, 2H), 2.76-2.73 (m, | ++ | GP 1 |
| 12 | 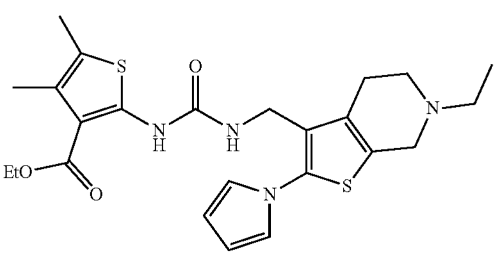 [SMILES: CCOC(=O)c1c(NC(=O)NCc2c(-n3cccc3)sc3c2CCN(CC)C3)sc(C)c1C] | Orange-brown solid; mp = 196.9° C.; $^1$H NMR (400 MHz, CDCl$_3$); δ 10.50 (br s, 1H), 6.79 (s, 2H), 6.31 (s, 2H), 4.64 (br s, 1H), 4.31-4.26 (m, 4H), 3.65 (s, 2H), 2.83-2.64 (m, 6H), 2.22 (s, 3H), 2.20 (s, 3H), 1.36 (t, J = 6.8 Hz, 3H), 1.20 (t, J = 6.8 Hz, 3H); LCMS (electrospray) m/z 487.15 (M + H)$^+$. | +++ | GP 1 |

TABLE 1-continued

Anti-HCVcc genotype ½ activity for Formula I Series

| No. | Structure | Data | EC$_{50}$ | General Procedure (GP) |
|---|---|---|---|---|
| 13 | 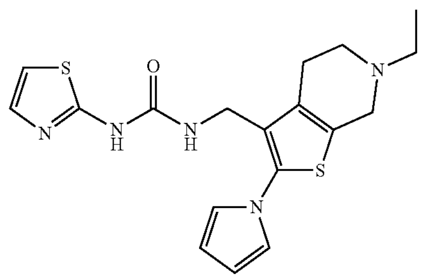 [SMILES: CCN1CCc2c(sc(-n3cccc3)c2CNC(=O)Nc2nccs2)C1] | Brown solid; $^1$H NMR (400 MHz, cdcl$_3$) δ 7.27 (brs, 1H), 6.82 (brs, 2H), 6.78 (d, J = 3.4 Hz, 1H), 6.26 (brs, 2H), 4.28 (d, J = 5.2 Hz, 2H), 3.69 (s, 2H), 2.89-2.82 (m, 2H), 2.81-2.76 (m, 2H), 2.69 (q, J = 7.0 Hz, 2H), 1.20 (t, J = 7.1 Hz, 3H); LCMS (electrospray) m/z (M + H)$^+$ 388.05 | + | GP 1 |
| 14 | 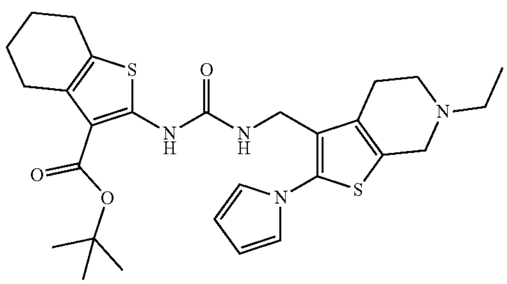 [SMILES: CCN1CCc2c(sc(-n3cccc3)c2CNC(=O)Nc2sc3c(c2C(=O)OC(C)(C)C)CCCC3)C1] | White solid; $^1$H NMR (400 MHz, cdcl$_3$) δ 10.57 (s, 1H), 6.79 (t, J = 2.1 Hz, 2H), 6.30 (t, J = 2.1 Hz, 2H), 4.73 (brs, 1H), 4.27 (d, J = 5.4 Hz, 2H), 3.65 (s, 2H), 2.83 (t, J = 5.5 Hz, 2H), 2.75 (t, J = 5.3 Hz, 2H), 2.72-2.62 (m, 4H), 2.59 (t, J = 4.8 Hz, 2H), 1.80-1.70 (m, 4H), 1.54 (s, 9H), 1.20 (t, J = 7.2 Hz, 3H); LCMS (electrospray) m/z (M + H)$^+$ 541.27 | ++++ | GP 10 (TU-K) |
| 15 | 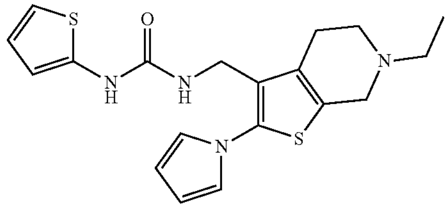 [SMILES: CCN1CCc2c(sc(-n3cccc3)c2CNC(=O)Nc2cccs2)C1] | solid; $^1$H NMR (400 MHz, acetone-d6); δ 9.00 (br s, 1H), 6.96 (t, J = 1.2 Hz, 2H), 6.74-6.71 (m, 2H), 6.43 (t, J = 1.6 Hz, 1H), 6.25-6.20 (m, 3H), 4.18 (d, J = 5.2 Hz, 2H), 3.75 (s, 2H), 2.91 (t, J = 5.6 Hz, 2H), 2.80 (t, J = 5.6 Hz, 2H), 2.74 (q, J = 7.2 Hz, 2H), 1.19 (t, J = 7.2 Hz, 3H); LCMS (electrospray) m/z 387.07 (M + H)$^+$. | + | GP 13 (TU-Q) |
| 16 | 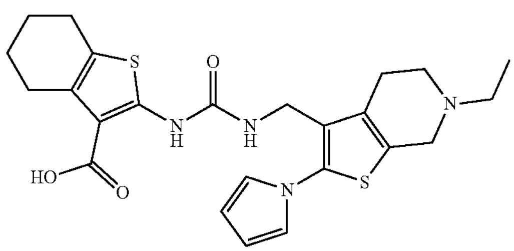 [SMILES: CCN1CCc2c(sc(-n3cccc3)c2CNC(=O)Nc2sc3c(c2C(=O)O)CCCC3)C1] | Yellow solid; $^1$H NMR (400 MHz, cd$_3$od) δ 6.95-6.91 (m, 2H), 6.31 (d, J = 1.8 Hz, 2H), 4.20 (brs, 2H), 3.39 (d, J = 6.0 Hz, 2H), 3.15-3.02 (m, 2H), 2.75 (brs, 2H), 2.64-2.55 (m, 4H), 2.47 (brs, 2H), 1.85-1.72 (m, 4H), 1.43 (td, J = 7.3, 3.5 Hz, 3H); LCMS (electrospray) m/z (M + H)$^+$ 485.14 | + | GP 10 (TU-L) |
| 17 | 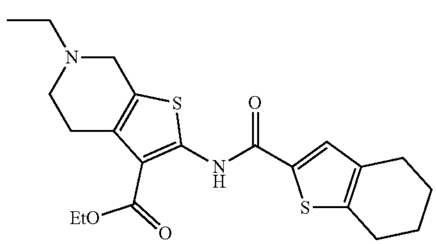 [SMILES: CCOC(=O)c1c(NC(=O)c2cc3c(s2)CCCC3)sc2c1CCN(CC)C2] | Clear oil; $^1$H NMR (400 MHz, cdcl$_3$) δ 6.99 (s, 1H), 3.53 (q, J = 7.1 Hz, 4H), 2.75 (t, J = 5.9 Hz, 2H), 2.59 (t, J = 5.9 Hz, 2H), 1.88-1.74 (m, 4H), 1.60 (brs, 6H), 1.23 (t, J = 7.1 Hz, 6H); LCMS (electrospray) m/z (M + H)$^+$ 419.08 | ++ | GP 11 |

TABLE 1-continued

Anti-HCVcc genotype ½ activity for Formula I Series

| No. | Structure | Data | EC$_{50}$ | General Procedure (GP) |
|---|---|---|---|---|
| 18 | 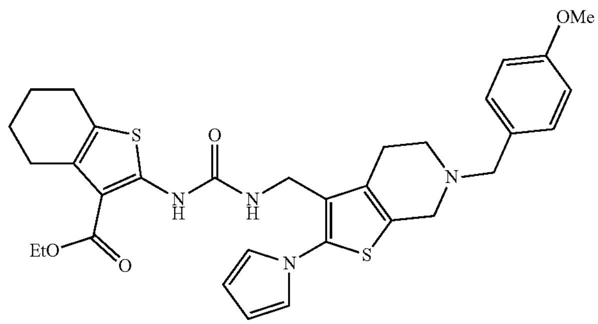 [SMILES: CCOC(=O)c1c(NC(=O)NCc2c(-n3cccc3)sc3c2CCN(Cc2ccc(OC)cc2)C3)sc2c1CCCC2] | Yellow solid; $^1$H NMR (400 MHz, cdcl$_3$) δ 10.48 (s, 1H), 7.28 (d, J = 8.5 Hz, 2H), 6.86 (d, J = 8.5 Hz, 2H), 6.78 (t, J = 2.0 Hz, 2H), 6.29 (t, J = 2.0 Hz, 2H), 4.80 (s, 1H), 4.30-4.21 (m, 4H), 3.80 (s, 3H), 3.66 (s, 2H), 3.57 (s, 2H), 2.82 (t, J = 5.6 Hz, 2H), 2.71 (t, J = 5.4 Hz, 4H), 2.58 (d, J = 5.1 Hz, 2H), 1.83-1.71 (m, 4H), 1.34 (t, J = 7.1 Hz, 3H); LCMS (electrospray) m/z (M + H)$^+$ 605.20. | ++++ | GP 1 |
| 19 | 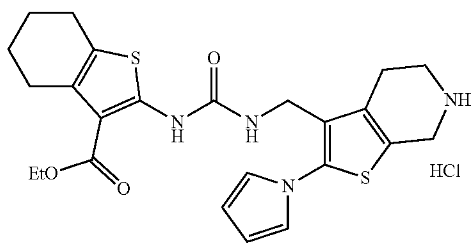 [SMILES: CCOC(=O)c1c(NC(=O)NCc2c(-n3cccc3)sc3c2CCNC3)sc2c1CCCC2 ; Cl] | White solid; $^1$H NMR (400 MHz, dmso) δ 10.33 (s, 1H), 9.48 (s, 2H), 8.17 (t, J = 5.3 Hz, 1H), 7.07 (t, J = 2.1 Hz, 2H), 6.30 (t, J = 2.1 Hz, 2H), 4.30 (s, 2H), 4.24 (q, J = 7.1 Hz, 2H), 4.10 (d, J = 5.3 Hz, 2H), 3.57 (s, 2H), 2.82 (t, J = 5.6 Hz, 2H), 2.66 (s, 2H), 2.53 (s, 2H), 1.71-1.73 (s, 4H), 1.28 (t, J = 7.1 Hz, 3H); LCMS (electrospray) m/z (M + H)$^+$ 485.10. | ++++ | GP 2 (TU-C) |
| 20 | 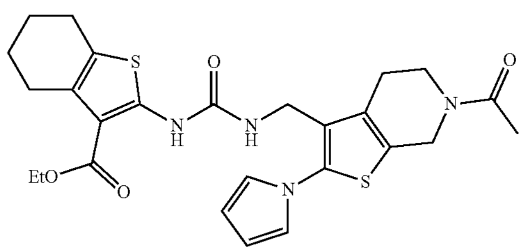 [SMILES: CCOC(=O)c1c(NC(=O)NCc2c(-n3cccc3)sc3c2CCN(C(C)=O)C3)sc2c1CCCC2] | $^1$H NMR (400 MHz, cdcl$_3$) δ 10.51 (s, 1H), 6.79 (s, 2H), 6.30 (s, 2H), 5.11 (s, 1H), 4.91-4.60 (br, 3H), 4.36-4.21 (m, 2H), 3-90-3.79 (br, 2H), 2.72 (m, 4H), 2.59 (m, 2H), 2.14 (s, 3H), 1.79 (m, 4H), 1.34 (t, J = 7.1 Hz, 3H); LCMS (electrospray) m/z (M + H)$^+$ 527.12. | ++++ | GP 3 (TU-D) |
| 21 | 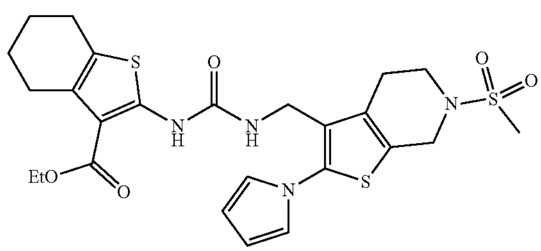 [SMILES: CCOC(=O)c1c(NC(=O)NCc2c(-n3cccc3)sc3c2CCN(S(C)(=O)=O)C3)sc2c1CCCC2] | $^1$H NMR (400 MHz, cdcl$_3$) δ 10.50 (s, 1H), 7.26 (s, 1H), 6.80 (s, 2H), 6.33 (s, 2H), 4.77 (s, 1H), 4.45 (s, 2H), 4.30-4.22 (m, 4H), 3.61 (t, J = 5.7 Hz , 2H), 2.88 (s, 3H), 2.83 (tm J = 5.4 Hz, 2H), 2.72 (br, 2H), 2.63-2.56 (m, 2H), 1.76 (d, J = 4.5 Hz, 4H), 1.34 (t, J = 7.1 Hz, 3H); LCMS (electrospray) m/z (M + H)$^+$ 563.22. | ++++ | GP 4 (TU-E) |
| 22 | 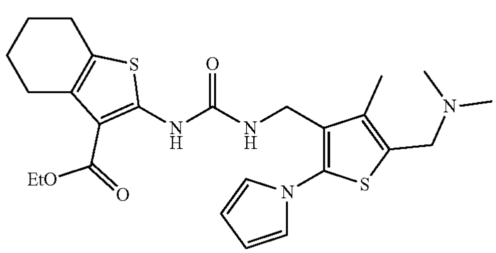 [SMILES: CCOC(=O)c1c(NC(=O)NCc2c(-n3cccc3)sc(CN(C)C)c2C)sc2c1CCCC2] | Yellow solid; $^1$H NMR (400 MHz, CDCl$_3$); δ 10.51 (br s, 1H), 6.80 (d, J = 2.0 Hz, 2H), 6.31 (t, J = 2.0 Hz, 2H), 4.64 (br s, 1H), 4.30-4.24 (m, 4H), 3.56 (s, 2H), 2.74-2.72 (m, 2H), 2.60-2.59 (m, 2H), 2.34 (s, 6H), 2.18 (s, 3H), 1.78-1.65 (m, 4H), 1.35 (t, J = 7.2 Hz, 3H); LCMS (electrospray) m/z 501.14 (M + H)$^+$. | ++++ | GP 14 (TU-R) |

TABLE 1-continued

Anti-HCVcc genotype ½ activity for Formula I Series

| No. | Structure | Data | EC$_{50}$ | General Procedure (GP) |
|---|---|---|---|---|
| 23 | 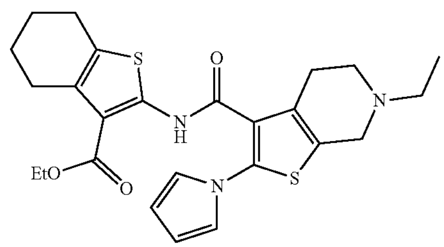 [SMILES: CCOC(=O)c1c(NC(=O)c2c(-n3cccc3)sc3c2CCN(CC)C3)sc2c1CCCC2] | Brown solid; $^1$H NMR (400 MHz, cd$_3$od) δ 6.85 (brs, 2H), 6.24 (brs, 2H), 4.14 (q, J = 7.1 Hz, 2H), 3.95 (s, 2H), 3.11 (t, J = 5.6 Hz, 2H), 3.04 (t, J = 5.6 Hz, 2H), 2.92 (q, J = 7.1 Hz, 2H), 1.38-1.24 (m, 11H), 1.13 (t, J = 7.1 Hz, 3H); LCMS (electrospray) m/z (M + H)$^+$ 484.12 | ++ | GP 1, GP 11 |
| 24 | 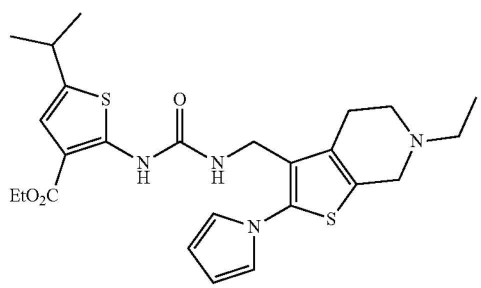 [SMILES: CCOC(=O)c1cc(C(C)C)sc1NC(=O)NCc1c(-n2cccc2)sc2c1CCN(CC)C2] | White solid; $^1$H NMR (400 MHz, cdcl$_3$) δ 10.08 (s, 1H), 6.80 (d, J = 1.8 Hz, 2H), 6.78 (s, 1H), 6.32 (d, J = 1.8 Hz, 2H), 5.03 (brs, 1H), 4.31-4.24 (m, 4H), 3.74 (s, 2H), 3.05-2.87 (m, 1H), 2.93 (brs, 2H), 2.82 (brs, 2H), 2.78-2.71 (m, 2H), 1.35 (t, J = 7.1 Hz, 3H), 1.31-1.21 (m, 9H); LCMS (electrospray) m/z (M + H)$^+$ 501.20 | +++ | GP 1 |
| 25 | 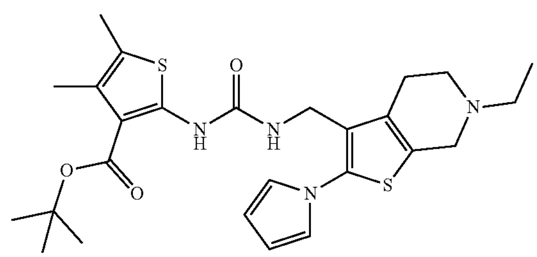 [SMILES: CCN1CCc2c(sc(-n3cccc3)c2CNC(=O)Nc2sc(C)c(C)c2C(=O)OC(C)(C)C)C1] | White solid; $^1$H NMR (400 MHz, dmso) δ 10.33 (s, 1H), 8.01 (t, J = 4.8 Hz, 1H), 6.99 (t, J = 1.9 Hz, 2H), 6.24 (t, J = 1.8 Hz, 2H), 4.01 (d, J = 4.4 Hz, 2H), 3.53 (s, 2H), 2.73-2.64 (m, 2H), 2.62-2.53 (m, 4H), 2.14 (d, J = 11.1 Hz, 6H), 1.53 (d, J = 4.8 Hz, 9H), 1.07 (t, J = 7.1 Hz, 3H); LCMS (electrospray) m/z (M + H)$^+$ 515.21 | ++++ | GP 1 |
| 26 | 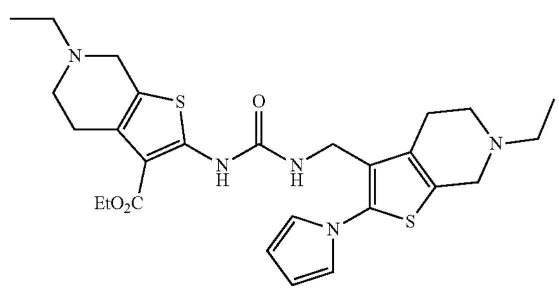 [SMILES: CCOC(=O)c1c(NC(=O)NCc2c(-n3cccc3)sc3c2CCN(CC)C3)sc2c1CCN(CC)C2] | Yellow solid; $^1$H NMR (400 MHz, cd$_3$od) δ 6.89 (t, J = 2.0 Hz, 2H), 6.25 (t, J = 1.9 Hz, 2H), 4.30 (q, J = 7.1 Hz, 2H), 4.15 (s, 2H), 3.64 (s, 2H), 3.53 (s, 2H), 2.90 (t, J = 5.5 Hz, 2H), 2.84 (t, J = 5.7 Hz, 2H), 2.79-2.68 (m, 4H), 2.63 (td, J = 14.3, 7.2 Hz, 4H), 1.35 (q, J = 6.9 Hz, 3H), 1.17 (tt, J = 11.6, 5.8 Hz, 6H); LCMS (electrospray) m/z (M + H)$^+$ 542.29 | ++++ | GP 1 |
| 27 | 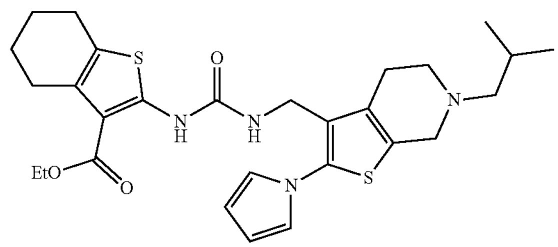 [SMILES: CCOC(=O)c1c(NC(=O)NCc2c(-n3cccc3)sc3c2CCN(CC(C)C)C3)sc2c1CCCC2] | Ivory solid; $^1$H NMR (400 MHz, cdcl$_3$) δ 10.49 (s, 1H), 7.26 (s, 1H), 6.79 (t, J = 2.0 Hz, 2H), 6.30 (t, J = 2.0 Hz, 2H), 4.88 (s, 1H), 4.31-4.21 (m, 4H), 3.69 (d, J = 11.8 Hz, 2H), 2.84 (s, 2H), 2.73 (d, J = 5.8 Hz, 4H), 2.59 (d, J = 5.2 Hz, 2H), 2.38 (d, J = 6.3 Hz, 2H), 1.91 (dt, J = 13.0, 6.5 Hz, 1H), 1.76 (d, J = 5.0 Hz, 4H), 1.34 (t, J = 7.1 Hz, 3H), 0.96 (t, J = 8.7 Hz, 3H); LCMS (electrospray) m/z (M + H)$^+$ 541.19. | ++++ | GP 5 (TU-F) |

TABLE 1-continued

Anti-HCVcc genotype ½ activity for Formula I Series

| No. | Structure | Data | EC$_{50}$ | General Procedure (GP) |
|---|---|---|---|---|
| 28 | 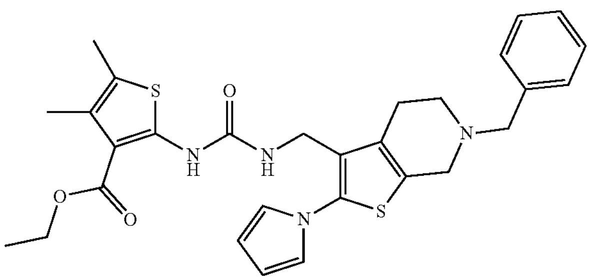 [SMILES: CCOC(=O)c1c(NC(=O)NCc2c(-n3cccc3)sc3c2CCN(Cc2ccccc2)C3)sc(C)c1C] | Yellow solid; $^1$H NMR (400 MHz, cdcl$_3$) δ 10.47 (d, J = 19.6 Hz, 1H), 7.41-7.23 (m, 5H), 6.78 (t, J = 2.0 Hz, 2H), 6.29 (t, J = 2.0 Hz, 2H), 4.88 (s, 1H), 4.31-4.22 (m, 4H), 3.75 (s, 2H), 3.62 (s, 2H), 2.86 (t, J = 5.5 Hz, 2H), 2.74 (d, J = 5.1 Hz, 2H), 2.20 (s, 3H), 2.19 (s, 3H), 1.35 (t, J = 7.1 Hz, 3H). LCMS (electrospray) m/z (M + H)$^+$ 549.14. | ++++ | GP 1 |
| 29 | 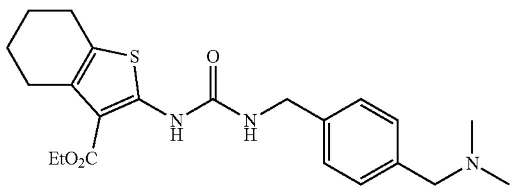 [SMILES: CCOC(=O)c1c(NC(=O)NCc2ccc(CN(C)C)cc2)sc2c1CCCC2] | Oil; $^1$H NMR (400 MHz, CDCl$_3$) 10.63 (NH, 1H), 7.24 (s, 4H), 5.52 (NH, 1H), 4.44 (d, J = 5.7 Hz, 2H), 4.21 (q, J = 6.6 Hz, 2H), 3.39 (s, 2H), 2.71 (s, 2H), 2.57 (s, 2H), 2.2 (s, 6H), 1.74 (s, 4H), 1.30 (t, J = 6.8 Hz, 3H); LRMS (electrospray) m/z (M + H)$^+$ 416.22. | +++ | GP 1 |
| 30 | 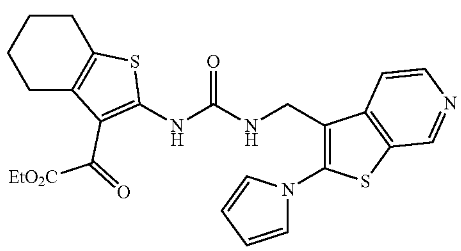 [SMILES: CCOC(=O)C(=O)c1c(NC(=O)NCc2c(-n3cccc3)sc3cnccc23)sc2c1CCCC2] | White solid; $^1$H NMR (400 MHz, cd$_3$od) δ 10.55 (s, 1H), 9.43 (s, 1H), 8.62 (s, 1H), 8.48 (s, 1H), 7.32 (s, 2H), 6.50 (s, 2H), 4.35-4.20 (m, 2H), 2.70 (s, 2H), 2.57 (s, 2H), 1.75 (s, 4H), 1.31-1.28 (m, 5H); LCMS (electrospray) m/z (M + H)$^+$ 481.04. | ++++ | GP 1 |
| 31 | 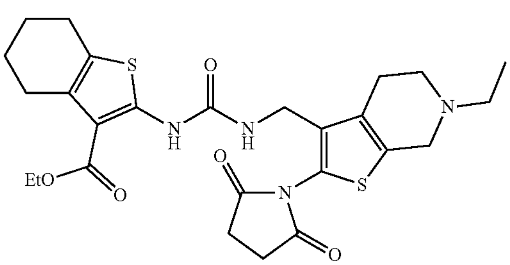 [SMILES: CCOC(=O)c1c(NC(=O)NCc2c(N3C(=O)CCC3=O)sc3c2CCN(CC)C3)sc2c1CCCC2] | Yellow-brown solid; mp = ° C.; $^1$H NMR (400 MHz, acetone-d$_6$); δ 4.44-4.26 (m, 4H), 3.64 (s, 2H), 2.82 (t, J = 5.6 Hz, 2H), 2.77-2.61 (m, 10H), 2.13 (t, J = 6.4 Hz, 2H), 1.81-1.78 (m, 4H), 1.36 (t, J = 7.2 Hz, 3H), 1.21 (t, J = 7.2 Hz, 3H); LCMS (electrospray) m/z 545.22 (M + H)$^+$. | +++ | GP 15 (TU-S) |
| 32 | 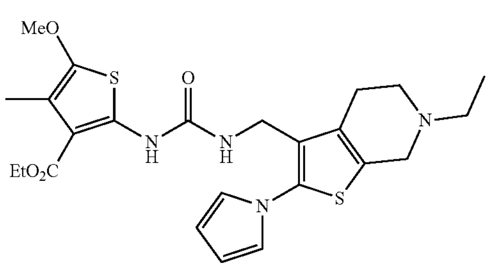 [SMILES: CCOC(=O)c1c(NC(=O)NCc2c(-n3cccc3)sc3c2CCN(CC)C3)sc(OC)c1C] | White solid; $^1$H NMR (400 MHz, cd$_3$od) δ 6.89 (t, J = 2.1 Hz, 2H), 6.25 (t, J = 2.1 Hz, 2H), 4.29 (q, J = 7.1 Hz, 2H), 4.15 (s, 2H), 3.80 (s, 3H), 3.65 (s, 2H), 2.85 (t, J = 5.8 Hz, 2H), 2.72 (t, J = 5.7 Hz, 2H), 2.66 (q, J = 7.2 Hz, 2H), 2.14 (s, 3H), 1.34 (t, J = 7.1 Hz, 3H), 1.19 (t, J = 7.2 Hz, 3H); LCMS (electrospray) m/z (M + H)$^+$ 503.17 | +++ | GP 1 |

TABLE 1-continued

Anti-HCVcc genotype ½ activity for Formula I Series

| No. | Structure | Data | EC$_{50}$ | General Procedure (GP) |
|---|---|---|---|---|
| 33 | 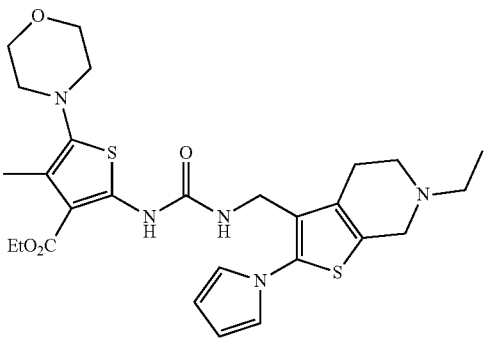 [SMILES: CCOC(=O)c1c(NC(=O)NCc2c(-n3cccc3)sc3c2CCN(CC)C3)sc(N2CCOCC2)c1C] | White solid; $^1$H NMR (400 MHz, cdcl$_3$) δ 10.59 (s, 1H), 7.27 (d, J = 6.9 Hz, 1H), 6.79 (t, J = 2.0 Hz, 2H), 6.29 (t, J = 2.0 Hz, 2H), 4.30-4.21 (m, 4H), 3.81-3.76 (m, 4H), 3.63 (s, 2H), 2.87-2.79 (m, 6H), 2.74 (t, J = 4.8 Hz, 2H), 2.64 (q, J = 7.1 Hz, 2H), 2.23 (s, 3H), 1.34 (t, J = 7.1 Hz, 3H), 1.18 (t, J = 7.1 Hz, 3H); LCMS (electrospray) m/z (M + H)$^+$ 558.21 | +++ | GP 1 |
| 34 | 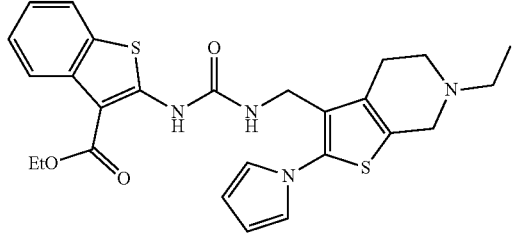 [SMILES: CCOC(=O)c1c(NC(=O)NCc2c(-n3cccc3)sc3c2CCN(CC)C3)sc2ccccc12] | White solid; $^1$H NMR (400 MHz, dmso) δ 10.81 (s, 1H), 8.40 (brs, 1H), 8.16 (d, J = 8.2 Hz, 1H), 7.83 (d, J = 7.9 Hz, 1H), 7.37 (t, J = 7.5 Hz, 1H), 7.24 (t, J = 7.5 Hz, 1H), 7.01 (s, 2H), 6.26 (s, 2H), 4.41 (q, J = 7.0 Hz, 2H), 4.08 (d, J = 4.5 Hz, 2H), 3.55 (s, 2H), 2.71 (t, J = 5.3 Hz, 2H), 2.61 (brs, 2H), 2.57-2.51 (m, 2H), 1.41 (t, J = 7.0 Hz, 3H0, 1.07 (t, J = 7.2 Hz, 3H); LCMS (electrospray) m/z (M + H)$^+$ 509.16 | +++ | GP 1 |
| 35 | 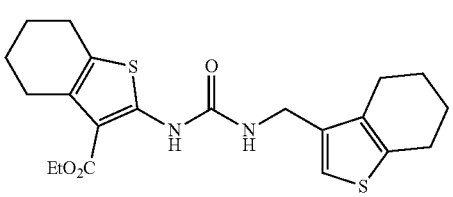 [SMILES: CCOC(=O)c1c(NC(=O)NCc2csc3c2CCCC3)sc2c1CCCC2] | White solid; $^1$H NMR (400 MHz, CDCl$_3$) 10.63 (NH, 1H), 6.94 (s, 1H), 5.17 (NH, 1H), 4.34 (d, J = 5.7 Hz, 2H), 4.23 (q, J = 6.6 Hz, 2H), 2.73 (d, J = 5.6 Hz, 4H), 2.59 (d, J = 5.1 Hz, 2H), 2.52 (t, J = 5.1 Hz, 2H), 1.89-1.57 (m, 8H), 1.34 (t, J = 6.8 Hz, 3H); LRMS (electrospray) m/z (M + H)$^+$ 419.15. | ++++ | GP 1-a |
| 36 | 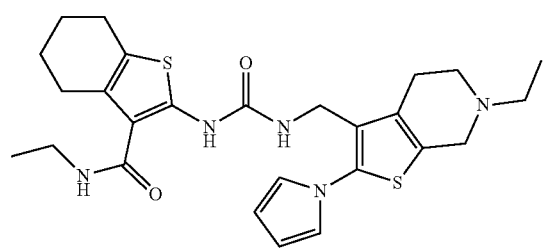 [SMILES: CCNC(=O)c1c(NC(=O)NCc2c(-n3cccc3)sc3c2CCN(CC)C3)sc2c1CCCC2] | White solid; $^1$H NMR (400 MHz, acetone) δ 10.94 (s, 1H), 7.04 (brs, 1H), 6.97 (s, 2H), 6.55 (brs, 1H), 6.23 (s, 2H), 4.20 (d, J = 5.0 Hz, 2H), 3.57 (s, 2H), 3.39-3.31 (m, 2H), 2.75-2.66 (m, 6H), 2.63-2.51 (m, 4H), 1.77 (brs, 4H), 1.13 (dt, J = 18.4, 7.1 Hz, 6H); LCMS (electrospray) m/z (M + H)$^+$ 512.22 | ++++ | GP 12 |
| 37 | 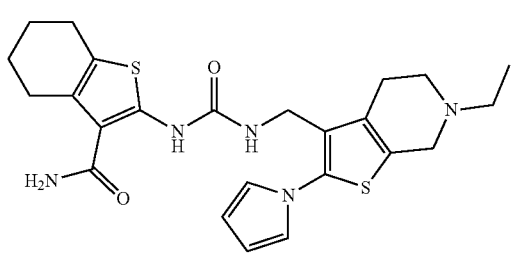 [SMILES: CCN1CCc2c(sc(-n3cccc3)c2CNC(=O)Nc2sc3c(c2C(N)=O)CCCC3)C1] | White solid; $^1$H NMR (400 MHz, acetone) δ 11.13 (s, 1H), 7.02 (brs, 1H), 6.96 (t, J = 2.1 Hz, 2H), 6.38 (brs, 2H), 6.23 (t, J = 2.1 Hz, 2H), 4.19 (d, J = 5.1 Hz, 2H), 3.57 (s, 2H), 2.77-2.70 (m, 4H), 2.69 (d, J = 5.1 Hz, 2H), 2.63-2.52 (m, 4H), 1.81-1.77 (m, 4H), 1.11 (t, J = 7.2 Hz, 3H); LCMS (electrospray) m/z (M + H)$^+$ 484.26 | +++ | GP 1 |

TABLE 1-continued

Anti-HCVcc genotype ½ activity for Formula I Series

| No. | Structure | Data | EC$_{50}$ | General Procedure (GP) |
|---|---|---|---|---|
| 38 | 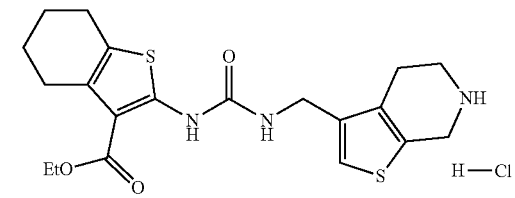 | Pink solid; $^1$H NMR (400 MHz, DMSO-d$_6$); δ 10.34 (s, 1H), 9.39 (br s, 2H), 8.27 (t, J = 5.2 Hz, 1H), 7.30 (s, 1H), 4.32 (s, 2H), 4.27-4.20 (m, 4H), 3.40-3.30 (m, 2H), 2.82 (t, J = 5.2 Hz, 2H), 2.70-2.60 (m, 2H), 2.52-2.50 (m, 2H), 1.75-1.65 (m, 4H), 1.29 (t, J = 7.2 Hz, 3H); LCMS (electrospray) m/z 420.10 | ++++ | GP 16 (TU-T) |
| 39 | 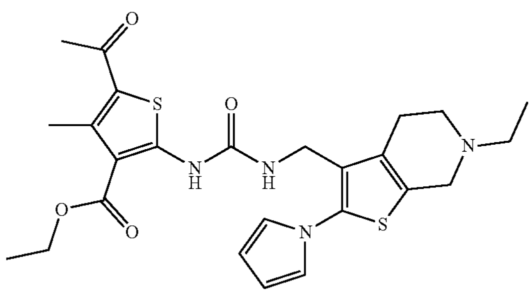 [SMILES: CCOC(=O)c1c(NC(=O)NCc2c(-n3cccc3)sc3c2CCN(CC)C3)sc(C(C)=O)c1C] | Yellow solid; $^1$H NMR (400 MHz, cd$_3$od) δ 6.94 (t, J = 2.1 Hz, 2H), 6.31 (t, J = 2.1 Hz, 2H), 4.43-4.35 (m, 4H), 4.25 (s, 2H), 3.58 (brs, 2H), 3.26 (brs, 2H), 3.07 (t, J = 6.1 Hz, 2H), 2.72 (s, 3H), 2.49 (s, 3H), 1.44-1.36 (m, 6H); LCMS (electrospray) m/z (M + H)$^+$ 515.01 | ++++ | GP 1 |
| 40 | 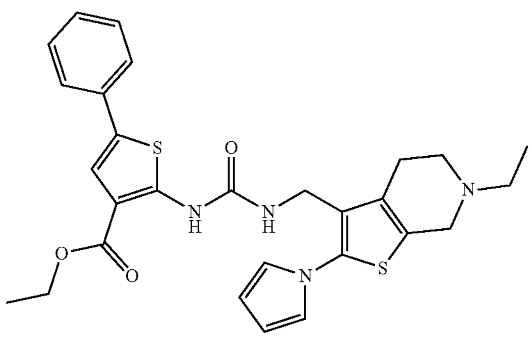 [SMILES: CCOC(=O)c1cc(-c2ccccc2)sc1NC(=O)NCc1c(-n2cccc2)sc2c1CCN(CC)C2] | Yellow solid; $^1$H NMR (400 MHz, cdcl$_3$) δ 10.18 (s, 1H), 7.55 (d, J = 7.5 Hz, 2H), 7.36-7.30 (m, 3H), 7.23 (t, J = 7.4 Hz, 1H), 6.81 (t, J = 2.1 Hz, 2H), 6.31 (t, J = 2.1 Hz, 2H), 5.14 (brs, 1H), 4.33-4.26 (m, 4H), 3.66 (s, 2H), 2.85 (t, J = 5.3 Hz, 2H), 2.77 (d, J = 5.2 Hz, 2H), 2.67 (q, J = 7.1 Hz, 2H), 1.36 (t, J = 7.1 Hz, 3H), 1.19 (t, J = 7.2 Hz, 3H); LCMS (electrospray) m/z (M + H)$^+$ 534.94 | +++ | GP 1 |
| 41 | 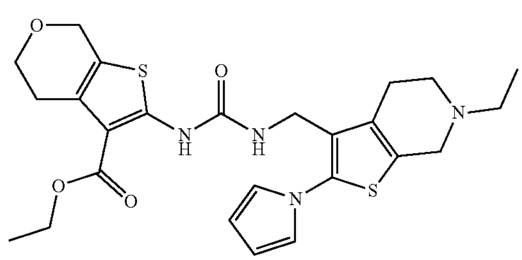 [SMILES: CCOC(=O)c1c(NC(=O)NCc2c(-n3cccc3)sc3c2CCN(CC)C3)sc2c1CCOC2] | Yellow solid; $^1$H NMR (400 MHz, cd$_3$od) δ 6.89 (t, J = 2.1 Hz, 2H), 6.26 (t, J = 2.1 Hz, 2H), 4.63 (s, 2H), 4.31 (q, J = 7.1 Hz, 2H), 4.16 (s, 2H), 3.90 (t, J = 5.6 Hz, 2H), 3.66 (s, 2H), 2.88-2.81 (m, 4H), 2.74 (t, J = 5.7 Hz, 2H), 2.66 (q, J = 7.3 Hz, 2H), 1.35 (t, J = 7.1 Hz, 3H), 1.19 (t, J = 7.2 Hz, 3H); LCMS (electrospray) m/z (M + H)$^+$ 515.01 | ++++ | GP 1 |
| 42 | 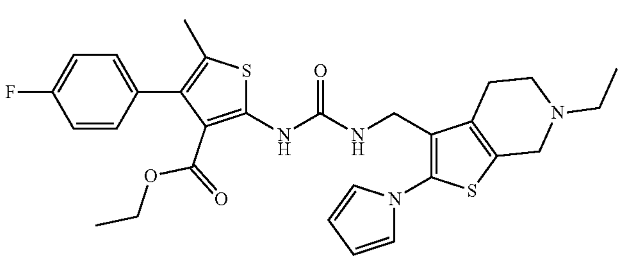 [SMILES: CCOC(=O)c1c(NC(=O)NCc2c(-n3cccc3)sc3c2CCN(CC)C3)sc(C)c1-c1ccc(F)cc1] | Yellow solid; $^1$H NMR (400 MHz, cd$_3$od) δ 7.21-7.04 (m, 4H), 6.90 (s, 2H), 6.26 (s, 2H), 4.18 (s, 2H), 3.93 (q, 6.8 Hz, 2H), 3.66 (s, 2H), 2.85 (t, J = 5.4 Hz, 2H), 2.74 (brs, 2H), 2.66 (q, J = 6.9 Hz, 2H), 2.06 (s, 3H), 1.20 (t, J = 7.0 Hz, 3H), 0.82 (t, J = 6.8 Hz, 3H); LCMS (electrospray) m/z (M + H)$^+$ 567.05 | ++++ | GP 1 |

TABLE 1-continued

Anti-HCVcc genotype ½ activity for Formula I Series

| No. | Structure | Data | EC$_{50}$ | General Procedure (GP) |
|---|---|---|---|---|
| 43 | 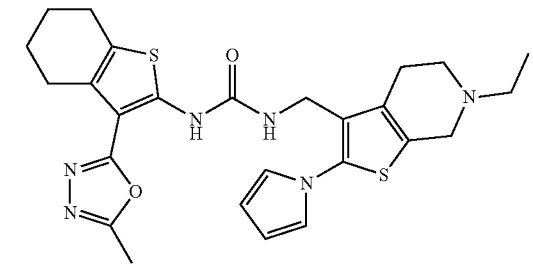 [SMILES: CCN1CCc2c(sc(-n3cccc3)c2CNC(=O)Nc2sc3c(c2-c2nnc(C)o2)CCCC3)C1] | White solid; $^1$H NMR (400 MHz, acetone) δ 10.17 (s, 1H), 7.37 (brs, 1H), 6.96 (t, J = 2.1 Hz, 2H), 6.24 (t, J = 2.1 Hz, 2H), 4.24 (d, J = 5.1 Hz, 2H), 3.57 (s, 2H), 2.80-2.72 (m, 4H), 2.72-2.61 (m, 2H), 2.64 (brs, 2H), 2.60-2.53 (m, 5H), 1.83-1.79 (m, 4H), 1.11 (t, J = 7.2 Hz, 3H); LCMS (electrospray) m/z (M + H)$^+$ 524.04 | ++++ | GP 1 |
| 44 | 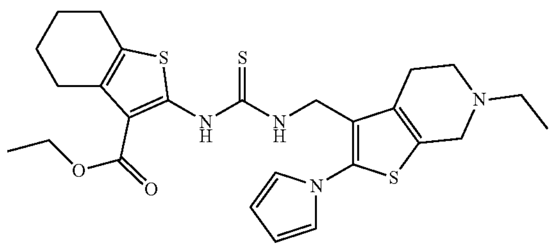 [SMILES: CCOC(=O)c1c(NC(=S)NCc2c(-n3cccc3)sc3c2CCN(CC)C3)sc2c1CCCC2] | Brown gel; $^1$H NMR (400 MHz, acetone) δ 11.82 (s, 1H), 8.53 (s, 1H), 6.91 (s, 2H), 6.23 (t, J = 1.8 Hz, 2H), 4.51 (d, J = 4.1 Hz, 2H), 4.28 (q, J = 7.1 Hz, 2H), 3.58 (s, 2H), 3.07-2.84 (m, 2H), 2.75 (t, J = 5.4 Hz, 4H), 2.65 (t, J = 5.5 Hz, 2H), 2.63-2.52 (m, 4H), 2.09-2.03 (m, 2H), 1.83-1.68 (m, 4H), 1.33 (t, J = 7.1 Hz, 3H), 1.11 (t, J = 7.1 Hz, 3H); LCMS (electrospray) m/z (M + H)$^+$ 528.94. | ++++ | GP 6 (TU-G) |
| 45 | 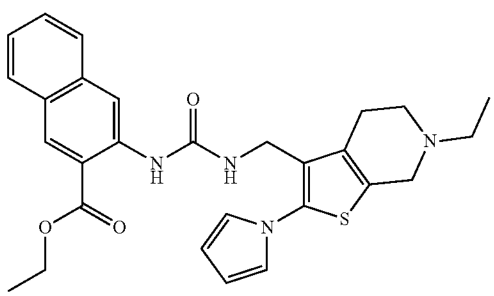 [SMILES: CCOC(=O)c1cc2ccccc2cc1NC(=O)NCc1c(-n2cccc2)sc2c1CCN(CC)C2] | Yellow solid; $^1$H NMR (400 MHz, acetone) δ 9.98 (s, 1H), 8.98 (s, 1H), 8.65 (s, 1H), 7.91 (d, J = 8.1 Hz, 1H), 7.81 (d, J = 8.2 Hz, 1H), 7.57 (t, J = 7.7 Hz, 1H), 7.40 (t, J = 7.9 Hz, 1H), 6.99 (t, J = 2.4 Hz, 2H), 6.86 (brs, 1H), 6.25 (t, J = 1.6 Hz, 2H), 4.42 (q, J = 7.1 Hz, 2H), 4.26 (d, J = 4.9 Hz, 2H), 3.58 (s, 2H), 2.75 (brs, 4H), 2.57 (q, 7.2 Hz, 2H), 1.42 (t, J = 7.1 Hz, 3H), 1.11 (t, J = 7.2 Hz, 3H); LCMS (electrospray) m/z (M + H)$^+$ 503.03 | ++ | GP 1 |
| 46 | 2HCl | Brown solid; $^1$H NMR (400 MHz, dmso) δ 10.58 (brs, 1H), 10.39 (s, 1H), 9.30 (brs, 2H), 8.32 (brs, 1H), 7.07 (s, 2H), 6.30 (s, 2H), 4.61 (brs, 2H), 4.28 (q, 7.0 Hz, 2H), 4.17 (s, 2H), 4.09 (brs, 2H), 3.72-3.65 (m, 2H), 3.53-3.42 (m, 2H), 2.96 (brs, 4H), 1.30 (t, J = 7.0 Hz, 6H); LCMS (electrospray) m/z (M + H)$^+$ 514.06 | +++ | GP 1, GP 2 (TU-O) |
| 47 | 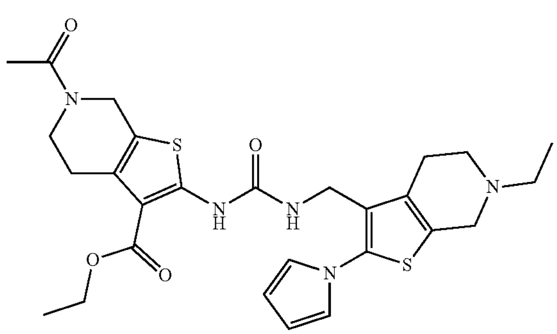 [SMILES: CCOC(=O)c1c(NC(=O)NCc2c(-n3cccc3)sc3c2CCN(CC)C3)sc2c1CCN(C(C)=O)C2] | Yellow solid; $^1$H NMR (400 MHz, acetone) δ 10.37 (s, 1H), 7.27 (brs, 1H), 6.95 (s, 2H), 6.24 (s, 2H), 4.56 (d, J = 10.0 Hz, 2H), 4.32-4.19 (m, 4H), 3.72 (q, 6.3 Hz, 2H), 3.57 (s, 2H), 2.89 (brs, 2H), 2.85-2.67 (m, 4H), 2.56 (q, J = 7.1 Hz, 2H), 2.10 (d, J = 5.7 Hz, 3H), 1.33 (t, J = 7.1 Hz, 3H), 1.11 (t, J = 7.1 Hz, 3H); LCMS (electrospray) m/z (M + H)$^+$ 556.20 | ++++ | GP 3-a (TU-P) |

TABLE 1-continued

Anti-HCVcc genotype ½ activity for Formula I Series

| No. | Structure | Data | EC$_{50}$ | General Procedure (GP) |
|---|---|---|---|---|
| 48 | 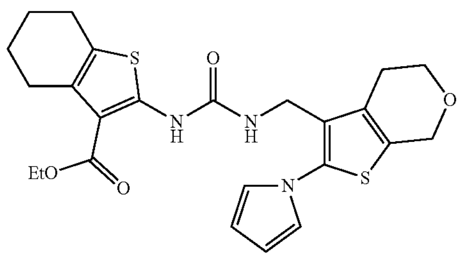 [SMILES: CCOC(=O)c1c(NC(=O)NCc2c(-n3cccc3)sc3c2CCOC3)sc2c1CCCC2] | White solid; $^1$H NMR (400 MHz, CDCl$_3$); δ 10.53 (s, 1H), 6.81 (t, J = 2.0 Hz, 2H), 6.33 (t, J = 2.0 Hz, 2H), 4.74 (s, 2H), 4.65 (t, J = 5.2 Hz, 1H), 4.30-4.25 (m, 4H), 3.99 (t, J = 5.2 Hz, 2H), 2.75-2.71 (m, 4H), 2.61 (t, J = 4.8 Hz, 2H), 1.81-1.76 (m, 4H), 1.36 (t, J = 7.2 Hz, 3H); LCMS (electrospray) m/z 485.98 (M + H)$^+$. | ++++ | GP 1 |
| 49 | 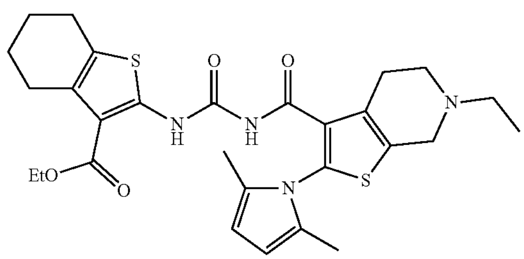 [SMILES: CCOC(=O)c1c(NC(=O)NC(=O)c2c(-n3c(C)ccc3C)sc3c2CCN(CC)C3)sc2c1CCCC2] | Yellow solid; $^1$H NMR (400 MHz, MeOH-d$_4$); δ 5.96 (s, 2H), 4.52 (s, 2H), 4.37 (t, J = 7.2 Hz, 2H), 3.70-3.65 (m, 2H), 3.64-3.55 (m, 2H), 3.41-3.35 (m, 2H), 2.81-2.78 (m, 2H), 2.67-2.64 (m, 2H), 2.04 (s, 6H), 1.82-1.75 (m, 4H), 1.45 (t, J = 7.2 Hz, 3H), 1.41 (t, J = 7.2 Hz, 3H); LCMS (electrospray) m/z 555.04 (M + H)$^+$. | ++ | GP 17 (TU-U) |
| 50 | 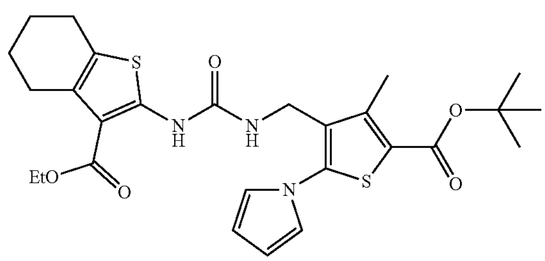 [SMILES: CCOC(=O)c1c(NC(=O)NCc2c(-n3cccc3)sc(C(=O)OC(C)(C)C)c2C)sc2c1CCCC2] | solid; $^1$H NMR (400 MHz, CDCl$_3$); δ 10.55 (s, 1H), 6.85 (t, J = 2.0 Hz, 2H), 6.34 (t, J = 2.0 Hz, 2H), 4.69 (t, J = 4.4 Hz, 1H), 4.35 (d, J = 4.8 Hz, 2H), 4.25 (q, J = 7.2 Hz, 2H), 2.73-2.71 (m, 2H), 2.60-2.58 (m, 2H), 2.54 (s, 3H), 1.80-1.70 (m, 4H), 1.57 (s, 9H), 1.34 (t, J = 7.2 Hz, 3H) | ++ | GP 18 (I-29) |
| 51 | 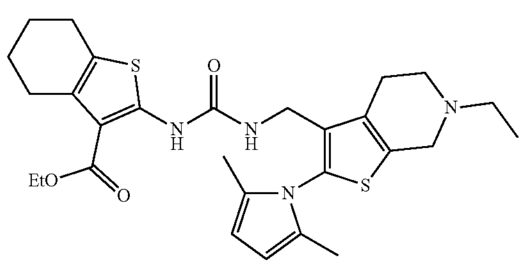 [SMILES: CCOC(=O)c1c(NC(=O)NCc2c(-n3c(C)ccc3C)sc3c2CCN(CC)C3)sc2c1CCCC2] | Yellow solid; $^1$H NMR (400 MHz, CDCl$_3$); δ 10.38 (s, 1H), 5.94 (s, 2H), 4.56 (br s, 1H), 4.28 (q, J = 7.2 Hz, 2H), 4.11 (d, J = 5.2 Hz, 2H), 3.85 (br s, 2H), 3.15-2.80 (m, 6H), 2.78-2.68 (m, 2H), 2.65-2.55 (m, 2H), 2.01 (s, 6H), 1.80-1.70 (m, 4H), 1.37-1.33 (m, 6H); LCMS (electrospray) m/z 541.06 (M + H)$^+$. | ++++ | GP 20 |
| 52 | 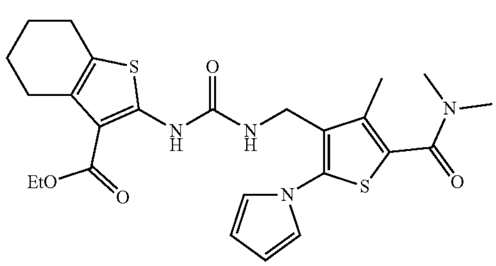 [SMILES: CCOC(=O)c1c(NC(=O)NCc2c(-n3cccc3)sc(C(=O)N(C)C)c2C)sc2c1CCCC2] | yellow oil; $^1$H NMR (400 MHz, CDCl$_3$); δ 10.52 (s, 1H), 6.83 (t, J = 2.0 Hz, 2H), 6.34 (t, J = 2.0 Hz, 2H), 4.58 (br s, 1H), 4.34-4.26 (m, 4H), 3.10 (s, 6H), 2.73-2.70 (m, 2H), 2.63-2.58 (m, 2H), 2.24 (s, 3H), 1.80-1.70 (m, 4H), 1.36 (t, J = 7.2 Hz, 3H); LCMS (electrospray) m/z 514.98 (M + H)$^+$. | +++ | GP 18 (TU-V) |

TABLE 1-continued

Anti-HCVcc genotype ½ activity for Formula I Series

| No. | Structure | Data | EC$_{50}$ | General Procedure (GP) |
|---|---|---|---|---|
| 53 | 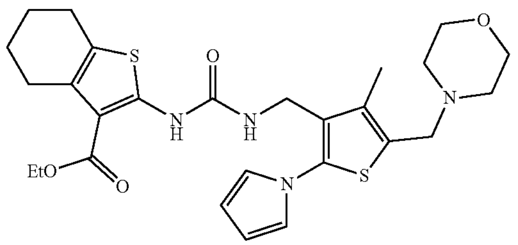 [SMILES: CCOC(=O)c1c(NC(=O)NCc2c(-n3cccc3)sc(CN3CCOCC3)c2C)sc2c1CCCC2] | Yellow oil; $^1$H NMR (400 MHz, MeOH-d$_4$); δ 10.50 (s, 1H), 7.73 (br s, 1H), 6.93 (s, 2H), 6.30 (s, 2H), 4.29 (q, J = 7.2 Hz, 2H), 4.21 (s, 4H), 3.82 (br s, 4H), 3.01 (br s, 4H), 2.78-2.70 (m, 2H), 2.62-2.55 (m, 2H), 2.29 (s, 3H), 1.79-1.70 (m, 4H), 1.34 (t, J = 7.2 Hz, 3H); LCMS (electrospray) m/z 542.94 (M + H)$^+$. | ++++ | GP 19 (TU-W) |
| 54 | 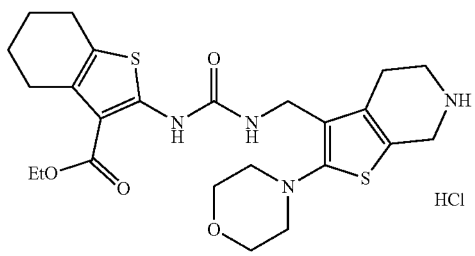 [SMILES: CCOC(=O)c1c(NC(=O)NCc2c(N3CCOCC3)sc3c2CCNC3)sc2c1CCCC2 ; Cl] | Red solid; $^1$H NMR (400 MHz, DMSO-d$_6$); δ 10.29 (s, 1H), 9.22 (br s, 2H), 7.99 (t, J = 5.2 Hz, 1H), 4.26-4.20 (m, 4H), 3.74-3.70 (m, 4H), 3.37-3.34 (m, 4H), 2.83-2.80 (m, 4H), 2.77-2.75 (m, 2H), 2.70-2.66 (m, 2H), 2.5 5-2.52 (m, 2H), 1.75-1.65 (m, 4H), 1.28 (t, J = 7.2 Hz, 3H); LCMS (electrospray) m/z 504.92 (M + H)$^+$. | +++ | GP 20 (TU-X) |
| 55 | 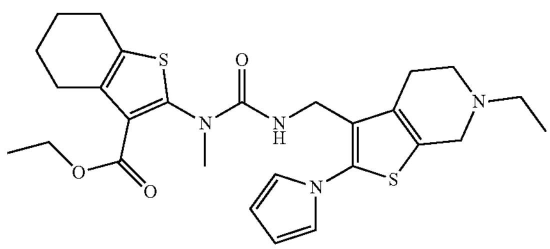 [SMILES: CCOC(=O)c1c(N(C)C(=O)NCc2c(-n3cccc3)sc3c2CCN(CC)C3)sc2c1CCCC2] | Brown gel; $^1$H NMR (400 MHz, acetone) δ 6.92-6.80 (m, 2H), 6.23-6.12 (m, 2H), 4.29-4.07 (m, 2H), 4.03-3.91 (m, 1H), 3.63-3.47 (m, 2H), 3.16 (s, 3H), 2.85-2.65 (m, 3H), 2.65-2.46 (m, 34H), 2.46-2.23 (m, 2H), 1.80-1.63 (m, 2H), 1.37-1.17 (m, 4H), 1.17-1.08 (m, 3H); LCMS (electrospray) m/z (M + H)$^+$ 526.92. | ++ | GP 7 (TU-H) |
| 56 | 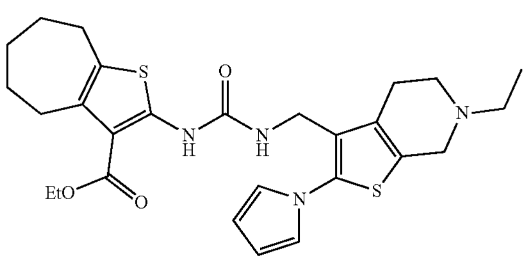 [SMILES: CCOC(=O)c1c(NC(=O)NCc2c(-n3cccc3)sc3c2CCN(CC)C3)sc2c1CCCCC2] | Yellow solid; $^1$H NMR (400 MHz, acetone) δ 10.28 (s, 1H), 7.15 (brs, 1H), 6.95 (t, J = 1.2 Hz, 2H), 6.24 (t, J = 1.2 Hz, 2H), 4.27 (q, J = 6.8 Hz, 2H), 4.21 (d, J = 4.8 Hz, 2H), 3.56 (s, 2H), 3.03-2.98 (m, 2H), 2.76-2.71 (m, 2H), 2.70-2.61 (m, 4H), 2.56 (q, J = 7.2 Hz, 2H), 1.86-1.78 (m, 2H), 1.66-1.54 (m, 4H), 1.31 (t, J = 7.2 Hz, 3H), 1.08 (t, J = 7.2 Hz, 3H); LCMS (electrospray) m/z (M + H)$^+$ 527.05 | ++++ | GP 1 |
| 57 | 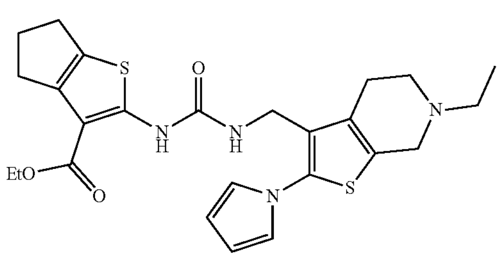 [SMILES: CCOC(=O)c1c(NC(=O)NCc2c(-n3cccc3)sc3c2CCN(CC)C3)sc2c1CCC2] | Yellow solid; $^1$H NMR (400 MHz, acetone) δ 10.12 (s, 1H), 7.21 (brs, 1H), 6.95 (t, J = 1.6 Hz, 2H), 6.24 (t, J = 1.6 Hz, 2H), 4.26-4.20 (m, 4H), 3.57 (s, 2H), 2.85-2.69 (m, 8H), 2.57 (q, J = 7.2 Hz, 2H), 2.36-2.28 (m, 2H), 1.31 (t, J = 7.2 Hz, 3H), 1.11 (t, J = 7.2 Hz, 3H); LCMS (electrospray) m/z (M + H)$^+$ 499.09 | ++++ | GP 1 |

TABLE 1-continued

Anti-HCVcc genotype ½ activity for Formula I Series

| No. | Structure | Data | EC$_{50}$ | General Procedure (GP) |
|---|---|---|---|---|
| 58 | 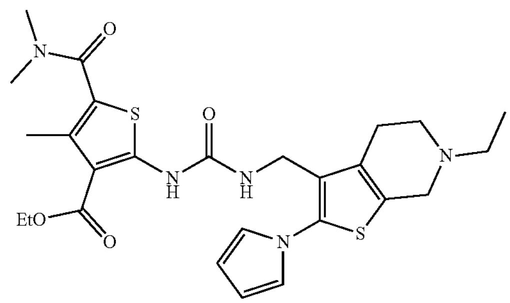 | Yellow solid; $^1$H NMR (400 MHz, acetone) δ 10.54 (s, 1H), 7.39 (brs, 1H), 6.79 (t, J = 2.0 Hz, 2H), 6.24 (t, J = 2.0 Hz, 2H), 4.30 (q, J = 7.2 Hz, 2H), 4.22 (d, J = 4.8 Hz, 2H), 3.57 (s, 2H), 3.01 (s, 6H), 2.76-2.72 (m, 2H), 2.71-2.68 (m, 2H), 2.56 (q, J = 7.2 Hz, 2H), 2.26 (s, 3H), 1.33 (t, J = 6.9 Hz, 3H), 1.11 (t, J = 7.2 Hz, 3H); LCMS (electrospray) m/z (M + H)$^+$ 534.99 | ++ | GP 1 |
| 59 | 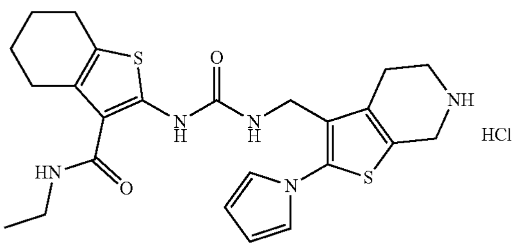 [SMILES: CCNC(=O)c1c(NC(=O)NCc2c(-n3cccc3)sc3c2CCNC3)sc2c1CCCC2 ; Cl] | Yellow solid; $^1$H NMR (400 MHz, cd$_3$od) δ 6.92 (t, J = 1.9 Hz, 2H), 6.29 (t, J = 1.9 Hz, 2H), 4.39 (s, 2H), 4.19 (s, 2H), 3.60-3.52 (m, 2H), 3.36 (q, J = 7.4 Hz, 2H), 2.99 (brs, 2H), 2.68-2.61 (m, 4H), 1.84-1.78 (m, 4H), 1.17 (t, J = 6.9 Hz, 3H); LCMS (electrospray) m/z (M + H)$^+$ 483.99 | ++++ | GP 12, GP 2 |
| 60 | 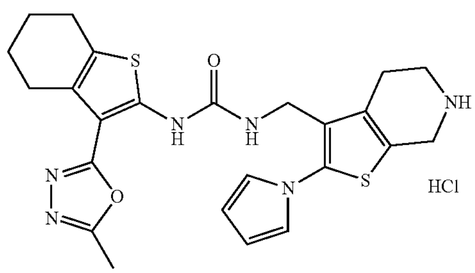 [SMILES: Cc1nnc(-c2c(NC(=O)NCc3c(-n4cccc4)sc4c3CCNC4)sc3c2CCCC3)o1 ; Cl] | White solid; $^1$H NMR (400 MHz, cd$_3$od) δ 6.95 (d, J = 1.9 Hz, 2H), 6.30 (d, J = 1.9 Hz, 2H), 4.40 (brs, 2H), 4.24 (s, 2H), 3.59-3.52 (m, 2H), 3.01 (brs, 2H), 2.81 (brs, 2H), 2.65 (brs, 2H), 2.59 (s, 3H), 1.85 (brs, 4H); LCMS (electrospray) m/z (M + H)$^+$ 495.01 | +++ | GP 1, GP 2 |
| 61 | 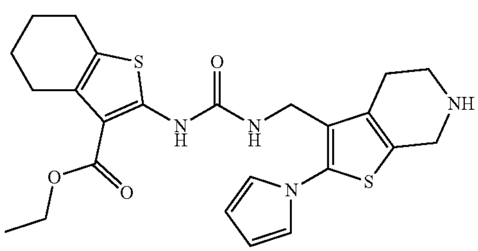 [SMILES: CCOC(=O)c1c(NC(=O)NCc2c(-n3cccc3)sc3c2CCNC3)sc2c1CCCC2] | White solid; $^1$H NMR (400 MHz, dmso) δ 10.29 (s, 1H), 8.04 (brs, 1H), 7.00 (s, 2H), 6.25 (s, 2H), 4.24 (q, J = 7.0 Hz, 2H), 4.03 (d, J = 4.8 Hz, 2H), 3.83 (s, 2H), 2.97 (t, J = 5.3 Hz, 2H), 2.66 (brs, 2H), 2.53 (brs, 4H), 1.70 (brs, 4H), 1.28 (t, J = 7.0 Hz, 3H); LCMS (electrospray) m/z (M + H)$^+$ 485.01 | ++++ | GP 27 |
| 62 | 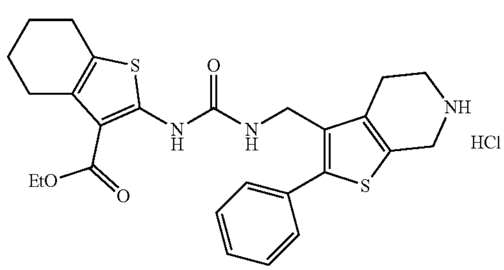 [SMILES: CCOC(=O)c1c(NC(=O)NCc2c(-c3ccccc3)sc3c2CCNC3)sc2c1CCCC2 ; Cl] | Pink solid; $^1$H NMR (400 MHz, MeOH-d$_4$); δ 7.49-7.39 (m, 5H), 4.45 (s, 2H), 4.32 (s, 2H), 4.28 (q, J = 6.8 Hz, 2H), 3.60-3.50 (m, 2H), 3.05-2.95 (m, 2 H), 2.75-2.65 (m, 2H), 2.60-2.50 (m, 2H), 1.80-1.70 (m, 4H), 1.33 (t, J = 7.2 Hz, 3H); LCMS (electrospray) m/z 496.06 (M + H)$^+$. | +++ | GP 21 (TU-Y) |

TABLE 1-continued

Anti-HCVcc genotype ½ activity for Formula I Series

| No. | Structure | Data | EC$_{50}$ | General Procedure (GP) |
|---|---|---|---|---|
| 63 | 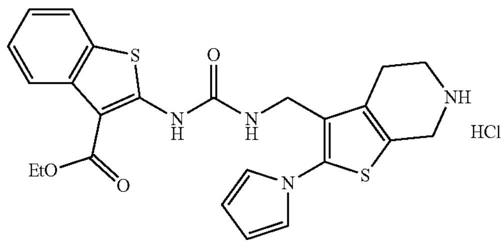 [SMILES: CCOC(=O)c1c(NC(=O)NCc2c(-n3cccc3)sc3c2CCNC3)sc2ccccc12 ; Cl] | White solid; $^1$H NMR (400 MHz, dmso) δ 10.86 (s, 1H), 8.52 (brs, 1H), 8.16 (d, J = 8.2 Hz, 1H), 7.84 (d, J = 7.9 Hz, 1H), 7.38 (t, J = 7.7 Hz, 1H), 7.25 (t, J = 7.5 Hz, 1H), 7.09 (t, J = 2.0 Hz, 2H), 6.31 (t, J = 2.0 Hz, 2H), 4.42 (q, J = 7.1 Hz, 2H), 4.26 (s, 2H), 4.15 (d, J = 5.2 Hz, 2H), 3.40-3.35 (m, 2H), 2.83 (brs, 2H), 1.41 (t, J = 7.1 Hz, 3H); LCMS (electrospray) m/z (M + H)$^+$ 480.99 | +++ | GP 1, GP 2 |
| 64 | 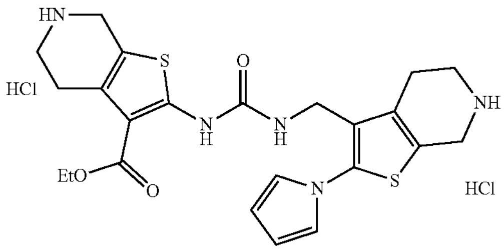 [SMILES: Cl ; CCOC(=O)c1c(NC(=O)NCc2c(-n3cccc3)sc3c2CCNC3)sc2c1CCNC2 ; Cl] | Violet solid; $^1$H NMR (400 MHz, dmso) δ 10.38 (s, 1H), 9.37 (brs, 2H), 8.32 (t, J = 5.2 Hz, 1H), 7.07 (t, J = 2.0 Hz, 2H), 6.29 (t, J = 2.0 Hz, 2H), 4.31-4.24 (m, 4H), 4.16 (s, 2H), 4.11 (d, J = 5.2 Hz, 2H), 3.28 (brs, 4H), 2.95 (brs, 2H), 2.82 (brs, 2H), 1.30 (t, J = 6.8 Hz, 3H); LCMS (electrospray) m/z (M + H)$^+$ 486.03 | ++ | GP 1, GP 2 |
| 65 | 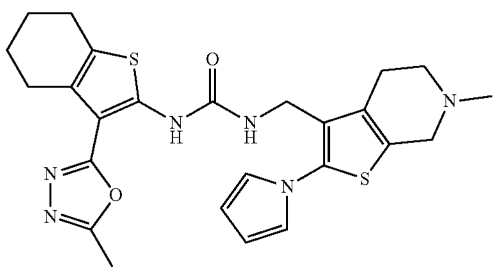 [SMILES: Cc1nnc(-c2c(NC(=O)NCc3c(-n4cccc4)sc4c3CCN(C)C4)sc3c2CCCC3)o1] | White solid; $^1$H NMR (400 MHz, acetone) δ 10.17 (s, 1H), 7.39 (brs, 1H), 6.96 (t, J = 2.0 Hz, 2H), 6.24 (t, J = 1.6 Hz, 2H), 4.24 (d, J = 5.1 Hz, 2H), 3.51 (s, 2H), 2.76 (brs, 2H), 2.73-2.66 (m, 4H), 2.64 (brs, 2H), 2.55 (s, 3H), 2.40 (s, 3H), 1.81 (brs, 4H); LCMS (electrospray) m/z (M + H)$^+$ 509.02 | ++++ | GP 1 |
| 66 | 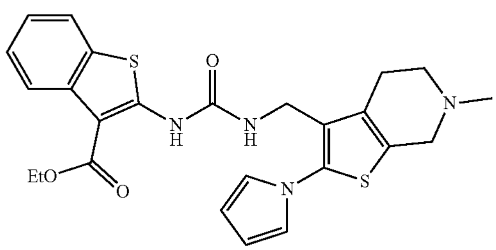 [SMILES: CCOC(=O)c1c(NC(=O)NCc2c(-n3cccc3)sc3c2CCN(C)C3)sc2ccccc12] | Yellow solid; $^1$H NMR (400 MHz, acetone) δ 10.91 (s, 1H), 8.23 (d, J = 8.2 Hz, 1H), 7.79 (d, J = 7.9 Hz, 1H), 7.54 (brs, 1H), 7.36 (t, J = 7.6 Hz, 1H), 7.24 (t, J = 7.5 Hz, 1H), 6.97 (t, J = 2.1 Hz, 2H), 6.25 (t, J = 2.1 Hz, 2H), 4.44 (q, J = 7.1 Hz, 2H), 4.27 (d, J = 5.1 Hz, 2H), 3.52 (s, 2H), 2.76-2.66 (m, 4H), 2.40 (s, 3H), 1.44 (t, J = 7.1 Hz, 3H); LCMS (electrospray) m/z (M + H)$^+$ 494.94 | ++++ | GP 1 |
| 67 | 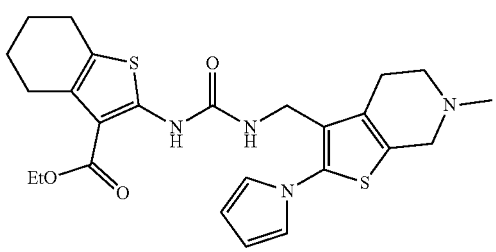 [SMILES: CCOC(=O)c1c(NC(=O)NCc2c(-n3cccc3)sc3c2CCN(C)C3)sc2c1CCCC2] | White solid; $^1$H NMR (400 MHz, acetone) δ 10.39 (s, 1H), 7.22 (brs, 1H), 6.95 (t, J = 2.1 Hz, 2H), 6.24 (t, J = 2.1 Hz, 2H), 4.26 (q, J = 7.1 Hz, 2H), 4.21 (d, J = 5.1 Hz, 2H), 3.51 (s, 2H), 2.74-2.65 (m, 6H), 2.60-2.55 (m, 2H), 2.40 (s, 3H), 1.81-1.70 (m, 4H), 1.32 (t, J = 7.1 Hz, 3H); LCMS (electrospray) m/z (M + H)$^+$ 499.02 | ++++ | GP 1 |

TABLE 1-continued

Anti-HCVcc genotype ½ activity for Formula I Series

| No. | Structure | Data | EC$_{50}$ | General Procedure (GP) |
|---|---|---|---|---|
| 68 | 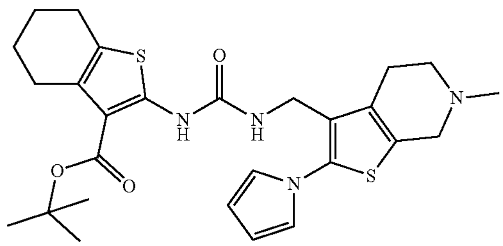 [SMILES: CN1CCc2c(sc(-n3cccc3)c2CNC(=O)Nc2sc3c(c2C(=O)OC(C)(C)C)CCCC3)C1] | White solid; $^1$H NMR (400 MHz, acetone) δ 10.45 (s, 1H), 7.21 (brs, 1H), 6.95 (t, J = 2.1 Hz, 2H), 6.24 (t, J = 2.1 Hz, 2H), 4.21 (d, J = 5.1 Hz, 2H), 3.51 (s, 2H), 2.74-2.64 (m, 6H), 2.57 (t, J = 5.0 Hz, 2H), 2.40 (s, 3H), 1.80-1.68 (m, 4H), 1.54 (s, 9H); LCMS (electrospray) m/z (M + H)$^+$ 527.12 | ++++ | GP 1 |
| 69 | 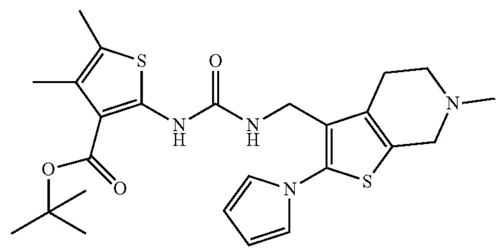 [SMILES: Cc1sc(NC(=O)NCc2c(-n3cccc3)sc3c2CCN(C)C3)c(C(=O)OC(C)(C)C)c1C] | White solid; $^1$H NMR (400 MHz, acetone) δ 10.46 (s, 1H), 7.19 (brs, 1H), 6.95 (t, J = 2.1 Hz, 2H), 6.24 (t, J = 2.1 Hz, 2H), 4.21 (d, J = 5.1 Hz, 2H), 3.51 (s, 2H), 2.71-2.67 (m, 4H), 2.40 (s, 3H), 2.18 (s, 3H), 2.17 (s, 3H), 1.55 (s, 9H); LCMS (electrospray) m/z (M + H)$^+$ 501.06 | ++++ | GP 1 |
| 70 | 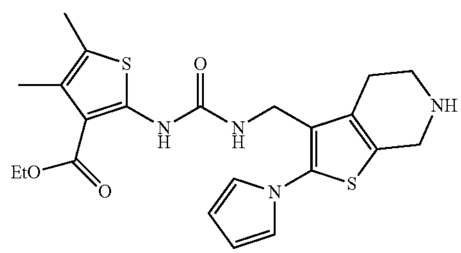 [SMILES: CCOC(=O)c1c(NC(=O)NCc2c(-n3cccc3)sc3c2CCNC3)sc(C)c1C] | Beige solid; $^1$H NMR (400 MHz, dmso) δ 10.31 (s, 1H), 9.30 (brs, 1H), 8.12 (brs, 1H), 7.07 (d, J = 1.9 Hz, 2H), 6.29 (d, J = 2.0 Hz, 2H), 4.29-4.20 (m, 4H), 4.09 (d, J = 5.1 Hz, 2H), 3.42-3.35 (m, 2H), 2.80 (brs, 2H), 2.16 (d, J = 3.5 Hz, 6H), 1.30 (t, J = 7.1 Hz, 3H); LCMS (electrospray) m/z (M + H)$^+$ 459.02 | +++ | GP 27 |
| 71 | 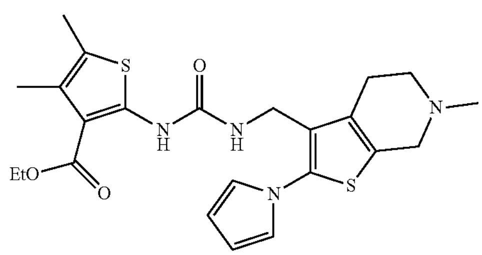 | White solid; $^1$H NMR (400 MHz, acetone) δ 10.39 (s, 1H), 7.18 (br, 1H), 6.95 (t, J = 2.1 Hz, 2H), 6.24 (t, J = 2.1 Hz, 2H), 4.27 (q, J = 7.1 Hz, 2H), 4.21 (d, J = 5.1 Hz, 2H), 3.51 (s, 2H), 2.73-2.65 (m, 4H), 2.40 (s, 3H), 2.19 (s, 6H), 1.33 (t, J = 7.1 Hz, 3H); LCMS (electrospray) m/z (M + H)$^+$ 473.03 | ++++ | GP 1 |
| 72 | 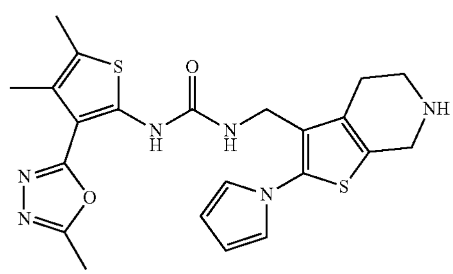 [SMILES: Cc1nnc(-c2c(NC(=O)NCc3c(-n4cccc4)sc4c3CCNC4)sc(C)c2C)o1] | Beige solid; $^1$H NMR (400 MHz, dmso) δ 10.02 (s, 1H), 9.26 (brs, 1H), 8.25 (brs, 1H), 7.08 (s, 2H), 6.30 (s, 2H), 4.31 (s, 2H), 4.12 (d, J = 4.9 Hz, 2H), 3.14-3.37 (m, 2H), 2.83 (brs, 2H), 2.57 (s, 3H), 2.23 (s, 6H); LCMS (electrospray) m/z (M + H)$^+$ 469.02 | +++ | GP 27 |

TABLE 1-continued

Anti-HCVcc genotype ½ activity for Formula I Series

| No. | Structure | Data | EC$_{50}$ | General Procedure (GP) |
|---|---|---|---|---|
| 73 | 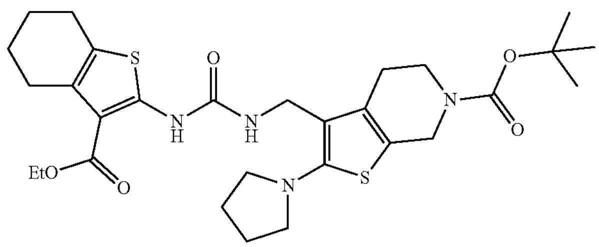 [SMILES: CCOC(=O)c1c(NC(=O)NCc2c(N3CCCC3)sc3c2CCN(C(=O)OC(C)(C)C)C3)sc2c1CCCC2] | Yellow oil; $^1$H NMR (400 MHz, acetone-d$_6$); δ 10.35 (s, 1H), 7.07 (s, 1H), 4.43 (s, 2H), 4.30 (d, J = 4.8 Hz, 2H), 4.24 (q, J = 7.2 Hz, 2H), 3.62 (t, J = 5.6 Hz, 2H), 3.17-3.14 (m, 4H), 2.72-2.70 (m, 2H), 2.59-2.56 (m, 4H), 1.94-1.91 (m, 4H), 1.80-1.70 (m, 4H), 1.44 (s, 9H), 1.30 (t, J = 7.2 Hz, 3H); LCMS (electrospray) m/z 589.18 (M + H)$^+$. | ++++ | GP 20 |
| 74 | 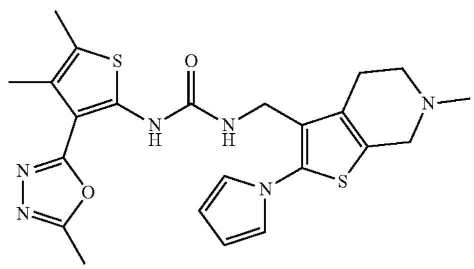 | White solid; $^1$H NMR (400 MHz, acetone) δ 10.21 (s, 1H), 7.35 (brs, 1H), 6.96 (t, J = 2.1 Hz, 2H), 6.24 (t, J = 2.1 Hz, 2H), 4.23 (d, J = 5.1 Hz, 2H), 3.51 (s, 2H), 2.72-2.65 (m, 4H), 2.56 (s, 3H), 2.39 (s, 3H), 2.26 (d, J = 7.2 Hz, 6H); LCMS (electrospray) m/z (M + H)$^+$ 483.17 | ++++ | GP 1 |
| 75 | 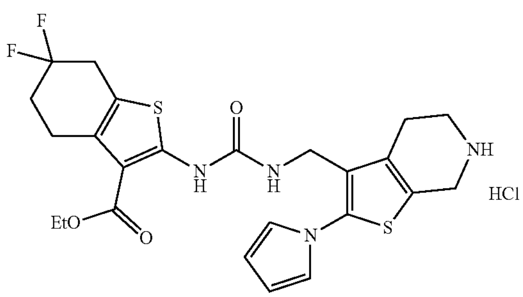 [SMILES: CCOC(=O)c1c(NC(=O)NCc2c(-n3cccc3)sc3c2CCNC3)sc2c1CCC(F)(F)C2 ; Cl] | Beige solid; $^1$H NMR (400 MHz, dmso) δ 10.36 (s, 1H), 9.14 (brs, 1H), 8.23 (t, J = 5.3 Hz, 1H), 7.06 (t, J = 2.0 Hz, 2H), 6.30 (t, J = 2.0 Hz, 2H), 4.29-4.22 (m, 4H), 4.11 (d, J = 5.3 Hz, 2H), 3.42-3.37 (m, 2H), 3.16 (t, J = 13.9 Hz, 2H), 2.91 (t, J = 6.3 Hz, 2H), 2.80 (brs, 2H), 2.26-2.12 (m, 2H), 1.30 (t, J = 7.1 Hz, 3H); LCMS (electrospray) m/z (M + H)$^+$ 521.13 | ++++ | GP 1, GP 2 |
| 76 | 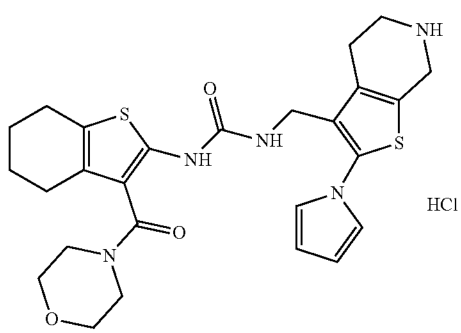 [SMILES: O=C(NCc1c(-n2cccc2)sc2c1CCNC2)Nc1sc2c(c1C(=O)N1CCOCC1)CCCC2 ; Cl] | Beige solid; $^1$H NMR (400 MHz, cd$_3$od) δ 6.92 (s, 2H), 6.31 (s, 2H), 4.40 (s, 2H), 4.19 (s, 2H), 3.68-3.31 (m, 10H), 3.02 (t, J = 5.9 Hz, 2H), 2.64 (brs, 2H), 2.41 (brs, 2H), 1.88-1.74 (m, 4H); LCMS (electrospray) m/z (M + H)$^+$ 526.17 | +++ | GP 12, GP 2 |
| 77 | 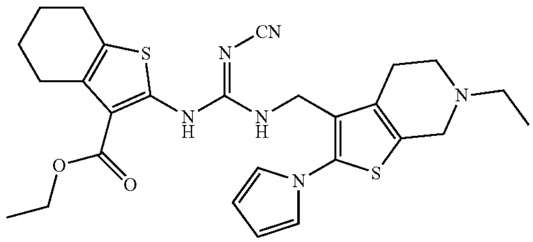 [SMILES: CCOC(=O)c1c(N/C(=N/C#N)NCc2c(-n3cccc3)sc3c2CCN(CC)C3)sc2c1CCCC2] | White solid; $^1$H NMR (400 MHz, Acetone-d$_6$) 7.40 (NH, 1H), 6.95 (s, 2H), 6.23 (s, 2H), 4.48 (s, 2H), 4.28 (q, J = 6.6 Hz, 2H), 3.59 (s, 2H), 2.83-2.75 (m, 4H), 2.66-2.54 (m, 4H), 1.76 (d, J = 5.4 Hz, 4H), 1.34 (t, J = 7.1 Hz, 3H), 1.12 (t, J = 6.8 Hz, 3H); LRMS (electrospray) m/z (M + H)$^+$ 537.19. | + | |

TABLE 1-continued

Anti-HCVcc genotype ½ activity for Formula I Series

| No. | Structure | Data | EC$_{50}$ | General Procedure (GP) |
|---|---|---|---|---|
| 78 | 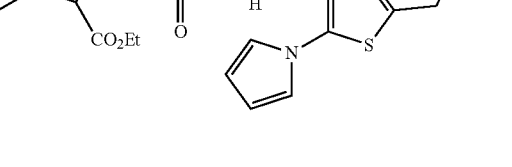 | White solid; $^1$H NMR (400 MHz, DMSO-d$_6$) 12.21 (NH, 1H), 9.47 (NH, 1H), 7.06 (s, 2H), 6.21 (s, 2H), 4.30 (q, J = 7.1 Hz, 2H), 4.17 (d, J = 5.4 Hz, 2H), 3.52 (s, 2H), 2.80-2.60 (m, 6H), 2.58-2.41 (m, 4H), 1.72 (s, 4H), 1.34 (t, J = 7.1 Hz, 3H), 1.05 (t, J = 7.1 Hz, 3H); LRMS (electrospray) m/z (M + H)$^+$ 541.13. | ++++ | GP 32 (TU-MM) |
| 79 | 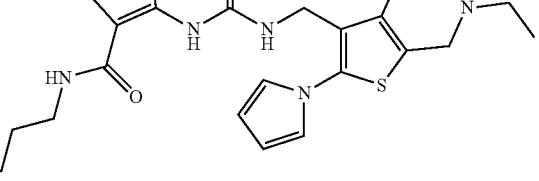 | Yellow solid; $^1$H NMR (400 MHz, acetone) δ 11.07 (s, 1H), 7.05 (brs, 1H), 6.96 (s, 2H), 6.73 (brs, 1H), 6.23 (s, 2H), 4.19 (d, J = 5.1 Hz, 2H), 3.56 (s, 2H), 3.47 (t, J = 5.8 Hz, 2H), 3.41 (q, J = 6.1 Hz, 2H), 3.30 (s, 3H), 2.75-2.65 (m, 6H), 2.63-2.52 (m, 4H), 1.86-1.74 (m, 6H), 1.11 (t, J = 7.1 Hz, 3H); LCMS (electrospray) m/z (M + H)$^+$ 556.30 | +++ | GP 12 |
| 80 | 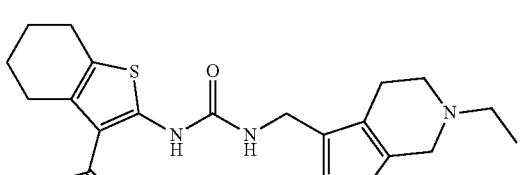 | Yellow solid; $^1$H NMR (400 MHz, acetone) δ 10.89 (s, 1H), 7.05 (brs, 1H), 6.97 (t, J = 2.0 Hz, 2H), 6.56 (brs, 1H), 6.23 (t, J = 2.0 Hz, 2H), 4.20 (d, J = 5.2 Hz, 2H), 3.57 (s, 2H), 3.17 (t, J = 6.4 Hz, 2H), 2.77-2.66 (m, 6H), 2.62-2.53 (m, 4H), 1.91-1.82 (m, 1H), 1.80-1.73 (m, 4H), 1.11 (t, J = 7.2 Hz, 3H), 0.93 (d, J = 6.7 Hz, 6H); LCMS (electrospray) m/z (M + H)$^+$ | ++++ | GP 12 |
| 81 | 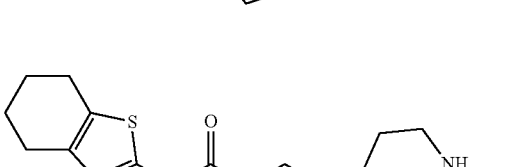 | Ivory solid; $^1$H NMR (400 MHz, DMSO-d$_6$); δ 10.31 (s, 1H), 9.18 (br s, 2H), 8.25 (t, J = 5.6 Hz, 1H), 4.26-4.19 (m, 6H), 3.39-3.36 (m, 2H), 2.86 (t, J = 5.6 Hz, 2H), 2.70-2.65 (m, 2H), 2.55-2.52 (m, 2H), 1.72-1.63 (m, 4H), 1.28 (t, J = 7.2 Hz, 3H); LCMS (electrospray) m/z 498.08 (M + H)$^+$. | ++++ | GP 22 (TU-Z) |
| 82 | 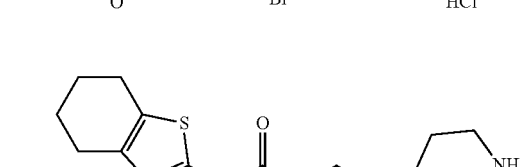 | Red solid; $^1$H NMR (400 MHz, DMSO-d$_6$); δ 10.35 (s, 1H), 9.29 (br s, 2H), 7.90 (br s, 1H), 7.78 (br s, 1H), 7.34-7.23 (m, 5H), 7.07 (s, 2H), 6.29 (s, 2H), 4.45-4.44 (m, 2H), 4.29 (s, 2H), 4.07-4.06 (m, 2H), 3.42-3.37 (m, 2H), 2.82-2.78 (m, 2H), 2.72-2.62 (m, 2H), 2.60-2.55 (m, 2H), 1.78-1.62 (m, 4H); LCMS (electrospray) m/z 546.20 (M + H)$^+$. | +++ | GP 12 |

TABLE 1-continued

Anti-HCVcc genotype ½ activity for Formula I Series

| No. | Structure | Data | EC$_{50}$ | General Procedure (GP) |
|---|---|---|---|---|
| 83 | 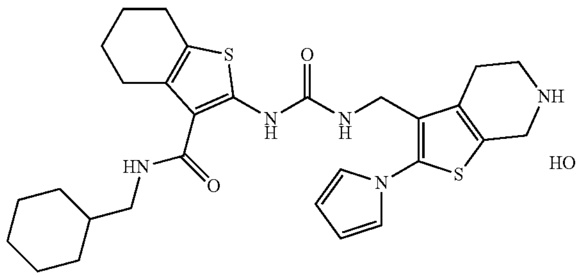 | Purple solid; $^1$H NMR (400 MHz, DMSO-d$_6$); δ 10.24 (s, 1H), 9.71 (br s, 2H), 7.87 (t, J = 5.2 Hz, 1H), 7.24 (t, J = 5.6 Hz, 1H, 7.07 (t, J = 2.0 Hz, 2H), 6.28 (t, J = 2.0 Hz, 2H), 4.28 (s, 2H), 4.05 (d, J = 4.8 Hz, 2H), 3.56-3.50 (m, 2H), 3.08 (t, J = 6.0 Hz, 2H), 2.82-2.78 (m, 2H), 2.68-2.60 (m, 2H), 2.58-2.52 (m, 2H), 1.80-1.45 (m, 9H), 1.28-1.10 (m, 4H), 0.95-0.84 (m, 2H); LCMS (electrospray) m/z 552.24 (M + H)$^+$. | ++ | GP 12 |
| 84 | 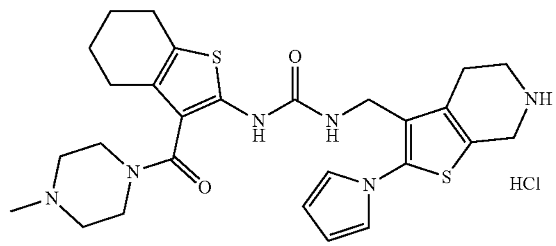 [SMILES: CN1CCN(C(=O)c2c(NC(=O)NCc3c(-n4cccc4)sc4c3CCNC4)sc3c2CCCC3)CC1 ; Cl] | Brown solid; $^1$H NMR (400 MHz, MeOH-d$_4$); δ 6.96-6.94 (m, 2H), 6.29 (s, 2H), 4.39-4.18 (m, 4H), 3.74-3.47 (m, 8H), 3.01-2.94 (m, 6H), 2.63 (s, 3H), 2.47-2.36 (m, 2H), 1.82-1.77 (m, 4H); LCMS (electrospray) m/z 539.16 (M + H)$^+$. | ++ | GP 12 |
| 85 | 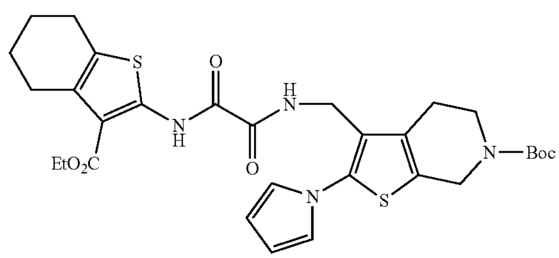 [SMILES: CCOC(=O)c1c(NC(=O)C(=O)NCc2c(-n3cccc3)sc3c2CCN(C(=O)OC(C)(C)C)C3)sc2c1CCCC2] | White solid; $^1$H NMR (400 MHz, Acetone-d$_6$) 12.38 (NH, 1H), 8.47 (NH, 1H), 7.02 (s, 2H), 6.25 (s, 2H), 4.59 (s, 2H), 4.42-4.31 (m, 4H), 3.70 (t, J = 5.7 Hz, 2H), 2.77 (s, 2H), 2.67 (t, J = 5.4 Hz, 4H), 1.79 (d, J = 5.5 Hz, 4H), 1.46 (s, 9H), 1.40 (t, J = 7.1 Hz, 3H); LRMS (electrospray) m/z (M + H)$^+$ 613.98. | + | GP 33 |
| 86 | 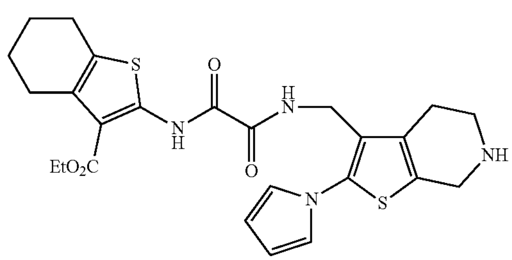 [SMILES: CCOC(=O)c1c(NC(=O)C(=O)NCc2c(-n3cccc3)sc3c2CCNC3)sc2c1CCCC2] | brown solid; $^1$H NMR (400 MHz, DMSO-d$_6$) 12.22 (NH, 1H), 9.59 (NH, 1H), 9.45 (s, 2HCl), 7.11 (s, 2H), 6.26 (s, 2H), 4.38-4.24 (m, 4H), 4.22 (d, J = 5.7 Hz, 2H), 3.39-3.36 (m, 2H), 2.84-2.68 (m, 4H), 2.64 (s, 2H), 1.73 (s, 4H), 1.32 (t, J = 7.0 Hz, 3H); LRMS (electrospray) m/z (M + H)$^+$ 513.02. | ++ | GP 33 |
| 87 | 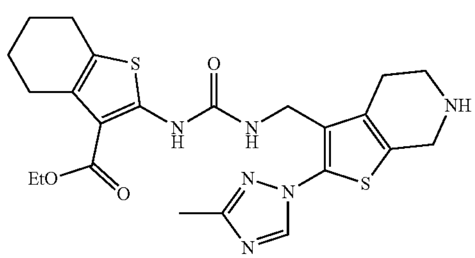 [SMILES: CCOC(=O)c1c(NC(=O)NCc2c(-n3cnc(C)n3)sc3c2CCNC3)sc2c1CCCC2] | Ivory solid; $^1$H NMR (400 MHz, DMSO-d$_6$); δ 10.30 (s, 1H), 9.50 (br s, 2H), 8.98 (s, 1H), 8.25 (s, 1H), 4.32 (s, 2H), 4.23-4.17 (m, 4H), 3.43-3.42 (m, 2H), 2.88-2.80 (m, 2H), 2.64-2.58 (m, 2H), 2.50-2.42 (m, 2H), 2.32 (s, 3H), 1.78-1.67 (m, 4H), 1.27 (t, J = 7.2 Hz, 3H); LCMS (electrospray) m/z 501.20 (M + H)$^+$. | +++ | GP 23 (TU-AA) |

TABLE 1-continued

Anti-HCVcc genotype ½ activity for Formula I Series

| No. | Structure | Data | EC$_{50}$ | General Procedure (GP) |
|---|---|---|---|---|
| 88 | 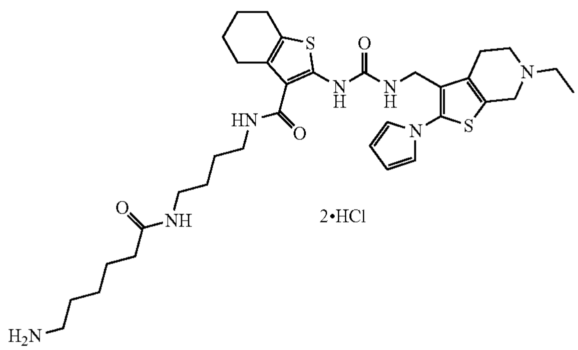 [SMILES: CCN1CCc2c(sc(-n3cccc3)c2CNC(=O)Nc2sc3c(c2C(=O)NCCCCNC(=O)CCCCCN)CCCC3)C1] | Yellow solid; $^1$H NMR (400 MHz, cd$_3$od) δ 6.93 (s, 2H), 6.30 (s, 2H), 4.66 (d, J = 15.2 Hz, 1H), 4.35 (d, J = 15.2 Hz, 1H), 4.20 (dd, J = 27.1, 14.5 Hz, 2H), 3.85 (d, J = 11.9 Hz, 2H), 3.49-3.32 (m, 6H), 3.21 (brs, 2H), 3.08 (brs, 2H), 2.91 (s, 2H), 2.63 (brs, 4H), 2.21 (t, J = 6.9 Hz, 2H), 1.81 (s, 4H), 1.72-1.51 (m, 8H), 1.48-1.43 (m, 3H); LCMS (electrospray) m/z (M + H)$^+$ 668.48 | ++ | GP 12 |
| 89 | 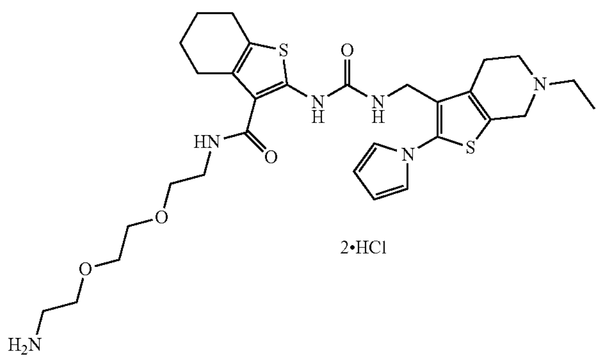 [SMILES: CCN1CCc2c(sc(-n3cccc3)c2CNC(=O)Nc2sc3c(c2C(=O)NCCOCCOCCN)CCCC3)C1] | Yellow solid; $^1$H NMR (400 MHz, cd$_3$od) δ 6.93 (t, J = 2.1 Hz, 2H), 6.30 (t, J = 2.1 Hz, 2H), 4.42 (brs, 2H), 4.20 (s, 2H), 3.76-3.61 (m, 10H), 3.60-3.52 (m, 4H), 3.15-3.02 (m, 4H), 2.70-2.60 (m, 4H), 1.92-1.78 (m, 4H), 1.42 (t, J = 7.3 Hz, 3H); LCMS (electrospray) m/z (M + H)$^+$ 615.35 | ++ | GP 12 |
| 90 | 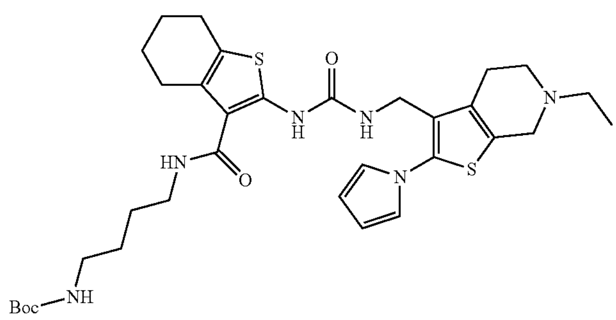 [SMILES: CCN1CCc2c(sc(-n3cccc3)c2CNC(=O)Nc2sc3c(c2C(=O)NCCCCNC(=O)OC(C)(C)C)CCCC3)C1] | White solid; $^1$H NMR (400 MHz, acetone) δ 10.93 (s, 1H), 7.05 (s, 1H), 6.97 (t, J = 2.1 Hz, 2H), 6.57 (brs, 1H), 6.23 (t, J = 2.1 Hz, 2H), 5.94 (s, 1H), 4.20 (d, J = 5.1 Hz, 2H), 3.57 (s, 2H), 3.36 (dd, J = 12.7, 6.4 Hz, 2H), 3.08 (dd, J = 12.9, 6.5 Hz, 2H), 2.75-2.65 (m, 6H), 2.62-2.52 (m, 4H), 1.77 (brs, 4H), 1.64-1.49 (m, 4H), 1.39 (s, 9H), 1.11 (t, J = 7.2 Hz, 3H); LCMS (electrospray) m/z (M + H)$^+$ 655.42 | ++ | GP 12 |
| 91 | 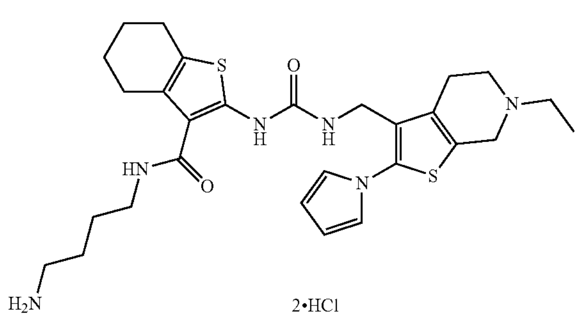 [SMILES: CCN1CCc2c(sc(-n3cccc3)c2CNC(=O)Nc2sc3c(c2C(=O)NCCCCN)CCCC3)C1] | Beige solid; $^1$H NMR (400 MHz, cd$_3$od) δ 6.94 (s, 2H), 6.30 (s, 2H), 4.47 (brs, 2H), 4.20 (s, 2H), 3.62 (brs, 2H), 3.42-3.34 (m, 4H), 3.08 (brs, 2H), 2.97 (t, J = 7.3 Hz, 2H), 2.65 (d, J = 15.1 Hz, 4H), 1.83 (s, 4H), 1.70 (s, 4H), 1.44 (t, J = 7.2 Hz, 3H); LCMS (electrospray) m/z (M + H)$^+$ 555.42 | +++ | GP 12 |

TABLE 1-continued

Anti-HCVcc genotype ½ activity for Formula I Series

| No. | Structure | Data | EC$_{50}$ | General Procedure (GP) |
|---|---|---|---|---|
| 92 | 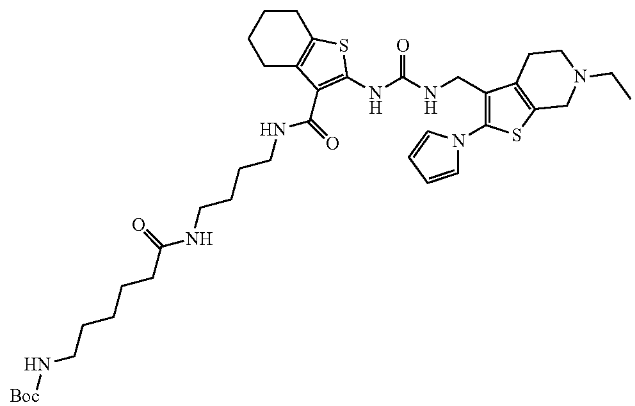 [SMILES: CCN1CCc2c(sc(-n3cccc3)c2CNC(=O)Nc2sc3c(c2C(=O)NCCCCNC(=O)CCCCCNC(=O)OC(C)(C)C)CCCC3)C1] | Yellow solid; $^1$H NMR (400 MHz, acetone) δ 10.80 (s, 1H), 7.12 (brs, 1H), 7.04 (brs, 1H), 6.97 (t, J = 2.1 Hz, 2H), 6.60 (brs, 1H), 6.24 (t, J = 2.1 Hz, 2H), 5.89 (brs, 1H), 4.20 (d, J = 4.9 Hz, 2H), 3.57 (s, 2H), 3.37 (dd, J = 12.3, 6.3 Hz, 2H), 3.22 (dd, J = 12.8, 6.6 Hz, 2H), 3.02 (dd, J = 13.1, 6.8 Hz, 2H), 2.75-2.66 (m, 6H), 2.62-2.53 (m, 4H), 2.12-2.07 (m, 2H), 1.94-1.87 (m, 2H), 1.77 (brs, 4H), 1.55 (dt, J = 22.8, 7.4 Hz, 4H), 1.49-1.41 (m, 2H), 1.39 (s, 9H), 1.34-1.26 (m, 2H), 1.11 (t, J = 7.2 Hz, 3H); LCMS (electrospray) m/z (M + H)$^+$ 768.67 | ++ | GP 12 |
| 93 | 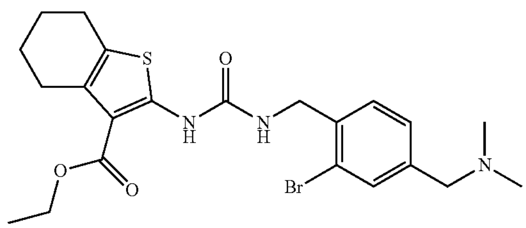 [SMILES: CCOC(=O)c1c(NC(=O)NCc2ccc(CN(C)C)cc2Br)sc2c1CCCC2] | Ivory solid; $^1$H NMR (400 MHz, acetone-d$_6$); δ 10.51 (s, 1H), 7.63 (br s, 1H), 7.55 (s, 1H), 7.45 (d, J = 8.0 Hz, 1H), 7.29 (dd, J = 8.0, 1.2 Hz, 1H), 4.51 (d, J = 6.0 Hz, 2H), 4.27 (q, J = 7.2 Hz, 2H), 3.38 (s, 2H), 2.73-2.71 (m, 2H), 2.58-2.56 (m, 2H), 2.17 (s, 6H), 1.77-1.73 (m, 4H), 1.33 (t, J = 7.2 Hz, 3H); LCMS (electrospray) m/z 494.17 (M + H)$^+$. | +++ | GP 24 (TU-BB) |
| 94 | 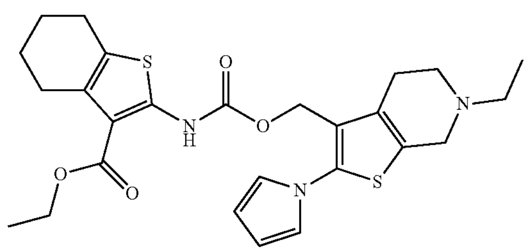 [SMILES: CCOC(=O)c1c(NC(=O)OCc2c(-n3cccc3)sc3c2CCN(CC)C3)sc2c1CCCC2] | White solid; $^1$H NMR (400 MHz, Acetone) δ 10.54 (s, 1H), 6.96 (t, J = 2.4 Hz, 2H), 6.27 (t, J = 2.0 Hz, 2H), 5.04 (s, 2H), 4.29 (q, J = 7.2 Hz, 2H), 3.59 (s, 2H), 2.79-2.72 (m, 6H), 2.61-2.55 (m, 4H), 1.78-1.72 (m, 4H), 1.34 (t, J = 7.2 Hz, 3H), 1.12 (t, J = 7.2 Hz, 3H); LCMS (electrospray) m/z (M + H)$^+$ 514.26 | ++++ | GP 1, GP 29 |
| 95 | 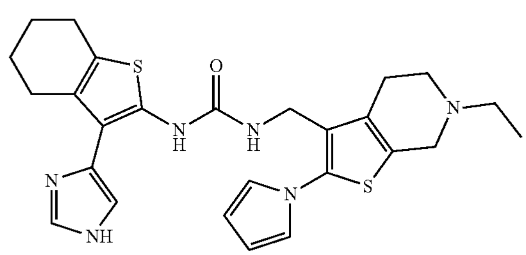 [SMILES: CCN1CCc2c(sc(-n3cccc3)c2CNC(=O)Nc2sc3c(c2-c2c[nH]cn2)CCCC3)C1] | Yellow solid; $^1$H NMR (400 MHz, acetone); δ 13.22 (s, 1H), 10.29 (s, 1H), 8.03 (t, J = 4.8 Hz, 1H), 7.64 (s, 1H), 7.51 (s, 1H), 6.99 (t, J = 2.0 Hz, 2H), 6.25 (t, J = 2.0 Hz, 2H), 4.24 (q, J = 7.1 Hz, 2H), 3.54 (s, 2H), 2.76-2.63 (m, 4H), 2.60-2.50 (m, 6H), 1.70 (brs, 4H), 1.03 (t, J = 7.1 Hz, 3H); LCMS (electrospray) m/z (M + H)$^+$ 507.07 | + | GP 1 |
| 96 | 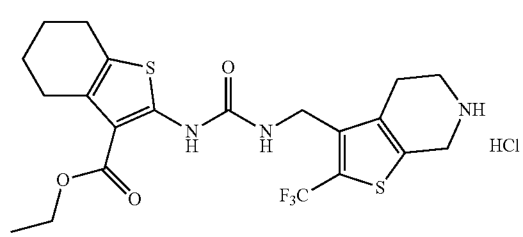 [SMILES: CCOC(=O)c1c(NC(=O)NCc2c(C(F)(F)F)sc3c2CCNC3)sc2c1CCCC2 ; Cl] | White solid; $^1$H NMR (400 MHz, DMSO-d$_6$); δ $^1$H NMR (400 MHz, DMSO-d$_6$); δ 10.34 (s, 1H), 9.30 (br s, 2H), 8.27 (t, J = 5.6 Hz, 1H), 4.39 (s, 2H), 4.35 (d, J = 5.2 Hz, 2H), 4.23 (q, J = 6.8 Hz, 2H), 3.35-3.34 (m, 2H), 2.90-2.89 (m, 2H), 2.66-2.65 (m, 2H), 2.53-2.51 (m, 2H), 1.75-1.65 (m, 4H), 1.28 (t, J = 7.2 Hz, 3H); LCMS (electrospray) m/z 488.19 (M + H)$^+$. | ++++ | GP 25 (TU-CC) |

TABLE 1-continued

Anti-HCVcc genotype ½ activity for Formula I Series

| No. | Structure | Data | EC$_{50}$ | General Procedure (GP) |
|---|---|---|---|---|
| 97 | 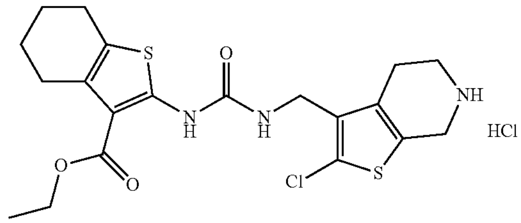 | Pink solid; mp = ° C.; $^1$H NMR (400 MHz, DMSO-d$_6$); δ 10.30 (s, 1H), 9.30 (br s, 2H), 8.29 (t, J = 5.6 Hz, 1H), 4.26-4.19 (m, 6H), 3.35-3.34 (m, 2H), 2.85 (t, J = 5.6 Hz, 2H), 2.67-2.65 (m, 2H), 2.56-2.54 (m, 2H), 1.74-1.64 (m, 4H), 1.28 (t, J = 7.2 Hz, 3H); LCMS (electrospray) m/z 454.12 (M + H)$^+$. | +++ | GP 26 (TU-DD) |
| 98 | 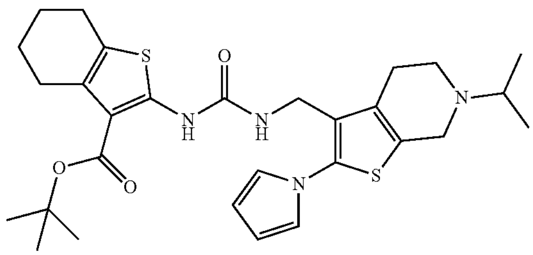 [SMILES: CC(C)N1CCc2c(sc(-n3cccc3)c2CNC(=O)Nc2sc3c(c2C(=O)OC(C)(C)C)CCCC3)C1] | White solid; $^1$H NMR (400 MHz, meod) δ 10.58 (s, 1H), 6.78 (t, J = 2.2 Hz, 2H), 6.29 (t, J = 2.2 Hz, 2H), 4.62 (t, J = 5.2 Hz, 1H), 4.26 (d, J = 5.2 Hz, 2H), 3.69 (s, 2H), 2.96-2.89 (m, 1H), 2.81 (t, J = 5.6 Hz, 2H), 2.70 (d, J = 5.2 Hz, 4H), 2.59 (d, J = 5.2 Hz, 2H), 1.76-1.69 (m, 6H), 1.54 (s, 9H), 1.11 (d, J = 18 Hz, 6H); LCMS (electrospray) m/z (M + H)$^+$ 555.28 | ++++ | GP 1-b (TU-EE) |
| 99 | 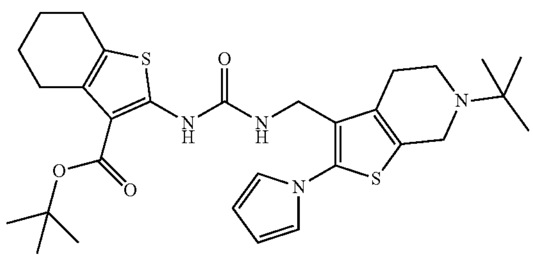 [SMILES: CC(C)(C)OC(=O)c1c(NC(=O)NCc2c(-n3cccc3)sc3c2CCN(C(C)(C)C)C3)sc2c1CCCC2] | White solid; $^1$H NMR (400 MHz, cdcl$_3$) δ 10.58 (s, 1H), 6.78 (t, J = 1.8 Hz, 2H), 6.29 (t, J = 1.6 Hz, 2H), 4.63 (t, J = 5.4 Hz, 1H), 4.26 (d, J = 5.2 Hz, 2H), 3.74 (s, 2H), 2.82 (t, J = 5.6 Hz, 1H), 2.68 (d, J = 4.8 Hz, 4H), 2.59 (d, J = 4.8 Hz, 2H), 1.75 (d, J = 5.2 Hz, 4H), 1.54 (s, 9H), 1.16 (s, 9H); LCMS (electrospray) m/z (M + H)$^+$ 569.36 | ++++ | GP 1-c (TU-FF) |
| 100 | 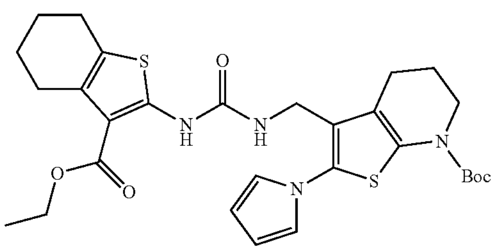 [SMILES: CCOC(=O)c1c(NC(=O)NCc2c(-n3cccc3)sc3c2CCCN3C(=O)OC(C)(C)C)sc2c1CCCC2] | White solid; $^1$H NMR (400 MHz, Acetone) δ 10.38 (s, 1H), 7.19 (brs, 1H), 6.93 (s, 2H), 6.22 (s, 2H), 4.25 (q, J = 7.2 Hz, 2H), 4.20 (d, J = 5.2 Hz, 2H), 3.82 (brs, 2H), 2.72 (brs, 2H), 2.65 (t, J = 6.0 Hz, 2H), 2.56 (brs, 2H), 2.00-1.96 (m, 2H), 1.81-1.72 (m, 4H), 1.53 (s, 9H), 1.31 (t, J = 7.2 Hz, 3H); LCMS (electrospray) m/z (M + H)$^+$ 585.28 | + | GP 1 |
| 101 | 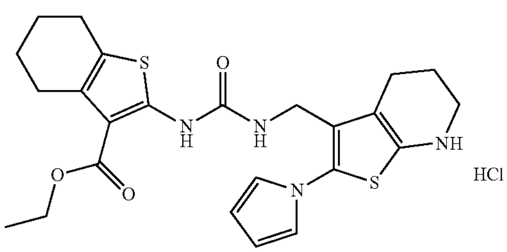 [SMILES: CCOC(=O)c1c(NC(=O)NCc2c(-n3cccc3)sc3c2CCCN3)sc2c1CCCC2 ; Cl] | White solid; $^1$H NMR (400 MHz, Acetone) δ 10.27 (s, 1H), 7.99 (brs, 1H), 6.90 (t, J = 1.6 Hz, 2H), 6.20 (t, J = 1.6 Hz, 2H), 4.24 (q, J = 7.2 Hz, 2H), 3.90 (d, J = 4.8 Hz, 2H), 3.16 (brs, 2H), 2.66 (brs, 2H), 2.52 (brs, 2H), 2.45 (t, J = 6.0 Hz, 2H), 1.80 (brs, 2H), 1.74-1.67 (m, 4H), 1.30 (t, J = 7.2 Hz, 3H); LCMS (electrospray) m/z (M + H)$^+$ 485.21 | +++ | GP 1, GP 2 |
| 102 | 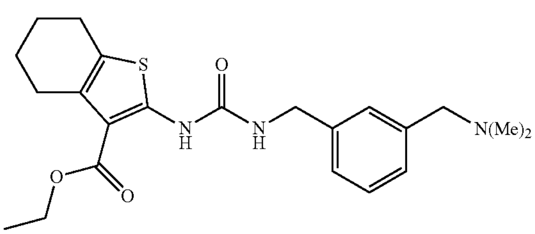 | Yellow oil; $^1$H NMR (400 MHz, CDCl$_3$) δ 10.58 (s, 1H), 7.16-7.23 (m, 4H), 5.55 (s, 1H), 4.44 (d, J = 5.6 Hz, 2H), 4.22 (q, J = 7.2 Hz, 2H), 3.47 (s, 2H), 2.66-2.68 (m, 2H), 2.53-2.55 (m, 2H), 2.26 (s, 6H), 1.70-1.73 (m, 4H), 1.29 (t, J = 7.2 Hz, 3H); LRMS (electrospray) m/z (M + H)$^+$ 416.29. | +++ | GP 1 |

TABLE 1-continued

Anti-HCVcc genotype ½ activity for Formula I Series

| No. | Structure | Data | EC$_{50}$ | General Procedure (GP) |
|---|---|---|---|---|
| 103 | 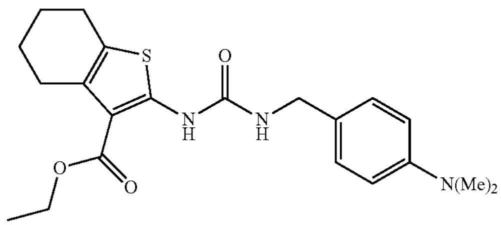 | Yellow oil; $^1$H NMR (400 MHz, CDCl$_3$) δ 10.66 (s, 1H), 8.12 (d, J = 8.8 Hz, 1H), 7.32 (d, J = 7.2 Hz, 2H), 6.96 (s, 1H), 6.94 (d, J = 7.2 Hz, 1H), 4.48 (q, J = 4.8 Hz, 2H), 4.26 (q, J = 7.2 Hz, 2H), 3.05 (d, J = 8.0 Hz, 6H), 2.70-2.71 (m, 2H), 2.56-2.58 (m, 2H), 1.70-1.73 (m, 4H), 1.35 (t, J = 6.8 Hz, 3H); LRMS (electrospray) m/z (M + H)$^+$ 402.27. | ++++ | GP 1 |
| 104 | 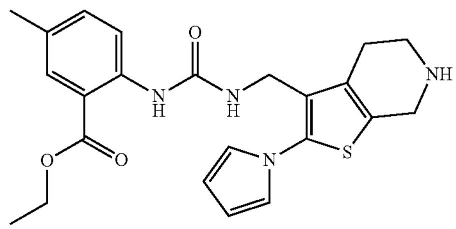 | Yellow solid; $^1$H NMR (400 MHz, CDCl$_3$) δ 9.73 (s, 1H), 9.37 (s, 2H), 8.26 (d, J = 8.4 Hz, 1H), 7.7-7.78 (m, 1 H), 7.71 (s, 1H), 7.36 (d, J = 8.4 Hz, 1H), 7.10 (s, 2H), 6.29 (s, 2H), 4.34 (q, J = 6.8 Hz, 4H), 4.09 (d, J = 5.2 Hz, 2H), 3.55-3.57 (m, 2H), 2.83-2.85 (m, 2H), 2.27 (s, 3H), 1.36 (t, J = 7.2 Hz, 3H); LRMS (electrospray) m/z (M + H)$^+$ 439.22 | ++ | GP 1, GP 2 |
| 105 | 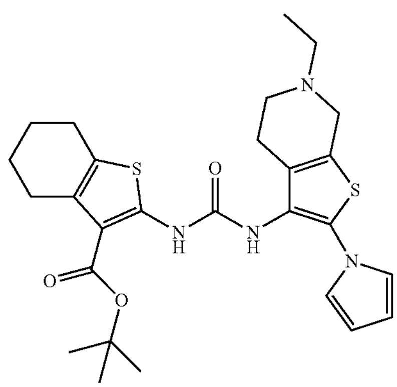 [SMILES: CCN1CCc2c(sc(-n3cccc3)c2NC(=O)Nc2sc3c(c2C(=O)OC(C)(C)C)CCCC3)C1] | White solid; $^1$H NMR (400 MHz, acetone) δ 10.70 (s, 1H), 6.89 (t, J = 2.0 Hz, 2H), 6.18 (t, J = 1.8 Hz, 2H), 3.61 (s, 2H), 2.77 (t, J = 5.6 Hz, 2H), 2.70 (d, J = 4.8 Hz, 2H), 2.57-2.52 (m, 2H), 1.74-1.69 (m, 4H), 1.54 (s, 9H), 1.28 (s, 4H), 1.11 (t, J = 4.8 Hz, 3H); LCMS (electrospray) m/z (M + H)$^+$ 527.32 | ++ | |
| 106 | 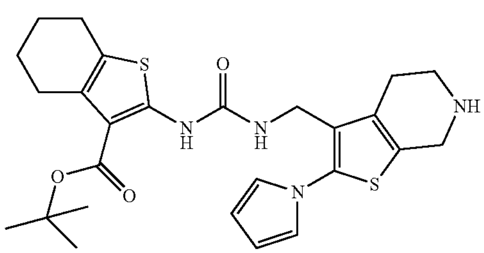 [SMILES: CC(C)(C)OC(=O)c1c(NC(=O)NCc2c(-n3cccc3)sc3c2CCNC3)sc2c1CCCC2] | White solid; $^1$H NMR (400 MHz, cdcl$_3$) δ 10.57 (s, 1H), 6.80 (t, J = 1.8 Hz, 2H), 6.31 (t, J = 2.2 Hz, 2H), 4.63 (t, J = 5.4 Hz, 1H), 4.27 (d, J = 5.6 Hz, 2H), 3.97 (s, 2H), 3.14 (t, J = 5.8 Hz, 2H), 2.69 (t, J = 5.0 Hz, 2H), 2.63-2.58 (m, 4H), 1.76-1.70 (m, 4H), 1.54 (s, 9H); LCMS (electrospray) m/z (M + H)$^+$ 513.24 | ++++ | GP 27 (TU-GG) |
| 107 | 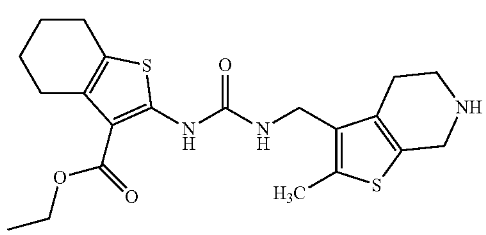 | White solid; $^1$H NMR (400 MHz, DMSO-d$_6$); δ 10.27 (s, 1H), 9.06 (br s, 2H), 8.13 (t, J = 5.2 Hz, 1H), 4.26-4.20 (m, 4H), 4.13-4.12 (m, 2H), 3.43-3.36 (m, 2H), 2.82-2.80 (m, 2H), 2.66-2.64 (m, 2H), 2.56-2.50 (m, 2H), 2.43 (s, 3H), 1.70-1.60 (m, 4H), 1.28 (t, J = 7.2 Hz, 3H); LCMS (electrospray) m/z 434.05 (M + H)$^+$. | ++++ | GP 26 |

TABLE 1-continued

Anti-HCVcc genotype ½ activity for Formula I Series

| No. | Structure | Data | EC$_{50}$ | General Procedure (GP) |
|---|---|---|---|---|
| 108 | 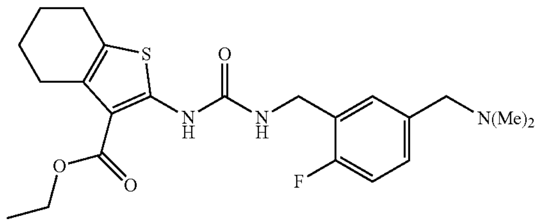 | Yellow oil; $^1$H NMR (400 MHz, CDCl$_3$) δ 10.61 (s, 1H), 7.34 (d, J = 5.2 Hz, 1H), 7.17-7.20 (m, 1H), 6.94-6.99 (m, 1H), 5.51 (s, 1H), 4.55 (q, J = 5.2 Hz, 2H), 4.28 (q, J = 7.2 Hz, 2H), 3.50 (s, 2H), 2.69-2.74 (m, 4H), 2.64-2.68 (m, 4H), 2.14 (s, 6H), 1.33 (t, J = 7.6 Hz, 3H); LRMS (electrospray) m/z (M + H)$^+$ 434.12. | +++ | GP 1 |
| 109 | 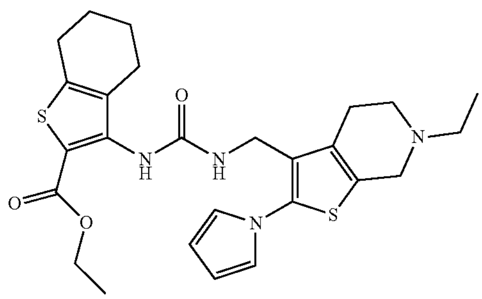 [SMILES: CCOC(=O)c1sc2c(c1NC(=O)NCc1c(-n3cccc3)sc3c1CCN(CC)C3)CCCC2] | Yellow solid; $^1$H NMR (400 MHz, CDCl$_3$) δ 8.28 (s, 1H), 6.81 (s, 2H), 6.31 (s, 2H), 5.09 (s, 1H), 4.21-4.27 (m, 4H), 3.97 (s, 2H), 2.74-2.93 (m, 2H), 2.71-2.73 (m, 4H), 2.39-2.42 (m, 4H), 2.19-2.39 (m, 2H), 1.82-1.84 (m, 2H), 1.37 (t, J = 5.2 Hz, 3H), 1.30 (t, J = 4.8 Hz, 3H); LRMS (electrospray) m/z (M + H)$^+$ 513.24. | ++ | GP 33 (TU-NN) |
| 110 | 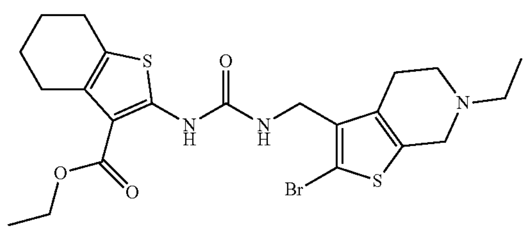 [SMILES: CCOC(=O)c1c(NC(=O)NCc2c(Br)sc3c2CCN(CC)C3)sc2c1CCCC2] | Yellow oil; $^1$H NMR (400 MHz, acetone-d$_6$); δ 10.39 (s, 1H), 7.30 (br s, 1H), 4.34 (d, J = 5.6 Hz, 2H), 4.25 (q, J = 7.2 Hz, 2H), 3.52 (s, 2H), 2.73-2.71 (m, 6H), 2.59-2.52 (m, 4H), 1.78-1.71 (m, 4H), 1.31 (t, J = 7.2 Hz, 3H), 1.09 (t, J = 7.2 Hz, 3H); LCMS (electrospray) m/z 526 (M + H)$^+$. | ++++ | GP 16, GP 22 |
| 111 | 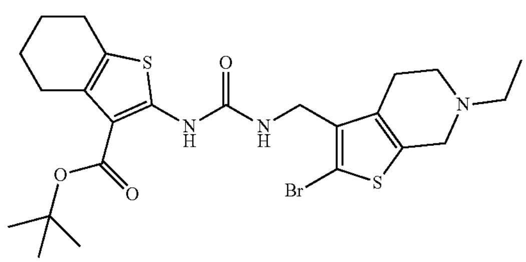 [SMILES: CCN1CCc2c(sc(Br)c2CNC(=O)Nc2sc3c(c2C(=O)OC(C)(C)C)CCCC3)C1] | Brown solid; $^1$H NMR (400 MHz, acetone-d$_6$); δ 10.46 (s, 1H), 7.33 (br s, 1H), 4.33 (d, J = 5.6 Hz, 2H), 3.52 (s, 2H), 2.71-2.68 (m, 6H), 2.58-2.52 (m, 4H), 1.76-1.73 (m, 4H), 1.53 (s, 9H), 1.10 (t, J = 7.2 Hz, 3H); LCMS (electrospray) m/z 554 (M + H)$^+$. | ++++ | GP 16, GP 22 |
| 112 | 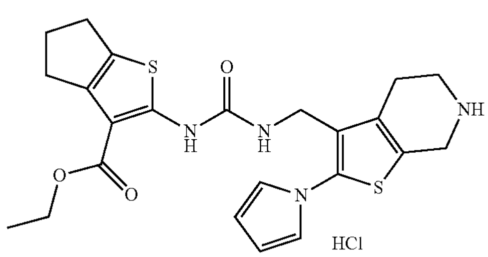 [SMILES: CCOC(=O)c1c(NC(=O)NCc2c(-n3cccc3)sc3c2CCNC3)sc2c1CCC2 ; Cl] | Brown solid; $^1$H NMR (400 MHz, MeOD) δ 6.93 (s, 2H), 6.30 (s, 2H), 4.36 (s, 2H), 4.28 (q, J = 7.2 Hz, 2H), 4.22 (s, 2H), 3.52 (t, J = 6.4 Hz, 2H), 2.97 (t, J = 5.6 Hz, 2H), 2.86 (t, J = 6.8 Hz, 2H), 2.79 (t, J = 6.8 Hz, 2H), 2.39-2.32 (m, 2H), 1.34 (t, J = 7.2 Hz, 3H); LCMS (electrospray) m/z (M + H)$^+$ 471.13 | ++++ | GP 1, GP 2 |

TABLE 1-continued

Anti-HCVcc genotype ½ activity for Formula I Series

| No. | Structure | Data | EC$_{50}$ | General Procedure (GP) |
|---|---|---|---|---|
| 113 | 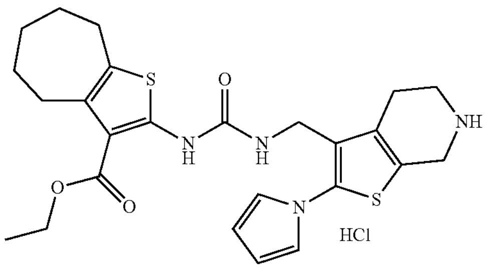 [SMILES: CCOC(=O)c1c(NC(=O)NCc2c(-n3cccc3)sc3c2CCNC3)sc2c1CCCCC2 ; Cl] | Beige solid; $^1$H NMR (400 MHz, MeOD) δ 6.93 (t, J = 2.0 Hz, 2H), 6.30 (t, J = 2.0 Hz, 2H), 4.35 (s, 2H), 4.32 (q, J = 6.4 Hz, 2H), 4.21 (s, 2H), 3.52 (t, J = 6.0 Hz, 2H), 3.05-3.00 (m, 2H), 2.96 (t, J = 6.0 Hz, 2H), 2.70-2.65 (m, 2H), 1.90-1.81 (m, 2H), 1.67-1.56 (m, 4H), 1.35 (t, J = 7.2 Hz, 3H); LCMS (electrospray) m/z (M + H)$^+$ 499.16 | +++ | GP 1, GP 2 |
| 114 | 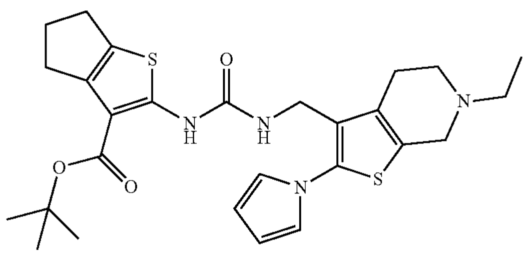 [SMILES: CCN1CCc2c(sc(-n3cccc3)c2CNC(=O)Nc2sc3c(c2C(=O)OC(C)(C)C)CCC3)C1] | White solid; $^1$H NMR (400 MHz, acetone) δ 10.14 (s, 1H), 7.23 (brs, 1H), 6.95 (s, 2H), 6.23 (s, 2H), 4.21 (d, J = 5.2 Hz, 2H), 3.57 (s, 2H), 2.85-2.72 (m, 6H), 2.71-2.68 (m, 2H), 2.56 (q, J = 7.2 Hz, 2H), 2.35-2.26 (m, 2H), 1.53 (s, 9H), 1.11 (t, J = 7.6 Hz, 3H); LCMS (electrospray) m/z (M + H)$^+$ 527.19 | ++++ | GP 1, GP 2 |
| 115 | 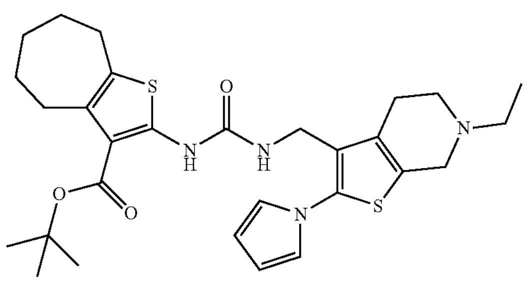 [SMILES: CCN1CCc2c(sc(-n3cccc3)c2CNC(=O)Nc2sc3c(c2C(=O)OC(C)(C)C)CCCCC3)C1] | White solid; $^1$H NMR (400 MHz, MeOD) δ 10.32 (s, 1H), 7.14 (brs, 1H), 6.94 (s, 2H), 6.24 (s, 2H), 4.21 (d, J = 4.8 Hz, 2H), 3.57 (s, 2H), 3.01-2.95 (m, 2H), 2.74-2.69 (m, 2H), 2.68-2.64 (m, 4H), 2.56 (q, J = 7.2 Hz, 2H), 1.88-1.78 (m, 2H), 1.65-1.52 (m, 4H), 1.54 (s, 9H), 1.11 (t, J = 7.2 Hz, 3H); LCMS (electrospray) m/z (M + H)$^+$ 555.28 | ++++ | GP 1, GP 2 |
| 116 | 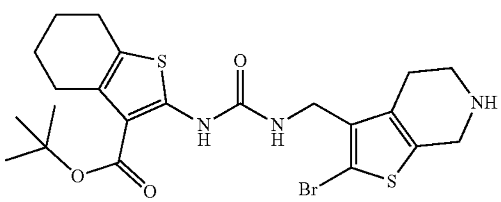 [SMILES: CC(C)(C)OC(=O)c1c(NC(=O)NCc2c(Br)sc3c2CCNC3)sc2c1CCCC2] | White solid; $^1$H NMR (400 MHz, DMSO-d$_6$); δ 10.31 (s, 1H), 8.09 (t, J = 4.8 Hz, 1H), 4.13 (d, J = 5.2 Hz, 2H), 3.73 (s, 2H), 3.44-3.34 (m, 2H), 2.88 (t, J = 5.6 Hz, 2H), 2.66-2.58 (m, 2H), 2.54-2.42 (m, 2H), 1.74-1.62 (m, 4H), 1.51 (s, 9H); LCMS (electrospray) m/z 526 (M + H)$^+$. | ++++ | GP 34 (TU-OO) |
| 117 | 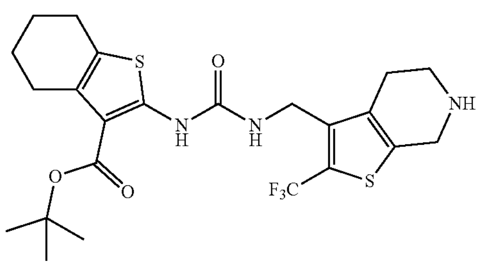 [SMILES: CC(C)(C)OC(=O)c1c(NC(=O)NCc2c(C(F)(F)F)sc3c2CCNC3)sc2c1CCCC2] | White solid; $^1$H NMR (400 MHz, DMSO-d$_6$); δ 10.36 (s, 1H), 8.12 (t, J = 4.8 Hz, 1H), 4.30 (d, J = 4.8 Hz, 2H), 3.87 (s, 2H), 3.34-2.26 (m, 2H), 2.91 (t, J = 4.8 Hz, 2H), 2.66-2.58 (m, 2H), 2.51-2.49 (m, 2H), 1.74-1.62 (m, 4H), 1.51 (s, 9H); LCMS (electrospray) m/z 516 (M + H)$^+$. | ++++ | GP 25, GP 34 |
| 118 | 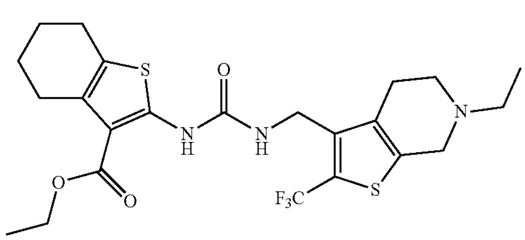 [SMILES: CCOC(=O)c1c(NC(=O)NCc2c(C(F)(F)F)sc3c2CCN(CC)C3)sc2c1CCCC2] | Yellow oil; $^1$H NMR (400 MHz, acetone-d$_6$); δ 10.41 (s, 1H), 7.33 (br s, 1H), 4.49 (d, J = 4.4 Hz, 2H), 4.24 (q, J = 7.2 Hz, 2H), 2.75-7.71 (m, 6H), 2.60-2.54 (m, 4H) 3.52 (s, 2H), 1.70-1.68 (m, 4H), 1.11 (t, J = 7.2 Hz, 3H); LCMS (electrospray) m/z 516 (M + H)$^+$. | ++++ | GP 25 |

TABLE 1-continued

Anti-HCVcc genotype ½ activity for Formula I Series

| No. | Structure | Data | EC₅₀ | General Procedure (GP) |
|---|---|---|---|---|
| 119 | 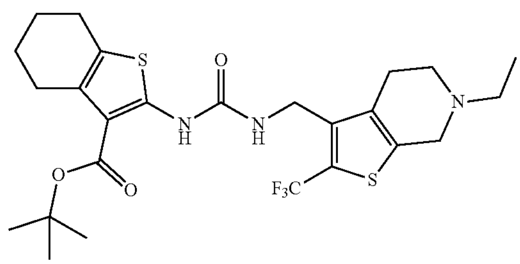 [SMILES: CCN1CCc2c(sc(C(F)(F)F)c2CNC(=O)Nc2sc3c(c2C(=O)OC(C)(C)C)CCCC3)C1] | Ivory oil; ¹H NMR (400 MHz, acetone-d₆); δ 10.46 (s, 1H), 7.36 (br s, 1H), 4.48 (dd, J = 4.2, 1.2 Hz, 2H), 3.65 (s, 2H), 2.74-2.68 (m, 6H), 2.60-2.54 (m, 4H), 1.76-1.73 (m, 4H), 1.53 (s, 9H), 1.10 (t, J = 7.2 Hz, 3H); LCMS (electrospray) m/z 544 (M + H)⁺. | ++++ | GP 25 |
| 120 | 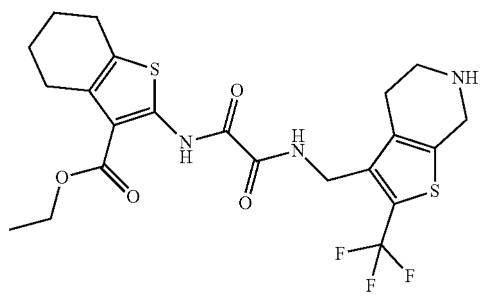 [SMILES: CCOC(=O)c1c(NC(=O)C(=O)NCc2c(C(F)(F)F)sc3c2CCNC3)sc2c1CCCC2] | white solid; ¹H NMR (400 MHz, acetone) δ 4.62-4.57 (m, 2H), 4.38 (q, J = 7.1 Hz, 2H), 3.98 (s, 2H), 3.04 (t, J = 5.7 Hz, 2H), 2.67 (d, J = 5.8 Hz, 2H), 2.63 (t, J = 5.7 Hz, 2H), 1.86-1.72 (m, 6H), 1.40 (t, J = 7.1 Hz, 3H); LCMS (electrospray) m/z (M + H) + 515.96 | ++ | GP1 GP26 GP28 GP33 |
| 121 | 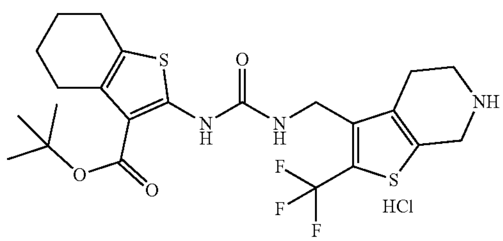 [SMILES: CC(C)(C)OC(=O)c1c(NC(=O)NCc2c(C(F)(F)F)sc3c2CCNC3)sc2c1CCCC2 ; Cl] | White solid; ¹H NMR (400 MHz, DMSO-d6); δ 10.37 (s, 1H), 9.23 (br s, 2 H), 8.26 (t, J = 5.2 Hz, 1H), 4.39 (s, 2H), 4.35 (d, J = 4.8 Hz, 2H), 3.39-3.38 (m, 2H), 2.92-2.84 (m, 2H), 2.64-2.59 (m, 2H), 1.74-1.62 (m, 4H), 1.51 (s, 9H); LCMS (electrospray) m/z 516.02 (M + H) +. | ++++ | GP26, GP35 |
| 122 | 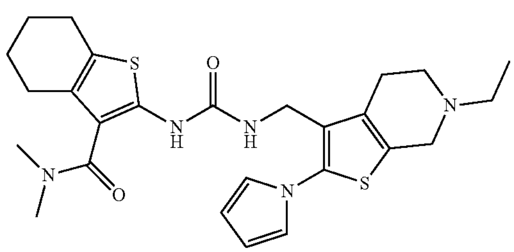 [SMILES: CCN1CCc2c(sc(-n3cccc3)c2CNC(=O)Nc2sc3c(c2C(=O)N(C)C)CCCC3)C1] | white solid; ¹H NMR (400 MHz, acetone) δ 8.25 (s, 1H), 6.92 (t, J = 2.1 Hz, 2H), 6.23 (t, J = 2.1 Hz, 2H), 4.16 (d, J = 5.3 Hz, 2H), 3.57 (t, J = 1.6 Hz, 2H), 2.93 (s, 6H), 2.74 (t, J = 5.9 Hz, 2H), 2.66 (td, J = 5.2, 2.4 Hz, 2H), 2.64-2.59 (m, 2H), 2.56 (t, J = 7.2 Hz, 2H), 2.41-2.32 (m, 2H), 1.84-1.76 (m, 2H), 1.75-1.66 (m, 2H), 1.12 (t, J = 7.2 Hz, 3H); LCMS (electrospray) m/z (M + H) + 512.08 | +++ | GP1 GP12 |
| 123 | 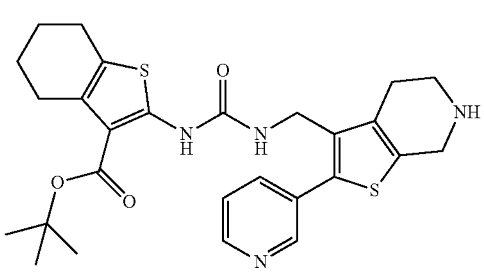 [SMILES: CC(C)(C)OC(=O)c1c(NC(=O)NCc2c(-c3cccnc3)sc3c2CCNC3)sc2c1CCCC2] | White solid; ¹H NMR (400 MHz, DMSO-d6) δ 10.33 (s, NH), 8.66 (s, 1H), 8.55 (d, J = 5.2 Hz, 1H), 8.09 (t, J = 5.0 Hz, NH), 7.86 (d, J = 5.2 Hz, 1H), 7.47 (t, J = 6.6 Hz, 1H), 4.13 (d, J = 4.4 Hz, 2H), 3.86 (s, 2H), 3.30 (s, 2H), 2.93 (t, J = 5.6 Hz, 2H), 2.62 (s, 2H), 2.50 (t, J = 6.0 Hz, 2H), 1.67 (s, 4H), 1.49 (s, 9H); LCMS (electrospray) m/z (M + H) + 525.08. | ++++ | GP35, GP38 |

TABLE 1-continued

Anti-HCVcc genotype ½ activity for Formula I Series

| No. | Structure | Data | EC$_{50}$ | General Procedure (GP) |
|---|---|---|---|---|
| 124 | 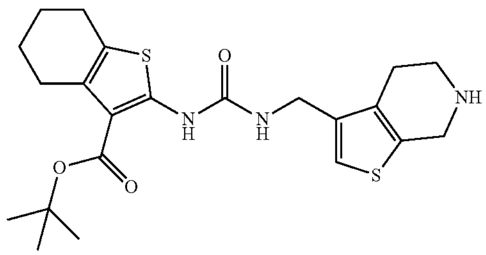 [SMILES: CC(C)(C)OC(=O)c1c(NC(=O)NCc2csc3c2CCNC3)sc2c1CCCC2] | White solid; $^1$H NMR (400 MHz, DMSO-d$_6$) δ 10.38 (s, NH), 8.24 (t, J = 5.0 Hz, NH), 7.28 (s, 1H), 4.30 (s, 2H), 4.18 (d, J = 4.4 Hz, 2H), 3.31 (t, J = 5.8 Hz, 2H), 2.82 (t, J = 6.0 Hz, 2H), 2.63 (t, J = 6.0 Hz, 2H), 2.51 (t, J = 6.0 Hz, 2H), 1.67 (s, 4H), 1.51 (s, 9H); LCMS (electrospray) m/z (M + H) + 447.99. | ++++ | GP16 |
| 125 | 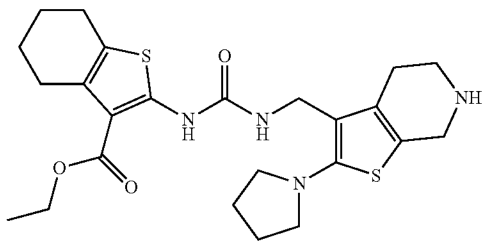 [SMILES: CCOC(=O)c1c(NC(=O)NCc2c(N3CCCC3)sc3c2CCNC3)sc2c1CCCC2] | Yellow solid; $^1$H NMR (400 MHz, MeOH-d4); δ 4.29-4.23 (m, 4H), 3.80 (s, 2H), 3.16-3.12 (m, 4H), 3.04 (t, J = 5.6 Hz, 2H), 2.73-2.71 (m, 2H), 2.59-2.52 (m, 4H), 1.94 (quint, J = 2.4 Hz, 4H), 1.82-1.70 (m, 4H), 1.32 (t, J = 7.2 Hz, 3H); LCMS (electrospray) m/z 489.09 (M + H) +. | +++ | GP20 |
| 126 | 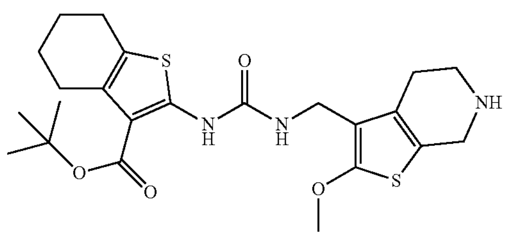 [SMILES: COc1sc2c(c1CNC(=O)Nc1sc3c(c1C(=O)OC(C)(C)C)CCCC3)CCNC2] | Ivory solid; $^1$H NMR (400 MHz, MeOH-d4); δ 4.17 (s, 2H), 3.92 (s, 2H), 3.89 (s, 3H), 3.16 (t, J = 5.6 Hz, 2H), 2.71-2.69 (m, 2H), 2.65 (t, J = 5.6 Hz, 2H), 2.59-2.57 (m, 2H), 1.82-1.70 (m, 4H), 1.56 (s, 9H); LCMS (electrospray) m/z 478.05 (M + H) +. | ++++ | GP27 GP36 |
| 127 | 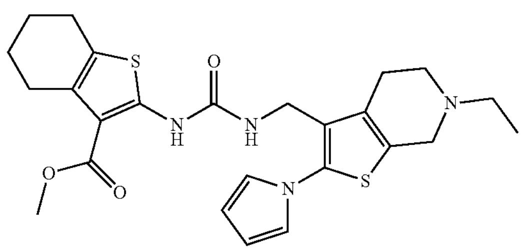 [SMILES: CCN1CCc2c(sc(-n3cccc3)c2CNC(=O)Nc2sc3c(c2C(=O)OC)CCCC3)C1] | Pale yellow solid; $^1$H NMR (400 MHz, MeOD) δ 6.89 (t, J = 2.2 Hz, 2H), 6.26 (t, J = 2.2 Hz, 2H), 4.16 (s, 2H), 3.82 (s, 3H), 3.66 (s, 2H), 2.86 (t, J = 6.0 Hz, 2H), 2.72 (q, J = 6.0 Hz, 4H), 2.67 (q, J = 7.2 Hz, 2H), 2.59 (s, 2H), 1.78 (d, J = 6.0 Hz, 4H), 1.19 (t, J = 7.4 Hz, 3H); LCMS (electrospray) m/z (M + H) + 499.16. | ++++ | GP1 |
| 128 | 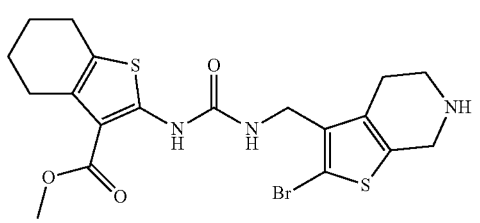 [SMILES: COC(=O)c1c(NC(=O)NCc2c(Br)sc3c2CCNC3)sc2c1CCCC2] | White solid; $^1$H NMR (400 MHz, MeOD) δ 4.29 (s, 2H), 3.86 (s, 2H), 3.81 (s, 3H), 3.06 (t, J = 5.8 Hz, 2H), 2.72 (t, J = 6.0 Hz, 2H), 2.65 (t, J = 6.0 Hz, 2H), 2.59 (t, J = 6.0 Hz, 2H), 1.78 (d, J = 6.0 Hz, 4H); LCMS (electrospray) m/z (M + H)$^+$ 483.85. | ++++ | GP35 |
| 129 | 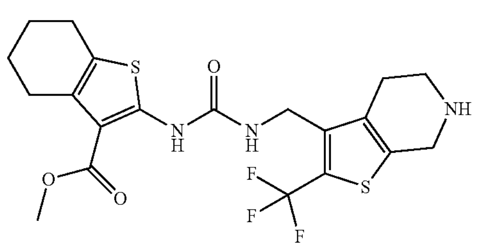 [SMILES: COC(=O)c1c(NC(=O)NCc2c(C(F)(F)F)sc3c2CCNC3)sc2c1CCCC2] | White solid; $^1$H NMR (400 MHz, MeOD) δ 4.42 (s, 2H), 3.99 (s, 2H), 3.81 (s, 3H), 3.07 (t, J = 5.8 Hz, 2H), 2.72 (t, J = 6.0 Hz, 2H), 2.68 (t, J = 6.0 Hz, 2H), 2.59 (t, J = 6.0 Hz, 2H), 1.77 (d, J = 6.0 Hz, 4H); LCMS (electrospray) m/z (M + H) + 473.98. | ++++ | GP26, GP35 |

TABLE 1-continued

Anti-HCVcc genotype ½ activity for Formula I Series

| No. | Structure | Data | EC$_{50}$ | General Procedure (GP) |
|---|---|---|---|---|
| 130 | 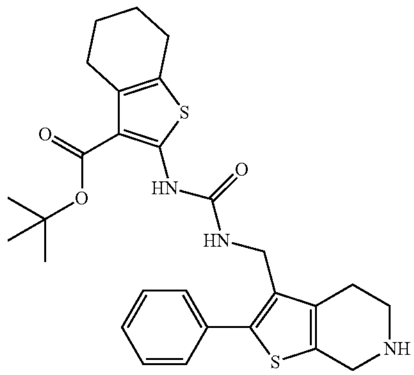 [SMILES: CC(C)(C)OC(=O)c1c(NC(=O)NCc2c(-c3ccccc3)sc3c2CCNC3)sc2c1CCCC2] | White solid; $^1$H NMR (400 MHz, MeOD) δ 7.48-7.39 (m, 4H), 7.37-7.34 (m, 1H), 4.27 (s, 2H), 4.05 (s, 2H), 3.17 (t, J = 5.7 Hz, 2H), 2.75-2.68 (m, 4H), 2.61-2.56 (m, 2H), 1.80-1.73 (m, 4H), 1.56 (s, 9H); LCMS (electrospray) m/z (M + H) + 524.12 | ++++ | GP39, GP35 |
| 131 | 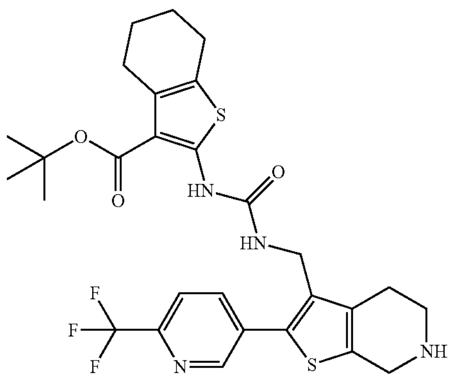 [SMILES: CC(C)(C)OC(=O)c1c(NC(=O)NCc2c(-c3ccc(C(F)(F)F)nc3)sc3c2CCNC3)sc2c1CCCC2] | White solid; $^1$H NMR (400 MHz, MeOD) δ 8.80 (s, 1H), 8.15-8.12 (m, 1H), 7.85 (d, J = 8.2 Hz, 1H), 4.31 (s, 2H), 4.02 (s, 2H), 3.12 (t, J = 5.4 Hz, 2H), 2.74-2.68 (m, 4H), 2.60-2.55 (m, 2H), 1.79-1.74 (m, 4H), 1.55 (s, 9H); LCMS (electrospray) m/z (M + H) + 593.04 | +++ | GP39, GP35 |
| 132 | 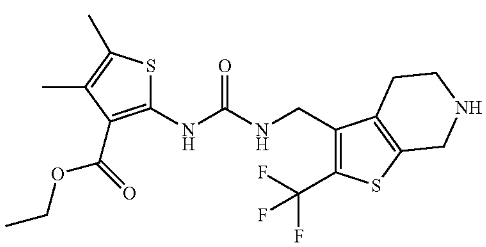 [SMILES: CCOC(=O)c1c(NC(=O)NCc2c(C(F)(F)F)sc3c2CCNC3)sc(C)c1C] | White solid; $^1$H NMR (400 MHz, Acetone) δ 10.39 (s, 1H), 7.32 (brs, 1H), 4.48 (dd, J = 5.2, 1.2 Hz, 2H), 4.26 (q, J = 14.0, 7.2 Hz, 2H), 3.97 (s, 2H), 3.02 (t, J = 6.0 Hz, 2H), 2.66-2.63 (m, 2H), 2.20 (s, 3H), 2.19 (s, 3H), 1.32 (t, J = 7.2 Hz, 3H); LCMS (electrospray) m/z (M + H)+ 461.87 | ++++ | GP1 GP26 GP28 |
| 133 | 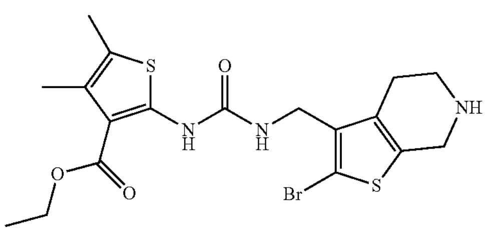 [SMILES: CCOC(=O)c1c(NC(=O)NCc2c(Br)sc3c2CCNC3)sc(C)c1C] | White solid; $^1$H NMR (400 MHz, Acetone) δ 10.38 (s, 1H), 7.29 (brs, 1H), 4.33 (d, J = 5.6 Hz, 2H), 4.27 (q, J = 14.0, 7.2 Hz, 2H), 3.84 (t, J = 1.6 Hz, 2H), 3.00 (t, J = 5.6 Hz, 2H), 2.63-2.59 (m, 2H), 2.20 (s, 3H), 2.19 (s, 3H), 1.33 (t, J = 7.2 Hz, 3H); LCMS (electrospray) m/z (M + H) + 471.81, 473.78 | ++++ | GP1 GP35 |
| 134 | 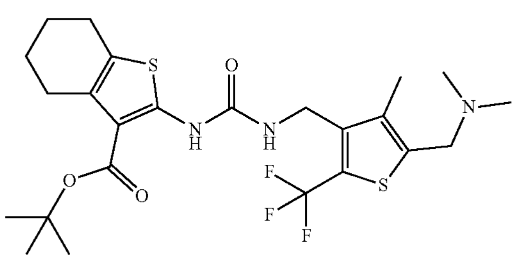 [SMILES: Cc1c(CN(C)C)sc(C(F)(F)F)c1CNC(=O)Nc1sc2c(c1C(=O)OC(C)(C)C)CCCC2] | Ivory solid; $^1$H NMR (400 MHz, acetone-d6); δ 10.45 (s, 1H), 7.33 (br s, 1H), 4.50 (d, J = 4.8 Hz, 2H), 3.59 (s, 2H), 2.71-2.68 (m, 2H), 2.57-2.56 (m, 2H), 2.26 (s, 6H), 2.21 (s, 3H), 1.76-1.68 (m, 4H), 1.53 (s, 9H); LCMS (electrospray) m/z 532.02 (M + H) +. | ++++ | GP26, GP14 |

TABLE 1-continued

Anti-HCVcc genotype ½ activity for Formula I Series

| No. | Structure | Data | EC$_{50}$ | General Procedure (GP) |
|---|---|---|---|---|
| 135 | 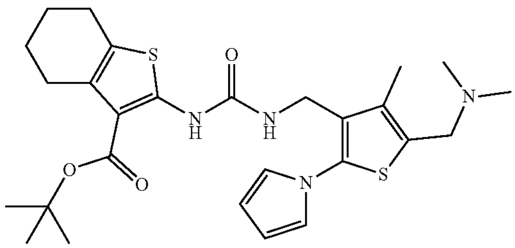 | Ivory solid; $^1$H NMR (400 MHz, acetone-d6); δ 10.45 (s, 1H), 7.33 (br s, 1H), 4.50 (d, J = 4.8 Hz, 2H), 3.59 (s, 2H), 2.71-2.68 (m, 2H), 2.57-2.56 (m, 2H), 2.26 (s, 6H), 2.21 (s, 3H), 1.76-1.68 (m, 4H), 1.53 (s, 9H); LCMS (electrospray) m/z 532.02 (M + H) +. | ++++ | GP14 |
| 136 | 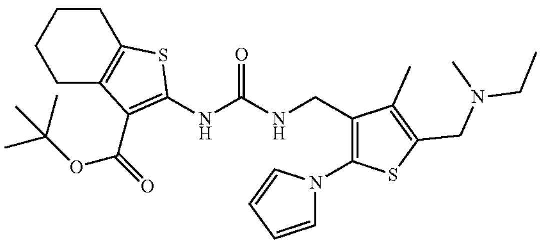 [SMILES: CCN(C)Cc1sc(-n2cccc2)c(CNC(=O)Nc2sc3c(c2C(=O)OC(C)(C)C)CCCC3)c1C] | Yellow solid; $^1$H NMR (400 MHz, acetone-d6); δ 10.44 (s, 1H), 7.21 (br s, 1H), 6.94 (t, J = 2.4, 2H), 6.23 (t, J = 2.4 Hz, 2H), 4.23 (d, J = 4.8 Hz, 2H), 3.60 (s, 2H), 2.71-2.68 (m, 2H), 2.58-2.56 (m, 2H), 2.47 (q, J = 7.2 Hz, 2H), 2.23 (s, 3H), 2.18 (s, 3H), 1.80-1.68 (m, 4H), 1.54 (s, 9H), 1.06 (t, J = 7.2 Hz, 3H); LCMS (electrospray) m/z 543.01 (M + H) +. | ++++ | GP18 |
| 137 | 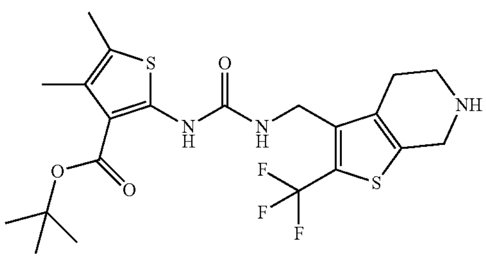 [SMILES: Cc1sc(NC(=O)NCc2c(C(F)(F)F)sc3c2CCNC3)c(C(=O)OC(C)(C)C)c1C] | Beige solid; $^1$H NMR (400 MHz, Acetone) δ 10.46 (s, 1H), 7.35 (brs, 1H), 4.48 (dd, J = 5.6, 1.2 Hz, 2H), 3.97 (s, 2H), 3.02 (t, J = 6.0 Hz, 2H), 2.66-2.62 (m, 2H), 2.19 (s, 3H), 2.17 (s, 3H), 1.55 (s, 9H); LCMS (electrospray) m/z (M + H) + 489.97 | ++++ | GP1, GP26, GP28 |
| 138 | 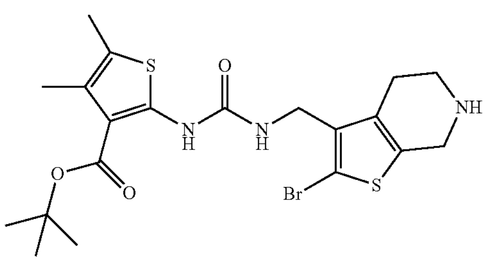 [SMILES: Cc1sc(NC(=O)NCc2c(Br)sc3c2CCNC3)c(C(=O)OC(C)(C)C)c1C] | Beige solid; $^1$H NMR (400 MHz, Acetone) δ 10.46 (s, 1H), 7.31 (brs, 1H), 4.33 (d, J = 5.6 Hz, 2H), 3.83 (s, 2H), 3.00 (t, J = 6.0 Hz, 2H), 2.62-2.59 (m, 2H), 2.19 (s, 3H), 2.17 (s, 3H), 1.55 (s, 9H); LCMS (electrospray) m/z (M + H) + 499.90, 501.88 | ++++ | GP1, GP35 |
| 139 | 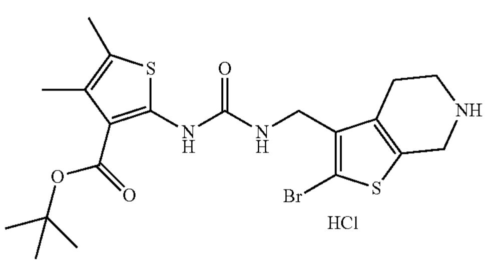 [SMILES: Cc1sc(NC(=O)NCc2c(Br)sc3c2CCNC3)c(C(=O)OC(C)(C)C)c1C ; Cl] | Beige solid; $^1$H NMR (400 MHz, DMSO) δ 10.34 (s, 1H), 9.32 (brs, 1H), 8.22 (t, J = 6.0 Hz, 1H), 4.23 (s, 2H), 4.18 (d, J = 5.6 Hz, 2H), 3.39-3.33 (m, 2H), 2.89-2.82 (m, 2H), 2.15 (s, 3H), 2.12 (s, 3H), 1.52 (s, 9H); LCMS (electrospray) m/z (M + H) + 499.90, 501.88 | ++++ | GP1, GP35, GP2 |

TABLE 1-continued

Anti-HCVcc genotype ½ activity for Formula I Series

| No. | Structure | Data | EC$_{50}$ | General Procedure (GP) |
|---|---|---|---|---|
| 140 | 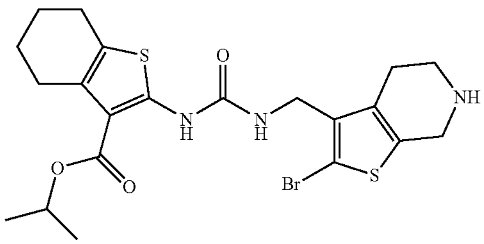 [SMILES: CC(C)OC(=O)c1c(NC(=O)NCc2c(Br)sc3c2CCNC3)sc2c1CCCC2] | White solid; $^1$H NMR (400 MHz, DMSO) d 10.33 (s, 1H), 8.09 (t, J = 5.2 Hz, 1H), 5.05 (pentet, J = 6.4 and 12.4 Hz, 1H), 4.14 (d, J = 5.2 Hz, 2H), 3.73 (s, 2H), 2.89 (t, J = 5.6 Hz, 2H), 2.66 (s, 2H), 2.53 (s, 2H), 1.69 (s, 4H), 1.29 (s, 3H), 2.27 (s, 3H); LCMS (electrospray) m/z (M + H)$^+$ 511.95 | ++++ | GP35 |
| 141 | 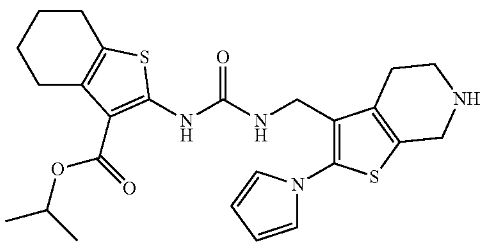 [SMILES: CC(C)OC(=O)c1c(NC(=O)NCc2c(-n3cccc3)sc3c2CCNC3)sc2c1CCCC2] | White solid; $^1$H NMR (400 MHz, MeOD) d 6.89 (t, J = 2.0 Hz, 2H), 6.25 (t, J = 2.0 Hz, 2H), 5.17 (pentet, J = 6.0 and 12.4 Hz, 1H), 4.15 (s, 2H), 3.92 (s, 2H), 3.10 (t, J = 5.6 Hz, 2H), 2.73 (t, J = 5.6 Hz, 2H), 2.64 (t, J = 5.6 Hz, 2H), 2.59 (t, J = 5.6 Hz, 2H), 1.78 (d, J = 6.0 Hz, 4H), 1.34 (s, 3H), 1.32 (s, 3H); LCMS (electrospray) m/z (M + H)$^+$ 499.09 | ++++ | GP28 |
| 142 | 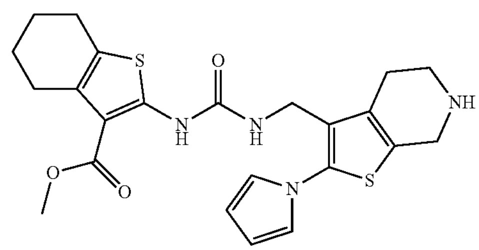 [SMILES: COC(=O)c1c(NC(=O)NCc2c(-n3cccc3)sc3c2CCNC3)sc2c1CCCC2] | White solid; $^1$H NMR (400 MHz, MeOD) d 6.88 (t, J = 2.0 Hz, 2H), 6.26 (t, J = 2.0 Hz, 2H), 4.15 (s, 2H), 3.92 (s, 2H), 3.82 (s, 3H), 3.10 (t, J = 5.6 Hz, 2H), 2.72 (t, J = 5.6 Hz, 2H), 2.64 (t, J = 5.6 Hz, 2H), 2.59 (t, J = 5.6 Hz, 2H), 1.78 (d, J = 6.0 Hz, 4H); LCMS (electrospray) m/z (M + H)$^+$ 470.99 | +++ | GP28 |
| 143 | 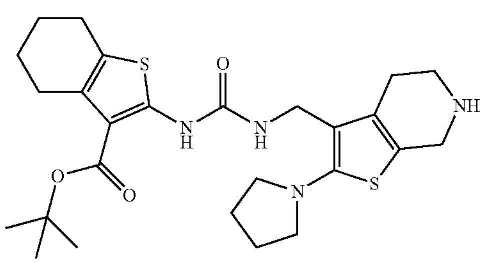 [SMILES: CC(C)(C)OC(=O)c1c(NC(=O)NCc2c(N3CCCC3)sc3c2CCNC3)sc2c1CCCC2] | White solid; $^1$H NMR (400 MHz, DMSO-d6) δ 10.26 (s, NH), 7.84 (t, J = 5.0 Hz, NH), 4.10 (d, J = 4.4 Hz, 4H), 3.73 (s, 2H), 3.14 (s, 2H), 3.08 (s, 2H), 2.93 (t, J = 5.6 Hz, 2H), 2.62 (s, 2H), 2.39 (s, 2H), 1.85 (s, 4H), 1.66 (s, 4H), 1.48 (s, 9H); LCMS (electrospray) m/z (M + H) + 517.05. | ++++ | GP20 |
| 144 | 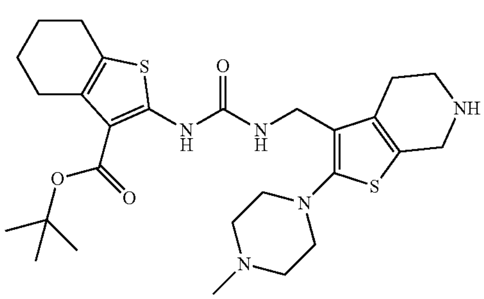 [SMILES: CN1CCN(c2sc3c(c2CNC(=O)Nc2sc4c(c2C(=O)OC(C)(C)C)CCCC4)CCNC3)CC1] | White solid; $^1$H NMR (400 MHz, DMSO-d6) δ 10.28 (s, NH), 7.86 (t, J = 5.0 Hz, NH), 4.14 (d, J = 4.4 Hz, 2H), 3.76 (s, 2H), 3.35 (s, 4H), 3.12 (s, 2H), 2.99 (s, 2H), 2.89 (m, 4H), 2.77 (t, J = 5.6 Hz, 2H), 2.50 (s, 3H), 2.43 (s, 2H), 1.68 (s, 4H), 1.50 (s, 9H); LCMS (electrospray) m/z (M + H) + 546.17. | +++ | GP20 |

TABLE 1-continued

Anti-HCVcc genotype ½ activity for Formula I Series

| No. | Structure | Data | EC$_{50}$ | General Procedure (GP) |
|---|---|---|---|---|
| 145 | 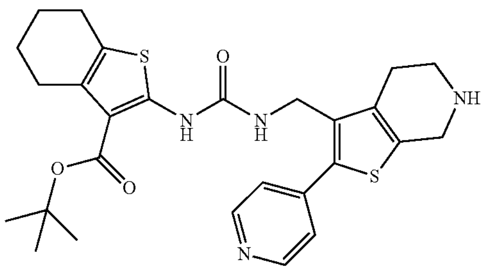 [SMILES: CC(C)(C)OC(=O)c1c(NC(=O)NCc2c(-c3ccncc3)sc3c2CCNC3)sc2c1CCCC2] | White solid; $^1$H NMR (400 MHz, MeOD) δ 8.55 (dd, J = 4.6, 1.6 Hz, 2H), 7.54 (dd, J = 4.6, 1.7 Hz, 2H), 4.35 (s, 2H), 4.06 (s, 2H), 3.16 (t, J = 5.8 Hz, 2H), 2.74 (t, J = 6.0 Hz, 2H), 2.70 (t, J = 5.7 Hz, 2H), 2.58 (t, J = 5.0 Hz, 2H), 1.81-1.73 (m, 4H), 1.55 (s, 9H); LCMS (electrospray) m/z (M + H) + 525.08 | ++++ | GP38, GP35 |
| 146 | 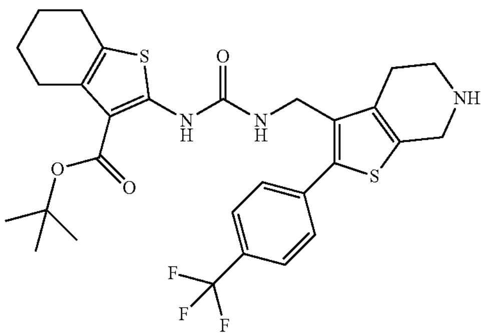 [SMILES: CC(C)(C)OC(=O)c1c(NC(=O)NCc2c(-c3ccc(C(F)(F)F)cc3)sc3c2CCNC3)sc2c1CCCC2] | $^1$H NMR (400 MHz, DMSO) δ 10.34 (s, 1H), 8.12 (t, J = 4.8 Hz, 1H), 7.79 (d, J = 8.2 Hz, 2H), 7.66 (d, J = 8.1 Hz, 2H), 4.16 (d, J = 4.7 Hz, 2H), 3.85 (s, 2H), 2.92 (t, J = 5.6 Hz, 2H), 2.62 (s, 2H), 2.50 (d, J = 5.4 Hz, 4H), 1.67 (s, 4H), 1.49 (s, 9H); LCMS (electrospray) m/z (M + H) + 592.09 | ++++ | GP38, GP35 |
| 147 | 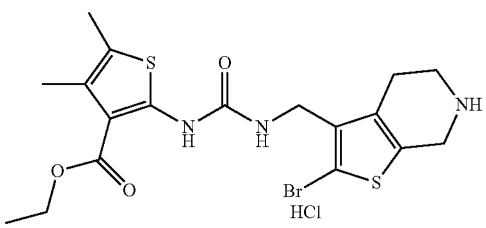 [SMILES: CCOC(=O)c1c(NC(=O)NCc2c(Br)sc3c2CCNC3)sc(C)c1C ; Cl] | White solid; $^1$H NMR (400 MHz, DMSO) δ 10.28 (s, 1H), 9.14 (brs, 1H), 8.23 (t, J = 5.6 Hz, 1H), 4.28-4.22 (m, 4H), 4.19 (d, J = 5.2 Hz, 2H), 3.39-3.33 (m, 2H), 2.88-2.81 (m, 2H), 2.16 (s, 3H), 2.15 (s, 3H), 1.29 (t, J = 6.8 Hz, 3H); LCMS (electrospray) m/z (M + H) + 471.87, 473.85 | ++++ | GP1, GP35, GP2 |
| 148 | 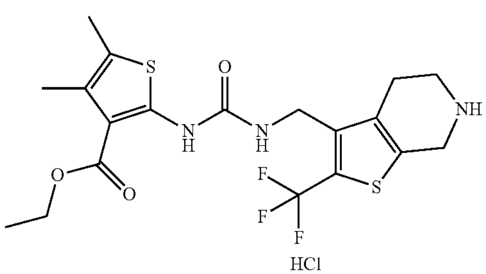 [SMILES: CCOC(=O)c1c(NC(=O)NCc2c(C(F)(F)F)sc3c2CCNC3)sc(C)c1C ; Cl] | White solid; $^1$H NMR (400 MHz, DMSO) δ 10.32 (s, 1H), 9.26 (brs, 1H), 8.26 (t, J = 5.2 Hz, 1H), 4.38-4.32 (m, 4H), 4.25 (q, J = 14.0, 6.8 Hz, 2H), 3.39 (t, J = 7.2 Hz, 2H), 2.91-2.85 (m, 2H), 2.16 (s, 3H), 2.15 (s, 3H), 1.29 (t, J = 6.8 Hz, 3H); LCMS (electrospray) m/z (M + H) + 461.94 | ++++ | GP1, GP26, GP2 |
| 149 | 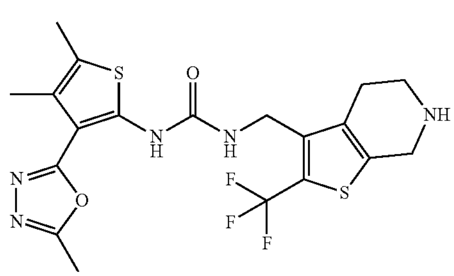 [SMILES: Cc1nnc(-c2c(NC(=O)NCc3c(C(F)(F)F)sc4c3CCNC4)sc(C)c2C)o1] | White solid; $^1$H NMR (400 MHz, acetone) δ 10.21 (s, 1H), 7.51 (brs, 1H), 4.51 (dd, J = 5.6, 1.2 Hz, 2H), 3.97 (s, 2H), 3.02 (t, J = 6.0 Hz, 2H), 2.65 (t, J = 5.2 Hz, 2H), 2.56 (s, 3H), 2.27 (s, 3H), 2.26 (s, 3H); LCMS (electrospray) m/z (M + H) + 471.94 | ++++ | GP1, GP26, GP2 |

TABLE 1-continued

Anti-HCVcc genotype ½ activity for Formula I Series

| No. | Structure | Data | EC$_{50}$ | General Procedure (GP) |
|---|---|---|---|---|
| 150 | 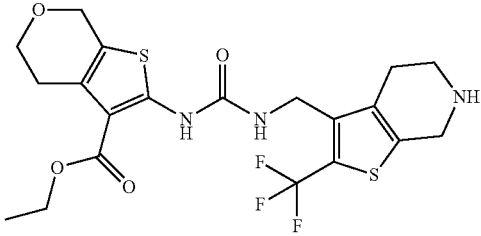 [SMILES: CCOC(=O)c1c(NC(=O)NCc2c(C(F)(F)F)sc3c2CCNC3)sc2c1CCOC2] | White solid; $^1$H NMR (400 MHz, Acetone) δ 10.37 (s, 1H), 7.42 (brs, 1H), 4.61 (t, J = 2.0 Hz, 2H), 4.49 (dd, J = 5.2, 1.2 Hz, 2H), 4.27 (q, J = 14.4, 7.2, 2H), 3.97 (s, 2H), 3.85 (t, J = 6.0 Hz, 2H), 3.02 (t, J = 6.0, 2H), 2.80-2.76 (m, 2H), 2.65 (t, J = 5.2 Hz, 2H), 1.32 (t, J = 7.2 Hz, 3H); LCMS (electrospray) m/z (M + H) + 489.90 | ++++ | GP1, GP26, GP28 |
| 151 | 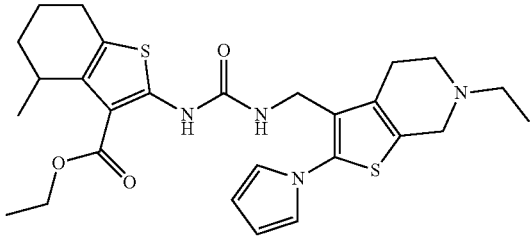 [SMILES: CCOC(=O)c1c(NC(=O)NCc2c(-n3cccc3)sc3c2CCN(CC)C3)sc2c1C(C)CCC2] | Beige solid; $^1$H NMR (400 MHz, acetone) δ 10.47 (s, 1H), 7.17 (brs, 1H), 6.94 (s, 2H), 6.23 (s, 2H), 4.35-4.19 (m, 4H), 3.57 (s, 2H), 3.32-3.28 (m, 1H), 2.74 (d, J = 5.2 Hz, 2H), 2.69-2.66 (m, 2H), 2.63-2.05 (m, 4H), 1.89-1.82 (m, 1H), 1.79-1.71 (m, 2H), 1.67-1.61 (m, 1H), 1.33 (t, J = 7.2 Hz, 3H), 1.17-1.09 (m, 6H); LCMS (electrospray) m/z (M + H) + 527.05 | ++++ | GP1 |
| 152 | 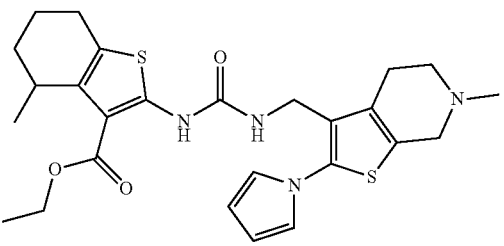 [SMILES: CCOC(=O)c1c(NC(=O)NCc2c(-n3cccc3)sc3c2CCN(C)C3)sc2c1C(C)CCC2] | Beige solid; $^1$H NMR (400 MHz, acetone) δ 10.47 (s, 1H), 7.19 (brs, 1H), 6.95 (t, J = 2.0 Hz, 2H), 6.24 (t, J = 2.0 Hz, 2H), 4.35-4.19 (m, 4H), 3.51 (s, 2H), 3.33-3.28 (m, 1H), 2.70-2.66 (m, 4H), 2.61-2.53 (m, 2H), 2.40 (s, 3H), 1.90-1.84 (m, 1H), 1.81-1.70 (m, 2H), 1.68-1.61 (m, 1H), 1.34 (t, J = 6.8 Hz, 3H), 1.15 (d, J = 7.2 Hz, 3H); LCMS (electrospray) m/z (M + H) + 513.04 | ++++ | GP1 |
| 153 | 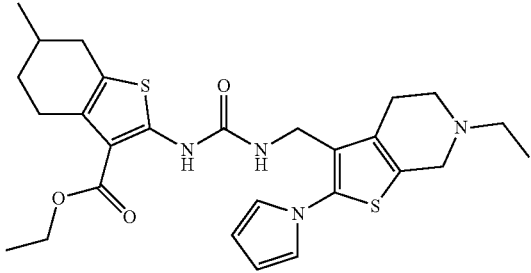 [SMILES: CCOC(=O)c1c(NC(=O)NCc2c(-n3cccc3)sc3c2CCN(CC)C3)sc2c1CCC(C)C2] | Beige solid; $^1$H NMR (400 MHz, acetone) δ 10.38 (s, 1H), 7.17 (brs, 1H), 6.95 (t, J = 2.0 Hz, 2H), 6.23 (t, J = 2.4 Hz, 2H), 4.25 (q, J = 14.0, 6.8 Hz, 2H), 4.23 (d, J = 5.2 Hz, 2H), 3.57 (s, 2H), 2.92-2.83 (m, 1H), 2.76-2.72 (m, 3H), 2.71-2.61 (m, 4H), 2.56 (q, J = 14.0, 7.2 Hz, 2H), 2.22-2.14 (m, 1H), 1.90-1.79 (m, 2H), 1.31 (t, J = 7.2 Hz, 3H), 1.11 (t, J = 7.6 Hz, 3H), 1.04 (d, J = 6.4 Hz, 3H); LCMS (electrospray) m/z (M + H) + 527.05 | ++++ | GP1 |
| 154 | 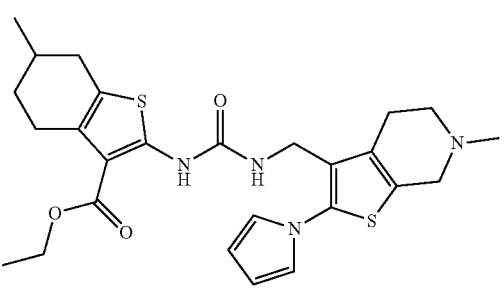 [SMILES: CCOC(=O)c1c(NC(=O)NCc2c(-n3cccc3)sc3c2CCN(C)C3)sc2c1CCC(C)C2] | Beige solid; $^1$H NMR (400 MHz, acetone) δ 10.37 (s, 1H), 7.18 (brs, 1H), 6.95 (t, J = 2.0 Hz, 2H), 6.23 (t, J = 2.4 Hz, 2H), 4.25 (q, J = 13.6, 6.4 Hz, 2H), 4.21 (d, J = 5.2 Hz, 2H), 3.50 (s, 2H), 2.92-2.83 (m, 1H), 2.71-2.58 (m, 7H), 2.39 (s, 3H), 2.22-2.14 (m, 1H), 1.90-1.79 (m, 2H), 1.31 (t, J = 7.2 Hz, 3H), 1.04 (d, J = 6.4 Hz, 3H); LCMS (electrospray) m/z (M + H) + 513.10 | ++++ | GP1 |

TABLE 1-continued

Anti-HCVcc genotype ½ activity for Formula I Series

| No. | Structure | Data | EC$_{50}$ | General Procedure (GP) |
|---|---|---|---|---|
| 155 | 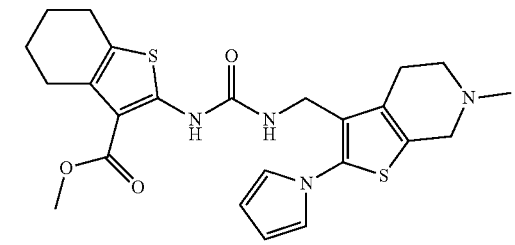 [SMILES: COC(=O)c1c(NC(=O)NCc2c(-n3cccc3)sc3c2CCN(C)C3)sc2c1CCCC2] | White solid; $^1$H NMR (400 MHz, DMSO) δ 10.18 (s, 1H), 8.04 (t, J = 4.8 Hz, 1H), 6.99 (t, J = 2.2 Hz, 2H), 6.25 (t, J = 2.2 Hz, 2H), 4.03 (d, J = 5.2 Hz, 2H), 3.76 (s, 3H), 3.48 (s, 2H), 2.65 (t, J = 5.8 Hz, 4H), 2.60 (s, 2H), 2.53 (s, 2H), 2.36 (s, 3H), 1.70 (s, 4H); LCMS (electrospray) m/z (M + H)$^+$ 485.07 | +++ | GP1 |
| 156 | 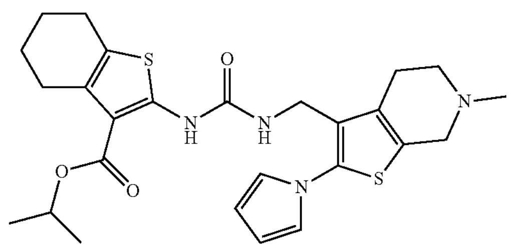 [SMILES: CC(C)OC(=O)c1c(NC(=O)NCc2c(-n3cccc3)sc3c2CCN(C)C3)sc2c1CCCC2] | Pale yellow solid; $^1$H NMR (400 MHz, DMSO) δ 10.36 (s, 1H), 8.05 (t, J = 4.8 Hz, 1H), 6.99 (t, J = 2.2 Hz, 2H), 6.25 (t, J = 2.2 Hz, 2H), 5.06 (pentet, J = 6.4 and 12.4 Hz, 1H), 4.02 (d, J = 5.2 Hz, 2H), 3.48 (s, 3H), 2.65 (t, J = 5.8 Hz, 4H), 2.59 (s, 2H), 2.53 (s, 2H), 2.35 (s, 3H), 1.70 (s, 4H), 1.29 (s, 3H), 1.28 (s, 3H); LCMS (electrospray) m/z (M + H)$^+$ 513.10 | ++++ | GP1 |
| 157 | 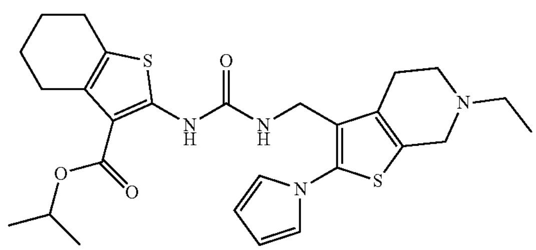 [SMILES: CCN1CCc2c(sc(-n3cccc3)c2CNC(=O)Nc2sc3c(c2C(=O)OC(C)C)CCCC3)C1] | White solid; $^1$H NMR (400 MHz, acetone) δ 10.44 (s, 1H), 7.20 (s, 1H), 6.95 (t, J = 2.2 Hz, 2H), 6.24 (t, J = 2.2 Hz, 2H), 5.11 (pentet, J = 6.4 and 12.0 Hz, 1H), 4.22 (d, J = 4.0 Hz, 2H), 3.57 (s, 2H), 2.67-2.78 (m, 6H), 2.56 (q, J = 7.2 Hz, 4H), 1.75 (d, J = 6.0 Hz, 4H), 1.32 (s, 3H), 1.30 (s, 3H), 1.11 (t, J = 7.4 Hz, 3H); LCMS (electrospray) m/z (M + H)$^+$ 526.21 | ++++ | GP1 |
| 158 | 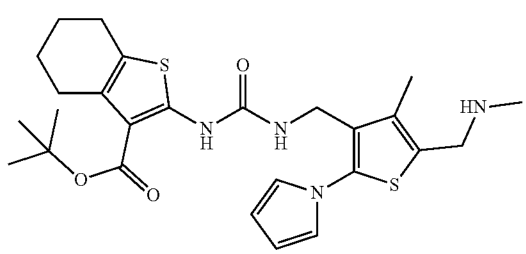 [SMILES: CNCc1sc(-n2cccc2)c(CNC(=O)Nc2sc3c(c2C(=O)OC(C)(C)C)CCCC3)c1C] | Yellow solid; $^1$H NMR (400 MHz, acetone-d6); δ 11.18 (s, 1H), 6.86 (t, J = 2.0 Hz, 2H), 6.20 (t, J = 2.0 Hz, 2H), 4.76 (s, 2H), 4.15 (s, 2H), 3.12 (s, 3H), 2.74-2.72 (m, 2H), 2.60-2.58 (m, 2H), 2.25 (s, 3H), 1.78-1.73 (m, 4H), 1.57 (s, 9H); LCMS (electrospray) m/z 515.00 (M + H) +. | +++ | GP14 |
| 159 | 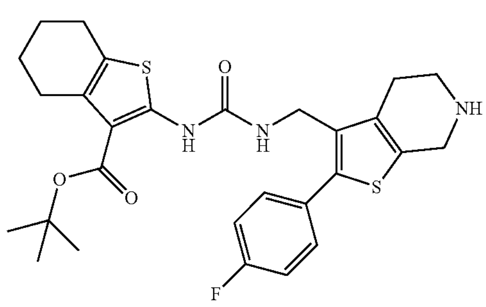 [SMILES: CC(C)(C)OC(=O)c1c(NC(=O)NCc2c(-c3ccc(F)cc3)sc3c2CCNC3)sc2c1CCCC2] | white solid; $^1$H NMR (400 MHz, CDCl$_3$) δ 10.65 (s, 1H), 7.38-7.30 (m, 2H), 7.12-7.04 (m, 2H), 4.76 (t, J = 4.7 Hz, 1H), 4.36 (d, J = 4.9 Hz, 2H), 4.01 (s, 2H), 3.12 (t, J = 5.8 Hz, 2H), 2.73-2.65 (m, 2H), 2.64-2.53 (m, 4H), 1.83-1.69 (m, 4H), 1.52 (s, 9H); LCMS (electrospray) m/z (M + H)$^+$ 542.08 | ++++ | GP38, GP35 |

TABLE 1-continued

Anti-HCVcc genotype ½ activity for Formula I Series

| No. | Structure | Data | EC$_{50}$ | General Procedure (GP) |
|---|---|---|---|---|
| 160 | 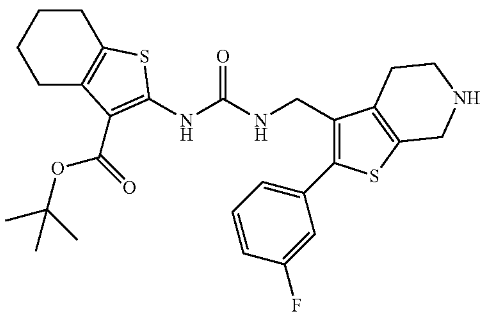 [SMILES: CC(C)(C)OC(=O)c1c(NC(=O)NCc2c(-c3cccc(F)c3)sc3c2CCNC3)sc2c1CCCC2] | white solid; $^1$H NMR (400 MHz, CDCl$_3$) δ 10.65 (s, 1H), 7.35 (dd, J = 14.3, 7.8 Hz, 1H), 7.16 (d, J = 7.5 Hz, 1H), 7.12-7.00 (m, 2H), 4.87 (s, 1H), 4.40 (d, J = 4.6 Hz, 2H), 4.01 (s, 2H), 3.12 (t, J = 5.4 Hz, 2H), 2.68 (s, 2H), 2.60 (d, J = 5.4 Hz, 4H), 1.75 (d, J = 5.0 Hz, 4H), 1.51 (s, 9H).; LCMS (electrospray) m/z (M + H)$^+$ 542.08 | ++++ | GP38, GP35 |
| 161 | 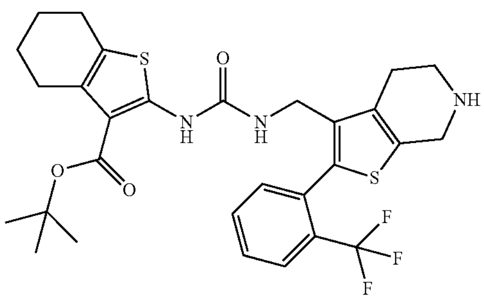 [SMILES: CC(C)(C)OC(=O)c1c(NC(=O)NCc2c(-c3ccccc3C(F)(F)F)sc3c2CCNC3)sc2c1CCCC2] | white solid; $^1$H NMR (400 MHz, cdcl$_3$) δ 10.50 (s, 1H), 7.74 (d, J = 7.6 Hz, 1H), 7.56-7.45 (m, 2H), 7.35 (d, J = 7.3 Hz, 1H), 4.68 (s, 1H), 4.14 (s, 2H), 4.02 (s, 2H), 3.13 (s, 2H), 2.68 (s, 2H), 2.60 (d, J = 16.1 Hz, 4H), 1.74 (s, 4H), 1.53 (d, J = 2.2 Hz, 9H); LCMS (electrospray) m/z (M + H)$^+$ 592.09 | +++ | GP38, GP35 |
| 162 | 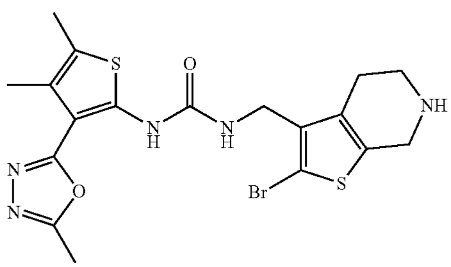 [SMILES: Cc1nnc(-c2c(NC(=O)NCc3c(Br)sc4c3CCNC4)sc(C)c2C)o1] | Yellow solid; $^1$H NMR (400 MHz, DMSO) δ 9.93 (s, 1H), 8.14 (brs, 1H), 4.16 (d, J = 5.2 Hz, 2H), 3.73 (s, 2H), 2.88 (t, J = 4.8 Hz, 2H), 2.56 (s, 3H), 2.49-2.45 (m, 2H), 2.22 (s, 6H); LCMS (electrospray) m/z (M + H) + 481.88, 483.85 | ++++ | GP1 GP35 |
| 163 | 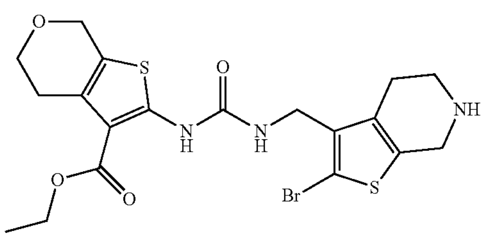 [SMILES: CCOC(=O)c1c(NC(=O)NCc2c(Br)sc3c2CCNC3)sc2c1CCOC2] | Beige solid; $^1$H NMR (400 MHz, DMSO) δ 10.27 (s, 1H), 8.15 (brs, 1H), 4.45 (s, 2H), 4.24 (q, J = 14.4, 7.2, 2H), 4.16 (d, J = 5.6 Hz, 2H), 3.82 (t, J = 5.2 Hz, 2H), 3.74 (s, 2H), 2.89 (t, J = 5.6 Hz, 2H), 2.76-2.71 (m, 2H), 2.49-2.46 (m, 2H), 1.28 (t, J = 7.2 Hz, 3H); LCMS (electrospray) m/z (M + H) + 499.90, 501.88 | ++++ | GP1 GP35 |
| 164 | 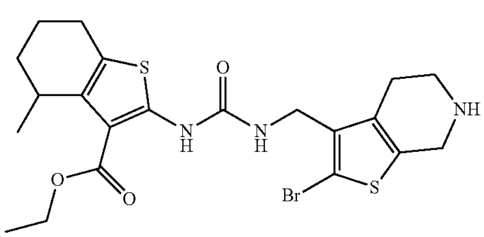 [SMILES: CCOC(=O)c1c(NC(=O)NCc2c(Br)sc3c2CCNC3)sc2c1C(C)CCC2] | White solid; $^1$H NMR (400 MHz, DMSO) δ 10.31 (s, 1H), 8.09 (t, J = 4.8 Hz, 1H), 4.32-4.18 (m, 2H), 4.15 (d, J = 5.6 Hz, 2H), 3.73 (s, 2H), 3.28-3.10 (m, 1H), 2.89 (t, J = 6.0 Hz, 2H), 2.60-2.53 (m, 2H), 2.49-2.41 (m, 2H), 1.81-1.64 (m, 3H), 1.63-1.57 (m, 1H), 1.29 (t, J = 6.8 Hz, 3H), 1.10 (d, J = 6.8 Hz, 3H); LCMS (electrospray) m/z (M + H) + 511.95, 513.99 | ++++ | GP1 GP35 |

… TABLE 1-continued

Anti-HCVcc genotype ½ activity for Formula I Series

| No. | Structure | Data | EC$_{50}$ | General Procedure (GP) |
|---|---|---|---|---|
| 165 | 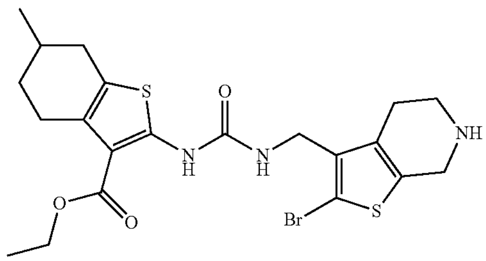 [SMILES: CCOC(=O)c1c(NC(=O)NCc2c(Br)sc3c2CCNC3)sc2c1CCC(C)C2] | White solid; $^1$H NMR (400 MHz, CDCl3) δ 10.56 (s, 1H), 5.09 (brs, 1H), 4.35 (d, J = 5.6 Hz, 2H), 4.26 (q, J = 14.0, 6.8 Hz, 2H), 3.88 (s, 2H), 3.08 (t, J = 6.0 Hz, 2H), 2.91-2.85 (m, 1H), 2.70-2.58 (m, 3H), 2.26-2.18 (m, 1H), 1.90-1.80 (m, 2H), 1.71 (s, 2H), 1.34 (t, J = 6.8 Hz, 3H), 1.05 (d, J = 6.4 Hz, 3H); LCMS (electrospray) m/z (M + H) + 511.95, 513.92 | ++++ | GP1 GP35 |
| 166 | 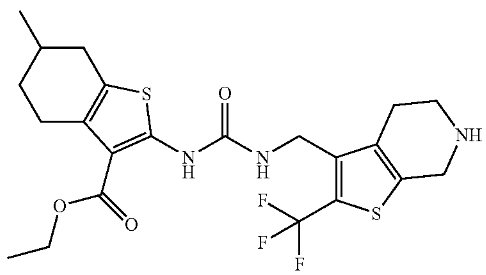 [SMILES: CCOC(=O)c1c(NC(=O)NCc2c(C(F)(F)F)sc3c2CCNC3)sc2c1CCC(C)C2] | Yellow solid; $^1$H NMR (400 MHz, CDCl3) δ 10.55 (s, 1H), 5.02 (brs, 1H), 4.49 (d, J = 5.6 Hz, 2H), 4.26 (q, J = 14.4, 7.2 Hz, 2H), 4.00 (s, 2H), 3.10 (t, J = 5.2 Hz, 2H), 2.91-2.85 (m, 1H), 2.71-2.58 (m, 3H), 2.27-2.19 (m, 1H), 1.89-1.83 (m, 2H), 1.68 (brs, 2H), 1.34 (t, J = 6.8 Hz, 3H), 1.06 (d, J = 6.4 Hz, 3H); LCMS (electrospray) m/z (M + H) + 502.01 | ++++ | GP1 GP26, GP28 |
| 167 | 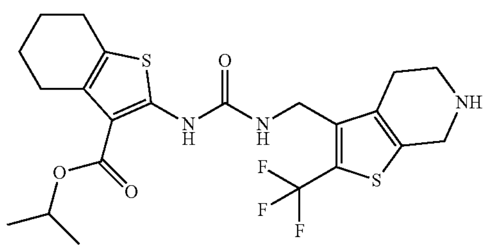 [SMILES: CC(C)OC(=O)c1c(NC(=O)NCc2c(C(F)(F)F)sc3c2CCNC3)sc2c1CCCC2] | White solid; $^1$H NMR (400 MHz, DMSO) δ 10.36 (s, 1H), 8.14 (t, J = 5.0 Hz, 1H), 5.05 (pentet, J = 6.4 and 12.4 Hz, 1H), 4.30 (d, J = 4.8 Hz, 2H), 3.87 (s, 2H), 2.91 (t, J = 5.8 Hz, 2H), 2.66 (s, 2H), 2.53 (s, 4H), 1.69 (s, 4H), 1.29 (s, 3H), 1.27 (s, 3H); LCMS (electrospray) m/z (M + H)$^+$ 501.95 | ++++ | GP26, GP35 |
| 168 | 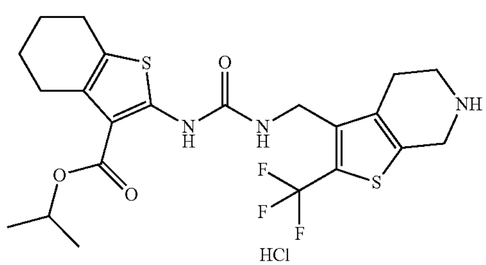 [SMILES: CC(C)OC(=O)c1c(NC(=O)NCc2c(C(F)(F)F)sc3c2CCNC3)sc2c1CCCC2 ; Cl] | White solid; $^1$H NMR (400 MHz, DMSO) δ 10.39 (s, 1H), 9.25 (br, 1H), 8.26 (t, J = 5.0 Hz, 1H), 5.05 (pentet, J = 6.4 and 12.4 Hz, 1H), 4.33 (t, J = 5.6 Hz, 4H), 2.85 (s, 2H), 2.65 (s, 2H), 2.50 (t, J = 5.8 Hz, 4H), 1.69 (s, 4H), 1.29 (s, 3H), 1.27 (s, 3H); LCMS (electrospray) m/z (M + H)$^+$ 502.01 | ++++ | GP26 |
| 169 | 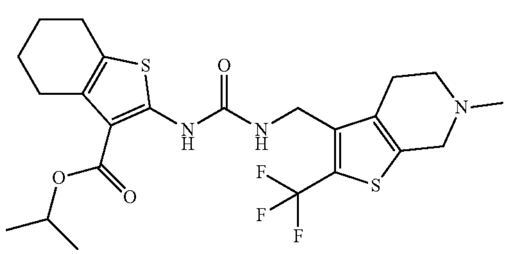 | White solid; $^1$H NMR (400 MHz, MeOD) δ 5.16 (pentet, J = 6.4 and 12.4 Hz, 1H), 4.42 (d, J = 1.2 Hz, 2H), 3.67 (s, 2H), 2.78-2.82 (m, 4H), 2.74 (d, J = 6.0 Hz, 2H), 2.59 (d, J = 6.0 Hz, 2H), 2.48 (s, 3H), 1.78 (d, J = 5.6 Hz, 4H), 1.33 (s, 3H), 1.32 (s, 3H); LCMS (electrospray) m/z (M + H)$^+$ 561.10 | ++++ | GP26, GP35, GP5 |

TABLE 1-continued

Anti-HCVcc genotype ½ activity for Formula I Series

| No. | Structure | Data | EC$_{50}$ | General Procedure (GP) |
|---|---|---|---|---|
| 170 | 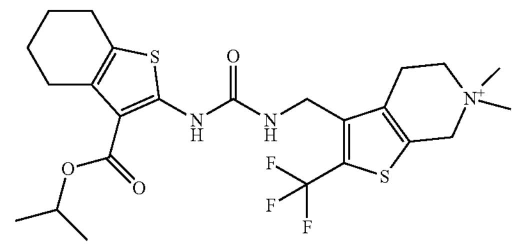 [SMILES: CC(C)OC(=O)c1c(NC(=O)NCc2c(C(F)(F)F)sc3c2CC[N+](C)(C)C3)sc2c1CCCC2] | Pale yellow solid; $^1$H NMR (400 MHz, DMSO) δ 10.41 (s, 1H), 8.23 (t, J = 5.0 Hz, 1H), 5.05 (pentet, J = 6.4 and 12.4 Hz, 1H), 4.76 (s, 2H), 4.35 (d, J = 5.2 Hz, 2H), 3.73 (t, J = 6.2 Hz, 2H), 3.17 (s, 6H), 3.07 (t, J = 6.2 Hz, 2H), 2.66 (s, 2H), 2.53 (s, 2H), 1.69 (s, 4H), 1.29 (s, 3H), 1.27 (s, 3H); LCMS (electrospray) m/z (M + H)$^+$ 530.04 | ++++ | GP26, GP35, GP3 |
| 171 | 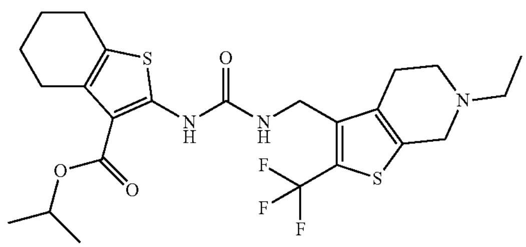 [SMILES: CCN1CCc2c(sc(C(F)(F)F)c2CNC(=O)Nc2sc3c(c2C(=O)OC(C)C)CCCC3)C1] | Pale yellow solid; $^1$H NMR (400 MHz, MeOD) δ 5.16 (pentet, J = 6.4 and 12.4 Hz, 1H), 4.42 (s, 2H), 3.73 (s, 2H), 2.77 (t, J = 5.6 Hz, 2H), 2.73 (t, J = 5.6 Hz, 2H), 2.67 (q, J = 7.2 Hz, 2H), 2.60 (t, J = 5.6 Hz, 2H), 1.78 (d, J = 6.0 Hz, 4H), 1.33 (s, 3H), 1.32 (s, 3H), 1.19 (t, J = 7.0 Hz, 3H); LCMS (electrospray) m/z (M + H)$^+$ 530.11 | ++++ | GP26, GP35, GP5 |
| 172 | 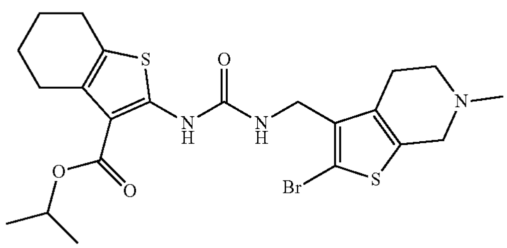 [SMILES: CC(C)OC(=O)c1c(NC(=O)NCc2c(Br)sc3c2CCN(C)C3)sc2c1CCCC2] | White solid; $^1$H NMR (400 MHz, MeOD) δ 5.16 (pentet, J = 6.4 and 12.4 Hz, 1H), 4.34 (s, 2H), 3.55 (s, 2H), 2.77 (s, 4H), 2.74 (d, J = 6.0 Hz, 2H), 2.59 (d, J = 6.0 Hz, 2H), 2.46 (s, 3H), 1.78 (d, J = 5.6 Hz, 4H), 1.33 (s, 3H), 1.32 (s, 3H); LCMS (electrospray) m/z (M + H)$^+$ 525.96 | ++++ | GP35, GP5, GP3 |
| 173 | 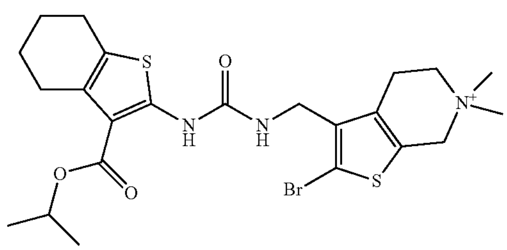 [SMILES: CC(C)OC(=O)c1c(NC(=O)NCc2c(Br)sc3c2CC[N+](C)(C)C3)sc2c1CCCC2] | Pale yellow solid; $^1$H NMR (400 MHz, DMSO) δ 10.38 (s, 1H), 8.20 (t, J = 5.2 Hz, 1H), 5.06 (pentet, J = 6.4 and 12.4 Hz, 1H), 4.60 (s, 2H), 4.20 (d, J = 5.2 Hz, 2H), 3.68 (t, J = 6.0 Hz, 2H), 3.15 (s, 6H), 3.03 (t, J = 6.2 Hz, 2H), 2.66 (s, 2H), 2.53 (s, 2H), 1.70 (s, 4H), 1.29 (s, 3H), 1.27 (s, 3H); LCMS (electrospray) m/z (M + H)$^+$ 541.95 | ++++ | GP35, GP3 |
| 174 | 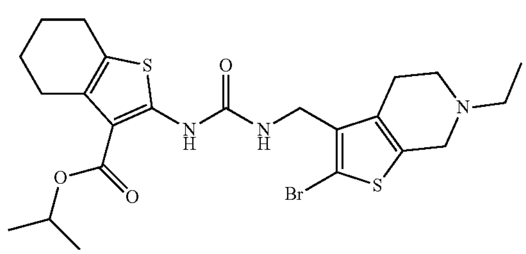 [SMILES: CCN1CCc2c(sc(Br)c2CNC(=O)Nc2sc3c(c2C(=O)OC(C)C)CCCC3)C1] | Pale yellow solid; $^1$H NMR (400 MHz, DMSO) δ 10.34 (s, 1H), 8.08 (t, J = 4.8 Hz, 1H), 5.05 (pentet, J = 6.4 and 12.4 Hz, 1H), 4.14 (d, J = 4.4 Hz, 2H), 3.48 (s, 2H), 2.66 (d, J = 4.4 Hz, 4H), 2.60 (d, J = 4.8 Hz, 2H), 2.53 (s, 2H), 1.69 (s, 4H), 1.29 (s, 3H), 1.27 (s, 3H), 1.05 (t, J = 7.2 Hz, 3H); LCMS (electrospray) m/z (M + H)$^+$ 539.98 | ++++ | GP35, GP5 |
| 175 | 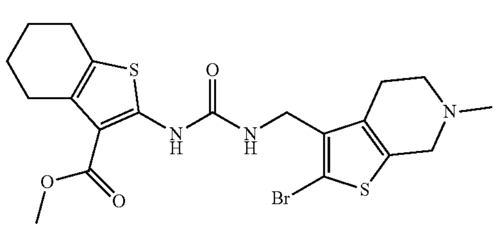 [SMILES: COC(=O)c1c(NC(=O)NCc2c(Br)sc3c2CCN(C)C3)sc2c1CCCC2] | White solid; $^1$H NMR (400 MHz, MeOD) δ 4.29 (s, 2H), 3.81 (s, 3H), 3.57 (s, 2H), 2.79-2.76 (m, 4H), 2.73 (d, J = 6.0 Hz, 2H), 2.59 (d, J = 6.0 Hz, 2H), 2.47 (s, 3H), 1.78 (d, J = 5.6 Hz, 4H); LCMS (electrospray) m/z (M + H)$^+$ 497.93 | ++++ | GP35, GP5, GP3 |

TABLE 1-continued

Anti-HCVcc genotype ½ activity for Formula I Series

| No. | Structure | Data | EC$_{50}$ | General Procedure (GP) |
|---|---|---|---|---|
| 176 | 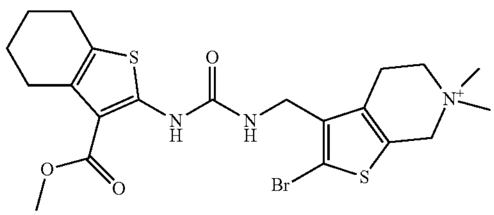 [SMILES: COC(=O)c1c(NC(=O)NCc2c(Br)sc3c2CC[N+](C)(C)C3)sc2c1CCCC2] | Pale yellow solid; $^1$H NMR (400 MHz, DMSO) δ 10.22 (s, 1H), 8.18 (t, J = 5.2 Hz, 1H), 4.60 (s, 2H), 4.21 (d, J = 5.2 Hz, 2H), 3.76 (s, 3H), 3.68 (t, J = 6.0 Hz, 2H), 3.15 (s, 6H), 3.03 (t, J = 6.2 Hz, 2H), 2.64 (s, 2H), 2.53 (s, 2H), 1.70 (d, J = 5.6 Hz, 4H); LCMS (electrospray) m/z (M + H)$^+$ 513.92 | ++++ | GP35 |
| 177 | 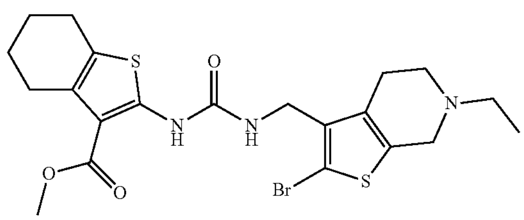 [SMILES: CCN1CCc2c(sc(Br)c2CNC(=O)Nc2sc3c(c2C(=O)OC)CCCC3)C1] | Pale yellow solid; $^1$H NMR (400 MHz, DMSO) δ 10.15 (s, 1H), 8.05 (t, J = 5.0 Hz, 1H), 4.15 (d, J = 5.2 Hz, 2H), 3.76 (s, 3H), 3.48 (s, 2H), 2.67 (d, J = 5.0 Hz, 4H), 2.61 (d, J = 5.0 Hz, 2H), 2.53 (s, 2H), 1.70 (d, J = 5.6 Hz, 4H), 1.05 (t, J = 7.2 Hz, 3H); LCMS (electrospray) m/z (M + H)$^+$ 511.95 | ++++ | GP35, GP5 |
| 178 | 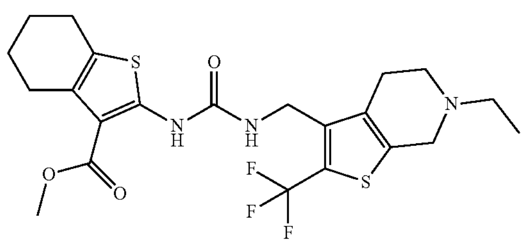 [SMILES: CCN1CCc2c(sc(C(F)(F)F)c2CNC(=O)Nc2sc3c(c2C(=O)OC)CCCC3)C1] | White solid; $^1$H NMR (400 MHz, DMSO) δ 10.19 (s, 1H), 8.10 (t, J = 5.0 Hz, 1H), 4.31 (d, J = 4.4 Hz, 2H), 3.75 (s, 3H), 3.62 (s, 2H), 2.70 (d, J = 5.0 Hz, 2H), 2.64 (d, J = 5.0 Hz, 4H), 2.55 (s, 2H), 1.70 (d, J = 5.6 Hz, 4H), 1.06 (t, J = 7.4 Hz, 3H); LCMS (electrospray) m/z (M + H)$^+$ 502.15 | ++++ | GP35, GP5 |
| 179 | 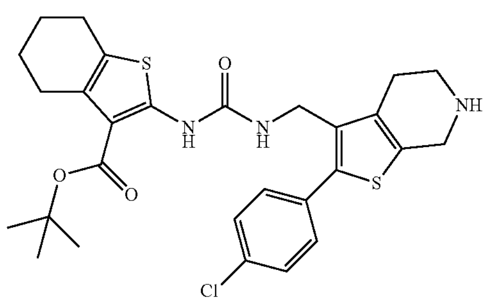 | White solid; $^1$H NMR (400 MHz, CDCl$_3$) δ 10.65 (s, 1H), 7.38-7.29 (m, 3H), 7.25 (d, J = 2.4 Hz, 1H), 4.80 (s, 1H), 4.37 (d, J = 3.0 Hz, 2H), 4.01 (s, 2H), 3.12 (t, J = 5.0 Hz, 2H), 2.68 (s, 2H), 2.66-2.54 (m, 4H), 1.82-1.72 (m, 4H), 1.52 (d, J = 2.2 Hz, 9H); LCMS (electrospray) m/z (M + H)$^+$ 558.07 | ++++ | GP27, GP35 |
| 180 | 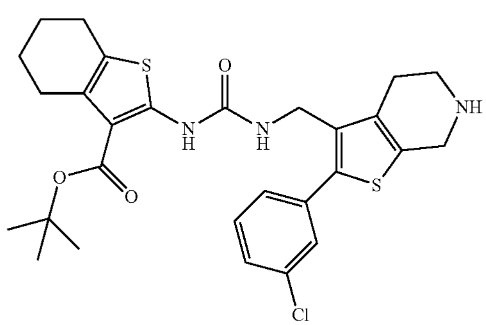 [SMILES: CC(C)(C)OC(=O)c1c(NC(=O)NCc2c(-c3cccc(Cl)c3)sc3c2CCNC3)sc2c1CCCC2] | White solid; $^1$H NMR (400 MHz, DMSO) δ 10.34 (s, 1H), 8.10 (s, 1H), 7.56-7.35 (m, 4H), 4.15 (d, J = 4.5 Hz, 2H), 3.95 (s, 2H), 3.06-2.95 (m, 2H), 2.63 (s, 2H), 2.55 (s, 4H), 1.67 (s, 4H), 1.50 (s, 9H); LCMS (electrospray) m/z (M + H)$^+$ 558.07 | ++++ | GP38, GP35 |

TABLE 1-continued

Anti-HCVcc genotype ½ activity for Formula I Series

| No. | Structure | Data | EC$_{50}$ | General Procedure (GP) |
|---|---|---|---|---|
| 181 | 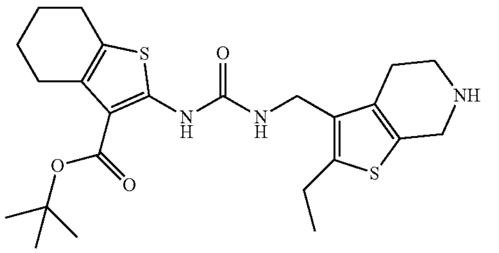 [SMILES: CCc1sc2c(c1CNC(=O)Nc1sc3c(c1C(=O)OC(C)(C)C)CCCC3)CCNC2] | White solid; $^1$H NMR (400 MHz, MeOD) δ 4.22 (s, 2H), 3.94 (s, 2H), 3.11 (t, J = 5.9 Hz, 2H), 2.86 (q, J = 7.5 Hz, 2H), 2.74-2.62 (m, 4H), 2.58 (t, J = 4.9 Hz, 2H), 1.83-1.70 (m, 4H), 1.55 (s, 9H), 1.24 (t, J = 7.5 Hz, 3H); LCMS (electrospray) m/z (M + H)$^+$ 476.09 | ++++ | GP27, GP35 |
| 182 | 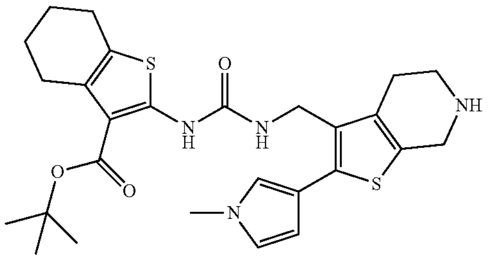 [SMILES: Cn1ccc(-c2sc3c(c2CNC(=O)Nc2sc4c(c2C(=O)OC(C)(C)C)CCCC4)CCNC3)c1] | White solid; $^1$H NMR (400 MHz, MeOD) δ 6.82 (t, J = 2.0 Hz, 1H), 6.66 (t, J = 2.5 Hz, 1H), 6.18 (dd, J = 2.7, 1.8 Hz, 1H), 4.31 (s, 2H), 3.96 (s, 2H), 3.66 (s, 2H), 3.12 (t, J = 5.9 Hz, 2H), 2.72-2.64 (m, 4H), 2.59 (t, J = 5.1 Hz, 2H), 1.82-1.69 (m, 4H), 1.55 (s, 9H); LCMS (electrospray) m/z (M + H)$^+$ 527.19 | ++++ | GP38, GP35 |
| 183 | 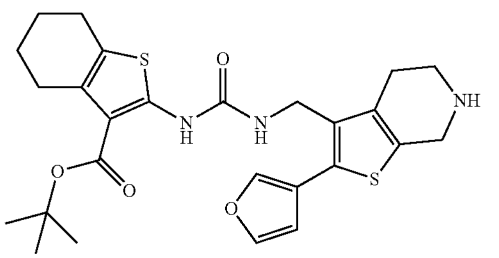 | White solid; $^1$H NMR (400 MHz, DMSO-d6) δ 10.31 (s, NH), 8.01 (t, J = 5.0 Hz, NH), 7.91 (d, J = 1.2 Hz, 1H), 7.75 (d, J = 1.2 Hz, 1H), 6.68 (s, 1H), 4.19 (d, J = 4.4 Hz, 2H), 3.80 (s, 2H), 3.29 (s, 2H), 2.91 (t, J = 5.6 Hz, 2H), 2.62 (s, 2H), 2.50 (t, J = 6.0 Hz, 2H), 1.67 (s, 4H), 1.49 (s, 9H); LCMS (electrospray) m/z (M + H) + 514.12. | ++++ | GP38, GP35 |
| 184 | 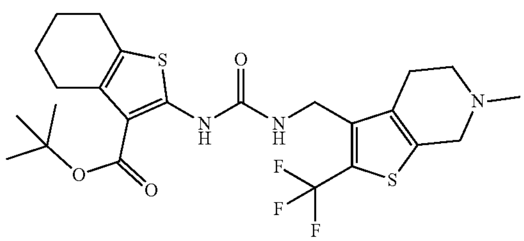 [SMILES: CN1CCc2c(sc(C(F)(F)F)c2CNC(=O)Nc2sc3c(c2C(=O)OC(C)(C)C)CCCC3)C1] | White solid; $^1$H NMR (400 MHz, acetone-d6); δ 10.48 (s, 1H), 7.38 (s, 1H), 4.49 (d, J = 5.2 Hz, 2H), 3.59 (s, 2H), 2.78-2.75 (m, 2H), 2.71-2.67 (m, 4H), 2.59-2.56 (m, 2H), 2.40 (s, 3H), 1.76-1.74 (m, 4H), 1.53 (s, 9H); LCMS (electrospray) m/z 530.00 (M + H) +. | ++++ | GP26, 3 |
| 185 | 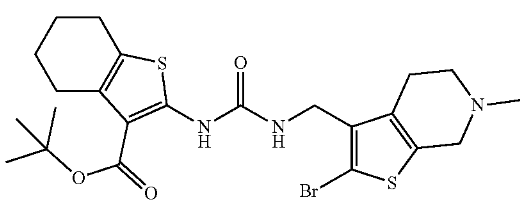 [SMILES: CN1CCc2c(sc(Br)c2CNC(=O)Nc2sc3c(c2C(=O)OC(C)(C)C)CCCC3)C1] | Yellow solid; $^1$H NMR (400 MHz, acetone-d6); δ 10.46 (s, 1H), 7.34 (s, 1H), 4.33 (d, J = 5.6 Hz, 2H), 3.46 (t, J = 1.6 Hz, 2H), 2.76-2.63 (m, 6H), 2.58-2.56 (m, 2H), 2.38 (s, 3H), 1.77-1.72 (m, 4H), 1.54 (s, 9H); LCMS (electrospray) m/z 540.02 (M + H) +. | ++++ | GP35, 3 |
| 186 | 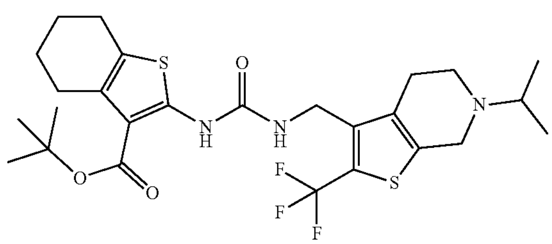 [SMILES: CC(C)N1CCc2c(sc(C(F)(F)F)c2CNC(=O)Nc2sc3c(c2C(=O)OC(C)(C)C)CCCC3)C1] | Yellow solid; $^1$H NMR (400 MHz, acetone-d6); δ 10.48 (s, 1H), 7.44 (s, 1H), 4.49 (dd, J = 1.2, 5.6 Hz, 2H), 4.15-3.95 (m, 1H), 3.30-3.16 (m, 1H), 3.15-2.95 (m, 2H), 2.94-2.85 (m, 3H), 2.71-2.68 (m, 2H), 2.58-2.56 (m, 2H), 1.78-1.69 (m, 4H), 1.53 (s, 9H), 1.22 (d, J = 6.4 Hz, 6H); LCMS (electrospray) m/z 558.00 (M + H) +. | ++++ | GP26, 3 |

TABLE 1-continued

Anti-HCVcc genotype ½ activity for Formula I Series

| No. | Structure | Data | EC$_{50}$ | General Procedure (GP) |
|---|---|---|---|---|
| 187 | 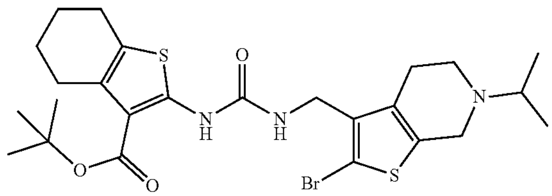 [SMILES: CC(C)N1CCc2c(sc(Br)c2CNC(=O)Nc2sc3c(c2C(=O)OC(C)(C)C)CCCC3)C1] | Brown solid; $^1$H NMR (400 MHz, acetone-d6); δ 10.47 (s, 1H), 7.31 (s, 1H), 4.33 (d, J = 5.6 Hz, 2H), 3.62 (s, 2H), 2.94-2.86 (m, 1H), 2.78-2.74 (m, 2H), 2.71-2.67 (m, 4H), 2.58-2.56 (m, 2H), 1.76-1.72 (m, 4H), 1.53 (s, 9H), 1.07 (d, J = 6.8 Hz, 6H); LCMS (electrospray) 567.98 m/z (M + H) +. | ++++ | GP35, 3 |
| 188 | 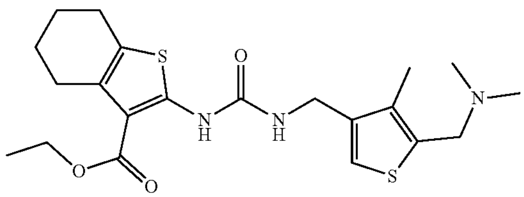 [SMILES: CCOC(=O)c1c(NC(=O)NCc2csc(CN(C)C)c2C)sc2c1CCCC2] | Brown solid; $^1$H NMR (400 MHz, acetone-d6); δ 10.41 (s, 1H), 7.33 (s, 1H), 7.17 (s, 1H), 4.36 (d, J = 4.8 Hz, 2H), 4.26 (q, J = 7.2 Hz, 2H), 3.50 (s, 2H), 2.74-2.71 (m, 2H), 2.59-2.56 (m, 2H), 2.20 (s, 6H), 2.15 (s, 3H), 1.79-1.72 (m, 4H), 1.32 (t, J = 7.2 Hz, 3H); LCMS (electrospray) m/z 436.04 (M + H) +. | ++++ | GP14, 16 |
| 189 | 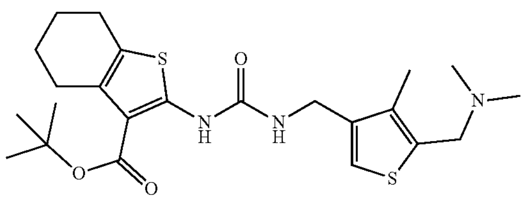 [SMILES: Cc1c(CNC(=O)Nc2sc3c(c2C(=O)OC(C)(C)C)CCCC3)csc1CN(C)C] | Brown oil; $^1$H NMR (400 MHz, acetone-d6); δ 10.48 (s, 1H), 7.36 (s, 1H), 7.17 (s, 1H), 4.36 (dd, J = 0.8, 5.2 Hz, 2H), 3.50 (s, 2H), 2.71-2.69 (m, 2H), 2.58-2.55 (m, 2H), 2.20 (s, 6H), 2.15 (s, 3H), 1.78-1.73 (m, 4H), 1.54 (s, 9H); LCMS (electrospray) m/z 464.07 (M + H) +. | ++++ | GP15, 16 |
| 190 | 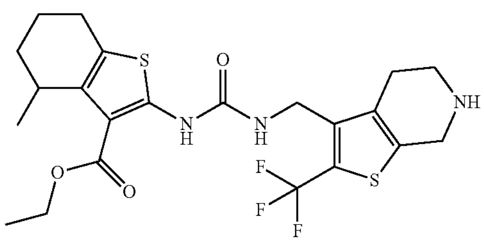 [SMILES: CCOC(=O)c1c(NC(=O)NCc2c(C(F)(F)F)sc3c2CCNC3)sc2c1C(C)CCC2] | Beige solid; $^1$H NMR (400 MHz, DMSO) δ 10.34 (s, 1H), 8.13 (t, J = 4.8 Hz, 1H), 4.32-4.19 (m, 4H), 3.87 (s, 2H), 3.29-3.20 (m, 1H), 2.91 (t, J = 5.2 Hz, 2H), 2.61-2.53 (m, 2H), 2.49-2.45 (m, 2H), 1.80-1.65 (m, 3H), 1.63-1.57 (m, 1H), 1.29 (t, J = 6.8 Hz, 3H), 1.10 (d, J = 6.8 Hz, 3H); LCMS (electrospray) m/z (M + H) + 502.08 | ++++ | GP1 GP26 GP28 |
| 191 | 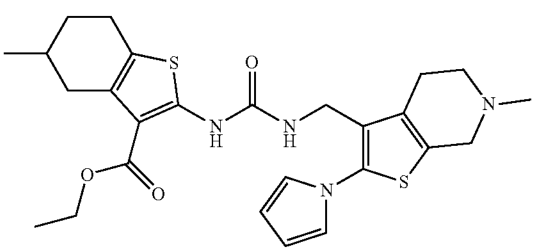 | White solid; $^1$H NMR (400 MHz, CDCl3) δ 10.47 (s, 1H), 6.80 (t, J = 2.0 Hz, 2H), 6.31 (t, J = 2.4 Hz, 2H), 4.61 (brs, 1H), 4.32-4.25 (m, 4H), 3.56 (s, 2H), 2.95-2.90 (m, 1H), 2.75-2.69 (m, 4H), 2.66-2.59 (m, 2H), 2.48 (s, 3H), 2.24-2.16 (m, 1H), 1.88-1.77 (m, 3H), 1.36 (t, J = 7.2 Hz, 3H), 1.06 (d, J = 6.8 Hz, 3H); LCMS (electrospray) m/z (M + H) + 513.04 | ++++ | GP1 |
| 192 | 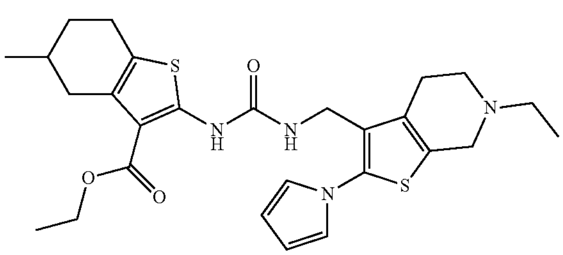 [SMILES: CCOC(=O)c1c(NC(=O)NCc2c(-n3cccc3)sc3c2CCN(CC)C3)sc2c1CC(C)CC2] | Beige solid; $^1$H NMR (400 MHz, CDCl3) δ 10.47 (s, 1H), 6.79 (t, J = 2.0 Hz, 2H), 6.30 (t, J = 2.4 Hz, 2H), 4.58 (brs, 1H), 4.32-4.25 (m, 4H), 3.61 (s, 2H), 2.97-2.91 (m, 1H), 2.82-2.77 (m, 2H), 2.74-2.70 (m, 2H), 2.65-2.58 (m, 4H), 2.24-2.16 (m, 1H), 1.90-1.72 (m, 3H), 1.36 (t, J = 7.2 Hz, 3H), 1.17 (t, J = 7.2 Hz, 3H), 1.06 (d, J = 6.4 Hz, 3H); LCMS (electrospray) m/z (M + H) + 527.12 | ++++ | GP1 |

TABLE 1-continued

Anti-HCVcc genotype ½ activity for Formula I Series

| No. | Structure | Data | EC$_{50}$ | General Procedure (GP) |
|---|---|---|---|---|
| 193 | 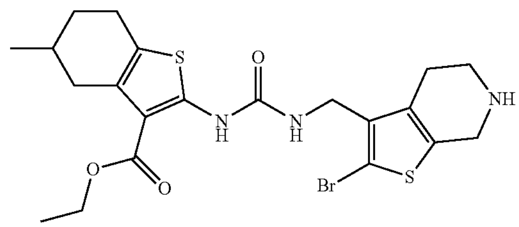 [SMILES: CCOC(=O)c1c(NC(=O)NCc2c(Br)sc3c2CCNC3)sc2c1CC(C)CC2] | White solid; $^1$H NMR (400 MHz, DMSO) δ 10.24 (s, 1H), 8.08 (t, J = 4.8 Hz, 1H), 4.25 (q, J = 14.8, 7.6 Hz, 2H), 4.15 (d, J = 5.6 Hz, 2H), 3.73 (s, 2H), 2.91-2.83 (m, 3H), 2.59-2.52 (m, 3H), 2.50-2.41 (m, 2H), 2.19-2.10 (m, 1H), 1.83-1.78 (m, 1H), 1.76-1.64 (m, 1H), 1.28 (t, J = 7.2 Hz, 3H), 1.02 (d, J = 6.8 Hz, 3H); LCMS (electrospray) m/z (M + H) + 512.01, 513.92 | ++++ | GP1 GP35 |
| 194 | 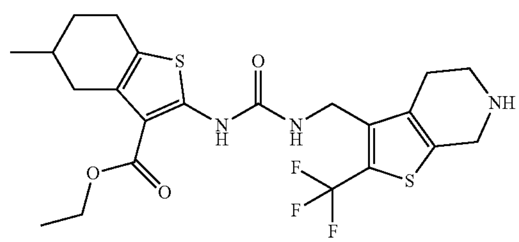 [SMILES: CCOC(=O)c1c(NC(=O)NCc2c(C(F)(F)F)sc3c2CCNC3)sc2c1CC(C)CC2] | White solid; $^1$H NMR (400 MHz, DMSO) δ 10.27 (s, 1H), 8.13 (t, J = 4.8 Hz, 1H), 4.31 (d, J = 4.4 Hz, 2H), 4.24 (q, J = 14.0, 7.2 Hz, 2H), 3.73 (s, 2H), 2.93-2.85 (m, 3H), 2.60-2.52 (m, 3H), 2.50-2.40 (m, 2H), 2.19-2.10 (m, 1H), 1.84-1.78 (m, 1H), 1.75-1.66 (m, 1H), 1.28 (t, J = 7.2 Hz, 3H), 1.02 (d, J = 6.8 Hz, 3H); LCMS (electrospray) m/z (M + H) + 502.01 | ++++ | GP1 GP26 GP28 |
| 195 | 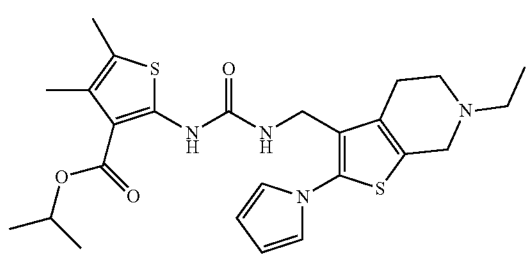 [SMILES: CCN1CCc2c(sc(-n3cccc3)c2CNC(=O)Nc2sc(C)c(C)c2C(=O)OC(C)C)C1] | White solid; $^1$H NMR (400 MHz, DMSO) δ 10.44 (s, 1H), 8.03 (t, J = 5.0 Hz, 1H), 6.99 (t, J = 2.2 Hz, 2H), 6.25 (t, J = 2.2 Hz, 2H), 5.08 (pentet, J = 6.4 and 12.4 Hz, 1H), 4.02 (d, J = 5.2 Hz, 2H), 3.54 (s, 2H), 2.71 (t, J = 5.6 Hz, 2H), 2.53-2.58 (m, 4H), 2.16 (s, 3H), 2.15 (s, 3H), 1.30 (s, 3H), 1.28 (s, 3H), 1.07 (t, J = 7.2 Hz, 3H); LCMS (electrospray) m/z (M + H)$^+$ 501.13 | ++++ | GP1 |
| 196 | 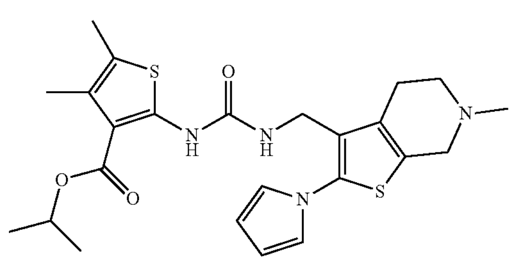 [SMILES: Cc1sc(NC(=O)NCc2c(-n3cccc3)sc3c2CCN(C)C3)c(C(=O)OC(C)C)c1C] | White solid; $^1$H NMR (400 MHz, DMSO) δ 10.44 (s, 1H), 8.04 (t, J = 5.0 Hz, 1H), 7.00 (t, J = 2.2 Hz, 2H), 6.25 (t, J = 2.2 Hz, 2H), 5.08 (pentet, J = 6.4 and 12.4 Hz, 1H), 4.02 (d, J = 5.2 Hz, 2h), 3.48 (s, 2H), 2.70 (d, J = 6.8 Hz, 2H), 2.64 (d, J = 5.2 Hz, 2H), 2.35 (s, 3H), 2.16 (s, 3H), 2.15 (s, 3H), 1.32 (s, 3H), 1.31 (s, 3H); LCMS (electrospray) m/z (M + H)$^+$ 487.05 | ++++ | GP35 |
| 197 | 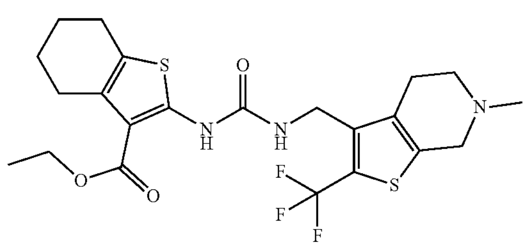 [SMILES: CCOC(=O)c1c(NC(=O)NCc2c(C(F)(F)F)sc3c2CCN(C)C3)sc2c1CCCC2] | White solid; $^1$H NMR (400 MHz, acetone-d6); δ 10.40 (s, 1H), 7.34 (brs, 1H), 4.49 (dd, J = 1.2, 5.2 Hz, 2H), 4.25 (q, J = 7.2 Hz, 2H), 3.58 (d, J = 1.2 Hz, 2H), 2.78-2.75 (m, 2H), 2.73-2.67 (m, 4H), 2.59-2.56 (m, 2H), 2.40 (s, 3H), 1.80-1.71 (m, 4H), 1.31 (t, J = 7.2 Hz, 3H); LCMS (electrospray) m/z (M + H) + 502.04 | ++++ | GP26, 3 |

TABLE 1-continued

Anti-HCVcc genotype ½ activity for Formula I Series

| No. | Structure | Data | EC$_{50}$ | General Procedure (GP) |
|---|---|---|---|---|
| 198 | 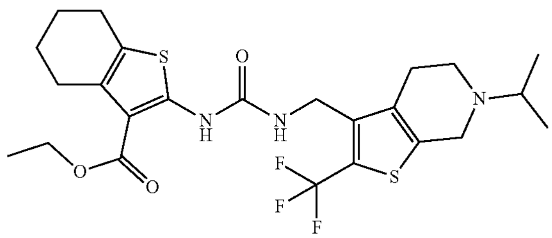 [SMILES: CCOC(=O)c1c(NC(=O)NCc2c(C(F)(F)F)sc3c2CCN(C(C)C)C3)sc2c1CCCC2] | Brown solid; $^1$H NMR (400 MHz, acetone-d6); δ 10.41 (s, 1H), 7.33 (br s, 1H), 4.48 (d, J = 4.8 Hz, 2H), 4.24 (q, J = 7.2 Hz, 2H), 3.75 (d, J = 1.2 Hz, 2H), 2.93 (quint, J = 6.4 Hz, 1H), 2.79-2.76 (m, 2H), 2.73-2.70 (m, 4H), 2.58-2.57 (m, 2H), 1.79-1.71 (m, 4H), 1.31 (t, J = 7.2 Hz, 3H), 1.09 (d, J = 6.4 Hz, 6H); LCMS (electrospray) m/z (M + H) + 530.13 | ++++ | GP26, 3 |
| 199 | 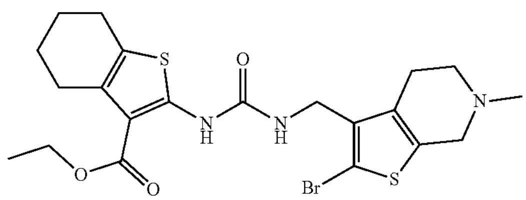 [SMILES: CCOC(=O)c1c(NC(=O)NCc2c(Br)sc3c2CCN(C)C3)sc2c1CCCC2] | Ivory solid; $^1$H NMR (400 MHz, acetone-d6); δ 10.39 (s, 1H), 7.30 (brs, 1H), 4.33 (d, J = 5.2 Hz, 2H), 4.25 (q, J = 7.2 Hz, 2H), 3.45 (t, J = 2.0 Hz, 2H), 2.74-2.70 (m, 4H), 2.66-2.63 (m, 2H), 2.59-2.56 (m, 2H), 2.37 (s, 3H), 1.79-1.71 (m, 4H), 1.31 (t, J = 7.2 Hz, 3H); LCMS (electrospray) m/z (M + H) + 511.93 | ++++ | GP35, 3 |
| 200 | 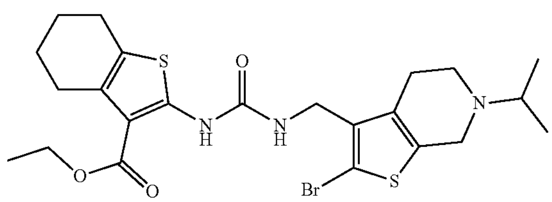 [SMILES: CCOC(=O)c1c(NC(=O)NCc2c(Br)sc3c2CCN(C(C)C)C3)sc2c1CCCC2] | Brown solid; $^1$H NMR (400 MHz, acetone-d6); δ 10.40 (s, 1H), 7.28 (brs, 1H), 4.33 (d, J = 5.6 Hz, 2H), 4.27 (q, J = 6.8 Hz, 2H), 3.61 (t, J = 1.6 Hz, 2H), 2.89 (quint, J = 6.0 Hz, 1H), 2.78-2.66 (m, 6H), 2.59-2.56 (m, 2H), 1.80-1.70 (m, 4H), 1.31 (t, J = 6.8 Hz, 3H), 1.07 (d, J = 6.4 Hz, 6H); LCMS (electrospray) m/z (M + H) + 540.02 | ++++ | GP35, 3 |
| 201 | 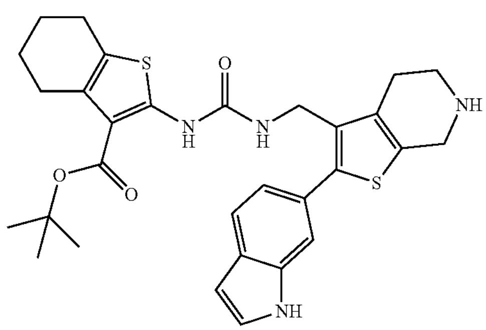 [SMILES: CC(C)(C)OC(=O)c1c(NC(=O)NCc2c(-c3ccc4cc[nH]c4c3)sc3c2CCNC3)sc2c1CCCC2] | White solid; $^1$H NMR (400 MHz, CDCl$_3$) δ 10.61 (s, 1H), 8.76 (s, 1H), 7.60 (d, J = 8.1 Hz, 1H), 7.36 (s, 1H), 7.21 (s, 1H), 7.10 (d, J = 8.2 Hz, 1H), 6.52 (s, 1H), 5.59 (s, 1H), 5.32-5.26 (m, 1H), 4.38 (d, J = 3.5 Hz, 2H), 3.92 (s, 2H), 3.42 (s, 3H), 3.03 (s, 2H), 2.66 (s, 2H), 2.55 (s, 4H), 1.46 (s, 9H); LCMS (electrospray) m/z (M + H) + 563.17 | ++ | GP38, GP35 |
| 202 | 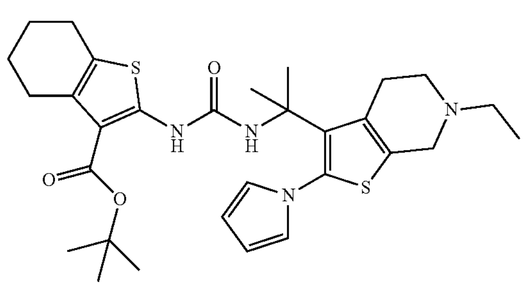 [SMILES: CCN1CCc2c(sc(-n3cccc3)c2C(C)(C)NC(=O)Nc2sc3c(c2C(=O)OC(C)(C)C)CCCC3)C1] | White solid; $^1$H NMR (400 MHz, DMSO) δ 10.24 (s, 1H), 8.23 (s, 1H), 6.85 (s, 2H), 6.13 (t, J = 2.1 Hz, 2H), 3.46 (s, 2H), 2.60 (s, 6H), 2.43 (dd, J = 14.4, 7.3 Hz, 2H), 1.66 (s, 4H), 1.51 (s, 8H), 1.23 (s, 6H), 1.01 (t, J = 7.1 Hz, 3H); LCMS (electrospray) m/z (M + H) + 569.15 | ++ | GP38, GP25 |

TABLE 1-continued

Anti-HCVcc genotype ½ activity for Formula I Series

| No. | Structure | Data | EC$_{50}$ | General Procedure (GP) |
|---|---|---|---|---|
| 203 | 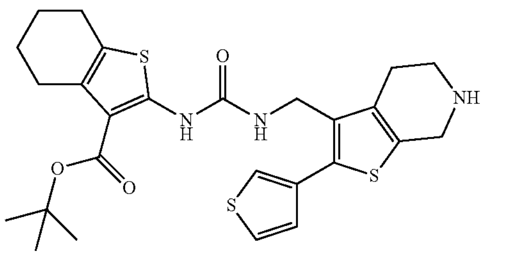 [SMILES: CC(C)(C)OC(=O)c1c(NC(=O)NCc2c(-c3ccsc3)sc3c2CCNC3)sc2c1CCCC2] | White solid; $^1$H NMR (400 MHz, DMSO-d6) δ 10.36 (s, NH), 8.09 (t, J = 5.0 Hz, NH), 7.69-7.65 (m, 2H), 7.28 (d, J = 1.2 Hz, 1H), 4.23 (d, J = 4.4 Hz, 2H), 4.03 (s, 2H), 3.11 (s, 2H), 2.63 (s, 4H), 2.52 (s, 2H), 1.69 (s, 4H), 1.51 (s, 9H); LCMS (electrospray) m/z (M + H) + 530.04. | ++++ | GP38, GP35 |
| 204 | 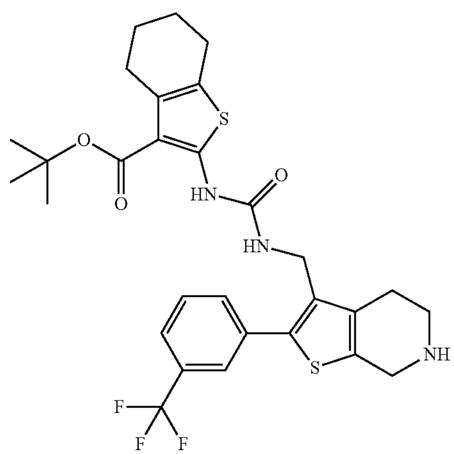 [SMILES: CC(C)(C)OC(=O)c1c(NC(=O)NCc2c(-c3cccc(C(F)(F)F)c3)sc3c2CCNC3)sc2c1CCCC2] | White solid; $^1$H NMR (400 MHz, DMSO) δ 10.34 (s, 1H), 8.12 (t, J = 4.8 Hz, 1H), 7.80-7.65 (m, 4H), 4.14 (d, J = 4.8 Hz, 2H), 3.95 (s, 2H), 3.01 (t, J = 5.6 Hz, 2H), 2.62 (s, 2H), 2.55 (s, 2H), 2.50 (s, 4H), 1.67 (s, 4H), 1.49 (s, 9H); LCMS (electrospray) m/z (M + H) + 592.09 | +++ | GP38, GP35 |
| 205 | 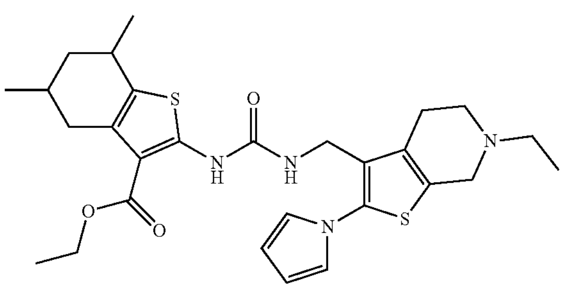 [SMILES: CCOC(=O)c1c(NC(=O)NCc2c(-n3cccc3)sc3c2CCN(CC)C3)sc2c1CC(C)CC2C] | Yellow oil; $^1$H NMR (400 MHz, acetone) δ 10.39 (s, 1H), 7.19 (brs, 1H), 6.95 (s, 2H), 6.24 (s, 2H), 4.30-4.21 (m, 4H), 3.58 (s, 2H), 3.01-2.95 (m, 1H), 2.87-2.79 (m, 2H), 2.77-2.73 (m, 2H), 2.71-2.67 (m, 2H), 2.57 (q, J = 14.4, 7.2 Hz, 2H), 2.16-2.08 (m, 1H), 1.92-1.85 (m, 1H), 1.82-1.70 (m, 1H), 1.32 (t, J = 7.2 Hz, 3H), 1.23 (d, J = 6.8 Hz, 3H), 1.11 (t, J = 6.8 Hz, 3H), 1.05 (d, J = 6.8 Hz, 3H); LCMS (electrospray) m/z (M + H) + 541.13 | ++++ | GP1 |
| 206 | 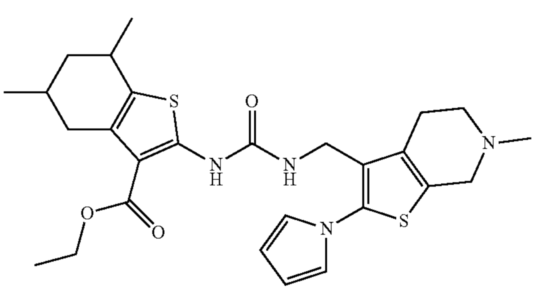 | Yellow solid; $^1$H NMR (400 MHz, acetone) δ 10.39 (s, 1H), 7.18 (brs, 1H), 6.95 (s, 2H), 6.24 (s, 2H), 4.30-4.21 (m, 4H), 3.51 (s, 2H), 3.02-2.94 (m, 1H), 2.88-2.78 (m, 2H), 2.72-2.66 (m, 4H), 2.40 (s, 3H), 2.16-2.07 (m, 1H), 1.92-1.87 (m, 1H), 1.83-1.72 (m, 1H), 1.32 (t, J = 7.2 Hz, 3H), 1.23 (d, J = 6.8 Hz, 3H), 1.05 (d, J = 6.8 Hz, 3H); LCMS (electrospray) m/z (M + H) + 527.12 | ++++ | GP1 |

TABLE 1-continued

Anti-HCVcc genotype ½ activity for Formula I Series

| No. | Structure | Data | EC$_{50}$ | General Procedure (GP) |
|---|---|---|---|---|
| 207 | 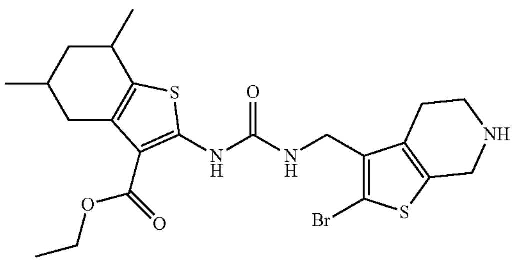 [SMILES: CCOC(=O)c1c(NC(=O)NCc2c(Br)sc3c2CCNC3)sc2c1CC(C)CC2C] | White solid; $^1$H NMR (400 MHz, CDCl3) δ 10.61 (s, 1H), 4.88 (brs, 1H), 4.37 (d, J = 5.6 Hz, 2H), 4.28 (q, J = 14.4, 7.2 Hz, 2H), 3.91 (s, 2H), 3.09 (t, J = 6.0 Hz, 2H), 2.99-2.92 (m, 1H), 2.91-2.81 (m, 2H), 2.62 (brs, 2H), 2.18-2.10 (m, 1H), 1.91-1.83 (m, 1H), 1.82-1.72 (m, 1H), 1.35 (t, J = 7.2 Hz, 3H), 1.26 (d, J = 6.4 Hz, 3H), 1.06 (d, J = 6.8 Hz, 3H); LCMS (electrospray) m/z (M + H) + 525.96, 527.93 | ++++ | GP1 GP35 |
| 208 | 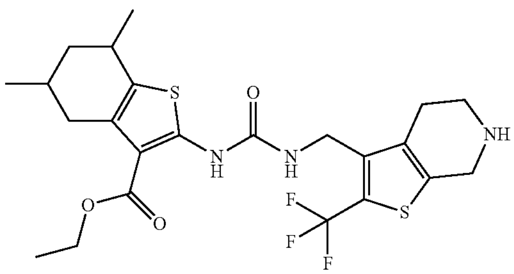 [SMILES: CCOC(=O)c1c(NC(=O)NCc2c(C(F)(F)F)sc3c2CCNC3)sc2c1CC(C)CC2C] | White solid; $^1$H NMR (400 MHz, CDCl3) δ 10.60 (s, 1H), 4.86 (t, J = 6.4 Hz, 1H), 4.51 (d, J = 6.0 Hz, 2H), 4.28 (q, J = 14.4, 7.2 Hz, 2H), 4.01 (s, 2H), 3.11 (t, J = 5.6 Hz, 2H), 2.99-2.92 (m, 1H), 2.90-2.80 (m, 2H), 2.66 (t, J = 6.0 Hz, 2H), 2.18-2.09 (m, 1H), 1.92-1.86 (m, 1H), 1.85-1.72 (m, 1H), 1.35 (t, J = 6.8 Hz, 3H), 1.26 (d, J = 6.8 Hz, 3H), 1.06 (d, J = 6.8 Hz, 3H); LCMS (electrospray) m/z (M + H) + 516.10 | ++++ | GP1 GP35 |
| 209 | 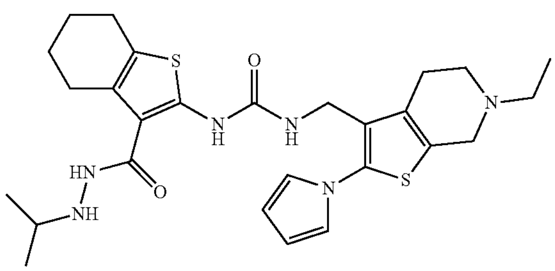 [SMILES: CCN1CCc2c(sc(-n3cccc3)c2CNC(=O)Nc2sc3c(c2C(=O)NNC(C)C)CCCC3)C1] | White solid; $^1$H NMR (400 MHz, CDCl3) δ 11.10 (s, 1H), 7.22 (brs, 1H), 6.78 (t, J = 2.4 Hz, 2H), 6.29 (t, J = 2.4 Hz, 2H), 4.63 (brs, 1H), 4.24 (d, J = 5.2 Hz, 2H), 3.60 (s, 2H), 3.16-3.10 (m, 1H), 2.79 (t, J = 6.0 Hz, 2H), 2.76-2.69 (m, 2H), 2.68-2.57 (m, 6H), 1.89-1.75 (m, 4H), 1.16 (t, J = 7.2 Hz, 3H), 1.09 (d, J = 6.4 Hz, 6H); LCMS (electrospray) m/z (M + H) + 541.13 | ++++ | GP1 GP12 |
| 210 | 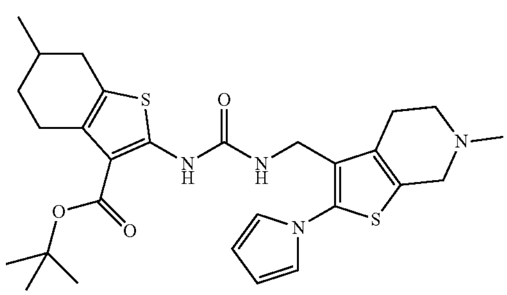 [SMILES: CC1CCc2c(sc(NC(=O)NCc3c(-n4cccc4)sc4c3CCN(C)C4)c2C(=O)OC(C)(C)C)C1] | White solid; $^1$H NMR (400 MHz, CDCl3) δ 11.10 (s, 1H), 7.22 (brs, 1H), 6.78 (t, J = 2.4 Hz, 2H), 6.29 (t, J = 2.4 Hz, 2H), 4.63 (brs, 1H), 4.24 (d, J = 5.2 Hz, 2H), 3.60 (s, 2H), 3.16-3.10 (m, 1H), 2.79 (t, J = 6.0 Hz, 2H), 2.76-2.69 (m, 2H), 2.68-2.57 (m, 6H), 1.89-1.75 (m, 4H), 1.16 (t, J = 7.2 Hz, 3H), 1.09 (d, J = 6.4 Hz, 6H); LCMS (electrospray) m/z (M + H) + 541.13 | ++++ | GP1 |
| 211 | 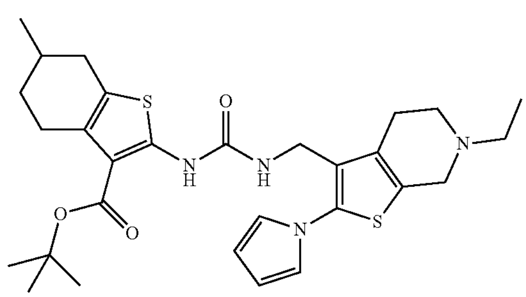 [SMILES: CCN1CCc2c(sc(-n3cccc3)c2CNC(=O)Nc2sc3c(c2C(=O)OC(C)(C)C)CCC(C)C3)C1] | White solid; $^1$H NMR (400 MHz, CDCl3) δ 10.58 (s, 1H), 6.79 (t, J = 2.4 Hz, 2H), 6.31 (t, J = 2.4 Hz, 2H), 4.53 (brs, 1H), 4.27 (d, J = 5.2 Hz, 2H), 3.67-3.63 (brs, 2H), 2.86-2.59 (m, 7H), 2.21 (m, 1H), 1.84 (m, 2H), 1.59 (m, 2H), 1.56 (s, 9H), 1.34-1.30 (m, 1H), 1.20 (m, 3H), 1.04 (d, J = 6.0 Hz, 3H); LCMS (electrospray) m/z (M + H) + 555.21 | ++++ | GP1 |

TABLE 1-continued

Anti-HCVcc genotype ½ activity for Formula I Series

| No. | Structure | Data | EC$_{50}$ | General Procedure (GP) |
|---|---|---|---|---|
| 212 | 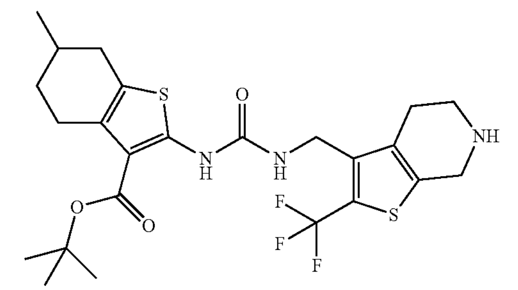 [SMILES: CC1CCc2c(sc(NC(=O)NCc3c(C(F)(F)F)sc4c3CCNC4)c2C(=O)OC(C)(C)C)C1] | White solid; $^1$H NMR (400 MHz, DMSO) δ 10.62 (s, 1H), 4.94 (brs, 1H), 4.48 (d, J = 5.6 Hz, 2H), 4.11 (s, 2H), 3.17 (t, J = 6.0 Hz, 2H), 2.87-2.83 (m, 2H), 2.78-2.75 (m, 2H), 2.69-2.59 (m, 2H), 2.24-2.18 (m, 1H), 1.86-1.83 (m, 2H), 1.53 (s, 9H), 1.38-1.32 (m, 1H), 1.05 (d, J = 6.4 Hz, 3H); LCMS (electrospray) m/z (M + H) + 530.11 | ++++ | GP1 GP26 GP28 |
| 213 | 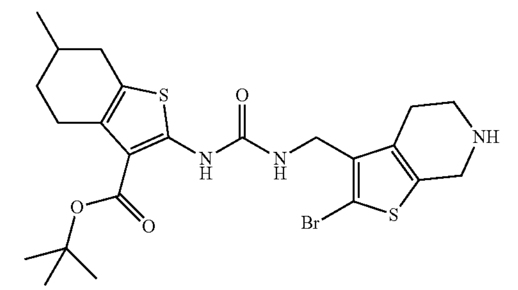 [SMILES: CC1CCc2c(sc(NC(=O)NCc3c(Br)sc4c3CCNC4)c2C(=O)OC(C)(C)C)C1] | White solid; $^1$H NMR (400 MHz, DMSO) δ 10.61 (s, 1H), 5.02 (t, J = 5.2 Hz, 1H), 4.34 (d, J = 5.6 Hz, 2H), 3.91 (s, 2H), 3.08 (brs, 2H), 2.87-2.82 (m, 2H), 2.69-2.56 (m, 4H), 2.24-2.18 (m, 1H), 1.86-1.82 (m, 2H), 1.53 (s, 9H), 1.36-1.32 (m, 1H), 1.05 (d, J = 6.8 Hz, 3H); LCMS (electrospray) m/z (M + H) + 541.95 | ++++ | GP1 GP35 |
| 214 | 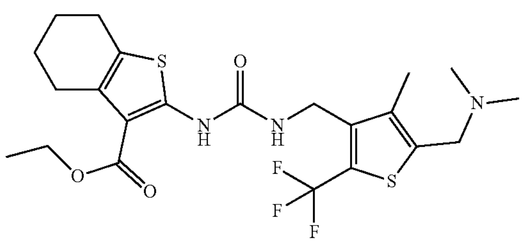 [SMILES: CCOC(=O)c1c(NC(=O)NCc2c(C(F)(F)F)sc(CN(C)C)c2C)sc2c1CCCC2] | Ivory solid; $^1$H NMR (400 MHz, acetone-d6); δ 10.39 (s, 1H), 7.30 (brs, 1H), 4.50 (dd, J = 1.2, 5.2 Hz, 2H), 4.23 (q, J = 7.2 Hz, 2H), 3.60 (s, 2H), 2.73-2.70 (m, 2H), 2.59-2.57 (m, 2H), 2.26 (s, 6H), 2.22 (s, 3H), 1.80-1.71 (m, 4H), 1.31 (t, J = 7.2 Hz, 3H); LCMS (electrospray) m/z (M + H) + 504.06 | ++++ | GP14, 35 |
| 215 | 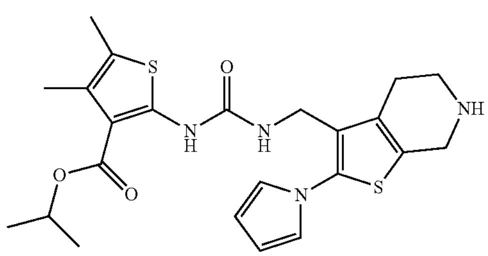 [SMILES: Cc1sc(NC(=O)NCc2c(-n3cccc3)sc3c2CCNC3)c(C(=O)OC(C)C)c1C] | Pale yellow solid; $^1$H NMR (400 MHz, DMSO) δ 10.34 (s, 1H), 8.04 (t, J = 5.0 Hz, 1H), 7.00 (t, J = 2.2 Hz, 2H), 6.25 (t, J = 2.2 Hz, 2H), 5.08 (pentet, J = 6.4 and 12.4 Hz, 1H), 4.02 (d, J = 5.2 Hz, 2H), 3.79 (s, 2H), 2.93 (t, J = 5.6 Hz, 2H), 2.46 (d, J = 5.2 Hz, 2H), 2.16 (s, 3H), 2.15 (s, 3H), 1.32 (s, 3H), 1.31 (s, 3H); LCMS (electrospray) m/z (M + H)$^+$ 473.03 | ++++ | GP28 |
| 216 | 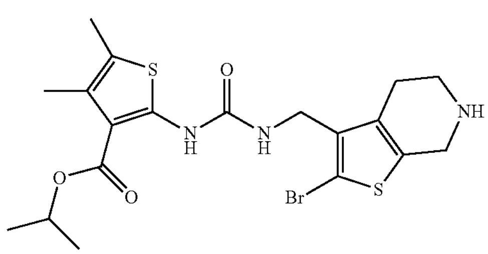 [SMILES: Cc1sc(NC(=O)NCc2c(Br)sc3c2CCNC3)c(C(=O)OC(C)C)c1C] | Yellow solid; $^1$H NMR (400 MHz, DMSO) δ 10.32 (s, 1H), 8.08 (t, J = 5.2 Hz, 1H), 5.11-5.03 (m, 1H), 4.14 (d, J = 5.2 Hz, 2H), 3.73 (s, 2H), 2.89 (t, J = 5.6 Hz, 2H), 2.50-2.47 (m, 2H), 2.15 (d, J = 6.4 Hz, 6H), 1.30 (s, 3H), 1.28 (s, 3H); LCMS (electrospray) m/z (M + H) + 485.89, 487.93 | ++++ | GP1 GP35 |

TABLE 1-continued

Anti-HCVcc genotype ½ activity for Formula I Series

| No. | Structure | Data | EC$_{50}$ | General Procedure (GP) |
|---|---|---|---|---|
| 217 | 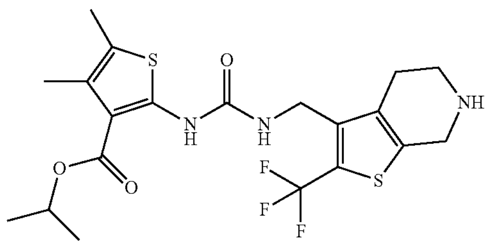 | White solid; $^1$H NMR (400 MHz, DMSO) δ 10.34 (s, 1H), 8.13 (t, J = 5.2 Hz, 1H), 5.10-5.05 (m, 1H), 4.30 (d, J = 5.2 Hz, 2H), 3.87 (s, 2H), 2.91 (t, J = 5.6 Hz, 2H), 2.54-2.50 (m, 2H), 2.15 (d, J = 6.8 Hz, 6H), 1.30 (s, 3H), 1.28 (s, 3H); LCMS (electrospray) m/z (M + H) + 479.03 | ++++ | GP1 GP26 GP28 |
| 218 | 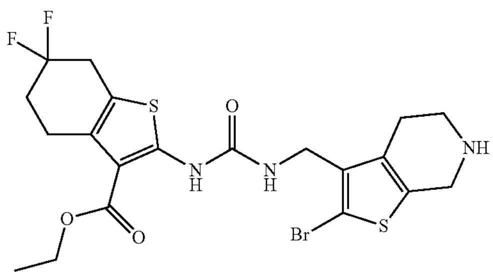 [SMILES: CCOC(=O)c1c(NC(=O)NCc2c(Br)sc3c2CCNC3)sc2c1CCC(F)(F)C2] | White solid; $^1$H NMR (400 MHz, CDCl3) δ 10.59 (s, 1H), 4.95 (brs, 1H), 4.37 (d, J = 5.6 Hz, 2H), 4.30 (q, J = 14.4, 6.8 Hz, 2H), 3.91 (s, 2H), 3.15-3.07 (m, 4H), 3.00 (t, J = 6.4 Hz, 2H), 2.62 (t, J = 6.0 Hz, 2H), 2.23-2.12 (m, 2H), 1.37 (t, J = 7.2 Hz, 3H); LCMS (electrospray) m/z (M + H) + 533.92, 535.89 | ++++ | GP1 GP35 |
| 219 | 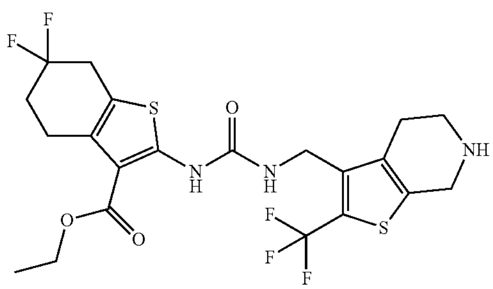 [SMILES: CCOC(=O)c1c(NC(=O)NCc2c(C(F)(F)F)sc3c2CCNC3)sc2c1CCC(F)(F)C2] | White solid; $^1$H NMR (400 MHz, CDCl3) δ 10.58 (s, 1H), 4.95 (t, J = 5.6 Hz, 1H), 4.50 (d, J = 5.6 Hz, 2H), 4.29 (q, J = 14.0, 6.8 Hz, 2H), 4.01 (s, 2H), 3.19-3.08 (m, 4H0, 3.00 (t, J = 6.4 Hz, 2H), 2.66 (brs, 2H), 2.23-2.12 (m, 2H), 1.36 (t, J = 7.2 Hz, 3H); LCMS (electrospray) m/z (M + H) + 524.06 | ++++ | GP1 GP26 GP28 |
| 220 | 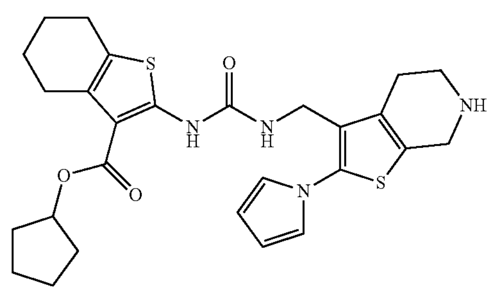 [SMILES: O=C(NCc1c(-n2cccc2)sc2c1CCNC2)Nc1sc2c(c1C(=O)OC1CCCC1)CCCC2] | White solid; $^1$H NMR (400 MHz, CDCl3) δ 10.55 (s, 1H), 6.79 (t, J = 2.0 Hz, 2H), 6.31 (t, J = 2.0 Hz, 2H), 5.04 (s, 1H), 4.26 (d, J = 6.6 Hz, 2H), 4.09 (s, 2H), 3.26 (t, J = 5.8 Hz, 2H), 2.77 (s, 2H), 2.68 (s, 2H), 2.58 (s, 2H), 1.90-1.76 (m, 12H), 1.69-1.64 (m, 2H); LCMS (electrospray) m/z (M + H)$^+$ 525.14 | ++++ | GP28 |
| 221 | 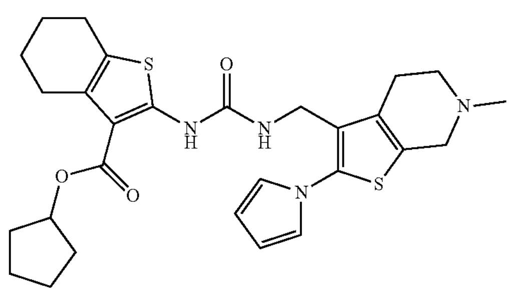 [SMILES: CN1CCc2c(sc(-n3cccc3)c2CNC(=O)Nc2sc3c(c2C(=O)OC2CCCC2)CCCC3)C1] | Pale yellow solid; $^1$H NMR (400 MHz, DMSO) δ 10.39 (s, 1H), 8.06 (t, J = 4.8 Hz, 1H), 6.99 (t, J = 2.2 Hz, 2H), 6.25 (t, J = 2.2 Hz, 2H), 5.24 (pentet, J = 6.4 and 12.4 Hz, 1H), 4.02 (d, J = 4.8 Hz, 2H), 3.48 (s, 3H), 2.64 (d, J = 5.6 Hz, 4H), 2.59 (d, J = 4.4 Hz, 2H), 2.53 (s, 2H), 2.35 (s, 3H), 1.90-1.84 (m, 2H), 1.74-1.59 (m, 12H); LCMS (electrospray) m/z (M + H)$^+$ 539.16 | ++++ | GP1 |

TABLE 1-continued

Anti-HCVcc genotype ½ activity for Formula I Series

| No. | Structure | Data | EC$_{50}$ | General Procedure (GP) |
|---|---|---|---|---|
| 222 | 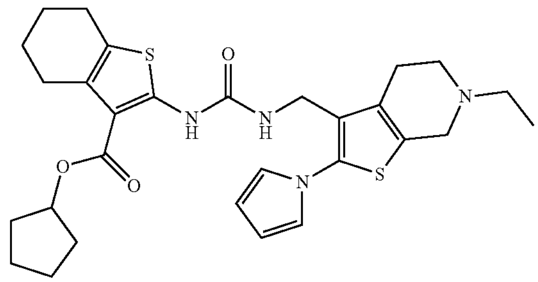 [SMILES: CCN1CCc2c(sc(-n3cccc3)c2CNC(=O)Nc2sc3c(c2C(=O)OC2CCCC2)CCCC3)C1] | Pale yellow solid; $^1$H NMR (400 MHz, DMSO) δ 10.40 (s, 1H), 8.05 (t, J = 4.8 Hz, 1H), 6.99 (t, J = 2.2 Hz, 2H), 6.25 (t, J = 2.2 Hz, 2H), 5.24 (pentet, J = 6.4 and 12.4 Hz, 1H), 4.02 (d, J = 4.8 Hz, 2H), 3.54 (s, 3H), 2.71 (d, J = 5.6 Hz, 2H), 2.64 (s, 2H), 2.56 (d, J = 8.0 Hz, 4H), 1.89-1.84 (m, 2H), 1.74-1.61 (m, 12H), 1.07 (t, J = 7.4 Hz, 3H); LCMS (electrospray) m/z (M + H)$^+$ 553.24 | ++++ | GP1 |
| 223 | 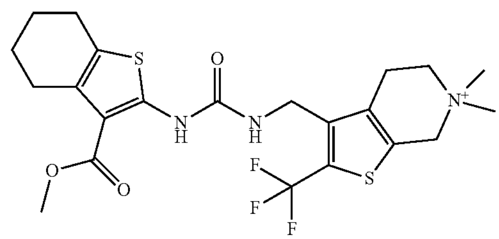 [SMILES: COC(=O)c1c(NC(=O)NCc2c(C(F)(F)F)sc3c2CC[N+](C)(C)C3)sc2c1CCCC2] | Pale yellow solid; $^1$H NMR (400 MHz, DMSO) δ 10.27 (s, 1H), 8.24 (t, J = 5.2 Hz, 1H), 4.76 (s, 2H), 4.36 (d, J = 5.2 Hz, 2H), 3.76 (s, 3H), 3.73 (t, J = 6.0 Hz, 2H), 3.17 (s, 6H), 3.07 (t, J = 6.2 Hz, 2H), 2.64 (s, 2H), 2.53 (s, 2H), 1.70 (d, J = 5.6 Hz, 4H); LCMS (electrospray) m/z (M + H)$^+$ 502.42 | ++ | GP26, GP35 |
| 224 | 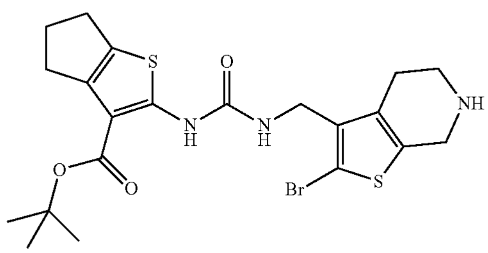 [SMILES: CC(C)(C)OC(=O)c1c(NC(=O)NCc2c(Br)sc3c2CCNC3)sc2c1CCC2] | Beige solid; $^1$H NMR (400 MHz, DMSO) δ 10.08 (s, 1H), 8.06 (d, J = 5.6 Hz, 1H), 4.12 (d, J = 5.2 Hz, 2H), 3.71 (s, 2H), 2.87 (t, J = 6.0 Hz, 2H), 2.78-2.65 (m, 4H), 2.48-2.45 (m, 2H), 2.26-2.22 (m, 2H), 1.48 (s, 9H); LCMS (electrospray) m/z (M + H) + 512.48 | ++++ | GP1, GP35 |
| 225 | 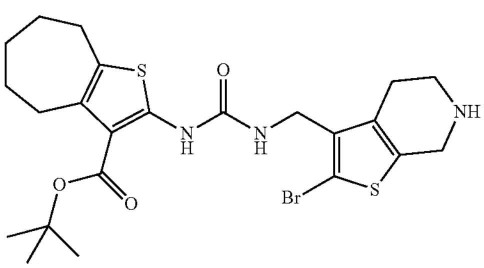 [SMILES: CC(C)(C)OC(=O)c1c(NC(=O)NCc2c(Br)sc3c2CCNC3)sc2c1CCCCC2] | Beige solid; $^1$H NMR (400 MHz, DMSO) δ 10.09 (s, 1H), 7.99 (d, J = 5.6 Hz, 1H), 4.12 (d, J = 5.2 Hz, 2H), 3.71 (s, 2H), 2.89-2.84 (m, 4H), 2.60-2.58 (m, 2H), 2.48-2.45 (m, 2H), 1.78-1.74 (m, 2H), 1.55-1.52 (m, 4H), 1.49 (s, 9H); LCMS (electrospray) m/z (M + H) + 540.54 | ++++ | GP35 |
| 226 | 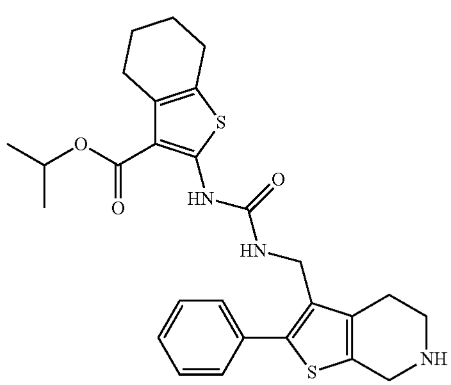 [SMILES: CC(C)OC(=O)c1c(NC(=O)NCc2c(-c3ccccc3)sc3c2CCNC3)sc2c1CCCC2] | White solid; $^1$H NMR (400 MHz, DMSO) δ 10.35 (s, 1H), 8.09 (t, J = 4.6 Hz, 1H), 7.44 (d, J = 4.3 Hz, 3H), 7.36 (td, J = 8.6, 4.4 Hz, 1H), 5.04 (dt, J = 12.5, 6.3 Hz, 1H), 4.14 (d, J = 4.7 Hz, 2H), 3.84 (s, 2H), 2.92 (t, J = 5.7 Hz, 2H), 2.65 (s, 2H), 2.55-2.49 (m, 4H), 1.68 (s, 4H), 1.27 (d, J = 6.2 Hz, 6H); LCMS (electrospray) m/z (M + H) + 510.11 | ++++ | GP38, GP35 |

TABLE 1-continued

Anti-HCVcc genotype ½ activity for Formula I Series

| No. | Structure | Data | EC$_{50}$ | General Procedure (GP) |
|---|---|---|---|---|
| 227 | 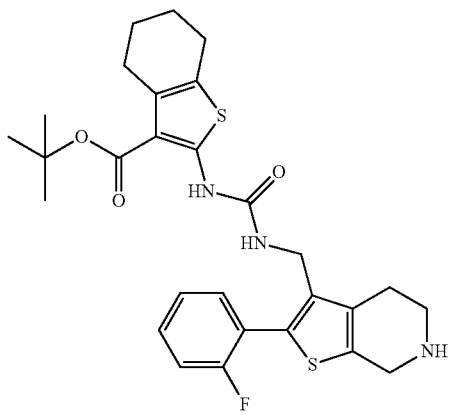 [SMILES: CC(C)(C)OC(=O)c1c(NC(=O)NCc2c(-c3ccccc3F)sc3c2CCNC3)sc2c1CCCC2] | White solid; $^1$H NMR (400 MHz, DMSO) δ 10.27 (s, 1H), 7.97 (d, J = 4.6 Hz, 1H), 7.44 (dd, J = 13.5, 6.8 Hz, 2H), 7.34-7.24 (m, 2H), 4.04 (d, J = 4.8 Hz, 2H), 3.85 (s, 2H), 2.93 (t, J = 5.7 Hz, 2H), 2.61 (s, 2H), 2.49 (s, 4H), 1.66 (s, 4H), 1.49 (s, 9H); LCMS (electrospray) m/z (M + H) + 542.15 | +++ | GP38, GP35 |
| 228 | 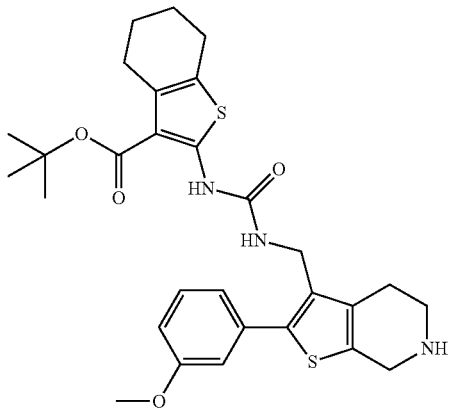 [SMILES: COc1cccc(-c2sc3c(c2CNC(=O)Nc2sc4c(c2C(=O)OC(C)(C)C)CCCC4)CCNC3)c1] | White solid; $^1$H NMR (400 MHz, DMSO) δ 10.35 (s, 1H), 8.10 (t, J = 4.8 Hz, 1H), 7.34 (t, J = 8.2 Hz, 1H), 7.04-6.99 (m, 2H), 6.93 (ddd, J = 8.3, 2.5, 0.9 Hz, 1H), 4.14 (d, J = 4.7 Hz, 2H), 3.87 (s, 2H), 3.75 (s, 3H), 2.95 (t, J = 5.6 Hz, 2H), 2.62 (s, 2H), 2.50 (d, J = 5.6 Hz, 4H), 1.67 (s, 4H), 1.49 (s, 9H); LCMS (electrospray) m/z (M + H) + 554.13 | +++ | GP38, GP35 |
| 229 | 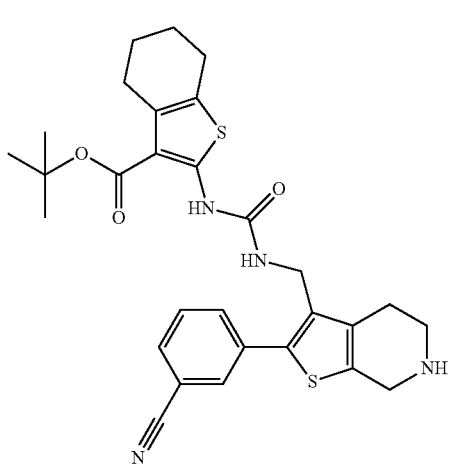 [SMILES: CC(C)(C)OC(=O)c1c(NC(=O)NCc2c(-c3cccc(C#N)c3)sc3c2CCNC3)sc2c1CCCC2] | White solid; $^1$H NMR (400 MHz, DMSO) δ 10.32 (s, 1H), 8.07 (t, J = 4.8 Hz, 1H), 7.88 (t, J = 1.4 Hz, 1H), 7.85-7.79 (m, 1H), 7.80-7.74 (m, 1H), 7.65 (t, J = 7.8 Hz, 1H), 4.14 (d, J = 4.9 Hz, 2H), 3.85 (s, 2H), 2.92 (t, J = 5.4 Hz, 2H), 2.62 (s, 2H), 2.50 (d, J = 3.5 Hz, 4H), 1.67 (s, 4H), 1.50 (s, 9H); LCMS (electrospray) m/z (M + H) + 549.16 | +++ | GP38, GP35 |

TABLE 1-continued

Anti-HCVcc genotype ½ activity for Formula I Series

| No. | Structure | Data | EC$_{50}$ | General Procedure (GP) |
|---|---|---|---|---|
| 230 | 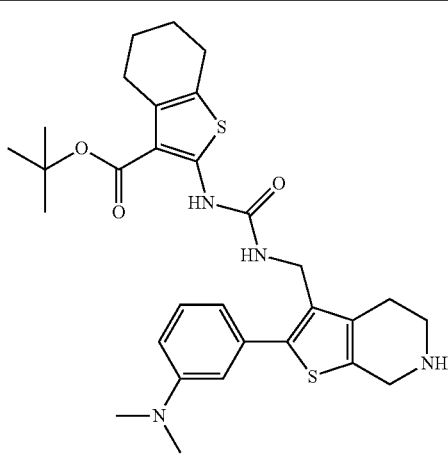 | White solid; $^1$H NMR (400 MHz, DMSO) δ 10.35 (s, 1H), 8.14 (t, J = 4.7 Hz, 1H), 7.22 (t, J = 7.9 Hz, 1H), 6.78-6.73 (m, 1H), 6.71 (dd, J = 7.8, 1.9 Hz, 2H), 4.16 (d, J = 4.6 Hz, 2H), 4.05 (s, 2H), 3.13 (t, J = 5.7 Hz, 2H), 2.88 (s, 6H), 2.62 (s, 4H), 2.55-2.48 (m, 4H), 1.67 (s, 4H), 1.49 (s, 9H); LCMS (electrospray) m/z (M + H) + 567.19 | ++ | GP38, GP35 |
| 231 | 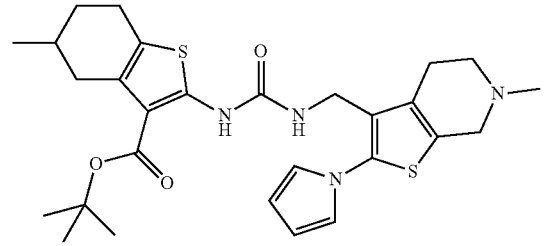 | White solid; $^1$H NMR (400 MHz, CDCl3) δ 10.56 (s, 1H), 6.79 (t, J = 1.6 Hz, 2H), 6.31 (q, J = 0.8 Hz, J = 2.0 Hz, 2H), 4.58 (brs, 1H), 4.27 (d, J = 5.2 Hz, 2H), 3.64 (brs, 2H), 2.91 (dd, J = 4.8 Hz, J = 4.8 Hz, 1H), 2.78 (m, 4H), 2.63 (m, 2H), 2.53 (s, 3H), 2.20-2.13 (q, J = 10.0 Hz, J = 10.0 Hz, 1H), 1.87-1.84 (m, 1H), 1.77 (brs, 1H), 1.54 (s, 9H), 1.40-1.38 (m, 1H), 1.05 (d, J = 6.0 Hz, 3H); LCMS (electrospray) m/z (M + H) + 541.13 | ++++ | GP1 |
| 232 | 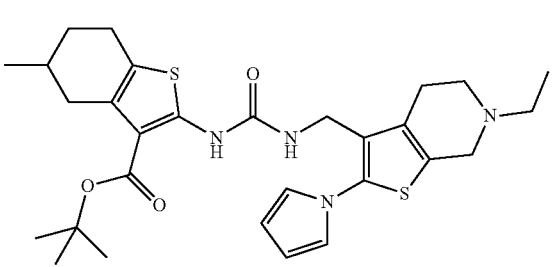 [SMILES: CCN1CCc2c(sc(-n3cccc3)c2CNC(=O)Nc2sc3c(c2C(=O)OC(C)(C)C)CC(C)CC3)C1] | White solid; $^1$H NMR (400 MHz, CDCl3) δ 10.56 (s, 1H), 6.79 (t, J = 2.0 Hz, 2H), 6.31 (t, J = 2.0 Hz, 2H), 4.58 (brs, 1H), 4.27 (q, J = 14.8 Hz, J = 18.2 Hz, 2H), 3.67 (brs, 2H), 2.93-2.88 (q, J = 4.8 Hz, J = 5.6 Hz, 1H), 2.77 (m, 4H), 2.61 (m, 2H), 2.20-2.16 (m, 1H), 1.87-1.83 (m, 1H), 1.76 (m, 1H), 1.60 (brs, 2H), 1.55 (s, 9H), 1.40-1.34 (m, 1H), 1.04 (d, J = 6.0 Hz, 3H); LCMS (electrospray) m/z (M + H) + 555.21 | ++++ | GP1 |
| 233 | 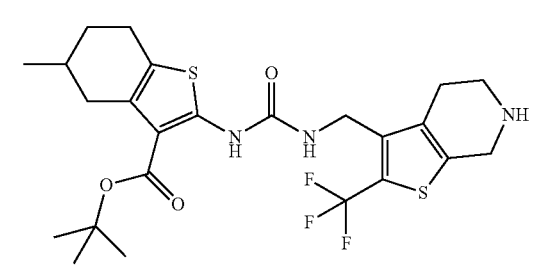 [SMILES: CC1CCc2sc(NC(=O)NCc3c(C(F)(F)F)sc4c3CCNC4)c(C(=O)OC(C)(C)C)c2C1] | White solid; $^1$H NMR (400 MHz, DMSO) δ 10.60 (s, 1H), 4.96 (brs, 1H), 4.49 (d, J = 5.2 Hz, 2H), 4.04 (brs, 2H), 3.12 (brs, 2H), 2.93-2.87 (q, J = 4.8 Hz, J = 4.8 Hz, 1H), 2.67-2.61 (m, 4H), 2.20-2.13 (m, 2H0, 1.87-1.84 (m, 1H), 1.77 (m, 1H), 1.50 (s, 9H), 1.42-1.35 (m, 1H), 1.05 (d, J = 6.4 Hz, 3H); LCMS (electrospray) m/z (M + H) + 530.11 | ++++ | GP1 GP26 GP28 |

TABLE 1-continued

Anti-HCVcc genotype ½ activity for Formula I Series

| No. | Structure | Data | EC$_{50}$ | General Procedure (GP) |
|---|---|---|---|---|
| 234 | 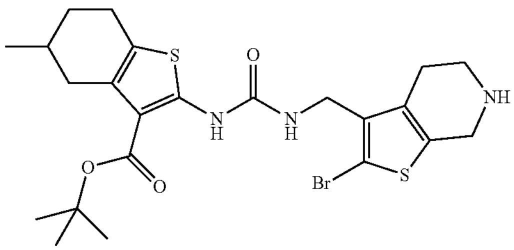 [SMILES: CC1CCc2sc(NC(=O)NCc3c(Br)sc4c3CCNC4)c(C(=O)OC(C)(C)C)c2C1] | White solid; $^1$H NMR (400 MHz, DMSO) δ 10.61 (s, 1H), 5.02 (brs, 1H), 4.35 (d, J = 5.6 Hz, 2H), 3.95 (s, 2H), 3.10 (brs, 2H), 2.94-2.89 (q, J = 4.8 Hz, J = 4.8 Hz, 2H), 2.65 (m, 4H), 2.17 (m, 2H), 1.88-1.84 (m, 1H), 1.78 (m, 1H), 1.54 (s, 9H), 1.43-1.34 (m, 1H), 1.05 (d, J = 6.8 Hz, 3H);; LCMS (electrospray) m/z (M + H) + 541.95 | ++++ | GP1 GP35 |
| 235 | 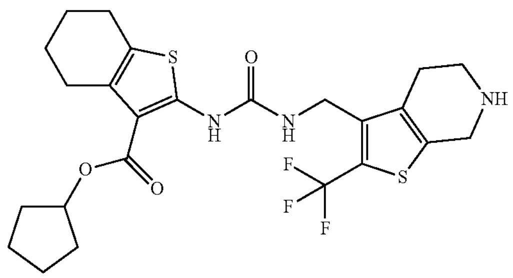 [SMILES: O=C(NCc1c(C(F)(F)F)sc2c1CCNC2)Nc1sc2c(c1C(=O)OC1CCCC1)CCCC2] | White solid; $^1$H NMR (400 MHz, DMSO) δ 10.40 (s, 1H), 8.14 (t, J = 5.4 Hz, 1H), 5.25 (t, J = 5.4 Hz, 1H), 4.30 (d, J = 4.8 Hz, 2H), 3.87 (s, 2H), 2.91 (t, J = 5.6 Hz, 2H), 2.63 (s, 2H), 1.86-1.81 (m, 2H), 1.73-1.59 (m, 12H); LCMS (electrospray) m/z (M + H)$^+$ 528.07 | ++++ | GP26, GP35 |
| 236 | 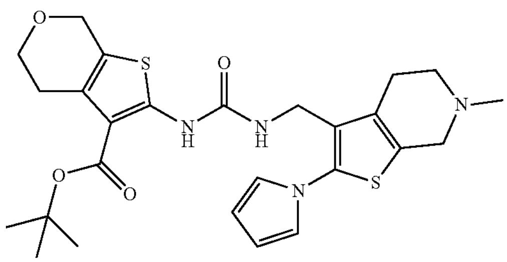 [SMILES: CN1CCc2c(sc(-n3cccc3)c2CNC(=O)Nc2sc3c(c2C(=O)OC(C)(C)C)CCOC3)C1] | White solid; $^1$H NMR (400 MHz, CDCl3) δ 10.53 (s, 1H), 6.80 (t, J = 2.0 Hz, 2H), 6.31 (t, J = 2.0 Hz, 2H), 4.65 (t, J = 2.0 Hz, 2H), 4.62 (brs, 1H), 4.28 (d, J = 5.6 Hz, 2H), 3.91 (t, J = 5.6 Hz, 2H), 3.56 (s, 2H), 2.83-2.78 (m, 2H), 2.77-2.69 (m, 4H), 2.48 (s, 3H), 1.55 (s, 9H); LCMS (electrospray) m/z (M + H) + 529.16 | ++++ | GP1 |
| 237 | 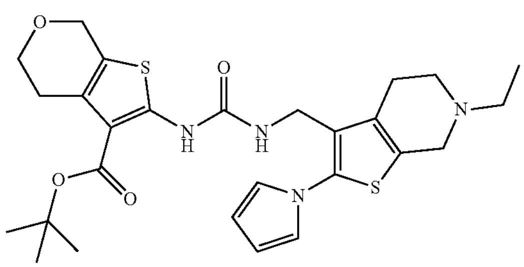 [SMILES: CCN1CCc2c(sc(-n3cccc3)c2CNC(=O)Nc2sc3c(c2C(=O)OC(C)(C)C)CCOC3)C1] | White solid; $^1$H NMR (400 MHz, CDCl3) δ 10.53 (s, 1H), 6.80 (t, J = 2.0 Hz, 2H), 6.31 (t, J = 2.4 Hz, 2H), 4.65 (t, J = 1.6 Hz, 2H), 4.61 (brs, 1H), 4.28 (d, J = 5.2 Hz, 2H), 3.91 (t, J = 5.2 Hz, 2H), 3.61 (s, 2H), 2.83-2.77 (m, 4H), 2.73-2.70 (m, 2H), 2.62 (q, J = 14.8, 7.6 Hz, 2H), 1.55 (s, 9H), 1.18 (t, J = 7.2 Hz, 3H); LCMS (electrospray) m/z (M + H) + 543.11 | ++++ | GP1 |
| 238 | 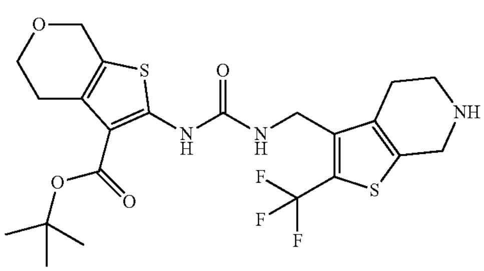 [SMILES: CC(C)(C)OC(=O)c1c(NC(=O)NCc2c(C(F)(F)F)sc3c2CCNC3)sc2c1CCOC2] | White solid; $^1$H NMR (400 MHz, DMSO) δ 10.34 (s, 1H), 8.19 (brs, 1H), 4.55 (s, 2H), 4.31 (d, J = 5.2 Hz, 2H), 3.87 (s, 2H), 3.81 (t, J = 5.6 Hz, 2H), 2.91 (t, J = 5.6 Hz, 2H), 2.74-2.69 (m, 2H), 2.56-2.51 (m, 2H), 1.51 (s, 9H); LCMS (electrospray) m/z (M + H) + 518.07 | ++++ | GP1 GP26 GP28 |

TABLE 1-continued

Anti-HCVcc genotype ½ activity for Formula I Series

| No. | Structure | Data | EC$_{50}$ | General Procedure (GP) |
|---|---|---|---|---|
| 239 | 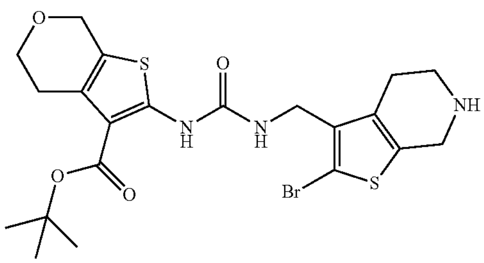 [SMILES: CC(C)(C)OC(=O)c1c(NC(=O)NCc2c(Br)sc3c2CCNC3)sc2c1CCOC2] | White solid; $^1$H NMR (400 MHz, DMSO) δ 10.32 (s, 1H), 8.15 (brs, 1H), 4.55 (s, 2H), 4.15 (d, J = 5.2 Hz, 2H), 3.81 (t, J = 6.0 Hz, 2H), 3.74 (s, 2H), 2.89 (t, J = 6.0 Hz, 2H), 2.74-2.69 (m, 2H), 2.58-2.51 (m, 2H), 1.52 (s, 9H); LCMS (electrospray) m/z (M + H) + 528.00, 529.98 | ++++ | GP1 GP35 |
| 240 | 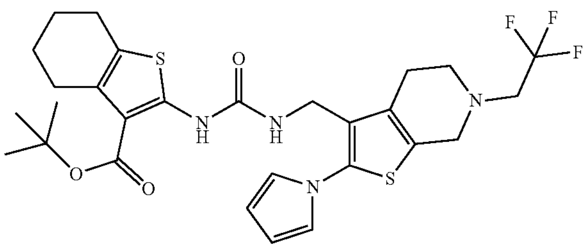 [SMILES: CC(C)(C)OC(=O)c1c(NC(=O)NCc2c(-n3cccc3)sc3c2CCN(CC(F)(F)F)C3)sc2c1CCCC2] | Ivory solid; $^1$H NMR (400 MHz, acetone-d6); δ 10.46 (s, 1H), 7.23 (t, J = 4.8 Hz, 1H), 6.95 (t, J = 2.0 Hz, 2H), 6.25 (t, J = 2.0 Hz, 2H), 4.23 (d, J = 4.8 Hz, 2H), 3.90 (s, 2H), 3.34 (q, J = 9.6 Hz, 2H), 3.06 (t, J = 6.0 Hz, 2H), 2.76-2.74 (m, 2H), 2.73-2.68 (m, 2H), 2.58-2.55 (m, 2H), 1.78-1.70 (m, 4H), 1.54 (s, 9H); LCMS (electrospray) m/z (M + H) + 595.26 | ++++ | GP28, 3 |
| 241 | 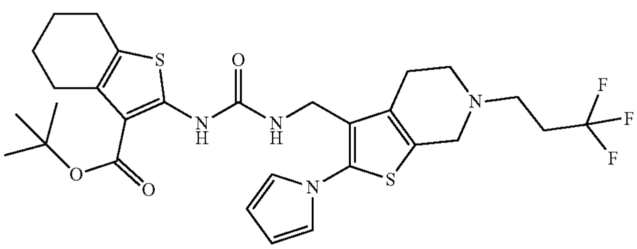 [SMILES: CC(C)(C)OC(=O)c1c(NC(=O)NCc2c(-n3cccc3)sc3c2CCN(CCC(F)(F)F)C3)sc2c1CCCC2] | Ivory solid; $^1$H NMR (400 MHz, acetone-d6); δ 10.46 (s, 1H), 7.23 (t, J = 4.8 Hz, 1H), 6.96 (t, J = 2.0 Hz, 2H), 6.24 (t, J = 2.0 Hz, 2H), 4.22 (d, J = 5.2 Hz, 2H), 3.69 (s, 2H), 2.86-2.81 (m, 4H), 2.73-2.69 (m, 4H), 2.60-2.48 (m, 4H), 1.78-1.70 (m, 4H), 1.54 (s, 9H); LCMS (electrospray) m/z (M + H) + 609.12 | ++++ | GP28, 3 |
| 242 | 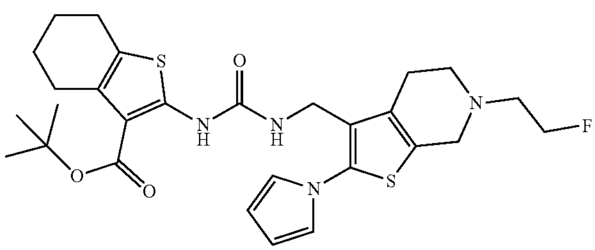 [SMILES: CC(C)(C)OC(=O)c1c(NC(=O)NCc2c(-n3cccc3)sc3c2CCN(CCF)C3)sc2c1CCCC2] | White solid; $^1$H NMR (400 MHz, acetone-d6); δ 10.46 (s, 1H), 7.22 (t, J = 4.8 Hz, 1H), 6.95 (t, J = 2.0 Hz, 2H), 6.24 (t, J = 2.0 Hz, 2H), 4.68 (t, J = 5.2 Hz, 1H), 4.55 (t, J = 5.2 Hz, 1H), 4.22 (d, J = 5.2 Hz, 2H), 3.71 (t, J = 1.6 Hz, 2H), 2.94-2.84 (m, 4H), 2.72-2.70 (m, 4H), 2.58-2.55 (m, 2H), 1.78-1.70 (m, 4H), 1.54 (s, 9H); LCMS (electrospray) m/z (M + H) + 559.12 | ++++ | GP28, 3 |
| 243 | 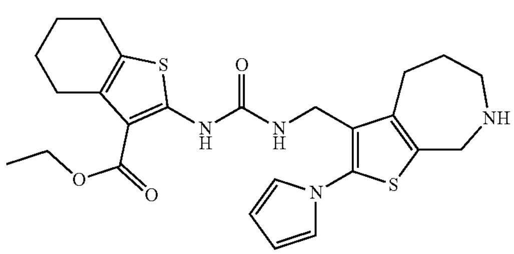 [SMILES: CCOC(=O)c1c(NC(=O)NCc2c(-n3cccc3)sc3c2CCCNC3)sc2c1CCCC2] | Colorless oil; $^1$H NMR (400 MHz, acetone-d6); δ 10.38 (s, 1H), 7.21 (t, J = 4.8 Hz, 1H), 6.92 (t, J = 2.0 Hz, 2H), 6.23 (t, J = 2.0 Hz, 2H), 4.25 (q, J = 6.8 Hz, 2H), 4.19 (d, J = 4.8 Hz, 2H), 3.87 (s, 2H), 3.16-3.13 (m, 2H), 2.84-2.81 (m, 2H), 2.74-2.70 (m, 2H), 2.59-2.56 (m, 2H), 1.79-1.68 (m, 6H), 1.31 (t, J = 6.8 Hz, 3H); LCMS (electrospray) m/z (M + H) + 499.12 | ++++ | GP2 |

TABLE 1-continued

Anti-HCVcc genotype ½ activity for Formula I Series

| No. | Structure | Data | EC$_{50}$ | General Procedure (GP) |
|---|---|---|---|---|
| 244 | 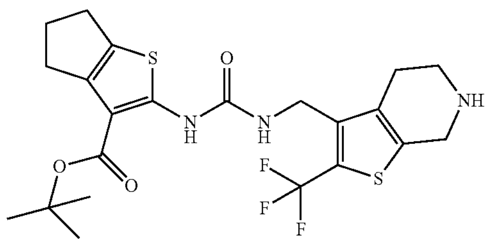 [SMILES: CC(C)(C)OC(=O)c1c(NC(=O)NCc2c(C(F)(F)F)sc3c2CCNC3)sc2c1CCC2] | Beige solid; $^1$H NMR (400 MHz, DMSO) δ 10.10 (s, 1H), 8.09 (d, J = 5.6 Hz, 1H), 4.28 (d, J = 4.8 Hz, 2H), 3.85 (s, 2H), 2.90 (t, J = 6.0 Hz, 2H), 2.78-2.68 (m, 4H), 2.53-2.51 (m, 2H), 2.26-2.22 (m, 2H), 1.48 (s, 9H); LCMS (electrospray) m/z (M + H) + 501.58 | ++++ | GP26, 35 |
| 245 | 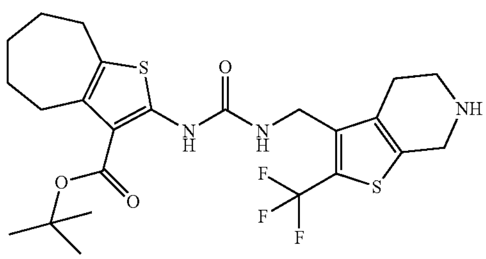 [SMILES: CC(C)(C)OC(=O)c1c(NC(=O)NCc2c(C(F)(F)F)sc3c2CCNC3)sc2c1CCCCC2] | Beige solid; $^1$H NMR (400 MHz, DMSO) δ 10.12 (s, 1H), 8.03 (d, J = 5.6 Hz, 1H), 4.28 (d, J = 4.8 Hz, 2H), 3.85 (s, 2H), 2.91-2.86 (m, 4H), 2.61-2.58 (m, 2H), 2.53-2.51 (m, 2H), 1.78-1.74 (m, 2H), 1.57-1.51 (m, 4H), 1.49 (s, 9H); LCMS (electrospray) m/z (M + H) + 529.64 | ++++ | GP26, 35 |
| 246 | 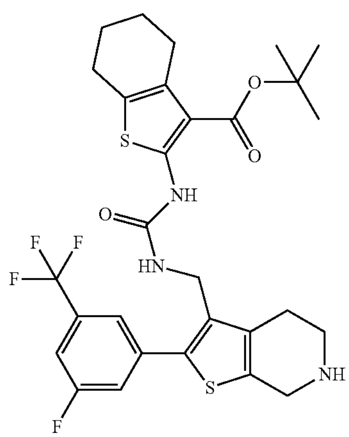 [SMILES: CC(C)(C)OC(=O)c1c(NC(=O)NCc2c(-c3cc(F)cc(C(F)(F)F)c3)sc3c2CCNC3)sc2c1CCCC2] | White solid; $^1$H NMR (400 MHz, DMSO) δ 10.20 (s, 1H), 7.85 (s, 1H), 7.70 (d, J = 9.0 Hz, 1H), 7.58-7.47 (m, 2H), 4.02 (s, 1H), 3.84 (s, 2H), 3.72 (s, 1H), 2.93 (t, J = 5.7 Hz, 2H), 2.61 (s, 2H), 2.49 (s, 4H), 1.66 (s, 4H), 1.49 (s, 9H); LCMS (electrospray) m/z (M + H) + 610.11 | ++ | GP38, GP35 |
| 247 | 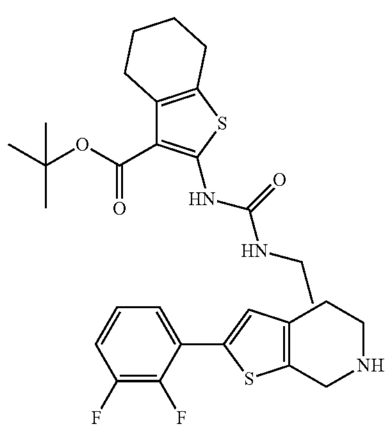 | White solid; $^1$H NMR (400 MHz, DMSO) δ 10.26 (s, 1H), 7.99 (t, J = 5.0 Hz, 1H), 7.49-7.40 (m, 1H), 7.30-7.20 (m, 2H), 4.06 (d, J = 4.9 Hz, 2H), 3.85 (s, 2H), 2.92 (t, J = 5.7 Hz, 2H), 2.61 (s, 2H), 2.54-2.49 (m, 4H), 1.66 (s, 4H), 1.49 (s, 9H); LCMS (electrospray) m/z (M + H) + 560.25 | +++ | GP38, GP35 |

TABLE 1-continued

Anti-HCVcc genotype ½ activity for Formula I Series

| No. | Structure | Data | EC$_{50}$ | General Procedure (GP) |
|---|---|---|---|---|
| 248 | 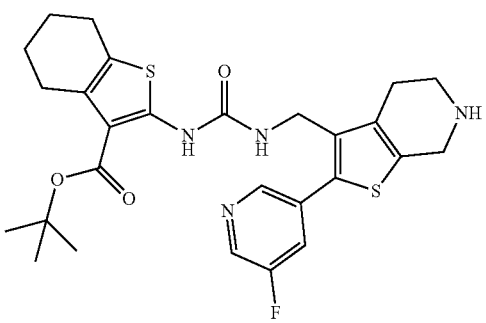 [SMILES: CC(C)(C)OC(=O)c1c(NC(=O)NCc2c(-c3cncc(F)c3)sc3c2CCNC3)sc2c1CCCC2] | White solid; $^1$H NMR (400 MHz, DMSO) δ 10.33 (s, 1H), 8.59 (d, J = 2.7 Hz, 1H), 8.54 (t, J = 1.7 Hz, 1H), 8.11 (t, J = 5.0 Hz, 1H), 7.87 (ddd, J = 9.8, 2.6, 1.9 Hz, 1H), 4.16 (d, J = 5.1 Hz, 2H), 3.96 (s, 2H), 3.02 (t, J = 5.6 Hz, 2H), 2.62 (s, 2H), 2.57 (t, J = 5.4 Hz, 2H), 2.50 (d, J = 5.6 Hz, 2H), 1.67 (s, 4H), 1.50 (s, 9H); LCMS (electrospray) m/z (M + H) + 543.17 | ++++ | GP38, GP35 |
| 249 | 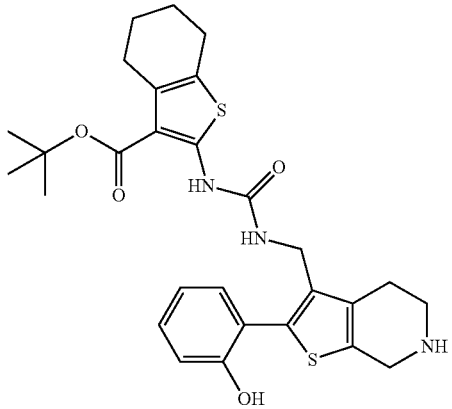 [SMILES: CC(C)(C)OC(=O)c1c(NC(=O)NCc2c(-c3ccccc3O)sc3c2CCNC3)sc2c1CCCC2] | White solid; $^1$H NMR (400 MHz, DMSO) δ 10.27 (s, 1H), 9.64 (s, 1H), 7.90 (s, 1H), 7.20-7.14 (m, 2H), 6.91 (dd, J = 8.6, 1.1 Hz, 1H), 6.82 (td, J = 7.5, 1.0 Hz, 1H), 4.00 (d, J = 4.7 Hz, 2H), 3.83 (s, 2H), 2.92 (t, J = 5.5 Hz, 2H), 2.61 (s, 2H), 2.51 (d, J = 12.1 Hz, 4H), 1.66 (s, 4H), 1.49 (s, 9H); LCMS (electrospray) m/z (M + H) + 540.11 | +++ | GP38, GP35 |
| 250 | 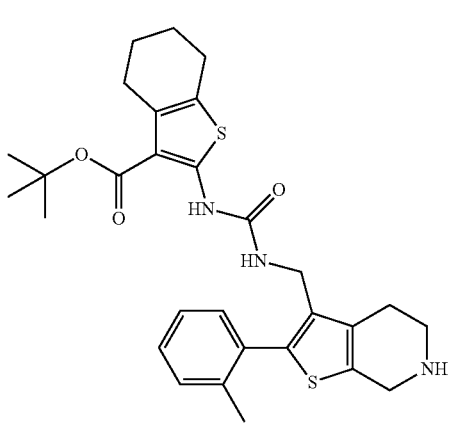 [SMILES: Cc1ccccc1-c1sc2c(c1CNC(=O)Nc1sc3c(c1C(=O)OC(C)(C)C)CCCC3)CCNC2] | White solid; $^1$H NMR (400 MHz, DMSO) δ 10.25 (s, 1H), 7.88 (t, J = 4.7 Hz, 1H), 7.32-7.25 (m, 2H), 7.24-7.17 (m, 2H), 3.90 (d, J = 4.8 Hz, 2H), 3.86 (s, 2H, 2.95 (t, J = 5.7 Hz, 2H), 2.61 (s, 2H), 2.52 (s, 4H), 2.16 (s, 3H), 1.66 (s, 4H), 1.49 (s, 9H); LCMS (electrospray) m/z (M + H) + 538.14 | +++ | GP38, GP35 |

TABLE 1-continued

Anti-HCVcc genotype ½ activity for Formula I Series

| No. | Structure | Data | EC$_{50}$ | General Procedure (GP) |
|---|---|---|---|---|
| 251 | 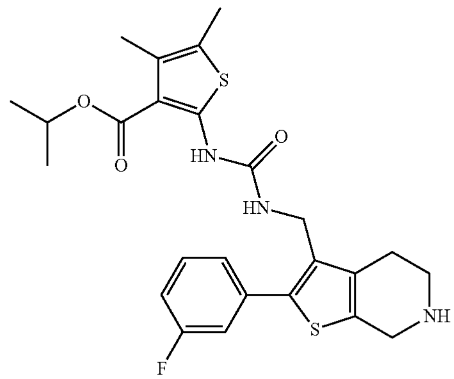 [SMILES: Cc1sc(NC(=O)NCc2c(-c3cccc(F)c3)sc3c2CCNC3)c(C(=O)OC(C)C)c1C] | White solid; $^1$H NMR (400 MHz, DMSO) δ 10.34 (s, 1H), 8.08 (t, J = 4.6 Hz, 1H), 7.51-7.47 (m, 1H), 7.30-7.45 (m, 2H), 7.22-7...19 (m, 1H), 5.09-5.03 (m, 1H), 4.15 (d, J = 4.8 Hz, 2H), 3.84 (s, 2H), 2.91 (t, J = 5.6 Hz, 2H), 2.14 (d, J = 6.0 Hz, 6H), 1.30 (s, 3H), 1.28 (s, 3H); LCMS (electrospray) m/z (M + H) + 502.15 | ++++ | GP38, GP35 |
| 252 | 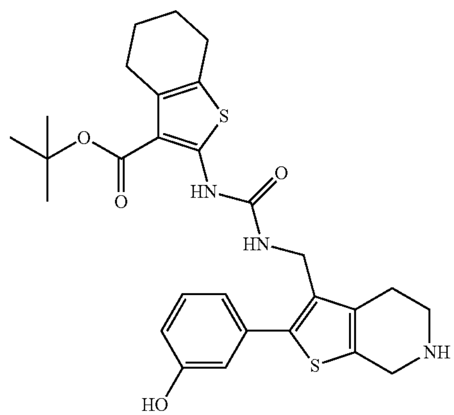 [SMILES: CC(C)(C)OC(=O)c1c(NC(=O)NCc2c(-c3cccc(O)c3)sc3c2CCNC3)sc2c1CCCC2] | White solid; $^1$H NMR (400 MHz, MeOD) δ 7.22 (t, J = 7.9 Hz, 1H), 6.94-6.90 (m, 1H), 6.89-6.87 (m, 1H), 6.77 (ddd, J = 7.8, 2.5, 0.7 Hz, 1H), 4.28 (s, 2H), 3.97 (s, 2H), 3.09 (t, J = 5.8 Hz, 2H), 2.70 (t, J = 5.2 Hz, 2H), 2.66 (t, J = 5.9 Hz, 2H), 2.58 (t, J = 5.3 Hz, 2H), 1.83-1.71 (m, 4H), 1.55 (s, 8H); LCMS (electrospray) m/z (M + H) + 540.18 | +++ | GP38, GP35 |
| 253 | 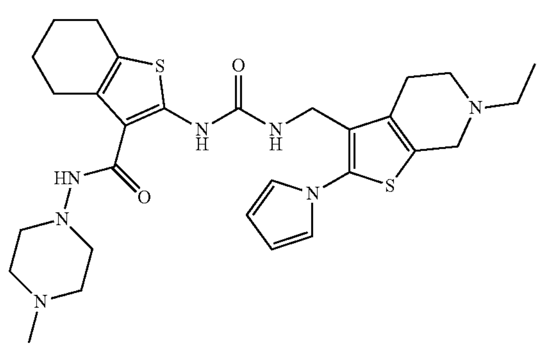 [SMILES: CCN1CCc2c(sc(-n3cccc3)c2CNC(=O)Nc2sc3c(c2C(=O)NN2CCN(C)CC2)CCCC3)C1] | White solid; $^1$H NMR (400 MHz, CDCl3) δ 11.09 (s, 1H), 6.79 (t, J = 2.0 Hz, 2H), 6.29 (t, J = 2 Hz, 2H), 4.75 (brs, 1H), 4.23 (d, J = 5.2 Hz, 2H), 3.62 (s, 2H), 2.91 (brs, 3H), 2.80 (t, J = 6 Hz, 2H), 2.73 (d, J = 5.6 Hz, 2H), 2.63 (m, 9H), 2.27 (s, 3H), 1.82 (m, 6H), 1.17 (t, J = 6.8 Hz, 3H); LCMS (electrospray) m/z (M + H) + 582.29 | +++ | GP1 GP12 |
| 254 | 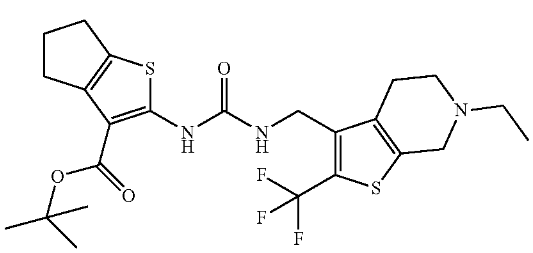 [SMILES: CCN1CCc2c(sc(C(F)(F)F)c2CNC(=O)Nc2sc3c(c2C(=O)OC(C)(C)C)CCC3)C1] | Beige solid; $^1$H NMR (400 MHz, CDCl$_3$) δ 10.29 (s, 1H), 4.84 (s, 1H), 4.50 (d, J = 5.2 Hz, 2H), 3.67 (s, 2H), 2.86-2.78 (m, 8H), 2.63 (q, J = 7.2 Hz, J = 6.8 Hz, 2H), 2.36-2.30 (m, 2H), 1.52 (s, 9H), 1.17 (t, J = 7.2 Hz, 3H); LCMS (electrospray) m/z (M + H) + 530.18 | ++++ | GP26, 35, 3 |

TABLE 1-continued

Anti-HCVcc genotype ½ activity for Formula I Series

| No. | Structure | Data | EC$_{50}$ | General Procedure (GP) |
|---|---|---|---|---|
| 255 | 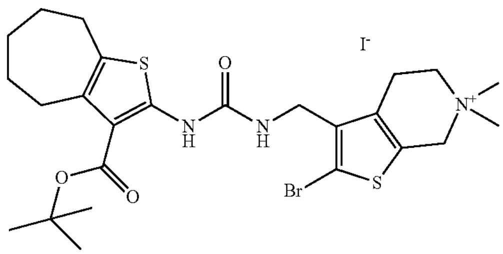 [SMILES: CC(C)(C)OC(=O)c1c(NC(=O)NCc2c(Br)sc3c2CC[N+](C)(C)C3)sc2c1CCCCC2 ; [I-]] | Ivory solid; $^1$H NMR (400 MHz, CDCl$_3$) δ 10.40 (s, 1H), 6.01 (s, 1H), 4.92 (s, 2H), 4.31 (d, J = 5.2 Hz, 2H), 3.97-3.95 (m, 2H), 3.54 (s, 6H), 3.17-3.15 (m, 2H), 2.92-2.90 (m, 2H), 2.63-2.60 (m, 2H), 1.82-1.79 (m, 2H), 1.63-1.57 (m, 4H), 1.51 (s, 9H); LCMS (electrospray) m/z (M + H) + 568.28 | ++++ | GP26, 35, 3 |
| 256 | 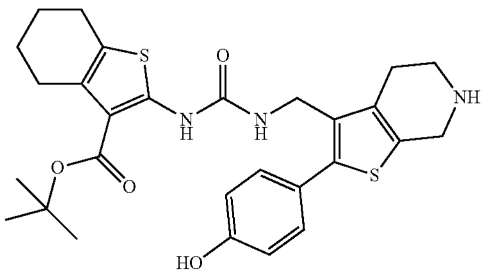 [SMILES: CC(C)(C)OC(=O)c1c(NC(=O)NCc2c(-c3ccc(O)cc3)sc3c2CCNC3)sc2c1CCCC2] | Ivory solid; $^1$H NMR (400 MHz, DMSO) δ 10.33 (s, 1H), 9.65 (s, 1H), 8.03 (t, J = 4.5 Hz, 1H), 7.26-7.20 (m, 2H), 6.83-6.76 (m, 2H), 4.08 (d, J = 4.8 Hz, 2H), 3.80 (s, 2H), 2.90 (t, J = 5.8 Hz, 2H), 2.62 (t, J = 6.5 Hz, 2H), 2.56-2.50 (m, 2H), 2.46-2.39 (m, 2H), 1.67 (s, 4H), 1.49 (s, 9H); LCMS (electrospray) m/z (M + H) + 540.18 | +++ | GP38, GP35 |
| 257 | 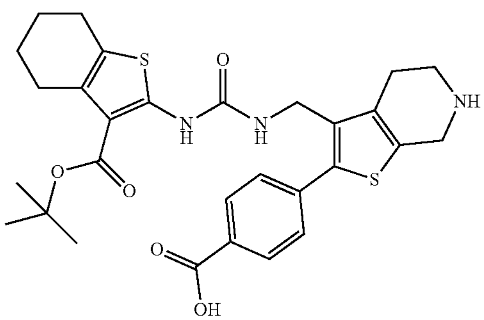 [SMILES: CC(C)(C)OC(=O)c1c(NC(=O)NCc2c(-c3ccc(C(=O)O)cc3)sc3c2CCNC3)sc2c1CCCC2] | Ivory solid; $^1$H NMR (400 MHz, DMSO) δ 10.34 (s, 1H), 8.11 (s, 2H), 7.97 (d, J = 8.5 Hz, 2H), 7.54 (d, J = 8.4 Hz, 2H), 4.18 (d, J = 4.6 Hz, 2H), 3.93 (s, 2H), 3.00 (t, J = 5.8 Hz, 2H), 2.62 (s, 3H), 2.57-2.50 (m, 5H), 1.67 (s, 4H), 1.49 (s, 8H); LCMS (electrospray) m/z (M + H) + 568.21 | ++ | GP38, GP35 |
| 258 | 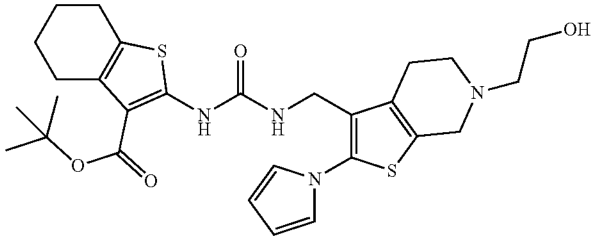 [SMILES: CC(C)(C)OC(=O)c1c(NC(=O)NCc2c(-n3cccc3)sc3c2CCN(CCO)C3)sc2c1CCCC2] | Ivory solid; $^1$H NMR (400 MHz, acetone-d6); δ 10.46 (s, 1H), 7.23 (t, J = 4.8 Hz, 1H), 6.96 (t, J = 2.0 Hz, 2H), 6.24 (t, J = 2.0 Hz, 2H), 4.22 (d, J = 5.2 Hz, 2H), 3.69-2.66 (m, 4H), 3.45 (brs, 1H), 2.85-2.84 (m, 2H), 2.72-2.68 (m, 6H), 2.58-2.56 (m, 2H), 1.78-1.70 (m, 4H), 1.54 (s, 9H); LCMS (electrospray) m/z (M + H) + 557.25 | ++++ | GP28, 3 |
| 259 | 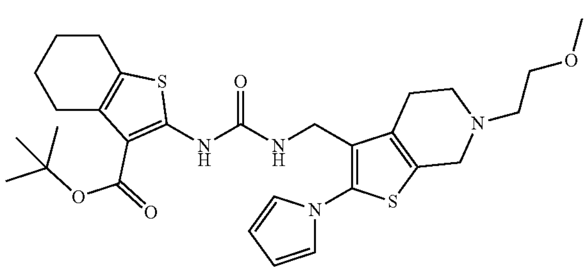 [SMILES: COCCN1CCc2c(sc(-n3cccc3)c2CNC(=O)Nc2sc3c(c2C(=O)OC(C)(C)C)CCCC3)C1] | White solid; $^1$H NMR (400 MHz, acetone-d6); δ 10.46 (s, 1H), 7.21 (t, J = 4.8 Hz, 1H), 6.95 (t, J = 2.0 Hz, 2H), 6.24 (t, J = 2.0 Hz, 2H), 4.21 (d, J = 5.2 Hz, 2H), 3.66 (t, J = 1.6 Hz, 2H), 3.53 (t, J = 5.6 Hz, 2H), 3.29 (s, 3H), 2.74-2.66 (m, 8H), 2.58-2.55 (m, 2H), 1.76-1.70 (m, 4H), 1.54 (s, 9H); LCMS (electrospray) m/z (M + H) + 571.23 | ++++ | GP28, 3 |

TABLE 1-continued

Anti-HCVcc genotype ½ activity for Formula I Series

| No. | Structure | Data | EC$_{50}$ | General Procedure (GP) |
|---|---|---|---|---|
| 260 | 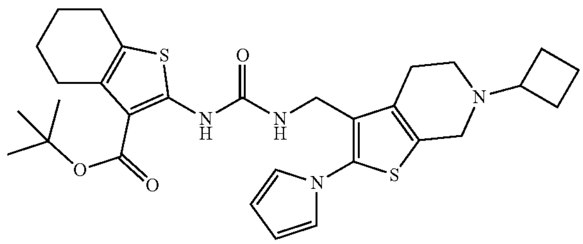 [SMILES: CC(C)(C)OC(=O)c1c(NC(=O)NCc2c(-n3cccc3)sc3c2CCN(C2CCC2)C3)sc2c1CCCC2] | Ivory solid; $^1$H NMR (400 MHz, acetone-d6); δ 10.46 (s, 1H), 7.21 (brs, 1H), 6.95 (t, J = 2.0 Hz, 2H), 6.24 (t, J = 2.0 Hz, 2H), 4.21 (d, J = 5.2 Hz, 2H), 3.46 (s, 2H), 2.99-2.91 (m, 1H), 2.71-2.65 (m, 4H), 2.62-2.56 (m, 4H), 2.12-2.08 (m, 2H), 1.91-1.84 (m, 2H), 1.78-1.66 (m, 6H), 1.54 (s, 9H); LCMS (electrospray) m/z (M + H) + 567.20 | ++++ | GP28, 5 |
| 261 | 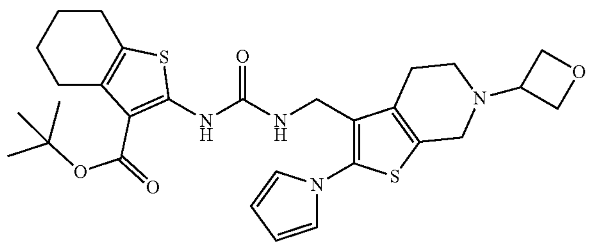 [SMILES: CC(C)(C)OC(=O)c1c(NC(=O)NCc2c(-n3cccc3)sc3c2CCN(C2COC2)C3)sc2c1CCCC2] | White solid; $^1$H NMR (400 MHz, acetone-d6); δ 10.47 (s, 1H), 7.23 (t, J = 4.8 Hz, 1H), 6.95 (t, J = 2.0 Hz, 2H), 6.24 (t, J = 2.0 Hz, 2H), 4.64-4.61 (m, 2H), 4.58-4.55 (m, 2H), 4.22 (d, J = 5.2 Hz, 2H), 3.71 (quint, J = 6.4 Hz, 1H), 3.51 (s, 2H), 2.71-2.69 (m, 4H), 2.65-2.62 (m, 2H), 2.58-2.56 (m, 2H), 1.78-1.70 (m, 4H), 1.54 (s, 9H); LCMS (electrospray) m/z (M + H) + 569.21 | ++++ | GP28, 5 |
| 262 | 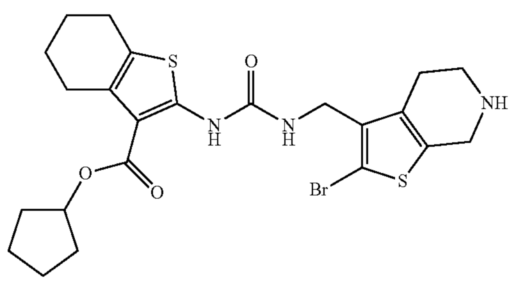 [SMILES: O=C(NCc1c(Br)sc2c1CCNC2)Nc1sc2c(c1C(=O)OC1CCCC1)CCCC2] | White solid; $^1$H NMR (400 MHz, DMSO) δ 10.37 (s, 1H), 8.10 (t, J = 5.4 Hz, 1H), 5.25 (t, J = 5.4 Hz, 1H), 4.14 (d, J = 5.2 Hz, 2H), 3.73 (s, 2H), 2.89 (t, J = 5.6 Hz, 2H), 2.63 (s, 2H), 1.87-1.81 (m, 2H), 1.73-1.59 (m, 12H); LCMS (electrospray) m/z (M + H)$^+$ 538.07 | ++++ | GP35 |
| 263 | 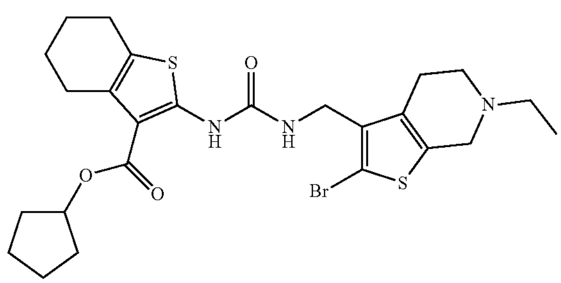 [SMILES: CCN1CCc2c(sc(Br)c2CNC(=O)Nc2sc3c(c2C(=O)OC2CCCC2)CCCC3)C1] | Pale yellow solid; $^1$H NMR (400 MHz, DMSO) δ 10.66 (s, 1H), 5.30 (pentet, J = 6.4 and 12.4 Hz, 1H), 3.40 (d, J = 4.8 Hz, 2H), 3.00 (s, 2H), 2.71 (d, J = 5.6 Hz, 2H), 2.64 (s, 2H), 2.56 (d, J = 8.0 Hz, 4H), 1.89-1.84 (m, 2H), 1.74-1.61 (m, 12H), 1.07 (t, J = 7.4 Hz, 3H); LCMS (electrospray) m/z (M + H)$^+$ 566.10 | ++++ | GP35, GP5 |
| 264 | 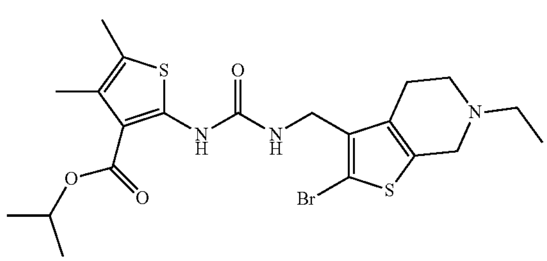 [SMILES: CCN1CCc2c(sc(Br)c2CNC(=O)Nc2sc(C)c(C)c2C(=O)OC(C)C)C1] | Pale yellow solid; $^1$H NMR (400 MHz, DMSO) δ 10.32 (s, 1H), 8.06 (t, J = 5.0 Hz, 1H), 5.08 (pentet, J = 6.4 and 12.4 Hz, 1H), 4.14 (d, J = 4.8 Hz, 2H), 3.48 (s, 2H), 2.67 (t, J = 5.6 Hz, 2H), 2.61 (d, J = 5.2 Hz, 2H), 2.16 (s, 3H), 2.14 (s, 3H), 1.31 (s, 3H), 1.30 (s, 3H), 1.05 (t, J = 7.2 Hz, 3H); LCMS (electrospray) m/z (M + H)$^+$ 514.06 | ++++ | GP35, GP5 |

TABLE 1-continued

Anti-HCVcc genotype ½ activity for Formula I Series

| No. | Structure | Data | EC$_{50}$ | General Procedure (GP) |
|---|---|---|---|---|
| 265 | 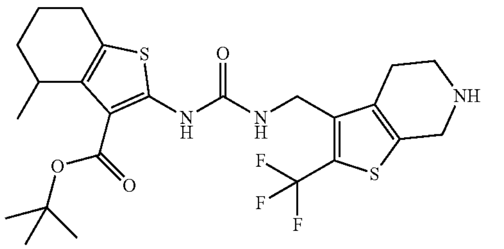 [SMILES: CC1CCCc2sc(NC(=O)NCc3c(C(F)(F)F)sc4c3CCNC4)c(C(=O)OC(C)(C)C)c21] | White solid; $^1$H NMR (400 MHz, DMSO) δ 10.78 (s, 1H), 4.93 (brs, 1H), 4.49 (d, J = 6 Hz, 2H), 4.07 (brs, 2H), 3.24 (brs, 1H), 3.14 (brs, 2H), 2.71 (brs, 2H), 2.63-2.55 (m, 2H), 2.05-1.99 (m, 2H), 1.84-1.76 (m, 2H), 1.66-1.63 (m, 1H), 1.55 (s, 9H), 1.14 (d, J = 6.8 Hz, 3H); LCMS (electrospray) m/z (M + H) + 530.18 | ++++ | GP1 GP26 GP28 |
| 266 | 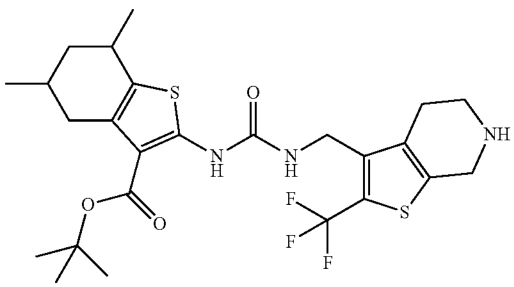 [SMILES: CC1Cc2c(sc(NC(=O)NCc3c(C(F)(F)F)sc4c3CCNC4)c2C(=O)OC(C)(C)C)C(C)C1] | White solid; $^1$H NMR (400 MHz, DMSO) δ 10.64 (s, 1H), 4.95 (t, J = 5.6 Hz, 1H), 4.50 (d, J = 5.2 Hz, 2H), 4.06 (brs, 2H), 3.14 (t, J = 5.2 Hz, 2H), 2.95-2.89 (dd, J = 5.2 Hz, J = 5.2 Hz, 1H), 2.89-2.80 (m, 1H), 2.70 (m, 2H), 2.14-2.04 (m, 1H), 1.90-1.85 (m, 1H), 1.79 (m, 1H), 1.54 (s, 9H), 1.25 (m, 4H), 1.05 (d, J = 6.4 Hz, 3H); LCMS (electrospray) m/z (M + H) + 544.19 | ++++ | GP1 GP26 GP28 |
| 267 | 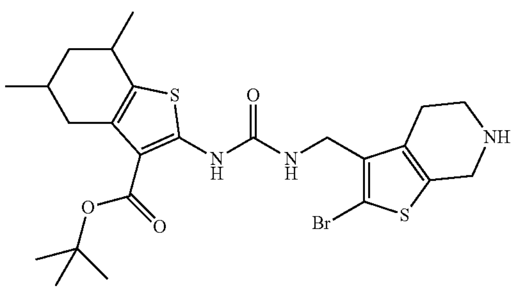 [SMILES: CC1Cc2c(sc(NC(=O)NCc3c(Br)sc4c3CCNC4)c2C(=O)OC(C)(C)C)C(C)C1] | White solid; $^1$H NMR (400 MHz, DMSO) δ 10.63 (s, 1H), 5.04 (brs, 1H), 4.35 (m, 2H), 3.94 (s, 2H), 3.09 (t, J = 5.6 Hz, 2H), 2.95-2.89 (dd, J = 6.8 Hz, J = 5.2 Hz, 1H), 2.85 (m, 1H), 2.64 (t, J = 5.6 Hz, 2H), 2.20 (m, 2H), 2.14-2.04 (m, 1H), 2.14-1.89-1.86 (m, 1H), 1.79 (m, 1H), 1.54 (s, 9H), 1.24 (m, 4H), 1.05 (d, J = 6.8 Hz, 3H); LCMS (electrospray) m/z (M + H) + 556.03 | ++++ | GP1 GP35 |
| 268 | 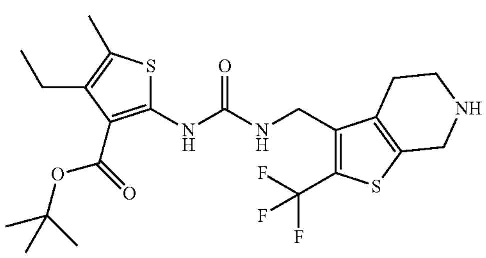 [SMILES: CCc1c(C)sc(NC(=O)NCc2c(C(F)(F)F)sc3c2CCNC3)c1C(=O)OC(C)(C)C] | White solid; $^1$H NMR (400 MHz, DMSO) δ 10.71 (s, 1H), 5.12 (brs, 1H), 4.48 (d, J = 5.6 Hz, 2H), 4.13 (brs, 2H), 3.20 (brs, 2H), 2.79 (brs, 2H), 2.67 (q, J = 7.2 Hz, J = 7.2 Hz, 4H), 2.22 (s, 3H), 1.55 (s, 9H), 1.05 (t, J = 7.2 Hz, 3H); LCMS (electrospray) m/z (M + H) + 504.12 | ++++ | GP1 GP26 GP28 |
| 269 | 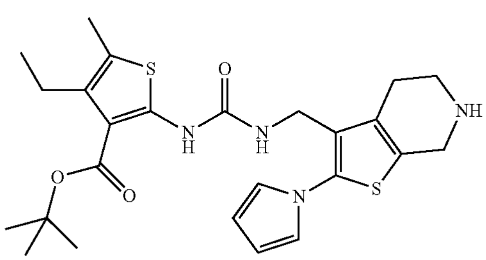 [SMILES: CCc1c(C)sc(NC(=O)NCc2c(-n3cccc3)sc3c2CCNC3)c1C(=O)OC(C)(C)C] | White solid; $^1$H NMR (400 MHz, DMSO) δ 10.66 (s, 1H), 6.80 (t, J = 2.4 Hz, 2H), 6.31 (t, J = 2 Hz, 2H), 4.81 (brs, 1H), 4.25 (d, J = 5.2 Hz, 2H), 4.03 (s, 2H), 3.20 (brs, 2H), 2.68 (m, 4H), 2.23 (s, 3H), 1.56 (s, 9H), 1.05 (t, J = 7.6 Hz, 3H); LCMS (electrospray) m/z (M + H) + 501.20 | ++++ | GP1 GP28 |

TABLE 1-continued

Anti-HCVcc genotype ½ activity for Formula I Series

| No. | Structure | Data | EC$_{50}$ | General Procedure (GP) |
|---|---|---|---|---|
| 270 | 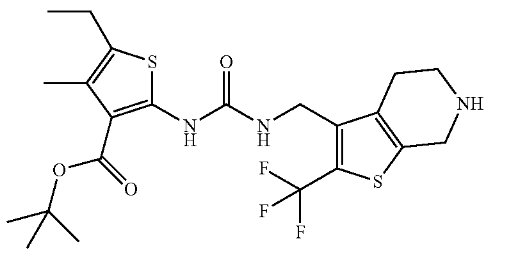 [SMILES: CCc1sc(NC(=O)NCc2c(C(F)(F)F)sc3c2CCNC3)c(C(=O)OC(C)(C)C)c1C] | White solid; $^1$H NMR (400 MHz, DMSO) δ 10.68 (s, 1H), 4.98 (brs, 1H), 4.49 (d, J = 5.2 Hz, 2H), 4.07 (s, 2H), 3.15 (t, J = 5.6 Hz, 2H), 2.73 (brs, 2H), 2.64 (q, J = 7.2 Hz, J = 7.6 Hz, 4H), 2.19 (s, 3H), 1.54 (s, 9H), 1.20 (t, J = 7.6 Hz, 3H); LCMS (electrospray) m/z (M + H) + 504.26 | ++++ | GP1 GP26 GP28 |
| 271 | 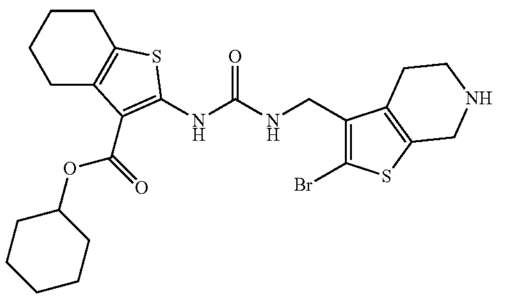 [SMILES: O=C(NCc1c(Br)sc2c1CCNC2)Nc1sc2c(c1C(=O)OC1CCCCC1)CCCC2] | Pale yellow solid; $^1$H NMR (400 MHz, DMSO) δ 9.88 (s, 1H), 7.59 (t, J = 5.4 Hz, 1H), 4.39 (pentet, J = 6.4 and 12.4 Hz, 1H), 3.64 (d, J = 4.8 Hz, 2H), 3.23 (s, 2H), 2.39 (t, J = 5.8 Hz, 2H), 2.23 (s, 2H), 2.00 (d, J = 8.0 Hz, 4H), 1.33-1.30 (m, 2H), 1.20 (s, 6H), 1.04-0.72 (m, 6H); LCMS (electrospray) m/z (M + H)$^+$ 552.15 | ++++ | GP35 |
| 272 | 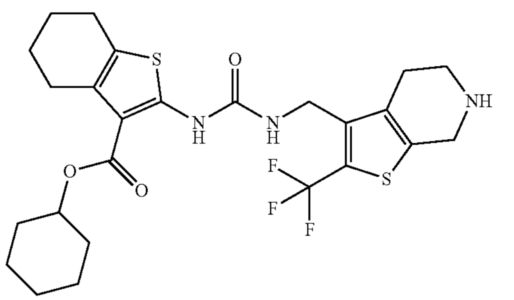 [SMILES: O=C(NCc1c(C(F)(F)F)sc2c1CCNC2)Nc1sc2c(c1C(=O)OC1CCCCC1)CCCC2] | Pale yellow solid; $^1$H NMR (400 MHz, DMSO) δ 10.40 (s, 1H), 8.14 (t, J = 5.4 Hz, 1H), 4.88 (pentet, J = 6.4 and 12.4 Hz, 1H), 4.31 (d, J = 4.8 Hz, 2H), 3.87 (s, 2H), 2.91 (t, J = 5.8 Hz, 2H), 2.69 (s, 2H), 2.53 (d, J = 8.0 Hz, 4H), 1.83-1.80 (m, 2H), 1.70 (s, 6H), 1.54-1.37 (m, 6H); LCMS (electrospray) m/z (M + H)$^+$ 542.22 | ++++ | GP26, GP35 |
| 273 | 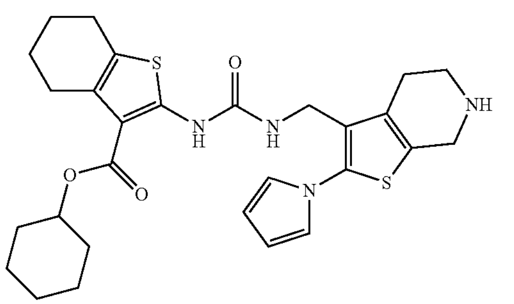 [SMILES: O=C(NCc1c(-n2cccc2)sc2c1CCNC2)Nc1sc2c(c1C(=O)OC1CCCCC1)CCCC2] | White solid; $^1$H NMR (400 MHz, DMSO) δ 10.40 (s, 1H), 8.05 (t, J = 5.4 Hz, 1H), 6.99 (t, J = 2.2 Hz, 2H), 6.24 (t, J = 2.2 Hz, 2H), 4.90 (pentet, J = 6.4 and 12.4 Hz, 1H), 4.01 (d, J = 4.8 Hz, 2H), 3.79 (s, 2H), 2.93 (t, J = 5.8 Hz, 2H), 2.73 (s, 2H), 2.53 (d, J = 8.0 Hz, 4H), 1.83-1.80 (m, 2H), 1.70 (s, 6H), 1.54-1.37 (m, 6H); LCMS (electrospray) m/z (M + H)$^+$ 539.30 | ++++ | GP28 |
| 274 | 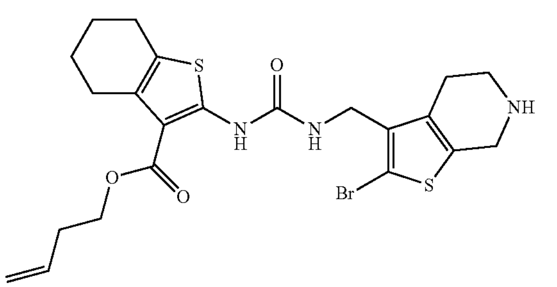 [SMILES: C=CCCOC(=O)c1c(NC(=O)NCc2c(Br)sc3c2CCNC3)sc2c1CCCC2] | White solid; $^1$H NMR (400 MHz, DMSO) δ 10.28 (s, 1H), 8.09 (t, J = 5.4 Hz, 1H), 5.84 (dt, J = 6.8 and 17.2 Hz, 1H), 5.13 (td, J = 1.6 and 15.6 Hz, 1H), 5.07 (d, J = 10.4 Hz, 1H), 4.23 (t, J = 12.0 Hz, 2H), 4.15 (d, J = 4.8 Hz, 2H), 3.73 (s, 2H), 2.89 (t, J = 5.6 Hz, 2H), 2.65 (s, 2H), 2.53 (s, 2H), 2.48 (s, 2H), 2.43 (q, J = 6.4 Hz, 2H), 1.69 (s, 4H); LCMS (electrospray) m/z (M + H)$^+$ 524.06 | ++++ | GP35 |

TABLE 1-continued

Anti-HCVcc genotype ½ activity for Formula I Series

| No. | Structure | Data | EC$_{50}$ | General Procedure (GP) |
|---|---|---|---|---|
| 275 | 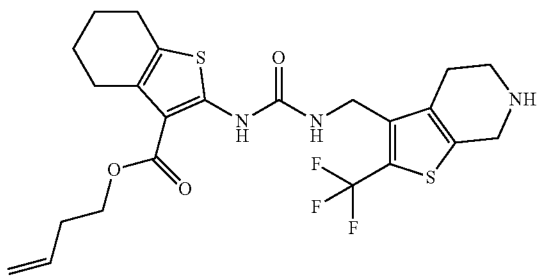 [SMILES: C=CCCOC(=O)c1c(NC(=O)NCc2c(C(F)(F)F)sc3c2CCNC3)sc2c1CCCC2] | White solid; $^1$H NMR (400 MHz, DMSO) δ 10.31 (s, 1H), 8.14 (t, J = 5.4 Hz, 1H), 5.83 (dt, J = 6.8 and 17.2 Hz, 1H), 5.13 (td, J = 1.6 and 15.6 Hz, 1H), 5.07 (d, J = 10.4 Hz, 1H), 4.31 (d, J = 4.8 Hz, 2H), 4.23 (t, J = 12.0 Hz, 2H), 3.87 (s, 2H), 2.91 (t, J = 5.6 Hz, 2H), 2.65 (s, 2H), 2.53 (s, 2H), 2.48 (s, 2H), 2.43 (q, J = 6.4 Hz, 2H), 1.69 (s, 4H); LCMS (electrospray) m/z (M + H)$^+$ 514.19 | ++++ | GP26, GP35 |
| 276 | 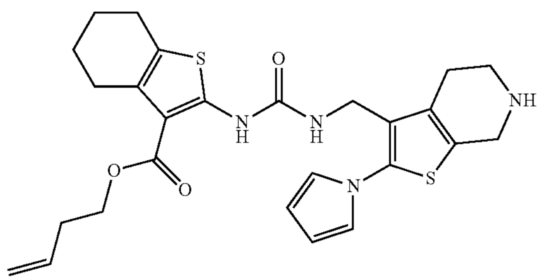 [SMILES: C=CCCOC(=O)c1c(NC(=O)NCc2c(-n3cccc3)sc3c2CCNC3)sc2c1CCCC2] | White solid; $^1$H NMR (400 MHz, DMSO) δ 10.30 (s, 1H), 8.06 (t, J = 5.4 Hz, 1H), 6.99 (t, J = 2.2 Hz, 2H), 6.24 (t, J = 2.2 Hz, 2H), 5.84 (dt, J = 6.8 and 17.2 Hz, 1H), 5.13 (td, J = 1.6 and 15.6 Hz, 1H), 5.07 (d, J = 10.4 Hz, 1H), 4.26 (t, J = 12.0 Hz, 2H), 4.01 (d, J = 4.8 Hz, 2H), 3.79 (s, 2H), 2.93 (t, J = 5.6 Hz, 2H), 2.65 (s, 2H), 2.53 (s, 2H), 2.48 (s, 2H), 2.43 (q, J = 6.4 Hz, 2H), 1.69 (s, 4H); LCMS (electrospray) m/z (M + H)$^+$ 511.20 | ++++ | GP28 |
| 277 | 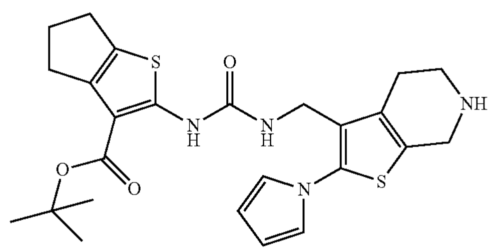 [SMILES: CC(C)(C)OC(=O)c1c(NC(=O)NCc2c(-n3cccc3)sc3c2CCNC3)sc2c1CCC2] | White solid; $^1$H NMR (400 MHz, DMSO) δ 10.08 (s, 1H), 8.01 (t, J = 5.2 Hz, 1H), 6.97 (t, J = 2.4 Hz, 2H), 6.22 (t, J = 2.0 Hz, 2H), 3.99 (d, J = 5.2 Hz, 2H), 3.77 (s, 2H), 2.93-2.90 (m, 2H), 2.75-2.68 (m, 4H), 2.48-2.43 (m, 2H), 2.26-2.22 (m, 2H), 1.48 (s, 9H); LCMS (electrospray) m/z (M + H) + 499.22 | ++++ | GP28 |
| 278 | 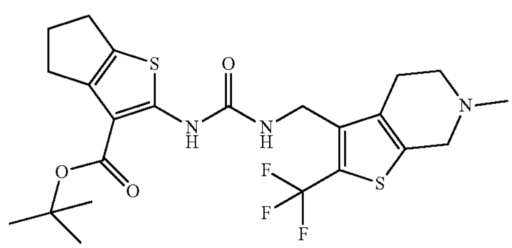 [SMILES: CN1CCc2c(sc(C(F)(F)F)c2CNC(=O)Nc2sc3c(c2C(=O)OC(C)(C)C)CCC3)C1] | White solid; $^1$H NMR (400 MHz, CDCl$_3$) δ 10.28 (s, 1H), 4.92 (t, J = 5.6 Hz, 1H), 4.49 (d, J = 5.2 Hz, 2H), 3.61 (s, 2H), 2.84-2.72 (m, 8H), 2.47 (s, 3H), 2.36-2.29 (m, 2H), 1.52 (s, 9H); LCMS (electrospray) m/z (M + H) + 516.16 | ++++ | GP26, 35, 5 |
| 279 | 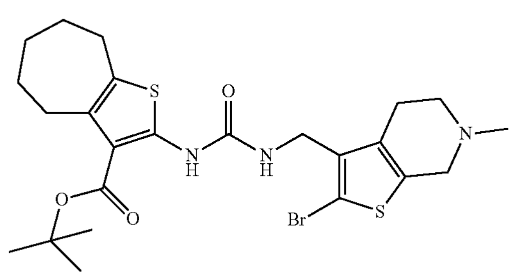 [SMILES: CN1CCc2c(sc(Br)c2CNC(=O)Nc2sc3c(c2C(=O)OC(C)(C)C)CCCCC3)C1] | Ivory solid; $^1$H NMR (400 MHz, CDCl$_3$) δ 10.53 (s, 1H), 5.29 (s, 1H), 4.95 (t, J = 4.8 Hz, 2H), 4.36 (d, J = 5.2 Hz, 2H), 3.51 (brs, 2H), 2.97-2.94 (m, 2H), 2.74-2.70 (m, 4H), 2.68-2.65 (m, 2H), 2.45 (s, 3H), 1.84-1.78 (m, 2H), 1.69-1.62 (m, 4H), 1.53 (s, 9H); LCMS (electrospray) m/z (M + H) + 554.13 | ++++ | GP35, 5 |

TABLE 1-continued

Anti-HCVcc genotype 1/2 activity for Formula I Series

| No. | Structure | Data | EC$_{50}$ | General Procedure (GP) |
|-----|-----------|------|-----------|------------------------|
| 280 | 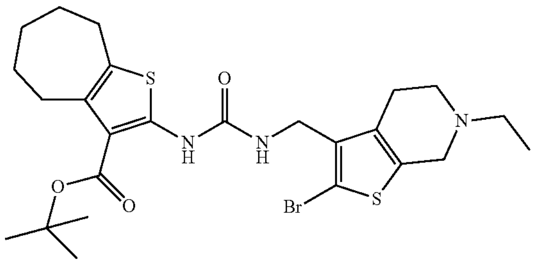 [SMILES: CCN1CCc2c(sc(Br)c2CNC(=O)Nc2sc3c(c2C(=O)OC(C)(C)C)CCCCC3)C1] | Yellow solid; $^1$H NMR (400 MHz, CDCl$_3$) δ 10.53 (s, 1H), 4.89 (t, J = 5.2 Hz, 1H), 4.36 (t, J = 4.0 Hz, 2H), 3.55 (s, 2H), 2.97-2.94 (m, 2H), 2.74-2.65 (m, 6H), 2.60-2.56 (m, 2H), 1.84-1.78 (m, 2H), 1.68-1.58 (m, 4H), 1.53 (s, 9H), 1.14 (t, J = 7.2 Hz, 3H); LCMS (electrospray) m/z (M + H) + 568.14 | ++++ | GP35, 3 |
| 281 | 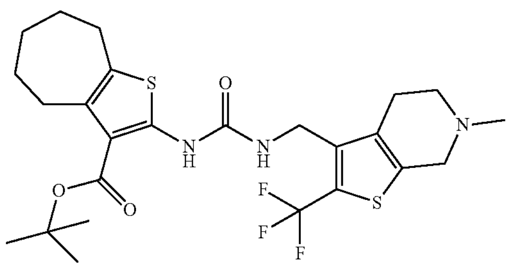 [SMILES: CN1CCc2c(sc(C(F)(F)F)c2CNC(=O)Nc2sc3c(c2C(=O)OC(C)(C)C)CCCCC3)C1] | Ivory solid; $^1$H NMR (400 MHz, CDCl$_3$) δ 10.53 (s, 1H), 5.29 (s, 1H), 4.90 (t, J = 5.2 Hz, 2H), 4.50 (d, J = 4.8 Hz, 2H), 3.67 (brs, 2H), 2.97-2.94 (m, 2H), 2.0 (brs, 4H), 2.68-2.65 (m, 2H), 2.51 (s, 3H), 1.84-1.78 (m, 2H), 1.69-1.62 (m, 4H), 1.54 (s, 9H); LCMS (electrospray) m/z (M + H) + 544.19 | ++++ | GP26, 35, 5 |
| 282 | 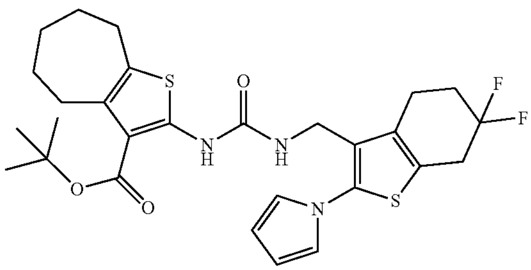 | Yellow solid; $^1$H NMR (400 MHz, acetone-d6); δ 10.45 (s, 1H), 7.26 (t, J = 4.8 Hz, 1H), 6.97 (t, J = 2.0 Hz, 2H), 6.25 (t, J = 2.0 Hz, 2H), 4.24 (d, J = 5.2 Hz, 2H), 3.30 (t, J = 13.6 Hz, 2H), 2.90-2.86 (m, 2H), 2.71-2.68 (m, 2H), 2.58-2.56 (m, 2H), 2.34-2.23 (m, 2H), 1.78-1.70 (m, 4H), 1.54 (s, 9H); LCMS (electrospray) m/z (M + H) + 548.28 | ++++ | GP28 |
| 283 | 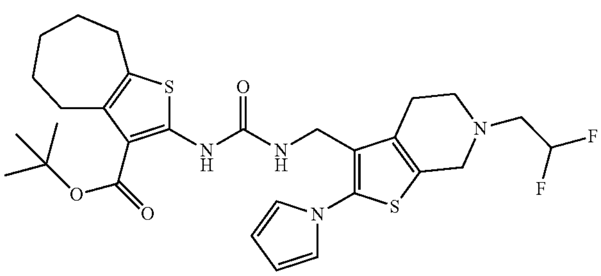 | White solid; $^1$H NMR (400 MHz, acetone-d6); δ 10.46 (s, 1 H), 7.22 (brs, 1H), 6.96 (t, J = 2.0 Hz, 2H), 6.24 (t, J = 2.0 Hz, 2H), 6.09, 5.95 (t, J = 4.4 Hz, 1H), 4.23 (d, J = 4.8 Hz, 2H), 3.81 (s, 2H), 3.03-2.94 (m, 4H), 2.74-2.69 (m, 4H), 2.58-2.56 (m, 2H), 1.77-1.70 (m, 4H), 1.54 (s, 9H); LCMS (electrospray) m/z (M + H) + 577.28 | ++++ | GP28, 3 |
| 284 | 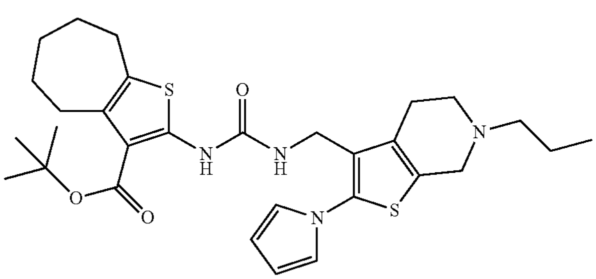 | Yellow solid; $^1$H NMR (400 MHz, acetone-d6); δ 10.46 (s, 1H), 7.20 (brs, 1H), 6.95 (t, J = 2.0 Hz, 2H), 6.24 (t, J = 2.0 Hz, 2H), 4.20 (d, J = 5.2 Hz, 2H), 3.57 (s, 2H), 2.77-2.73 (m, 2H), 2.71-2.68 (m, 4H), 2.58-2.56 (m, 2H), 2.48 (t, J = 7.2 Hz, 2H), 1.78-1.70 (m, 4H), 1.61-1.54 (m, 11H), 0.95 (t, J = 7.2 Hz, 3H); LCMS (electrospray) m/z (M + H) + 555.30 | ++++ | GP28, 3 |

TABLE 1-continued

Anti-HCVcc genotype ½ activity for Formula I Series

| No. | Structure | Data | EC$_{50}$ | General Procedure (GP) |
|---|---|---|---|---|
| 285 | 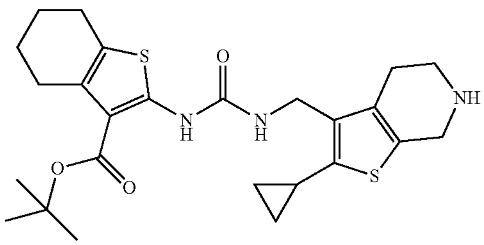 [SMILES: CC(C)(C)OC(=O)c1c(NC(=O)NCc2c(C3CC3)sc3c2CCNC3)sc2c1CCCC2] | White solid; $^1$H NMR (400 MHz, MeOD) δ 4.34 (s, 2H), 3.86 (s, 2H), 3.05 (t, J = 5.8 Hz, 2H), 2.70 (t, J = 5.7 Hz, 2H), 2.64-2.55 (m, 4H), 2.13 (td, J = 8.2, 4.3 Hz, 1H), 1.76 (d, J = 5.6 Hz, 4H), 1.55 (s, 9H), 1.01-0.94 (m, 2H), 0.66-0.59 (m, 2H); LCMS (electrospray) m/z (M + H) + 488.20 | ++++ | GP38, GP35 |
| 286 | 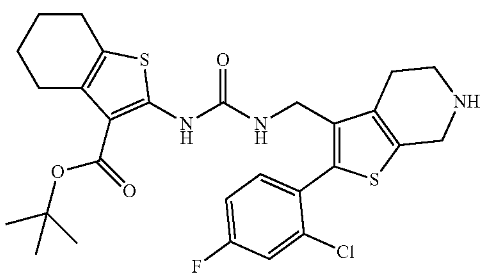 [SMILES: CC(C)(C)OC(=O)c1c(NC(=O)NCc2c(-c3ccc(F)cc3Cl)sc3c2CCNC3)sc2c1CCCC2] | White solid; $^1$H NMR (400 MHz, DMSO) δ 10.23 (s, 1H), 7.90 (s, 1H), 7.54 (dd, J = 8.8, 2.5 Hz, 1H), 7.46 (dd, J = 8.3, 6.6 Hz, 1H), 7.27 (td, J = 8.5, 2.5 Hz, 1H), 3.94 (d, J = 4.8 Hz, 2H), 3.84 (s, 2H), 2.92 (t, J = 5.3 Hz, 2H), 2.61 (s, 2H), 2.48 (s, 5H), 1.66 (s, 4H), 1.49 (s, 9H); LCMS (electrospray) m/z (M + H) + 576.17 | +++ | GP38, GP35 |
| 287 | 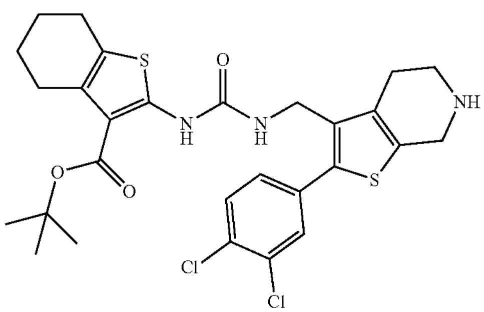 [SMILES: CC(C)(C)OC(=O)c1c(NC(=O)NCc2c(-c3ccc(Cl)c(Cl)c3)sc3c2CCNC3)sc2c1CCCC2] | White solid; $^1$H NMR (400 MHz, DMSO) δ 10.33 (s, 1H), 8.08 (t, J = 4.9 Hz, 1H), 7.71-7.67 (m, 2H), 7.42 (dd, J = 8.3, 2.1 Hz, 1H), 4.13 (d, J = 4.9 Hz, 2H), 3.84 (s, 2H), 2.91 (t, J = 5.5 Hz, 2H), 2.62 (s, 2H), 2.51 (s, 3H), 1.67 (s, 4H), 1.50 (s, 8H); LCMS (electrospray) m/z (M + H) + 592.22 | +++ | GP38, GP35 |
| 288 | 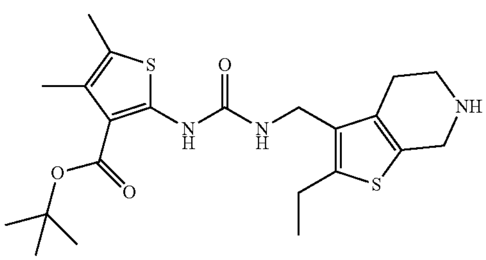 [SMILES: CCc1sc2c(c1CNC(=O)Nc1sc(C)c(C)c1C(=O)OC(C)(C)C)CCNC2] | White solid; $^1$H NMR (400 MHz, DMSO) δ 10.25 (s, 1H), 7.94 (s, 1H), 4.06 (d, J = 4.9 Hz, 2H), 3.73 (s, 2H), 2.88 (t, J = 5.6 Hz, 2H), 2.78 (dd, J = 14.9, 7.3 Hz, 2H), 2.43 (t, J = 5.2 Hz, 2H), 2.11 (d, J = 12.3 Hz, 4H), 1.50 (d, J = 1.2 Hz, 9H), 1.15 (td, J = 7.4, 1.4 Hz, 3H); LCMS (electrospray) m/z (M + H) + 450.17 | ++++ | GP27, GP35 |
| 289 | 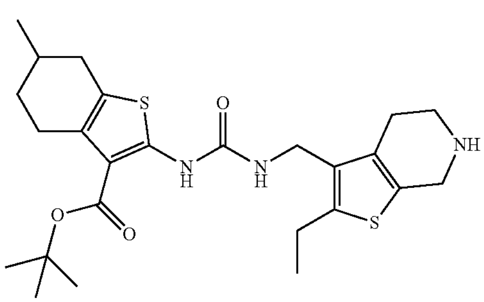 [SMILES: CCc1sc2c(c1CNC(=O)Nc1sc3c(c1C(=O)OC(C)(C)C)CCC(C)C3)CCNC2] | White solid; $^1$H NMR (400 MHz, DMSO) δ 10.25 (s, 1H), 7.95 (t, J = 5.0 Hz, 1H), 4.07 (d, J = 5.2 Hz, 2H), 3.73 (s, 2H), 2.87 (t, J = 5.7 Hz, 2H), 2.78 (dd, J = 15.0, 7.5 Hz, 2H), 2.62-2.52 (m, 2H), 2.43 (t, J = 4.8 Hz, 2H), 2.16-2.06 (m, 1H), 1.83-1.70 (m, 2H), 1.49 (s, 9H), 1.33-1.20 (m, 2H), 1.14 (t, J = 7.5 Hz, 3H), 0.98 (d, J = 6.4 Hz, 3H); LCMS (electrospray) m/z (M + H) + 490.31 | ++++ | GP27, GP35 |

TABLE 1-continued

Anti-HCVcc genotype ½ activity for Formula I Series

| No. | Structure | Data | EC$_{50}$ | General Procedure (GP) |
|---|---|---|---|---|
| 290 | 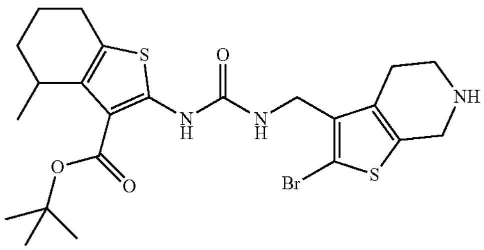 [SMILES: CC1CCCc2sc(NC(=O)NCc3c(Br)sc4c3CCNC4)c(C(=O)OC(C)(C)C)c21] | White solid; $^1$H NMR (400 MHz, DMSO) δ 10.38 (s, 1H), 8.08 (t, J = 5.2 Hz, 1H), 4.12 (d, J = 5.2 Hz, 2H), 3.75 (s, 2H), 3.19 (m, 2H), 2.90 (t, J = 6.0 Hz, 2H), 2.53 (m, 1H), 2.43 (m, 2H), 1.95-1.89 (m, 1H), 1.71 (m, 3H), 1.57 (d, J = 10.4 Hz, 1H), 1.51 (1, 9H), 1.08 (d, J = 6.8 Hz, 3H); LCMS (electrospray) m/z (M + H) + 542.08 | ++++ | GP1 GP35 |
| 291 | 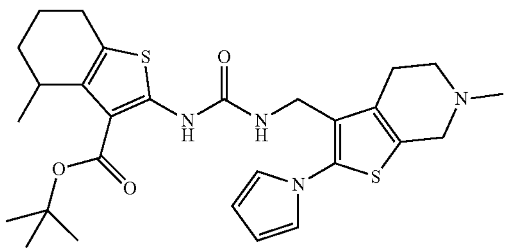 [SMILES: CC1CCCc2sc(NC(=O)NCc3c(-n4cccc4)sc4c3CCN(C)C4)c(C(=O)OC(C)(C)C)c21] | White solid; $^1$H NMR (400 MHz, CDCl3) δ 10.72 (s, 1H), 6.87 (t, J = 9.2 Hz, 2H), 6.30 (t, J = 6.0 Hz, 2H), 4.70 (brs, 1H), 4.27 (d, J = 5.6 Hz, 2H), 3.75 (brs, 2H), 3.26 (t, J = 5.2 Hz, 2H), 2.96-2.81 (m, 3H), 2.66-2.52 (m, 4H), 1.86-1.75 (m, 4H), 1.68-1.64 (m, 2H), 1.54 (s, 9H), 1.15 (d, J = 6.8 Hz, 3H); LCMS (electrospray) m/z (M + H) + 541.27 | ++++ | GP1 |
| 292 | 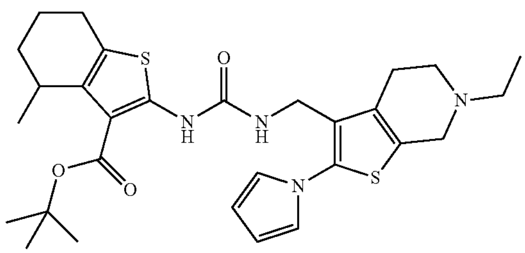 [SMILES: CCN1CCc2c(sc(-n3cccc3)c2CNC(=O)Nc2sc3c(c2C(=O)OC(C)(C)C)C(C)CCC3)C1] | White solid; $^1$H NMR (400 MHz, CDCl3) δ 10.73 (s, 1H), 6.79 (t, J = 2.0 Hz, 2H), 6.31 (t, J = 2.0 Hz, 2H), 4.58 (brs, 1H), 4.27 (d, J = 5.2 Hz, 2H), 3.68 (brs, 2H), 3.26 (t, J = 5.2 Hz, 2H), 2.91-2.51 (m, 6H), 1.88-1.72 (m, 4H), 1.68-1.62 (m, 2H), 1.56 (s, 9H), 1.22 (m, 3H), 1.15 (d, J = 6.8 Hz, 3H); LCMS (electrospray) m/z (M + H) + 555.28 | ++++ | GP1 |
| 293 | 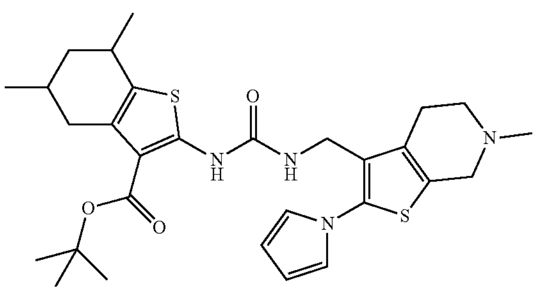 | White solid; $^1$H NMR (400 MHz, CDCl3) δ 10.59 (s, 1H), 6.80 (t, J = 2.4 Hz, 2H), 6.31 (t, J = 2.4 Hz, 2H), 4.61 (brs, 1H), 4.28 (d, J = 5.2 Hz, 2H), 3.62 (brs, 2H), 2.91 (dd, J = 5.2 Hz, 5.2 Hz, 1H), 2.88-2.71 (m, 3H), 2.52 (s, 3H), 2.17-2.08 (m, 1H), 1.89-1.73 (m, 2H), 1.54 (s, 9H), 1.24 (m, 3H), 1.03 (m, 3H); LCMS (electrospray) m/z (M + H) + 555.28 | ++++ | GP1 |
| 294 | 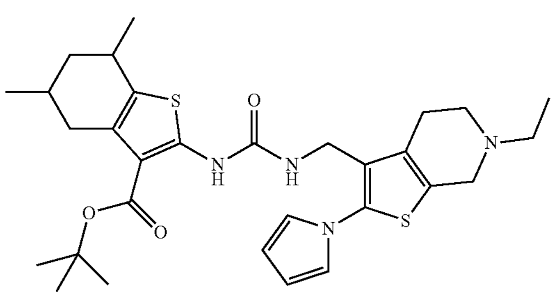 [SMILES: CCN1CCc2c(sc(-n3cccc3)c2CNC(=O)Nc2sc3c(c2C(=O)OC(C)(C)C)CC(C)CC3C)C1] | White solid; $^1$H NMR (400 MHz, CDCl3) δ 10.59 (s, 1H), 6.79 (t, J = 2.0 Hz, 2H), 6.30 (t, J = 2.4 Hz, 2H), 4.60 (brs, 1H), 4.28 (d, J = 5.6 Hz, 2H), 3.67 (brs, 2H), 2.96-2.62 (m, 7H), 2.14-2.07 (m, 1H), 1.90-1.72 (m, 2H), 1.54 (s, 9H), 1.25 (m, 6H), 1.04 (m, 3H); LCMS (electrospray) m/z (M + H) + 569.23 | ++++ | GP1 |

TABLE 1-continued

Anti-HCVcc genotype ½ activity for Formula I Series

| No. | Structure | Data | EC$_{50}$ | General Procedure (GP) |
|---|---|---|---|---|
| 295 | 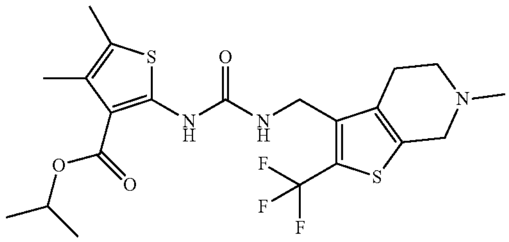 [SMILES: Cc1sc(NC(=O)NCc2c(C(F)(F)F)sc3c2CCN(C)C3)c(C(=O)OC(C)C)c1C] | White solid; $^1$H NMR (400 MHz, DMSO) δ 10.32 (s, 1H), 8.08 (t, J = 5.0 Hz, 1H), 5.07 (pentet, J = 6.4 and 12.4 Hz, 1H), 4.14 (d, J = 4.8 Hz, 2H), 3.42 (s, 2H), 2.69 (s, 4H), 2.33 (s, 3H), 2.16 (s, 3H), 2.14 (s, 3H), 1.30 (s, 3H), 1.27 (s, 3H); LCMS (electrospray) m/z (M + H)$^+$ 490.18 | ++++ | GP26, GP35, GP5 |
| 296 | 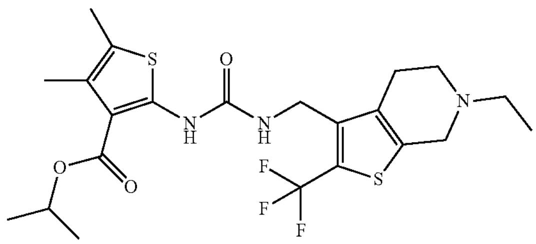 [SMILES: CCN1CCc2c(sc(C(F)(F)F)c2CNC(=O)Nc2sc(C)c(C)c2C(=O)OC(C)C)C1] | Pale yellow solid; $^1$H NMR (400 MHz, DMSO) δ 10.34 (s, 1H), 8.11 (t, J = 5.0 Hz, 1H), 5.07 (pentet, J = 6.4 and 12.4 Hz, 1H), 4.29 (d, J = 4.8 Hz, 2H), 3.62 (s, 2H), 2.71 (d, J = 5.2 Hz, 2H), 2.67 (t, J = 5.6 Hz, 2H), 2.53 (q, J = 7.2 Hz, 2H), 2.16 (s, 3H), 2.14 (s, 3H), 1.30 (s, 3H), 1.29 (s, 3H), 1.06 (t, J = 7.2 Hz, 3H); LCMS (electrospray) m/z (M + H)$^+$ 503.15 | ++++ | GP26, GP35, GP5 |
| 297 | 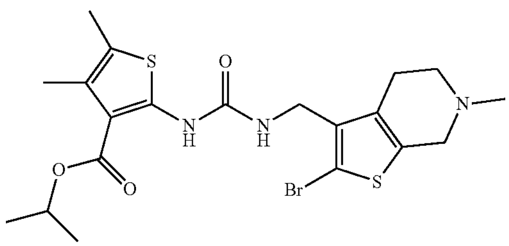 [SMILES: Cc1sc(NC(=O)NCc2c(Br)sc3c2CCN(C)C3)c(C(=O)OC(C)C)c1C] | White solid; $^1$H NMR (400 MHz, DMSO) δ 10.35 (s, 1H), 8.14 (t, J = 5.0 Hz, 1H), 5.07 (pentet, J = 6.4 and 12.4 Hz, 1H), 4.29 (d, J = 4.8 Hz, 2H), 3.56 (s, 2H), 2.69 (s, 4H), 2.35 (s, 3H), 2.16 (s, 3H), 2.14 (s, 3H), 1.30 (s, 3H), 1.27 (s, 3H); LCMS (electrospray) m/z (M + H)$^+$ 500.04 | ++++ | GP5, GP35 |
| 298 | 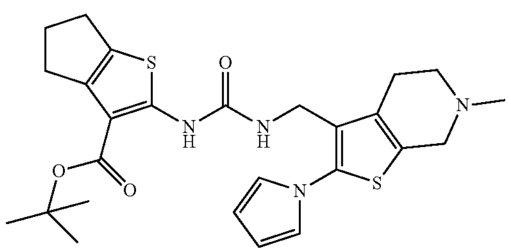 [SMILES: CN1CCc2c(sc(-n3cccc3)c2CNC(=O)Nc2sc3c(c2C(=O)OC(C)(C)C)CCC3)C1] | Ivory solid; $^1$H NMR (400 MHz, CDCl$_3$) δ 10.23 (s, 1H), 6.80 (t, J = 2.4 Hz, 2H), 6.30 (t, J = 2.4 Hz, 2H), 4.72 (s, 1H), 4.27 (d, J = 5.2 Hz, 2H), 3.62 (s, 2H), 2.83-2.79 (m, 8H), 2.51 (s, 3H), 2.34-2.30 (m, 2H), 1.54 (s, 9H); LCMS (electrospray) m/z (M + H) + 513.24 | ++++ | GP1 |
| 299 | 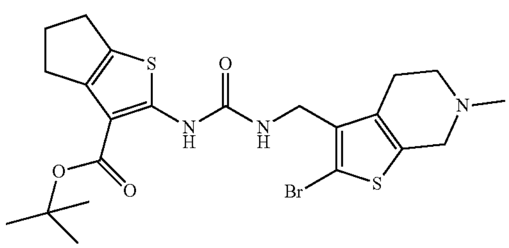 [SMILES: CN1CCc2c(sc(Br)c2CNC(=O)Nc2sc3c(c2C(=O)OC(C)(C)C)CCC3)C1] | Beige solid; $^1$H NMR (400 MHz, CDCl$_3$) δ 10.29 (s, 1H), 5.03 (s, 1H), 4.36 (d, J = 5.6 Hz, 2H), 3.58 (s, 2H), 2.84-2.79 (m, 8H), 2.50 (s, 3H), 2.34-2.31 (m, 2H), 1.52 (s, 9H); LCMS (electrospray) m/z (M + H) + 528.14 | ++++ | GP35, 5 |
| 300 | 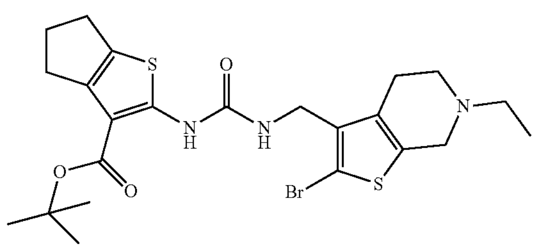 [SMILES: CCN1CCc2c(sc(Br)c2CNC(=O)Nc2sc3c(c2C(=O)OC(C)(C)C)CCC3)C1] | Yellow solid; $^1$H NMR (400 MHz, CDCl$_3$) δ 10.27 (s, 1H), 4.92 (s, 1H), 4.36 (d, J = 5.6 Hz, 2H), 3.58 (s, 2H), 2.84-2.76 (m, 8H), 2.64 (m, 2H), 2.38-2.34 (m, 2H), 1.52 (s, 9H), 1.24 (s, 3H); LCMS (electrospray) m/z (M + H) + 542.08 | ++++ | GP35, 3 |

TABLE 1-continued

Anti-HCVcc genotype ½ activity for Formula I Series

| No. | Structure | Data | EC$_{50}$ | General Procedure (GP) |
|---|---|---|---|---|
| 301 | 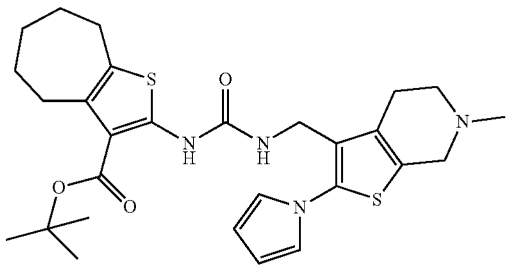 [SMILES: CN1CCc2c(sc(-n3cccc3)c2CNC(=O)Nc2sc3c(c2C(=O)OC(C)(C)C)CCCCC3)C1] | Yellow solid; $^1$H NMR (400 MHz, CDCl$_3$) δ 10.46 (s, 1H), 6.79 (t, J = 2.0 Hz, 1H), 6.31 (t, J = 2.0 Hz, 2H), 4.78 (s, 1H), 4.26 (d, J = 5.2 Hz, 2H), 3.72 (s, 2H), 2.97-2.94 (m, 2H), 2.89-2.82 (m, 4H), 2.67-2.65 (m, 2H), 2.58 (s, 3H), 1.82-1.80 (m, 2H), 1.65-1.59 (m, 4H), 1.55 (s, 9H); LCMS (electrospray) m/z (M + H) + 541.34 | ++++ | GP1 |
| 302 | 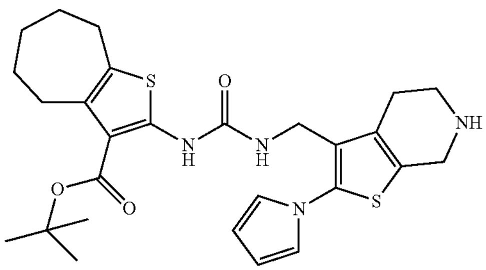 [SMILES: CC(C)(C)OC(=O)c1c(NC(=O)NCc2c(-n3cccc3)sc3c2CCNC3)sc2c1CCCCC2] | Ivory solid; $^1$H NMR (400 MHz, DMSO) δ 10.12 (s, 1H), 7.97 (t, J = 5.2 Hz, 1H), 6.97 (t, J = 2.0 Hz, 2H), 6.22 (t, J = 2.0 Hz, 2H), 3.98 (d, J = 5.2 Hz, 2H), 3.77 (s, 2H), 2.92-2.89 (m, 4H), 2.62-2.58 (m, 2H), 2.43-2.40 (m, 2H), 1.78-1.74 (m, 2H), 1.58-1.56 (m, 4H), 1.52 (s, 9H); LCMS (electrospray) m/z (M + H) + 527.32 | ++++ | GP28 |
| 303 | 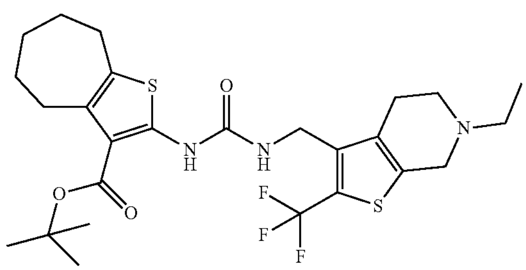 [SMILES: CCN1CCc2c(sc(C(F)(F)F)c2CNC(=O)Nc2sc3c(c2C(=O)OC(C)(C)C)CCCCC3)C1] | Yellow solid; $^1$H NMR (400 MHz, CDCl$_3$) δ 10.52 (s, 1H), 4.94 (s, 1H), 4.49 (d, J = 5.6 Hz, 2H), 3.72 (brs, 2H), 2.97-2.94 (m, 2H), 2.88-2.81 (m, 4H), 2.68-2.65 (m, 4H), 1.84-1.78 (m, 2H), 1.69-1.62 (m, 4H), 1.54 (s, 9H), 1.20 (t, J = 6.8 Hz, 3H); LCMS (electrospray) m/z (M + H) + 558.28 | ++++ | GP26, 35, 3 |
| 304 | 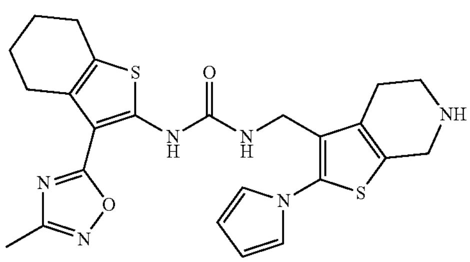 [SMILES: Cc1noc(-c2c(NC(=O)NCc3c(-n4cccc4)sc4c3CCNC4)sc3c2CCCC3)n1] | Beige solid; $^1$H NMR (400 MHz, CDCl$_3$) δ 10.44 (s, 1H), 6.81 (t, J = 2.0 Hz, 2H), 6.31 (t, J = 2.0 Hz, 2H0, 4.89 (t, J = 4.8 Hz, 1H), 4.32 (d, J = 4.8 Hz, 2H), 3.96 (s, 2H), 3.15 (t, J = 5.6 Hz, 2H), 2.86-2.84 (m, 2H), 2.65-2.63 (m, 4H), 2.42 (s, 3H), 1.84-1.81 (m, 4H); LCMS (electrspray) m/z (M + H) + 495.21 | +++ | GP28 |
| 305 | 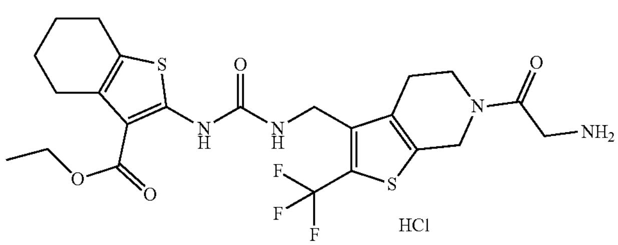 [SMILES: CCOC(=O)c1c(NC(=O)NCc2c(C(F)(F)F)sc3c2CCN(C(=O)CN)C3)sc2c1CCCC2 ; Cl] | White solid; $^1$H NMR (400 MHz, DMSO-d6); δ 10.32 (s, 1H), 8.20-8.12 (m, 4H), 4.79, 4.74 (s, 2H), 4.32 (s, 2H), 4.22 (q, J = 7.2 Hz, 2H), 3.99, 3.92 (s, 2H), 3.84-3.76, 3.70-3.64 (m, 2H), 3.78-2.62 (m, 4H), 2.58-2.52 (m, 2H), 1.74-1.62 (m, 4H), 1.28 (t, J = 7.2 Hz, 3H); LCMS (electrospray) m/z (M + H) + 545.29 | ++++ | GP35, 11, 2 |

TABLE 1-continued

Anti-HCVcc genotype ½ activity for Formula I Series

| No. | Structure | Data | EC$_{50}$ | General Procedure (GP) |
|---|---|---|---|---|
| 306 | 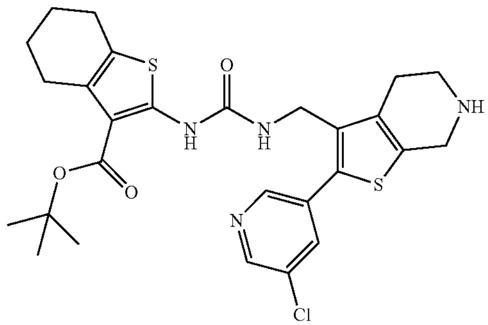 | White solid; $^1$H NMR (400 MHz, acetone-d6); δ 10.41 (s, 1H), 7.45-7.39 (m, 1H), 4.90, 4.78 (s, 2H), 4.50 (d, J = 5.2 Hz, 2H), 4.24 (q, J = 7.2 Hz, 2H), 4.16, 4.15 (s, 2H), 3.86-3.83 (m, 2H), 2.88-2.83 (m, 2H), 2.73-2.71 (m, 2H), 2.58-2.57 (m, 2H), 1.80-1.70 (m, 4H), 1.31 (t, J = 7.2 Hz, 3H); LCMS (electrospray) m/z (M + H) + 545.15 | ++++ | GP38, GP35 |
| 307 | 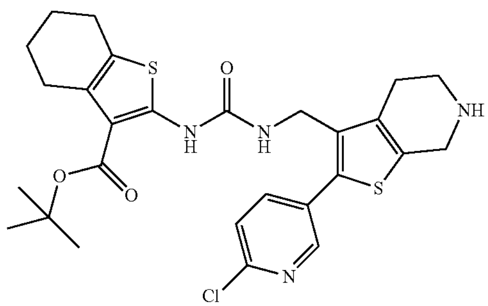 [SMILES: CC(C)(C)OC(=O)c1c(NC(=O)NCc2c(-c3ccc(Cl)nc3)sc3c2CCNC3)sc2c1CCCC2] | $^1$H NMR (400 MHz, DMSO) δ 10.32 (s, 1H), 8.64-8.57 (m, 2H), 8.09 (t, J = 4.9 Hz, 1H), 8.01 (t, J = 2.0 Hz, 1H), 4.14 (d, J = 4.9 Hz, 2H), 3.87 (s, 2H), 2.93 (t, J = 5.7 Hz, 2H), 2.62 (s, 2H), 2.51 (s, 2H), 1.67 (s, 4H), 1.49 (s, 9H); LCMS (electrospray) m/z (M + H) + 559.23 | ++++ | GP38, GP35 |
| 308 | 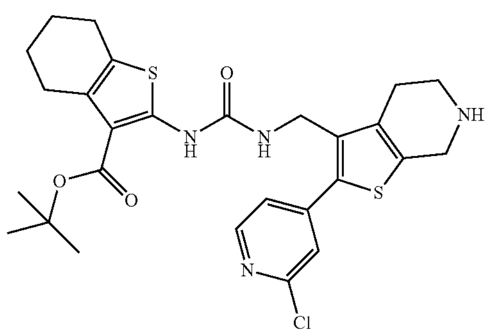 [SMILES: CC(C)(C)OC(=O)c1c(NC(=O)NCc2c(-c3ccnc(Cl)c3)sc3c2CCNC3)sc2c1CCCC2] | $^1$H NMR (400 MHz, DMSO) δ 10.32 (s, 1H), 8.49 (d, J = 2.4 Hz, 1H), 8.09 (t, J = 1.8 Hz, 1H), 7.92 (dd, J = 4.1, 0.8 Hz, 1H), 7.60 (d, J = 8.0 Hz, 1H), 4.11 (d, J = 5.2 Hz, 2H), 3.80 (s, 2H), 2.92 (t, J = 2.1 Hz, 2H), 2.62 (s, 2H), 2.49 (s, 4H), 1.67 (s, 4H), 1.50 (s, 9H); LCMS (electrospray) m/z (M + H) + 559.23 | ++++ | GP38, GP35 |
| 309 | 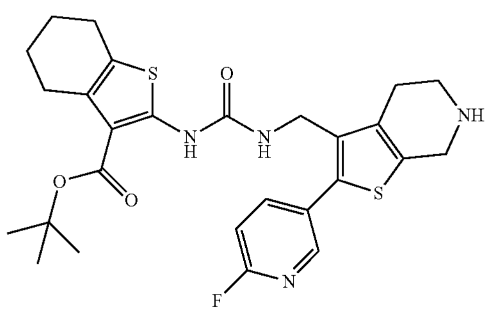 [SMILES: CC(C)(C)OC(=O)c1c(NC(=O)NCc2c(-c3ccc(F)nc3)sc3c2CCNC3)sc2c1CCCC2] | $^1$H NMR (400 MHz, DMSO) δ 10.32 (s, 1H), 8.31 (d, J = 2.5 Hz, 1H), 8.10-8.01 (m, 2H), 7.29 (dd, J = 8.5, 2.8 Hz, 1H), 4.11 (d, J = 5.0 Hz, 2H), 3.89 (s, 2H), 2.96 (t, J = 5.6 Hz, 2H), 2.62 (s, 2H), 2.51 (d, J = 7.3 Hz, 4H), 1.67 (s, 4H), 1.49 (s, 9H); LCMS (electrospray) m/z (M + H)+ 543.31 | ++++ | GP38, GP35 |

TABLE 1-continued

Anti-HCVcc genotype ½ activity for Formula I Series

| No. | Structure | Data | EC$_{50}$ | General Procedure (GP) |
|---|---|---|---|---|
| 310 | 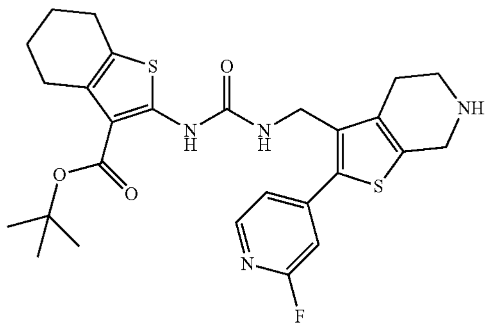 [SMILES: CC(C)(C)OC(=O)c1c(NC(=O)NCc2c(-c3ccnc(F)c3)sc3c2CCNC3)sc2c1CCCC2] | $^1$H NMR (400 MHz, DMSO) δ 10.35 (s, 1H), 8.27 (d, J = 5.2 Hz, 1H), 8.14 (t, J = 5.0 Hz, 1H), 7.42 (dt, J = 5.3, 1.6 Hz, 1H), 7.26 (s, 1H), 4.23 (d, J = 5.0 Hz, 2H), 3.87 (s, 2H), 2.92 (t, J = 5.6 Hz, 2H), 2.62 (s, 2H), 2.51 (s, 4H), 1.67 (s, 4H), 1.49 (s, 9H); LCMS (electrospray) m/z (M + H) + 543.24 | ++++ | GP38, GP35 |
| 311 | 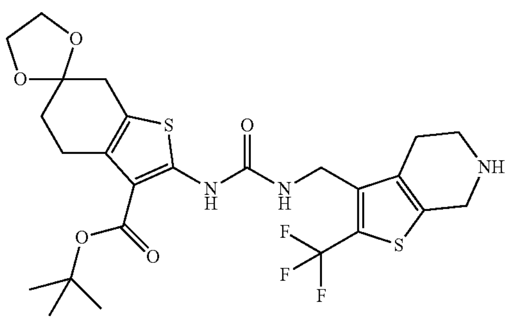 [SMILES: CC(C)(C)OC(=O)c1c(NC(=O)NCc2c(C(F)(F)F)sc3c2CCNC3)sc2c1CCC1(C2)OCCO1] | White solid; $^1$H NMR (400 MHz, DMSO) δ 10.34 (s, 1H), 8.15 (t, J = 5.2 Hz, 1H), 4.30 (d, J = 5.2 Hz, 2H), 3.90 (s, 4H), 3.87 (brs, 2H), 2.91 (t, J = 5.6 Hz, 2H), 2.79 (t, J = 6 Hz, 2H), 2.71 (brs, 2H), 2.54 (m, 2H), 1.79 (t, J = 6.8 Hz, 2H), 1.52 (s, 9H); LCMS (electrospray) m/z (M + H) + 574.33 | ++++ | GP1 GP26 GP28 |
| 312 | 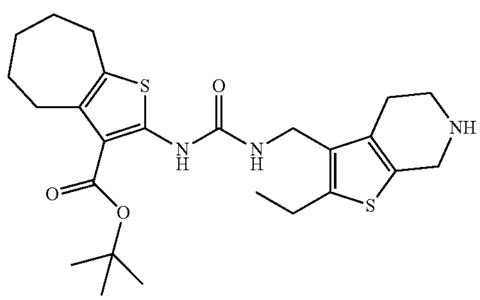 [SMILES: CCc1sc2c(c1CNC(=O)Nc1sc3c(c1C(=O)OC(C)(C)C)CCCCC3)CCNC2] | White solid; $^1$H NMR (400 MHz, DMSO) δ 10.06 (s, 1H), 7.91 (s, 1H), 4.07 (d, J = 5.4 Hz, 2H), 3.88 (s, 2H), 3.02 (s, 2H), 2.86 (d, J = 10.7 Hz, 2H), 2.79 (dd, J = 15.1, 7.5 Hz, 2H), 2.62-2.50 (m, 4H), 1.79-1.69 (m, 2H), 1.59-1.52 (m, 4H), 1.49 (s, 9H), 1.15 (t, J = 7.5 Hz, 3H); LCMS (electrospray) m/z (M + H) + 490.31 | ++++ | GP1, GP27, GP35 |
| 313 | 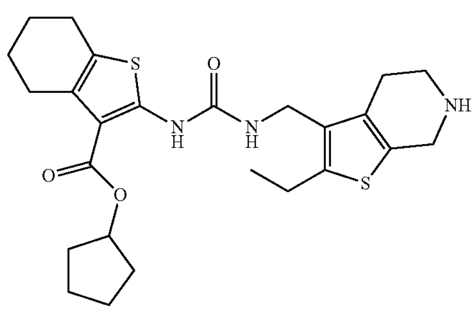 [SMILES: CCc1sc2c(c1CNC(=O)Nc1sc3c(c1C(=O)OC1CCCC1)CCCC3)CCNC2] | White solid; $^1$H NMR (400 MHz, DMSO) δ 10.32 (s, 1H), 8.01 (s, 1H), 5.22 (s, 1H), 4.08 (d, J = 5.1 Hz, 2H), 3.87 (s, 2H), 3.01 (s, 2H), 2.79 (dd, J = 14.6, 7.2 Hz, 2H), 2.60 (s, 2H), 2.53 (s, 2H), 1.91-1.54 (m, 14H), 1.15 (t, J = 7.5 Hz, 3H); LCMS (electrospray) m/z (M + H) + 488.27 | ++++ | GP1, GP27, GP35 |

TABLE 1-continued

Anti-HCVcc genotype ½ activity for Formula I Series

| No. | Structure | Data | EC$_{50}$ | General Procedure (GP) |
|---|---|---|---|---|
| 314 | 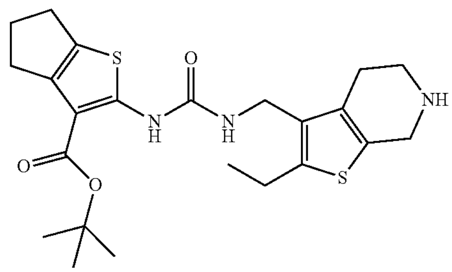 [SMILES: CCc1sc2c(c1CNC(=O)Nc1sc3c(c1C(=O)OC(C)(C)C)CCC3)CCNC2] | White solid; $^1$H NMR (400 MHz, dmso) δ 10.03 (s, 1H), 7.94 (s, 1H), 4.06 (d, J = 5.1 Hz, 2H), 3.72 (s, 2H), 2.87 (t, J = 4.1 Hz, 2H), 2.80-2.66 (m, 6H), 2.44-2.38 (m, 2H), 2.27-2.19 (m, 2H), 1.47 (s, 9H), 1.14 (t, J = 7.5 Hz, 3H); LCMS (electrospray) m/z (M + H) + 462.28 | ++++ | GP1, GP27, GP37 |
| 315 | 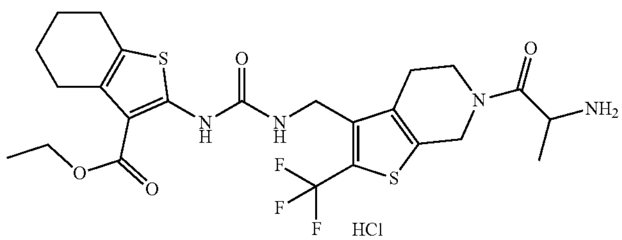 [SMILES: CCOC(=O)c1c(NC(=O)NCc2c(C(F)(F)F)sc3c2CCN(C(=O)C(C)N)C3)sc2c1CCCC2 ; Cl] | White solid; $^1$H NMR (400 MHz, DMSO-d6); δ 10.29 (s, 1H), 8.21 (brs, 4H), 5.01-4.89 (m, 1H), 4.79-4.64 (m, 1H), 4.43-4.10 (m, 5H), 3.86-3.43 (m, 2H), 2.77 (S, 2H), 2.71 (s, 2H), 2.53 (s, 2H), 1.69 (brs, 4H), 1.42-1.26 (m, 6H); LCMS (electrospray) m/z (M + H) + 559.19 | ++++ | GP35, 11, 2 |
| 316 | 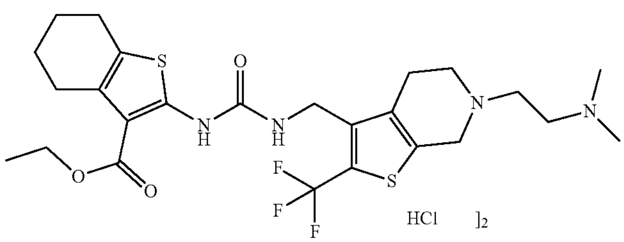 | Ivory solid; $^1$H NMR (400 MHz, DMSO-d6); δ 11.39 (brs, 1H), 10.64 (brs, 1H), 10.33 (s, 1H), 8.32 (s, 1H), 4.36 (brs, 2H), 4.24 (t, J = 7.2 Hz, 2H), 3.65-3.30 (m, 8H), 3.00 (s, 2H), 2.85 (s, 6H), 2.66 (s, 2H), 2.53 (s, 2H), 1.69 (brs, 4H), 1.28 (t, J = 7.2 Hz, 3H); LCMS (electrospray) m/z (M + H) + 559.40 | ++++ | GP35, 3 |
| 317 | 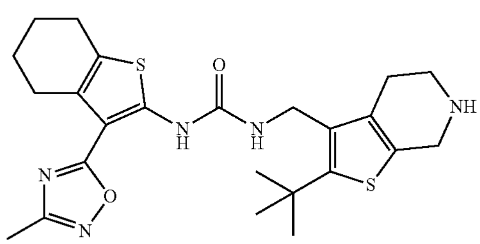 | White solid; $^1$H NMR (400 MHz, CDCl$_3$) δ 10.57 (s, 1H), 4.93 (t, J = 2.0 Hz, 1H), 4.55 (d, J = 5.2 Hz, 2H), 4.02 (d, J = 1.2 Hz, 2H), 3.12 (t, J = 6.0 Hz, 2H), 2.85-2.83 (m, 2H), 2.70-2.65 (m, 4H), 2.42 (s, 3H), 1.84-1.81 (m, 4H); LCMS (electrospray) m/z (M + H) + 498.27 | ++++ | GP35 |
| 318 | 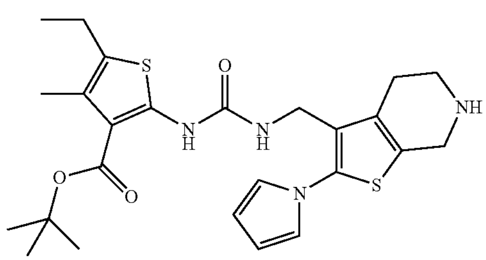 [SMILES: CCc1sc(NC(=O)NCc2c(-n3cccc3)sc3c2CCNC3)c(C(=O)OC(C)(C)C)c1C] | White solid; $^1$H NMR (400 MHz, DMSO) δ 10.61 (s, 1H), 6.80 (t, J = 2.0 Hz, 2H), 6.32 (t, J = 2 Hz, 2H), 4.69 (brs, 1H), 4.27 (d, J = 5.2 Hz, 2H), 4.01 (s, 2H), 3.19 (brs, 2H), 2.65 (m, 4H), 2.19 (s, 3H), 1.56 (s, 9H), 1.19 (t, J = 7.2 Hz, 3H); LCMS (electrospray) m/z (M + H) + 501.20 | +++ | GP1 GP28 |

TABLE 1-continued

Anti-HCVcc genotype ½ activity for Formula I Series

| No. | Structure | Data | EC$_{50}$ | General Procedure (GP) |
|---|---|---|---|---|
| 319 | 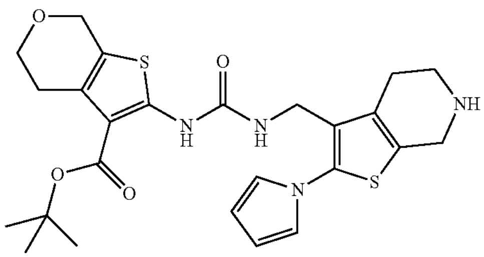 [SMILES: CC(C)(C)OC(=O)c1c(NC(=O)NCc2c(-n3cccc3)sc3c2CCNC3)sc2c1CCOC2] | White solid; $^1$H NMR (400 MHz, DMSO) δ 10.34 (s, 1H), 8.10 (t, J = 4.8 Mz, 1H), 7.00 (t, J = 2.0 Mz, 1H), 6.24 (t, J = 2.0 Mz, 1H), 4.55 (s, 2H), 4.02 (d, J = 4.8 Hz, 2H), 3.81 (m, 4H), 2.94 (t, J = 5.6 Hz, 2H), 2.72 (t, J = 5.6 Hz, 2H), 2.46 (t, J = 5.2 Mz, 2H), 1.52 (s, 9H); LCMS (electrospray) m/z (M + H) + 515.28 | ++++ | GP1 GP28 |
| 320 | 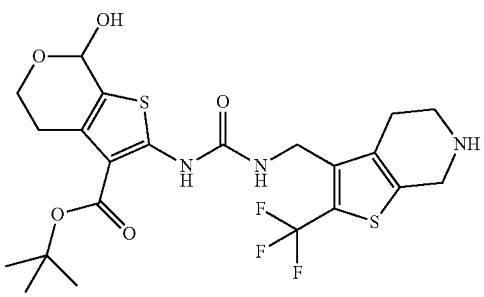 [SMILES: CC(C)(C)OC(=O)c1c(NC(=O)NCc2c(C(F)(F)F)sc3c2CCNC3)sc2c1CCOC2O] | White solid; $^1$H NMR (400 MHz, DMSO) δ 10.32 (s, 1H), 8.18 (t, J = 5.2 Mz, 1H, 4.66 (d, J = 14.4 Mz, 1H), 4.58 (m, 2H), 4.45 (d, J = 14.8 Mz, 1H), 4.31 (d, J = 5.2 Hz, 2H), 3.88 (d, J = 12.0 Mz, 3H), 3.61 (d, J = 10.4 Hz, 1H), 2.91 (t, J = 6.0 Hz, 2H), 2.50 (t, J = 1.6 Mz, 2H), 1.53 (s, 9H); LCMS (electrospray) m/z (M + H) + 534.26 | ++++ | GP1 GP35 GP36 (TU-PP) |
| 321 | 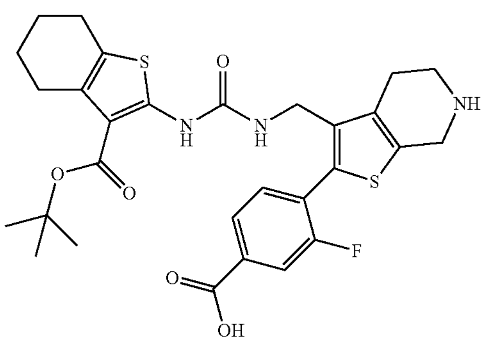 [SMILES: CC(C)(C)OC(=O)c1c(NC(=O)NCc2c(-c3ccc(C(=O)O)cc3F)sc3c2CCNC3)sc2c1CCCC2] | White solid; $^1$H NMR (400 MHz, dmso) δ 10.27 (s, 1H), 8.00 (t, J = 4.6 Hz, 1H), 7.78 (dd, J = 7.9, 1.3 Hz, 1H), 7.71 (dd, J = 10.6, 1.3 Hz, 1H), 7.49 (t, J = 7.8 Hz, 1H), 4.08 (d, J = 4.7 Hz, 2H), 3.97 (s, 2H), 3.05-3.01 (m, 2H), 2.59 (d, J = 13.7 Hz, 4H), 2.53 (s, 2H), 1.66 (s, 4H), 1.49 (s, 9H); LCMS (electrospray) m/z (M + H) + | ++ | GP38, GP35 |
| 322 | 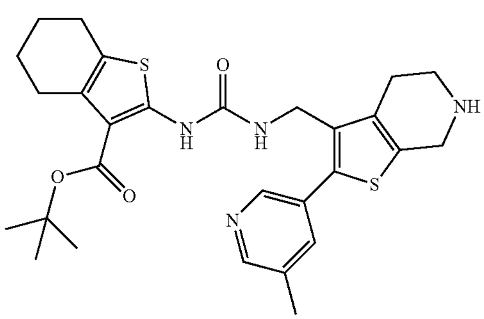 [SMILES: Cc1cncc(-c2sc3c(c2CNC(=O)Nc2sc4c(c2C(=O)OC(C)(C)C)CCCC4)CCNC3)c1] | White solid; $^1$H NMR (400 MHz, dmso) δ 10.32 (s, 1H), 8.45 (d, J = 1.9 Hz, 1H), 8.39 (d, J = 1.4 Hz, 1H), 8.08 (t, J = 4.8 Hz, 1H), 7.63 (s, 1H), 4.13 (d, J = 4.9 Hz, 2H), 3.85 (s, 2H), 2.92 (t, J = 5.5 Hz, 2H), 2.62 (s, 2H), 2.49 (s, 4H), 2.32 (s, 3H), 1.67 (s, 4H), 1.49 (s, 9H); LCMS (electrospray) m/z (M + H) + | +++ | GP38, GP35 |

TABLE 1-continued

Anti-HCVcc genotype ½ activity for Formula I Series

| No. | Structure | Data | EC$_{50}$ | General Procedure (GP) |
|---|---|---|---|---|
| 323 | 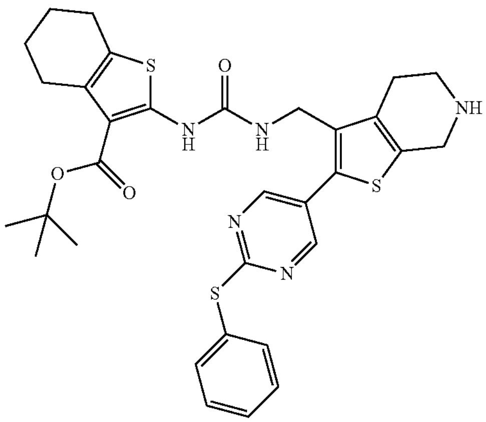 [SMILES: CC(C)(C)OC(=O)c1c(NC(=O)NCc2c(-c3cnc(Sc4ccccc4)nc3)sc3c2CCNC3)sc2c1CCCC2] | White solid; $^1$H NMR (400 MHz, dmso) δ 10.29 (s, 1H), 8.67 (s, 2H), 8.03 (t, J = 5.0 Hz, 2H), 7.64-7.58 (m, 1H), 7.48-7.42 (m, 3H), 4.11 (d, J = 5.2 Hz, 2H), 3.83 (s, 2H), 2.91 (t, J = 5.3 Hz, 2H), 2.62 (s, 2H), 2.49 (s, 4H), 1.67 (s, 4H), 1.49 (s, 10H); LCMS (electrospray) m/z (M + H) + | +++ | GP38, GP35 |
| 324 | 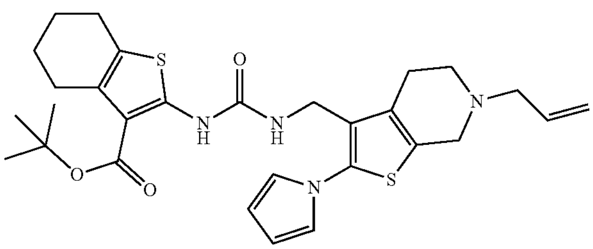 [SMILES: C=CCN1CCc2c(sc(-n3cccc3)c2CNC(=O)Nc2sc3c(c2C(=O)OC(C)(C)C)CCCC3)C1] | Ivory solid; $^1$H NMR (400 MHz, acetone-d6); δ 10.46 (s, 1H), 7.23 (t, J = 4.8 Hz, 1H), 6.95 (t, J = 2.0 Hz, 2H), 6.24 (t, J = 2.0 Hz, 2H), 5.90 (dddd, J = 6.0, 6.0, 10.0, 16.8 Hz, 1H), 5.24 (d, J = 17.2 Hz, 1H), 5.14 (d, J = 10.4 Hz, 1H), 4.21 (d, J = 5.2 Hz, 2H), 3.58 (t, J = 1.6 Hz, 2H), 3.18 (dt, J = 1.6, 6.4 Hz 2H), 2.76 (t, J = 5.6 Hz, 2H), 2.70-2.69 (m, 4H), 2.58-2.55 (m, 2H), 1.78-1.69 (m, 4H), 1.54 (s, 9H); LCMS (electrospray) m/z (M + H) + 553.28 | ++++ | GP28, 3 |
| 325 | 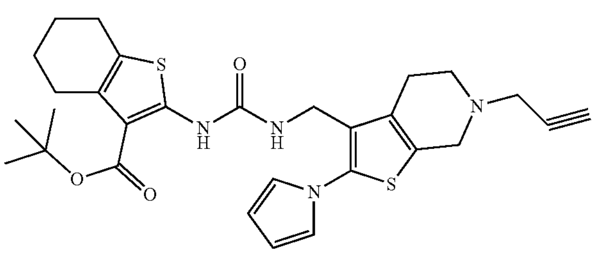 [SMILES: C#CCN1CCc2c(sc(-n3cccc3)c2CNC(=O)Nc2sc3c(c2C(=O)OC(C)(C)C)CCCC3)C1] | Yellow solid; $^1$H NMR (400 MHz, acetone-d6); δ 10.46 (s, 1H), 7.23 (t, J = 4.8 Hz, 1H), 6.96 (t, J = 2.0 Hz, 2H), 6.24 (t, J = 4.8 Hz, 2H), 4.22 (d, J = 5.2 Hz, 2H), 3.71 (t, J = 1.6 Hz, 2H), 3.52 (d, J = 2.4 Hz, 2H), 2.94 (s, 1H), 2.86-2.68 (m, 6H), 2.58-2.55 (m, 2H), 1.77-1.70 (m, 4H), 1.54 (m, 9H); LCMS (electrospray) m/z (M + H) + 551.27 | ++++ | GP28, 3 |
| 326 | 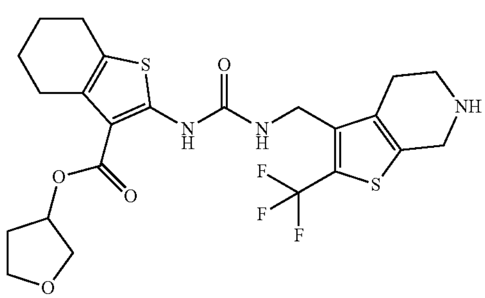 [SMILES: O=C(NCc1c(C(F)(F)F)sc2c1CCNC2)Nc1sc2c(c1C(=O)OC1CCOC1)CCCC2] | White solid; $^1$H NMR (400 MHz, DMSO) δ 10.34 (s, 1H), 8.16 (t, J = 5.2 Hz, 1H), 5.38 (pentet, J = 6.4 and 12.4 Hz, 1H), 4.30 (d, J = 4.8 Hz, 2H), 3.88-3.75 (m, 6H), 2.91 (t, J = 5.8 Hz, 2H), 2.64 (s, 2H), 2.52 (d, J = 5.2 Hz, 4H), 2.20-2.13 (m, 1H), 2.03-1.99 (m, 1H), 1.69 (s, 4H); LCMS (electrospray) m/z (M + H)$^+$ 530.25 | ++++ | GP1, GP2 |

TABLE 1-continued

Anti-HCVcc genotype ½ activity for Formula I Series

| No. | Structure | Data | EC$_{50}$ | General Procedure (GP) |
|---|---|---|---|---|
| 327 | 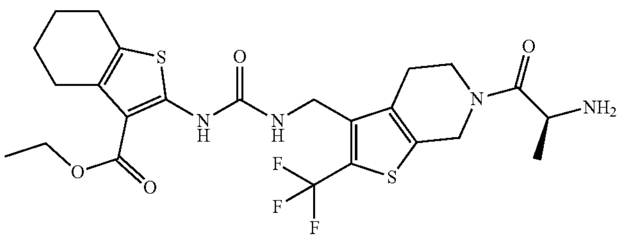 [SMILES: CCOC(=O)c1c(NC(=O)NCc2c(C(F)(F)F)sc3c2CCN(C(=O)[C@H](C)N)C3)sc2c1CCCC2] | Ivory solid; $^1$H NMR (400 MHz, acetone-d6); δ 10.41-10.40 (m, 1H), 7.60-7.40 (m, 1H), 4.93-4.88 (m, 1H), 4.70-4.63 (m, 1H), 4.54-4.43 (m, 3H), 4.24 (q, J = 7.2 Hz, 2H), 3.90-3.64 (m, 2H), 2.76-2.71 (m, 4H), 2.58-2.57 (m, 2H), 1.80-1.70 (m, 4H), 1.30 (t, J = 7.2 Hz, 3H), 1.20 (d, J = 6.4 Hz, 3H); LCMS (electrospray) m/z (M + H) + 559.20 | ++++ | GP35, 11 |
| 328 | 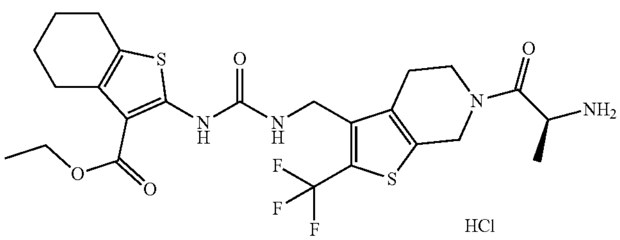 [SMILES: CCOC(=O)c1c(NC(=O)NCc2c(C(F)(F)F)sc3c2CCN(C(=O)[C@H](C)N)C3)sc2c1CCCC2 ; Cl] | White solid; $^1$H NMR (400 MHz, DMSO-d6); δ 10.29 (s, 1H), 8.21 (brs, 4H), 5.01-4.89 (m, 1H), 4.79-4.64 (m, 1H), 4.43-4.10 (m, 5H), 3.86-3.43 (m, 2H), 2.77 (s, 2H), 2.71 (s, 2H), 2.53 (s, 2H), 1.69 (brs, 4H), 1.42-1.26 (m, 6H); LCMS (electrospray) m/z (M + H) + 559.19 | ++++ | GP35, 11, 2 |
| 329 | 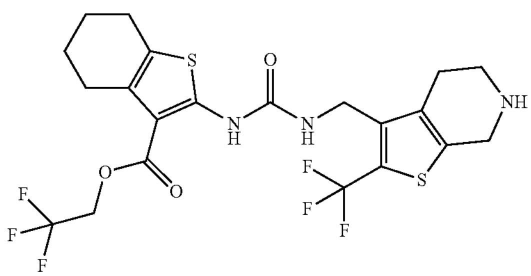 [SMILES: O=C(NCc1c(C(F)(F)F)sc2c1CCNC2)Nc1sc2c(c1C(=O)OCC(F)(F)F)CCCC2] | White solid; $^1$H NMR (400 MHz, DMSO) δ 10.23 (s, 1H), 8.23 (t, J = 5.4 Hz, 1H), 4.88 (q, J = 9.2 Hz, 2H), 4.32 (d, J = 4.8 Hz, 2H), 3.87 (s, 2H), 2.91 (t, J = 5.6 Hz, 2H), 2.64 (s, 2H), 2.54 (s, 4H), 1.70 (s, 4H); LCMS (electrospray) m/z (M + H)$^+$ 542.15 | ++++ | GP26, GP35 |
| 330 | 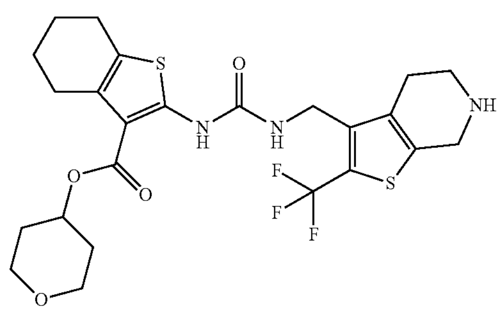 [SMILES: O=C(NCc1c(C(F)(F)F)sc2c1CCNC2)Nc1sc2c(c1C(=O)OC1CCOCC1)CCCC2] | White solid; $^1$H NMR (400 MHz, DMSO) δ 10.37 (s, 1H), 8.15 (t, J = 5.2 Hz, 1H), 5.07 (pentet, J = 4.0 and 8.0 Hz, 1H), 4.30 (d, J = 4.8 Hz, 2H), 3.87 (s, 2H), 3.82-3.76 (m, 2H), 3.56-3.50 (m, 2H), 2.91 (t, J = 5.8 Hz, 2H), 2.70 (s, 2H), 2.53 (s, 4H), 1.96-1.91 (m, 1H), 1.71 (s, 4H), 1.71-1.61 (m, 2H); LCMS (electrospray) m/z (M + H)$^+$ 544.26 | ++++ | GP26, GP35 |
| 331 | 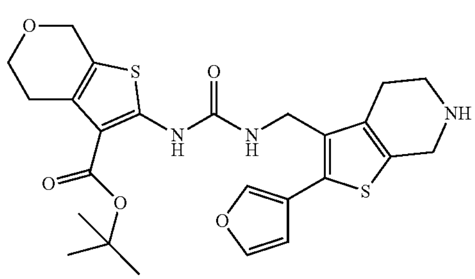 [SMILES: CC(C)(C)OC(=O)c1c(NC(=O)NCc2c(-c3ccoc3)sc3c2CCNC3)sc2c1CCOC2] | White solid; $^1$H NMR (400 MHz, cdcl3) δ 10.58 (s, 1H), 7.60 (s, 1H), 7.45 (t, J = 1.7 Hz, 1H), 6.52 (dd, J = 1.7, 0.8 Hz, 1H), 4.63 (d, J = 6.1 Hz, 2H), 4.37 (d, J = 4.8 Hz, 2H), 4.12 (s, 2H), 3.89 (t, J = 5.5 Hz, 2H), 3.22 (s, 2H), 2.86-2.67 (m, 4H), 1.49 (s, 9H); LCMS (electrospray) m/z (M + H) + 516.16 | ++++ | GP38, GP35 |

TABLE 1-continued

Anti-HCVcc genotype ½ activity for Formula I Series

| No. | Structure | Data | EC$_{50}$ | General Procedure (GP) |
|---|---|---|---|---|
| 332 | 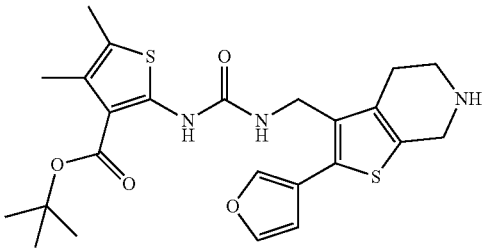 [SMILES: Cc1sc(NC(=O)NCc2c(-c3ccoc3)sc3c2CCNC3)c(C(=O)OC(C)(C)C)c1C] | White solid; $^1$H NMR (400 MHz, dmso) δ 10.30 (s, 1H), 7.99 (t, J = 5.0 Hz, 1H), 7.91 (dd, J = 1.5, 0.8 Hz, 1H), 7.75 (t, J = 1.7 Hz, 1H), 6.68 (dd, J = 1.8, 0.9 Hz, 1H), 4.18 (d, J = 5.0 Hz, 2H), 3.79 (s, 2H), 2.90 (t, J = 5.6 Hz, 2H), 2.47 (s, 2H), 2.13 (s, 3H), 2.10 (s, 3H), 1.50 (s, 9H); LCMS (electrospray) m/z (M + H) + 488.20 | ++++ | GP38, GP35 |
| 333 | 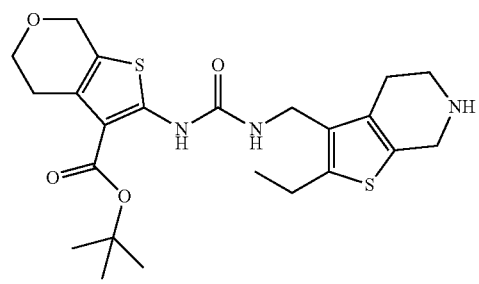 [SMILES: CCc1sc2c(c1CNC(=O)Nc1sc3c(c1C(=O)OC(C)(C)C)CCOC3)CCNC2] | White solid; $^1$H NMR (400 MHz, dmso) δ 10.28 (s, 1H), 8.11 (t, J = 5.3 Hz, 1H), 4.52 (s, 2H), 4.11 (d, J = 5.4 Hz, 1H), 4.08 (s, 2H), 3.78 (t, J = 5.5 Hz, 2H), 3.23-3.19 (m, 3H), 2.83 (dd, J = 14.9, 7.4 Hz, 2H), 2.68 (s, 4H), 1.49 (s, 9H), 1.16 (t, J = 7.5 Hz, 4H); LCMS (electrospray) m/z (M + H) + 478.13 | ++++ | GP1, GP27, GP35 |
| 334 | 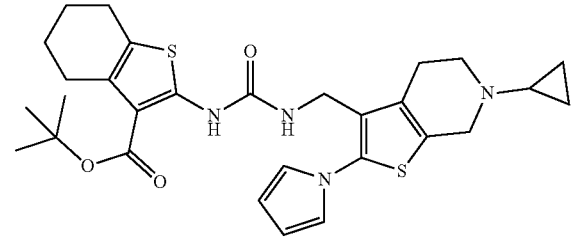 [SMILES: CC(C)(C)OC(=O)c1c(NC(=O)NCc2c(-n3cccc3)sc3c2CCN(C2CC2)C3)sc2c1CCCC2] | Yellow solid; $^1$H NMR (400 MHz, CDCl3); δ 10.57 (s, 1H), 6.79 (t, J = 2.0 Hz, 2H), 6.29 (t, J = 2.0 Hz, 2H), 4.76 (brs, 1H), 4.26 (d, J = 5.2 Hz, 2H), 3.80-3.75 (m, 2H), 3.10-2.95 (m, 2H), 2.73-2.69 (m, 4H), 2.59-2.58 (m, 2H), 2.00-1.90 (m, 1H), 1.80-1.65 (m, 4H), 1.53 (s, 9H), 0.61-0.56 (m, 4H); LCMS (electrospray) m/z (M + H) + 553.35 | ++++ | GP5, 1 |
| 335 | 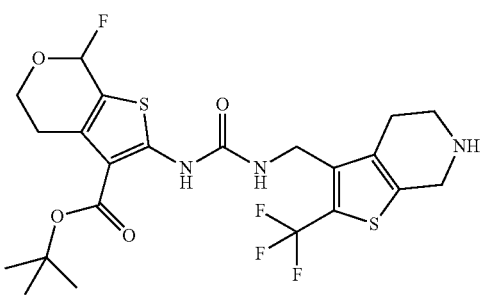 [SMILES: CC(C)(C)OC(=O)c1c(NC(=O)NCc2c(C(F)(F)F)sc3c2CCNC3)sc2c1CCOC2F] | White solid; $^1$H NMR (400 MHz, DMSO) δ 10.40 (s, 1H), 8.26 (t, J = 5.2 Mz, 1H), 5.60 (s, 0.5 H), 5.48 (s, 0.5 H), 4.77 (dd, J = 5.6 Mz, 1H), 4.49 (dd, J = 10 Hz, 1H), 4.32 (d, J = 5.2 Mz, 2H), 4.21 (t, J = 14.4 Hz, 1H), 3.87 (s, 2H), 3.76 (d, J = 13.2 Mz, 0.5H), 3.67 (d, J = 12.8 Mz, 0.5H), 2.91 (t, J = 6.0 Mz, 2H), 2.53 (t, J = 6.4 Mz, 2H), 1.52 (s, 9H); LCMS (electrospray) m/z (M + H) + 536.10 | ++++ | GP35, GP36, GP37 (TU-QQ) |
| 336 | 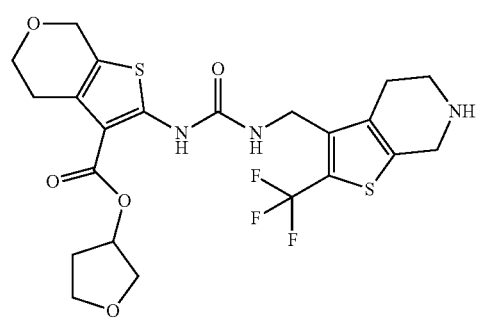 [SMILES: O=C(NCc1c(C(F)(F)F)sc2c1CCNC2)Nc1sc2c(c1C(=O)OC1CCOC1)CCOC2] | White solid; $^1$H NMR (400 MHz, DMSO) δ 10.34 (s, 1H), 8.22 (t, J = 5.2 Hz, 1H), 5.41-5.38 (m, 1H), 4.56 (s, 2H), 4.31 (d, J = 4.8 Hz, 2H), 3.89-3.75 (m, 8H), 2.92 (t, J = 5.8 Hz, 2H), 2.72 (t, J = 5.2 Hz, 2H), 2.54 (t, J = 8.0 Hz, 2H), 2.21-2.13 (m, 1H), 2.05-2.00 (m, 1H); LCMS (electrospray) m/z (M + H)$^+$ 532.15 | ++++ | GP26, GP35 |

TABLE 1-continued

Anti-HCVcc genotype ½ activity for Formula I Series

| No. | Structure | Data | EC$_{50}$ | General Procedure (GP) |
|---|---|---|---|---|
| 337 | 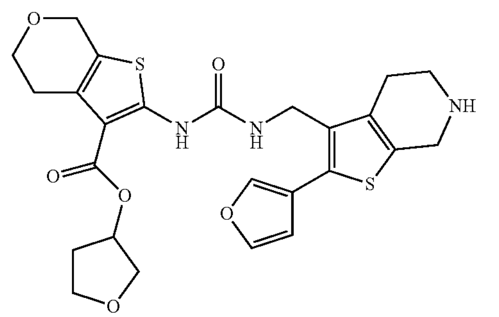 [SMILES: O=C(NCc1c(-c2ccoc2)sc2c1CCNC2)Nc1sc2c(c1C(=O)OC1CCOC1)CCOC2] | White solid; $^1$H NMR (400 MHz, DMSO) δ 10.33 (s, 1H), 8.13 (t, J = 4.8 Hz, 1H), 7.94 (s, 1H), 7.78 (t, J = 1.4 Hz, 1H), 6.70 (d, J = 1.6 Hz, 1H), 5.40-5.38 (m, 1H), 4.56 (s, 2H), 4.22 (d, J = 4.8 Hz, 2H), 3.89-3.75 (m, 8H), 2.92 (t, J = 5.8 Hz, 2H), 2.72 (t, J = 5.2 Hz, 2H), 2.54 (t, J = 8.0 Hz, 2H), 2.20-2.13 (m, 1H), 2.04-1.99 (m, 1H); LCMS (electrospray) m/z (M + H)$^+$ 530.11 | ++++ | GP21, GP35 |
| 338 | 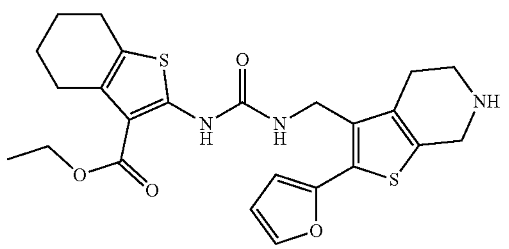 [SMILES: CCOC(=O)c1c(NC(=O)NCc2c(-c3ccco3)sc3c2CCNC3)sc2c1CCCC2] | Yellow solid; $^1$H NMR (400 MHz, acetone-d6); δ 10.37 (s, 1H), 7.58 (dd, J = 0.5, 2.0 Hz, 1H), 7.28 (m, 1H), 6.66 (d, J = 3.2 Hz, 1H), 6.54 (dd, J = 2.0, 3.6 Hz, 1H), 4.89 (s, 1H), 4.50 (d, J = 5.2 Hz, 2H), 4.23 (q, J = 7.2 Hz, 2H), 3.93 (s, 2H), 3.04 (t, J = 6.0 Hz, 2H), 2.73-2.69 (m, 2H), 2.66-2.63 (m, 2H), 2.60-2.56 (m, 2H), 1.80-1.71 (m, 4H), 1.30 (t, J = 7.2 Hz, 3H); LCMS (electrospray) m/z (M + H) + 486.01 | ++++ | GP21, GP39 |
| 339 | 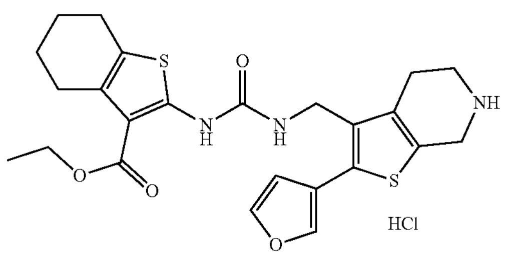 [SMILES: CCOC(=O)c1c(NC(=O)NCc2c(-c3ccoc3)sc3c2CCNC3)sc2c1CCCC2 ; Cl] | Ivory solid; $^1$H NMR (400 MHz, DMSO-d6); δ 10.32 (s, 1H), 9.45 (brs, 2H), 8.16 (t, J = 5.2 Hz, 1H), 8.06 (d, J = 0.8 Hz, 1H), 7.83 (d, J = 0.8 Hz, 1H), 6.79 (t, J = 0.8 Hz, 1H), 4.31 (s, 2H), 4.27-4.20 (m, 4H), 3.45-3.39 (m, 2H), 2.90-2.80 (m, 2H), 2.70-2.60 (m, 2H), 2.53-2.50 (m, 2H), 1.75-1.60 (m, 4H), 1.28 (t, J = 7.2 Hz, 3H); LCMS (electrospray) m/z (M + H) + 486.11 | ++++ | GP21, 2 |
| 340 | 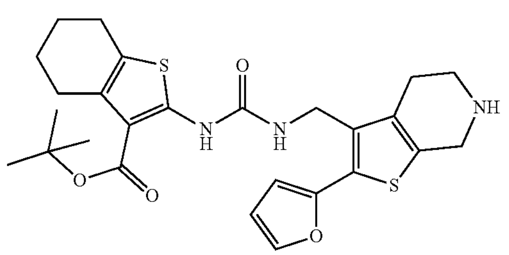 [SMILES: CC(C)(C)OC(=O)c1c(NC(=O)NCc2c(-c3ccco3)sc3c2CCNC3)sc2c1CCCC2] | Beige solid; $^1$H NMR (400 MHz, dmso) δ 10.30 (s, 1H), 8.04 (t, J = 2.0 Hz, 1H), 7.70 (s, 1H), 6.65 (d, J = 2.8 Hz, 1H), 6.59 (s, 1H), 4.29 (d, J = 4.4 Hz, 2H), 3.82 (s, 2H), 2.93-2.90 (m, 2H), 2.62-2.61 (m, 2H), 1.67-1.65 (m, 4H), 1.47 (s, 9H); LCMS (electrospray) m/z (M + H) + 514.19 | ++++ | GP21, GP39 |
| 341 | 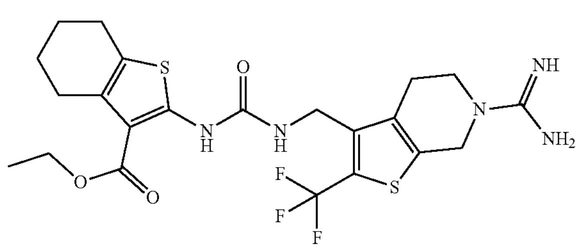 [SMILES: CCOC(=O)c1c(NC(=O)NCc2c(C(F)(F)F)sc3c2CCN(C(=N)N)C3)sc2c1CCCC2] | Beige solid; $^1$H NMR (400 MHz, dmso) δ 10.30 (s, 1H), 8.20 (t, J = 2.0 Hz, 1H), 7.68 (s, 4H), 4.74 (s, 2H), 4.32 (d, J = 5.2 Hz, 2H), 4.21 (q, J = 7.2 Hz, 2H), 3.71 (t, J = 5.2 Hz, 2H), 2.75-2.74 (m, 2H), 2.65-2.63 (m, 2H), 2.53-2.51 (m, 2H), 1.67-1.65 (m, 4H), 1.25 (t, J = 6.8 Hz, 3H); LCMS (electrospray) m/z (M + H) + 530.11 | ++++ | GP35, 3, 2 |

TABLE 1-continued

Anti-HCVcc genotype ½ activity for Formula I Series

| No. | Structure | Data | EC$_{50}$ | General Procedure (GP) |
|---|---|---|---|---|
| 342 | 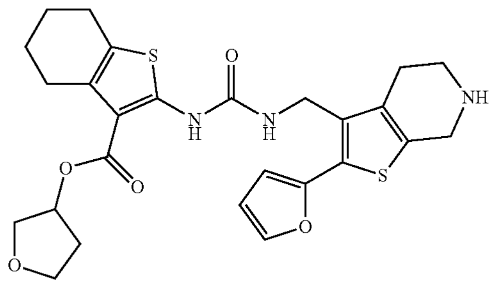 [SMILES: O=C(NCc1c(-c2ccco2)sc2c1CCNC2)Nc1sc2c(c1C(=O)OC1CCOC1)CCCC2] | White solid; $^1$H NMR (400 MHz, DMSO) d 10.30 (s, 1H), 8.07 (t, J = 4.8 Hz, 1H), 7.70 (t, J = 0.8 Hz, 1H), 6.65 (d, J = 3.2 Hz, 1H), 6.58 (dd, J = 4.0 Hz, J = 0.8 Hz, 1H), 5.35 (t, J = 4.4, 1H), 4.30 (d, J = 4.8 Hz, 2H), 3.85-3.72 (m, 6H), 2.90 (t, J = 5.8 Hz, 2H), 2.62 (s, 2H), 2.18-2.10 (m, 1H), 2.01-1.95 (m, 1H), 1.67 (s, 4H); LCMS (electrospray) m/z (M + H) + 528.07 | ++++ | GP21 |
| 343 | 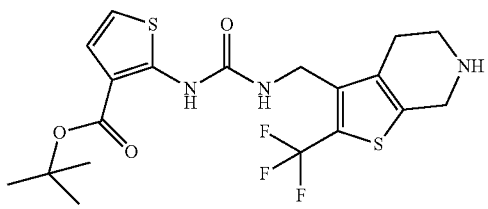 [SMILES: CC(C)(C)OC(=O)c1ccsc1NC(=O)NCc1c(C(F)(F)F)sc2c1CCNC2] | White solid; $^1$H NMR (400 MHz, DMSO) δ 10.19 (s, 1H), 8.17 (t, J = 5.2 (Hz, 1H), 6.98 (d, J = 5.6 Hz, 1H), 6.74 (d, J = 5.6 Hz, 1H), 4.32 (d, J = 4.8 Hz, 2H), 3.87 (s, 2H), 2.92 (t, J = 5.8 Hz, 2H), 2.52 (t, J = 5.2 Hz, 2H), 1.52 (s, 9H); LCMS (electrospray) m/z (M + H)$^+$ 462.01 | +++ | GP26, GP35 |
| 344 | 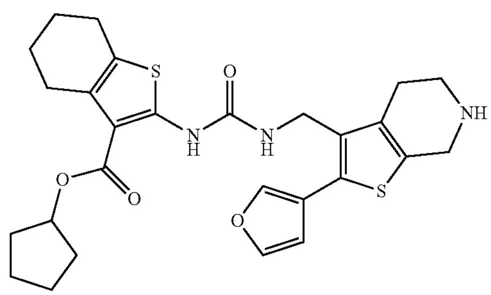 [SMILES: O=C(NCc1c(-c2ccoc2)sc2c1CCNC2)Nc1sc2c(c1C(=O)OC1CCCC1)CCCC2] | $^1$H NMR (400 MHz, dmso) δ 10.38 (s, 1H), 8.08 (t, J = 2.0 Hz, 1H), 7.98 (t, J = 0.2 Hz, 1H), 7.78 (t, J = 0.6 Hz, 1H), 6.73 (s, 1H), 5.23 (t, J = 2.1 Hz, 1H), 4.21 (d, J = 5.1 Hz, 2H), 4.08 (s, 2H), 3.17 (t, J = 2.1 Hz, 2H), 2.68 (t, J = 2.1 Hz, 2H), 2.61 (s, 2H), 2.50 (s, 2H), 1.88-1.78 (m, 4H), 1.75-1.54 (m, 8H); LCMS (electrospray) m/z (M + H) + 526.17 | ++++ | GP38, GP35 |
| 345 | 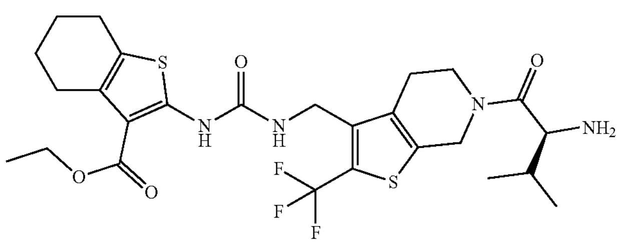 [SMILES: CCOC(=O)c1c(NC(=O)NCc2c(C(F)(F)F)sc3c2CCN(C(=O)[C@@H](N)C(C)C)C3)sc2c1CCCC2] | Ivory solid; $^1$H NMR (400 MHz, acetone-d6); δ 10.39 (s, 1H), 7.41 (s, 1H), 4.98-4.85, 4.68-4.64 (m, 2H), 4.50 (s, 2H), 4.24 (q, J = 7.2 Hz, 2H), 3.97-3.92 (m, 1H), 3.88-3.78 (m, 1H), 3.64-3.58 (m, 1H), 2.87-2.78 (m, 2H), 2.73-2.71 (m, 2H), 2.58-2.57 (m, 2H), 2.08-2.04 (m, 1H), 1.80-1.70 (m, 4H), 1.31 (t, J = 7.2 Hz, 3H), 0.96-0.82 (m, 6H); LCMS (electrospray) m/z (M + H) + 587.22 | ++++ | GP35, 11, 2 |
| 346 | 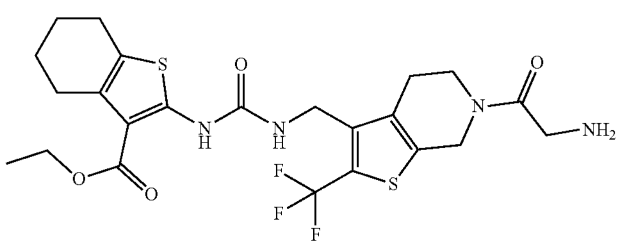 [SMILES: CCOC(=O)c1c(NC(=O)NCc2c(C(F)(F)F)sc3c2CCN(C(=O)CN)C3)sc2c1CCCC2] | White solid; $^1$H NMR (400 MHz, acetone-d6); δ 10.41 (s, 1H), 7.45-7.39 (m, 1H), 4.90, 4.78 (s, 2H), 4.50 (d, J = 5.2 Hz, 2H), 4.24 (q, J = 7.2 Hz, 2H), 4.16, 4.15 (s, 2H), 3.86-3.83 (m, 2H), 2.88-2.83 (m, 2H), 2.73-2.71 (m, 2H), 2.58-2.57 (m, 2H), 1.80-1.70 (m, 4H), 1.31 (t, J = 7.2 Hz, 3H); LCMS (electrospray) m/z (M + H) + 545.15 | ++++ | GP35, 11, 2 |

TABLE 1-continued

Anti-HCVcc genotype ½ activity for Formula I Series

| No. | Structure | Data | EC$_{50}$ | General Procedure (GP) |
|---|---|---|---|---|
| 347 | 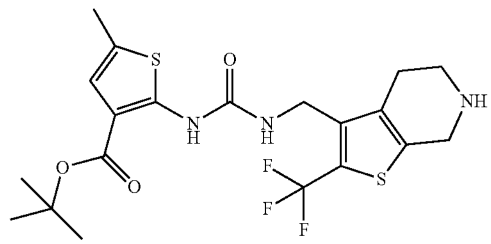 [SMILES: Cc1cc(C(=O)OC(C)(C)C)c(NC(=O)NCc2c(C(F)(F)F)sc3c2CCNC3)s1] | Beige solid; $^1$H NMR (400 MHz, DMSO) δ 10.07 (s, 1H), 8.09 (t, J = 5.2 Hz, 1H), 6.63 (s, 1H), 4.28 (d, J = 4.4 Hz, 2H), 3.85 (s, 2H), 2.89 (t, J = 6.0 Hz, 2H), 2.53-2.51 (m, 2H), 2.24 (s, 3H), 1.48 (s, 9H); LCMS (electrospray) m/z (M + M) + 476.03 | ++++ | GP26, 35 |
| 348 | 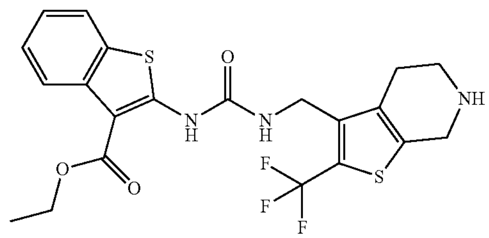 [SMILES: CCOC(=O)c1c(NC(=O)NCc2c(C(F)(F)F)sc3c2CCNC3)sc2ccccc12] | Beige solid; $^1$H NMR (400 MHz, DMSO) δ 10.81 (s, 1H), 8.48 (t, J = 5.2 Hz, 1H), 8.15 (d, J = 8.4 Hz, 1H), 7.81 (d, J = 7.6 Hz, 1H), 7.36 (t, J = 7.6 Hz, 1H), 7.23 (t, J = 7.6 Hz, 1H), 4.40-4.33 (m, 4H), 3.86 (s, 2H), 2.91 (t, J = 5.6 Hz, 2H), 2.55 (t, J = 5.2 Hz, 2H), 1.38 (t, J = 6.8 Hz, 3H); LCMS (electrospray) m/z (M + H) + 483.99 | ++++ | GP35 |
| 349 | 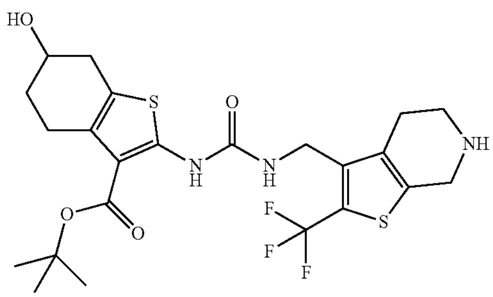 [SMILES: CC(C)(C)OC(=O)c1c(NC(=O)NCc2c(C(F)(F)F)sc3c2CCNC3)sc2c1CCC(O)C2] | White solid; $^1$H NMR (400 MHz, DMSO) δ 10.33 (s, 1H), 8.13 (t, J = 5.2 Mz, 1H), 4.80 (d, J = 3.6 Mz, 1H), 4.30 (d, J = 4.8 Mz, 2H), 3.87 (s, 2H), 2.91 (t, J = 5.2 Hz, 2H), 2.78 (m, 2H), 2.63 (m, 1H), 2.38 (dd, J = 7.2 Mz, 1H), 1.83 (m, 1H), 1.61 (m, 1H), 1.51 (s, 9H); LCMS (electrospray) m/z (M + H) + 532.08 | ++++ | GP1 GP26 GP28 |
| 350 | 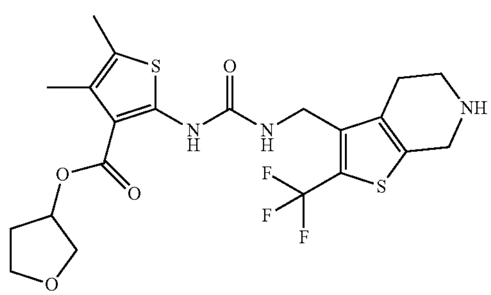 [SMILES: Cc1sc(NC(=O)NCc2c(C(F)(F)F)sc3c2CCNC3)c(C(=O)OC2CCOC2)c1C] | White solid; $^1$H NMR (400 MHz, DMSO) δ 10.33 (s, 1H), 8.14 (t, J = 5.2 Hz, 1H, 5.41-5.38 (m, 1H), 3.90-3.77 (m, 6H), 2.91 (t, J = 5.8 Hz, 2H), 2.52 (t, J = 5.2 Hz, 2H), 2.21-2.17 (m, 1H), 2.16 (s, 3H), 2.13 (s, 3H), 2.05-1.99 (m, 1H); LCMS (electrospray) m/z (M + H)$^+$ 504.05 | ++++ | GP26, GP35 |
| 351 | 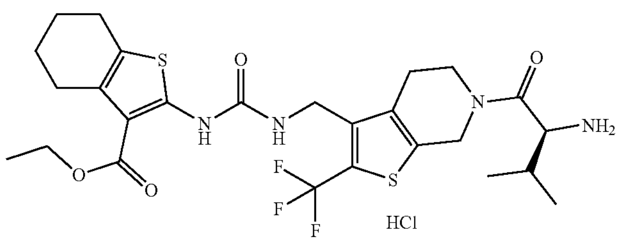 [SMILES: CCOC(=O)c1c(NC(=O)NCc2c(C(F)(F)F)sc3c2CCN(C(=O)[C@@H](N)C(C)C)C3)sc2c1CCCC2 ; Cl] | Ivory solid; $^1$H NMR (400 MHz, DMSO-d6); δ 10.32 (s, 1H), 8.22-8.20 (m, 1H), 8.13 (brs, 3H), 5.06-4.99 (m, 1H), 4.81, 4.61 (d, J = 16.8 Hz, 1H), 4.39-4.32 (m, 3H), 4.28-4.20 (m, 2H), 4.12-4.08, 3.98-3.94, 3.74-3.68, 3.56-3.52 (m, 2H), 2.74-2.64 (m, 4H), 2.51-2.48 (m, 2H), 2.06-2.05 (m, 1H), 1.76-1.62 (m, 4H), 1.27 (t, J = 7.2 Hz, 3H), 1.01-0.90 (m, 6H); LCMS (electrospray) m/z (M + H) + 587.16 | ++++ | GP35, 11, 2 |

TABLE 1-continued

Anti-HCVcc genotype ½ activity for Formula I Series

| No. | Structure | Data | EC$_{50}$ | General Procedure (GP) |
|---|---|---|---|---|
| 352 | 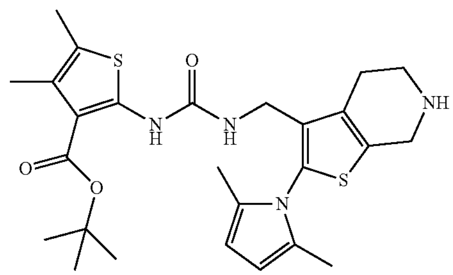 [SMILES: Cc1sc(NC(=O)NCc2c(-n3c(C)ccc3C)sc3c2CCNC3)c(C(=O)OC(C)(C)C)c1C] | $^1$H NMR (400 MHz, dmso) δ 10.26 (s, 1H), 7.89 (t, J = 1.8 Hz, 1H), 5.78 (s, 2H), 3.80 (d, J = 4.9 Hz, 4H), 2.94 (t, J = 2.1 Hz, 2H), 2.10 (d, J = 9.5 Hz, 6H), 1.95 (s, 6H), 1.50 (s, 9H); LCMS (electrospray) m/z (M + H) + 515.14 | ++ | GP1, GP17, GP35 |
| 353 | 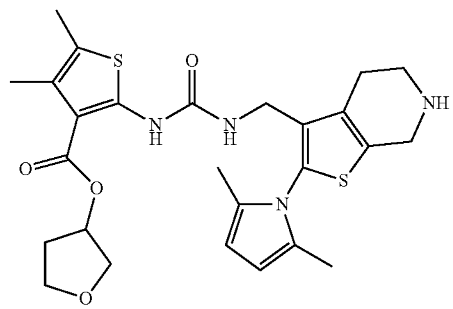 [SMILES: Cc1sc(NC(=O)NCc2c(-n3c(C)ccc3C)sc3c2CCNC3)c(C(=O)OC2CCOC2)c1C] | $^1$H NMR (400 MHz, dmso) δ 10.28 (s, 1H), 7.92 (t, J = 1.8 Hz, 1H), 5.78 (s, 2H), 5.38 (t, J = 1.9 Hz, 1H), 3.89-3.73 (m, 10H), 2.94 (t, J = 5.6 Hz, 2H), 2.21-2.14 (m, 1H), 2.12 (d, J = 8.3 Hz, 6H), 2.04-1.96 (m, 2H), 1.94 (s, 6H); LCMS (electrospray) m/z (M + H) + 529.16 | ++ | GP1, GP17, GP35 |
| 354 | 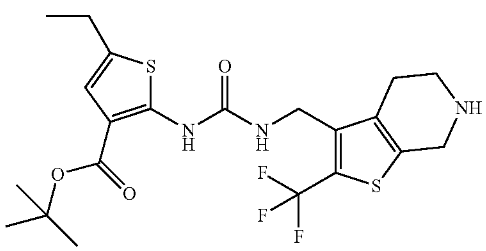 [SMILES: CCc1cc(C(=O)OC(C)(C)C)c(NC(=O)NCc2c(C(F)(F)F)sc3c2CCNC3)s1] | White solid; $^1$H NMR (400 MHz, DMSO) δ 10.08 (s, 1H), 8.09 (t, J = 5.2 Hz, 1H), 6.64 (s, 1H), 4.28 (d, J = 4.4 Hz, 2H), 3.85 (s, 2H), 2.90 (t, J = 5.6 Hz, 2H), 2.61 (q, J = 7.6 Hz, 2H), 2.51-2.49 (m, 2H), 1.48 (s, 9H), 1.16 (t, J = 7.2 Hz, 3H); LCMS (electrospray) m/z (M + H) + 490.04 | ++++ | GP26, 35 |
| 355 | 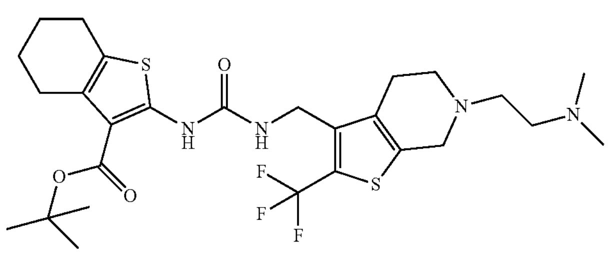 [SMILES: CN(C)CCN1CCc2c(sc(C(F)(F)F)c2CNC(=O)Nc2sc3c(c2C(=O)OC(C)(C)C)CCCC3)C1] | White solid; $^1$H NMR (400 MHz, DMSO) δ 10.34 (s, 1H), 8.12 (t, J = 5.0 Hz, 1H), 4.29 (d, J = 4.8 Hz, 2H), 3.68 (s, 2H), 2.77 (d, J = 5.6 Hz, 2H), 2.63-2.59 (m, 6H), 2.52 (d, J = 8.0 Hz, 4H), 2.20 (s, 6H), 1.68 (s, 4H), 1.51 (s, 9H); LCMS (electrospray) m/z (M + H)$^+$ 587.19 | ++++ | GP26, 35 |
| 356 | 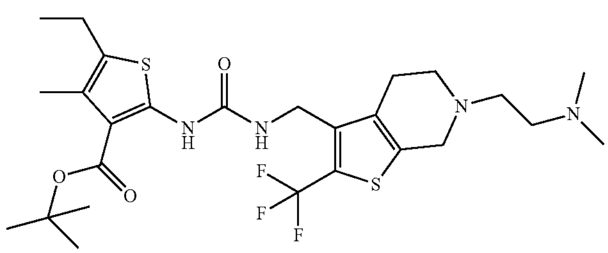 [SMILES: CCc1sc(NC(=O)NCc2c(C(F)(F)F)sc3c2CCN(CCN(C)C)C3)c(C(=O)OC(C)(C)C)c1C] | White solid; $^1$H NMR (400 MHz, DMSO) δ 10.34 (s, 1H), 8.11 (t, J = 5.0 Hz, 1H), 4.29 (d, J = 4.8 Hz, 2H), 3.69 (s, 2H), 2.76 (d, J = 5.6 Hz, 2H), 2.63-2.55 (m, 8H), 2.24 (s, 6H), 2.13 (s, 3H), 1.53 (s, 9H), 1.10 (t, J = 8.0 Hz, 3H); LCMS (electrospray) m/z (M + H)$^+$ 575.15 | ++++ | GP26, 35 |

TABLE 1-continued

Anti-HCVcc genotype ½ activity for Formula I Series

| No. | Structure | Data | EC$_{50}$ | General Procedure (GP) |
|---|---|---|---|---|
| 357 | 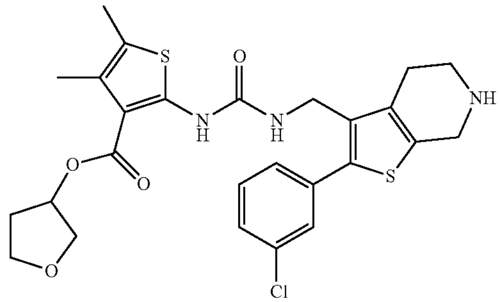 [SMILES: Cc1sc(NC(=O)NCc2c(-c3cccc(Cl)c3)sc3c2CCNC3)c(C(=O)OC2CCOC2)c1C] | White solid; $^1$H NMR (400 MHz, DMSO) δ 10.35 (s, 1H), 8.12 (t, J = 5.2 Hz, 1H), 7.50-7.41 (m, 4H), 5.40 (pentet, J = 6.4 and 12.4 Hz, 1H), 4.16 (d, J = 4.8 Hz, 2H), 3.90-3.77 (m, 6H), 2.93 (t, J = 5.8 Hz, 2H), 2.50 (t, J = 5.2 Hz, 2H), 2.21-2.16 (m, 1H), 2.16 (s, 3H), 2.14 (s, 3H), 2.06-2.00 (m, 1H); LCMS (electrospray) m/z (M + H)$^+$ 546.03 | +++ | GP21, GP35 |
| 358 | 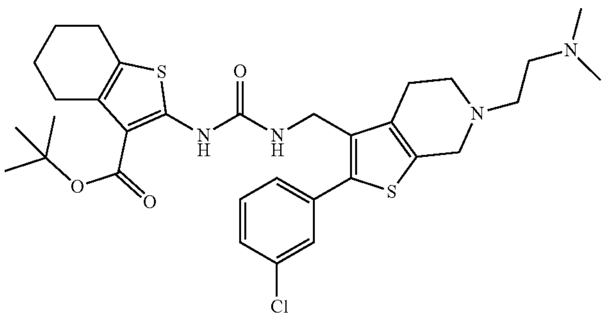 [SMILES: CN(C)CCN1CCc2c(sc(-c3cccc(Cl)c3)c2CNC(=O)Nc2sc3c(c2C(=O)OC(C)(C)C)CCCC3)C1] | Ivory solid; $^1$H NMR (400 MHz, acetone-d6); δ 10.48 (s, 1H), 7.52 (s, 1H), 7.47-7.44 (m, 2H), 7.40-7.38 (m, 1H), 7.31 (brs, 1H), 4.36-4.35 (m, 2H), 3.70 (s, 2H), 3.00-2.99 (m, 2H), 2.81-2.67 (m, 6H), 2.57-2.51 (m, 4H), 2.24 (s, 6H), 1.75-1.74 (m, 4H), 1.53 (s, 9H); LCMS (electrospray) m/z (M + H) + 629.23 | ++++ | GP21, 3 |
| 359 | 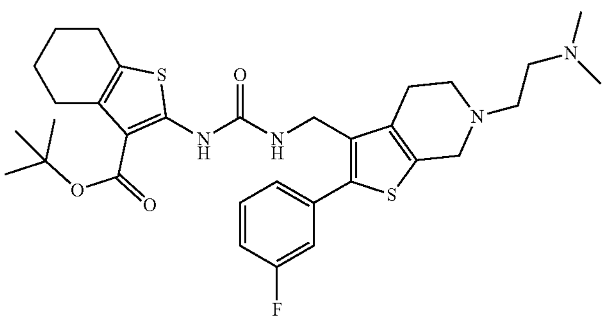 | Beige solid; $^1$H NMR (400 MHz, acetone-d6) δ 10.49 (s, 1H), 7.51-7.45 (m, 1H), 7.34-7.27 (m, 3H), 7.14 (td, J = 8.4, 2.4 Hz, 1H), 4.36 (d, J = 4.8 Hz, 2H, 3.71 (s, 2H), 2.82-2.79 (m, 2H), 2.75-2.70 (m, 6H), 2.63-2.60 (m, 2H), 2.58-2.56 (m, 2H), 2.30 (s, 6H), 1.75-1.73 (m, 4H), 1.53 (s, 9H); LCMS (electrospray) m/z (M + H) + 613.17 | ++++ | GP21, 3 |
| 360 | 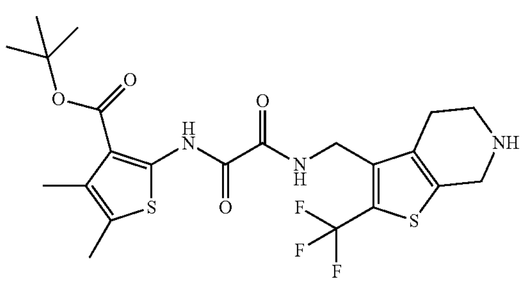 [SMILES: Cc1sc(NC(=O)C(=O)NCc2c(C(F)(F)F)sc3c2CCNC3)c(C(=O)OC(C)(C)C)c1C] | White solid; $^1$H NMR (400 MHz, cdcl3) δ 12.48 (s, 1H), 7.53 (t, J = 6.0 Hz, 1H), 4.55 (d, J = 5.9 Hz, 2H), 4.14 (s, 2H), 3.23 (t, J = 5.6 Hz, 2H), 2.77 (s, 2H), 2.26 (d, J = 14.8 Hz, 6H), 1.62 (s, 9H); LCMS (electrospray) m/z (M + H) + 518.00 | +++ | GP1, GP33, GP35 |
| 361 | 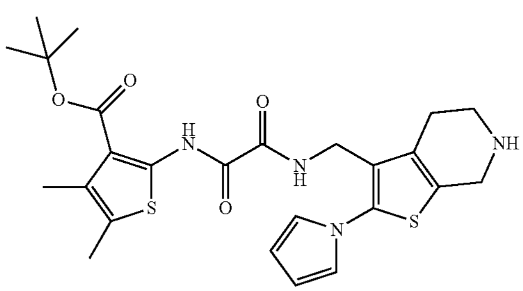 [SMILES: Cc1sc(NC(=O)C(=O)NCc2c(-n3cccc3)sc3c2CCNC3)c(C(=O)OC(C)(C)C)c1C] | White solid; $^1$H NMR (400 MHz, dmso) δ 12.12 (s, 2H), 9.41 (t, J = 6.5 Hz, 1H), 7.04 (t, J = 1.9 Hz, 2H), 6.19 (t, J = 2.1 Hz, 2H), 4.14 (d, J = 5.6 Hz, 2H), 3.76 (s, 2H), 2.89 (t, J = 5.5 Hz, 2H), 2.39 (s, 2H), 2.24 (s, 3H), 2.18 (s, 3H), 1.55 (s, 9H); LCMS (electrospray) m/z (M + H) + 515.08 | +++ | GP1, GP33, GP35 |

TABLE 1-continued

Anti-HCVcc genotype ½ activity for Formula I Series

| No. | Structure | Data | EC$_{50}$ | General Procedure (GP) |
|---|---|---|---|---|
| 362 | 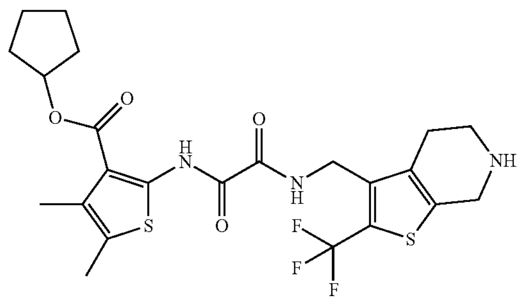 [SMILES: Cc1sc(NC(=O)C(=O)NCc2c(C(F)(F)F)sc3c2CCNC3)c(C(=O)OC2CCCC2)c1C] | White solid; $^1$H NMR (400 MHz, dmso) δ 12.12 (s, 1H), 9.50 (s, 1H), 5.49-5.45 (m, 1H), 4.39 (d, J = 5.3 Hz, 2H), 3.93-3.74 (m, 8H), 2.88 (t, J = 5.6 Hz, 2H), 2.25 (s, 3H), 2.19 (s, 3H), 2.14-2.01 (m, 2H); LCMS (electrospray) m/z (M + H) + 532.02 | ++ | GP1, GP33, GP35 |
| 363 | 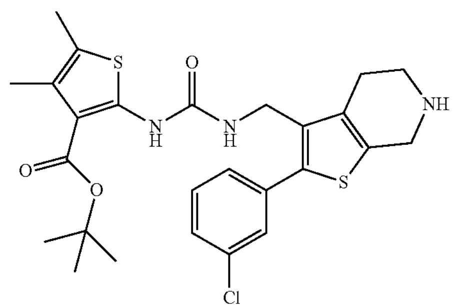 | White solid; $^1$H NMR (400 MHz, dmso) δ 10.32 (s, 1H), 8.06 (t, J = 4.8 Hz, 1H), 7.50-7.36 (m, 4H), 4.13 (d, J = 4.7 Hz, 2H), 3.84 (s, 2H), 2.91 (t, J = 5.5 Hz, 2H), 2.12 (d, J = 11.4 Hz, 6H), 1.61-1.45 (m, 9H); LCMS (electrospray) m/z (M + H) + 532.08 | ++++ | GP38, GP35 |
| 364 | 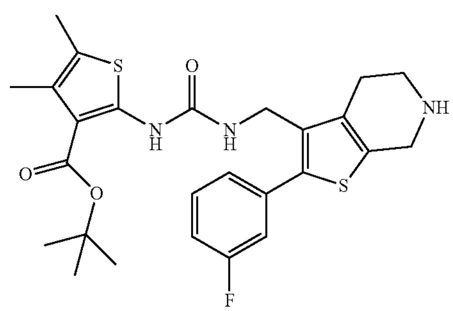 [SMILES: Cc1sc(NC(=O)NCc2c(-c3cccc(F)c3)sc3c2CCNC3)c(C(=O)OC(C)(C)C)c1C] | White solid; $^1$H NMR (400 MHz, dmso) δ 10.33 (s, 1H), 7.47 (dd, J = 14.5, 7.7 Hz, 1H), 7.27 (d, J = 8.6 Hz, 2H), 7.20 (t, J = 9.1 Hz, 1H), 4.14 (d, J = 4.7 Hz, 2H), 3.83 (s, 2H), 2.91 (t, J = 5.5 Hz, 2H), 2.12 (d, J = 11.7 Hz, 6H), 1.50 (s, 9H); LCMS (electrospray) m/z (M + H) + 516.10 | ++++ | GP38, GP35 |
| 365 | 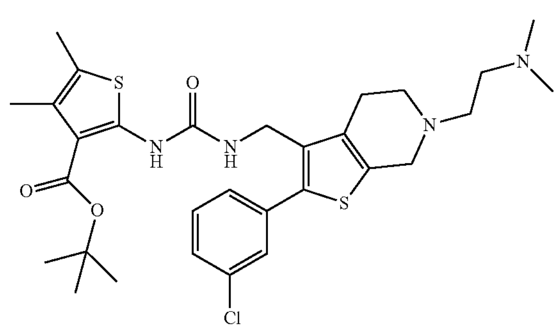 | White solid; $^1$H NMR (400 MHz, dmso) δ 10.33 (s, 1H), 8.05 (t, J = 4.7 Hz, 1H), 7.52-7.35 (m, 4H), 4.14 (d, J = 4.7 Hz, 2H), 3.67 (s, 2H), 2.84-2.73 (m, 4H), 2.67 (t, J = 6.1 Hz, 2H), 2.60 (s, 2H), 2.42 (s, 6H), 2.12 (d, J = 11.8 Hz, 6H), 1.50 (s, 9H); LCMS (electrospray) m/z (M + H) + 603.17 | +++ | GP38, GP3, GP35 |

TABLE 1-continued

Anti-HCVcc genotype ½ activity for Formula I Series

| No. | Structure | Data | EC$_{50}$ | General Procedure (GP) |
|---|---|---|---|---|
| 366 | 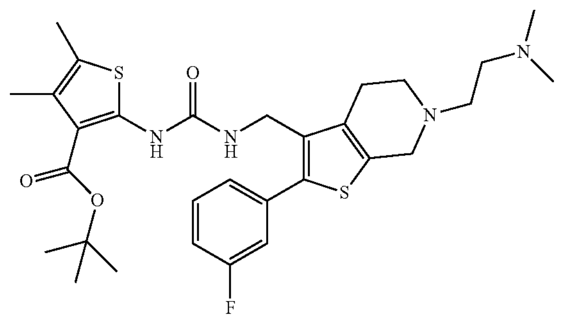 | White solid; $^1$H NMR (400 MHz, dmso) δ 10.33 (s, 1H), 8.05 (t, J = 4.8 Hz, 1H), 7.48 (dd, J = 14.3, 7.7 Hz, 1H), 7.30-7.25 (m, 2H), 7.21 (dd, J = 10.3, 8.0 Hz, 1H), 4.14 (d, J = 4.7 Hz, 2H), 3.65 (s, 2H), 2.75 (t, J = 5.3 Hz, 2H), 2.65 (s, 4H), 2.59 (s, 2H), 2.33 (s, 6H), 2.12 (d, J = 12.0 Hz, 6H), 1.50 (s, 9H) | ++++ | GP38, GP3, GP35 |
| 367 | 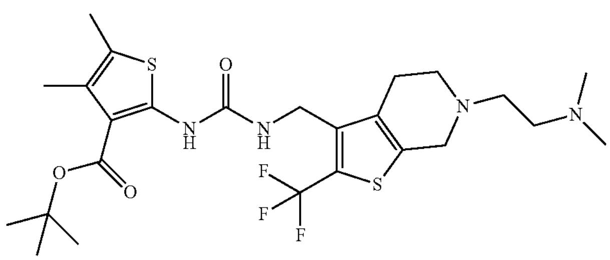 [SMILES: Cc1sc(NC(=O)NCc2c(C(F)(F)F)sc3c2CCN(CCN(C)C)C3)c(C(=O)OC(C)(C)C)c1C] | White solid; $^1$H NMR (400 MHz, DMSO) δ 10.33 (s, 1H), 8.10 (t, J = 5.0 Hz, 1H), 4.29 (d, J = 4.8 Hz, 2H), 3.69 (s, 2H), 2.76 (d, J = 5.6 Hz, 2H), 2.63-2.59 (m, 4H), 2.22 (s, 6H), 2.15 (s, 3H), 2.12 (s, 3H), 1.52 (s, 9H); LCMS (electrospray) m/z (M + H)$^+$ 561.07 | ++++ | GP26, GP35 |
| 368 | 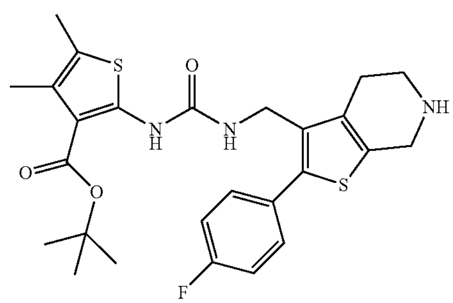 [SMILES: Cc1sc(NC(=O)NCc2c(-c3ccc(F)cc3)sc3c2CCNC3)c(C(=O)OC(C)(C)C)c1C] | White solid; $^1$H NMR (400 MHz, dmso) δ 10.32 (s, 1H), 8.05 (t, J = 4.7 Hz, 1H), 7.51-7.43 (m, 2H), 7.28 (t, J = 8.8 Hz, 2H), 4.10 (d, J = 4.7 Hz, 2H), 3.83 (s, 2H), 2.91 (t, J = 5.6 Hz, 2H), 2.47 (s, 2H), 2.12 (d, J = 11.4 Hz, 6H), 1.51 (s, 9H); LCMS (electrospray) m/z (M + H) + 516.10 | +++ | GP38, GP35 |
| 369 | 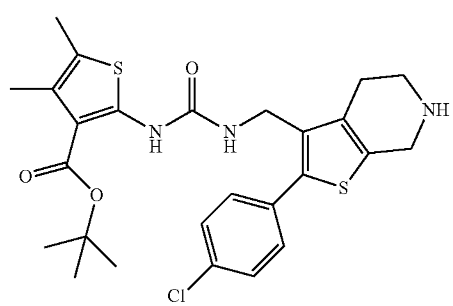 [SMILES: Cc1sc(NC(=O)NCc2c(-c3ccc(Cl)cc3)sc3c2CCNC3)c(C(=O)OC(C)(C)C)c1C] | White solid; $^1$H NMR (400 MHz, dmso) δ 10.32 (s, 1H), 8.06 (t, J = 4.7 Hz, 1H), 7.48 (dd, J = 19.5, 8.5 Hz, 4H), 4.12 (d, J = 4.7 Hz, 2H), 3.84 (s, 2H), 2.92 (t, J = 5.5 Hz, 2H), 2.48 (s, 2H), 2.12 (d, J = 11.6 Hz, 6H), 1.51 (s, 9H); LCMS (electrospray) m/z (M + H) + 532.02 | ++++ | GP38, GP35 |
| 370 | 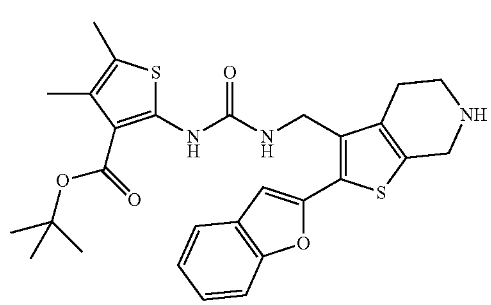 | White solid; $^1$H NMR (400 MHz, dmso) δ 10.32 (s, 1H), 8.11 (t, J = 4.9 Hz, 1H), 7.63 (d, J = 7.4 Hz, 1H), 7.58 (d, J = 8.0 Hz, 1H), 7.32-7.21 (m, 2H), 7.13 (s, 1H), 4.44 (d, J = 4.9 Hz, 2H), 3.87 (s, 2H), 2.93 (t, J = 5.4 Hz, 2H), 2.54 (s, 2H), 2.12 (d, J = 16.6 Hz, 6H), 1.49 (s, 9H); LCMS (electrospray) m/z (M + H) + 532.02 | ++++ | GP39, GP35 |

TABLE 1-continued

Anti-HCVcc genotype ½ activity for Formula I Series

| No. | Structure | Data | EC$_{50}$ | General Procedure (GP) |
|---|---|---|---|---|
| 371 | 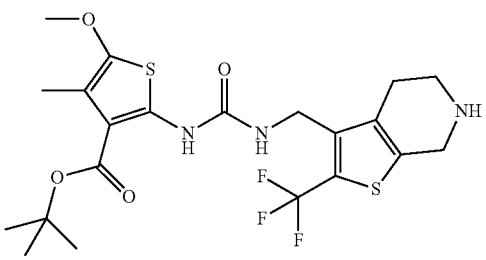 [SMILES: COc1sc(NC(=O)NCc2c(C(F)(F)F)sc3c2CCNC3)c(C(=O)OC(C)(C)C)c1C] | White solid; ¹H NMR (400 MHz, DMSO) δ 10.35 (s, 1H), 8.13 (t, J = 5.2 Hz, 1H), 4.29 (d, J = 4.8 Hz, 2H), 3.87 (s, 2H), 3.74 (s, 3H), 2.92 (t, J = 6.0 Hz, 2H), 2.50 (brs, 2H), 2.06 (s, 3H), 1.51 (s, 9H), 1.24 (s, 1H); LCMS (electrospray) m/z (M + H) + 506.03 | ++++ | GP1 GP26 GP28 |
| 372 | 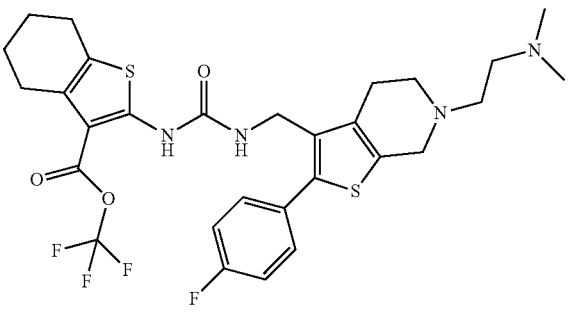 | Beige solid; ¹H NMR (400 MHz, acetone-d6) δ 10.47 (s, 1H), 7.56-7.52 (m, 2H), 7.25-7.19 (m, 3H), 4.33 (d, J = 4.4 Hz, 2H), 3.72 (s, 2H), 2.84-2.77 (m, 4H), 2.74-2.68 (m, 6H), 2.60-2.56 (m, 2H), 2.38 (s, 6H), 1.80-1.70 (m, 4H), 1.54 (s, 9H); LCMS (electrospray) m/z (M + H) + 613.30 | ++++ | GP21, 3 |
| 373 | 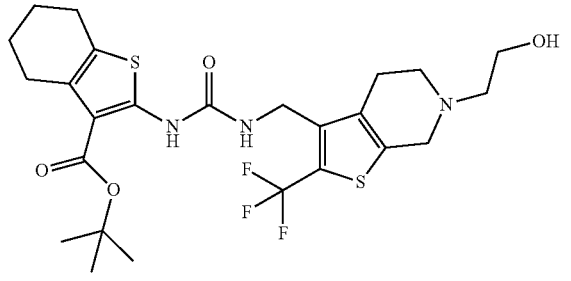 [SMILES: CC(C)(C)OC(=O)c1c(NC(=O)NCc2c(C(F)(F)F)sc3c2CCN(CCO)C3)sc2c1CCCC2] | White solid; ¹H NMR (400 MHz, acetone-d6) δ 10.47 (s, 1H), 7.38 (t, J = 5.2 Hz, 1H), 4.49 (d, J = 5.2 Hz, 2H), 3.75 (s, 2H), 3.67 (t, J = 5.6 Hz, 2H), 3.47 (brs, 1H), 2.85-2.82 (m, 2H), 2.77-2.75 (m, 2H), 2.70-2.67 (m, 4H), 2.58-2.56 (m, 2H), 1.78-1.70 (m, 4H), 1.53 (s, 9H); LCMS (electrospray) m/z (M + H) + 560.11 | ++++ | GP26, 35, 3 |
| 374 | 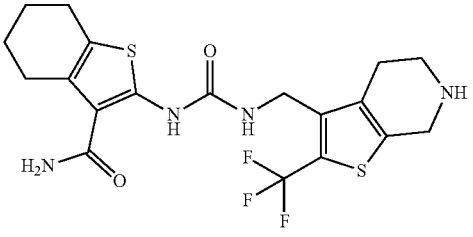 [SMILES: NC(=O)c1c(NC(=O)NCc2c(C(F)(F)F)sc3c2CCNC3)sc2c1CCCC2] | Beige solid; ¹H NMR (400 MHz, dmso) δ 10.34 (s, 1H), 7.86 (t, J = 5.2 Hz, 1H), 7.23 (br s, 1H), 6.73 (br s, 1H), 4.25 (d, J = 4.4 Hz, 2H), 3.85 (s, 2H), 2.89 (t, J = 6.0 Hz, 2H), 2.53-2.51 (m, 2H), 2.51-2.50 (m, 4H), 1.70-1.66 (m, 4H),; LCMS (electrospray) m/z (M + H) + 458.95 | ++ | GP35 |

Activity range: >10 uM: +, 1-10 uM: ++, 0.1-1 uM: +++, <0.1 uM: ++++

TABLE 2

Anti-HCV genotype 1/2 activity for Formula II Series

| No. | Structure | Characterization | EC$_{50}$ | Method |
|---|---|---|---|---|
| 1001 | 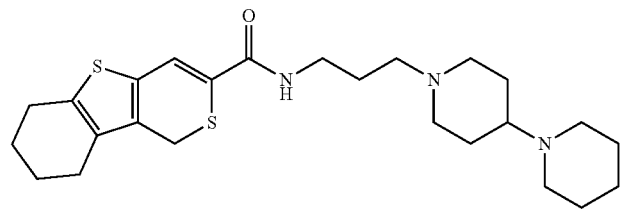 [SMILES: O=C(NCCCN1CCC(N2CCCCC2)CC1)C1=Cc2sc3c(c2CS1)CCCC3] | Original hit, Not synthesized, | +++ | D-1 |

TABLE 2-continued

Anti-HCV genotype 1/2 activity for Formula II Series

| No. | Structure | Characterization | EC$_{50}$ | Method |
|---|---|---|---|---|
| 1002 | 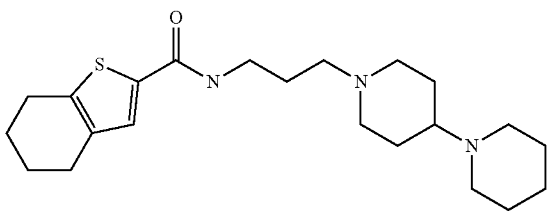 [SMILES: O=C(NCCCN1CCC(N2CCCCC2)CC1)c1cc2c(s1)CCCC2] | Oil; $^1$H NMR (400 MHz, DMSO-d$_6$) δ 8.35 (NH, 1H), 7.40 (s, 1H), 3.44-3.30 (m, 4H), 3.19 (q, J = 5.6 Hz, 2H), 3.30-2.97 (m, 2H), 2.95-2.85 (m, 3 H), 2.68 (t, J = 6.0 Hz, 2H), 2.52 (t, J = 6.0 Hz, 2H), 2.47-2.42 (m, 2), 1.96-1.88 (m, 4H), 1.75-1.70 (m, 10H), 1.46-1.38 (m, 2H); LRMS (electrospray) m/z (M + H)$^+$ 390.10. | + | D-1 |
| 1003 | 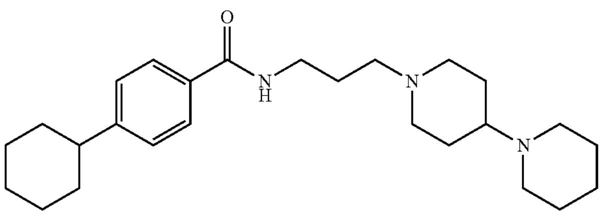 [SMILES: O=C(NCCCN1CCC(N2CCCCC2)CC1)c1ccc(C2CCCCC2)cc1] | Oil; $^1$H NMR (400 MHz, DMSO-d$_6$) δ 8.40 (NH, 1H), 7.73 (d, J = 6.4 Hz, 2H), 7.28 (d, J = 6.4 Hz, 2H), 3.48 (q, J = 5.6 Hz, 2H), 3.17-3.13 (m, 4H), 2.90-2.58 (m, 4 H), 2.55-2.52 (m, 8), 2.08-2.03 (m, 6H), 1.85-1.67 (m, 10H), 1.40-1.37 (m, 2H); LRMS (electrospray) m/z (M + H)$^+$ 412.14. | +++ | D-1 |
| 1004 | 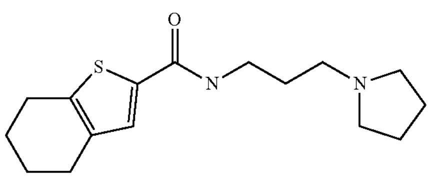 [SMILES: O=C(NCCCN1CCCC1)c1cc2c(s1)CCCC2] | Oil; $^1$H NMR (400 MHz, CDCl$_3$) δ 8.23 (NH, 1H), 7.24 (s, 1H), 3.53 (q, J = 5.6 Hz, 2H), 2.85-2.84 (m, 6H), 2.75 (t, J = 6.0 Hz, 2H), 2.58 (t, J = 6.0 Hz, 2H), 1.95-1.88 (m, 6 H), 1.84-1.74 (m, 4H); LRMS (electrospray) m/z (M + H)$^+$ 293.07. | + | D-1 |
| 1005 | 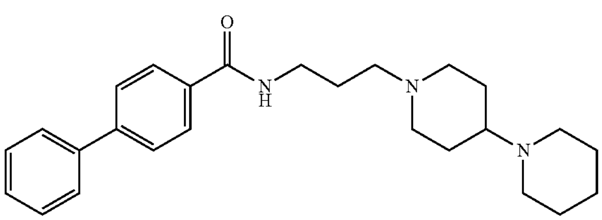 [SMILES: O=C(NCCCN1CCC(N2CCCCC2)CC1)c1ccc(-c2ccccc2)cc1] | White solid; $^1$H NMR (400 MHz, DMSO-d$_6$) δ 8.55 (NH, 1H), 7.90 (d, J = 6.4 Hz, 2H), 7.76-7.70 (m, 4H), 7.49 (t, J = 7.4 Hz, 2H), 7.40 (t, J = 7.4 Hz, 1H), 3.29-3.27 (m, 2H), 2.91 (d, J = 11.2 Hz, 2H), 2.42-2.40 (m, 4H), 2.31 (t, J = 6.0 Hz, 2H), 2.15-2.12 (m, 1H), 1.81 (t, J = 6.0 Hz, 2H), 1.70-1.63 (m, 4H), 1.44-1.42 (m, 5H), 1.37-1.34 (m, 3 H); LRMS (electrospray) m/z (M + H)$^+$ 406.15. | +++ | D-1 |
| 1006 | 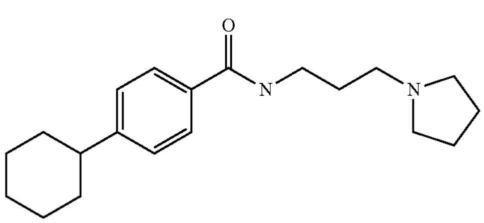 [SMILES: O=C(NCCCN1CCCC1)c1ccc(C2CCCCC2)cc1] | White solid; $^1$H NMR (400 MHz, CDCl$_3$) δ 8.53 (NH, 1H), 7.76 (d, J = 6.4 Hz, 2H), 7.28 (d, J = 6.4 Hz, 2H), 3.62 (q, J = 5.6 Hz, 2H), 2.83-2.81 (m, 2H), 2.76-2.74 (m, 4H), 2.56-2.54 (m, 1H), 1.92-1.80 (m, 10H), 1.76 (d, J = 12.4 Hz, 1H), 1.50-1.40 (m, 4H), 1.37-1.30 (m, 1H); LRMS (electrospray) m/z (M + H)$^+$ 315.19. | ++ | D-1 |

TABLE 2-continued

Anti-HCV genotype 1/2 activity for Formula II Series

| No. | Structure | Characterization | EC$_{50}$ | Method |
|-----|-----------|------------------|-----------|--------|
| 1007 | 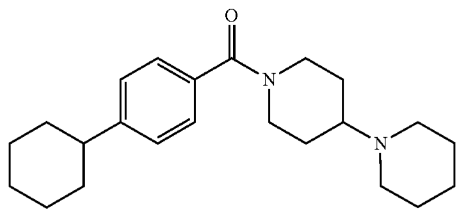 [SMILES: O=C(c1ccc(C2CCCCC2)cc1)N1CCC(N2CCCCC2)CC1] | Oil; $^1$H NMR (400 MHz, CDCl$_3$) δ 7.30 (d, J = 6.4 Hz, 2H), 7.21 (d, J = 6.4 Hz, 2H), 4.77-4.75 (m, 1H), 3.89-3.87 (m, 1H), 2.94-2.74 (m, 2H), 2.55-2.52 (m, 6H), 1.84-1.82 (m, 6H), 1.73 (d, J = 12.4 Hz, 1H), 1.63-1.61 (m, 4H), 1.39-1.33 (m, 7H), 1.22-1.20 (m, 2H); LRMS (electrospray) m/z (M + H)$^+$ 355.40. | ++ | D-1 |
| 1008 | 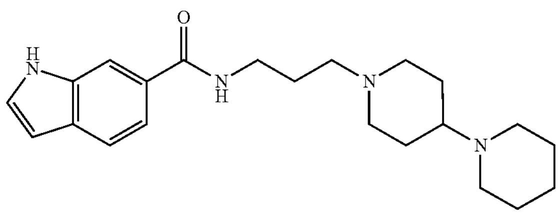 [SMILES: O=C(NCCCN1CCC(N2CCCCC2)CC1)c1ccc2cc[nH]c2c1] | White solid; $^1$H NMR (400 MHz, CD$_3$OD) δ 7.92 (s, 1H), 7.59 (d, J = 8.0 Hz, 1H), 7.47 (d, J = 8.0 Hz, 1H), 7.38 (d, J = 2.8 Hz, 1H), 6.50 (d, J = 2.8 Hz, 1H), 3.45 (t, J = 6.8 Hz, 2H), 3.08 (d, J = 12.0 Hz, 2H), 2.62-2.60 (m, 4H), 2.49 (t, J = 7.4 Hz, 2H), 2.40-2.38 (m, 1H), 2.01 (t, J = 11.2 Hz, 2H), 1.89-1.82 (m, 4H), 1.65-1.58 (m, 6H), 1.51-1.48 (m 2H); LRMS (electrospray) m/z (M + H)$^+$ 369.07. | + | D-1 |
| 1009 | 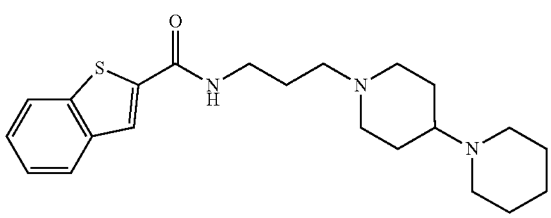 [SMILES: O=C(NCCCN1CCC(N2CCCCC2)CC1)c1cc2ccccc2s1] | White solid; $^1$H NMR (400 MHz, CD$_3$OD) δ 7.91-7.87 (m, 2H), 7.44-7.41 (m, 2H), 3.43 (t, J = 6.4 Hz, 2H), 3.06 (d, J = 11.6 Hz, 2H), 2.58-2.54 (m, 4H), 2.44 (t, J = 7.4 Hz, 2H), 2.26-2.24 (m, 1H), 1.87 (t, J = 11.2 Hz, 2H), 1.83-1.80 (m, 4H), 1.57-1.54 (m, 6H), 1.47-1.46 (m, 2H); LRMS (electrospray) m/z (M + H)$^+$ 386.08. | ++ | D-1 |
| 1010 | 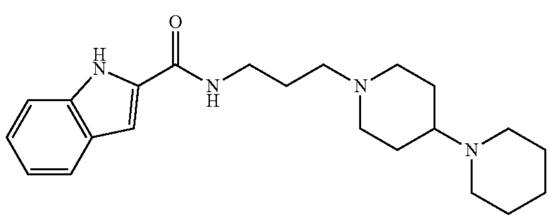 [SMILES: O=C(NCCCN1CCC(N2CCCCC2)CC1)c1cc2ccccc2[nH]1] | White solid; $^1$H NMR (400 MHz, CD$_3$OD) δ 7.58 (d, J = 8.4 Hz, 1H), 7.42 (d, J = 8.4 Hz, 1H), 7.20 (t, J = 7.6 Hz, 1H), 7.18-7.02 (m, 2H), 3.43 (t, J = 6.4 Hz, 2H), 2.85 (d, J = 11.6 Hz, 2H), 2.57-2.48 (m, 4H), 2.47 (t, J = 7.4 Hz, 2H), 2.48-2.46 (m, 1H), 1.96 (t, J = 11.2 Hz, 2H), 1.88-1.81 (m, 4H), 1.64-1.57 (m, 6H), 1.50-1.47 (m, 2H); LRMS (electrospray) m/z (M + H)$^+$ 369.07. | ++ | D-1 |
| 1011 | 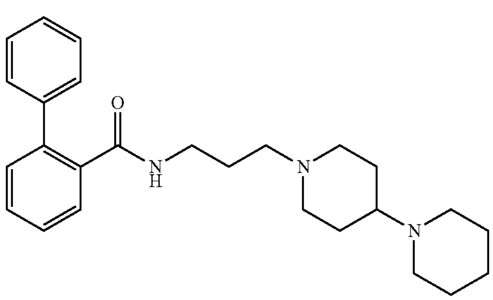 [SMILES: O=C(NCCCN1CCC(N2CCCCC2)CC1)c1ccccc1-c1ccccc1] | White solid; $^1$H NMR (400 MHz, CDCl$_3$); δ 7.59-7.62 (m, 1H), 7.33-7.47 (m, 8H), 6.74 (s, 1H), 3.23 (q, J = 6.0 Hz, 2H), 2.75 (d, J = 12.0 Hz, 2H), 2.39 (t, J = 4.8 Hz, 4H), 2.20-2.26 (m, 1H), 2.13 (t, J = 6.4 Hz, 2H), 1.75 (t, J = 11.8 Hz, 2H), 1.67 (d, J = 12.4 Hz, 2H), 1.58 (t, J = 5.2 Hz, 4H), 1.38-1.44 (m, 4H), 1.22-1.32 (m, 4H); LCMS (electrospray) m/z (M + H)$^+$ 406.22 | + | D-1 |

TABLE 2-continued

Anti-HCV genotype 1/2 activity for Formula II Series

| No. | Structure | Characterization | EC$_{50}$ | Method |
|---|---|---|---|---|
| 1012 | 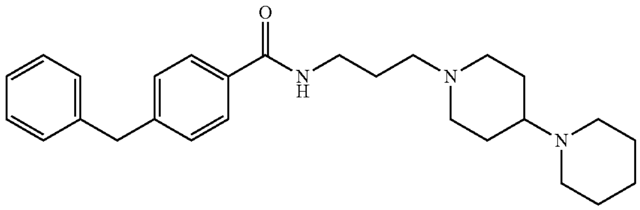 [SMILES: O=C(NCCCN1CCC(N2CCCCC2)CC1)c1ccc(Cc2ccccc2)cc1] | White solid; $^1$H NMR (400 MHz, CDCl$_3$); δ 8.31 (s, 1H), 7.74 (d, J = 8.0 Hz, 2H), 7.24 (td, J = 7.3 and 32.13 Hz, 5H), 7.15 (d, J = 8.0 Hz, 2H), 4.00 (s, 2H), 3.64 (q, J = 5.5 Hz, 2H), 3.05 (d, J = 12.0 Hz, 2H), 2.46-2.51 (m, 6H), 2.31-2.37 (m, 1H), 1.91 (t, J = 11.4 Hz, 2H), 1.91 (s, 4H), 1.75 (s, 6H), 1.43 (d, J = 5.6 Hz, 2H); LCMS (electrospray) m/z (M + H)$^+$ 420.37 | +++ | D-1 |
| 1013 | 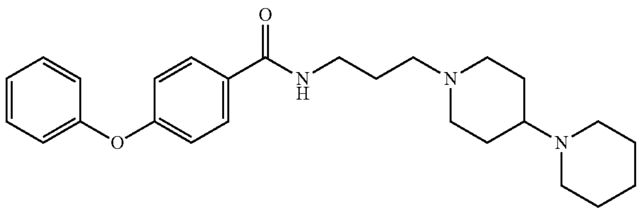 [SMILES: O=C(NCCCN1CCC(N2CCCCC2)CC1)c1ccc(Oc2ccccc2)cc1] | White solid; $^1$H NMR (400 MHz, CDCl$_3$); δ 8.35 (s, 1H), 7.89 (d, J = 8.8 Hz, 2H), 7.36 (t, J = 8.0 Hz, 2H), 7.15 (t, J = 7.6 Hz, 1H), 7.03 (d, J = 7.6 Hz, 2H), 6.96 (d, J = 9.2 Hz, 2H), 3.54 (q, J = 5.5 Hz, 2H), 3.06 (d, J = 12.0 Hz, 2H), 2.51 (t, J = 5.6 Hz, 2H), 2.45 (t, J = 5.2 Hz, 4H), 2.29-2.36 (m, 1H), 1.91 (t, J = 11.8 Hz, 2H), 1.72-1.78 (m, 4H), 1.49-1.55 (m, 6H), 1.40 (d, J = 5.2 Hz, 2H); LCMS (electrospray) m/z (M + H)$^+$ 422.41 | +++ | D-3 |
| 1014 | 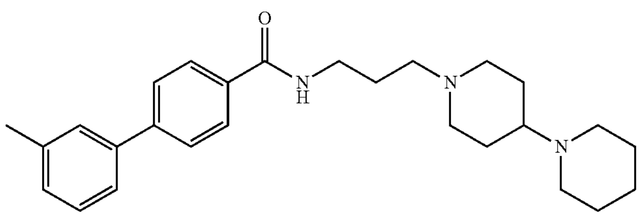 [SMILES: Cc1cccc(-c2ccc(C(=O)NCCCN3CCC(N4CCCCC4)CC3)cc2)c1] | White solid; $^1$H NMR (400 MHz, CDCl$_3$); δ 8.50 (s, 1H), 7.87 (d, J = 8.4 Hz, 2H), 7.62 (d, J = 8.0 Hz, 2H), 7.39 (d, J = 8.4 Hz, 2H), 7.33 (t, J = 7.6 Hz, 1H), 7.18 (d, J = 7.6 Hz, 1H), 3.58 (q, J = 5.6 Hz, 2H), 3.08 (d, J = 12.0 Hz, 2H), 2.52 (q, J = 5.9 Hz, 6H), 2.41 (s, 3H), 2.31-2.38 (m, 1H), 1.92 (t, J = 12.0 Hz, 2H), 1.75-1.80 (m, 4H), 1.52-1.65 (m, 6H), 1.43 (q, J = 5.6 Hz, 2H); LCMS (electrospray) m/z (M + H)$^+$ 420.30 | ++ | D-1 |
| 1015 | 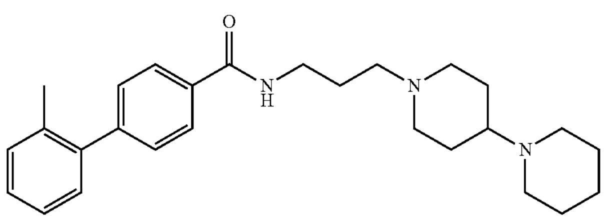 [SMILES: Cc1ccccc1-c1ccc(C(=O)NCCCN2CCC(N3CCCCC3)CC2)cc1] | Yellow solid; $^1$H NMR (400 MHz, CDCl$_3$); δ 8.40 (s, 1H), 7.86 (d, J = 8.4 Hz, 2H), 7.36 (d, J = 8.4 Hz, 2H), 7.18-7.27 (m, 4H), 3.58 (q, J = 5.5 Hz, 2H), 3.09 (d, J = 12.0 Hz, 2H), 2.53 (t, J = 5.8 Hz, 2H), 2.49 (t, J = 5.0 Hz, 4H), 2.31-2.37 (m, 1H), 2.25 (s, 3H), 1.93 (t, J = 11.0 Hz, 2H), 1.77-1.80 (m, 4H), 1.52-1.62 (m, 6H), 1.43 (q, J = 5.6 Hz, 2H); LCMS (electrospray) m/z (M + H)$^+$ 420.37 | +++ | D-1 |
| 1016 | 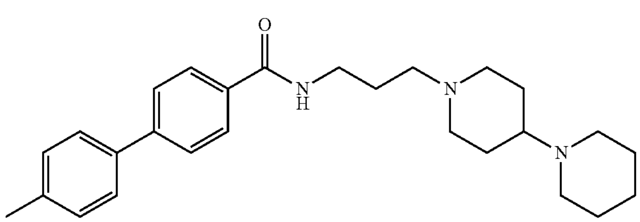 [SMILES: Cc1ccc(-c2ccc(C(=O)NCCCN3CCC(N4CCCCC4)CC3)cc2)cc1] | Yellow solid; $^1$H NMR (400 MHz, CDCl$_3$); δ 8.45 (s, 1H), 7.87 (d, J = 8.0 Hz, 2H), 7.61 (d, J = 8.0 Hz, 2H), 7.49 (d, J = 8.0 Hz, 2H), 7.25 (d, J = 8.0 Hz, 2H), 3.58 (q, J = 5.5 Hz, 2H), 3.08 (d, J = 12.0 Hz, 2H), 2.53 (q, J = 6.0 Hz, 6H), 2.39 (s, 3H), 2.33-2.39 (m, 1H), 1.93 (t, J = 12.0 | +++ | D-1 |

TABLE 2-continued

Anti-HCV genotype 1/2 activity for Formula II Series

| No. | Structure | Characterization | EC$_{50}$ | Method |
|---|---|---|---|---|
| | | Hz, 2H), 1.75-1.81 (m, 4H), 1.53-1.65 (m, 6H), 1.43 (q, J = 5.6 Hz, 2H); LCMS (electrospray) m/z (M + H)$^+$ 420.44 | | |
| 1017 | 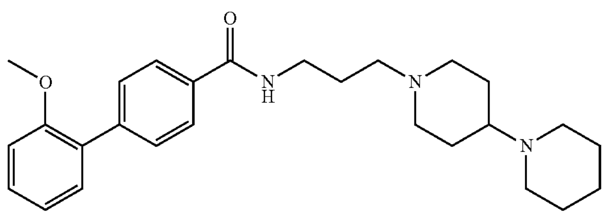 [SMILES: COc1ccccc1-c1ccc(C(=O)NCCCN2CCC(N3CCCCC3)CC2)cc1] | Yellow solid; $^1$H NMR (400 MHz, CDCl$_3$); δ 8.33 (s, 1H), 7.85 (d, J = 10.0 Hz, 2H), 7.56 (d, J = 10.4 Hz, 2H), 7.33 (ddd, J = 1.2 and 7.8 and 7.8 Hz, 1H), 7.29 (dd, J = 1.6 and 7.6 Hz, 1H), 7.02 (ddd, J = 1.2 and 7.5 and 7.5 Hz, 1H), 6.98 (d, J = 8.0 Hz, 1H), 3.80 (s, 3H), 3.56 (q, J = 5.6 Hz, 2H), 3.08 (d, J = 12.0 Hz, 2H), 2.49-2.53 (m, 6H), 2.31-2.37 (m, 1H), 1.92 (t, J = 12.0 Hz, 2H), 1.74-1.80 (m, 4H), 1.52-1.65 (m, 6H), 1.42 (q, J = 5.6 Hz, 2H); LCMS (electrospray) m/z (M + H)$^+$ 436.29 | ++ | D-1 |
| 1018 | 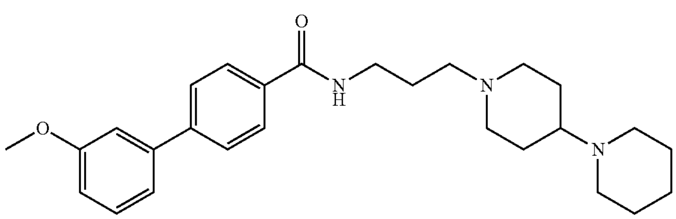 | White solid; $^1$H NMR (400 MHz, CDCl$_3$); δ 8.53 (s, 2H), 7.37 (d, J = 8.0 Hz, 2H), 7.25 (d, J = 8.0 Hz, 2H), 6.47 (s, 1H), 4.55 (dd, J = 3.6 and 13.6 Hz, 1H), 4.40 (td, J = 4.2 and 13.3 Hz, 1H), 3.50 (dd, J = 9.2 and 13.6 Hz, 1H), 3.37 (q, J = 6.0 Hz, 2H), 3.29 (ddd, J = 3.2 and 10.2 and 13.3 Hz, 1H), 2.59 (t, J = 6.0 Hz, 2H), 2.51 (s, 4H), 2.44-2.40 (m, 1H), 2.39 (s, 3H), 2.04-1.96 (m, 2H), 1.80-1.75 (m, 5H), 1.62-1.53 (m, 1H); LCMS (electrospray) m/z (M + H)$^+$ 394.25 | +++ | D-1 |
| 1019 | 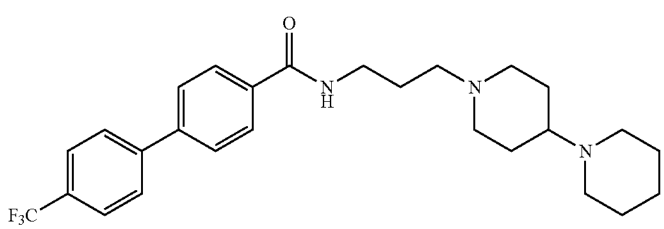 | White solid; $^1$H NMR (400 MHz, CDCl$_3$); δ 8.49 (s, 2H), 8.48 (s, 1H), 7.58 (t, J = 7.6 Hz, 1H), 7.36 (d, J = 8.0 Hz, 2H), 7.25 (d, J = 8.0 Hz, 2H), 7.14 (d, J = 8.4 Hz, 1H), 7.10 (d, J = 4.8 Hz, 1H), 6.84 (s, 1H), 4.47 (dd, J = 3.8 and 13.4 Hz, 1H), 4.31 (td, J = 4.3 and 12.9 Hz, 1H), 3.48 (q, J = 6.0 Hz, 2H), 3.50 (dd, J = 9.2 and 13.6 Hz, 1H), 3.31 (ddd, J = 3.1 and 10.1 and 13.0 Hz, 1H), 2.98 (dt, J = 2.4 and 6.3 Hz, 2H), 2.39 (s, 3H), 2.38-2.35 (m, 1H), 2.00-1.91 (m, 2H), 1.75-1.70 (m, 1H), 1.60-1.52 (m, 1H); LCMS (electrospray) m/z (M + H)$^+$ 402.07 | +++ | D-1 |

TABLE 2-continued

Anti-HCV genotype 1/2 activity for Formula II Series

| No. | Structure | Characterization | EC$_{50}$ | Method |
|---|---|---|---|---|
| 1020 | 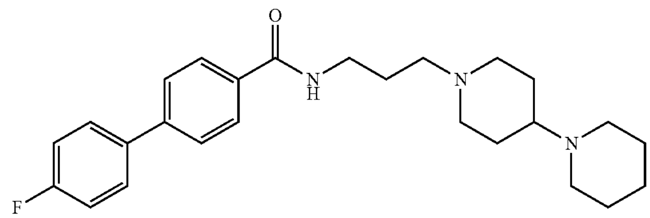 [SMILES: O=C(NCCCN1CCC(N2CCCCC2)CC1)c1ccc(-c2ccc(F)cc2)cc1] | Ivory solid; $^1$H NMR (400 MHz, CDCl$_3$); δ 8.47 (s, 2H), 7.36 (d, J = 8.0 Hz, 2H), 7.28-7.25 (m, 4H), 7.19 (d, J = 7.2 Hz, 1H), 7.15 (d, J = 8.0 Hz, 2H), 6.15 (s, 1H), 4.29 (dd, J = 3.4 and 13.8 Hz, 1H), 4.12 (td, J = 4.8 and 12.8 Hz, 1H), 3.69 (dd, J = 9.0 and 13.6 Hz, 1H), 3.53 (q, J = 6.0 Hz, 2H), 3.48 (ddd, J = 3.1 and 10.1 and 13.0 Hz, 1H), 2.79 (dt, J = 2.1 and 6.9 Hz, 2H), 2.39 (s, 3H), 2.37-2.33 (m, 1H), 2.09-2.02 (m, 1H), 1.90-1.83 (m, 1H), 1.72-1.65 (m, 1H), 1.57-1.53 (m, 1H); LCMS (electrospray) m/z (M + H)$^+$ 401.12 | +++ | D-1 |
| 1021 | 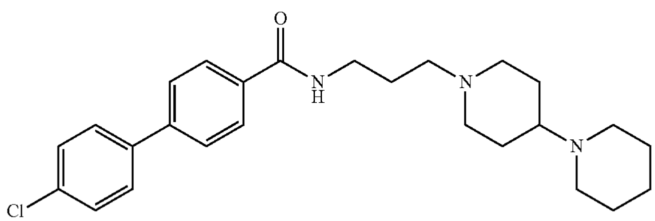 [SMILES: O=C(NCCCN1CCC(N2CCCCC2)CC1)c1ccc(-c2ccc(Cl)cc2)cc1] | Ivory solid; $^1$H NMR (400 MHz, CDCl$_3$); δ 8.48 (s, 2H), 7.33 (d, J = 8.0 Hz, 2H), 7.24 (d, J = 8.0 Hz, 2H), 7.14 (t, J = 8.0 Hz, 2H), 6.69 (t, J = 7.2 Hz, 1H), 6.58 (d, J = 7.6 Hz, 2H), 6.54 (s, 1H), 4.26 (dd, J = 3.6 and 13.6 Hz, 1H), 4.07 (td, J = 5.0 and 13.6 Hz, 1H), 3.92 (s, 1H), 3.81 (dd, J = 7.6 and 13.6 Hz, 1H), 3.60 (ddd, J = 3.8 and 9.0 and 13.0 Hz, 1H), 3.53-3.48 (m, 2H), 3.25 (t, J = 5.8 Hz, 2H), 2.46-2.41 (m, 1H), 2.39 (s, 3H), 2.14-2.09 (m, 1H), 1.93-1.88 (m, 1H), 1.73-1.68 (m, 1H), 1.62-1.56 (m, 1H); LCMS (electrospray) m/z (M + H)$^+$ 416.29 | +++ | D-1 |
| 1022 | 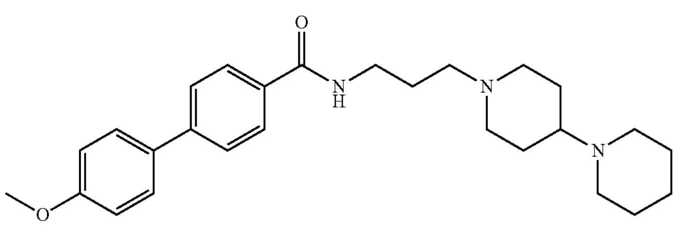 | White solid; $^1$H NMR (400 MHz, CDCl$_3$); δ 8.47 (s, 1H), 7.86 (d, J = 8.4 Hz, 2H), 7.58 (d, J = 8.4 Hz, 2H), 7.53 (d, J = 8.8 Hz, 2H), 6.97 (d, J = 8.8 Hz, 2H), 3.85 (s, 3H), 3.57 (dd, J = 5.4 and 10.6 Hz, 2H), 3.08 (d, J = 11.6 Hz, 2H), 2.54-2.48 (m, 6H), 2.39 (s, 3H), 2.19 (s, 6H), 2.04-1.95 (m, 2H), 1.80-1.74 (m, 2H), 1.61-1.54 (m, 1H); LCMS (electrospray) m/z (M + H)$^+$ 368.12 | ++++ | D-1 |
| 1023 | 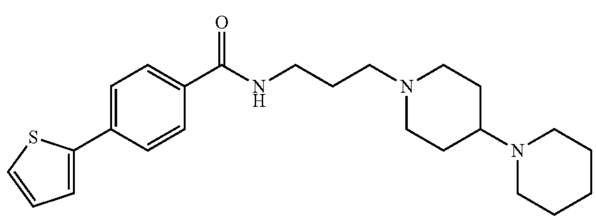 [SMILES: O=C(NCCCN1CCC(N2CCCCC2)CC1)c1ccc(-c2cccs2)cc1] | Ivory solid; $^1$H NMR (400 MHz, CDCl$_3$); δ 8.43 (s, 1H), 7.85 (d, J = 7.2 Hz, 2H), 7.63 (d, J = 7.2 Hz, 2H), 7.50 (dd, J = 1.2 and 2.4 Hz, 1H), 7.37-7.42 (m, 2H), 3.58 (dd, J = 5.2 and 10.8 Hz, 2H), 3.08 (d, J = 11.6 Hz, 2H), 2.50-2.56 (m, 6H), 2.37 (t, J = 11.6 Hz, 1H), 1.94 (t, J = 12.0 Hz, 2H), 1.75-1.81 (m, 4H), 1.59 (s, 6H), 1.43 (d, J = 5.2 Hz, 2H); LCMS | +++ | D-1 |

TABLE 2-continued

Anti-HCV genotype 1/2 activity for Formula II Series

| No. | Structure | Characterization | EC$_{50}$ | Method |
|---|---|---|---|---|
| | | (electrospray) m/z (M + H)$^+$ 412.14 | | |
| 1024 | 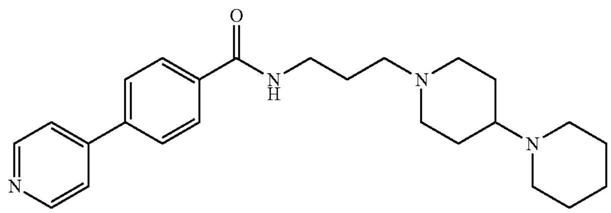 [SMILES: O=C(NCCCN1CCC(N2CCCCC2)CC1)c1ccc(-c2ccncc2)cc1] | Yellow oil; $^1$H NMR (400 MHz, CDCl$_3$); δ 8.69 (s, 2H), 8.60 (s, 1H), 7.93 (d, J = 8.0 Hz, 2H), 7.67 (d, J = 8.0 Hz, 2H), 7.50 (d, J = 3.6 Hz, 2H), 3.58 (dd, J = 5.6 and 11.2 Hz, 2H), 3.08 (d, J = 11.6 Hz, 2H), 2.54 (t, J = 5.6 Hz, 2H), 2.58 (t, J = 5.2 Hz, 4H), 2.29-2.35 (m, 1H), 1.96 (t, J = 12.0 Hz, 2H), 1.77-1.79 (m, 4H), 1.44-1.57 (m, 7H), 1.41 (d, J = 4.8 Hz, 2H); LCMS (electrospray) m/z (M + H)$^+$ 407.17 | + | D-1 |
| 1025 | 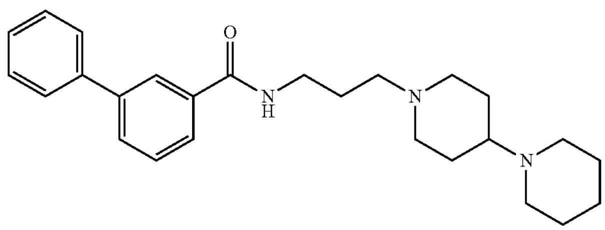 [SMILES: O=C(NCCCN1CCC(N2CCCCC2)CC1)c1cccc(-c2ccccc2)c1] | Yellow oil; $^1$H NMR (400 MHz, CDCl$_3$); δ 8.33 (s, 1H), 8.05 (t, J = 1.6 Hz, 1H), 7.71 (t, J = 9.2 Hz, 2H), 7.62 (d, J = 6.8 Hz, 2H), 7.42-7.46 (m, 3H), 7.35 (t, J = 7.2 Hz, 1H), 3.57 (dd, J = 5.6 and 11.2 Hz, 2H), 3.05 (d, J = 11.6 Hz, 2H), 2.51 (t, J = 5.6 Hz, 2H), 2.35 (d, J = 4.4 Hz, 4H), 2.30-2.31 (m, 1H), 1.87 (t, J = 12.0 Hz, 2H), 1.77 (dt, J = 6.0 Hz, 12.0 Hz, 2H), 1.71 (d, J = 12.8 Hz, 2H), 1.62 (dt, J = 6.4 and 12.8 Hz, 2H), 1.52 (dt, J = 6.4 and 11.6 Hz, 6H); LCMS (electrospray) m/z (M + H)$^+$ 406.29 | ++ | D-1 |
| 1026 | 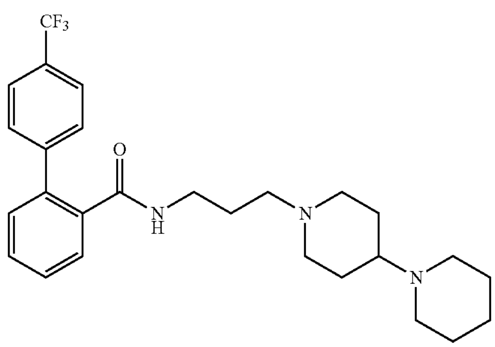 [SMILES: O=C(NCCCN1CCC(N2CCCCC2)CC1)c1ccccc1-c1ccc(C(F)(F)F)cc1] | White solid; $^1$H NMR (400 MHz, CDCl$_3$); δ 7.59-7.62 (m, 1H), 7.33-7.47 (m, 8H), 6.74 (s, 1H), 3.23 (q, J = 6.0 Hz, 2H), 2.75 (d, J = 12.0 Hz, 2H), 2.39 (t, J = 4.8 Hz, 4H), 2.20-2.26 (m, 1H), 2.13 (t, J = 6.4 Hz, 2H), 1.75 (t, J = 11.8 Hz, 2H), 1.67 (d, J = 12.4 Hz, 2H), 1.58 (t, J = 5.2 Hz, 4H), 1.38-1.44 (m, 4H), 1.22-1.32 (m, 4H); LCMS (electrospray) m/z (M + H)$^+$ 406.22 | ++ | D-1 |
| 1027 | 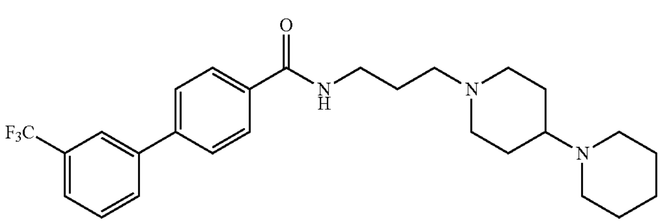 [SMILES: O=C(NCCCN1CCC(N2CCCCC2)CC1)c1ccc(-c2cccc(C(F)(F)F)c2)cc1] | Yellow solid; $^1$H NMR (400 MHz, CDCl$_3$); δ 8.59 (s, 1H), 7.92 (d, J = 8.4 Hz, 2H), 7.82 (s, 1H), 7.77 (d, J = 7.6 Hz, 1H), 7.64 (d, J = 8.4 Hz, 2H), 7.62 (s, 1H), 7.57 (t, J = 7.6 Hz, 2H), 3.59 (q, J = 5.5 Hz, 2H), 3.09 (d, J = 12.0 Hz, 2H), 2.55 (t, J = 5.6 Hz, 2H), 2.50 (t, J = 5.0 Hz, 4H), 2.32-2.38 (m, 1H), 1.94 (t, J = 11.4 Hz, 2H), 1.75-1.81 (m, 4H), 1.53-1.61 (m, 6H), 1.43 (q, J = 5.6 Hz, 2H); LCMS (electrospray) m/z (M + H)$^+$ 474.32 | +++ | D-1 |

TABLE 2-continued

Anti-HCV genotype 1/2 activity for Formula II Series

| No. | Structure | Characterization | EC$_{50}$ | Method |
|---|---|---|---|---|
| 1028 | 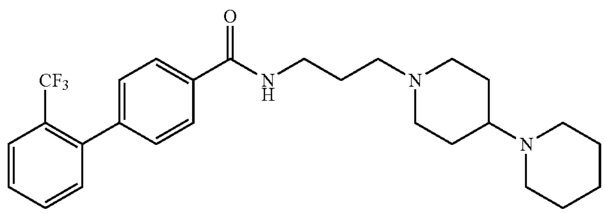 [SMILES: O=C(NCCCN1CCC(N2CCCCC2)CC1)c1ccc(-c2ccccc2C(F)(F)F)cc1] | Yellow solid; $^1$H NMR (400 MHz, CDCl$_3$); δ 8.42 (s, 1H), 7.85 (d, J = 8.0 Hz, 2H), 7.75 (d, J = 7.6 Hz, 1H), 7.57 (d, J = 7.4 Hz, 1H), 7.48 (t, J = 7.6 Hz, 1H), 7.36 (d, J = 8.0 Hz, 2H), 7.30 (d, J = 7.6 Hz, 1H), 3.58 (q, J = 5.3 Hz, 2H), 3.09 (d, J = 11.2 Hz, 2H), 2.54 (t, J = 5.8 Hz, 2H), 2.49 (t, J = 4.8 Hz, 4H), 2.33-2.39 (m, 1H), 1.93 (t, J = 11.6 Hz, 2H), 1.75-1.81 (m, 4H), 1.52-1.62 (m, 6H), 1.41 (q, J = 5.6 Hz, 2H); LCMS (electrospray) m/z (M + H)$^+$ 474.32 | +++ | D-1 |
| 1029 | 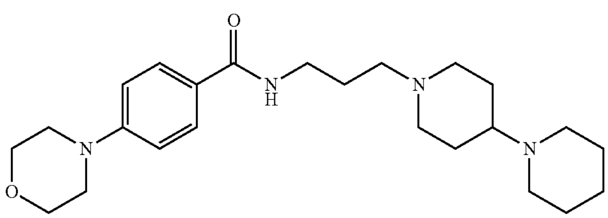 [SMILES: O=C(NCCCN1CCC(N2CCCCC2)CC1)c1ccc(N2CCOCC2)cc1] | White solid; $^1$H NMR (400 MHz, CDCl$_3$); δ 8.01 (s, 1H), 7.60 (d, J = 8.0 Hz, 2H), 6.94 (d, J = 8.2 Hz, 2H), 3.65 (t, J = 5.5 Hz, 4H), 3.42 (d, J = 12.0 Hz, 2H), 3.18 (t, J = 5.6 Hz, 4H), 2.53 (t, J = 5.2 Hz, 4H), 2.29-2.36 (m, 1H), 2.13-2.02 (m, 4H), 1.91 (t, J = 11.8 Hz, 2H), 1.72-1.78 (m, 6H), 1.49-1.55 (m, 6H), 1.34 (d, J = 5.2 Hz, 2H); LCMS (electrospray) m/z (M + H)$^+$ 424.24 | + | D-2 |
| 1030 | 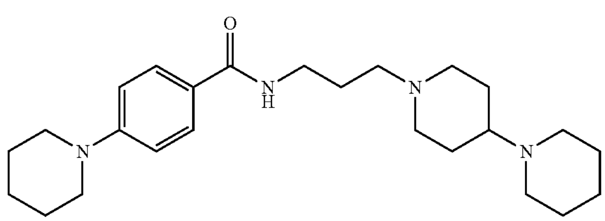 [SMILES: O=C(NCCCN1CCC(N2CCCCC2)CC1)c1ccc(N2CCCCC2)cc1] | White solid; $^1$H NMR (400 MHz, CDCl$_3$); δ 8.03 (s, 1H), 7.55 (d, J = 8.0 Hz, 2H), 6.93 (d, J = 8.2 Hz, 2H), 3.65 (t, J = 5.5 Hz, 4H), 3.42 (d, J = 12.0 Hz, 2H), 3.18 (t, J = 5.6 Hz, 4H), 2.53-2.44 (m, 6H), 2.29-2.36 (m, 1H), 2.13-2.02 (m, 4H), 1.91 (t, J = 11.8 Hz, 2H), 1.72-1.78 (m, 6H), 1.49-1.55 (m, 6H), 1.34 (d, J = 5.2 Hz, 2H); LCMS (electrospray) m/z (M + H)$^+$ 431.10 | ++ | D-2 |
| 1031 | 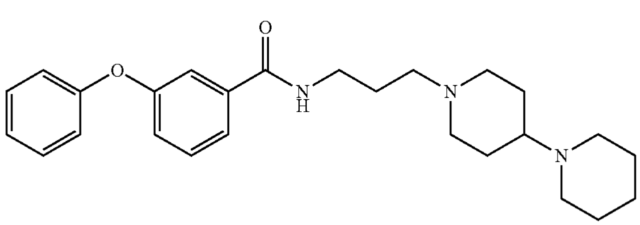 [SMILES: O=C(NCCCN1CCC(N2CCCCC2)CC1)c1cccc(Oc2ccccc2)c1] | Yellow oil; $^1$H NMR (400 MHz, CDCl$_3$); δ 8.38 (s, 1H), 7.49 (d, J = 8.4 Hz, 2H), 7.29-7.34 (m, 3H), 7.10 (t, J = 7.4 Hz, 1H), 7.05 (d, J = 8.4 Hz, 1H), 6.99 (d, J = 8.4 Hz, 2H), 3.52 (q, J = 5.5 Hz, 2H), 3.04 (d, J = 11.6 Hz, 2H), 2.47 (q, J = 5.1 Hz, 6H), 2.27-2.32 (m, 1H), 1.89 (t, J = 11.4 Hz, 2H), 1.73-1.80 (m, 4H), 1.52-1.58 (m, 6H), 1.40 (q, J = 5.6 Hz, 2H); LCMS (electrospray) m/z (M + H)$^+$ 422.35 | ++ | D-3 |

TABLE 2-continued

Anti-HCV genotype 1/2 activity for Formula II Series

| No. | Structure | Characterization | EC$_{50}$ | Method |
|---|---|---|---|---|
| 1032 | 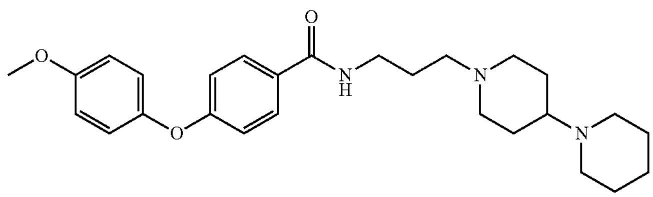 | Yellow solid; $^1$H NMR (400 MHz, CDCl$_3$); δ 8.24 (s, 1H), 7.77 (d, J = 8.4 Hz, 2H), 6.99 (d, J = 9.2 Hz, 2H), 6.90 (d, J = 8.8 Hz, 4H), 3.81 (s, 3H), 3.54 (q, J = 5.5 Hz, 2H), 3.08 (d, J = 12.0 Hz, 2H), 2.51 (s, 6H), 2.38-2.44 (m, 1H), 1.95 (t, J = 11.8 Hz, 2H), 1.74-1.84 (m, 4H), 1.54-1.63 (m, 6H), 1.43 (q, J = 5.6 Hz, 2H); LCMS (electrospray) m/z (M + H)$^+$ 452.35 | +++ | D-3 |
| 1033 | 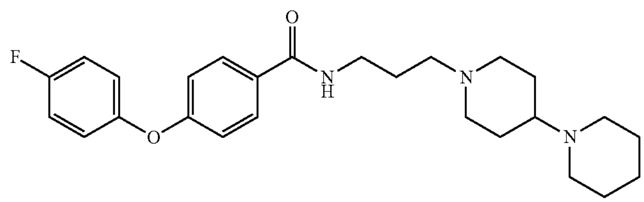 [SMILES: O=C(NCCCN1CCC(N2CCCCC2)CC1)c1ccc(Oc2ccc(F)cc2)cc1] | Yellow solid; $^1$H NMR (400 MHz, CDCl$_3$); δ 8.24 (s, 1H), 7.80 (d, J = 8.8 Hz, 2H), 7.05 (d, J = 8.0 Hz, 2H), 7.02 (d, J = 2.8 Hz, 2H), 6.93 (d, J = 11.6 Hz, 2H), 3.55 (q, J = 5.5 Hz, 2H), 3.09 (d, J = 12.0 Hz, 2H), 2.52 (s, 6H), 2.38-2.48 (m, 1H), 1.97 (t, J = 11.4 Hz, 2H), 1.74-1.86 (m, 4H), 1.55-1.65 (m, 6H), 1.44 (q, J = 5.6 Hz, 2H); LCMS (electrospray) m/z (M + H)$^+$ 440.24 | ++ | D-3 |
| 1034 | 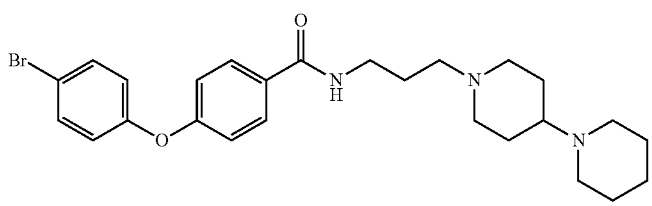 | White solid; $^1$H NMR (400 MHz, CDCl$_3$); δ 8.28 (s, 1H), 7.81 (d, J = 8.4 Hz, 2H), 7.47 (d, J = 8.8 Hz, 2H), 6.96 (d, J = 8.8 Hz, 2H), 6.92 (d, J = 8.7 Hz, 2H), 3.55 (q, J = 5.5 Hz, 2H), 3.09 (d, J = 10.4 Hz, 2H), 2.53 (s, 6H), 2.36-2.46 (m, 1H), 1.97 (t, J = 10.8 Hz, 2H), 1.74-1.86 (m, 4H), 1.55-1.65 (m, 6H), 1.44 (q, J = 5.6 Hz, 2H); LCMS (electrospray) m/z (M + H)$^+$ 500.18 | ++ | D-3 |
| 1035 | 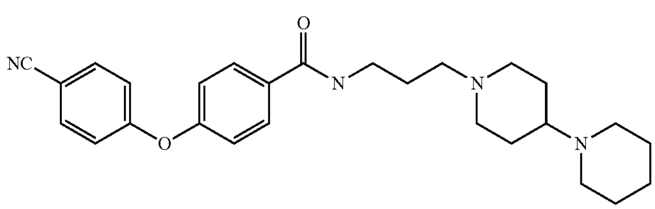 [SMILES: N#Cc1ccc(Oc2ccc(C(=O)NCCCN3CCC(N4CCCCC4)CC3)cc2)cc1] | White solid; $^1$H NMR (400 MHz, CDCl$_3$); δ 8.33 (s, 1H), 7.81 (d, J = 8.4 Hz, 2H), 7.44 (d, J = 8.6 Hz, 2H), 7.01 (d, J = 8.6 Hz, 2H), 6.90 (d, J = 8.7 Hz, 2H), 3.56 (q, J = 5.6 Hz, 2H), 3.07 (d, J = 12.0 Hz, 2H), 2.52 (q, J = 5.1 Hz, 6H), 2.33-2.41 (m, 1H), 1.93 (t, J = 11.2 Hz, 2H), 1.74-1.81 (m, 4H), 1.52-1.65 (m, 6H), 1.45 (q, J = 5.5 Hz, 2H); LCMS (electrospray) m/z (M + H)$^+$ 447.07 | + | D-3 |
| 1036 | 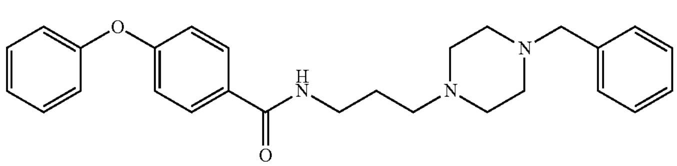 [SMILES: O=C(NCCCN1CCN(Cc2ccccc2)CC1)c1ccc(Oc2ccccc2)cc1] | Oil; $^1$H NMR (400 MHz, CDCl$_3$) δ 8.04 (NH, 1H), 7.79 (d, J = 6.4 Hz, 2H), 7.36 (d, J = 6.4 Hz, 2H), 7.29-7.24 (m, 5H), 7.15 (t, J = 7.6 Hz, 1H), 7.03 (d, J = 7.6 Hz, 1H), 6.93 (d, J = 7.6 Hz, 1H), 3.51-3.48 (m, 4H), 2.82 (d, J = 12.4 Hz, 6H), 2.64-2.61 (m, 4H), 1.92 (t, J = 6.0 Hz, 2H); | ++ | D-3 |

TABLE 2-continued

Anti-HCV genotype 1/2 activity for Formula II Series

| No. | Structure | Characterization | EC$_{50}$ | Method |
|---|---|---|---|---|
| | | LRMS (electrospray) m/z (M + H)$^+$ 430.24. | | |
| 1037 | 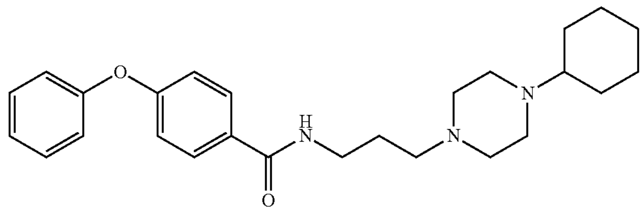 [SMILES: O=C(NCCCN1CCN(C2CCCCC2)CC1)c1ccc(Oc2ccccc2)cc1] | Oil; $^1$H NMR (400 MHz, CDCl$_3$); δ 7.94 (NH, 1H), 7.89 (d, J = 6.4 Hz, 2H), 7.35 (t, J = 7.6 Hz, 2H), 7.14 (t, J = 3.6 Hz, 1H), 7.00 (d, J = 8.4 Hz, 2H), 6.94 (d, J = 8.4 Hz, 2H), 3.51 (q, J = 5.6 Hz, 2H), 2.74-2.69 (m, 7H), 2.59 (t, J = 6.0 Hz, 2H), 2.42-2.40 (m, 1H), 1.85-1.80 (m, 2H), 1.78-1.74 (m, 4H), 2.62 (d, J = 12.4 Hz, 1H), 1.22-1.18 (m, 5H), 1.18-1.16 (m, 1H); LRMS (electrospray) m/z (M + H)$^+$ 422.28. | + | D-3 |
| 1038 | 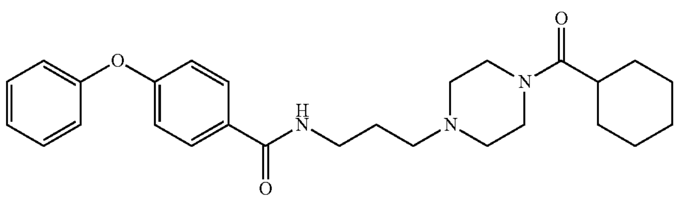 [SMILES: O=C(NCCCN1CCN(C(=O)C2CCCCC2)CC1)c1ccc(Oc2ccccc2)cc1] | Oil; $^1$H NMR (400 MHz, DMSO-d$_6$) δ 8.61 (NH, 1H), 7.89 (d, J = 6.4 Hz, 2H), 7.44 (t, J = 7.6 Hz, 2H), 7.21 (t, J = 3.6 Hz, 1H), 7.08-7.03 (m, 4H), 4.45-4.43 (m, 1H), 4.11-4.09 (m, 1H), 3.45-3.39 (m, 3H), 3.14-3.11 (m, 2H), 2.98-2.87 (m, 5H), 2.57 (d, J = 12.4 Hz, 1H), 1.96-1.93 (m, 2H), 1.70-1.62 (m, 5H), 1.31-1.29 (m, 4H), 1.18-1.16 (m, 1H); LRMS (electrospray) m/z (M + H)$^+$ 450.31. | + | D-3 |
| 1039 | 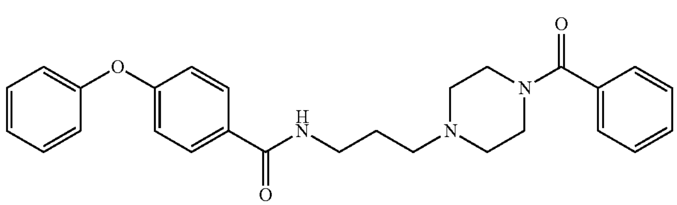 [SMILES: O=C(NCCCN1CCN(C(=O)c2ccccc2)CC1)c1ccc(Oc2ccccc2)cc1] | Oil; $^1$H NMR (400 MHz, CDCl$_3$) δ 7.72 (d, J = 6.4 Hz, 2H), 7.38-7.33 (m, 7H), 7.15 (t, J = 3.6 Hz, 1H), 7.03 (d, J = 8.4 Hz, 2H), 6.97 (d, J = 8.4 Hz, 2H), 3.75-3.37 (m, 2H), 3.52 (q, J = 5.6 Hz, 2H), 3.45-3.38 (m, 4H), 2.59 (t, J = 6.0 Hz, 2H), 2.47-2.43 (m, 2H), 1.79 (p, J$_{12}$ = 12.2 Hz, J$_{13}$ = 22.2 Hz, 2H); LRMS (electrospray) m/z (M + H)$^+$ 444.25. | + | D-3 |
| 1040 | 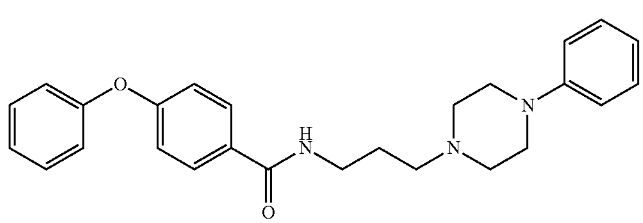 [SMILES: O=C(NCCCN1CCN(c2ccccc2)CC1)c1ccc(Oc2ccccc2)cc1] | Oil; $^1$H NMR (400 MHz, CDCl$_3$) δ 7.97 (NH, 1H), 7.77 (d, J = 6.4 Hz, 2H), 7.32 (t, J = 3.6 Hz, 2H), 7.25-7.21 (m, 3H), 7.11 (t, J = 3.6 Hz, 1H), 6.97 (d, J = 8.4 Hz, 2H), 6.87 (d, J = 7.6 Hz, 2H), 6.86 (d, J = 8.4 Hz, 2H), 3.57 (q, J = 5.6 Hz, 2H), 3.21-3.20 (m, 4H), 2.70-2.66 (m, 4H), 2.63 (t, J = 6.0 Hz, 2H), 1.85 (p, J$_{12}$ = 12.2 Hz, J$_{13}$ = 22.2 Hz, 2H); LRMS (electrospray) m/z (M + H)$^+$ 416.22. | ++ | D-3 |

TABLE 2-continued

Anti-HCV genotype 1/2 activity for Formula II Series

| No. | Structure | Characterization | $EC_{50}$ | Method |
|---|---|---|---|---|
| 1041 | 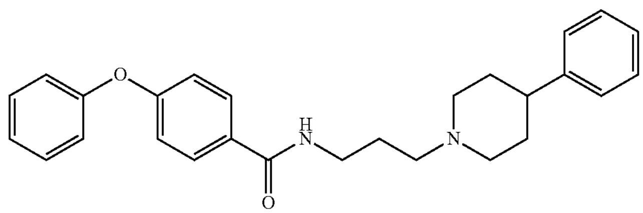 [SMILES: O=C(NCCCN1CCC(c2ccccc2)CC1)c1ccc(Oc2ccccc2)cc1] | Oil; $^1$H NMR (400 MHz, CDCl$_3$) δ 8.40 (NH, 1H), 7.84 (d, J = 6.4 Hz, 2H), 7.35 (t, J = 7.0 Hz, 2H), 7.20 (d, J = 8.4 Hz, 2H), 7.18-7.12 (m, 4H), 7.03 (d, J = 8.4 Hz, 2H), 6.98 (d, J = 6.4 Hz, 2H), 3.58 (q, J = 5.6 Hz, 2H), 3.20 (d, J = 12.4 Hz, 2H), 2.62 (t, J = 6.0 Hz, 2H), 2.51-2.45 (m, 2H), 2.14 (t, J = 10.0 Hz, 2H), 1.92-1.80 (m, 5H); LRMS (electrospray) m/z (M + H)$^+$ 415.27. | ++ | D-3 |
| 1042 | 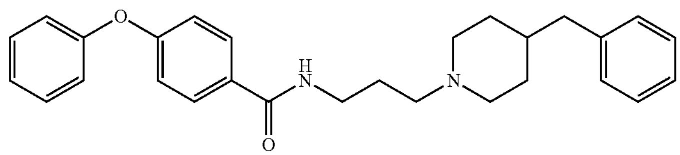 [SMILES: O=C(NCCCN1CCC(Cc2ccccc2)CC1)c1ccc(Oc2ccccc2)cc1] | Oil; $^1$H NMR (400 MHz, CDCl$_3$) δ 8.63 (NH, 1H), 8.01 (d, J = 6.4 Hz, 2H), 7.53 (t, J = 3.6 Hz, 2H), 7.42 (t, J = 6.6 Hz, 2H), 7.35-7.32 (m, 2H), 7.23 (t, J = 1.6 Hz, 4H), 7.17 (d, J = 6.4 Hz, 2H), 3.70 (q, J = 5.6 Hz, 2H), 3.29 (d, J = 11.6 Hz, 2H), 2.83 (t, J = 6.0 Hz, 2H), 2.67 (d, J = 7.2 Hz, 2H), 2.23 (t, J = 6.0 Hz, 2H), 2.01 (p, J$_{12}$ = 12.2 Hz, J$_{13}$ = 22.2 Hz, 2H), 1.85 (d, J = 7.2 Hz, 2H), 1.79-1.73 (m, 1H), 1.53-1.50 (m, 2H); LRMS (electrospray) m/z (M + H)$^+$ 429.28. | ++ | D-3 |
| 1043 | 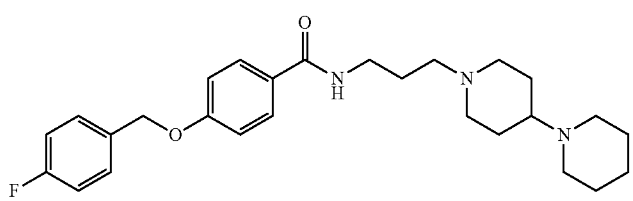 [SMILES: O=C(NCCCN1CCC(N2CCCCC2)CC1)c1ccc(OCc2ccc(F)cc2)cc1] | Yellow solid; $^1$H NMR (400 MHz, CDCl$_3$); δ 8.11 (s, 1H), 7.53 (d, J = 8.4 Hz, 2H), 7.15 (d, J = 8.4 Hz, 2H), 7.10 (d, J = 2.4 Hz, 4H), 5.10 (s, 2H), 3.55 (q, J = 5.5 Hz, 2H), 3.10 (d, J = 12.0 Hz, 2H), 2.52 (s, 6H), 2.36-2.46 (m, 1H), 1.97 (t, J = 11.4 Hz, 2H), 1.70-1.82 (m, 4H), 1.55-1.65 (m, 6H), 1.42 (q, J = 5.6 Hz, 2H); LCMS (electrospray) m/z (M + H)$^+$ 454.14 | ++ | D-3 |
| 1044 | 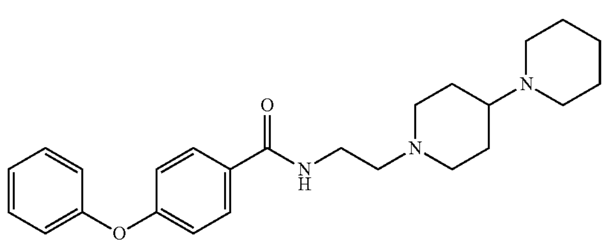 [SMILES: O=C(NCCN1CCC(N2CCCCC2)CC1)c1ccc(Oc2ccccc2)cc1] | White solid; $^1$H NMR (400 MHz, CDCl$_3$); δ 7.78 (d, J = 7.2 Hz, 2H), 7.37 (t, J = 8.0 Hz, 2H), 7.17 (t, J = 7.2 Hz, 1H), 7.05 (d, J = 8.4 Hz, 2H), 7.01 (d, J = 11.2 Hz, 2H), 6.86 (s, 1H), 3.55 (q, J = 5.6 Hz, 2H), 3.07 (d, J = 8.4 Hz, 2H), 2.75 (q, J = 5.1 Hz, 6H), 2.43-2.51 (m, 1H), 2.05 (t, J = 11.2 Hz, 2H), 1.84-1.91 (m, 4H), 1.62-1.75 (m, 4H), 1.53 (q, J = 5.5 Hz, 2H); LCMS (electrospray) m/z (M + H)$^+$ 407.99 | ++ | D-3 |

TABLE 2-continued

Anti-HCV genotype 1/2 activity for Formula II Series

| No. | Structure | Characterization | EC$_{50}$ | Method |
|---|---|---|---|---|
| 1045 | 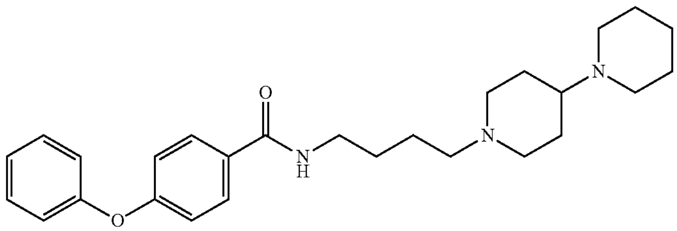 [SMILES: O=C(NCCCCN1CCC(N2CCCCC2)CC1)c1ccc(Oc2ccccc2)cc1] | White solid; $^1$H NMR (400 MHz, CDCl$_3$); δ 7.77 (d, J = 8.4 Hz, 2H), 7.37 (t, J = 8.0 Hz, 2H), 7.16 (t, J = 7.4 Hz, 1H), 7.04 (d, J = 8.8 Hz, 2H), 6.99 (d, J = 8.8 Hz, 2H), 6.77 (s, 1H), 3.46 (q, J = 5.6 Hz, 2H), 3.05 (d, J = 12.0 Hz, 2H), 2.64 (q, J = 5.1 Hz, 4H), 2.43-2.51 (m, 1H), 2.44 (s, 2H), 2.04 (t, J = 11.2 Hz, 2H), 1.94 (d, J = 12.0 Hz, 2H), 1.64-1.75 (m, 10H), 1.49 (q, J = 5.5 Hz, 2H); LCMS (electrospray) m/z (M + H)$^+$ 436.02 | +++ | D-3 |
| 1046 | 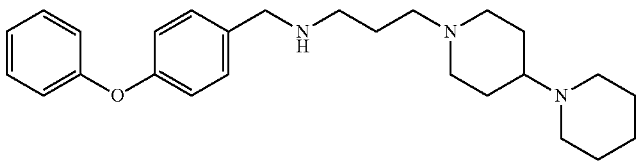 [SMILES: c1ccc(Oc2ccc(CNCCCN3CCC(N4CCCCC4)CC3)cc2)cc1] | Yellow solid; $^1$H NMR (400 MHz, CDCl$_3$); δ 7.29-7.38 (m, 4H), 7.10 (t, J = 7.4 Hz, 1H), 6.94-7.02 (m, 5H), 3.81 (s, 2H), 3.46 (q, J = 5.6 Hz, 2H), 3.05 (d, J = 12.0 Hz, 2H), 2.64 (q, J = 5.1 Hz, 4H), 2.43-2.51 (m, 1H), 2.44 (s, 2H), 2.04 (t, J = 11.2 Hz, 2H), 1.94 (d, J = 12.0 Hz, 2H), 1.64-1.75 (m, 10H), 1.49 (q, J = 5.5 Hz, 2H); LCMS (electrospray) m/z (M + H)$^+$ 408.06 | +++ | D-3 |
| 1047 | 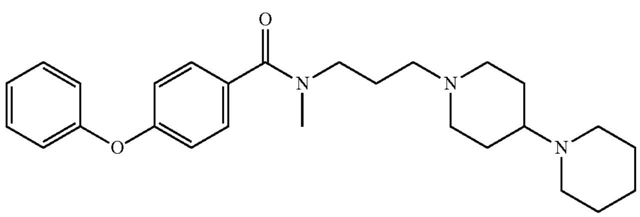 [SMILES: CN(CCCN1CCC(N2CCCCC2)CC1)C(=O)c1ccc(Oc2ccccc2)cc1] | Pale yellow solid; $^1$H NMR (400 MHz, CDCl$_3$); δ 7.81 (d, J = 8.8 Hz, 2H), 7.37 (t, J = 8.0 Hz, 2H), 7.16 (t, J = 7.4 Hz, 1H), 7.04 (d, J = 8.4 Hz, 2H), 6.98 (d, J = 8.4 Hz, 2H), 3.55 (q, J = 5.6 Hz, 2H), 3.13 (d, J = 11.2 Hz, 2H), 2.58 (q, J = 5.1 Hz, 6H), 2.33-2.41 (m, 1H), 1.90 (t, J = 11.2 Hz, 2H), 1.74-1.81 (m, 4H), 1.52-1.65 (m, 6H), 1.48 (q, J = 5.5 Hz, 2H), 1.42 (s, 3H); LCMS (electrospray) m/z (M + H)$^+$ 436.09 | ++ | D-3 |
| 1048 | 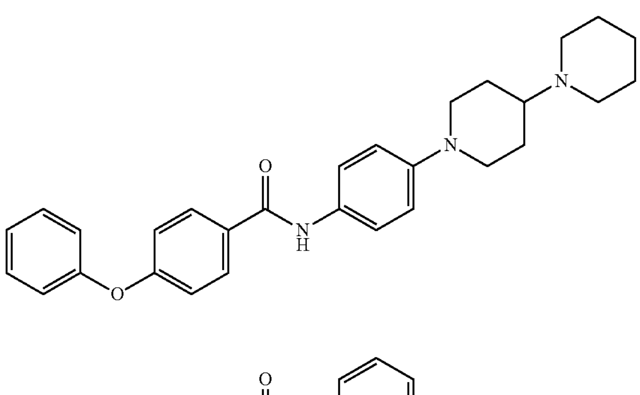 | White solid; $^1$H NMR (400 MHz, DMSO); δ 9.96 (s, 1H), 7.87 (d, J = 8.4 Hz, 2H), 7.57 (d, J = 8.8 Hz, 2H), 7.45 (t, J = 8.0 Hz, 2H), 7.22 (t, J = 8.0 Hz, 1H), 7.09 (dd, J = 8.6 and 11.0 Hz, 4H), 6.91 (d, J = 8.8 Hz, 2H), 3.68 (d, J = 12.8 Hz, 2H), 3.35 (q, J = 5.6 Hz, 2H), 1.79 (q, J = 11.2 Hz, 2H), 1.48-1.58 (m, 7H), 1.39 (q, J = 5.5 Hz, 3H); LCMS (electrospray) m/z (M + H)$^+$ 456.09 | ++ | D-3 |
| 1049 | 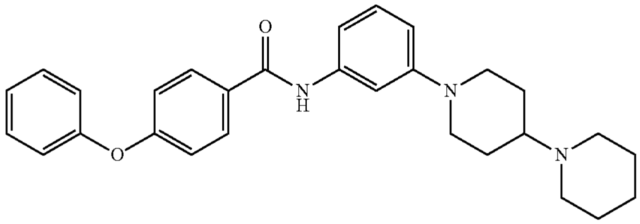 [SMILES: O=C(Nc1cccc(N2CCC(N3CCCCC3)CC2)c1)c1ccc(Oc2ccccc2)cc1] | White solid; $^1$H NMR (400 MHz, acetone); δ 9.31 (s, 1H), 8.02 (d, J = 8.8 Hz, 2H), 7.51 (t, J = 2.1 Hz, 1H), 7.42-7.48 (m, 2H), 7.29 (dd, J = 0.8 and 8.0 Hz, 1H), 7.22 (t, J = 7.4 Hz, 1H), 7.16 (d, J = 8.0 Hz, 1H), 7.08-7.12 (m, 2H), 7.06 (d, J = 8.8 Hz, 2H), 6.71 (dd, J = 2.2 and 7.8 Hz, | +++ | D-3 |

TABLE 2-continued

Anti-HCV genotype 1/2 activity for Formula II Series

| No. | Structure | Characterization | EC$_{50}$ | Method |
|-----|-----------|------------------|-----------|--------|
| | | 1H), 3.74 (d, J = 12.8 Hz, 2H), 2.71 (dt, J = 2.3 and 12.3 Hz, 2H), 2.55 (s, 4H), 2.41 (s, 1H), 1.87 (d, J = 12.8 Hz, 2H), 1.55-1.66 (m, 6H), 1.43 (q, J = 5.5 Hz, 2H); LCMS (electrospray) m/z (M + H)$^+$ 456.09 | | |
| 1050 | 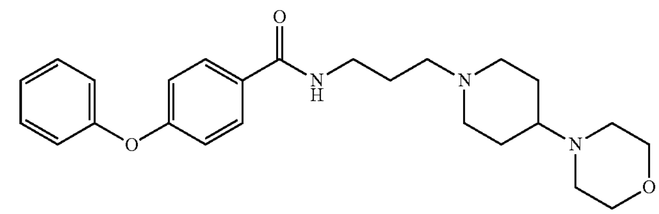 [SMILES: O=C(NCCCN1CCC(N2CCOCC2)CC1)c1ccc(Oc2ccccc2)cc1] | White solid; $^1$H NMR (400 MHz, CDCl$_3$) δ 8.25 (s, 1H), 7.81 (d, J = 8.5 Hz, 2H), 7.37 (t, J = 7.8 Hz, 2H), 7.17 (t, J = 7.4 Hz, 1H), 7.04 (d, J = 8.2 Hz, 2H), 6.98 (d, J = 8.6 Hz, 2H), 3.64 (t, J = 4.6 Hz, 4H), 3.56 (q, J = 5.6 Hz, 2H), 3.08 (d, J = 11.5 Hz, 2H), 2.56 (s, 2H), 2.49 (t, J = 4.6 Hz, 4H), 2.25 (t, J = 11.1 Hz, 1H), 1.99 (s, 3H), 1.90-1.72 (m, 4H), 1.62-1.45 (m, 2H); LRMS (electrospray) m/z (M + H)$^+$ 424.11. | ++ | D-3 |
| 1051 | 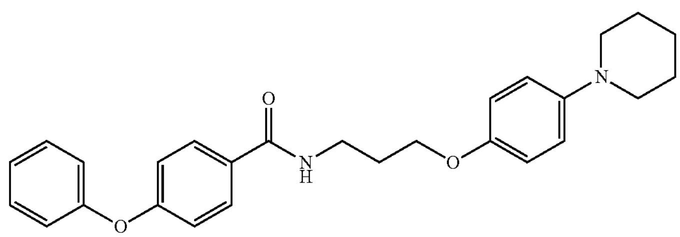 [SMILES: O=C(NCCCOc1ccc(N2CCCCC2)cc1)c1ccc(Oc2ccccc2)cc1] | White solid; $^1$H NMR (400 MHz, CDCl$_3$) δ 7.74 (d, J = 8.7 Hz, 2H), 7.37 (t, J = 7.8 Hz, 2H), 7.17 (t, J = 7.4 Hz, 1H), 7.04 (d, J = 8.2 Hz, 2H), 7.00 (d, J = 8.2 Hz, 2H), 6.92 (d, J = 8.9 Hz, 2H), 6.83 (d, J = 9.7 Hz, 2H), 6.68 (NH, 1H), 4.09 (t, J = 5.6 Hz, 2H), 3.67 (q, J = 5.6 Hz, 2H), 3.08-2.98 (m, 4H), 2.15-2.05 (m, 2H), 1.78-1.65 (m, 4H), 1.59-1.47 (m, 2H); LRMS (electrospray) m/z (M + H)$^+$ 431.12. | + | D-3 |
| 1052 | 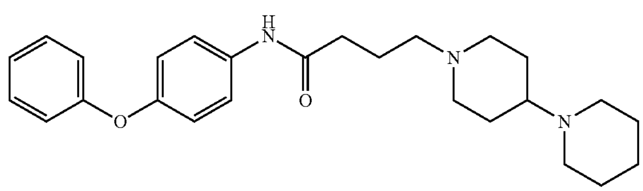 [SMILES: O=C(CCCN1CCC(N2CCCCC2)CC1)Nc1ccc(Oc2ccccc2)cc1] | Brown solid; $^1$H NMR (400 MHz, cdcl$_3$) δ 8.99 (s, 1H), 7.47 (d, J = 8.8 Hz, 2H), 7.31 (t, J = 7.9 Hz, 2H), 7.07 (t, J = 7.4 Hz, 1H), 7.01-6.92 (m, 4H), 3.01 (d, J = 11.7 Hz, 2H), 2.54-2.47 (m, 4H), 2.44 (t, J = 6.3 Hz, 4H), 2.35-2.24 (m, 1H), 1.97 (t, J = 11.4 Hz, 2H), 1.93-1.80 (m, 4H), 1.64-1.54 (m, 6H), 1.49-1.36 (m, 2H); LCMS (electrospray) m/z (M + H)$^+$ 422.14 | +++ | D-3 |
| 1053 | 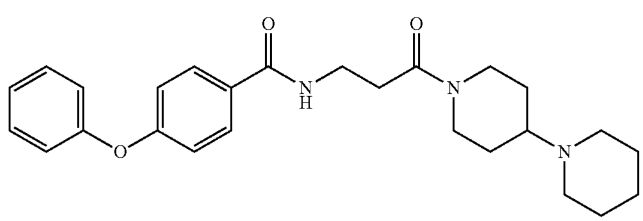 [SMILES: O=C(NCCC(=O)N1CCC(N2CCCCC2)CC1)c1ccc(Oc2ccccc2)cc1] | White solid; $^1$H NMR (400 MHz, cdcl$_3$) δ 7.68 (d, J = 8.7 Hz, 2H), 7.30 (t, J = 7.9 Hz, 2H), 7.09 (t, J = 7.4 Hz, 1H), 7.03 (t, J = 5.6 Hz, 1H), 6.96 (d, J = 7.9 Hz, 2H), 6.92 (d, J = 8.7 Hz, 2H), 4.63 (d, J = 13.5 Hz, 1H), 3.84 (d, J = 13.9 Hz, 1H), 3.67 (dd, J = 11.4, 5.8 Hz, 2H), 2.94 (t, J = 11.9 Hz, 1H), 2.78-2.58 (m, 4H), 2.55 (dd, J = 5.9, 3.3 Hz, 2H), 2.52-2.43 (m, 2H), 2.04-1.88 (m, 2H), 1.70 (s, 4H), 1.52-1.35 (m, | ++ | D-3 |

… TABLE 2-continued

Anti-HCV genotype 1/2 activity for Formula II Series

| No. | Structure | Characterization | EC$_{50}$ | Method |
|---|---|---|---|---|
| | | 4H); LCMS (electrospray) m/z (M + H)$^+$ 436.16 | | |
| 1054 | 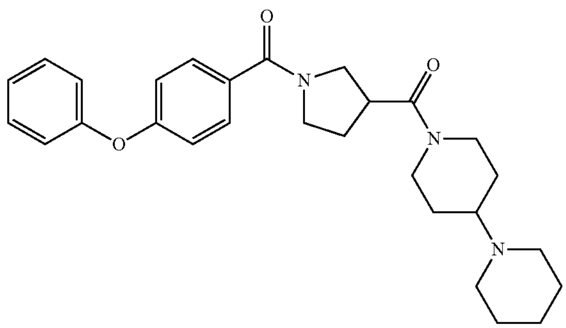 [SMILES: O=C(c1ccc(Oc2ccccc2)cc1)N1CCC(C(=O)N2CCC(N3CCCCC3)CC2)C1] | White solid; $^1$H NMR (400 MHz, cdcl$_3$) δ 7.49 (d, J = 7.4 Hz, 2H), 7.34 (t, J = 7.9 Hz, 2H), 7.13 (t, J = 7.4 Hz, 1H), 7.01 (d, J = 8.0 Hz, 2H), 6.96 (d, J = 8.4 Hz, 2H), 4.75 (s, 1H), 4.10-3.85 (m, 2H), 3.85-3.63 (m, 2H), 3.63-3.45 (m, 1H), 3.37-3.24 (m, 1H), 3.24-2.98 (m, 2H), 2.87 (s, 4H), 2.64-2.44 (m, 1H), 2.39-2.21 (m, 1H), 2.21-1.99 (m, 2H), 1.94 (s, 4H), 1.63 (s, 4H), 1.37 (t, J = 7.3 Hz, 1H); LCMS (electrospray) m/z (M + H)$^+$ 462.15 | + | D-3 |
| 1055 | 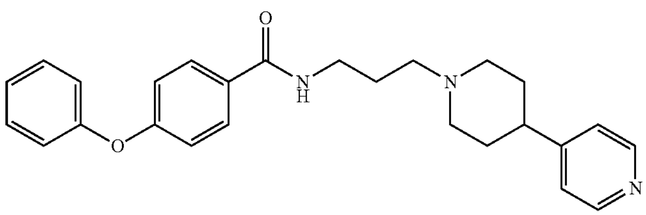 [SMILES: O=C(NCCCN1CCC(c2ccncc2)CC1)c1ccc(Oc2ccccc2)cc1] | White solid; $^1$H NMR (400 MHz, CDCl$_3$) δ 8.46 (s, 2H), 8.23 (NH, 1H), 7.82 (d, J = 9.1 Hz, 2H), 7.37 (t, J = 7.8 Hz, 2H), 7.19 (t, J = 7.4 Hz, 1H), 7.11-7.02 (m, J = 16.6, 11.5 Hz, 4H), 7.02 (d, J = 8.9 Hz, 2H), 3.59 (q, J = 5.6 Hz, 2H), 3.19 (d, J = 11.7 Hz, 2H), 2.64 (t, J = 6.0 Hz, 2H), 2.59-2.48 (m, 1H), 2.12 (t, J = 11.2 Hz, 2H), 1.88-1.83 (m, 4H), 1.79-1.75 (m, 2H); LRMS (electrospray) m/z (M + H)$^+$ 416.02. | + | D-3 |
| 1056 | 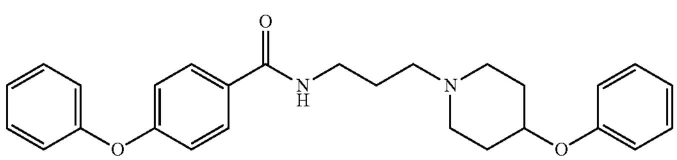 [SMILES: O=C(NCCCN1CCC(Oc2ccccc2)CC1)c1ccc(Oc2ccccc2)cc1] | White solid; $^1$H NMR (400 MHz, CDCl$_3$) δ 8.19 (NH, 1H), 7.82 (d, J = 8.5 Hz, 2H), 7.38 (t, J = 7.8 Hz, 2H), 7.28-7.25 (m, 2H), 7.17 (t, J = 7.4 Hz, 1H), 7.06-7.00 (m, 4H), 6.94 (t, J = 7.4 Hz, 1H), 6.87 (d, J = 7.3 Hz, 2H), 4.36 (s, 1H), 3.55 (q, J = 5.6 Hz, 2H), 2.83 (d, J = 11.7 Hz, 2H), 2.62 (t, J = 6.0 Hz, 2H), 2.45-2.42 (m, 2H), 2.02 (t, J = 11.2 Hz, 2H), 1.84-1.81 (m, 4H); LRMS (electrospray) m/z (M + H)$^+$ 431.19. | ++ | D-3 |
| 1057 | 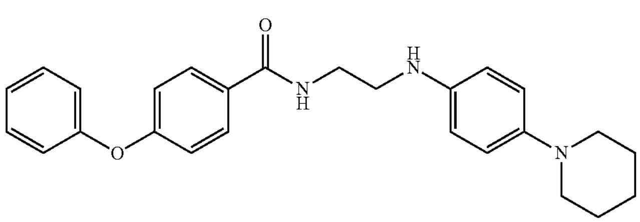 [SMILES: O=C(NCCNc1ccc(N2CCCCC2)cc1)c1ccc(Oc2ccccc2)cc1] | White solid; $^1$H NMR (400 MHz, CDCl$_3$) δ 12.80 (NH, 1H), 7.91 (d, J = 7.6 Hz, 1H), 7.74 (d, J = 8.4 Hz, 1H), 7.62 (NH, 1H), 7.48 (d, J = 7.6 Hz, 1H), 7.39-7.33 (m, 2H), 7.20-7.13 (m, 2H), 7.04 (d, J = 8.0 Hz, 1H), 6.99 (t, J = 7.4 Hz, 2H), 6.94 (d, J = 7.3 Hz, 2H), 6.62 (d, J = 7.6 Hz, 1H), 3.98 (s, 1H), 3.72-3.69 (m, 2H), 3.50-3.47 (m, 1H), 3.32-3.13 (m, 4H), 2.58-2.55 (m, 1H), 1.92-1.85 (m, 2H), 1.63-1.60 (m, 2H), 1.47-1.43 (m, 1H); LRMS (electrospray) m/z (M + H)$^+$ 416.15. | ++ | D-3 |

TABLE 2-continued

Anti-HCV genotype 1/2 activity for Formula II Series

| No. | Structure | Characterization | EC$_{50}$ | Method |
|---|---|---|---|---|
| 1058 | 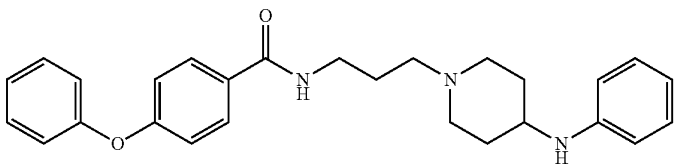 [SMILES: O=C(NCCCN1CCC(Nc2ccccc2)CC1)c1ccc(Oc2ccccc2)cc1] | White solid; $^1$H NMR (400 MHz, CDCl$_3$) δ 8.16 (NH, 1H), 7.82 (d, J = 8.5 Hz, 2H), 7.35 (t, J = 7.8 Hz, 2H), 7.17-7.13 (m, 3H), 7.05-7.02 (m, 4H), 6.71 (t, J = 7.4 Hz, 1H), 6.56 (d, J = 7.3 Hz, 2H), 3.58-3.56 (m, 2H), 3.48-3.46 (m, 1H), 3.02-3.28 (m, 2H), 2.65 (t, J = 11.2 Hz, 2H), 2.27 (s, 2H), 2.11 (d, J = 12.4 Hz, 2H), 1.85 (t, J = 6.0 Hz, 2H), 1.54-1.51 (m, 2H); LRMS (electrospray) m/z (M + H)$^+$ 430.99. | ++ | D-3 |
| 1059 | 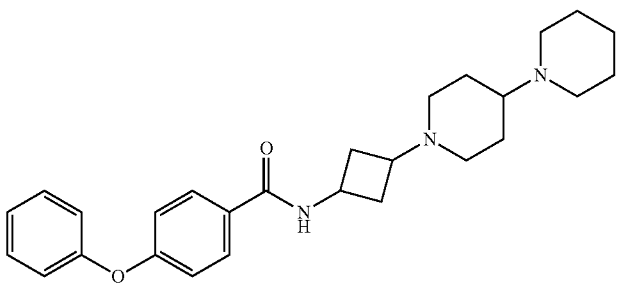 [SMILES: O=C(NC1CC(N2CCC(N3CCCCC3)CC2)C1)c1ccc(Oc2ccccc2)cc1] | White solid; $^1$H NMR (400 MHz, acetone); δ 7.92 (d, J = 8.8 Hz, 2H), 7.85 (d, J = 6.4 Hz, 1H), 7.40-7.45 (m, 2H), 7.20 (t, J = 7.4 Hz, 1H), 7.05-7.08 (m, 2H), 7.00 (d, J = 8.8 Hz, 2H), 4.44-4.46 (m, 1H), 2.95 (d, J = 12.0 Hz, 2H), 2.85 (t, J = 7.0 Hz, 1H), 2.48 (d, J = 5.2 Hz, 3H), 2.26-2.30 (m, 2H), 2.12-2.18 (m, 2H), 1.96-2.00 (m, 2H), 1.63-1.74 (m, 4H), 1.41-1.54 (m, 6H), 1.42 (q, J = 5.5 Hz, 2H); LCMS (electrospray) m/z (M + H)$^+$ 434.12 | ++ | D-3 |
| 1060 | 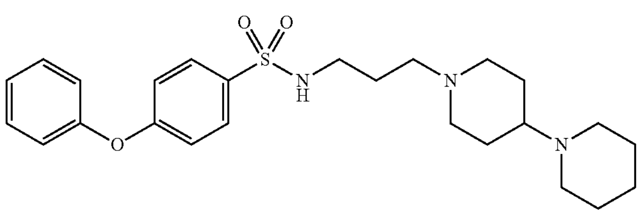 [SMILES: O=S(=O)(NCCCN1CCC(N2CCCCC2)CC1)c1ccc(Oc2ccccc2)cc1] | Brown solid; $^1$H NMR (400 MHz, acetone); δ 7.84 (d, J = 8.8 Hz, 2H), 7.47 (t, J = 8.0 Hz, 2H), 7.26 (t, J = 7.6 Hz, 1H), 7.09-7.14 (m, 4H), 2.99 (t, J = 6.4 Hz, 2H), 2.84 (d, J = 12.0 Hz, 2H), 2.46 (t, J = 5.0 Hz, 4H), 2.31 (t, J = 6.4 Hz, 2H), 2.12-2.18 (m, 1H), 1.83 (t, J = 12.0 Hz, 2H), 1.71 (d, J = 12.8 Hz, 2H), 1.61 (t, J = 6.4 Hz, 2H), 1.47-1.53 (m, 5H), 1.42 (q, J = 5.5 Hz, 2H); LCMS (electrospray) m/z (M + H)$^+$ 458.06 | +++ | D-3 |
| 1061 | 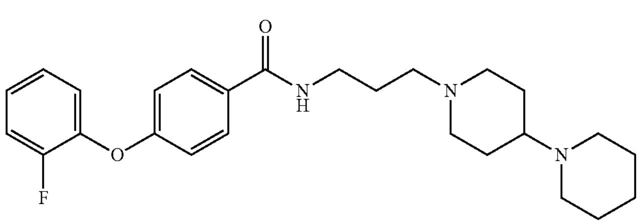 [SMILES: O=C(NCCCN1CCC(N2CCCCC2)CC1)c1ccc(Oc2ccccc2F)cc1] | Pale-yellow solid; 1H NMR (400 MHz, CDCl$_3$) δ 7.37 (d, J = 6.4 Hz, 2H), 7.15-7.18 (m, 2H), 7.09-7.14 (m, 2H), 6.96 (d, J = 8.4 Hz, 2H), 3.45 (t, J = 7.6 Hz, 2H), 3.10 (d, J = 11.2 Hz, 2H), 2.53-2.62 (m, 4H), 2.45 (t, J = 6.8 Hz, 2H), 2.38-2.42 (m, 1H), 2.05 (t, J = 12.0 Hz, 2H), 1.95 (d, J = 12.0 Hz, 2H), 1.85 (t, J = 7.2 Hz, 2H), 1.60-1.67 (m, 6H), 1.50-1.56 (m, 2H); LRMS (electrospray) m/z (M + H)$^+$ 440.24. | ++ | D-3 |

TABLE 2-continued

Anti-HCV genotype 1/2 activity for Formula II Series

| No. | Structure | Characterization | EC$_{50}$ | Method |
|---|---|---|---|---|
| 1062 | 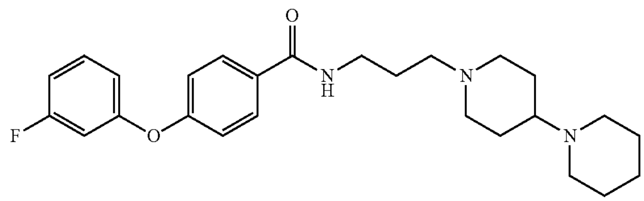 [SMILES: O=C(NCCCN1CCC(N2CCCCC2)CC1)c1ccc(Oc2cccc(F)c2)cc1] | Pale-yellow solid; 1H NMR (400 MHz, CDCl$_3$) δ 7.39 (d, J = 8.8 Hz, 2H), 7.31 (q, J = 8.0 Hz, 1H), 7.02 (d, J = 8.4 Hz, 2H), 6.84 (d, J = 8.0 Hz, 1H), 6.80 (d, J = 11.2 Hz, 1H), 6.73 (d, J = 9.6 Hz, 1H), 3.41 (t, J = 6.4 Hz, 2H), 3.10 (d, J = 12.0 Hz, 2H), 2.51-2.60 (m, 4H), 2.45 (t, J = 7.2 Hz, 2H), 2.35-2.37 (m, 1H), 2.01 (t, J = 11.6 Hz, 2H), 1.90 (d, J = 12.0 Hz, 2H), 1.84 (t, J = 7.2 Hz, 2H), 1.60-1.63 (m, 6H), 1.47-1.50 (m, 2H); LRMS (electrospray) m/z (M + H)$^+$ 440.27. | + | D-3 |
| 1063 | 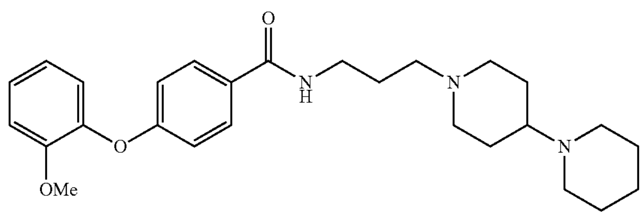 [SMILES: COc1ccccc1Oc1ccc(C(=O)NCCCN2CCC(N3CCCCC3)CC2)cc1] | Pale-yellow oil; 1H NMR (400 MHz, CDCl$_3$) δ 7.30 (d, J = 4.8 Hz, 2H), 7.02 (t, J = 7.6 Hz, 1H), 6.98 (t, J = 12.0 Hz, 2H), 6.93 (t, J = 6.0 Hz, 1H), 6.87 (d, J = 4.8 Hz, 2H), 3.78 (s, 3H), 3.45 (t, J = 11.6 Hz, 2H), 2.95 (d, J = 12.0 Hz, 2H), 2.73-2.80 (m, 4H), 2.43 (t, J = 7.6 Hz, 1H), 2.05 (t, J = 11.6 Hz, 1H), 2.00 (t, J = 12.0 Hz, 2H), 1.73-1.87 (m, 4H), 1.55-1.60 (m, 6H), 1.40-1.43 (m, 2H); LRMS (electrospray) m/z (M + H)$^+$ 452.14. | + | D-3 |
| 1064 | 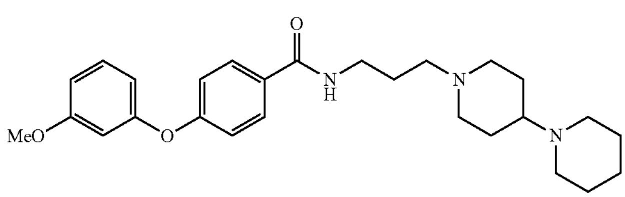 [SMILES: COc1cccc(Oc2ccc(C(=O)NCCCN3CCC(N4CCCCC4)CC3)cc2)c1] | Pale-yellow oil; 1H NMR (400 MHz, CDCl$_3$) δ 7.39 (d, J = 11.6 Hz, 2H), 7.27 (t, J = 7.2 Hz, 1H), 7.02 (t, J = 8.4 Hz, 2H), 6.72 (d, J = 2.4 Hz, 1H), 6.66 (d, J = 4.8 Hz, 2H), 3.79 (s, 3H), 3.46 (t, J = 11.2 Hz, 2H), 2.94 (d, J = 12.0 Hz, 2H), 2.71-2.80 (m, 4H), 2.45 (t, J = 7.2 Hz, 2H), 2.03 (t, J = 11.2 Hz, 1H), 2.01 (t, J = 12.0 Hz, 2H), 1.75-1.89 (m, 4H), 1.58-1.61 (m, 6H), 1.39-1.42 (m, 2H); LRMS (electrospray) m/z (M + H)$^+$ 452.08. | + | D-3 |
| 1065 | 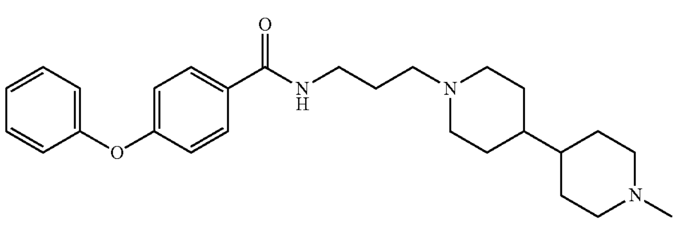 [SMILES: CN1CCC(C2CCN(CCCNC(=O)c3ccc(Oc4ccccc4)cc3)CC2)CC1] | White solid; $^1$H NMR (400 MHz, CD$_3$OD) δ 7.83 (d, J = 8.5 Hz, 2H), 7.40 (t, J = 7.8 Hz, 2H), 7.19 (t, J = 7.4 Hz, 1H), 7.05 (d, J = 7.6 Hz, 2H), 6.98 (d, J = 7.6 Hz, 2H), 3.40 (t, J = 6.4 Hz, 2H), 3.01 (d, J = 11.6 Hz, 2H), 2.88 (d, J = 11.2 Hz, 2H), 2.38 (t, J = 12.2 Hz, 2H), 2.24 (s, 3H), 1.95 (t, J = 6.0 Hz, 4H), 1.85-1.82 (m, 2H), 1.72 (d, J = 11.6 Hz, 3H), 1.31-1.12 (m, 5H), 1.11-1.04 (m, 2H); LRMS (electrospray) m/z (M + H)$^+$ 436.09. | +++ | D-3 |

TABLE 2-continued

Anti-HCV genotype 1/2 activity for Formula II Series

| No. | Structure | Characterization | EC$_{50}$ | Method |
|---|---|---|---|---|
| 1066 | 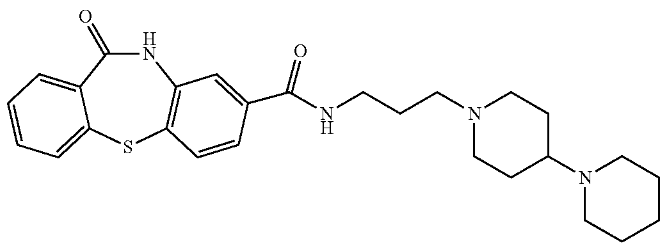 [SMILES: O=C(NCCCN1CCC(N2CCCCC2)CC1)c1ccc2c(c1)NC(=O)c1ccccc1S2] | White solid; $^1$H NMR (400 MHz, CD$_3$OD) δ 7.73 (d, J = 8.5 Hz, 1H), 7.68-7.66 (m, 2H), 7.60 (d, J = 8.0 Hz, 1H), 7.54 (d, J = 7.2 Hz, 1H), 7.48-7.43 (m, 2H), 3.58 (d, J = 12.0 Hz, 2H), 3.46 (t, J = 6.8 Hz, 2H), 3.38-3.35 (m, 2H), 3.26-3.24 (m, 3H), 3.00-2.99 (m, 2H), 2.91-2.88 (m, 2H), 2.32 (d, J = 12.0 Hz, 2H), 2.05-2.00 (m, 4H), 189-1.85 (m, 4H), 1.72-1.68 (m, 2H); LRMS (electrospray) m/z (M + H)$^+$ 479.09. | ++ | D-1 |
| 1067 | 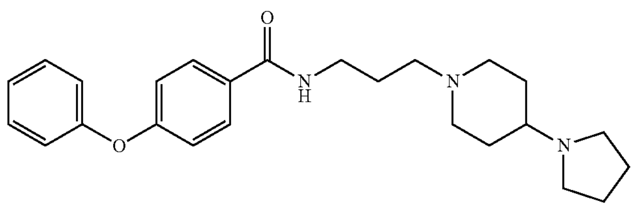 [SMILES: O=C(NCCCN1CCC(N2CCCC2)CC1)c1ccc(Oc2ccccc2)cc1] | Brown solid; $^1$H NMR (400 MHz, cd$_3$od) δ 7.82 (d, J = 8.7 Hz, 2H), 7.39 (t, J = 7.9 Hz, 2H), 7.18 (t, J = 7.4 Hz, 1H), 7.04 (d, J = 8.2 Hz, 2H), 7.00 (d, J = 8.7 Hz, 2H), 3.40 (t, J = 6.8 Hz, 2H), 2.99 (d, J = 11.9 Hz, 2H), 2.59 (s, 4H), 2.42 (t, , J = 8 Hz, 2H), 2.10-2.03 (m, 1H), 2.02-1.89 (m, 4H), 1.85-1.76 (m, 6H), 1.60-1.48 (m, 2H); LCMS (electrospray) m/z (M + H)$^+$ 408.06 | +++ | D-3 |
| 1068 | 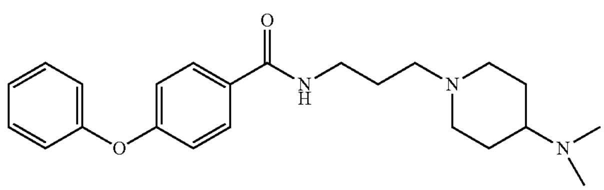 [SMILES: CN(C)C1CCN(CCCNC(=O)c2ccc(Oc3ccccc3)cc2)CC1] | Yellow oil; $^1$H NMR (400 MHz, cd$_3$od) δ 7.81 (d, J = 8.7 Hz, 2H), 7.41 (t, J = 7.9 Hz, 2H), 7.19 (t, J = 7.4 Hz, 1H), 7.05 (d, J = 8.2 Hz, 2H), 7.00 (d, J = 8.7 Hz, 2H), 3.41 (t, J = 6.8 Hz, 2H), 3.05 (d, J = 11.9 Hz, 2H), 2.45 (t, J = 6.0 Hz, 2H), 2.27 (s, 6H), 2.24-2.16 (m, 1H), 1.99 (t, J = 11.9 Hz, 2H), 1.91-1.77 (m, 4H), 1.51 (ddd, J = 24.5, 12.4, 3.5 Hz, 2H); LCMS (electrospray) m/z (M + H)$^+$ 382.07 | +++ | D-3 |
| 1069 | 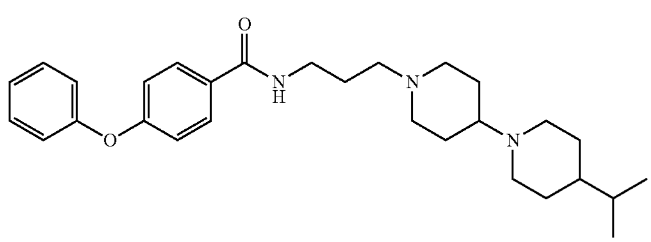 [SMILES: CC(C)C1CCN(C2CCN(CCCNC(=O)c3ccc(Oc4ccccc4)cc3)CC2)CC1] | Brown solid; $^1$H NMR (400 MHz, cd$_3$od) δ 7.84 (d, J = 7.4 Hz, 2H), 7.43 (t, J = 7.3 Hz, 2H), 7.21 (t, J = 7.4 Hz, 1H), 7.07 (d, J = 7.9 Hz, 2H), 7.02 (d, J = 7.4 Hz, 2H), 3.43 (t, J = 6.6 Hz, 2H), 3.04 (dd, J = 25.7, 11.1 Hz, 4H), 2.47 (t, J = 7.3 Hz, 2H), 2.33 (t, J = 11.6 Hz, 1H), 2.20 (t, J = 11.6 Hz, 2H), 2.00 (t, J = 11.9 Hz, 2H), 1.94-1.79 (m, 4H), 1.73 (d, J = 12.7 Hz, 2H), 1.58 (q, J = 22.7, 11.3 Hz, 2H), 1.48-1.39 (m, 1H), 1.30 (q, J = 22.0, 12.6 Hz, 2H), 1.11-0.99 (m, 1H), 0.91 (d, J = 6.7 Hz, 6H); LCMS (electrospray) m/z (M + H)$^+$ 464.32 | +++ | D-3 |

TABLE 2-continued

Anti-HCV genotype 1/2 activity for Formula II Series

| No. | Structure | Characterization | EC$_{50}$ | Method |
|---|---|---|---|---|
| 1070 | 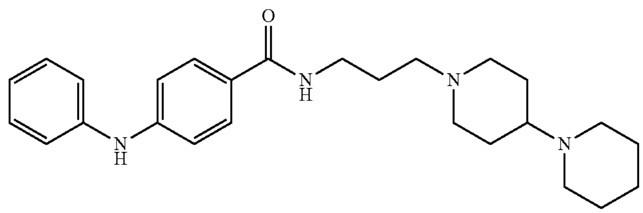 [SMILES: O=C(NCCCN1CCC(N2CCCCC2)CC1)c1ccc(Nc2ccccc2)cc1] | White solid; 1H NMR (400 MHz, CDCl$_3$) δ 7.95 (s, 1H), 7.73 (d, J = 8.8 Hz, 2H), 7.30 (t, J = 5.2 Hz, 2H), 7.14 (d, J = 8.8 Hz, 2H), 6.96-7.02 (m, 3H), 6.23 (s, 1H), 3.49-3.55 (m, 2H), 3.11 (d, J = 12.0 Hz, 2H), 2.63-2.64 (m, 2H), 2.52-2.56 (m, 6H), 1.93-1.96 (m, 3H), 1.78-1.80 (m, 2H), 1.67-1.75 (m, 6H), 1.37-1.45 (m, 2H); LRMS (electrospray) m/z (M + H)$^+$ 421.05. | ++ | D-3 |
| 1071 | 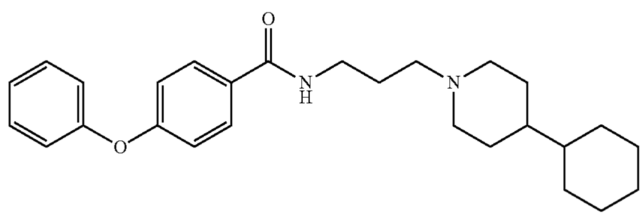 [SMILES: O=C(NCCCN1CCC(C2CCCCC2)CC1)c1ccc(Oc2ccccc2)cc1] | White solid; $^1$H NMR (400 MHz, CD$_3$OD) δ 7.83 (d, J = 8.5 Hz, 2H), 7.39 (t, J = 7.8 Hz, 2H), 7.20 (t, J = 7.4 Hz, 1H), 7.06-6.99 (m, 4H), 7.05-7.02 (m, 4H), 3.47 (t, J = 6.4 Hz, 4H), 3.02 (t, J = 7.4 Hz, 2H), 2.77 (t, J = 12.2 Hz, 2H), 2.02-1.93 (m, 4H), 1.76 (d, J = 12.4 Hz, 4H), 1.68 (d, J = 11.6 Hz, 1H), 1.50 (q, J = 11.8 Hz, 2H), 1.37-1.15 (m, 5H), 1.04-0.95 (m, 2H); LRMS (electrospray) m/z (M + H)$^+$ 421.26. | ++ | D-3 |
| 1072 | 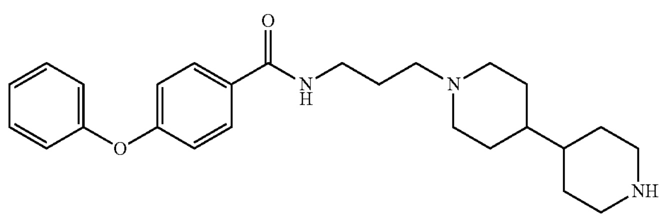 [SMILES: O=C(NCCCN1CCC(C2CCNCC2)CC1)c1ccc(Oc2ccccc2)cc1] | White solid; $^1$H NMR (400 MHz, CD$_3$OD) δ 7.80 (d, J = 8.7 Hz, 2H), 7.41 (t, J = 7.9 Hz, 2H), 7.19 (t, J = 7.4 Hz, 1H), 7.04 (d, J = 8.4 Hz, 2H), 6.99 (d, J = 8.7 Hz, 2H), 3.40 (t, J = 6.8 Hz, 2H), 3.07 (d, J = 11.4 Hz, 2H), 3.00 (d, J = 11.4 Hz, 2H), 2.60 (t, J = 6.4 Hz, 2H), 2.42 (t, J = 11.4 Hz, 2H), 1.91 (t, J = 11.3 Hz, 2H), 1.84 (q, J = 14.2, 6.9 Hz, 2H), 1.78-1.72 (m, 2H), 1.32-1.12 (m, 6H); LRMS (electrospray) m/z (M + H)$^+$ 422.14. | ++ | D-3 |
| 1073 | 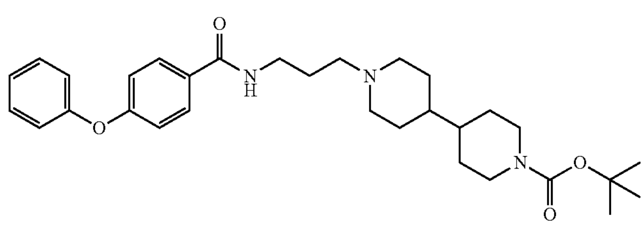 [SMILES: CC(C)(C)OC(=O)N1CCC(C2CCN(CCCNC(=O)c3ccc(Oc4ccccc4)cc3)CC2)CC1] | White solid; $^1$H NMR (400 MHz, CD$_3$OD) δ 7.81 (d, J = 8.7 Hz, 2H), 7.41 (t, J = 7.9 Hz, 2H), 7.20 (t, J = 7.4 Hz, 1H), 7.06 (d, J = 8.4 Hz, 2H), 7.00 (d, J = 8.7 Hz, 2H), 4.08 (d, J = 13.2 Hz, 2H), 3.40 (t, J = 6.8 Hz, 2H), 3.02 (d, J = 11.4 Hz, 2H), 2.68 (s, 2H), 2.44 (t, J = 11.4 Hz, 2H), 1.95 (t, J = 11.3 Hz, 2H), 1.82 (q, J = 14.2, 6.9 Hz, 2H), 1.72 (t, J = 12.5 Hz, 4H), 1.45 (s, 9H), 1.35-1.18 (m, 3H), 1.17-1.01 (m, 3H); LRMS (electrospray) m/z (M + H)$^+$ 522.09. | +++ | D-3 |

TABLE 2-continued

Anti-HCV genotype 1/2 activity for Formula II Series

| No. | Structure | Characterization | EC$_{50}$ | Method |
|---|---|---|---|---|
| 1074 | 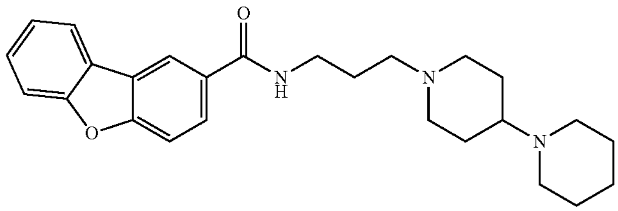 [SMILES: O=C(NCCCN1CCC(N2CCCCC2)CC1)c1ccc2oc3ccccc3c2c1] | Pale-yellow solid; 1H NMR (400 MHz, CDCl$_3$) δ 8.78 (s, 1H), 8.30 (d, J = 7.2 Hz, 1H), 8.13 (d, J = 8.8 Hz, 1H), 7.80 (d, J = 7.8 Hz, 1H), 7.75 (d, J = 8.0 Hz, 1H), 7.58 (d, J = 7.2 Hz, 1H), 7.45 (t, J = 7.2 Hz, 1H), 3.77 (t, J = 7.6 Hz, 2H), 3.28 (t, J = 6.0 Hz, 2H), 2.37-2.52 (m, 2H), 2.15-2.37 (m, 4H), 1.97-1.98 (m, 3H), 1.75-1.80 (m, 2H), 1.59-1.73 (m, 2H), 1.41-1.49 (m, 6H), 1.37-1.39 (m, 2H); LRMS (electrospray) m/z (M + H)$^+$ 419.96. | ++ | D-1 |
| 1075 | 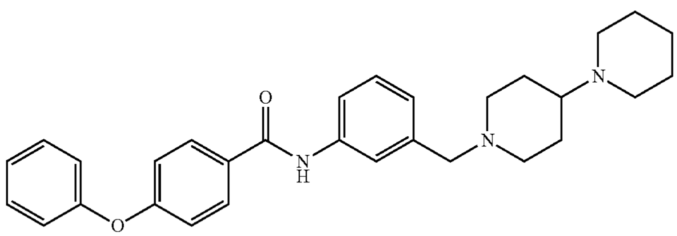 [SMILES: O=C(Nc1cccc(CN2CCC(N3CCCCC3)CC2)c1)c1ccc(Oc2ccccc2)cc1] | Pale yellow solid; $^1$H NMR (400 MHz, acetone); δ 9.46 (s, 1H), 8.06 (d, J = 8.8 Hz, 2H), 7.76-7.79 (m, 2H), 7.43-7.48 (m, 2H), 7.27 (t, J = 8.0 Hz, 1H), 7.22 (t, J = 7.4 Hz, 1H), 7.16 (d, J = 8.0 Hz, 1H), 7.04-7.09 (m, 3H), 3.44 (s, 2H), 2.91 (d, J = 12.0 Hz, 2H), 2.50 (t, J = 4.8 Hz, 4H), 2.11-2.25 (s, 1H), 1.91-1.97 (m, 2H), 1.72 (d, J = 12.0 Hz, 2H), 1.49-1.54 (m, 6H), 1.42 (q, J = 5.5 Hz, 2H); LCMS (electrospray) m/z (M + H)$^+$ 470.24 | +++ | D-3 |
| 1076 | 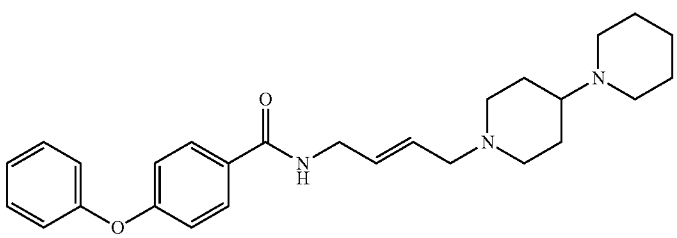 [SMILES: O=C(NC/C=C/CN1CCC(N2CCCCC2)CC1)c1ccc(Oc2ccccc2)cc1] | Yellow oil; $^1$H NMR (400 MHz, acetone); δ 7.93 (d, J = 8.8 Hz, 2H), 7.81 (s, 1H), 7.43 (t, J = 8.0 Hz, 2H), 7.20 (t, J = 7.4 Hz, 1H), 7.08 (d, J = 8.0 Hz, 2H), 7.02 (d, J = 6.8 Hz, 2H), 5.62 (d, J = 1.6 Hz, 2H), 3.99 (t, J = 4.4 Hz, 2H), 2.92 (d, J = 5.2 Hz, 2H), 2.32-2.41 (m, 1H), 1.89 (t, J = 12.0 Hz, 2H), 1.74 (d, J = 12.0 Hz, 2H), 1.54-1.65 (m, 6H), 1.42 (q, J = 5.5 Hz, 2H); LCMS (electrospray) m/z (M + H)$^+$ 434.12 | +++ | D-3 |
| 1077 | 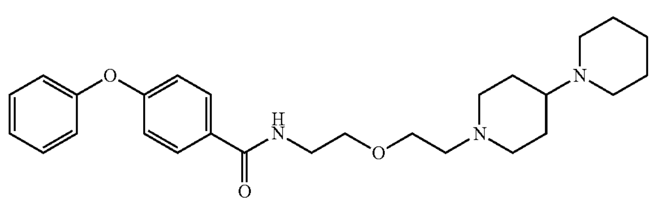 [SMILES: O=C(NCCOCCN1CCC(N2CCCCC2)CC1)c1ccc(Oc2ccccc2)cc1] | Brown solid; $^1$H NMR (400 MHz, acetone); δ 8.14 (s, 1H), 8.03 (d, J = 8.8 Hz, 2H), 7.43 (t, J = 8.0 Hz, 2H), 7.21 (t, J = 7.4 Hz, 1H), 7.08 (d, J = 8.0 Hz, 2H), 7.00 (d, J = 6.8 Hz, 2H), 3.63 (d, J = 5.6 Hz, 2H), 3.58 (q, J = 5.2 Hz, 2H), 3.52 (q, J = 5.2 Hz, 2H), 3.14 (d, J = 12.0 Hz, 2H), 2.70 (t, J = 5.4 Hz, 2H), 2.51 (s, 4H), 2.32-2.41 (m, 1H), 2.21 (t, J = 12.0 Hz, 2H), 1.69 (d, J = 12.4 Hz, 2H), 1.51-1.62 (m, 6H), 1.40 (q, J = 5.5 Hz, 2H); LCMS (electrospray) m/z (M + H)$^+$ 452.14 | ++ | D-3 |

TABLE 2-continued

Anti-HCV genotype 1/2 activity for Formula II Series

| No. | Structure | Characterization | EC$_{50}$ | Method |
|---|---|---|---|---|
| 1078 | 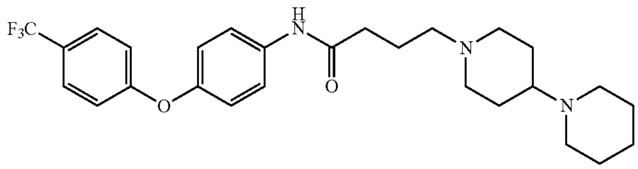 [SMILES: O=C(CCCN1CCC(N2CCCCC2)CC1)Nc1ccc(Oc2ccc(C(F)(F)F)cc2)cc1] | White solid; $^1$H NMR (400 MHz, CD$_3$OD) δ 7.66-7.63 (m, 4H), 7.08-7.04 (m, 4H), 3.73 (d, J = 11.4 Hz, 2H), 3.52-3.31 (m, 5H), 3.25 (t, J = 6.0 Hz, 2H), 3.06 (t, J = 11.4 Hz, 2H), 2.62 (t, J = 11.3 Hz, 2H), 2.41 (d, J = 12.4 Hz, 2H), 2.13-2.09 (m, 4H), 1.92-1.90 (m, 4H), 1.87-1.68 (m, 2H); LRMS (electrospray) m/z (M + H)$^+$ 490.11. | +++ | D-3 |
| 1079 | 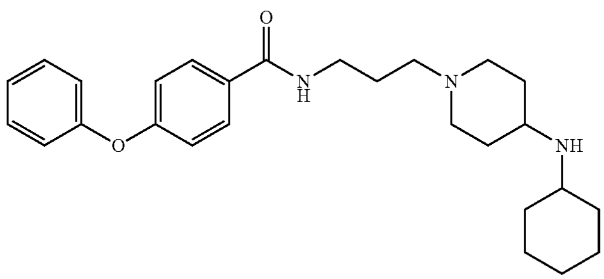 [SMILES: O=C(NCCCN1CCC(NC2CCCCC2)CC1)c1ccc(Oc2ccccc2)cc1] | Oil; $^1$H NMR (400 MHz, CD$_3$OD) δ 7.82 (d, J = 8.7 Hz, 2H), 7.42 (t, J = 7.9 Hz, 2H), 7.17 (t, J = 7.4 Hz, 1H), 7.00 (d, J = 8.4 Hz, 2H), 6.99 (d, J = 8.7 Hz, 2H), 3.39 (t, J = 6.8 Hz, 2H), 2.98 (d, J = 11.6 Hz, 3H), 2.67-2.62 (m, 2H), 2.44 (t, J = 6.8 Hz, 2H), 2.02 (t, J = 6.0 Hz, 2H), 1.90 (d, J = 6.8 Hz, 3H), 1.83 (t, J = 7.4 Hz, 2H), 1.77-1.73 (m, 2H), 1.64 (d, J = 12.4 Hz, 1H), 1.39-1.06 (m, 8H); LRMS (electrospray) m/z (M + H)$^+$ 436.29. | +++ | D-3 |
| 1080 | 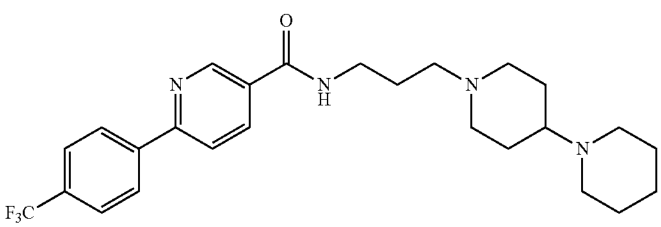 | White solid; $^1$H NMR (400 MHz, CD$_3$OD) δ 9.09 (NH, 1H), 8.31-8.25 (m, 3H), 8.06 (d, J = 8.0 Hz, 1H), 7.81 (d, J = 8.4 Hz, 2H), 3.46 (t, J = 6.6 Hz, 2H), 3.07 (d, J = 11.6 Hz, 2H), 2.61 (s, 4H), 2.47 (t, J = 6.8 Hz, 2H), 2.40-2.38 (m, 1H), 2.00 (t, J = 7.4 Hz, 2H), 1.90-1.83 (m, 4H), 1.63-1.57 (m, 6H), 1.48-1.47 (m, 2H); LRMS (electrospray) m/z (M + H)$^+$ 475.07. | +++ | D-1 |
| 1081 | 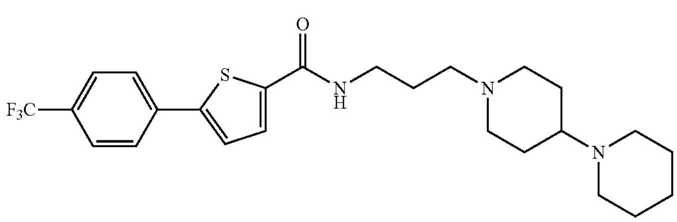 [SMILES: O=C(NCCCN1CCC(N2CCCCC2)CC1)c1ccc(-c2ccc(C(F)(F)F)cc2)s1] | White solid; $^1$H NMR (400 MHz, CD$_3$OD) δ 7.87 (d, J = 6.4 Hz, 2H), 7.72 (d, J = 6.4 Hz, 2H), 7.66 (d, J = 6.8 Hz, 1H), 7.54 (d, J = 6.8 Hz, 1H), 3.41 (t, J = 6.6 Hz, 2H), 3.11 (d, J = 11.6 Hz, 2H), 2.77 (s, 4H), 2.59-2.57 (m, 1H), 2.48 (t, J = 6.8 Hz, 2H), 2.05 (t, J = 7.4 Hz, 2H), 1.94 (d, J = 12.4 Hz, 2H), 1.83 (p, J$_{12}$ = 12.2 Hz J$_{13}$ = 22.2 Hz, 2H), 1.70-1.68 (m, 6H), 1.53-1.52 (m, 2H); LRMS (electrospray) m/z (M + H)$^+$ 480.11. | +++ | D-1 |

TABLE 2-continued

Anti-HCV genotype 1/2 activity for Formula II Series

| No. | Structure | Characterization | EC$_{50}$ | Method |
|---|---|---|---|---|
| 1082 | 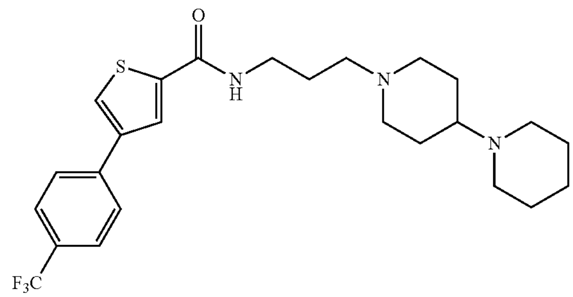 [SMILES: O=C(NCCCN1CCC(N2CCCCC2)CC1)c1cc(-c2ccc(C(F)(F)F)cc2)cs1] | White solid; $^1$H NMR (400 MHz, CD$_3$OD) δ 8.10 (s, 1H), 8.02 (s, 1H), 7.86 (d, J = 8.4 Hz, 2H), 7.72 (d, J = 8.4 Hz, 2H), 3.43 (t, J = 6.8 Hz, 2H), 3.12 (d, J = 12.0 Hz, 2H), 2.82 (s, 4H), 2.69-2.64 (m, 1H), 2.50 (t, J = 7.4 Hz, 2H), 2.07 (t, J = 12.0 Hz, 2H), 1.96 (d, J = 12.0 Hz, 2H), 1.84 (p, J$_{12}$ = 7.1 Hz, J$_{13}$ = 14.4 Hz, 2H), 1.72-1.64 (m, 6H), 1.55-1.54 (m, 2H); LRMS (electrospray) m/z (M + H)$^+$ 480.11. | +++ | D-1 |
| 1083 | 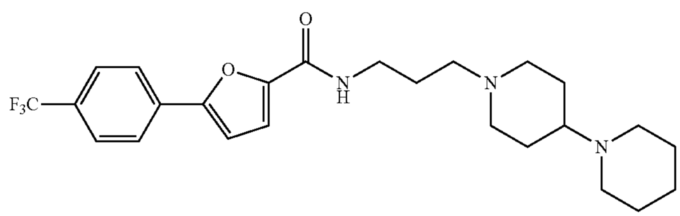 [SMILES: O=C(NCCCN1CCC(N2CCCCC2)CC1)c1ccc(-c2ccc(C(F)(F)F)cc2)o1] | Oil; $^1$H NMR (400 MHz, CD$_3$OD) δ 8.04 (d, J = 8.4 Hz, 2H), 7.73 (d, J = 8.4 Hz, 2H), 7.20 (d, J = 1.2 Hz, 1H), 7.09 (d, J = 1.2 Hz, 1H), 3.43 (t, J = 6.8 Hz, 2H), 3.08 (d, J = 12.0 Hz, 2H), 2.59 (s, 4H), 2.47 (t, J = 7.4 Hz, 2H), 2.44-2.37 (m, 1H), 2.03 (t, J = 12.0 Hz, 2H), 1.89-1.84 (m, 4H), 1.62-1.56 (m, 6H), 1.48-1.45 (m, 2H); LRMS (electrospray) m/z (M + H)$^+$ 464.12. | +++ | D-1 |
| 1084 | 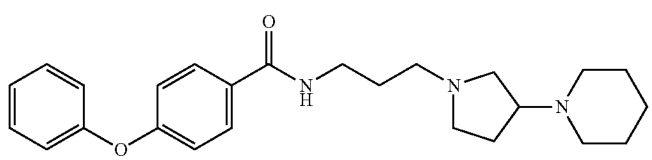 [SMILES: O=C(NCCCN1CCC(N2CCCCC2)C1)c1ccc(Oc2ccccc2)cc1] | Brown oil; $^1$H NMR (400 MHz, acetone); δ 8.31 (s, 1H), 7.95 (d, J = 8.8 Hz, 2H), 7.43 (t, J = 8.0 Hz, 2H), 7.20 (t, J = 7.4 Hz, 1H), 7.19 (d, J = 8.0 Hz, 2H), 7.00 (d, J = 6.8 Hz, 2H), 3.63 (d, J = 5.6 Hz, 2H), 3.52 (q, J = 5.2 Hz, 2H), 3.14 (d, J = 12.0 Hz, 2H), 2.51 (s, 4H), 2.32-2.41 (m, 1H), 2.21 (t, J = 12.0 Hz, 2H), 1.69 (d, J = 12.4 Hz, 2H), 1.51-1.62 (m, 6H), 1.40 (q, J = 5.5 Hz, 2H); LCMS (electrospray) m/z (M + H)$^+$ 408.13 | + | D-3 |
| 1085 | 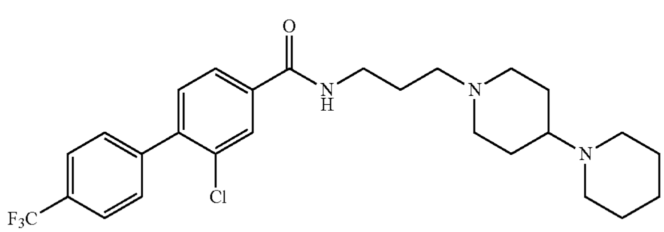 [SMILES: O=C(NCCCN1CCC(N2CCCCC2)CC1)c1ccc(-c2ccc(C(F)(F)F)cc2)c(Cl)c1] | White solid; $^1$H NMR (400 MHz, acetone); δ 8.41 (s, 1H), 7.85 (d, J = 8.4 Hz, 1H), 7.72 (d, J = 8.0 Hz, 2H), 7.55 (d, J = 8.0 Hz, 1H), 7.43 (t, J = 8.6 Hz, 2H), 3.47-3.51 (m, 2H), 3.01 (t, J = 11.6 Hz, 2H), 2.43-2.48 (m, 6H), 2.15-2.23 (m, 1H), 1.88 (t, J = 12.0 Hz, 2H), 1.78 (t, J = 6.6 Hz, 2H), 1.70 (t, J = 12.0 Hz, 2H), 1.43-1.49 (m, 6H), 1.38 (q, J = 5.5 Hz, 2H); LCMS (electrospray) m/z (M + H)$^+$ 508.14 | +++ | D-1 |

TABLE 2-continued

Anti-HCV genotype 1/2 activity for Formula II Series

| No. | Structure | Characterization | EC$_{50}$ | Method |
|---|---|---|---|---|
| 1086 | 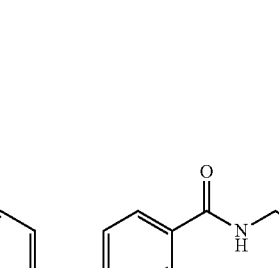 | White solid; $^1$H NMR (400 MHz, acetone); δ 9.30 (s, 1H), 7.87 (d, J = 8.4 Hz, 2H), 7.83 (d, J = 8.8 Hz, 2H), 7.77 (d, J = 8.0 Hz, 2H), 7.68 (d, J = 8.8 Hz, 2H), 2.93 (d, J = 11.6 Hz, 2H), 2.37-2.45 (m, 6H), 2.34 (t, J = 6.6 Hz, 2H), 2.16-2.20 (m, 1H), 1.81-1.88 (m, 4H), 1.65 (d, J = 12.4 Hz, 2H), 1.42-1.51 (m, 6H), 1.35 (q, J = 5.5 Hz, 2H); LCMS (electrospray) m/z (M + H)$^+$ 474.19 | +++ | D-4 |
| 1087 | 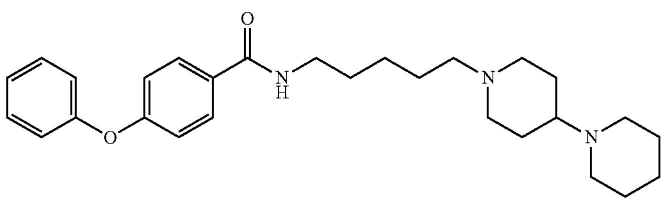 [SMILES: O=C(NCCCCCN1CCC(N2CCCCC2)CC1)c1ccc(Oc2ccccc2)cc1] | White solid; 1H NMR (400 MHz, CDCl$_3$) δ 7.85 (q, J = 7.2 Hz, 3H), 7.43 (t, J = 7.6 Hz, 1H), 7.21 (t, J = 7.6 Hz, 1H), 7.07 (d, J = 8.8 Hz, 1H), 7.00 (d, J = 6.8 Hz, 2H), 6.73 (d, J = 7.2 Hz, 1H), 3.39 (t, J = 7.2 Hz, 2H), 3.11 (d, J = 8.4 Hz, 2H), 2.71-2.77 (m, 4H), 2.45-2.49 (m, 1H), 2.42 (t, J = 8.0 Hz, 2H), 2.10 (t, J = 11.6 Hz, 2H), 1.95 (d, J = 12.8 Hz, 2H), 1.67-1.72 (m, 6H), 1.63-1.66 (m, 4H), 1.55-1.57 (m, 2H), 1.53-1.55 (m, 2H); LRMS (electrospray) m/z (M + H)$^+$ 450.10. | +++ | D-3 |
| 1088 | 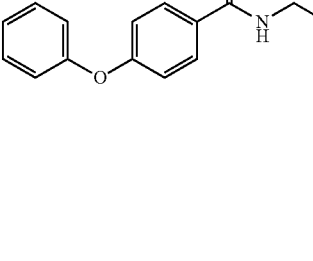 | White solid; 1H NMR (400 MHz, CDCl$_3$) δ 7.82 (d, J = 5.2 Hz, 2H), 7.42 (t, J = 7.6 Hz, 2H), 7.20 (t, J = 7.2 Hz, 1H), 7.06 (d, J = 8.8 Hz, 2H), 6.98 (d, J = 6.4 Hz, 2H), 3.38 (t, J = 7.2 Hz, 2H), 3.05 (d, J = 12.0 Hz, 2H), 2.37-2.60 (m, 4H), 2.33-2.37 (m, 3H), 2.01 (t, J = 12.0 Hz, 2H), 1.89 (d, J = 11.2 Hz, 2H), 1.62-1.65 (m, 6H), 1.57-1.60 (m, 6H), 1.53-1.55 (m, 4H); LRMS (electrospray) m/z (M + H)$^+$ 464.39. | +++ | D-3 |
| 1089 | 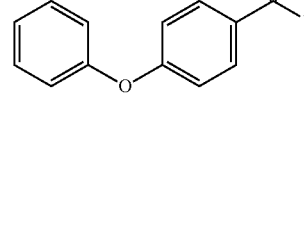 | Brown oil; $^1$H NMR (400 MHz, cdcl$_3$) δ 7.49 (d, J = 7.4 Hz, 2H), 7.34 (t, J = 7.9 Hz, 2H), 7.13 (t, J = 7.4 Hz, 1H), 7.01 (d, J = 8.0 Hz, 2H), 6.96 (d, J = 8.4 Hz, 2H), 3.83-3.54 (m, 3H), 3.38-3.27 (m, 1H), 3.11-3.2.92 (m, 2H), 2.65-2.27 (m, 8H), 2.18-1.84 (m, 6H), 1.76-1.50 (m, 9H); LCMS (electrospray) m/z (M + H)$^+$ 448.15 | ++ | D-3 |

TABLE 2-continued

Anti-HCV genotype 1/2 activity for Formula II Series

| No. | Structure | Characterization | EC$_{50}$ | Method |
|---|---|---|---|---|
| 1090 | 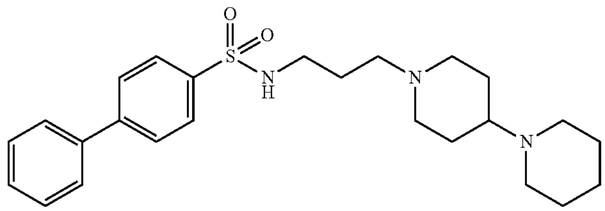 [SMILES: O=S(=O)(NCCCN1CCC(N2CCCCC2)CC1)c1ccc(-c2ccccc2)cc1] | Brown solid; $^1$H NMR (400 MHz, cd$_3$od) δ 7.92 (d, J = 8.3 Hz, 2H), 7.83 (d, J = 8.3 Hz, 2H), 7.69 (d, J = 7.6 Hz, 2H), 7.49 (t, J = 7.6 Hz, 2H), 7.41 (t, J = 7.1 Hz, 1H), 2.99-2.88 (m, J = 17.7, 10.8 Hz, 4H), 2.52 (t, J = 6.0 Hz, 4H), 2.32 (t, 2H), 2.27-2.18 (m, 1H), 1.89 (t, J = 12.0 Hz, 2H), 1.81 (d, J = 12.5 Hz, 2H), 1.67-1.55 (m, 6H), 1.54-1.42 (m, 4H); LCMS (electrospray) m/z (M + H)$^+$ 442.08 | +++ | D-5 |
| 1091 | 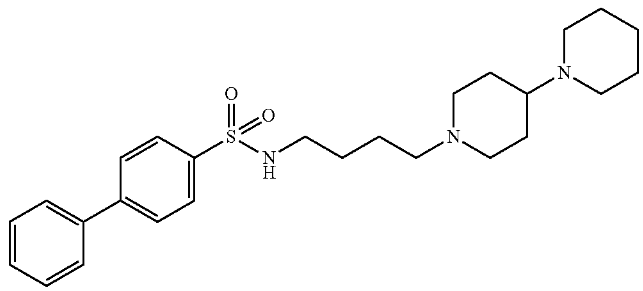 [SMILES: O=S(=O)(NCCCCN1CCC(N2CCCCC2)CC1)c1ccc(-c2ccccc2)cc1] | Brown solid; $^1$H NMR (400 MHz, cd$_3$od) δ 7.92 (d, J = 8.4 Hz, 2H), 7.82 (d, J = 8.4 Hz, 2H), 7.74 (s, 1H), 7.69 (d, J = 7.5 Hz, 2H), 7.48 (t, J = 7.5 Hz, 2H), 7.41 (t, J = 7.2 Hz, 1H), 3.00-2.89 (m, 4H), 2.62 (s, 4H), 2.41-2.32 (m, 1H), 2.27 (d, J = 6.8 Hz, 2H), 1.93 (t, J = 12.3 Hz, 2H), 1.84 (d, J = 12.4 Hz, 2H), 1.72-1.41 (m, 12H); LCMS (electrospray) m/z (M + H)$^+$ 456.09 | +++ | D-5 |
| 1092 | 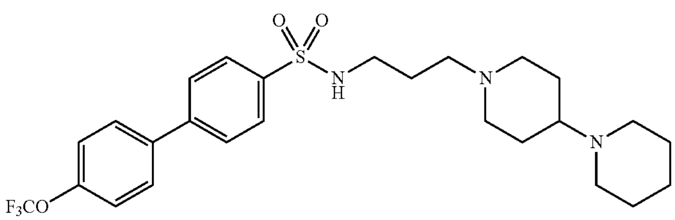 [SMILES: O=S(=O)(NCCCN1CCC(N2CCCCC2)CC1)c1ccc(-c2ccc(OC(F)(F)F)cc2)cc1] | Brown solid; $^1$H NMR (400 MHz, cd$_3$od) δ 7.93 (d, J = 8.4 Hz, 2H), 7.85 (d, J = 8.4 Hz, 2H), 7.80 (d, J = 8.7 Hz, 2H), 7.40 (d, J = 8.3 Hz, 2H), 3.06-2.92 (m, 8H), 2.87-2.76 (m, 1H), 2.41 (t, J = 8.0 Hz, 2H), 2.01 (dd, J = 23.4, 11.3 Hz, 4H), 1.76 (dt, J = 10.5, 5.3 Hz, 4H), 1.72-1.55 (m, 6H); LCMS (electrospray) m/z (M + H)$^+$ 526.17 | +++ | D-5 |
| 1093 | 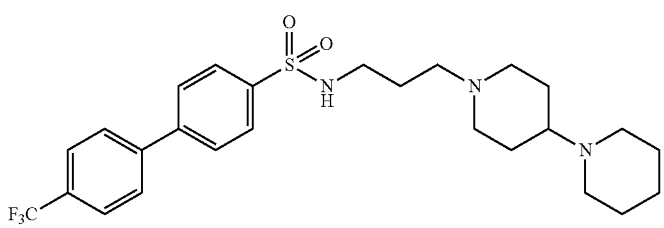 [SMILES: O=S(=O)(NCCCN1CCC(N2CCCCC2)CC1)c1ccc(-c2ccc(C(F)(F)F)cc2)cc1] | Brown Solid; $^1$H NMR (400 MHz, cd$_3$od) δ 7.96 (d, J = 8.4 Hz, 2H), 7.89 (d, J = 8.8 Hz, 3H), 7.79 (d, J = 8.3 Hz, 2H), 2.96-2.90 (m, J = 15.9, 9.2 Hz, 4H), 2.54 (s, 4H), 2.32 (t, J = 7.6 Hz, 2H), 2.25 (t, J = 11.7 Hz, 1H), 1.89 (t, J = 12.1 Hz, 2H), 1.81 (d, J = 12.7 Hz, 2H), 1.65-1.46 (m, 10H) ); LCMS (electrospray) m/z (M + H)$^+$ 510.18 | +++ | D-5 |
| 1094 | 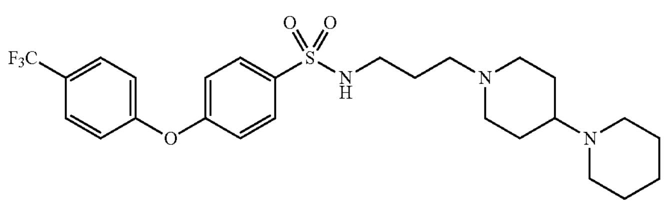 [SMILES: O=S(=O)(NCCCN1CCC(N2CCCCC2)CC1)c1ccc(Oc2ccc(C(F)(F)F)cc2)cc1] | Brown Solid; $^1$H NMR (400 MHz, cd$_3$od) δ 7.88 (d, J = 8.8 Hz, 2H), 7.74 (d, J = 8.7 Hz, 2H), 7.22 (t, J = 9.5 Hz, 4H), 3.00-2.90 (m, 4H), 2.57 (s, 4H), 2.35 (t, J = 8.0 Hz, 2H), 2.31-2.22 (m, 1H), 1.94 (t, J = 12.1 Hz, 2H), 1.86 (d, J = 12.7 Hz, 2H), 1.69-1.44 (m, 10H); LCMS (electrospray) m/z (M + H)$^+$ 526.23 | +++ | D-5 |

TABLE 2-continued

Anti-HCV genotype 1/2 activity for Formula II Series

| No. | Structure | Characterization | EC$_{50}$ | Method |
|---|---|---|---|---|
| 1095 | 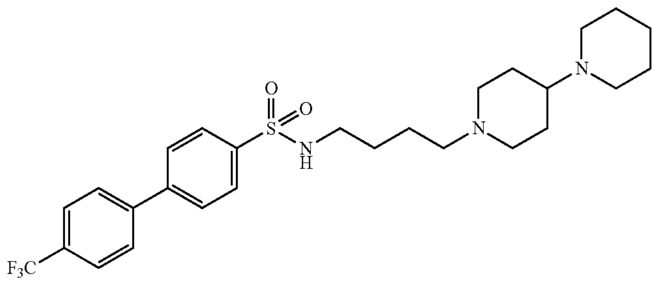 [SMILES: O=S(=O)(NCCCCN1CCC(N2CCCCC2)CC1)c1ccc(-c2ccc(C(F)(F)F)cc2)cc1] | Yellow solid; $^1$H NMR (400 MHz, cd$_3$od) δ 7.97 (d, J = 8.4 Hz, 2H), 7.90 (d, J = 7.7 Hz, 4H), 7.80 (d, J = 8.2 Hz, 2H), 2.98-2.88 (m, 4H), 2.50 (s, 4H), 2.24 (t, J = 6.9 Hz, 2H), 2.20-2.15 (m, 1H), 1.88 (t, J = 11.5 Hz, 2H), 1.79 (d, J = 12.4 Hz, 2H), 1.63-1.41 (m, 12H); LCMS (electrospray) m/z (M + H)$^+$ 524.26 | +++ | D-5 |
| 1096 | 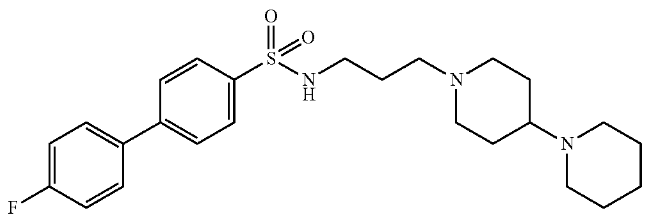 [SMILES: O=S(=O)(NCCCN1CCC(N2CCCCC2)CC1)c1ccc(-c2ccc(F)cc2)cc1] | White solid; $^1$H NMR (400 MHz, cd$_3$od) δ 7.92 (d, J = 8.5 Hz, 2H), 7.82 (d, J = 8.5 Hz, 2H), 7.72 (dd, J = 8.8, 5.3 Hz, 2H), 7.23 (t, J = 8.8 Hz, 2H), 3.17-3.00 (m, 7H), 2.95 (t, J = 6.7 Hz, 2H), 2.49-2.41 (m, 2H), 2.12-2.00 (m, 5H), 1.88-1.79 (m, 4H), 1.75-1.60 (m, 7H); LCMS (electrospray) m/z (M + H)$^+$ 460.24 | +++ | D-5 |
| 1097 | 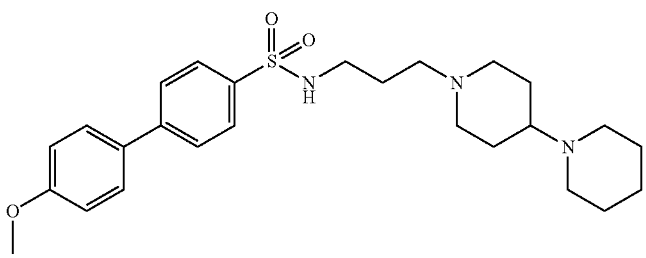 [SMILES: COc1ccc(-c2ccc(S(=O)(=O)NCCCN3CCC(N4CCCCC4)CC3)cc2)cc1] | Brown solid; $^1$H NMR (400 MHz, cd$_3$od) δ 7.87 (d, J = 8.4 Hz, 2H), 7.78 (d, J = 8.4 Hz, 2H), 7.64 (d, J = 8.7 Hz, 2H), 7.04 (d, J = 8.7 Hz, 2H), 3.84 (s, 3H), 3.04-2.87 (m, 8H), 2.81-2.70 (m, 1H), 2.39 (t, J = 8.0 Hz, 2H), 2.07-1.92 (m, 4H), 1.81-1.70 (m, 4H), 1.69-1.52 (m, 6H); LCMS (electrospray) m/z (M + H)$^+$ 472.15 | +++ | D-5 |
| 1098 | 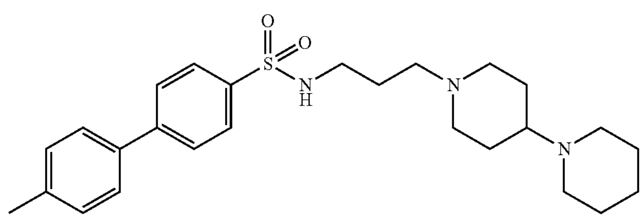 [SMILES: Cc1ccc(-c2ccc(S(=O)(=O)NCCCN3CCC(N4CCCCC4)CC3)cc2)cc1] | Brown solid; $^1$H NMR (400 MHz, cd$_3$od) δ 7.90 (d, J = 8.5 Hz, 2H), 7.81 (d, J = 8.5 Hz, 2H), 7.59 (d, J = 8.2 Hz, 2H), 7.31 (d, J = 8.1 Hz, 2H), 2.97-2.87 (m, 4H), 2.56 (s, 4H), 2.40 (s, 3H), 2.32 (t, J = 6.0 Hz, 2H), 2.29-2.21 (m, 1H), 1.94-1.78 (m, 4H), 1.68-1.56 (m, 6H), 1.56-1.43 (m, 4H); LCMS (electrospray) m/z (M + H)$^+$ 456.23 | +++ | D-5 |
| 1099 | 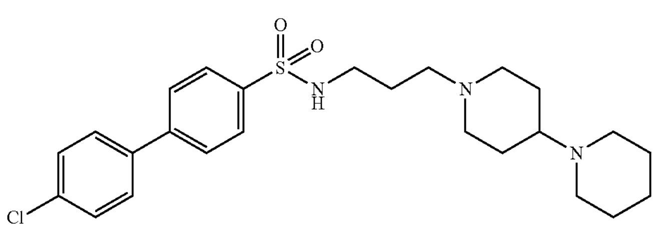 [SMILES: O=S(=O)(NCCCN1CCC(N2CCCCC2)CC1)c1ccc(-c2ccc(Cl)cc2)cc1] | White solid; $^1$H NMR (400 MHz, cd$_3$od) δ 7.92 (d, J = 8.4 Hz, 2H), 7.83 (d, J = 8.4 Hz, 2H), 7.69 (d, J = 8.5 Hz, 2H), 7.50 (d, J = 8.5 Hz, 2H), 2.96-2.87 (m, 4H), 2.55 (s, 4H), 2.32 (t, J = 6.0 Hz, 2H), 2.27-2.19 (m, 1H), 1.89 (t, J = 12.1 Hz, 1H), 1.82 (d, J = 12.5 Hz, 1H), 1.66-1.55 (m, 6H), 1.55-1.41 (m, 4H); LCMS (electrospray) m/z (M + H)$^+$ 476.03 | +++ | D-5 |

TABLE 2-continued

Anti-HCV genotype 1/2 activity for Formula II Series

| No. | Structure | Characterization | EC$_{50}$ | Method |
|---|---|---|---|---|
| 1100 | 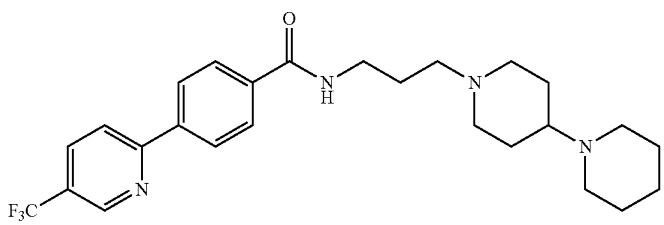 [SMILES: O=C(NCCCN1CCC(N2CCCCC2)CC1)c1ccc(-c2ccc(C(F)(F)F)cn2)cc1] | White solid; $^1$H NMR (400 MHz, CD$_3$OD) δ 8.97 (s, 1H), 8.23-8.19 (m, 3H), 8.15 (d, J = 8.4 Hz, 1H), 7.97 (d, J = 8.8 Hz, 2H), 3.48 (t, J = 6.8 Hz, 2H), 3.30-3.25 (m, 3H), 3.11 (s, 4H), 2.66 (t, J = 7.4 Hz, 2H), 2.29 (t, J = 12.0 Hz, 2H), 2.13 (d, J = 12.0 Hz, 2H), 1.92-1.78 (m, 8H), 1.65-1.63 (m, 2H); LRMS (electrospray) m/z (M + H)$^+$ 475.21. | +++ | D-1 |
| 1101 | 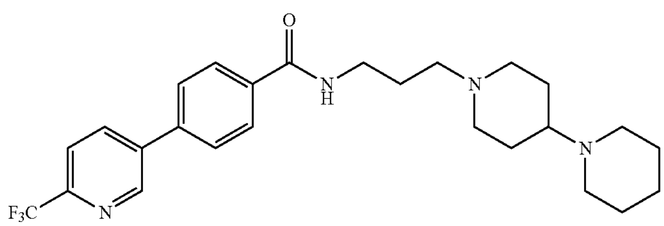 [SMILES: O=C(NCCCN1CCC(N2CCCCC2)CC1)c1ccc(-c2ccc(C(F)(F)F)nc2)cc1] | White solid; $^1$H NMR (400 MHz, CD$_3$OD) δ 9.03 (s, 1H), 8.34 (d, J = 8.4 Hz, 1H), 7.98 (d, J = 8.4 Hz, 2H), 7.92 (d, J = 8.4 Hz, 1H), 7.86 (d, J = 8.4 Hz, 2H), 3.46 (t, J = 6.6 Hz, 2H), 3.13 (d, J = 11.6 Hz, 2H), 2.86 (s, 4H), 2.72-2.70 (m, 1H), 2.52 (t, J = 6.8 Hz, 2H), 2.09 (t, J = 7.4 Hz, 2H), 1.98 (d, J = 12.4 Hz, 2H), 1.86 (p, J$_{12}$ = 12.2 Hz, J$_{13}$ = 22.2 Hz, 2H), 1.75-1.63 (m, 6H), 1.57-1.55 (m, 2H); LRMS (electrospray) m/z (M + H)$^+$ 475.14. | +++ | D-1 |
| 1102 | 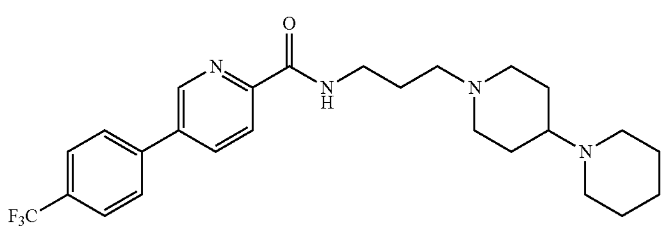 [SMILES: O=C(NCCCN1CCC(N2CCCCC2)CC1)c1ccc(-c2ccc(C(F)(F)F)cc2)cn1] | White solid; $^1$H NMR (400 MHz, CD$_3$OD) δ 8.96 (s, 1H), 8.28 (d, J = 8.4 Hz, 1H), 8.19 (d, J = 8.0 Hz, 1H), 7.93 (d, J = 8.4 Hz, 2H), 7.82 (d, J = 8.4 Hz, 2H), 3.50 (t, J = 6.6 Hz, 2H), 3.07 (d, J = 11.6 Hz, 2H), 2.56 (s, 4H), 2.47 (t, J = 6.8 Hz, 2H), 2.30-2.26 (m, 1H), 1.95 (t, J = 7.4 Hz, 2H), 1.83-1.81 (m, 4H), 1.68-1.57 (m, 6H), 1.47-1.46 (m, 2H); LRMS (electrospray) m/z (M + H)$^+$ 475.14. | +++ | D-1 |
| 1103 | 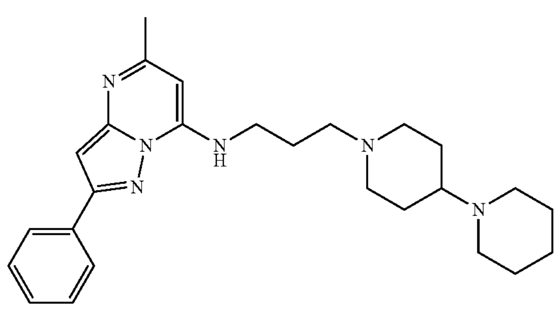 [SMILES: Cc1cc(NCCCN2CCC(N3CCCCC3)CC2)n2nc(-c3ccccc3)cc2n1] | White solid; $^1$H NMR (400 MHz, CD$_3$OD) δ 8.00 (d, J = 8.4 Hz, 2H), 7.47 (t, J = 4.2 Hz, 2H), 7.41 (t, J = 10.0 Hz, 1H), 6.61 (s, 1H), 6.08 (s, 1H), 3.56 (t, J = 6.6 Hz, 2H), 3.17 (d, J = 11.6 Hz, 2H), 3.03 (s, 5H), 2.60 (t, J = 6.8 Hz, 2H), 2.46 (s, 3H), 2.10 (t, J = 7.4 Hz, 2H), 2.02-1.93 (m, 4H), 1.76-1.72 (m, 6H), 1.51-1.48 (m, 2H); LRMS (electrospray) m/z (M + H)$^+$ 433.16. | ++ | D-1 |

TABLE 2-continued

Anti-HCV genotype 1/2 activity for Formula II Series

| No. | Structure | Characterization | EC$_{50}$ | Method |
|---|---|---|---|---|
| 1104 | 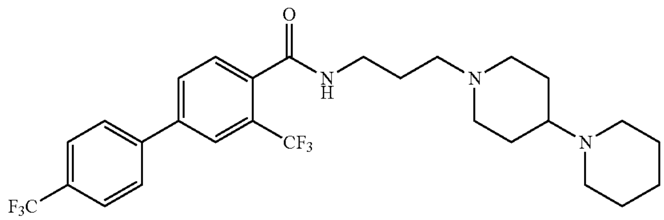 [SMILES: O=C(NCCCN1CCC(N2CCCCC2)CC1)c1ccc(-c2ccc(C(F)(F)F)cc2)cc1C(F)(F)F] | White solid; $^1$H NMR (400 MHz, CD$_3$OD) δ 8.03 (d, J = 8.4 Hz, 2H), 8.00 (d, J = 8.4 Hz, 2H), 7.84 (d, J = 8.4 Hz, 2H), 7.64 (d, J = 8.0 Hz, 1H), 3.42 (t, J = 6.6 Hz, 2H), 3.07 (d, J = 11.6 Hz, 2H), 2.63 (s, 4H), 2.46-2.43 (m, 3H), 2.02 (t, J = 7.4 Hz, 2H), 1.90-1.87 (m, 4H), 1.61-1.55 (m, 6H), 1.48-1.46 (m, 2H); LRMS (electrospray) m/z (M + H)$^+$ 542.15. | +++ | D-1 |
| 1105 | 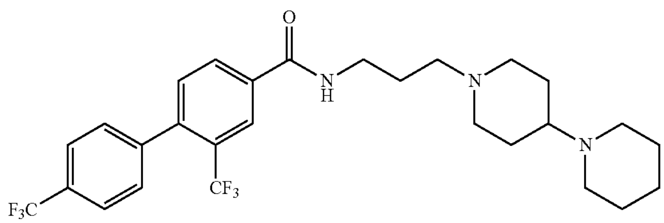 [SMILES: O=C(NCCCN1CCC(N2CCCCC2)CC1)c1ccc(-c2ccc(C(F)(F)F)cc2)c(C(F)(F)F)c1] | Oil; $^1$H NMR (400 MHz, CD$_3$OD) δ 8.24 (s, 1H), 8.08 (d, J = 8.4 Hz, 1H), 7.71 (d, J = 8.4 Hz, 2H), 7.50-7.46 (m, 3H), 3.42 (t, J = 6.6 Hz, 2H), 3.05 (d, J = 11.6 Hz, 2H), 2.57 (s, 4H), 2.43 (t, J = 7.4 Hz, 2H), 2.33-2.31 (m, 3H), 1.91 (t, J = 7.4 Hz, 2H), 1.87-1.80 (m, 4H), 1.54-1.44 (m, 6H), 1.29-1.28 (m, 2H); LRMS (electrospray) m/z (M + H)$^+$ 542.15. | +++ | D-1 |
| 1106 | 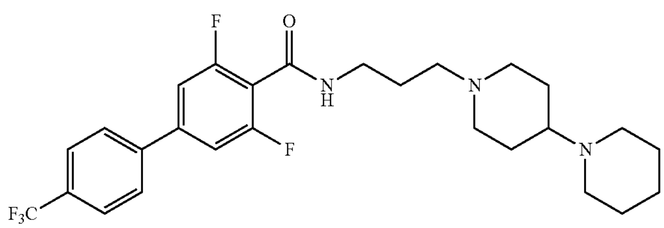 [SMILES: O=C(NCCCN1CCC(N2CCCCC2)CC1)c1c(F)cc(-c2ccc(C(F)(F)F)cc2)cc1F] | White solid; $^1$H NMR (400 MHz, CD$_3$OD) δ 7.87 (d, J = 8.4 Hz, 2H), 7.79 (d, J = 8.4 Hz, 2H), 7.45 (d, J = 8.4 Hz, 2H), 3.47 (t, J = 6.6 Hz, 2H), 3.31-3.08 (m, 7H), 2.57 (t, J = 7.4 Hz, 2H), 2.18 (t, J = 7.4 Hz, 2H), 2.09 (d, J = 12.4 Hz, 2H), 1.88-1.75 (m, 8H), 1.65-1.63 (m, 2H); LRMS (electrospray) m/z (M + H)$^+$ 510.18. | +++ | D-1 |
| 1107 | 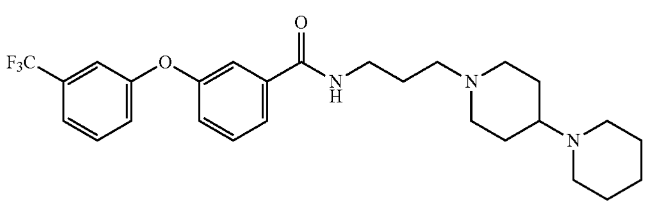 [SMILES: O=C(NCCCN1CCC(N2CCCCC2)CC1)c1cccc(Oc2cccc(C(F)(F)F)c2)c1] | Colorless oil; 1H NMR (400 MHz, CDCl$_3$) δ 7.65 (d, J = 7.6 Hz, 1H), 7.59 (t, J = 8.0 Hz, 1H), 7.53-7.55 (m, 2H), 7.45 (d, J = 7.6 Hz, 1H), 7.21-7.25 (m, 3H), 3.42 (t, J = 7.2 Hz, 2H), 3.06 (d, J = 11.2 Hz, 2H), 2.52-2.60 (m, 4H), 2.44 (t, J = 7.2 Hz, 2H), 2.33 (t, J = 11.2 Hz, 1H), 2.00 (t, J = 12.0 Hz, 2H), 1.79-1.88 (m, 4H), 1.52-1.55 (m, 6H), 1.47-1.50 (m, 2H); LRMS (electrospray) m/z (M + H)$^+$ 490.11. | +++ | D-1 |
| 1108 | 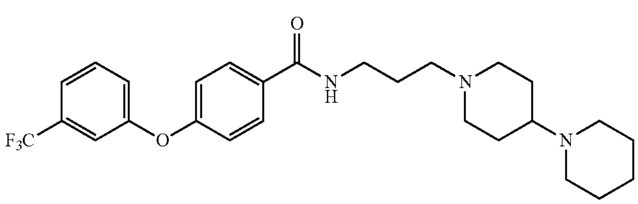 [SMILES: O=C(NCCCN1CCC(N2CCCCC2)CC1)c1ccc(Oc2cccc(C(F)(F)F)c2)cc1] | Pale-yellow oil; 1H NMR (400 MHz, CDCl$_3$) δ 7.88 (d, J = 8.8 Hz, 2H), 7.62 (t, J = 8.4 Hz, 1H), 7.49 (d, J = 8.0 Hz, 1H), 7.26-7.30 (m, 2H), 7.10 (d, J = 8.0 Hz, 2H), 3.44 (t, J = 6.8 Hz, 2H), 3.11 (d, J = 12.0 Hz, 2H), 2.49-2.70 (m, 4H), 2.48 (t, J = 8.0 Hz, 3H), 2.04 (t, J = 12.0 Hz, 2H), 1.94 (d, J = 12.4 Hz, 2H), 1.85 (t, J = 7.2 Hz, 2H), 1.60-1.65 (m, 6H), 1.51-1.53 (m, 2H); | +++ | D-1 |

TABLE 2-continued

Anti-HCV genotype 1/2 activity for Formula II Series

| No. | Structure | Characterization | EC$_{50}$ | Method |
|---|---|---|---|---|
| | | LRMS (electrospray) m/z (M + H)$^+$ 490.13. | | |
| 1109 | 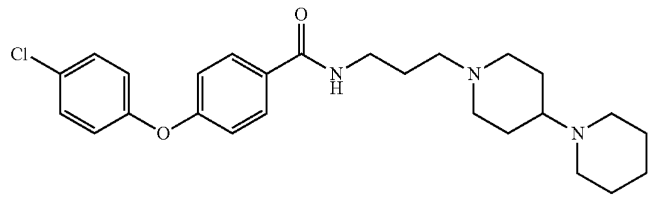 [SMILES: O=C(NCCCN1CCC(N2CCCCC2)CC1)c1ccc(Oc2ccc(Cl)cc2)cc1] | Pale-yellow solid; 1H NMR (400 MHz, CDCl$_3$) δ 7.84 (d, J = 8.8 Hz, 2H), 7.41 (d, J = 8.4 Hz, 2H), 7.06 (t, J = 6.8 Hz, 4H), 3.43 (t, J = 6.4 Hz, 2H), 3.10 (d, J = 11.6 Hz, 2H), 2.54-2.65 (m, 4H), 2.42-2.48 (m, 3H), 2.04 (t, J = 11.6 Hz, 2H), 1.92 (d, J = 12.0 Hz, 2H), 1.84 (t, J = 7.2 Hz, 2H), 1.58-1.64 (m, 6H), 1.50-1.52 (m, 2H); LRMS (electrospray) m/z (M + H)$^+$ 456.09. | ++ | D-1 |
| 1110 | 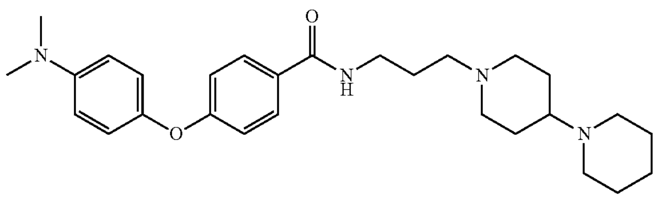 [SMILES: CN(C)c1ccc(Oc2ccc(C(=O)NCCCN3CCC(N4CCCCC4)CC3)cc2)cc1] | Pale-yellow oil; 1H NMR (400 MHz, CDCl$_3$) δ 7.79 (d, J = 8.8 Hz, 2H), 6.95 (t, J = 8.4 Hz, 4H), 6.83 (d, J = 6.8 Hz, 2H), 3.44 (t, J = 3.2 Hz, 2H), 3.17 (d, J = 12.0 Hz, 2H), 2.93-2.98 (m, 5H), 2.92 (s, 6H), 2.55 (t, J = 7.2 Hz, 2H), ), 2.17 (t, J = 12.0 Hz, 2H), 2.04 (d, J = 12.0 Hz, 2H), 1.78-1.87 (m, 8H), 1.59-1.61 (m, 2H); LRMS (electrospray) m/z (M + H)$^+$ 465.14. | +++ | D-1 |
| 1111 | 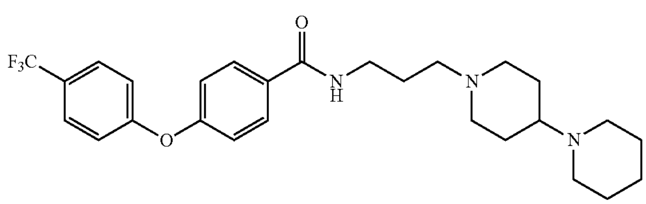 [SMILES: O=C(NCCCN1CCC(N2CCCCC2)CC1)c1ccc(Oc2ccc(C(F)(F)F)cc2)cc1] | Pale-yellow oil; 1H NMR (400 MHz, CDCl$_3$) δ 7.89 (d, J = 8.0 Hz, 2H), 7.71 (d, J = 8.4 Hz, 2H), 7.19 (t, J = 8.4 Hz, 2H), 7.13 (d, J = 7.6 Hz, 2H), 3.44 (t, J = 6.8 Hz, 2H), 3.10 (d, J = 11.6 Hz, 2H), 2.53-2.64 (m, 4H), 2.48 (t, J = 6.8 Hz, 2H), 2.38-2.41 (m, 1H), 2.04 (t, J = 11.6 Hz, 2H), 1.92 (d, J = 12.0 Hz, 2H), 1.86 (t, J = 7.2 Hz, 2H), 1.61-1.65 (m, 6H), 1.49-1.55 (m, 2H); LRMS (electrospray) m/z (M + H)$^+$ 490.11. | +++ | D-1 |
| 1112 | 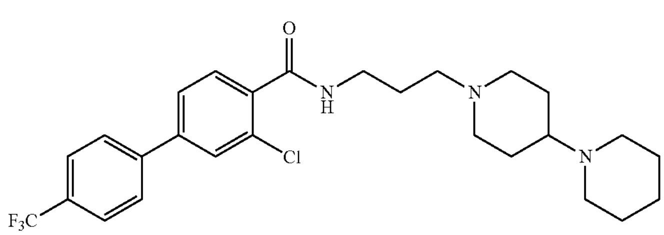 | White solid; $^1$H NMR (400 MHz, acetone); δ 8.41 (s, 1H), 7.85 (d, J = 8.4 Hz, 1H), 7.72 (d, J = 8.0 Hz, 2H), 7.52 (d, J = 8.4 Hz, 1H), 7.40 (t, J = 8.6 Hz, 2H), 3.47-3.51 (m, 2H), 3.01 (t, J = 11.6 Hz, 2H), 2.43-2.48 (m, 6H), 2.15-2.23 (m, 1H), 1.88 (t, J = 12.0 Hz, 2H), 1.78 (t, J = 6.6 Hz, 2H), 1.70 (t, J = 12.0 Hz, 2H), 1.43-1.49 (m, 6H), 1.38 (q, J = 5.5 Hz, 2H); LCMS (electrospray) m/z (M + H)$^+$ 508.19 | +++ | D-1 |

TABLE 2-continued

Anti-HCV genotype 1/2 activity for Formula II Series

| No. | Structure | Characterization | EC$_{50}$ | Method |
|---|---|---|---|---|
| 1113 | 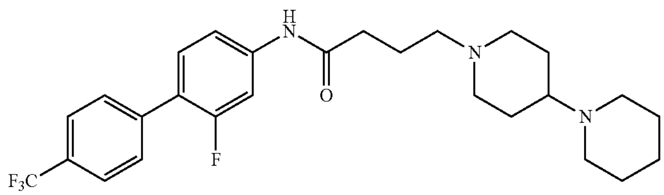 | White solid; $^1$H NMR (400 MHz, acetone); δ 9.50 (s, 1H), 7.89 (d, J = 13.6 Hz, 1H), 7.79 (t, J = 9.6 Hz, 4H), 7.53 (t, J = 8.4 Hz, 1H), 7.46 (d, J = 8.0 Hz, 1H), 2.88-2.94 (m, 5H), 2.32-2.40 (m, 6H), 2.13-2.19 (m, 1H), 1.87 (d, J = 9.2 Hz, 2H), 1.84 (d, J = 6.8 Hz, 2H), 1.64 (d, J = 12.4 Hz, 2H), 1.44-1.50 (m, 5H), 1.35 (q, J = 5.5 Hz, 2H); LCMS (electrospray) m/z (M + H)$^+$ 492.29 | +++ | D-4 |
| 1114 | 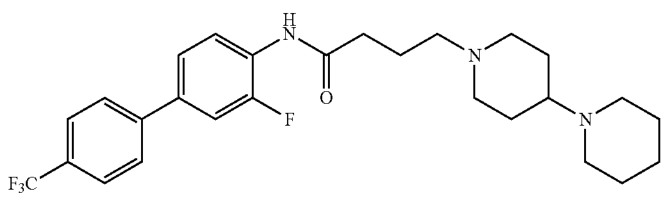 [SMILES: O=C(CCCN1CCC(N2CCCCC2)CC1)Nc1ccc(-c2ccc(C(F)(F)F)cc2)cc1F] | White solid; $^1$H NMR (400 MHz, acetone); δ 9.08 (s, 1H), 8.47 (t, J = 8.6 Hz, 1H), 7.91 (d, J = 8.0 Hz, 2H), 7.80 (d, J = 8.0 Hz, 2H), 7.56-7.59 (m, 2H), 2.94 (d, J = 11.2 Hz, 2H), 2.52 (t, J = 7.0 Hz, 2H), 2.34-2.40 (m, 4H), 2.14-2.20 (m, 1H), 1.99 (d, J = 12.0 Hz, 2H), 1.83-1.89 (m, 4H), 1.65 (d, J = 12.4 Hz, 2H), 1.43-1.50 (m, 6H), 1.35 (q, J = 5.5 Hz, 2H); LCMS (electrospray) m/z (M + H)$^+$ 492.15 | +++ | D-4 |
| 1115 | 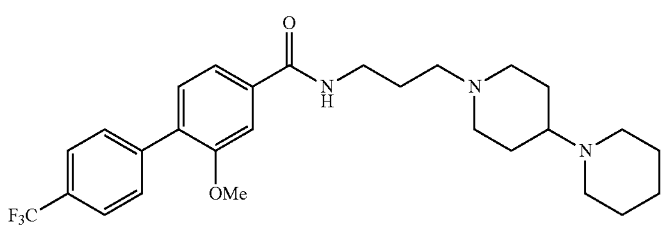 [SMILES: COc1cc(C(=O)NCCCN2CCC(N3CCCCC3)CC2)ccc1-c1ccc(C(F)(F)F)cc1] | White solid; $^1$H NMR (400 MHz, acetone); δ 8.30 (s, 1H), 7.76 (s, 4H), 7.63 (s, 1H), 7.55 (d, J = 8.0 Hz, 1H), 7.43 (d, J = 8.0 Hz, 1H), 3.90 (s, 3H), 3.48 (q, J = 6.4 Hz, 2H), 3.01 (d, J = 11.6 Hz, 2H), 2.44-2.48 (m, 6H), 2.04-2.08 (m, 1H), 1.88 (t, J = 12.0 Hz, 2H), 1.77 (t, J = 6.6 Hz, 2H), 1.71 (d, J = 12.0 Hz, 2H), 1.44-1.54 (m, 6H), 1.37 (q, J = 5.5 Hz, 2H); LCMS (electrospray) m/z (M + H)$^+$ 504.26 | +++ | D-1 |
| 1116 | 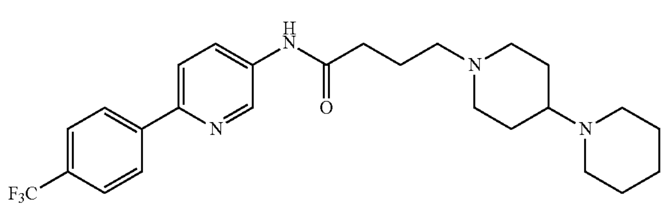 [SMILES: O=C(CCCN1CCC(N2CCCCC2)CC1)Nc1ccc(-c2ccc(C(F)(F)F)cc2)nc1] | White solid; $^1$H NMR (400 MHz, acetone); δ 9.50 (s, 1H), 8.85 (d, J = 2.4 Hz, 1H), 8.25 (dd, J = 2.4 and 8.8 Hz, 2H), 7.92 (d, J = 8.8 Hz, 1H), 7.76 (d, J = 8.4 Hz, 2H), 3.03 (d, J = 11.6 Hz, 2H), 2.40-2.47 (m, 8H), 2.21-2.30 (m, 1H), 1.90 (t, J = 12.0 Hz, 2H), 1.88 (t, J = 6.6 Hz, 2H), 1.82 (d, J = 12.4 Hz, 2H), 1.50-1.58 (m, 6H), 1.42 (q, J = 5.5 Hz, 2H); LCMS (electrospray) m/z (M + H)$^+$ 475.14 | +++ | D-4 |

TABLE 2-continued

Anti-HCV genotype 1/2 activity for Formula II Series

| No. | Structure | Characterization | EC$_{50}$ | Method |
|---|---|---|---|---|
| 1117 | 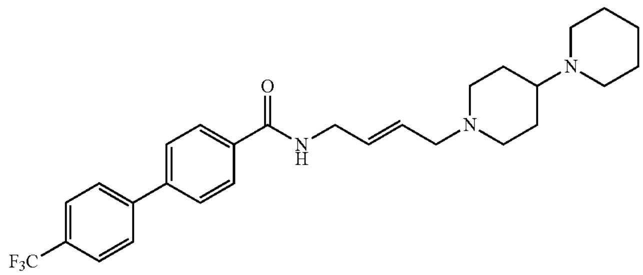 [SMILES: O=C(NC/C=C/CN1CCC(N2CCCCC2)CC1)c1ccc(-c2ccc(C(F)(F)F)cc2)cc1] | Yellow oil; $^1$H NMR (400 MHz, acetone); δ 8.25 (s, 1H), 7.96 (d, J = 8.8 Hz, 2H), 7.43 (d, J = 8.0 Hz, 2H), 7.08 (d, J = 8.0 Hz, 2H), 7.02 (d, J = 6.8 Hz, 2H), 5.62 (d, J = 1.6 Hz, 2H), 3.99 (t, J = 4.4 Hz, 2H), 2.92 (d, J = 5.2 Hz, 2H), 2.32-2.41 (m, 1H), 1.89 (t, J = 12.0 Hz, 2H), 1.74 (d, J = 12.0 Hz, 2H), 1.54-1.65 (m, 6H), 1.42 (q, J = 5.5 Hz, 2H); LCMS (electrospray) m/z (M + H)$^+$ 486.16 | +++ | D-1 |
| 1118 | 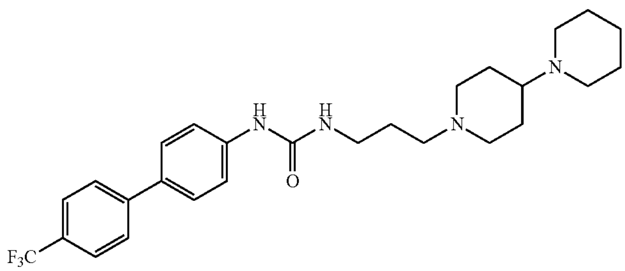 [SMILES: O=C(NCCCN1CCC(N2CCCCC2)CC1)Nc1ccc(-c2ccc(C(F)(F)F)cc2)cc1] | White solid; $^1$H NMR (400 MHz, cd$_3$od) δ 7.77 (d, J = 8.2 Hz, 2H), 7.69 (d, J = 8.3 Hz, 2H), 7.60 (d, J = 8.6 Hz, 2H), 7.49 (d, J = 8.6 Hz, 2H), 3.24 (t, J = 6.8 Hz, 2H), 3.04 (d, J = 11.8 Hz, 2H), 2.55 (s, 4H), 2.41 (t, J = 6.0 Hz, 2H), 2.32-2.22 (m, 2H), 1.98 (t, J = 11.9 Hz, 2H), 1.87 (d, J = 12.5 Hz, 2H), 1.78-1.70 (m, 2H), 1.65-1.44 (m, 10H); LCMS (electrospray) m/z (M + H)$^+$ 489.16 | +++ | D-4 |
| 1119 | 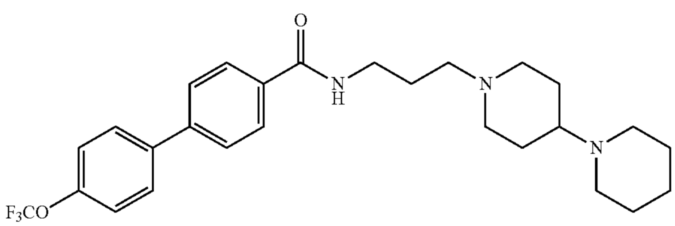 [SMILES: O=C(NCCCN1CCC(N2CCCCC2)CC1)c1ccc(-c2ccc(OC(F)(F)F)cc2)cc1] | White solid; $^1$H NMR (400 MHz, cd$_3$od) δ 7.91 (d, J = 8.3 Hz, 2H), 7.75 (dd, J = 11.5, 8.6 Hz, 4H), 7.38 (d, J = 8.3 Hz, 2H), 3.44 (t, J = 6.8 Hz, 2H), 3.06 (d, J = 11.9 Hz, 2H), 2.54 (t, J = 4.0 Hz, 4H), 2.46 (t, J = 8.0 Hz, 2H), 2.34-2.23 (m, 1H), 1.98 (t, J = 11.2 Hz, 2H), 1.90-1.79 (m, 4H), 1.65-1.41 (m, 10H); LCMS (electrospray) m/z (M + H)$^+$ 490.38 | +++ | D-1 |
| 1120 | 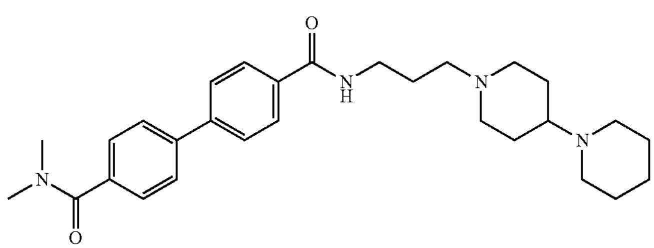 [SMILES: CN(C)C(=O)c1ccc(-c2ccc(C(=O)NCCCN3CCC(N4CCCCC4)CC3)cc2)cc1] | White solid; $^1$H NMR (400 MHz, cd$_3$od) δ 7.92 (d, J = 8.3 Hz, 2H), 7.78 (d, J = 8.2 Hz, 4H), 7.54 (d, J = 8.2 Hz, 2H), 3.45 (t, J = 6.3 Hz, 2H), 3.13 (s, 3H), 3.09 (s, 1H), 3.05 (s, 3H), 2.54 (s, 4H), 2.47 (t, J = 8.0 Hz, 2H), 2.34-2.23 (m, 1H), 1.99 (t, J = 11.4 Hz, 2H), 1.90-1.80 (m, 4H), 1.64-1.41 (m, 8H); LCMS (electrospray) m/z (M + H)$^+$ 477.32 | + | D-1 |
| 1121 | 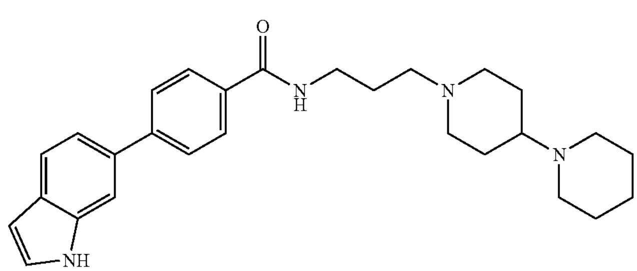 [SMILES: O=C(NCCCN1CCC(N2CCCCC2)CC1)c1ccc(-c2ccc3cc[nH]c3c2)cc1] | Brown solid; $^1$H NMR (400 MHz, cd$_3$od) δ 7.88 (d, J = 8.3 Hz, 2H), 7.76 (d, J = 8.4 Hz, 2H), 7.68 (s, 1H), 7.63 (d, J = 8.2 Hz, 1H), 7.36 (d, J = 1.4 Hz, 1H), 7.29 (d, J = 3.1 Hz, 1H), 6.47 (d, J = 3.0 Hz, 1H), 3.45 (t, J = 6.8 Hz, 2H), 3.07 (d, J = 11.7 Hz, 2H), 2.54 (s, 4H), 2.47 (t, J = 8.0 Hz, 2H), 2.35-2.22 (m, 1H), 1.98 (t, J = 11.4 Hz, 2H), 1.89-1.80 (m, | +++ | D-1 |

TABLE 2-continued

Anti-HCV genotype 1/2 activity for Formula II Series

| No. | Structure | Characterization | EC$_{50}$ | Method |
|---|---|---|---|---|
| | | 4H), 1.64-1.40 (m, 8H); LCMS (electrospray) m/z (M + H)$^+$ 445.21 | | |
| 1122 | 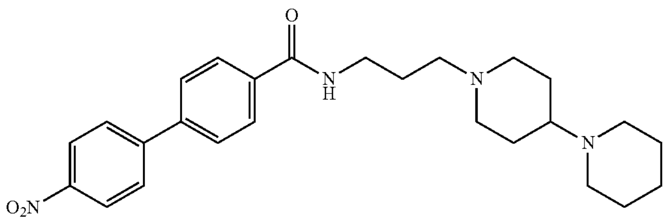 [SMILES: O=C(NCCCN1CCC(N2CCCCC2)CC1)c1ccc(-c2ccc([N+](=O)[O-])cc2)cc1] | Yellow oil; $^1$H NMR (400 MHz, cd$_3$od) δ 8.32 (d, J = 8.8 Hz, 2H), 7.92 (dd, J = 13.1, 8.6 Hz, 4H), 7.82 (d, J = 8.4 Hz, 2H), 3.44 (t, J = 6.8 Hz, 2H), 3.05 (d, J = 11.8 Hz, 2H), 2.53 (s, 4H), 2.45 (t, J = 6.8 Hz, 2H), 2.33-2.22 (m, 1H), 1.97 (t, J = 11.4 Hz, 2H), 1.90-1.78 (m, 4H), 1.63-1.39 (m, 8H); LCMS (electrospray) m/z (M + H)$^+$ 451.19 | +++ | D-1 |
| 1123 | 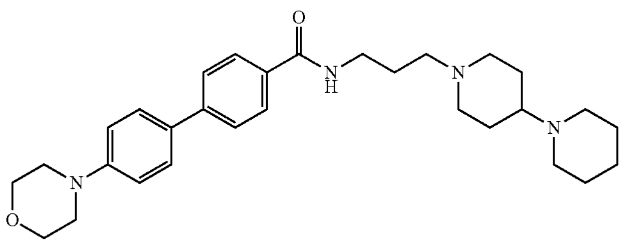 [SMILES: O=C(NCCCN1CCC(N2CCCCC2)CC1)c1ccc(-c2ccc(N3CCOCC3)cc2)cc1] | Brown solid; $^1$H NMR (400 MHz, cd$_3$od) δ 7.84 (d, J = 8.3 Hz, 2H), 7.68 (d, J = 8.3 Hz, 2H), 7.59 (d, J = 8.7 Hz, 2H), 7.05 (d, J = 8.8 Hz, 2H), 3.85 (t, J = 6.0 Hz, 4H), 3.43 (t, J = 6.7 Hz, 2H), 3.22-3.18 (m, 4H), 3.06 (d, J = 11.8 Hz, 2H), 2.53 (s, 4H), 2.46 (t, J = 8.0 Hz, 2H), 2.33-2.23 (m, 1H), 1.97 (t, J = 11.9 Hz, 2H), 1.88-1.78 (m, 4H), 1.63-1.40 (m, 8H); LCMS (electrospray) m/z (M + H)$^+$ 491.20 | +++ | D-1 |
| 1124 | 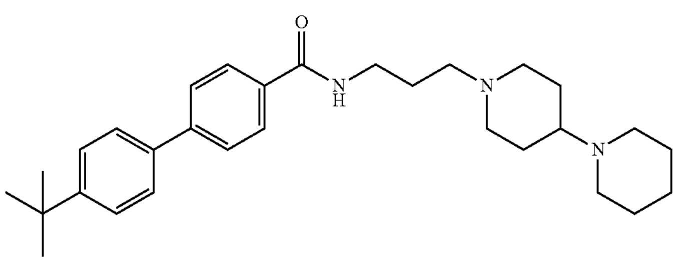 [SMILES: CC(C)(C)c1ccc(-c2ccc(C(=O)NCCCN3CCC(N4CCCCC4)CC3)cc2)cc1] | White solid; $^1$H NMR (400 MHz, cd$_3$od) δ 7.87 (d, J = 8.3 Hz, 2H), 7.70 (d, J = 8.3 Hz, 2H), 7.59 (d, J = 8.4 Hz, 2H), 7.49 (d, J = 8.4 Hz, 2H), 3.43 (t, J = 6.8 Hz, 2H), 3.04 (d, J = 11.8 Hz, 2H), 2.51 (s, 4H), 2.44 (t, J = 8.0 Hz, 2H), 2.31-2.19 (m, 1H), 1.95 (t, J = 11.3 Hz, 2H), 1.86-1.77 (m, 4H), 1.62-1.38 (m, 8H), 1.34 (s, 9H); LCMS (electrospray) m/z (M + H)$^+$ 462.42 | +++ | D-1 |
| 1125 | 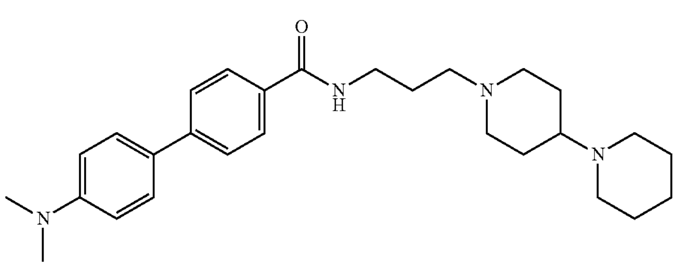 [SMILES: CN(C)c1ccc(-c2ccc(C(=O)NCCCN3CCC(N4CCCCC4)CC3)cc2)cc1] | Pink solid; $^1$H NMR (400 MHz, cd$_3$od) δ 7.82 (d, J = 8.4 Hz, 2H), 7.65 (d, J = 8.4 Hz, 2H), 7.55 (d, J = 8.8 Hz, 2H), 6.83 (d, J = 8.8 Hz, 2H), 3.42 (t, J = 6.8 Hz, 2H), 3.04 (d, J = 11.9 Hz, 2H), 2.97 (s, 6H), 2.51 (t, J = 6.0 Hz, 4H), 2.44 (t, J = 8.0 Hz, 2H), 2.30-2.21 (m, 1H), 1.95 (t, J = 11.3 Hz, 2H), 1.88-1.77 (m, 4H), 1.62-1.39 (m, 8H); LCMS (electrospray) m/z (M + H)$^+$ 449.15 | +++ | D-1 |

TABLE 2-continued

Anti-HCV genotype 1/2 activity for Formula II Series

| No. | Structure | Characterization | EC$_{50}$ | Method |
|---|---|---|---|---|
| 1126 | 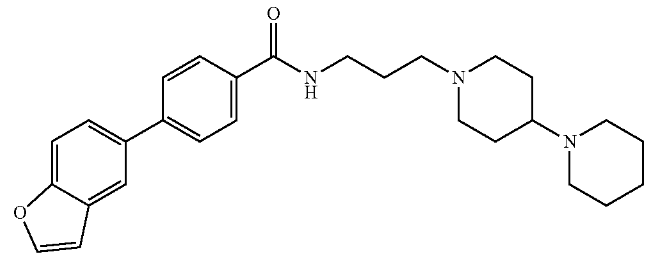 [SMILES: O=C(NCCCN1CCC(N2CCCCC2)CC1)c1ccc(-c2ccc3occc3c2)cc1] | White solid; $^1$H NMR (400 MHz, cd$_3$od) δ 7.88 (d, J = 8.2 Hz, 3H), 7.78 (d, J = 2.1 Hz, 1H), 7.72 (d, J = 8.3 Hz, 2H), 7.57 (s, 2H), 6.88 (d, J = 2.0 Hz, 1H), 3.43 (t, J = 6.7 Hz, 2H), 3.02 (d, J = 11.7 Hz, 2H), 2.48 (s, 4H), 2.43 (t, J = 6.0 Hz, 2H), 2.28-2.17 (m, 1H), 1.92 (t, J = 11.4 Hz, 2H), 1.86-1.75 (m, 4H), 1.61-1.38 (m, 8H); LCMS (electrospray) m/z (M + H)$^+$ 446.23 | +++ | D-1 |
| 1127 | 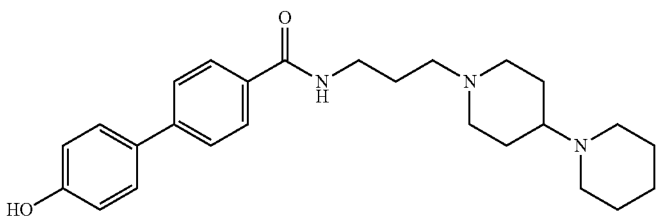 [SMILES: O=C(NCCCN1CCC(N2CCCCC2)CC1)c1ccc(-c2ccc(O)cc2)cc1] | Yellow oil; $^1$H NMR (400 MHz, cd$_3$od) δ 7.83 (d, J = 7.6 Hz, 2H), 7.64 (d, J = 7.8 Hz, 2H), 7.51 (d, J = 8.0 Hz, 2H), 6.87 (d, J = 7.9 Hz, 2H), 3.43 (t, J = 6.6 Hz, 2H), 3.05 (d, J = 11.2 Hz, 2H), 2.52 (s, 4H), 2.45 (t, J = 7.2 Hz, 2H), 2.31-2.20 (m, 1H), 1.96 (t, J = 11.8 Hz, 2H), 1.89-1.77 (m, 4H), 1.64-1.39 (m, 8H); LCMS (electrospray) m/z (M + H)$^+$ 422.21 | ++ | D-1 |
| 1128 | 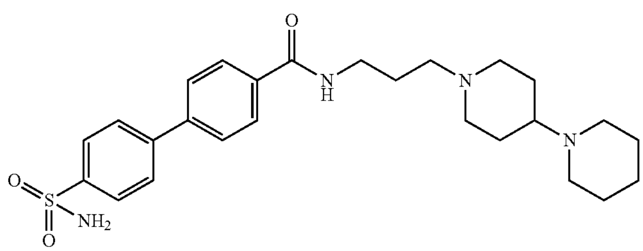 [SMILES: NS(=O)(=O)c1ccc(-c2ccc(C(=O)NCCCN3CCC(N4CCCCC4)CC3)cc2)cc1] | Brown solid; $^1$H NMR (400 MHz, cd$_3$od) δ 8.00 (d, J = 7.3 Hz, 2H), 7.93 (d, J = 7.3 Hz, 2H), 7.85 (d, J = 7.3 Hz, 2H), 7.79 (d, J = 7.3 Hz, 2H), 3.45 (t, J = 6.5 Hz, 2H), 3.07 (d, J = 11.4 Hz, 2H), 2.54 (s, 4H), 2.46 (t, J = 7.4 Hz, 2H), 2.35-2.22 (m, 1H), 1.98 (t, J = 11.8 Hz, 2H), 1.90-1.78 (m, 4H), 1.64-1.39 (m, 8H); LCMS (electrospray) m/z (M + H)$^+$ 485.14 | + | D-1 |
| 1129 | 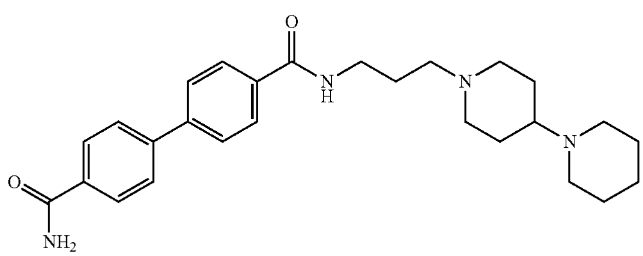 [SMILES: NC(=O)c1ccc(-c2ccc(C(=O)NCCCN3CCC(N4CCCCC4)CC3)cc2)cc1] | Yellow oil; $^1$H NMR (400 MHz, cd$_3$od) δ 7.98 (d, J = 8.1 Hz, 2H), 7.91 (d, J = 8.2 Hz, 2H), 7.82-7.74 (m, J = 12.6, 7.1 Hz, 4H), 3.63 (s, 1H), 3.44 (t, J = 6.4 Hz, 2H), 3.06 (d, J = 11.1 Hz, 2H), 2.54 (s, 4H), 2.46 (t, J = 7.2 Hz, 2H), 2.34-2.24 (m, 2H), 1.98 (t, J = 11.6 Hz, 2H), 1.91-1.78 (m, 4H), 1.64-1.40 (m, 8H); LCMS (electrospray) m/z (M + H)$^+$ 449.15 | + | D-1 |
| 1130 | 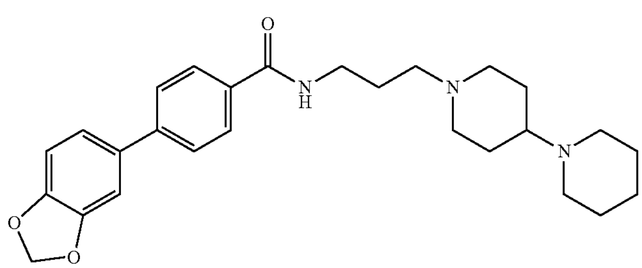 [SMILES: O=C(NCCCN1CCC(N2CCCCC2)CC1)c1ccc(-c2ccc3c(c2)OCO3)cc1] | Brown solid; $^1$H NMR (400 MHz, cd$_3$od) δ 7.87-7.82 (m, J = 8.3 Hz, 2H), 7.64 (d, J = 8.4 Hz, 2H), 7.18-7.14 (m, 2H), 6.91 (d, J = 8.5 Hz, 1H), 6.00 (s, 2H), 3.43 (t, J = 6.8 Hz, 2H), 3.06 (d, J = 11.9 Hz, 2H), 2.54 (s, 4H), 2.46 (t, J = 7.4 Hz, 2H), 2.33-2.23 (m, 1H), 1.97 (t, J = 12.0 Hz, 2H), 1.89-1.77 (m, 4H), 1.64-1.40 (m, 8H); LCMS (electrospray) m/z (M + H)$^+$ 450.31 | +++ | D-1 |

TABLE 2-continued

Anti-HCV genotype 1/2 activity for Formula II Series

| No. | Structure | Characterization | EC$_{50}$ | Method |
|-----|-----------|------------------|-----------|--------|
| 1131 | 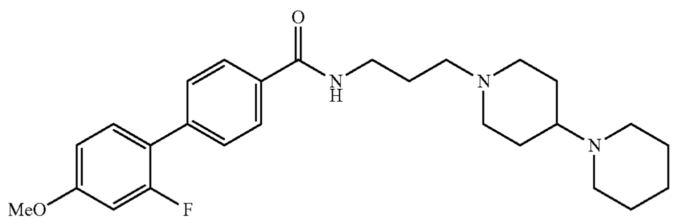 [SMILES: COc1ccc(-c2ccc(C(=O)NCCCN3CCC(N4CCCCC4)CC3)cc2)c(F)c1] | Oil; $^1$H NMR (400 MHz, CD$_3$OD) δ 7.87 (d, J = 8.4 Hz, 2H), 7.59 (d, J = 8.4 Hz, 2H), 7.43 (t, J = 8.8 Hz, 2H), 6.87-6.78 (m, 2H), 3.84 (s, 3H), 3.44 (t, J = 6.6 Hz, 2H), 3.05 (d, J = 11.6 Hz, 2H), 2.55 (s, 4H), 2.46 (t, J = 6.8 Hz, 2H), 2.31-2.25 (m, 1H), 1.97 (t, J = 7.4 Hz, 2H), 1.86-1.81 (m, 4H), 1.62-1.51 (m, 6H), 1.46-1.45 (m, 2H); LRMS (electrospray) m/z (M + H)$^+$ 454.25. | +++ | D-1 |
| 1132 | 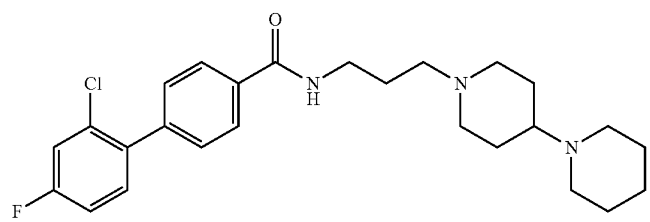 | Oil; $^1$H NMR (400 MHz, CD$_3$OD) δ 7.89 (d, J = 10.1 Hz, 2H), 7.50 (d, J = 8.4 Hz, 2H), 7.41 (dd, J = 8.6, 6.1 Hz, 1H), 7.35 (dd, J = 8.7, 2.6 Hz, 1H), 7.18 (t, J = 8.4 Hz, 1H), 3.44 (t, J = 6.6 Hz, 2H), 3.07 (d, J = 11.6 Hz, 2H), 2.55 (s, 4H), 2.46 (t, J = 6.8 Hz, 2H), 2.31-2.29 (m, 1H), 1.98 (t, J = 7.4 Hz, 2H), 1.91-1.78 (m, 4H), 1.68-1.54 (m, 6H), 1.50-1.41 (m, 2H); LRMS (electrospray) m/z (M + H)$^+$ 459.20. | +++ | D-1 |
| 1133 | 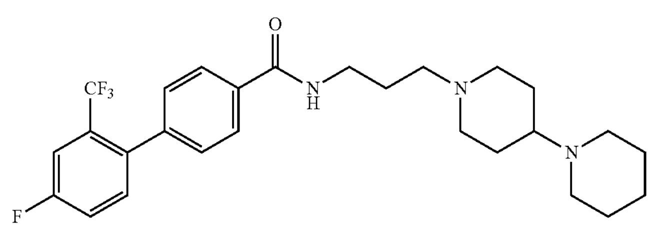 [SMILES: O=C(NCCCN1CCC(N2CCCCC2)CC1)c1ccc(-c2ccc(F)cc2C(F)(F)F)cc1] | Oil; $^1$H NMR (400 MHz, CD$_3$OD) δ 7.85 (d, J = 8.4 Hz, 2H), 7.57 (d, J = 8.4 Hz, 1H), 7.47-7.39 (m, 4H), 3.44 (t, J = 6.6 Hz, 2H), 3.07 (d, J = 11.6 Hz, 2H), 2.55 (s, 4H), 2.46 (t, J = 6.8 Hz, 2H), 2.29-2.27 (m, 1H), 1.99 (t, J = 7.4 Hz, 2H), 1.88-1.80 (m, 4H), 1.61-1.53 (m, 6H), 1.47-1.46 (m, 2H); LRMS (electrospray) m/z (M + H)$^+$ 492.22. | +++ | D-1 |
| 1134 | 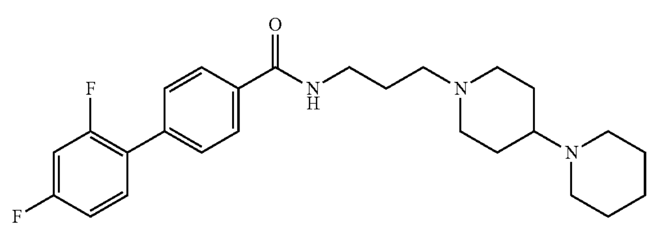 [SMILES: O=C(NCCCN1CCC(N2CCCCC2)CC1)c1ccc(-c2ccc(F)cc2F)cc1] | Oil; $^1$H NMR (400 MHz, CD$_3$OD) δ 7.90 (d, J = 8.1 Hz, 2H), 7.62 (d, J = 8.1 Hz, 2H), 7.55 (dd, J = 15.3, 8.1 Hz, 1H), 7.08 (t, J = 9.0 Hz, 2H), 3.46 (t, J = 6.6 Hz, 2H), 3.07 (d, J = 11.6 Hz, 2H), 2.62 (s, 4H), 2.48 (t, J = 6.8 Hz, 2H), 2.46-2.39 (m, 1H), 2.01 (t, J = 7.4 Hz, 2H), 1.87-1.81 (m, 4H), 1.64-1.54 (m, 6H), 1.49-1.48 (m, 2H); LRMS (electrospray) m/z (M + H)$^+$ 442.21. | +++ | D-1 |
| 1135 | 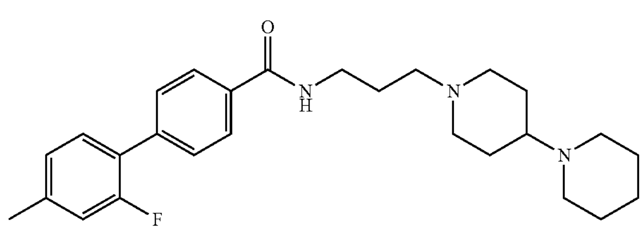 [SMILES: Cc1ccc(-c2ccc(C(=O)NCCCN3CCC(N4CCCCC4)CC3)cc2)c(F)c1] | Oil; $^1$H NMR (400 MHz, CD$_3$OD) δ 7.88 (d, J = 8.3 Hz, 2H), 7.62 (d, J = 7.4 Hz, 2H), 7.38 (t, J = 8.1 Hz, 1H), 7.09 (d, J = 7.9 Hz, 1H), 7.03 (d, J = 12.1 Hz, 1H), 3.31 (t, J = 6.6 Hz, 2H), 3.07 (d, J = 11.6 Hz, 2H), 2.58 (s, 4H), 2.46 (t, J = 6.8 Hz, 2H), 2.36 (s, 3H), 2.33-2.31 (m, 1H), | +++ | D-1 |

TABLE 2-continued

Anti-HCV genotype 1/2 activity for Formula II Series

| No. | Structure | Characterization | EC$_{50}$ | Method |
|---|---|---|---|---|
| | | 2.00 (t, J = 7.4 Hz, 2H), 1.89-1.81 (m, 4H), 1.64-1.55 (m, 6H), 1.48-1.46 (m, 2H); LRMS (electrospray) m/z (M + H)$^+$ 438.27. | | |
| 1136 | 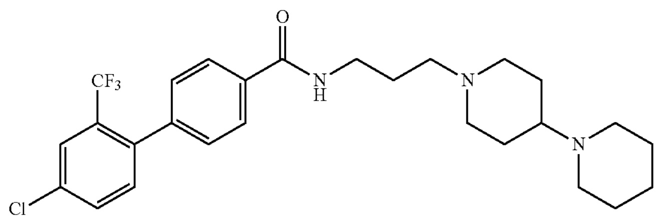 [SMILES: O=C(NCCCN1CCC(N2CCCCC2)CC1)c1ccc(-c2ccc(Cl)cc2C(F)(F)F)cc1] | Oil<br>$^1$H NMR (400 MHz, CD$_3$OD) δ 7.87 (d, J = 7.5 Hz, 2H), 7.80 (d, J = 9.0 Hz, 1H), 7.70 (d, J = 8.3 Hz, 1H), 7.44-7.35 (m, 3H), 3.46 (t, J = 6.6 Hz, 2H), 3.05 (d, J = 11.6 Hz, 2H), 2.55 (s, 4H), 2.44 (t, J = 6.8 Hz, 2H), 2.30-2.27 (m, 1H), 2.01 (t, J = 7.4 Hz, 2H), 1.87-1.81 (m, 4H), 1.61-1.54 (m, 6H), 1.47-1.45 (m, 2H); LRMS (electrospray) m/z (M + H)$^+$ 509.20. | +++ | D-1 |
| 1137 | 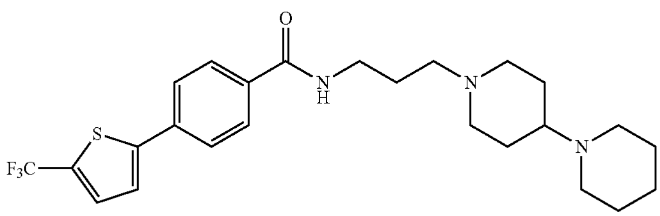 [SMILES: O=C(NCCCN1CCC(N2CCCCC2)CC1)c1ccc(-c2ccc(C(F)(F)F)s2)cc1] | Oil<br>$^1$H NMR (400 MHz, CD$_3$OD) δ 7.89 (d, J = 8.4 Hz, 2H), 7.79 (d, J = 8.4 Hz, 2H), 7.55 (d, J = 4.2 Hz, 1H), 7.53 (d, J = 4.2 Hz, 1H), 3.43 (t, J = 6.8 Hz, 2H), 3.06 (d, J = 11.9 Hz, 2H), 2.57 (s, 4H), 2.48 (t, J = 6.8 Hz, 2H), 2.40-2.28 (m, 1H), 1.98 (t, J = 11.3 Hz, 2H), 1.84-1.81 (m, 4H), 1.65-1.53 (m, 6H), 1.49-1.48 (m, 2H); LRMS (electrospray) m/z (M + H)$^+$ 480.18. | +++ | D-1 |
| 1138 | 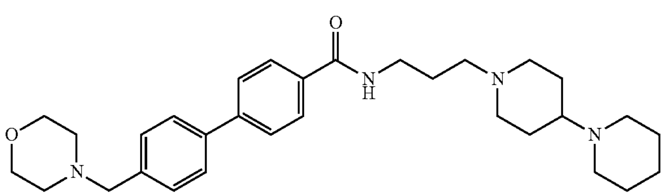 [SMILES: O=C(NCCCN1CCC(N2CCCCC2)CC1)c1ccc(-c2ccc(CN3CCOCC3)cc2)cc1] | Brown solid; $^1$H NMR (400 MHz, cd$_3$od) δ 7.88 (t, J = 8.4 Hz, 2H), 7.72 (d, J = 8.4 Hz, 2H), 7.64 (d, J = 8.2 Hz, 2H), 7.45 (d, J = 8.2 Hz, 2H), 3.73-3.67 (m, 4H), 3.57 (s, 2H), 3.44 (t, J = 6.8 Hz, 2H), 3.06 (d, J = 11.9 Hz, 2H), 2.54 (s, 4H), 2.51-2.42 (m, 6H), 2.36-2.23 (m, 1H), 1.98 (t, J = 11.2 Hz, 2H), 1.91-1.78 (m, 4H), 1.63-1.40 (m, 8H); LCMS (electrospray) m/z (M + H)$^+$ 505.35 | ++ | D-1 |
| 1139 | 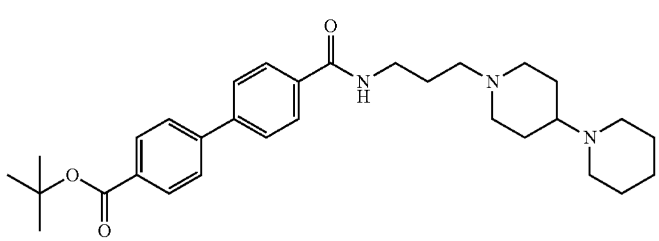 [SMILES: CC(C)(C)OC(=O)c1ccc(-c2ccc(C(=O)NCCCN3CCC(N4CCCCC4)CC3)cc2)cc1] | $^1$H NMR (400 MHz, cd$_3$od) δ 8.04 (d, J = 8.3 Hz, 2H), 7.91 (d, J = 8.3 Hz, 2H), 7.77 (t, J = 8.2 Hz, 4H), 3.44 (t, J = 6.8 Hz, 2H), 3.05 (d, J = 11.8 Hz, 2H), 2.53 (s, 4H), 2.45 (t, J = 7.4 Hz, 2H), 2.32-2.23 (m, 1H), 1.97 (t, J = 11.8 Hz, 2H), 1.88-1.76 (m, 4H), 1.61 (s, 9H), 1.60-1.42 (m, 8H); LCMS (electrospray) m/z (M + H)$^+$ 506.37 | +++ | D-1 |

TABLE 2-continued

Anti-HCV genotype 1/2 activity for Formula II Series

| No. | Structure | Characterization | EC$_{50}$ | Method |
|---|---|---|---|---|
| 1140 | 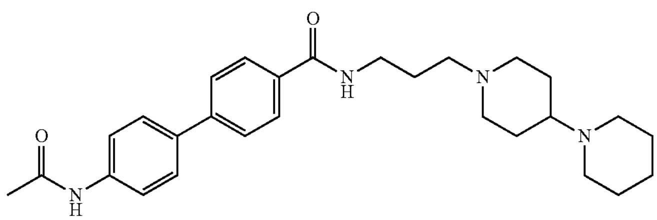 [SMILES: CC(=O)Nc1ccc(-c2ccc(C(=O)NCCCN3CCC(N4CCCCC4)CC3)cc2)cc1] | White solid; $^1$H NMR (400 MHz, cd$_3$od) δ 7.88 (t, J = 8.4 Hz, 2H), 7.71 (d, J = 8.4 Hz, 2H), 7.66 (q, J = 8.8 Hz, 4H), 3.44 (t, J = 6.8 Hz, 2H), 3.07 (d, J = 11.9 Hz, 2H), 2.54 (d, J = 4.8 Hz, 4H), 2.46 (t, J = 7.4 Hz, 2H), 2.34-2.23 (m, 2H), 2.15 (s, 3H), 1.98 (t, J = 12.2 Hz, 2H), 1.90-1.79 (m, 4H), 1.64-1.41 (m, 8H); LCMS (electrospray) m/z (M + H)$^+$ 463.30 | + | D-1 |
| 1141 | 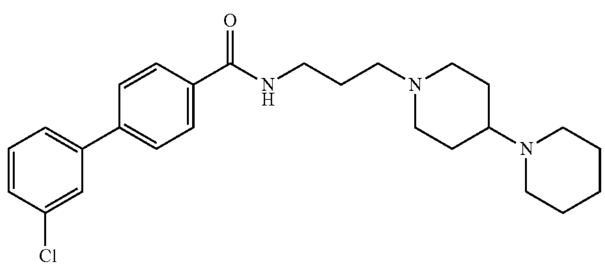 [SMILES: O=C(NCCCN1CCC(N2CCCCC2)CC1)c1ccc(-c2cccc(Cl)c2)cc1] | White solid; $^1$H NMR (400 MHz, cd$_3$od) δ 7.90 (d, J = 8.2 Hz, 2H), 7.71 (d, J = 8.2 Hz, 2H), 7.66 (s, 1H), 7.58 (d, J = 7.6 Hz, 1H), 7.44 (t, J = 7.8 Hz, 1H), 7.38 (d, J = 7.9 Hz, 1H), 3.44 (t, J = 6.7 Hz, 2H), 3.05 (d, J = 11.5 Hz, 2H), 2.54 (s, 4H), 2.45 (t, J = 7.4 Hz, 2H), 2.36-2.21 (m, 1H), 1.96 (t, J = 11.6 Hz, 2H), 1.89-1.77 (m, 4H), 1.64-1.37 (m, 8H); LCMS (electrospray) m/z (M + H)$^+$ 440.17 | +++ | D-1 |
| 1142 | 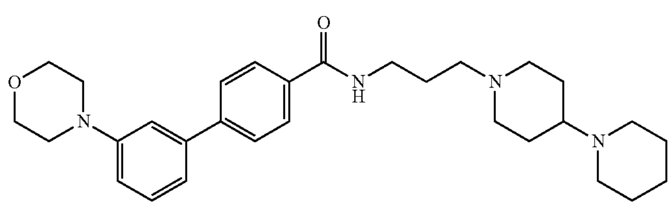 [SMILES: O=C(NCCCN1CCC(N2CCCCC2)CC1)c1ccc(-c2cccc(N3CCOCC3)c2)cc1] | Brown solid; $^1$H NMR (400 MHz, cd$_3$od) δ 7.87 (d, J = 8.2 Hz, 2H), 7.69 (d, J = 8.2 Hz, 2H), 7.33 (t, J = 7.9 Hz, 1H), 7.20 (s, 1H), 7.13 (d, J = 7.5 Hz, 1H), 6.99 (d, J = 8.1 Hz, 1H), 3.84 (t, J = 4.6 Hz, 4H), 3.43 (t, J = 6.7 Hz, 2H), 3.19 (t, J = 4.6 Hz, 4H), 3.05 (d, J = 11.6 Hz, 2H), 2.52 (s, 4H), 2.45 (t, J = 7.4 Hz, 2H), 2.32-2.21 (m, 1H), 1.96 (t, J = 11.7 Hz, 2H), 1.88-1.76 (m, 4H), 1.63-1.39 (m, 8H); LCMS (electrospray) m/z (M + H)$^+$ 491.33 | ++ | D-1 |
| 1143 | 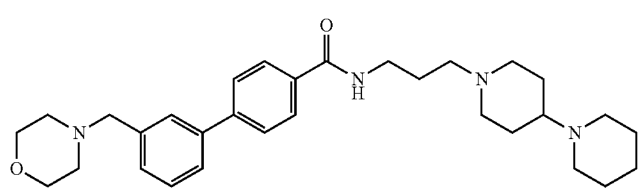 [SMILES: O=C(NCCCN1CCC(N2CCCCC2)CC1)c1ccc(-c2cccc(CN3CCOCC3)c2)cc1] | White solid; $^1$H NMR (400 MHz, cd$_3$od) δ 7.89 (d, J = 8.0 Hz, 2H), 7.72 (d, J = 7.7 Hz, 2H), 7.65 (s, 1H), 7.57 (d, J = 7.5 Hz, 1H), 7.42 (t, J = 7.6 Hz, 1H), 7.35 (d, J = 7.4 Hz, 1H), 3.68 (t, J = 4.4 Hz, 4H), 3.58 (s, 2H), 3.43 (t, J = 6.7 Hz, 2H), 3.05 (d, J = 11.5 Hz, 2H), 2.57-2.36 (m, 10H), 2.26 (t, J = 11.7 Hz, 1H), 1.96 (t, J = 11.8 Hz, 2H), 1.88-1.76 (m, 4H), 1.63-1.38 (m, 8H); LCMS (electrospray) m/z (M + H)$^+$ 505.35 | ++ | D-1 |

TABLE 2-continued

Anti-HCV genotype 1/2 activity for Formula II Series

| No. | Structure | Characterization | EC$_{50}$ | Method |
|---|---|---|---|---|
| 1144 | 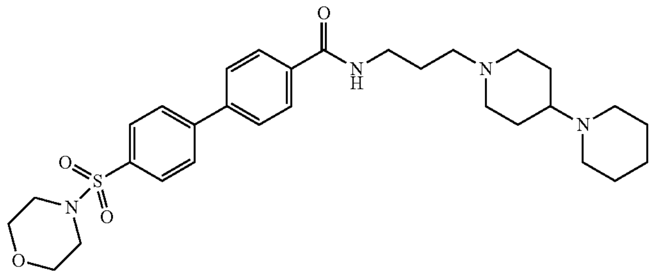 [SMILES: O=C(NCCCN1CCC(N2CCCCC2)CC1)c1ccc(-c2ccc(S(=O)(=O)N3CCOCC3)cc2)cc1] | White solid; $^1$H NMR (400 MHz, cd$_3$od) δ 7.94 (d, J = 8.4 Hz, 4H), 7.87 (d, J = 8.5 Hz, 2H), 7.82 (d, J = 8.4 Hz, 2H), 3.72 (t, J = 4.6 Hz, 4H), 3.45 (t, J = 6.8 Hz, 2H), 3.07 (d, J = 11.9 Hz, 2H), 3.01 (t, J = 4.8 Hz, 4H), 2.55 (s, 4H), 2.47 (t, J = 7.4 Hz, 2H), 2.36-2.25 (m, 1H), 1.99 (t, J = 11.1 Hz, 2H), 1.91-1.79 (m, 4H), 1.63-1.40 (m, 8H); LCMS (electrospray) m/z (M + H)$^+$ 555.28 | ++ | D-1 |
| 1145 | 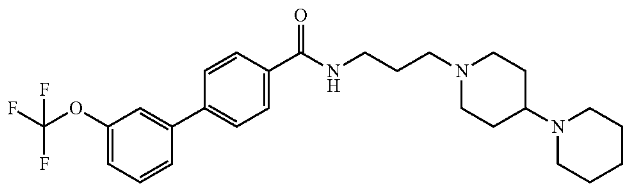 [SMILES: O=C(NCCCN1CCC(N2CCCCC2)CC1)c1ccc(-c2cccc(OC(F)(F)F)c2)cc1] | White solid; $^1$H NMR (400 MHz, cd$_3$od) δ 7.91 (d, J = 8.1 Hz, 2H), 7.73 (d, J = 8.1 Hz, 2H), 7.67 (d, J = 7.9 Hz, 1H), 7.56-7.51 (m, 2H), 7.30 (d, J = 8.2 Hz, 1H), 3.43 (t, J = 6.7 Hz, 2H), 3.05 (d, J = 11.6 Hz, 2H), 2.52 (s, 4H), 2.45 (t, J = 7.4 Hz, 2H), 2.33-2.19 (m, 1H), 1.96 (t, J = 11.8 Hz, 2H), 1.89-1.76 (m, 4H), 1.65-1.38 (m, 8H); LCMS (electrospray) m/z (M + H)$^+$ 490.24 | +++ | D-1 |
| 1146 | 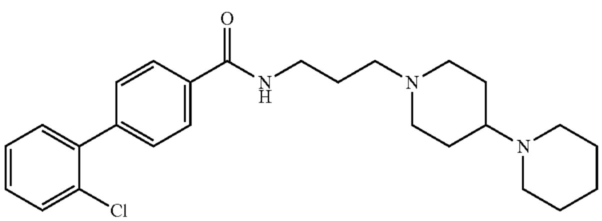 [SMILES: O=C(NCCCN1CCC(N2CCCCC2)CC1)c1ccc(-c2ccccc2Cl)cc1] | White solid; $^1$H NMR (400 MHz, cd$_3$od) δ 7.87 (d, J = 7.3 Hz, 2H), 7.50 (d, J = 7.9 Hz, 3H), 7.36 (s, 3H), 3.43 (t, J = 6.7 Hz, 2H), 3.05 (d, J = 11.5 Hz, 2H), 2.52 (s, 4H), 2.45 (t, J = 7.3 Hz, 2H), 2.26 (t, J = 11.6 Hz, 1H), 1.96 (t, J = 11.9 Hz, 2H), 1.89-1.78 (m, 4H), 1.62-1.40 (m, 8H); LCMS (electrospray) m/z (M + H)$^+$ 440.24 | +++ | D-1 |
| 1147 | 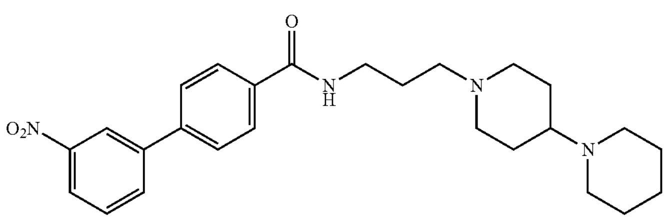 [SMILES: O=C(NCCCN1CCC(N2CCCCC2)CC1)c1ccc(-c2cccc([N+](=O)[O-])c2)cc1] | White solid; $^1$H NMR (400 MHz, cd$_3$od) δ 8.49 (s, 1H), 8.24 (dd, J = 8.1, 1.6 Hz, 1H), 8.07 (d, J = 7.8 Hz, 1H), 7.94 (d, J = 8.3 Hz, 2H), 7.80 (d, J = 8.3 Hz, 2H), 7.71 (t, J = 8.0 Hz, 1H), 3.44 (t, J = 6.8 Hz, 2H), 3.05 (d, J = 11.8 Hz, 2H), 2.52 (t, J = 4.6 Hz, 4H), 2.45 (t, J = 7.4 Hz, 2H), 2.31-2.20 (m, 1H), 1.97 (t, J = 11.5 Hz, 2H), 1.89-1.74 (m, 4H), 1.63-1.40 (m, 8H); LCMS (electrospray) m/z (M + H)$^+$ 451.19 | +++ | D-1 |
| 1148 | 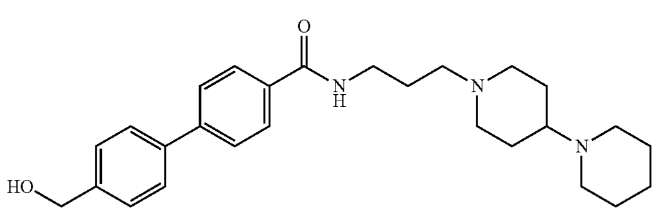 [SMILES: O=C(NCCCN1CCC(N2CCCCC2)CC1)c1ccc(-c2ccc(CO)cc2)cc1] | White solid; $^1$H NMR (400 MHz, cd$_3$od) δ 7.88 (d, J = 8.3 Hz, 2H), 7.72 (d, J = 8.4 Hz, 2H), 7.65 (d, J = 8.2 Hz, 2H), 7.46 (d, J = 8.1 Hz, 2H), 4.65 (s, 2H), 3.44 (t, J = 6.8 Hz, 2H), 3.06 (d, J = 11.8 Hz, 2H), 2.54 (s, 4H), 2.46 (t, J = 7.4 Hz, 2H), 2.34-2.23 (m, 1H), 1.98 (t, J = 11.3 Hz, 2H), 1.89-1.78 (m, 4H), 1.63-1.40 | + | D-1 |

TABLE 2-continued

Anti-HCV genotype 1/2 activity for Formula II Series

| No. | Structure | Characterization | EC$_{50}$ | Method |
|---|---|---|---|---|
| | | (m, 8H); LCMS (electrospray) m/z (M + H)$^+$ 436.22 | | |
| 1149 | 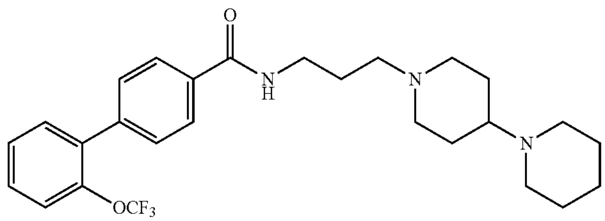 [SMILES: O=C(NCCCN1CCC(N2CCCCC2)CC1)c1ccc(-c2ccccc2OC(F)(F)F)cc1] | Brown solid; $^1$H NMR (400 MHz, cd$_3$od) δ 7.89 (d, J = 8.0 Hz, 2H), 7.55 (d, J = 8.0 Hz, 2H), 7.52-7.38 (m, 4H), 3.44 (t, J = 6.8 Hz, 2H), 3.06 (d, J = 11.7 Hz, 2H), 2.53 (d, J = 4.5 Hz, 4H), 2.45 (t, J = 7.4 Hz, 2H), 2.33-2.21 (m, 3.5 Hz, 1H), 1.98 (t, J = 11.7 Hz, 2H), 1.89-1.75 (m, 4H), 1.63-1.39 (m, 8H); LCMS (electrospray) m/z (M + H)$^+$ 490.24 | +++ | D-1 |
| 1150 | 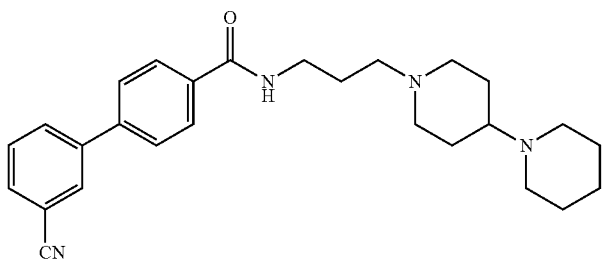 [SMILES: N#Cc1cccc(-c2ccc(C(=O)NCCCN3CCC(N4CCCCC4)CC3)cc2)c1] | Brown solid; $^1$H NMR (400 MHz, cd$_3$od) δ 8.04 (s, 1H), 7.99 (d, J = 8.0 Hz, 1H), 7.92 (d, J = 8.3 Hz, 2H), 7.76 (t, 3H), 7.65 (t, J = 7.8 Hz, 1H), 3.44 (t, J = 6.8 Hz, 2H), 3.06 (d, J = 11.8 Hz, 2H), 2.54 (s, 4H), 2.46 (t, J = 7.4 Hz, 2H), 2.35-2.23 (m, 1H), 1.98 (t, J = 11.4 Hz, 2H), 1.91-1.76 (m, 4H), 1.65-1.41 (m, 8H); LCMS (electrospray) m/z (M + H)$^+$ 431.26 | +++ | D-1 |
| 1151 | 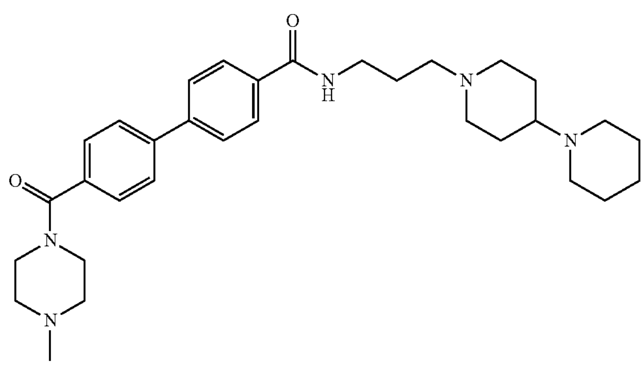 [SMILES: CN1CCN(C(=O)c2ccc(-c3ccc(C(=O)NCCCN4CCC(N5CCCCC5)CC4)cc3)cc2)CC1] | White solid; $^1$H NMR (400 MHz, cd$_3$od) δ 7.91 (d, J = 8.3 Hz, 2H), 7.77 (dd, J = 8.2, 5.0 Hz, 4H), 7.53 (d, J = 8.2 Hz, 2H), 3.80 (s, 2H), 3.52 (s, 2H), 3.44 (t, J = 6.8 Hz, 2H), 3.07 (d, J = 11.9 Hz, 2H), 2.55 (s, 6H), 2.46 (t, J = 7.4 Hz, 4H), 2.33 (s, 4H), 1.99 (t, J = 11.3 Hz, 2H), 1.90-1.79 (m, 4H), 1.64-1.42 (m, 8H); LCMS (electrospray) m/z (M + H)$^+$ 532.36 | + | D-1 |
| 1152 | 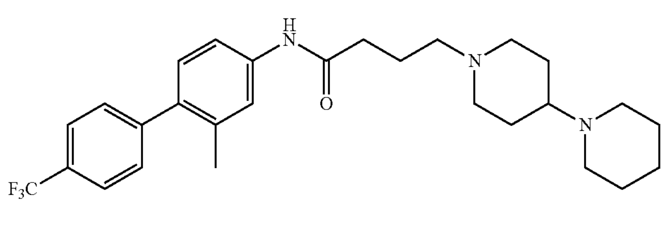 [SMILES: Cc1cc(NC(=O)CCCN2CCC(N3CCCCC3)CC2)ccc1-c1ccc(C(F)(F)F)cc1] | White solid; $^1$H NMR (400 MHz, cd$_3$od) δ 7.70 (d, J = 7.9 Hz, 2H), 7.49 (t, J = 10.7 Hz, 4H), 7.16 (d, J = 8.1 Hz, 1H), 3.03 (d, J = 10.9 Hz, 2H), 2.50 (s, 4H), 2.40 (s, 4H), 2.22 (d, J = 13.3 Hz, 4H), 1.97 (t, J = 12.0 Hz, 2H), 1.93-1.73 (m, 4H), 1.64-1.39 (m, 8H); LCMS (electrospray) m/z (M + H)$^+$ 488.34 | ++++ | D-4 |
| 1153 | 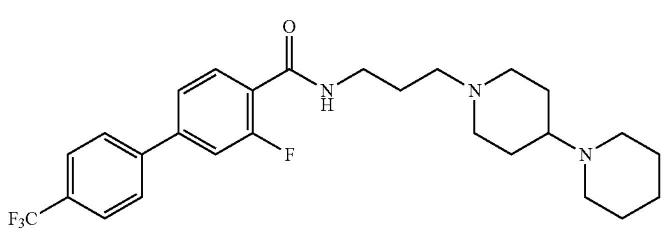 [SMILES: O=C(NCCCN1CCC(N2CCCCC2)CC1)c1ccc(-c2ccc(C(F)(F)F)cc2)cc1F] | White solid; $^1$H NMR (400 MHz, cd$_3$od) δ 7.86 (dd, J = 17.3, 8.0 Hz, 3H), 7.79 (d, J = 7.8 Hz, 2H), 7.61 (dd, J = 18.6, 10.1 Hz, 2H), 3.48 (t, J = 6.2 Hz, 2H), 3.26-3.05 (m, 7H), 2.65-2.55 (m, 2H), 2.21 (t, J = 11.6 Hz, 2H), 2.11 (d, J = 11.3 Hz, 2H), 1.94-1.61 (m, 10H); | +++ | D-1 |

TABLE 2-continued

Anti-HCV genotype 1/2 activity for Formula II Series

| No. | Structure | Characterization | EC$_{50}$ | Method |
|---|---|---|---|---|
| | | LCMS (electrospray) m/z (M + H)$^+$ 492.29 | | |
| 1154 | 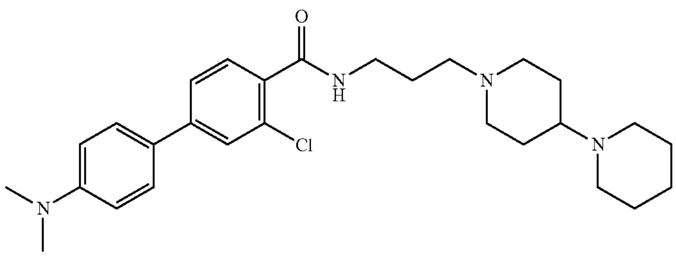 [SMILES: CN(C)c1ccc(-c2ccc(C(=O)NCCCN3CCC(N4CCCCC4)CC3)c(Cl)c2)cc1] | White solid; $^1$H NMR (400 MHz, cd$_3$od) δ 7.65 (s, 1H), 7.59-7.56 (m, 1H), 7.53 (d, J = 8.8 Hz, 2H), 7.45 (d, J = 8.0 Hz, 1H), 6.83 (d, J = 8.8 Hz, 2H), 3.44 (t, J = 6.6 Hz, 2H), 3.12 (d, J = 12.1 Hz, 2H), 2.99 (s, 6H), 2.79 (s, 4H), 2.54 (t, J = 7.3 Hz, 2H), 2.07 (t, J = 11.8 Hz, 2H), 1.94 (d, J = 12.0 Hz, 2H), 1.83 (dt, J = 13.8, 6.8 Hz, 2H), 1.71-1.49 (m, J = 34.7, 18.2, 13.9 Hz, 8H); LCMS (electrospray) m/z (M + H)$^+$ 483.24 | +++ | D-1 |
| 1155 | 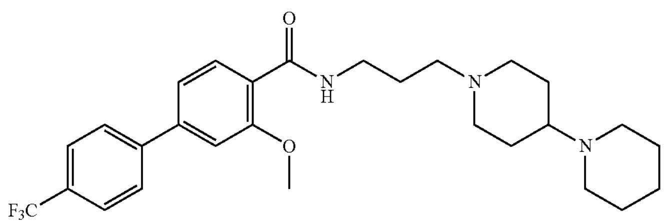 [SMILES: COc1cc(-c2ccc(C(F)(F)F)cc2)ccc1C(=O)NCCCN1CCC(N2CCCCC2)CC1] | White solid; $^1$H NMR (400 MHz, cd$_3$od) δ 7.98 (d, J = 7.6 Hz, 1H), 7.87 (d, J = 7.6 Hz, 2H), 7.76 (d, J = 7.6 Hz, 2H), 7.38 (d, J = 12.4 Hz, 1H), 4.06 (s, 3H), 3.47 (t, J = 6.8 Hz, 2H), 3.35 (s, 2H), 3.17 (s, 4H), 2.73 (s, 2H), 2.42 (t, J = 11.2 Hz, 2H), 2.16 (d, J = 12.0 Hz, 2H), 1.92-1.84 (m, 8H), 1.64 (s, 2H); LCMS (electrospray) m/z (M + H)$^+$ 504.33 | +++ | D-1 |
| 1156 | 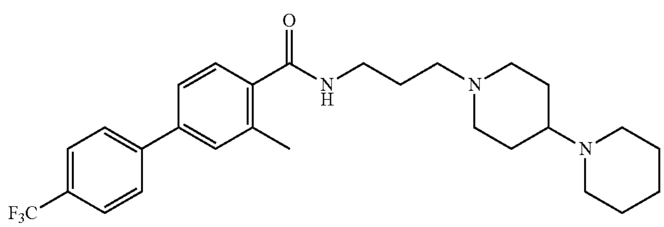 [SMILES: Cc1cc(-c2ccc(C(F)(F)F)cc2)ccc1C(=O)NCCCN1CCC(N2CCCCC2)CC1] | White solid; $^1$H NMR (400 MHz, cd$_3$od) δ 7.81 (d, J = 7.6 Hz, 2H), 7.73 (d, J = 7.6 Hz, 2H), 7.56 (d, J = 8.2 Hz, 2H), 7.45 (d, J = 8.0 Hz, 1H), 3.43 (t, J = 6.4 Hz, 2H), 3.21 (d, J = 11.6 Hz, 2H), 3.14 (s, 4H), 2.60 (s, 2H), 2.48 (s, 3H), 2.22 (t, J = 11.2 Hz, 2H), 2.10 (d, J = 11.6 Hz, 2H), 1.87-1.63 (m, 10H); LCMS (electrospray) m/z (M + H)$^+$ 488.27 | +++ | D-1 |
| 1157 | 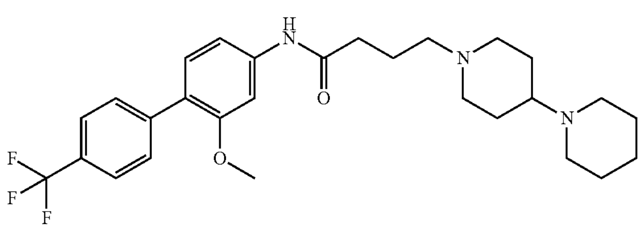 [SMILES: COc1cc(NC(=O)CCCN2CCC(N3CCCCC3)CC2)ccc1-c1ccc(C(F)(F)F)cc1] | White solid; $^1$H NMR (400 MHz, cd$_3$od) δ 7.64 (d, J = 1.6 Hz, 4H), 7.56 (d, J = 2.0 Hz, 1H), 7.27 (d, J = 8.4 Hz, 1H), 7.19 (dd, J = 3.1 Hz, 1.2 Hz, 2H), 3.81 (s, 3H), 3.04 (d, J = 12.0 Hz, 2H), 2.56 (s, 4H), 2.44-2.34 (m, 5H), 1.98 (t, J = 11.2 Hz, 2H), 1.93-1.82 (m, 4H), 1.62-1.45 (m, 8H); LCMS (electrospray) m/z (M + H)$^+$ 504.40 | +++ | D-4 |
| 1158 | 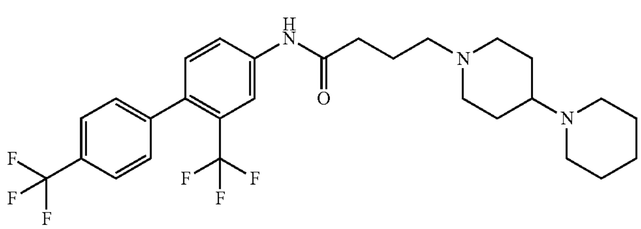 [SMILES: O=C(CCCN1CCC(N2CCCCC2)CC1)Nc1ccc(-c2ccc(C(F)(F)F)cc2)c(C(F)(F)F)c1] | White solid; $^1$H NMR (400 MHz, cd$_3$od) δ 8.17 (d, J = 2.0 Hz, 1H), 7.85 (dd, J = 3.1 Hz, 1.4 Hz, 1H), 7.71 (d, J = 8.4 Hz, 2H), 7.49 (d, J = 8.0 Hz, 2H), 7.34 (d, J = 8.4 Hz, 1H), 3.14 (d, J = 12.0 Hz, 2H), 2.89 (s, 4H), 2.82-2.79 (m, 1H), 2.54-2.44 (m, 4H), 2.11 (t, J = 12.4 Hz, 2H), 2.033-1.89 (m, 4H), 1.77-1.57 (m, 8H); | +++ | D-4 |

TABLE 2-continued

Anti-HCV genotype 1/2 activity for Formula II Series

| No. | Structure | Characterization | EC$_{50}$ | Method |
|---|---|---|---|---|
| 1159 | 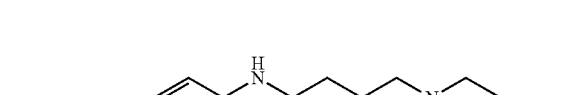 | LCMS (electrospray) m/z (M + H)$^+$ 542.3<br><br>White solid; $^1$H NMR (400 MHz, cd$_3$od) δ 8.15 (d, J = 2.4 Hz, 1H), 7.79 (dd, J = 3.2 Hz, 1.7 Hz, 1H), 7.71 (d, J = 8.4 Hz, 2H), 7.66 (d, J = 8.4 Hz, 2H), 7.49 (d, J = 8.8 Hz, 1H), 2.99 (d, J = 12.0 Hz, 2H), 2.62 (s, 4H), 2.47 (s, 1H), 2.38-2.33 (m, 4H), 1.95 (t, J = 12.0 Hz, 2H), 1.84-1.82 (m, 2H), 1.58-1.41 (m, 10H); LCMS (electrospray) m/z (M + H)$^+$ 499.43 | +++ | D-4 |

Activity range: >10 uM: +, 1-10 uM: ++, 0.1-1 uM: +++, <0.1 uM: ++++

TABLE 3

Cross-genotypic activity with representatives of Formulas I and II

| EC$_{50}$ | gt1a | gt1b | gt2a | gt2b | gt3a | gt4a | gt5a | gt6a | gt7a |
|---|---|---|---|---|---|---|---|---|---|
| Formula I No. 14 | +++ | +++ | +++ | ++++ | +++ | +++ | ++ | + | ++++ |
| Formula I No. 21 | ++++ | ++++ | ++++ | +++++ | ++++ | ++++ | ++ | − | ++++ |
| Formula I No. 27 | +++ | +++ | +++ | +++ | +++ | +++ | ++ | − | +++ |
| Formula I No. 19 | +++ | +++ | +++ | +++ | +++ | +++ | ++ | − | +++ |
| Formula I No. 121 | ++++ | ++++ | ++++ | ++++ | ++++ | ++++ | ++ | − | ++++ |
| Formula I No. 167 | ++++ | ++++ | ++++ | ++++ | ++++ | ++++ | ++ | − | ++++ |
| Formula I No. 316 | ++++ | ++++ | ++++ | ++++ | ++++ | ++++ | ++ | − | ++++ |
| Formula II No. 1013 | + | + | ++ | +++ | + | + | + | + | + |
| Formula II No. 1019 | + | + | ++ | ++ | + | + | + | + | + |

Activity range: >10 uM: +, 1-10 uM: ++, 0.1-1 uM: +++, <0.1 uM: ++++; gt refers to gentoype, the combination of numbers and letters "1b", "2a", "2b" etc. denotes the specific genotype and subtype.

TABLE 4

Drug combination evaluation of representative of Formula I in the HCV genotype 2 infectious system

| Drug Combination | Combination Ratio | CI values$^a$ at Inhibition of | | | | Weighted Average CI Values$^b$ |
|---|---|---|---|---|---|---|
| | | 50% | 75% | 90% | 95% | |
| Formula I (No. 14) + Telaprevir | 1:20 | 0.84 | 0.79 | 0.76 | 0.76 | 0.77 |
| Formula I (No. 14) + Sofosbuvir | 1:10 | 0.91 | 0.94 | 0.97 | 1.00 | 0.97 |
| Formula I (No. 14) + Daclatasvir | 1:0.001 | 0.68 | 0.66 | 0.70 | 0.77 | 0.72 |
| Formula I (No. 14) + IFN-α | 1:100 | 0.74 | 0.65 | 0.56 | 0.51 | 0.58 |
| Formula I (No. 121) + Telaprevir | 1:208 | 0.74 | 0.81 | 0.90 | 0.98 | 0.90 |
| Formula I (No. 121) + Sofosbuvir | 1:208 | 0.87 | 0.813 | 0.830 | 0.85 | 0.84 |
| Formula I (No. 121) + Daclatasvir | 1:0.021 | 0.81 | 0.75 | 0.74 | 0.74 | 0.75 |
| Formula I (No. 121) + IFN-α | 1:4166 | 0.36 | 0.34 | 0.41 | 0.49 | 0.43 |
| Formula I (No. 167) + Telaprevir | 1:166 | 0.95 | 0.77 | 0.68 | 0.63 | 0.90 |
| Formula I (No. 167) + Sofosbuvir | 1:166 | 0.69 | 0.65 | 0.70 | 0.76 | 0.84 |
| Formula I (No. 167) + Daclatasvir | 1:0.016 | 0.70 | 0.70 | 0.75 | 0.80 | 0.76 |
| Formula I (No. 167) + IFN-α | 1:3333 | 0.53 | 0.42 | 0.38 | 0.36 | 0.40 |
| Formula I (No. 316) + Telaprevir | 1:666 | 0.87 | 0.64 | 0.54 | 0.50 | 0.58 |
| Formula I (No. 316) + Sofosbuvir | 1:666 | 0.72 | 0.70 | 0.85 | 1.02 | 0.88 |
| Formula I (No. 316) + Daclatasvir | 1:0.066 | 0.65 | 0.53 | 0.48 | 0.47 | 0.51 |
| Formula I (No. 316) + IFN-α | 1:13333 | 0.62 | 0.53 | 0.47 | 0.43 | 0.49 |

$^a$CI values are based on the combination index isobologram equations: CI = [(D)1/(Dx)1] + [(D)2/(Dx)2], where Dx = Dm[fa/(1-fa)]1/m
$^b$Because of the high degrees of effects are more important than the low degrees of effects, the weighted CI calue was designed as CIwt = [CI50 + 2CI75 + 3CI90 + 4CI95]/10

TABLE 5

Drug combination evaluation of representative of Formula I in the HCV genotype ½ chimeric infectious system

| Drug Combination | Combination Ratio | CI values[a] at Inhibition of | | | | Weighted Average CI Values[b] |
|---|---|---|---|---|---|---|
| | | 50% | 75% | 90% | 95% | |
| Formula I (No.14) + Telaprevir | 1:20 | 0.63 | 0.33 | 0.32 | 0.35 | 0.37 |
| Formula I (No.14) + Sofosbuvir | 1:10 | 1.79 | 0.83 | 0.79 | 0.80 | 0.90 |
| Formula I (No.14) + Daclatasvir | 1:0.001 | 0.75 | 0.45 | 0.37 | 0.35 | 0.41 |
| Formula I (No.14) + IFN-α | 1:100 | 0.53 | 0.32 | 0.27 | 0.27 | 0.31 |

[a]CI values are based on the combination index isobologram equations: CI = [(D)1/(Dx)1] + [(D)2/(Dx)2], where Dx = Dm[fa/(1-fa)]1/m
[b]Because of the high degrees of effects are more important than the low degrees of effects, the weighted CI calue was designed as CIwt = [CI50 + 2CI75 + 3CI90 + 4CI95]/10

The invention claimed is:

1. A compound having Formula (If):

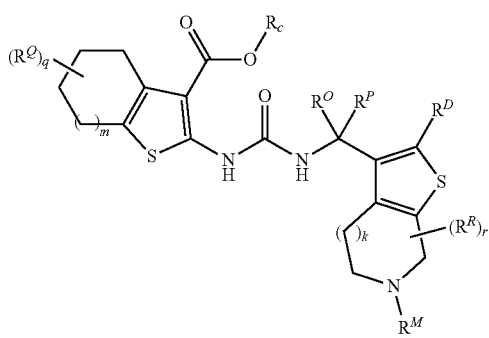

(If)

wherein
$R^D$ is selected from the group consisting of halo; cyano; C1-C5 alkyl; C3-C6 cycloalkyl; C1-C3 alkoxy; C1-C3 haloalkyl; C1-C3 sulfanyl; phenyl; aryl; heteroaryl; —NR$^G$R$^H$; —C(O)NRaRb; —C(O)Rc; —C(O)ORc; sulfonyl; sulfoxide;

$R^O$ and $R^P$ are each independently at each occurrence selected from the group consisting of H, C1-C5 alkyl, C1-C5 alkenyl, C1-C5 alkynyl, C3-C6 cycloalkyl; heterocycloalkyl; heteroaryl; phenyl; with either the proviso that, when one of $R^O$ or $R^P$ is H, then the other one of $R^O$ or $R^P$ is not methyl; or with the proviso that the compound is not;

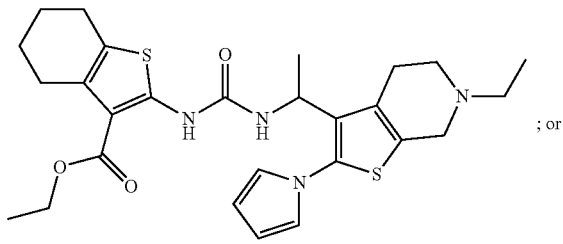 [SMILES: CCOC(=O)c1c(NC(=O)NC(C)c2c(-n3cccc3)sc3c2CCN(CC)C3)sc2c1CCCC2]

; or $R^O$ and $R^P$ are joined together, forming a cycloalkyl group, cycloalkenyl group, or heterocycloalkyl group optionally substituted with one to four $R^I$ groups;

wherein $R^I$ is selected from the group consisting of H; halo; cyano; C1-C5 alkyl; C1-C3 sulfanyl; C1-C4 alkoxy; C1-C3 haloalkyl; hydroxyl; oxo; —NRaRb; —C(O)NRaRb; —C(O)Rc; —C(O)ORc; sulfonyl; sulfoxide; (CH$_2$)$_p$OH; (CH$_2$)$_p$ORa; (CH$_2$)$_p$NR$^G$R$^H$; (CH$_2$)$_p$OC(O)NRaRb; (CH$_2$)$_p$C(O)NRaRb; C3-C6 cycloalkyl; heterocycloalkyl; aryl; heteroaryl; phenyl;

$R^G$ is selected from the group consisting of H; C1-C6 alkyl; C1-C6 alkoxy; C3-C6 cycloalkyl; heterocycloalkyl; heteroaryl; phenyl;

$R^H$ is selected from the group consisting of H; C1-C6 alkyl; C1-C6 alkoxy; C3-C6 cycloalkyl; heterocycloalkyl; heteroaryl; phenyl; or $R^G$ and $R^H$, together with the nitrogen atom to which they are bonded, form a 4- to 10-membered saturated or unsaturated heterocyclic ring which is optionally substituted with one or more C1-C3 alkyl, benzyl, phenyl, C1-C3 alkoxy or halogen;

$R_C$ is selected from C1-C10 alkyl, C1-C10 alkenyl, C1-C10 alkynyl, C3-C10 cycloalkyl, C1-C3 haloalkyl, aryl, heteroaryl, heterocycloalkyl, wherein each of the aforementioned alkyl, alkenyl, alkynyl, cycloalkyl, aryl, heteroaryl and heterocycloalkyl may be substituted with one or more of hydroxyl, halo, alkoxy, oxo, sulfonyl, sulfoxide, aryl, heteroaryl or —NRaRb;

$R^M$ is selected from the group consisting of H; C1-C6 alkyl, C3-C6 cycloalkyl, C1-C3 haloalkyl, phenyl; aryl; heteroaryl; —NR$^G$R$^H$; —C(O)NRaRb; —C(O)Rc; —C(O)ORc; sulfonyl; sulfoxide; C1-C6 alkyl substituted with hydroxyl, alkoxy, —NRaRb, phenyl, —NR$^G$R$^H$, —C(O)NRaRb, —C(O)Rc, —C(O)ORc; sulfonyl, or sulfoxide;

$R^Q$ and $R^R$ represents a substituent which is at each occurrence independently selected from the group consisting of H; halo; cyano; C1-C5 alkyl; C3-C6 cycloalkyl; C1-C3 alkoxy; C1-C3 haloalkyl; C1-C3 sulfanyl; phenyl; aryl; heteroaryl; —NR$^G$R$^H$; —C(O)NRaRb; —C(O)Rc; —C(O)ORc; sulfonyl; sulfoxide; (CH$_2$)$_p$OH; (CH$_2$)$_p$ORa; (CH$_2$)$_p$NR$^G$R$^H$; (CH$_2$)$_p$OC(O)NRaRb; (CH$_2$)$_p$C(O)NRaRb;

Ra and Rb are each independently at each occurrence selected from the group consisting of hydrogen, C1-C6 alkyl, substituted C1-C6 alkyl, C1-C6 alkoxyC1-C6 alkyl, C6-C14 alkyl chain containing one or several of —O—, —C(O)NH—, —NHC(O)—, —N—, or —NHC(O)O— optionally with a terminal —NH$_2$ or —NH-Boc; C1-C6 alkenyl, substituted C1-C6 alkenyl, C1-C6 alkynyl, substituted C1-C6 alkynyl, C3-C7 cycloalkyl, substituted C3-C7 cycloalkyl, aryl, substituted aryl, heteroaryl, substituted heteroaryl, heterocycloalkyl, substituted heterocycloalkyl; or Ra and Rb, together with the nitrogen atom to which they are bonded, form a 4- to 10-membered saturated or unsaturated heterocyclic ring which is optionally substituted with one or more C1-C3 alkyl, benzyl, phenyl, C1-C3 alkoxy or halogen;

Rc is selected from the group consisting of hydrogen, C1-C10, C1-C10 alkenyl, C1-C10 alkynyl, C3-C10 cycloalkyl, C1-C3 haloalkyl, aryl, heteroaryl, heterocycloalkyl, wherein each of the aforementioned alkyl, alkenyl, alkynyl, cycloalkyl, aryl, heteroaryl and heterocycloalkyl may be substituted with one or more of hydroxyl, halo, alkoxy, oxo, sulfonyl, sulfoxide, aryl, heteroaryl or —NRaRb;

m is an integer from 0 to 2;
k is an integer from 0 to 2;

p is an integer from 0 to 5;
q is an integer from 1 to 3; and
r is an integer from 1 to 3,
and pharmaceutically acceptable salts thereof.
2. The compound according to claim 1, wherein the compound of Formula (If) is selected from the group consisting of:
Formula 2
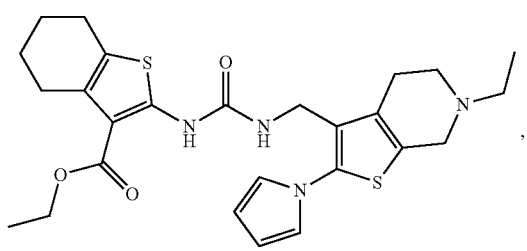
Formula 5
Formula 7
Formula 14
Formula 16
Formula 18
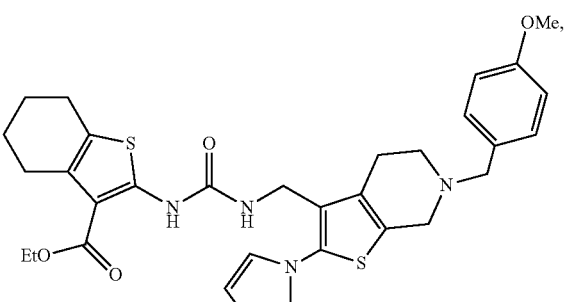
Formula 19
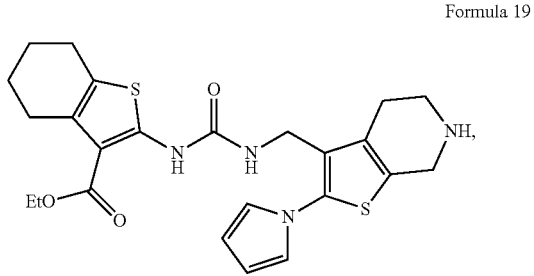
Formula 20
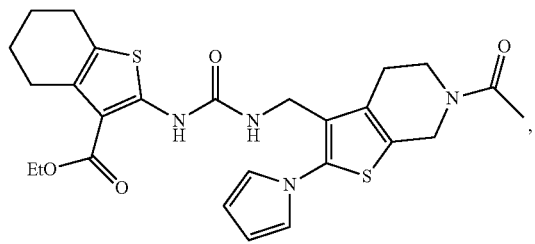
Formula 21
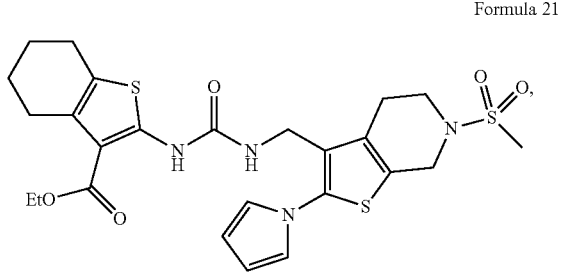
Formula 23
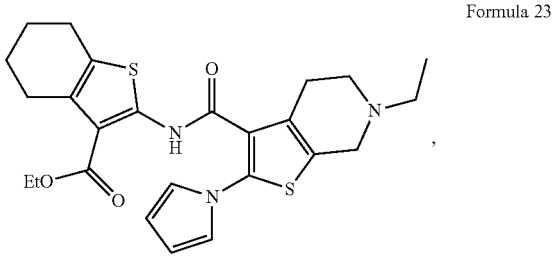

311
-continued
Formula 27
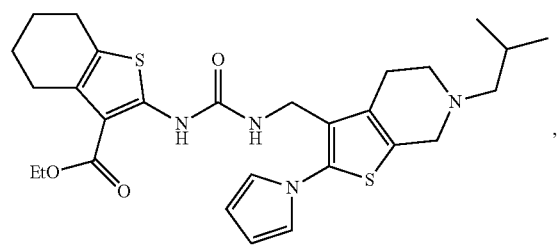
Formula 30
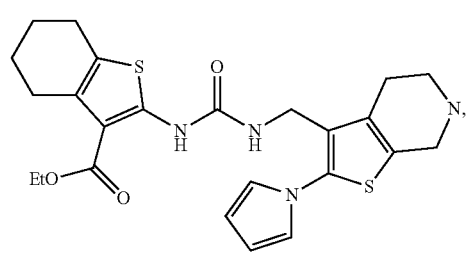
Formula 31
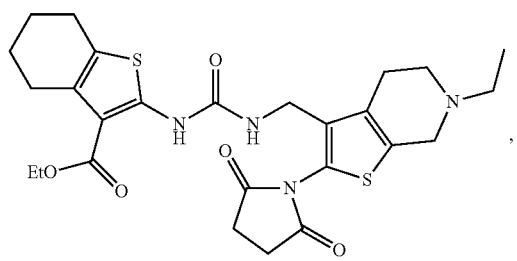
Formula 36
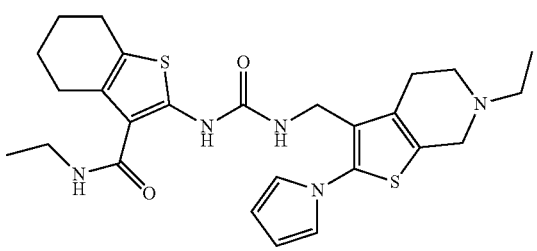
Formula 37
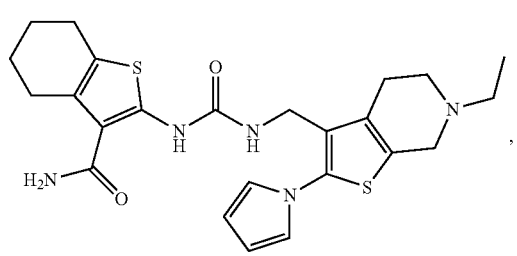
Formula 38
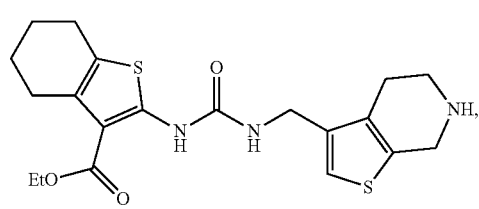
312
-continued
Formula 43
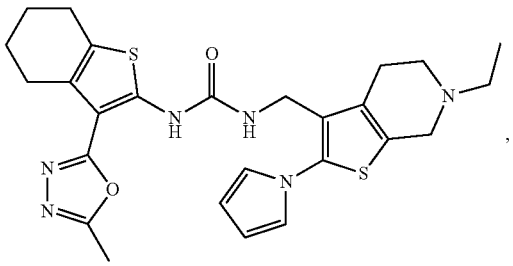
Formula 49
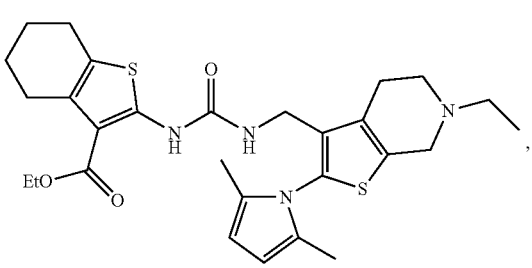
Formula 51
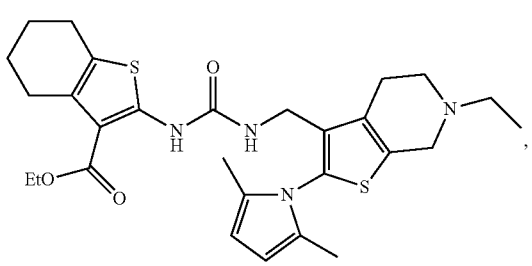
Formula 54
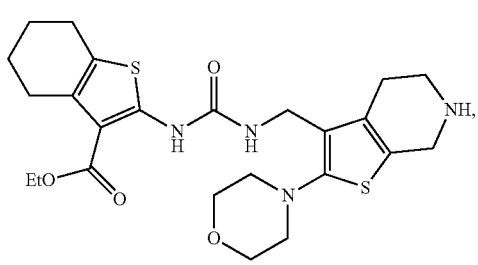
Formula 55
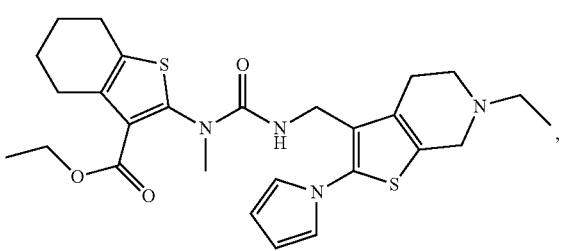

Formula 56
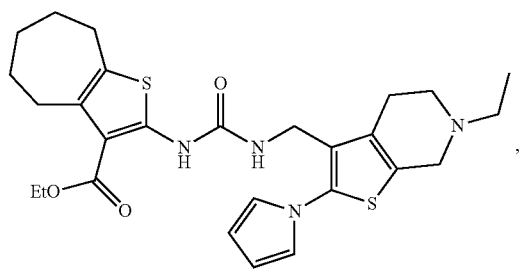
Formula 68
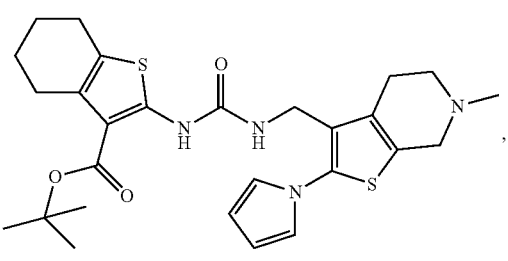
Formula 57
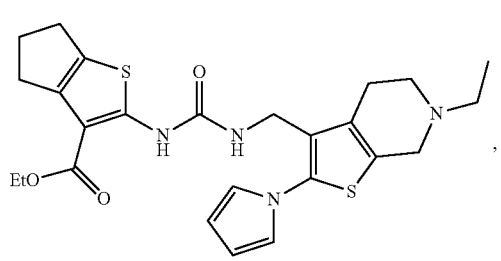
Formula 73
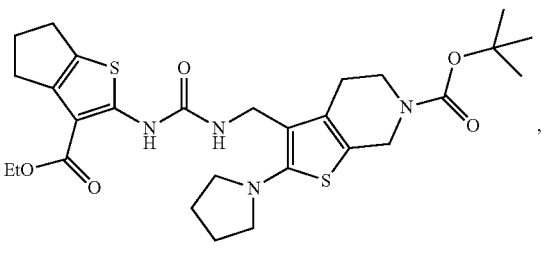
Formula 59
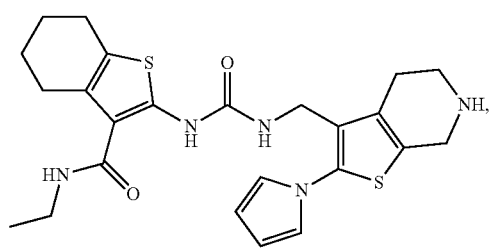
Formula 75
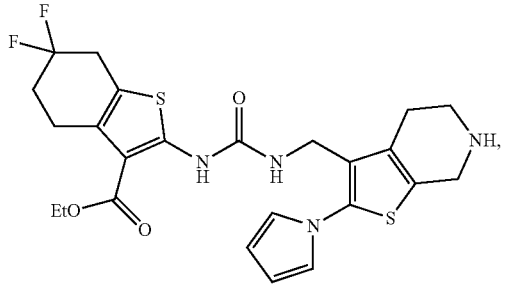
Formula 61
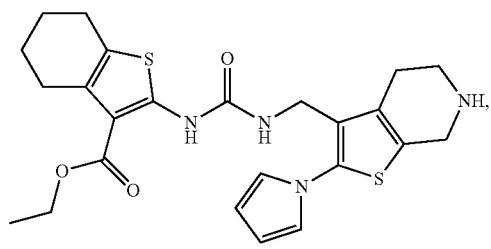
Formula 81
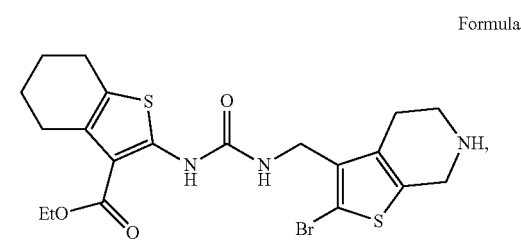
Formula 62
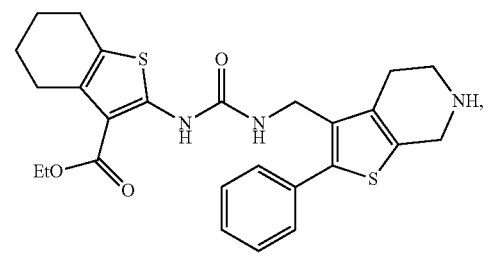
Formula 87
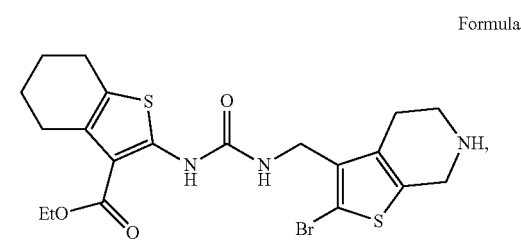
Formula 67
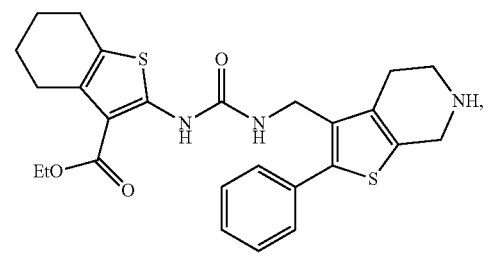
Formula 94

Formula 96
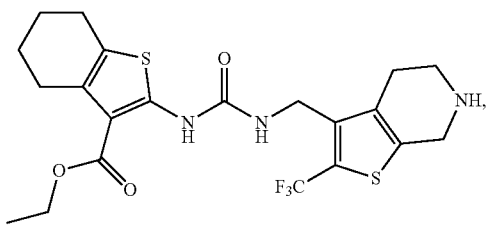
Formula 97
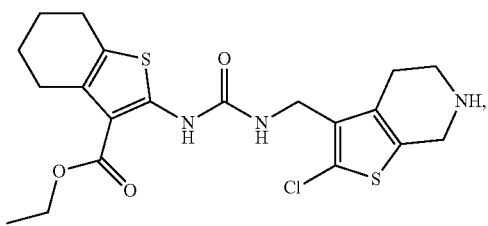
Formula 98
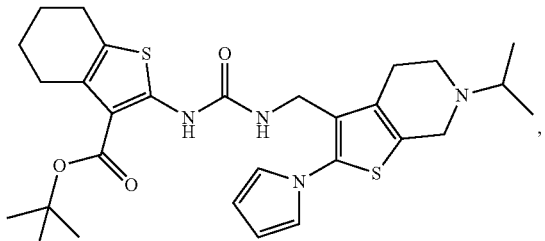
Formula 99
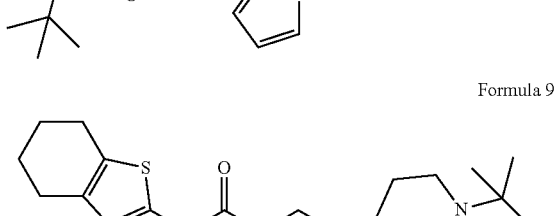
Formula 100
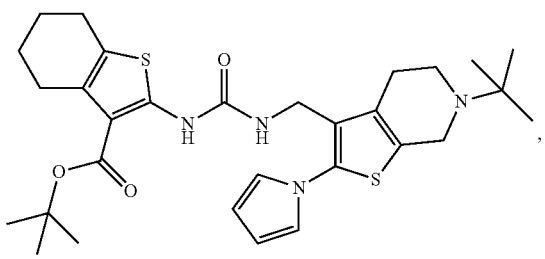
Formula 101
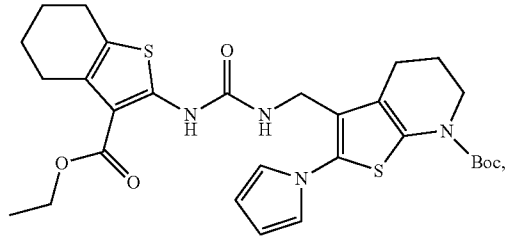
Formula 106
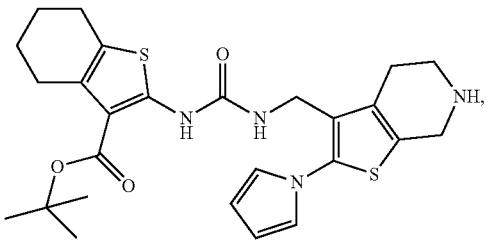
Formula 107
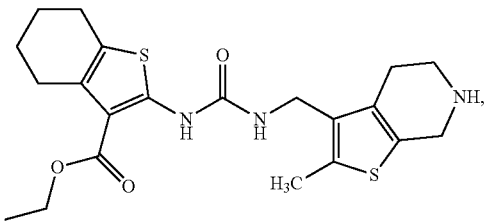
Formula 110
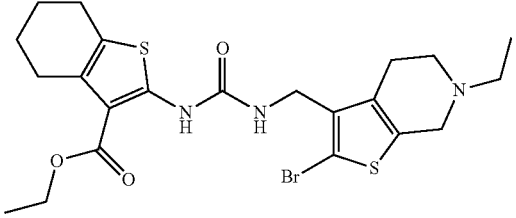
Formula 111
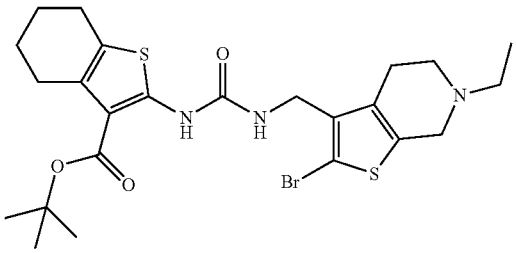
Formula 112
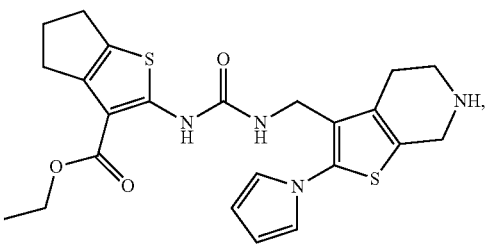
Formula 113
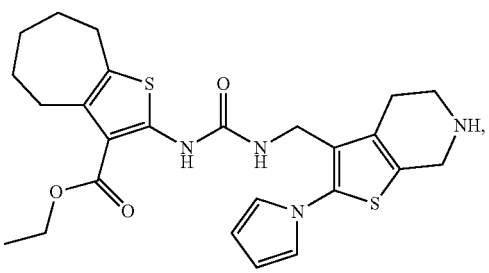

Formula 114
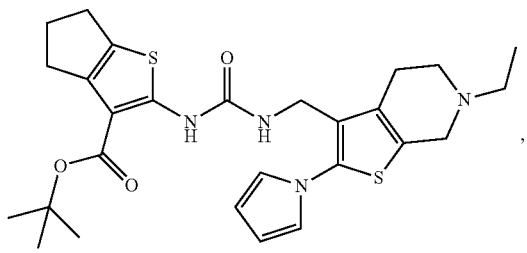
Formula 115
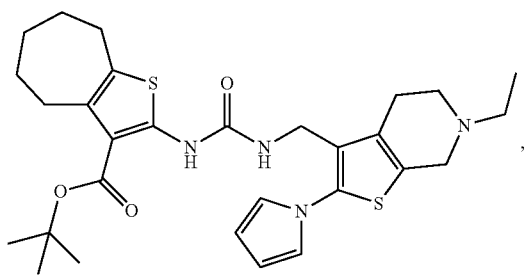
Formula 116
Formula 117
Formula 118
Formula 119
Formula 121
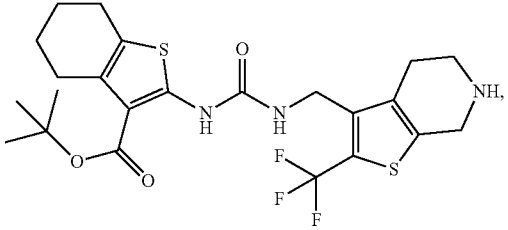
Formula 122
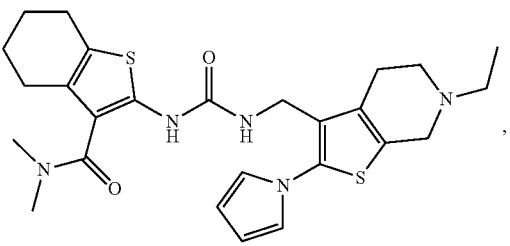
Formula 123
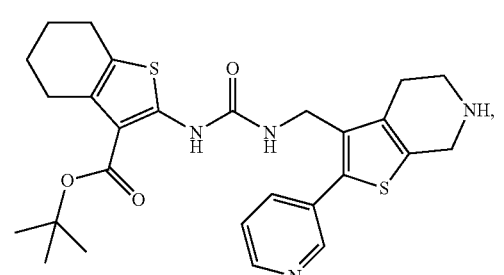
Formula 124
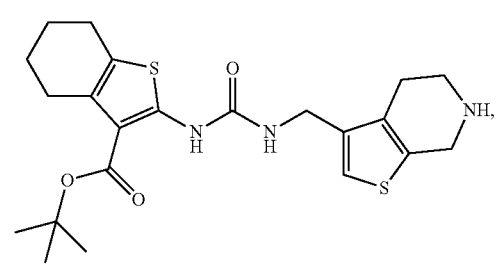
Formula 125
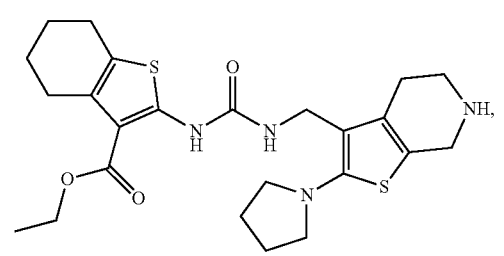
Formula 126
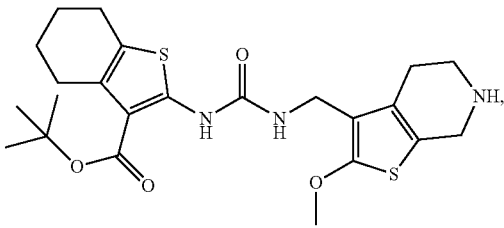

Formula 127
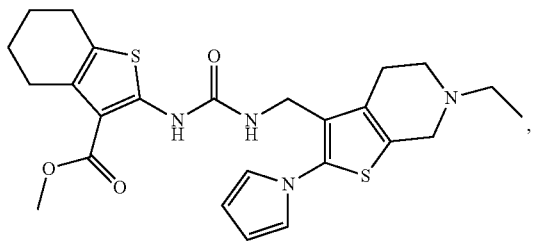
Formula 128
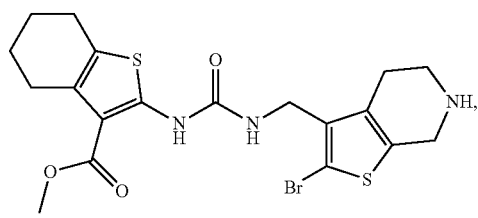
Formula 129
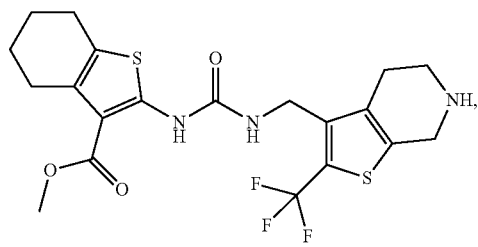
Formula 130
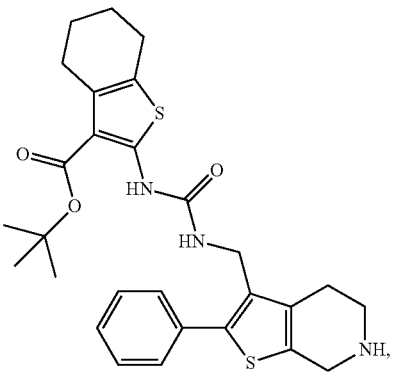
Formula 131
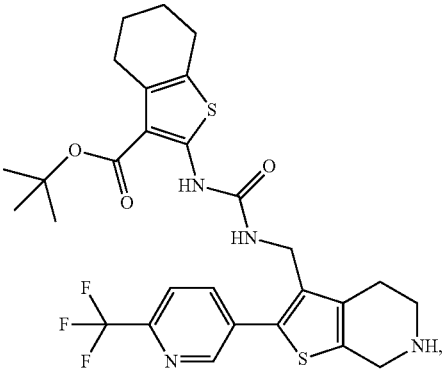
Formula 140
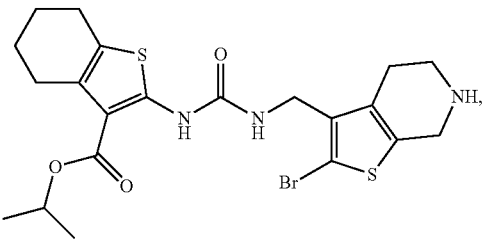
Formula 141
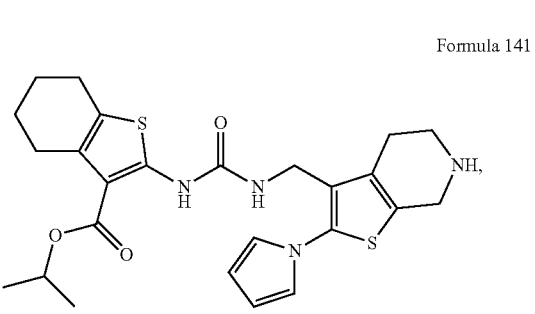
Formula 142
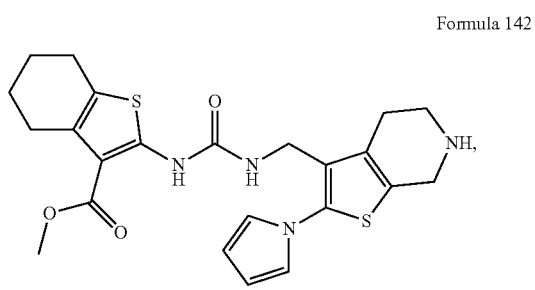
Formula 143
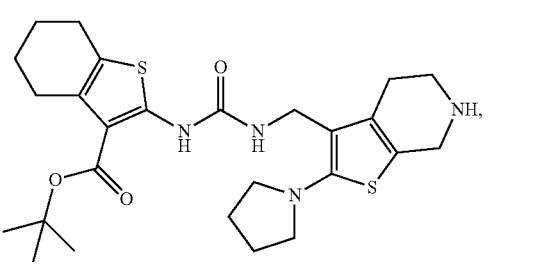
Formula 144
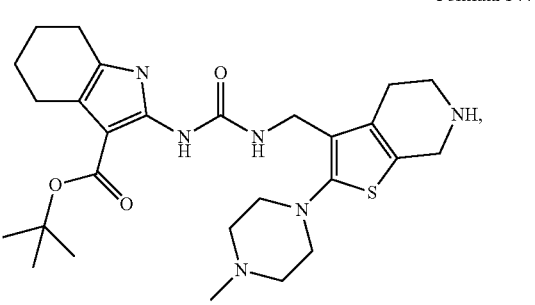

-continued
Formula 145
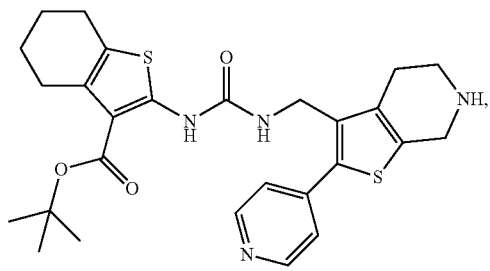
Formula 146
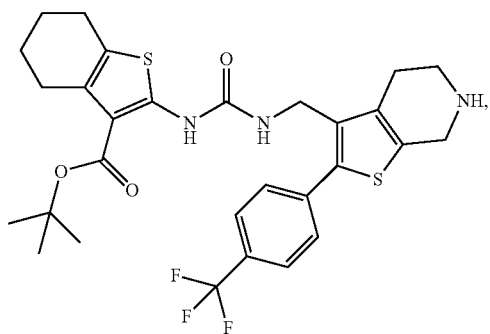
Formula 151
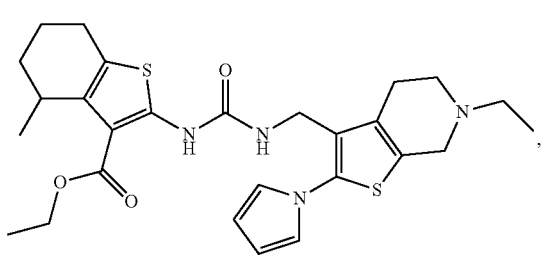
Formula 152
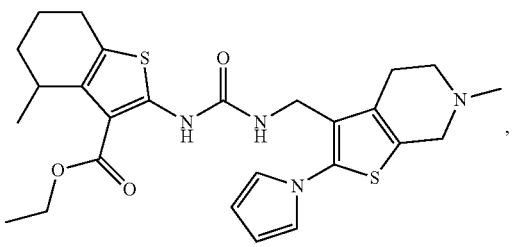
Formula 153
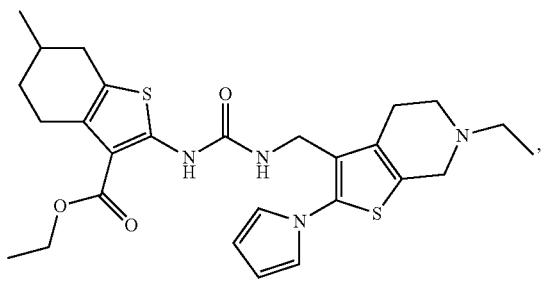
-continued
Formula 154
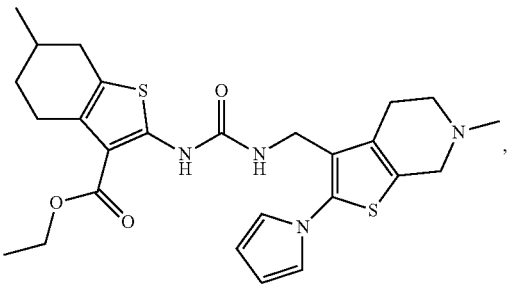
Formula 155
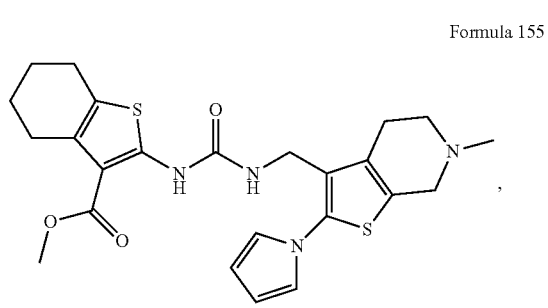
Formula 156
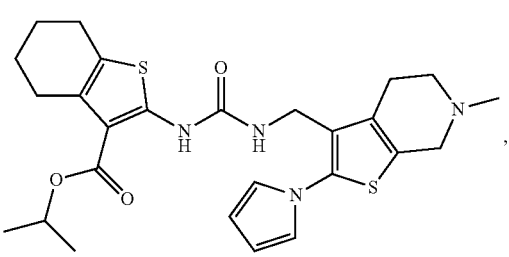
Formula 157
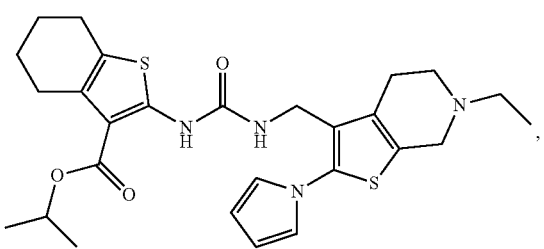
Formula 159
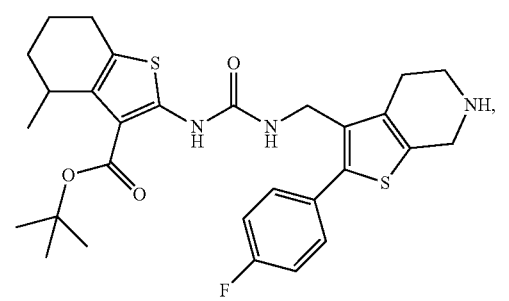

-continued
Formula 160
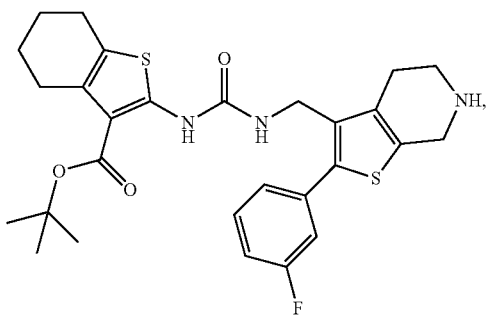
Formula 161
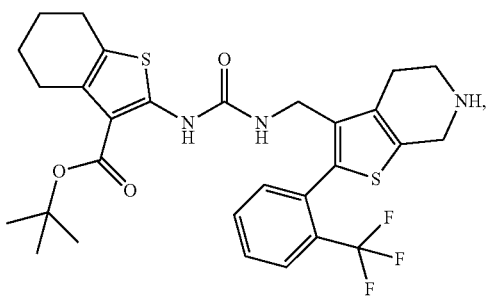
Formula 164
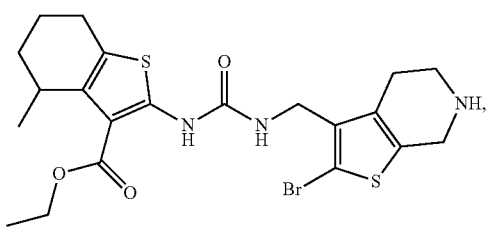
Formula 165
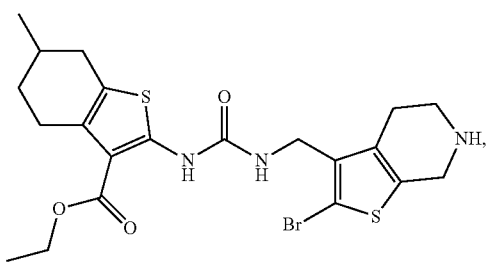
Formula 166
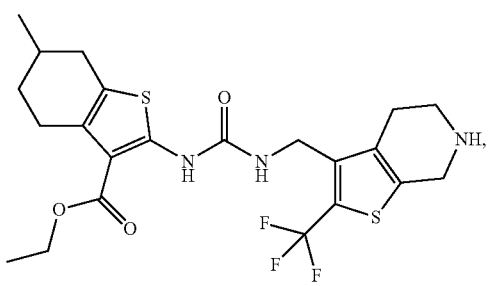
-continued
Formula 167
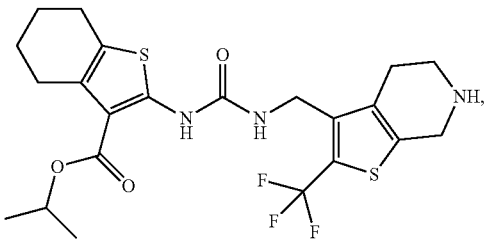
Formula 169
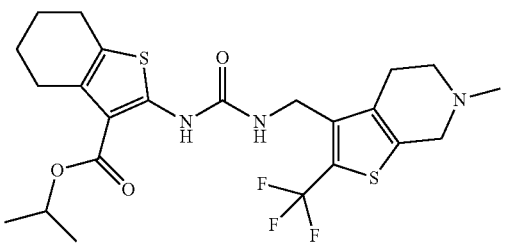
Formula 171
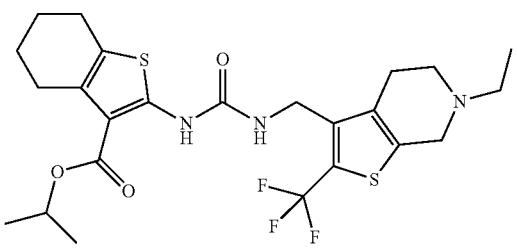
Formula 172
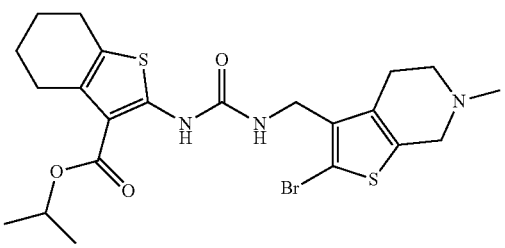
Formula 174
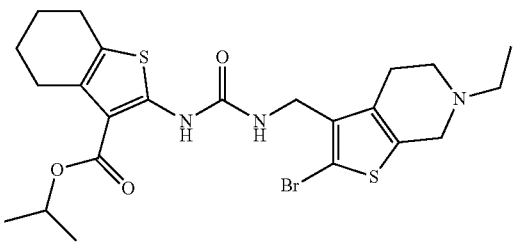
Formula 175
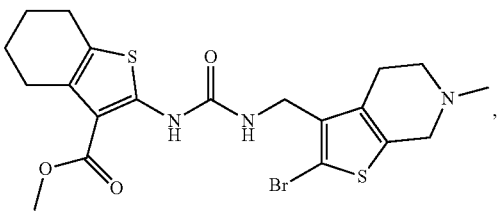

Formula 177
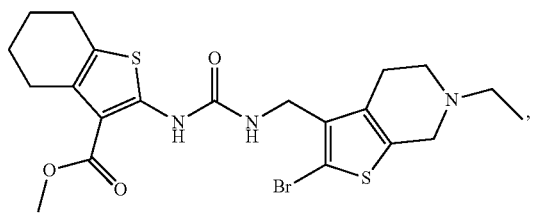
Formula 178
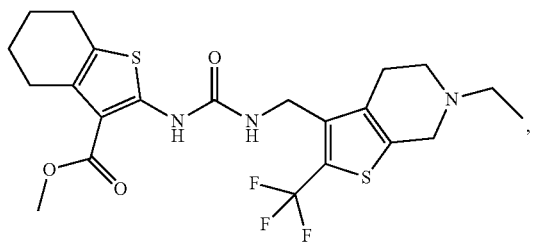
Formula 179
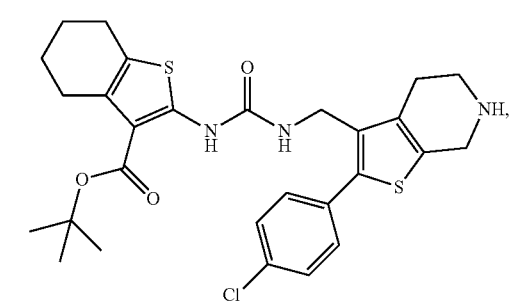
Formula 180
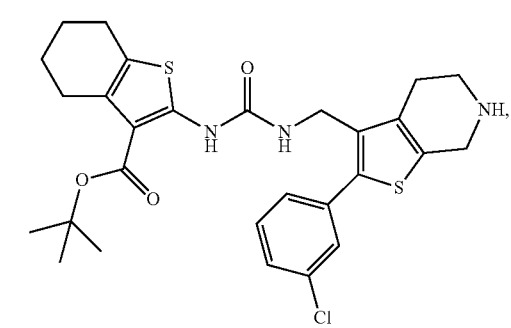
Formula 181
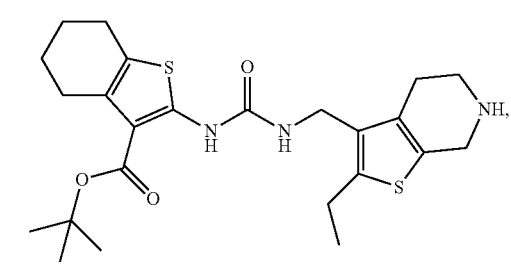
Formula 182
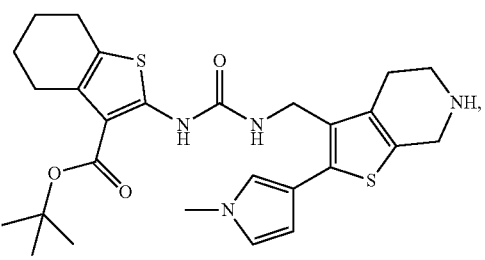
Formula 183
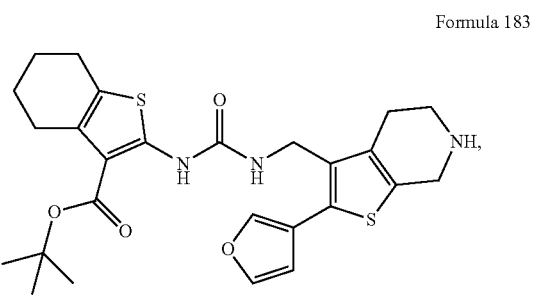
Formula 184
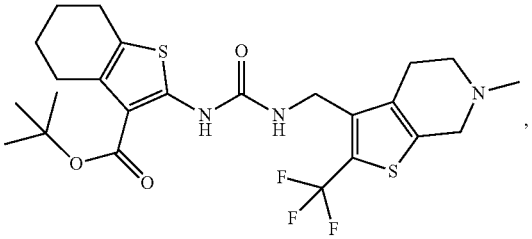
Formula 185
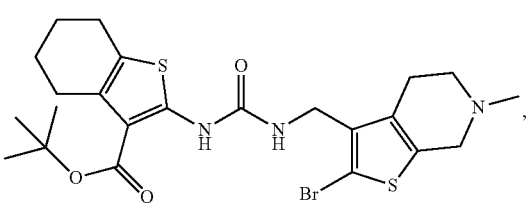
Formula 186
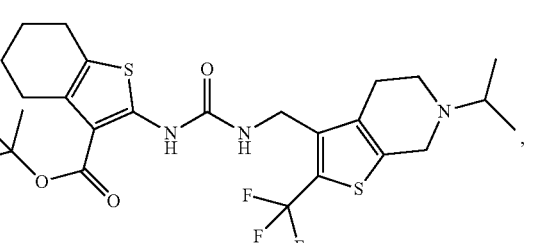
Formula 187
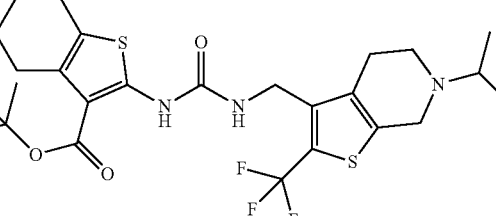

Formula 190
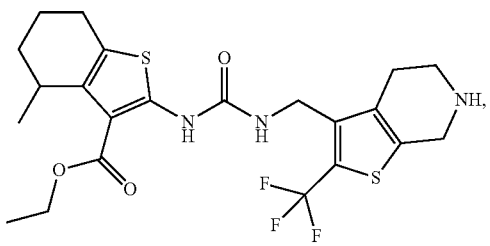
Formula 191
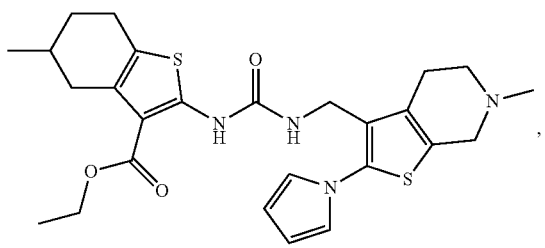
Formula 192
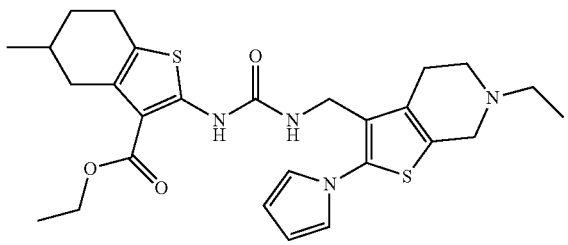
Formula 193
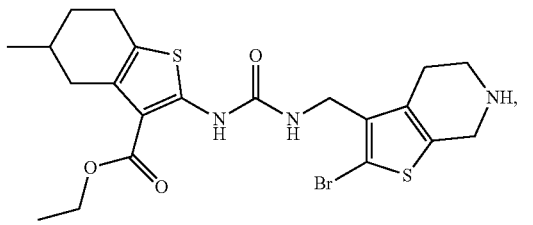
Formula 194
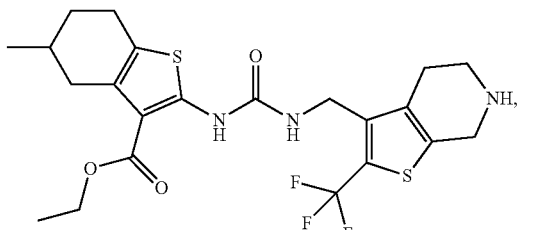
Formula 197
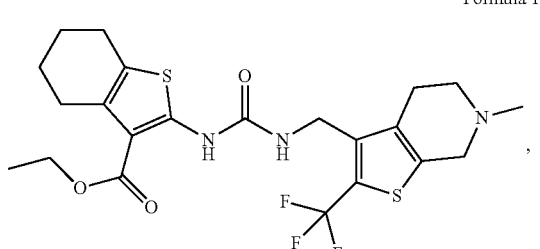
Formula 198
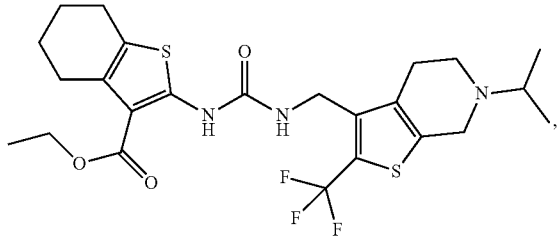
Formula 199
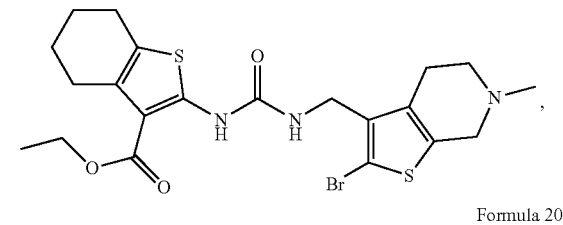
Formula 200
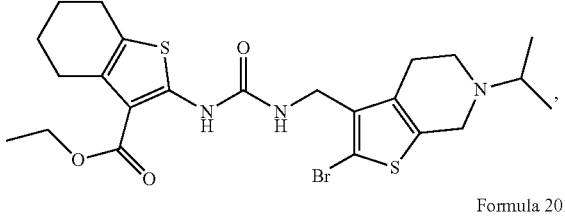
Formula 201
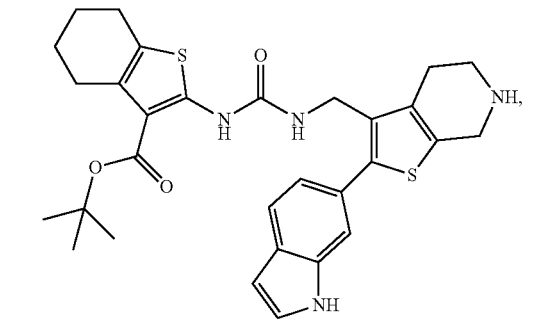
Formula 202
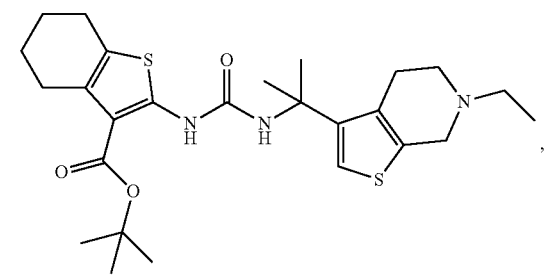
Formula 203
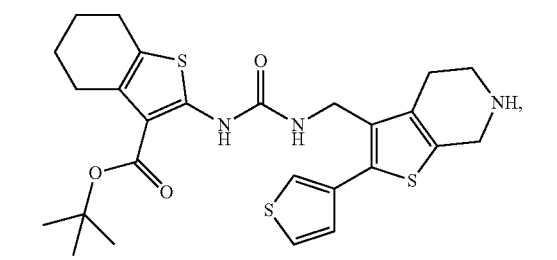

Formula 204
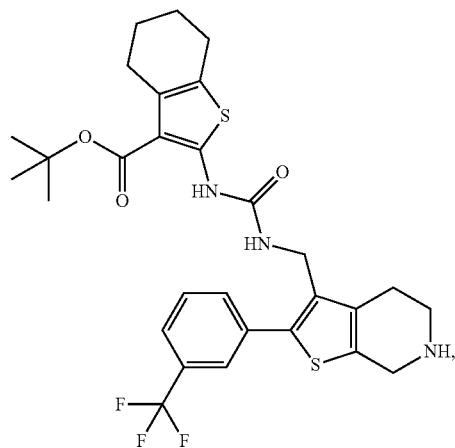
Formula 205
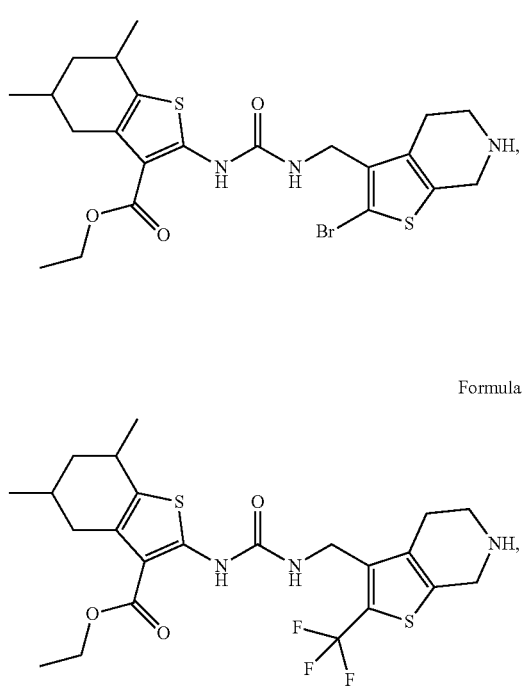
Formula 207
Formula 208
Formula 210
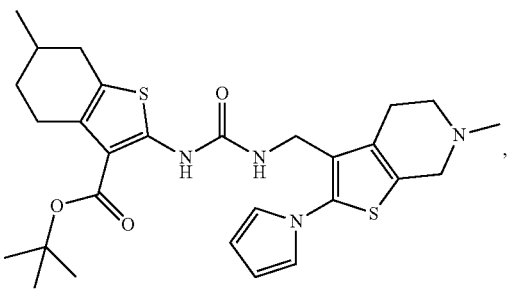
Formula 211
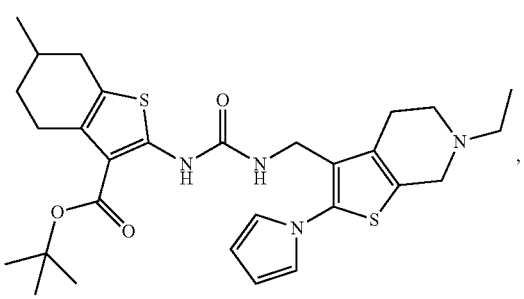
Formula 212
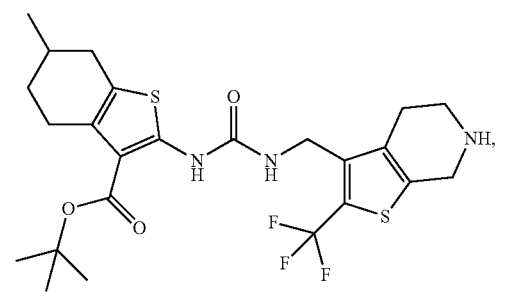
Formula 213
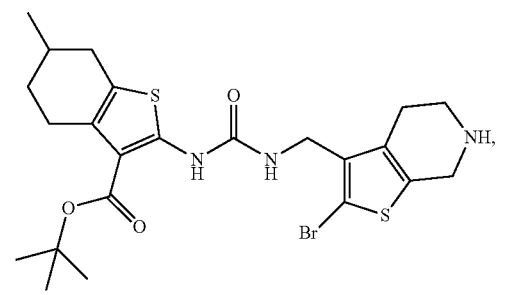
Formula 218
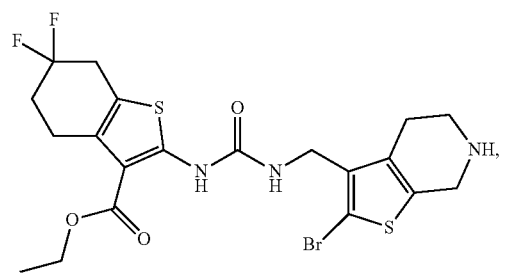

Formula 219
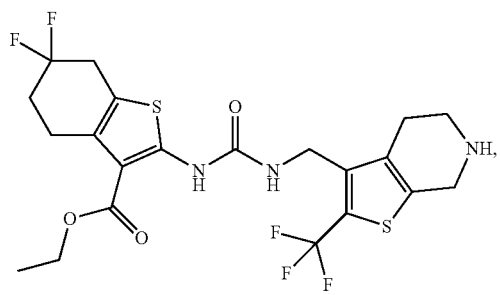
Formula 220
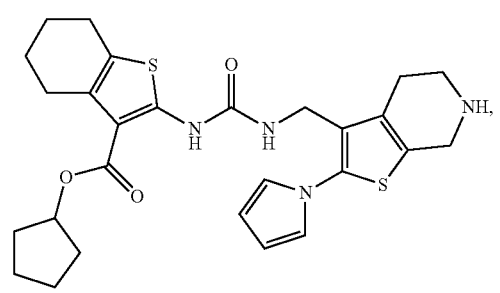
Formula 221
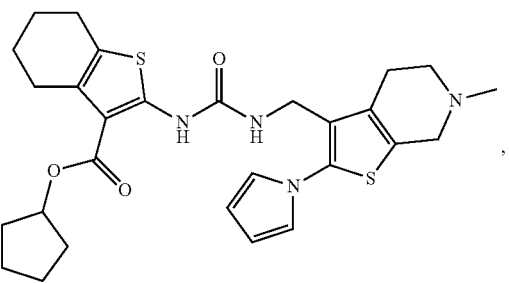
Formula 222
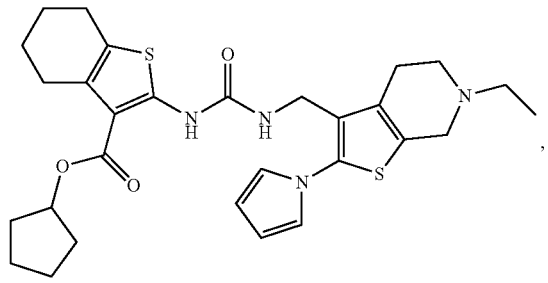
Formula 224
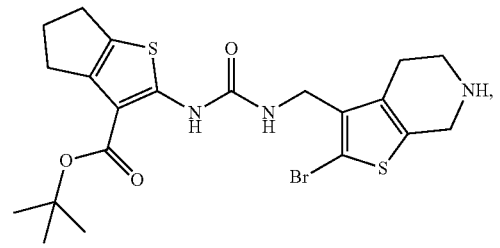
Formula 225
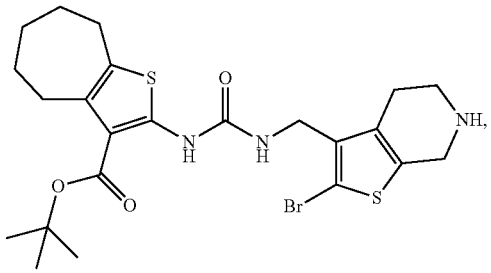
Formula 226
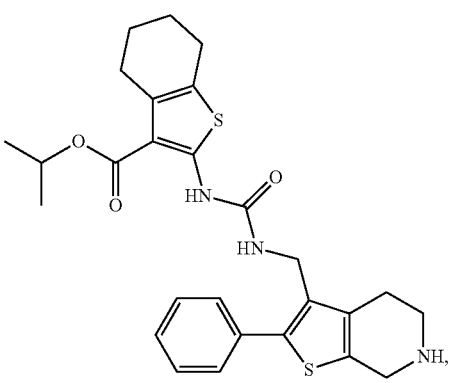
Formula 227
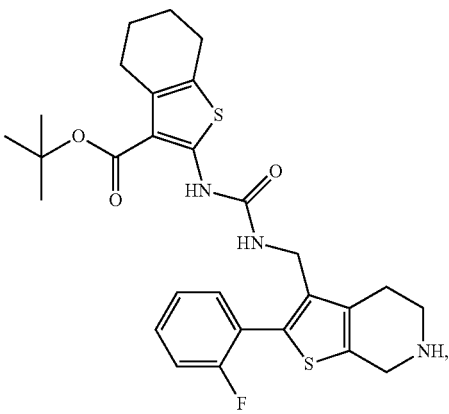
Formula 228
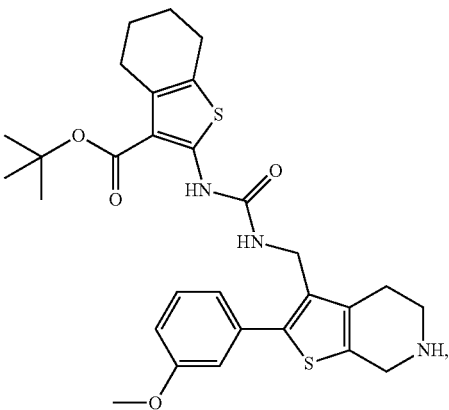

Formula 229
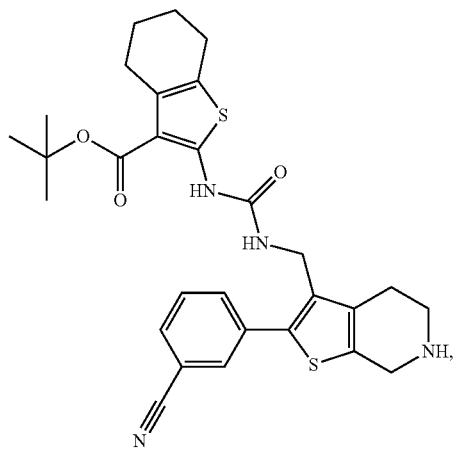
Formula 230
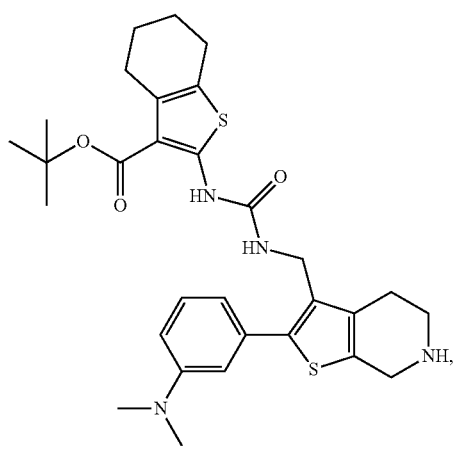
Formula 231
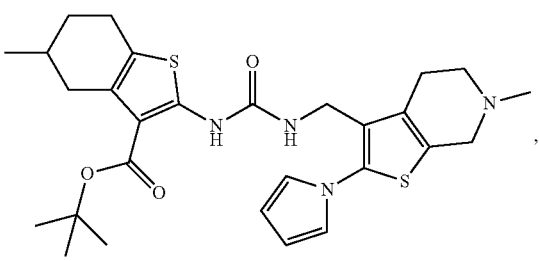
Formula 232
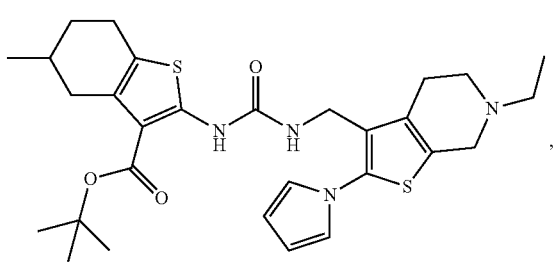
Formula 233
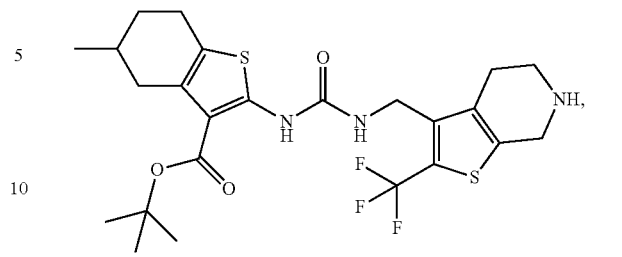
Formula 234
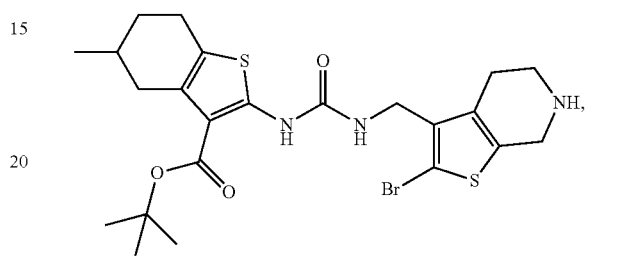
Formula 235
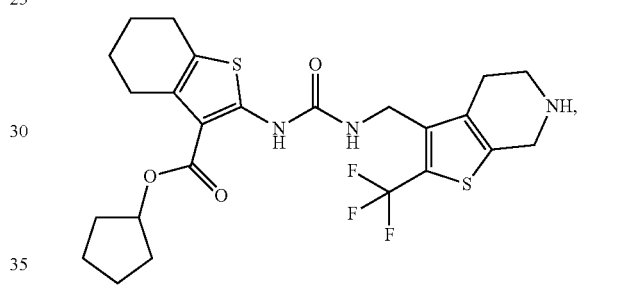
Formula 240
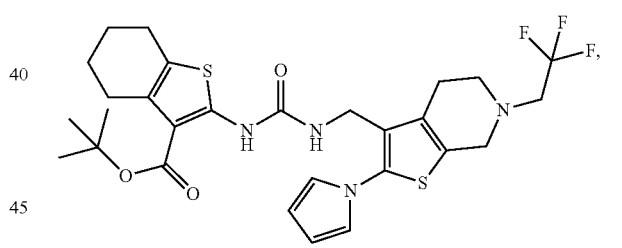
Formula 241
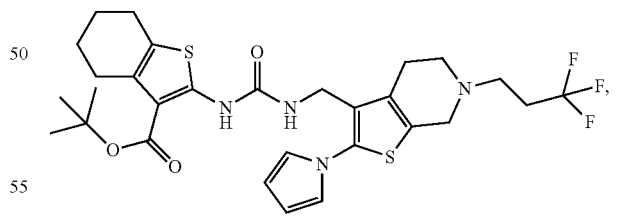
Formula 242
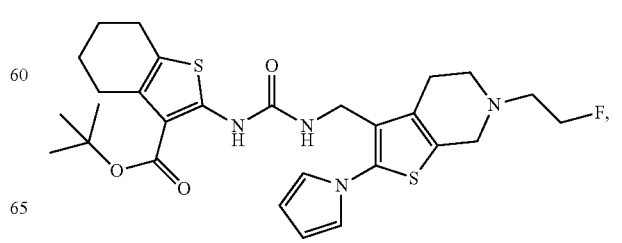

Formula 243
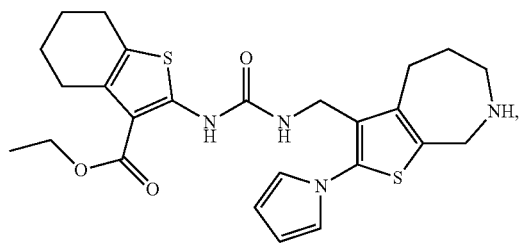
Formula 244
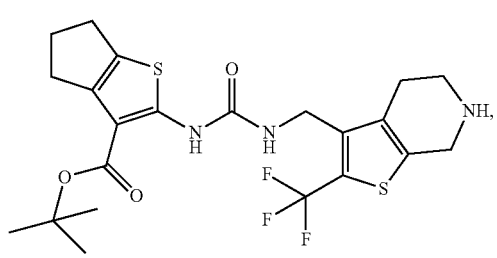
Formula 245
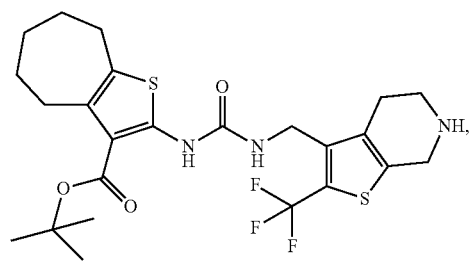
Formula 246
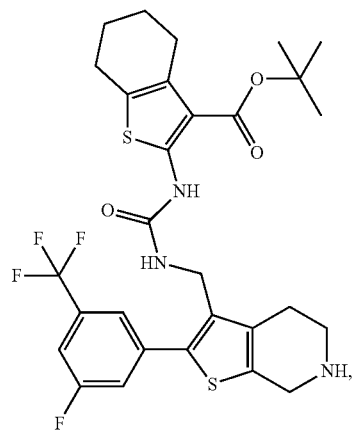
Formula 247
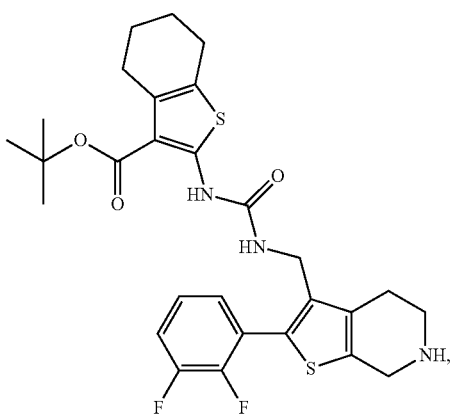
Formula 248
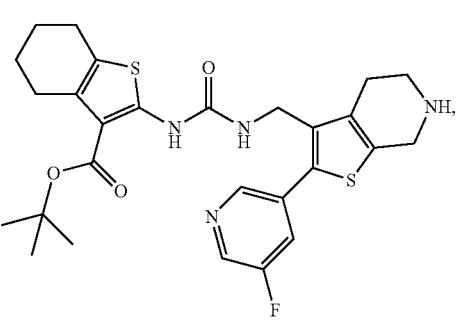
Formula 249
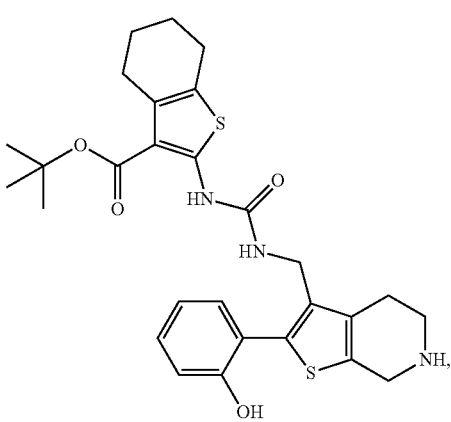
Formula 250
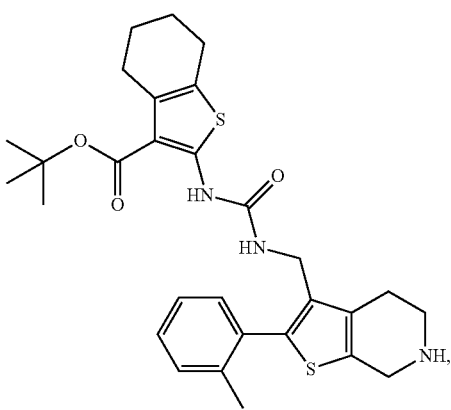

Formula 252
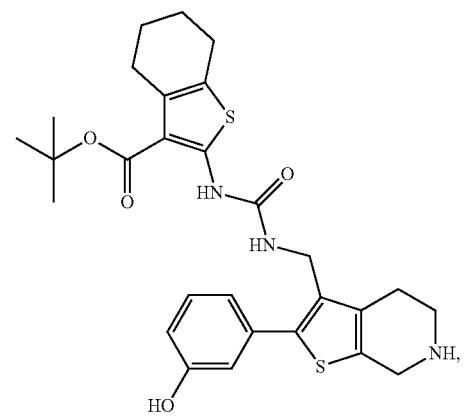
Formula 254
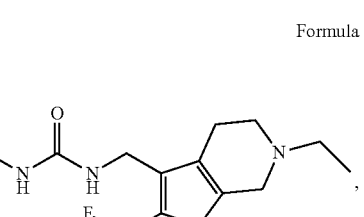
Formula 256
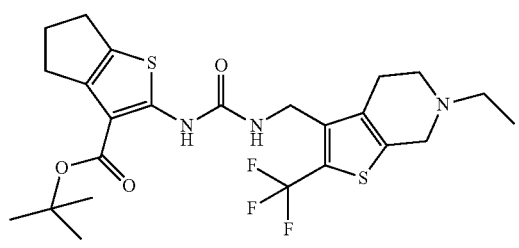
Formula 257
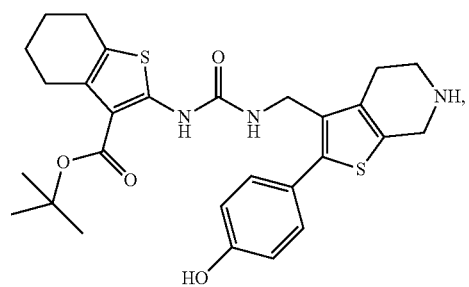
Formula 258
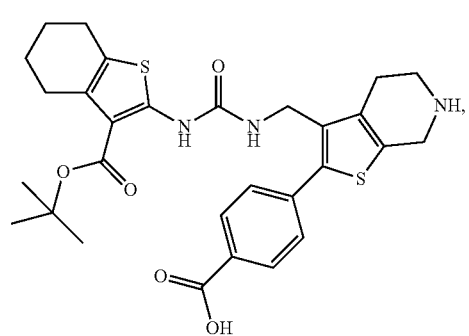
Formula 259
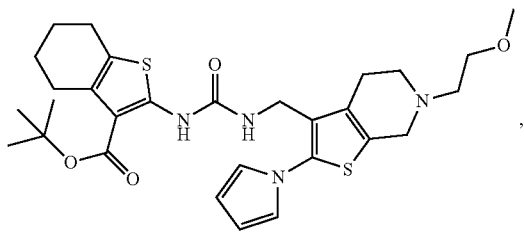
Formula 260
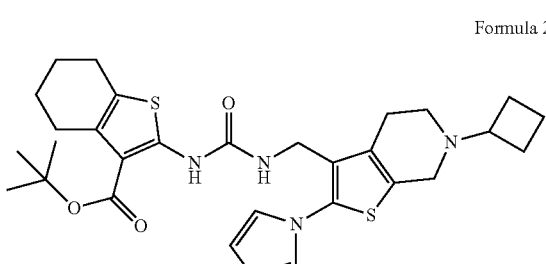
Formula 261
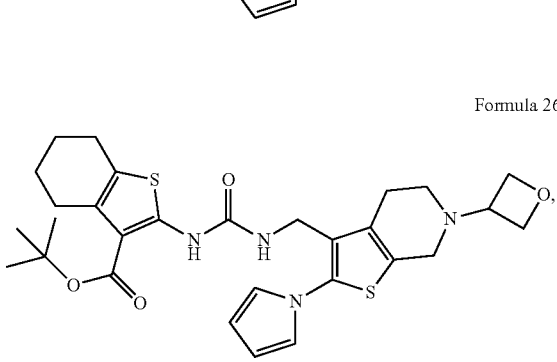
Formula 262
Formula 263
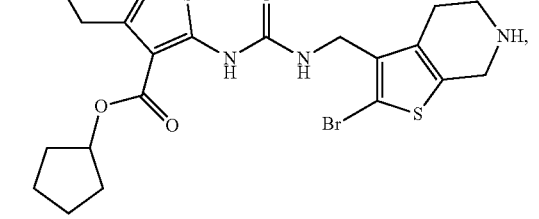

Formula 265
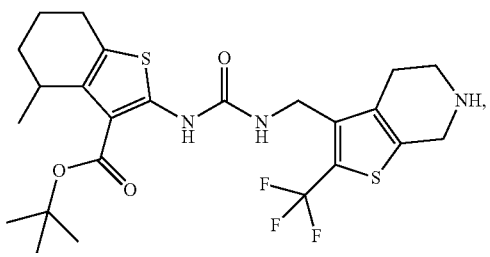
Formula 266
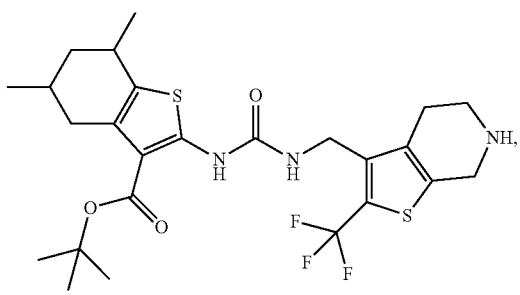
Formula 267
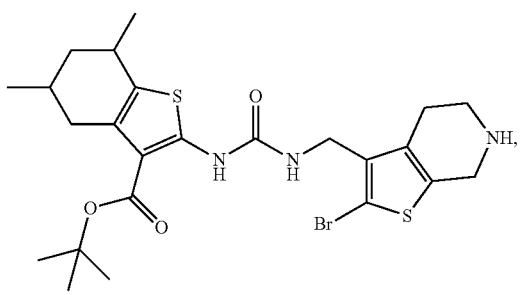
Formula 271
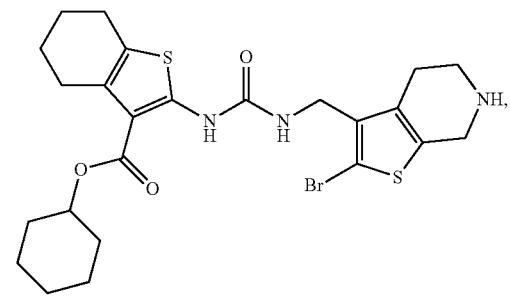
Formula 272
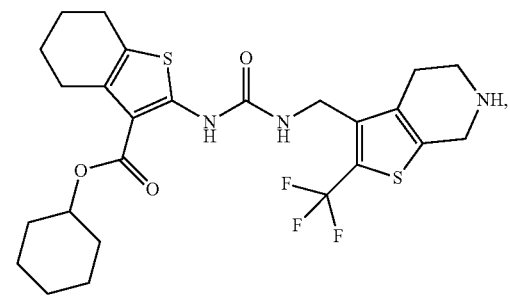
Formula 273
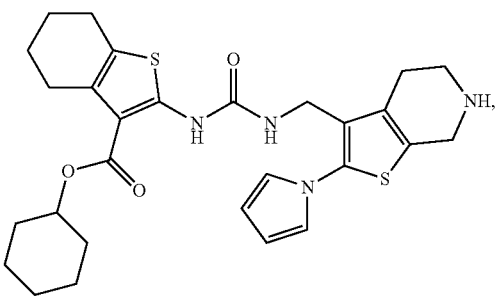
Formula 274
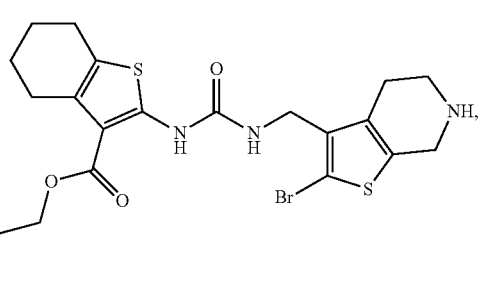
Formula 275
Formula 276
Formula 277
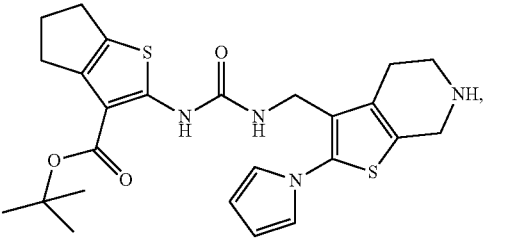

Formula 278
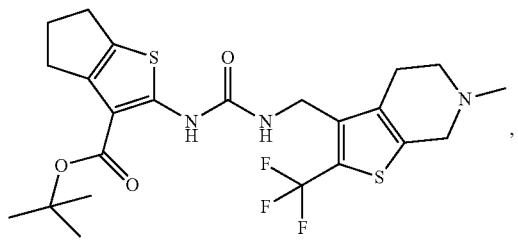
Formula 279
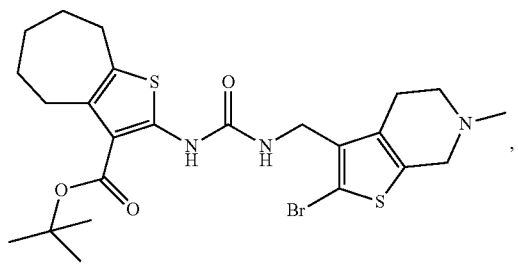
Formula 280
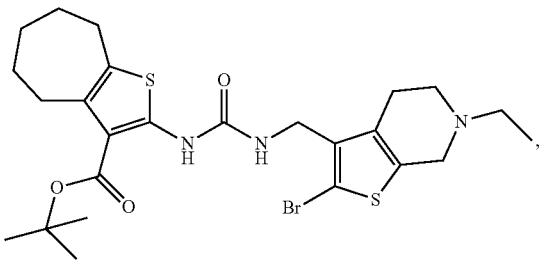
Formula 281
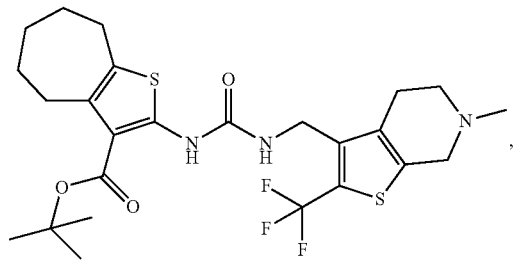
Formula 283
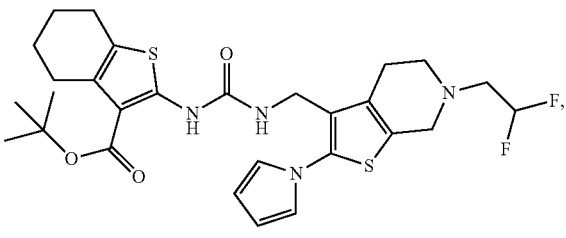
Formula 284
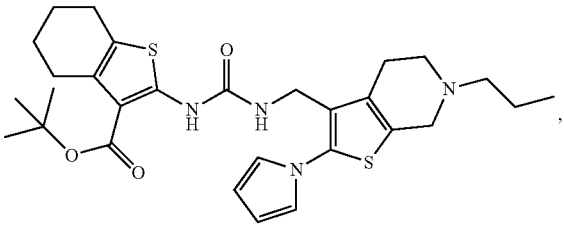
Formula 285
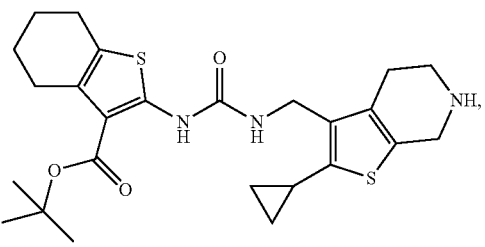
Formula 286
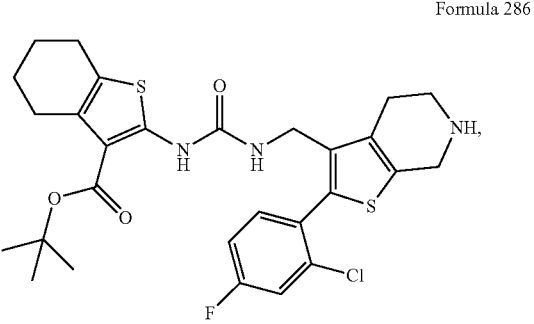
Formula 287
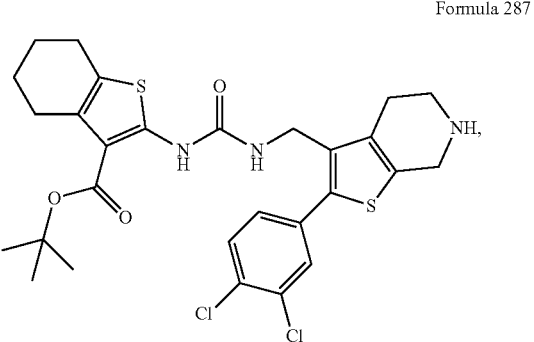
Formula 289
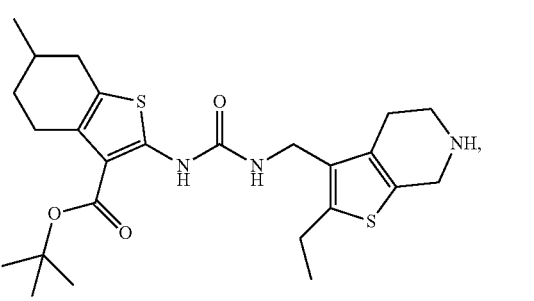
Formula 290
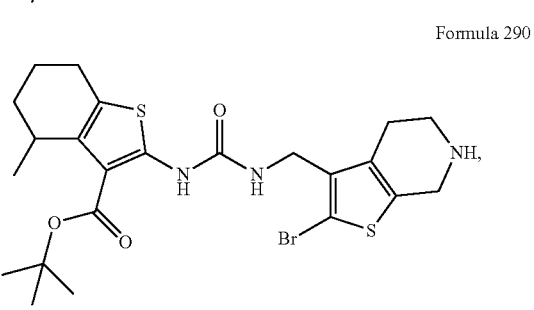

Formula 291
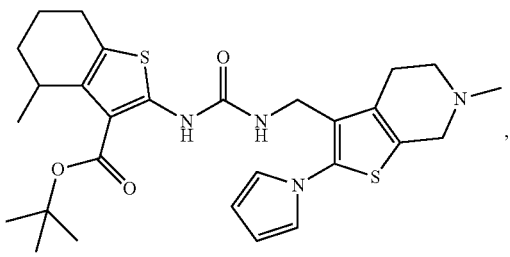
Formula 292
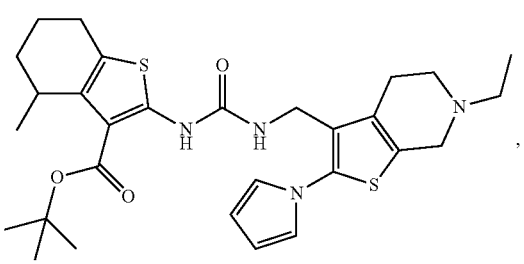
Formula 293
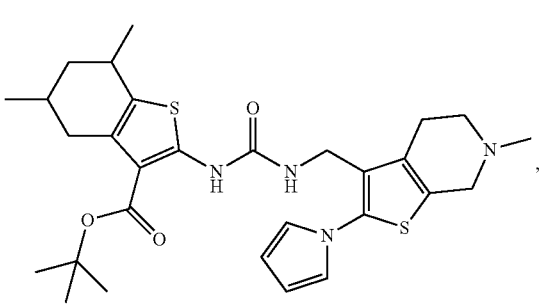
Formula 294
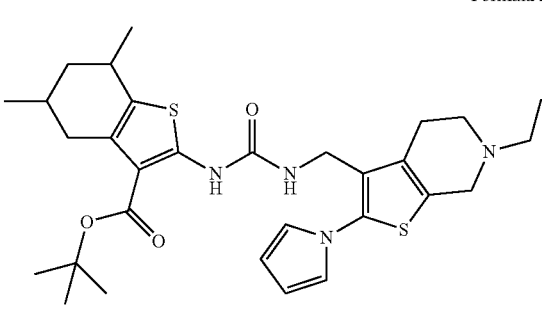
Formula 298
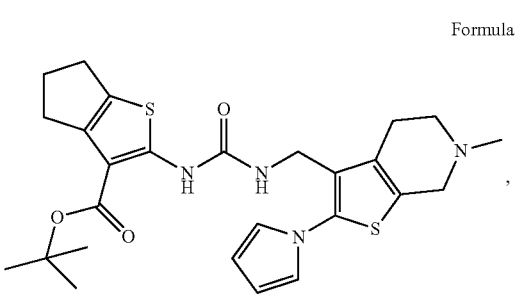
Formula 299
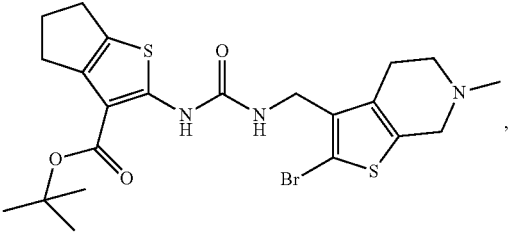
Formula 300
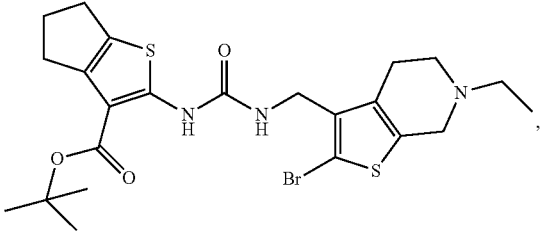
Formula 301
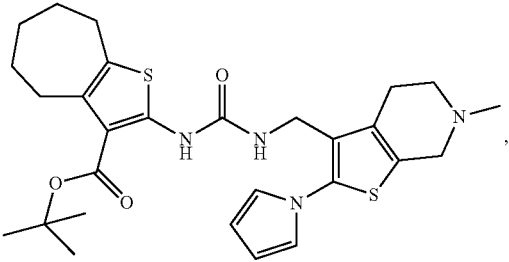
Formula 302
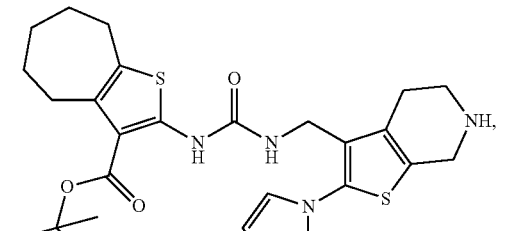
Formula 303
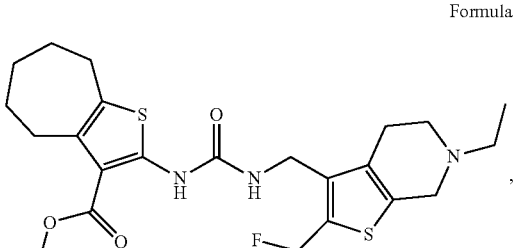
Formula 305
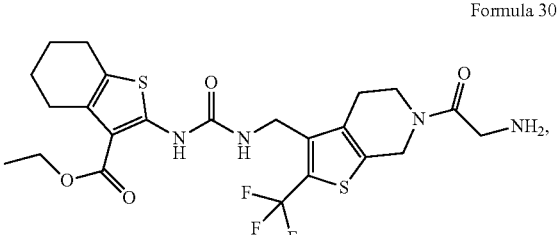

Formula 306
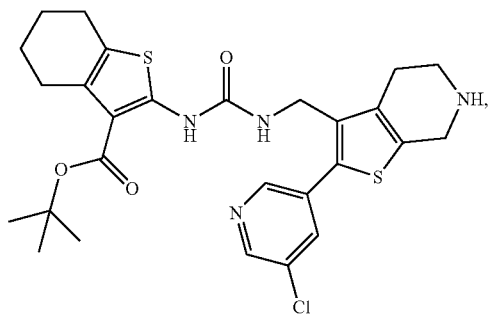
Formula 307
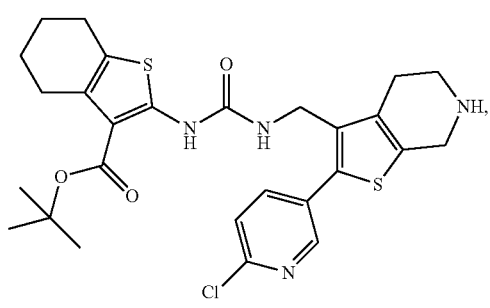
Formula 308
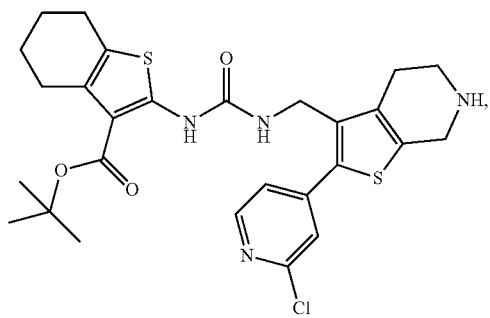
Formula 309
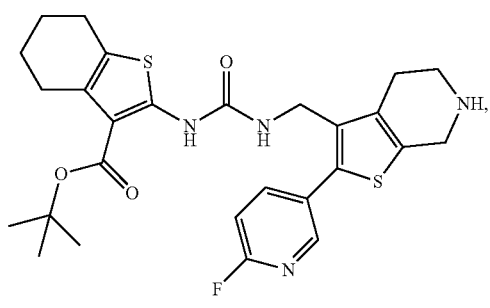
Formula 310
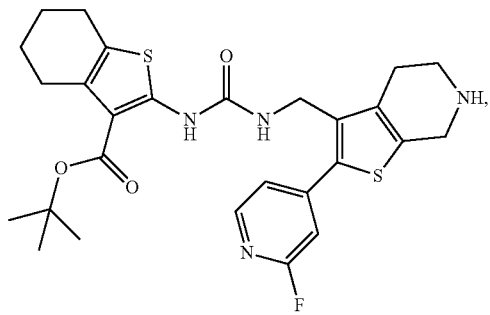
Formula 312
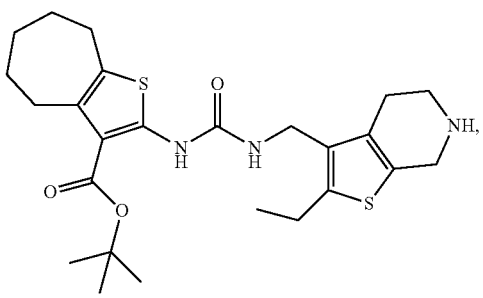
Formula 313
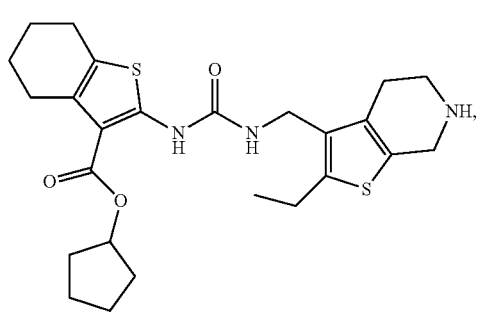
Formula 314
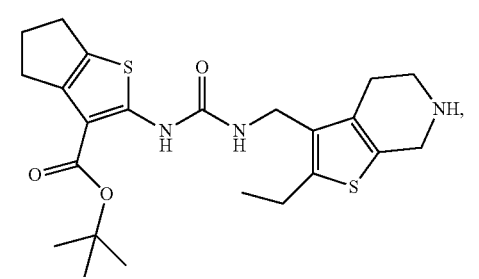
Formula 315
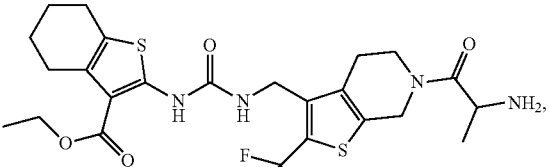
Formula 316
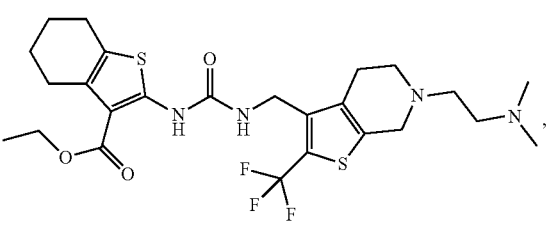

Formula 317
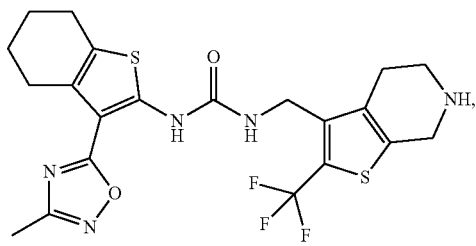
Formula 321
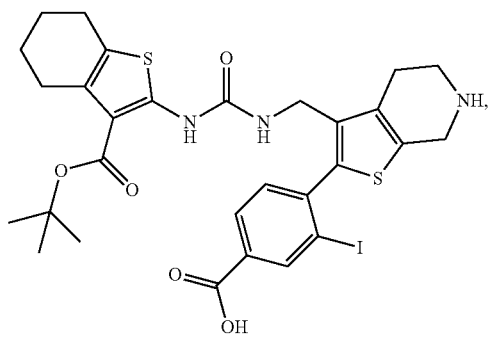
Formula 322
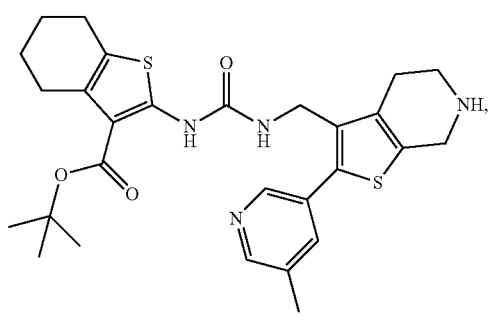
Formula 323
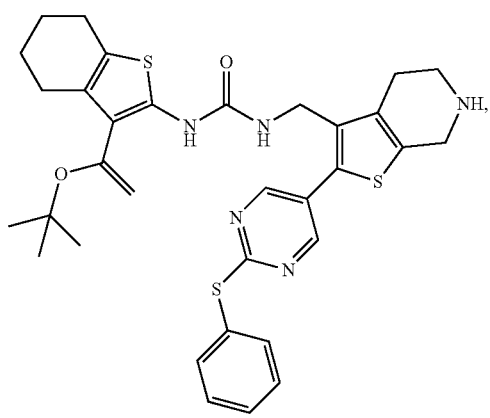
Formula 324
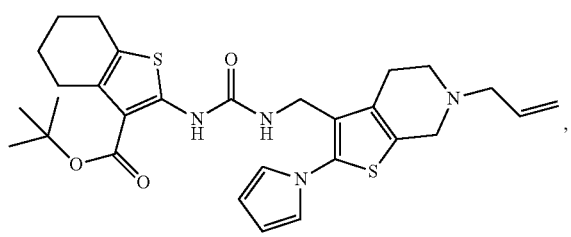
Formula 325
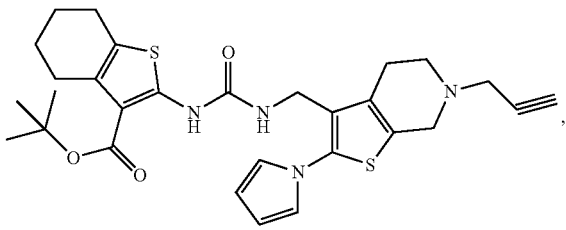
Formula 326
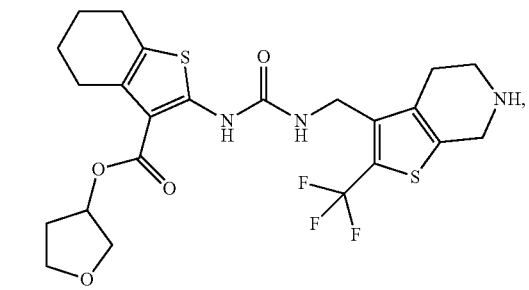
Formula 327
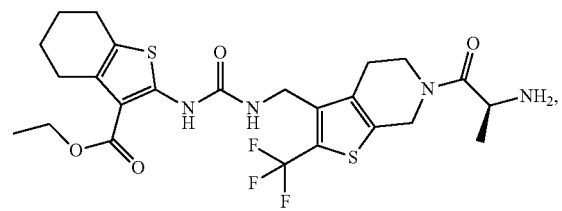
Formula 328
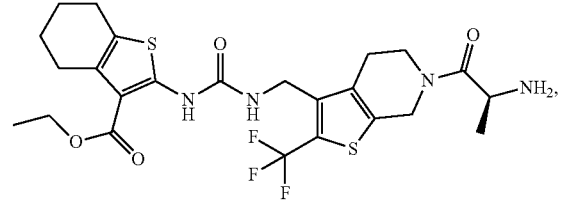
Formula 329
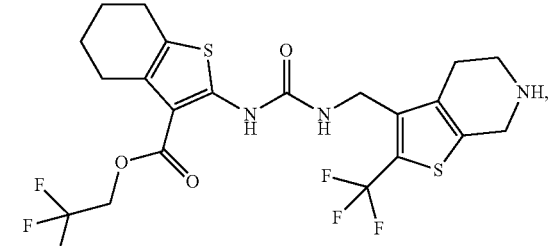
Formula 330
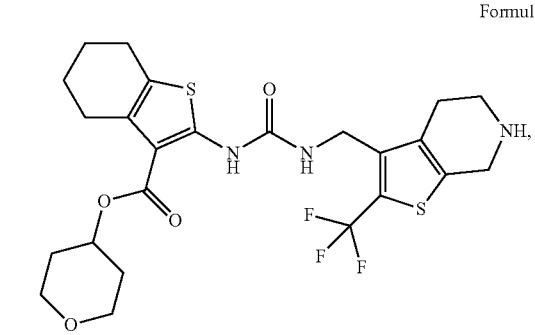

Formula 334
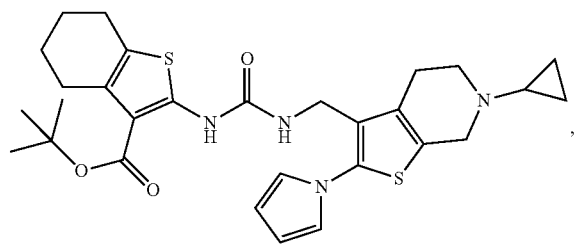
Formula 338
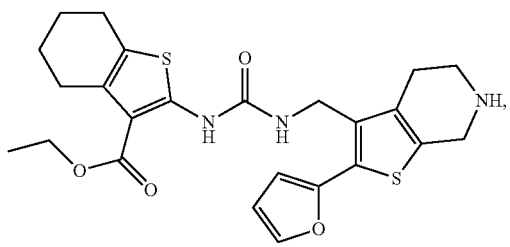
Formula 339
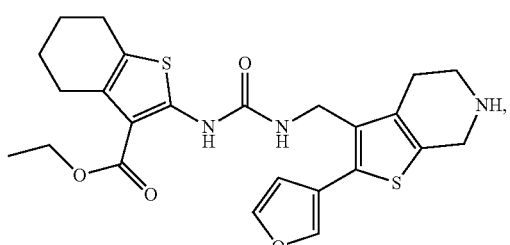
Formula 340
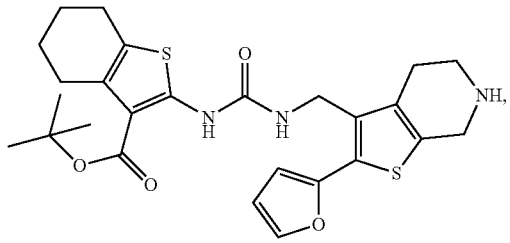
Formula 342
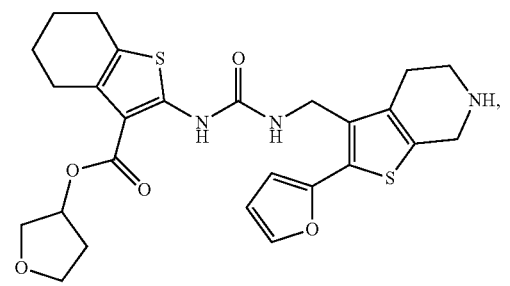
Formula 344
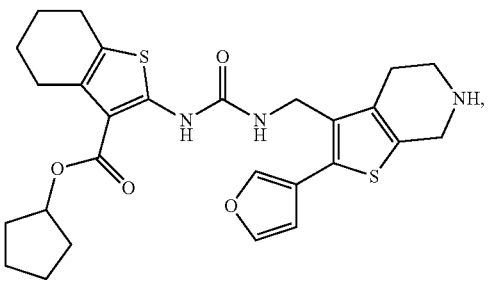
Formula 345
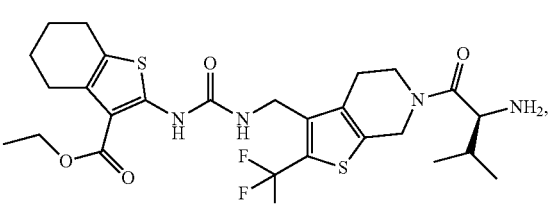
Formula 346
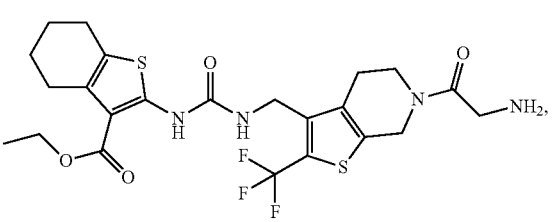
Formula 349
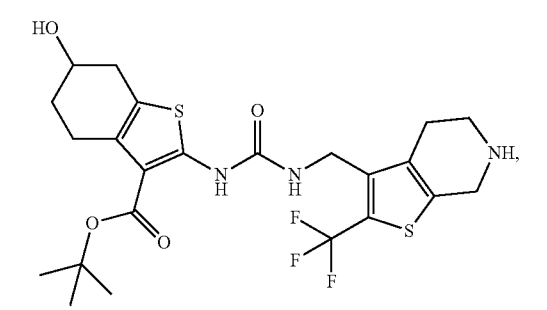
Formula 351
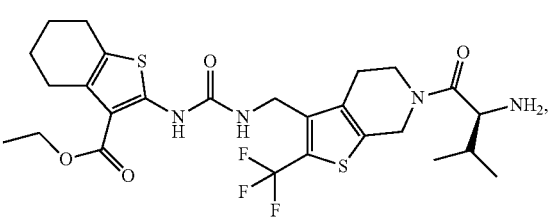
Formula 355
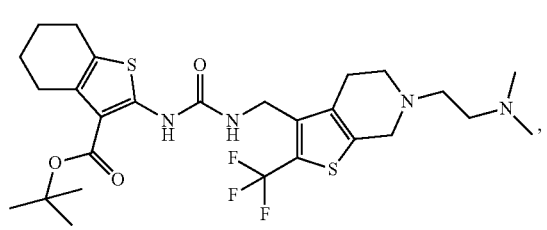

-continued
Formula 358
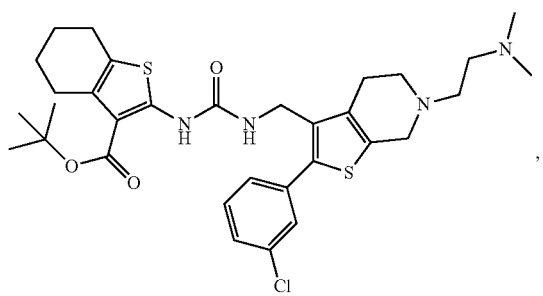
Formula 2
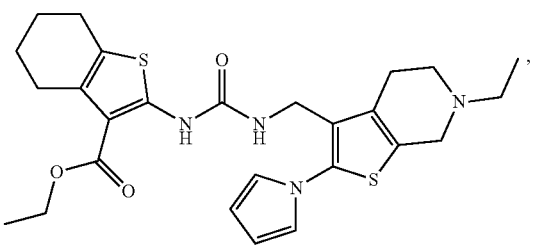
Formula 359
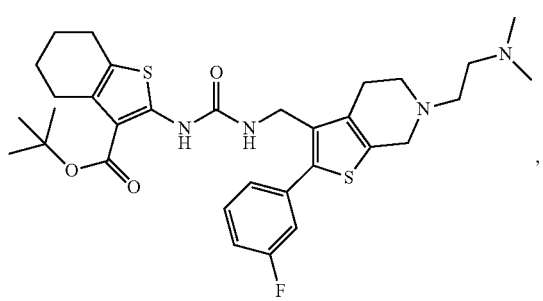
Formula 7
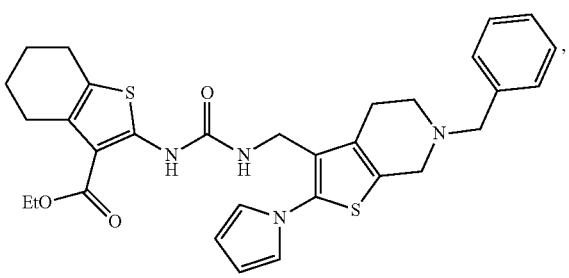
Formula 372
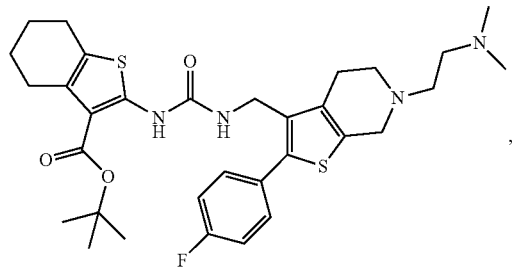
Formula 14
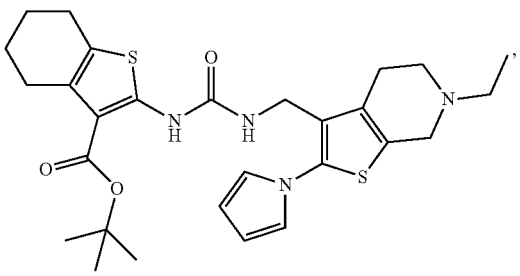
Formula 373
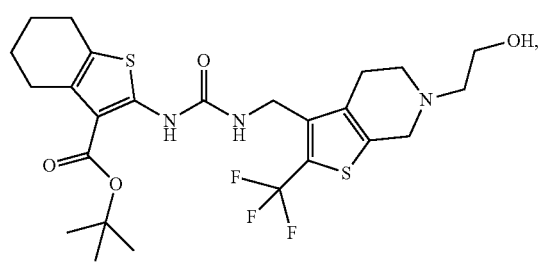
Formula 18
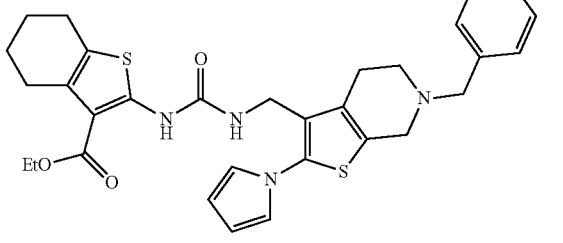
and a pharmaceutically acceptable salt thereof.
3. The compound according to claim 2, wherein the compound of Formula (If) is selected from the group consisting of:
Formula 19
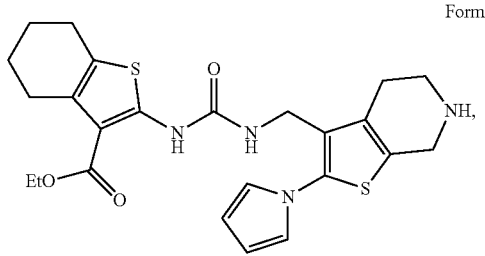

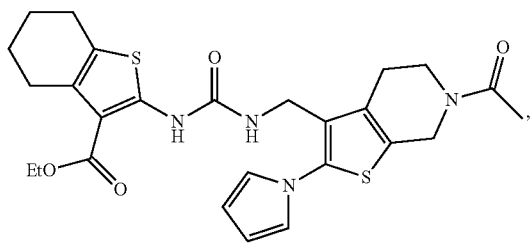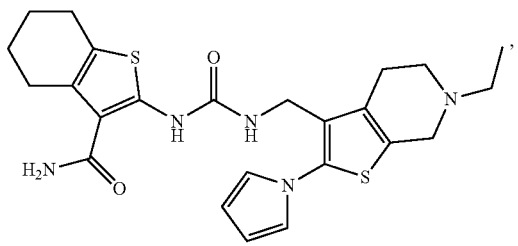

Formula 56
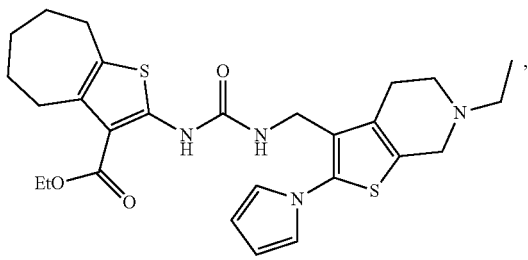
Formula 57
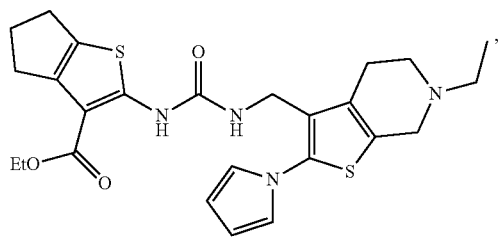
Formula 59
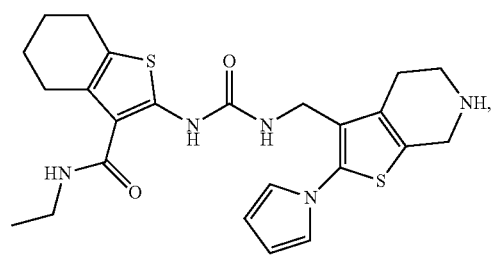
Formula 61
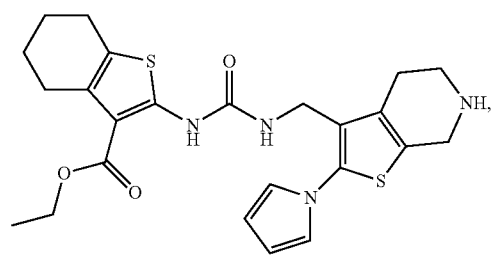
Formula 62
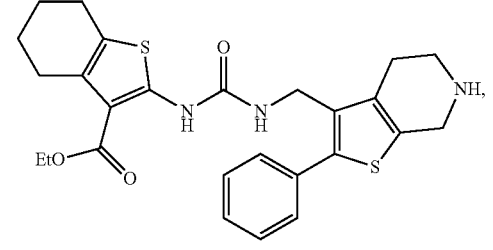
Formula 67
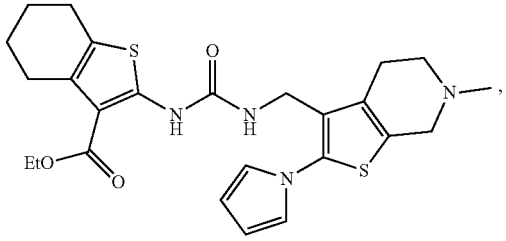
Formula 68
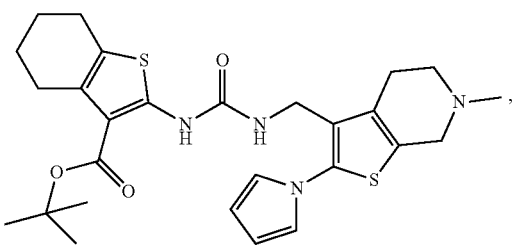
Formula 73
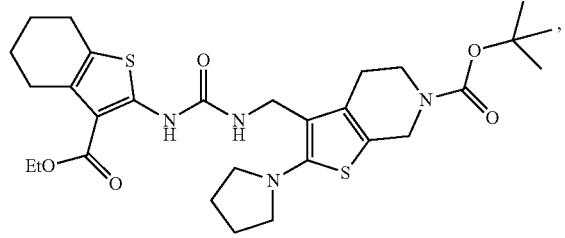
Formula 75
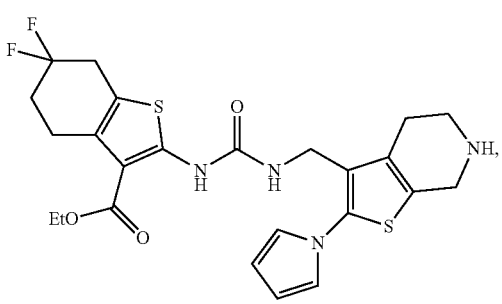
Formual 81
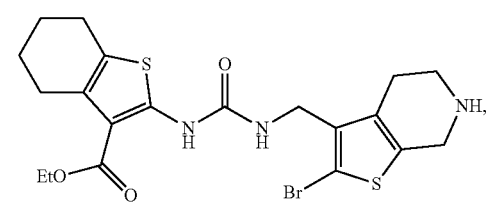
Formula 87
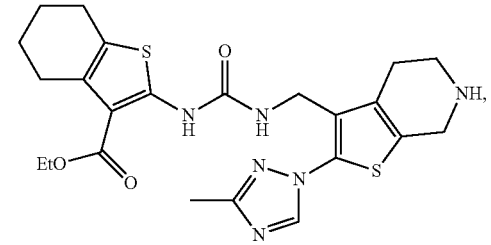
Formula 94
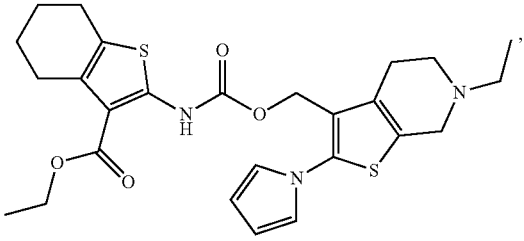

Formula 96
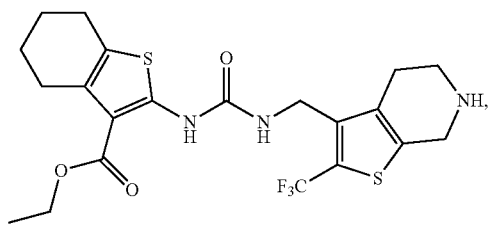
Formula 97
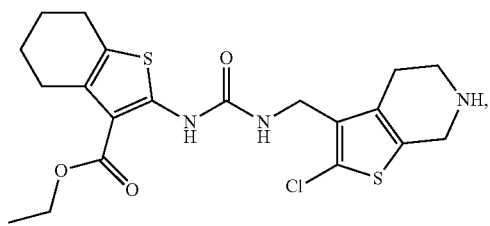
Formula 98
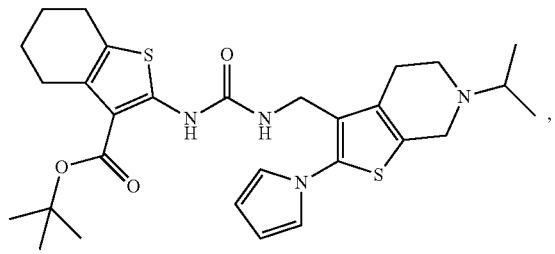
Formula 99
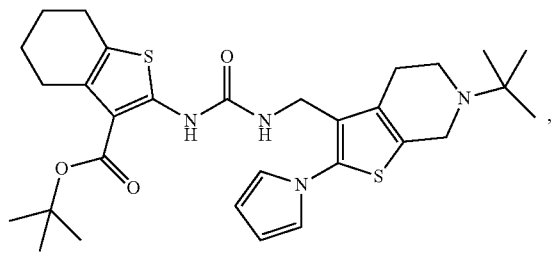
Formula 101
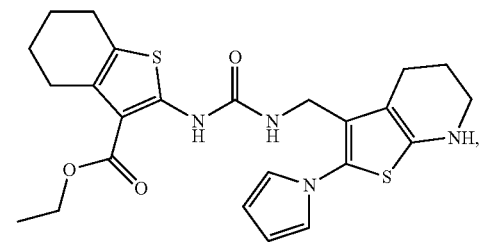
Formula 106
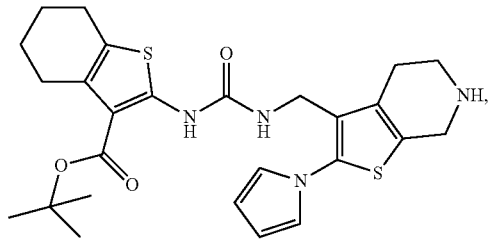
Formula 107
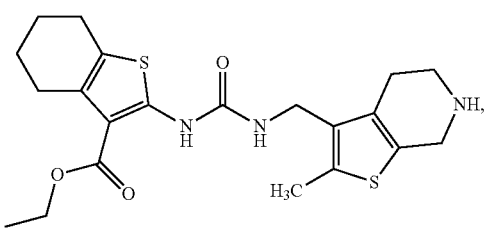
Formula 110
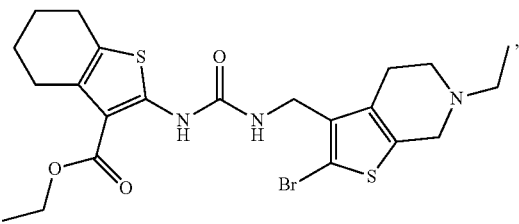
Formula 111
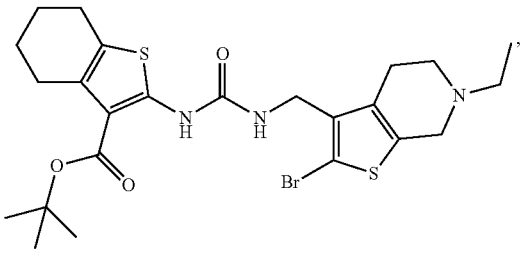
Formula 112
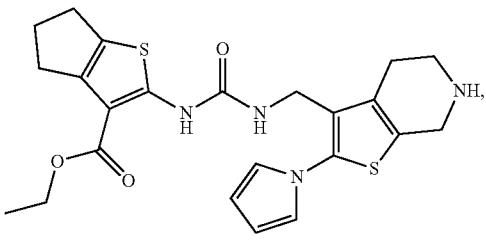
Formula 113
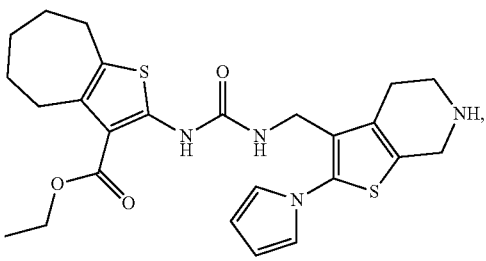
Formula 114
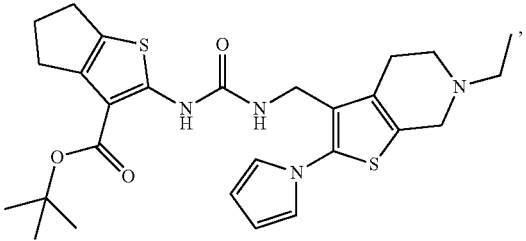

Formula 115
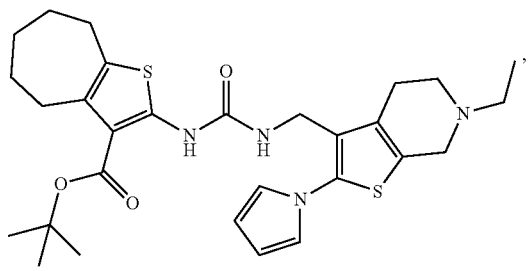
Formula 116
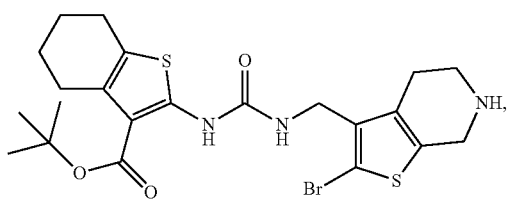
Formula 117
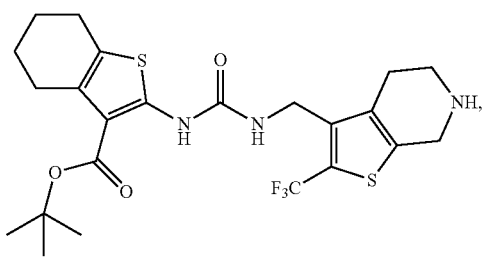
Formula 118
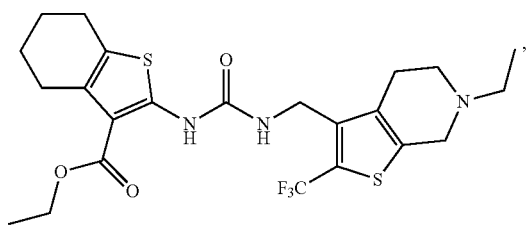
Formula 119
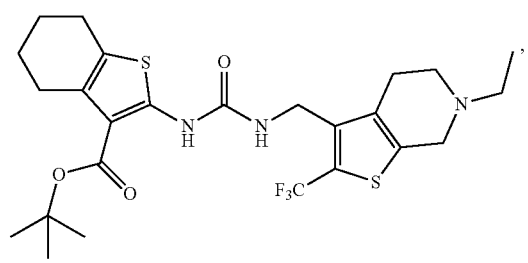
Formula 121
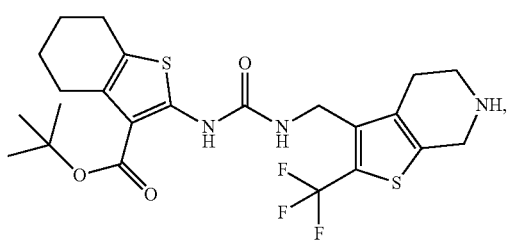
Formula 122
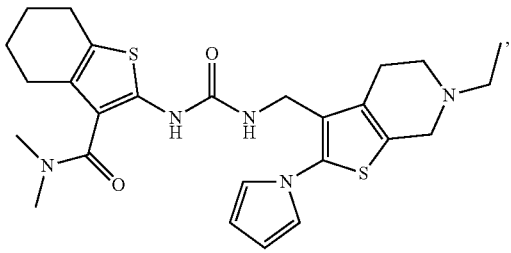
Formula 123
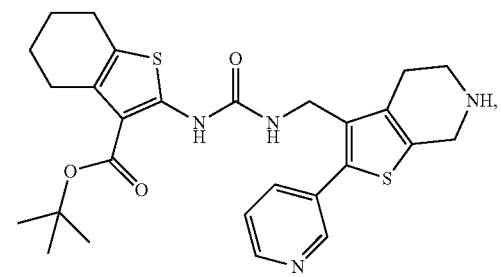
Formula 124
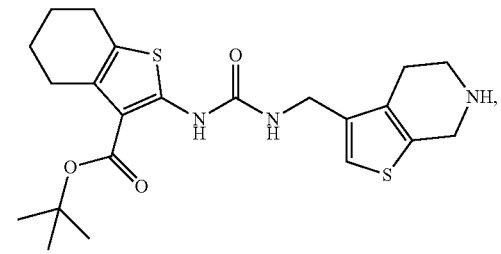
Formula 125
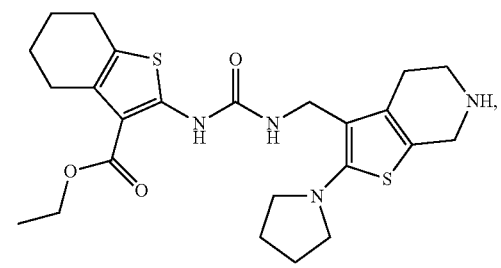
Formula 126
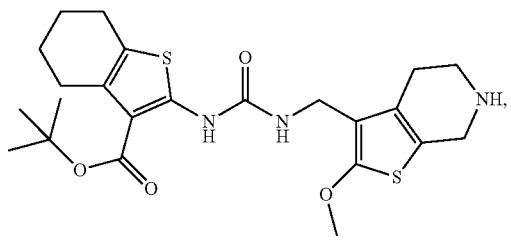

Formula 127
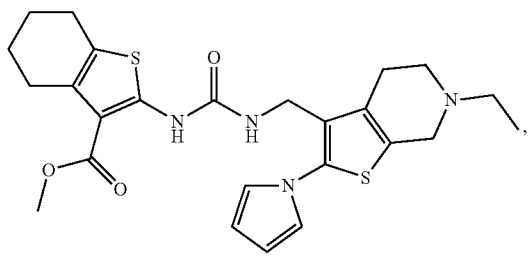
Formula 128
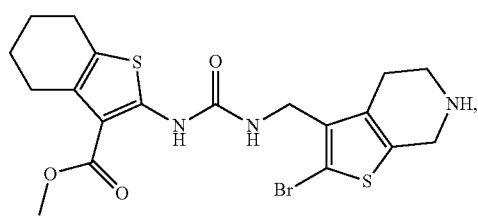
Formula 129
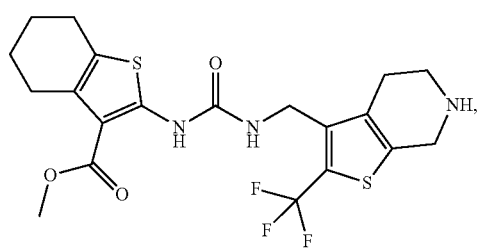
Formula 130
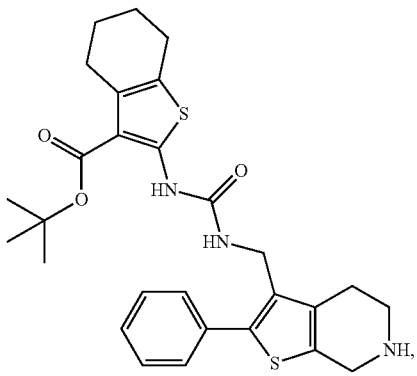
Formula 131
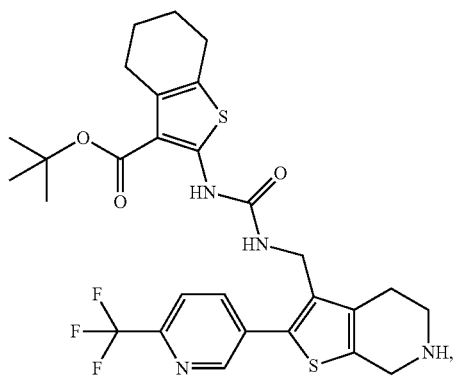
Formula 140
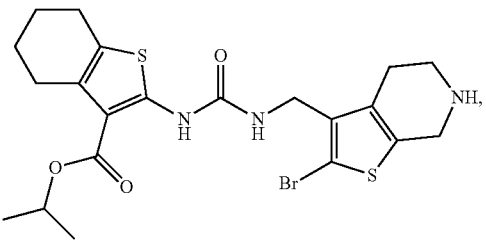
Formula 141
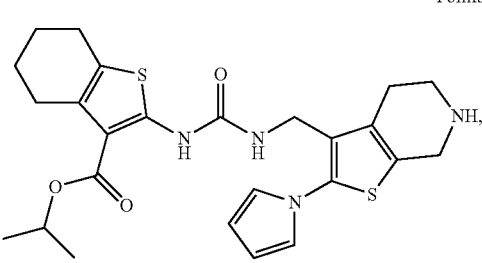
Formula 142
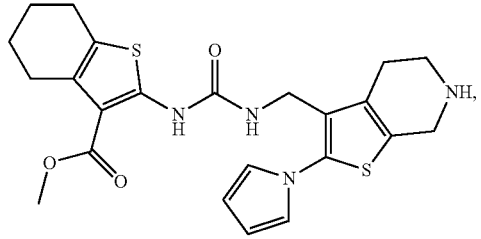
Formula 143
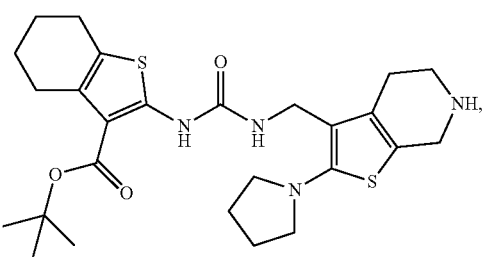
Formula 144
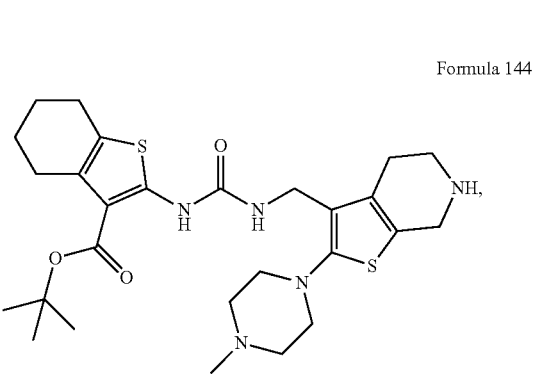

Formula 145
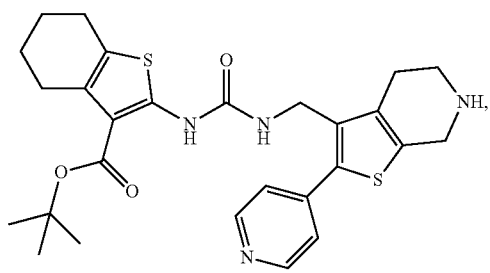
Formula 146
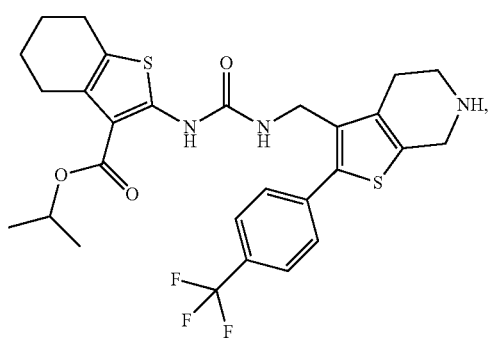
Formula 151
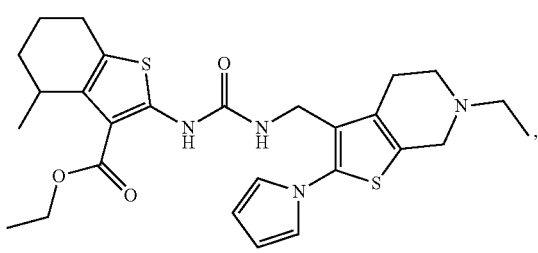
Formula 152
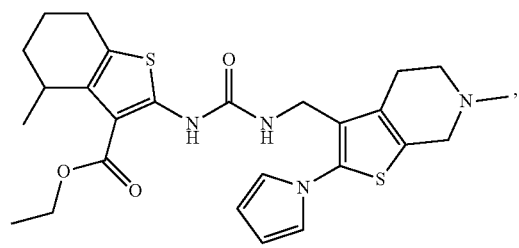
Formula 153
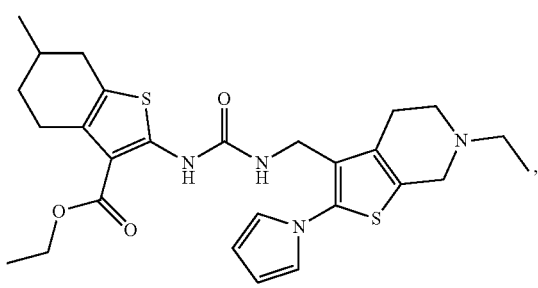
Formula 154
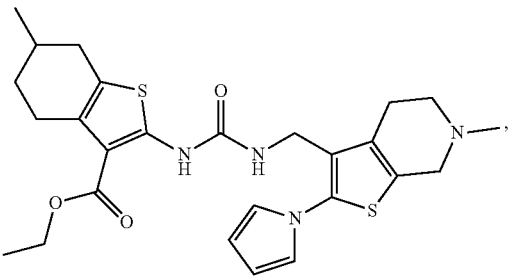
Formula 155
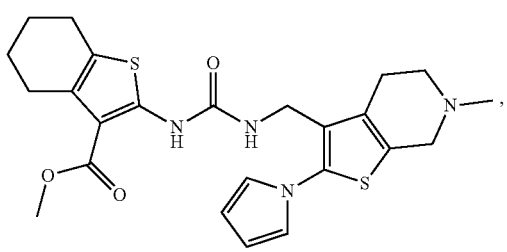
Formula 156
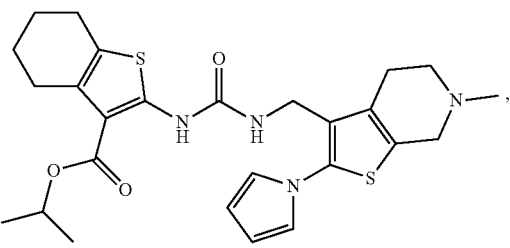
Formula 157
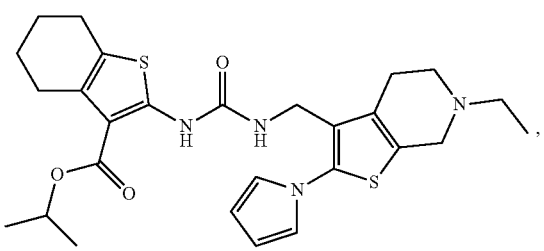
Formula 159
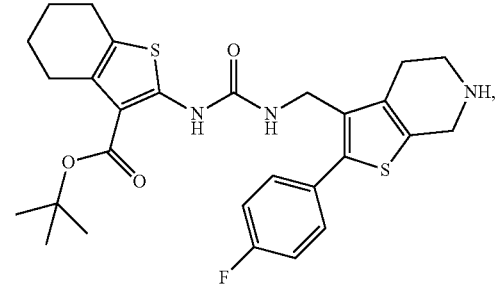

Formula 160
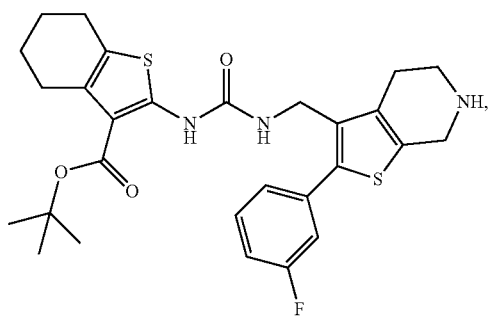
Formula 161
Formula 164
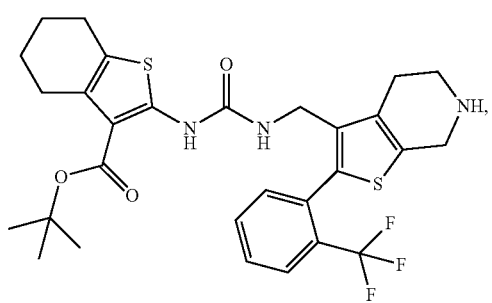
Formula 165
Formula 166
Formula 167
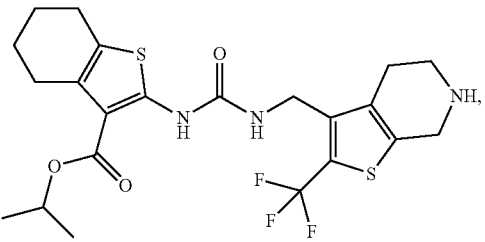
Formula 169
Formula 171
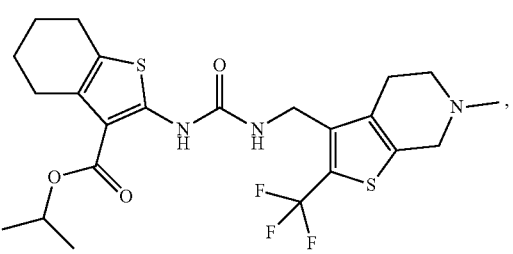
Formula 172
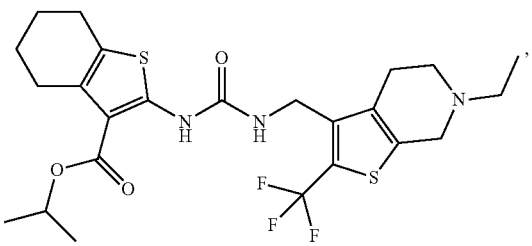
Formula 174
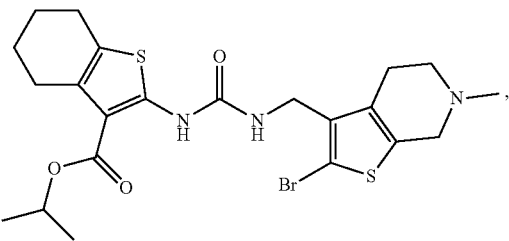
Formula 175
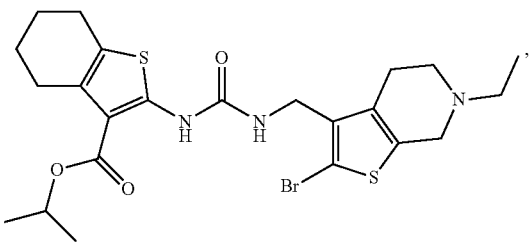
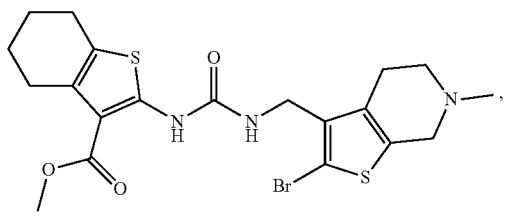

Formula 177
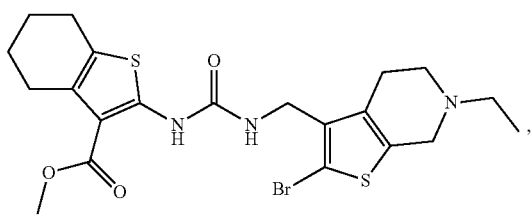
Formula 178
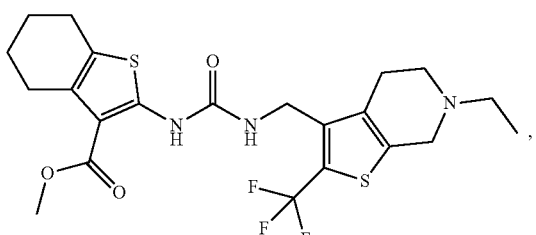
Formula 179
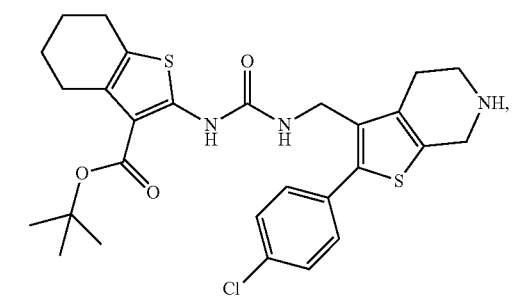
Formula 180
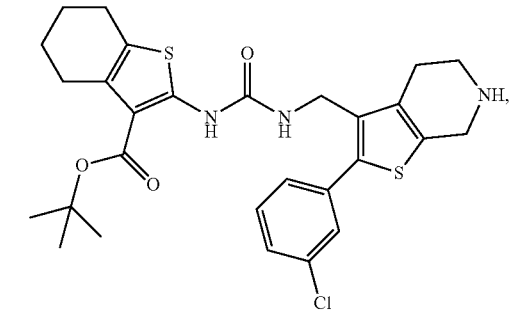
Formula 181
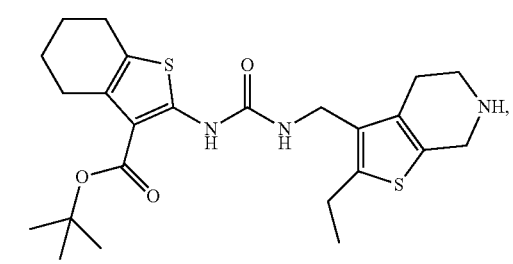
Formula 182
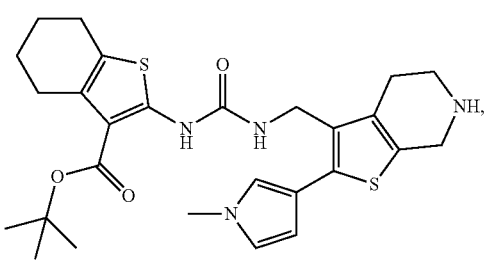
Formula 183
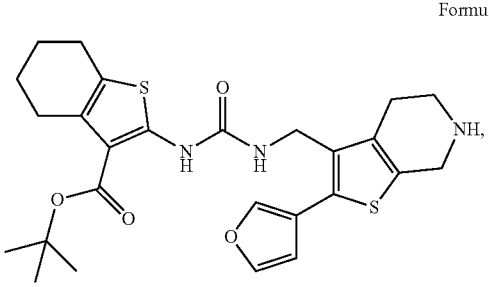
Formula 184
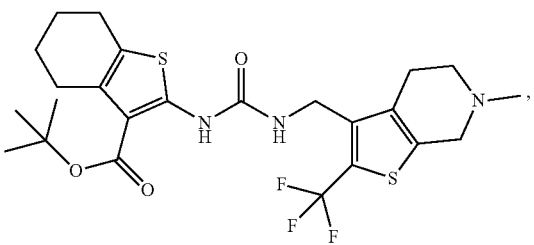
Formula 185
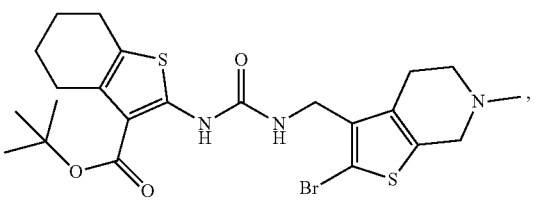
Formula 186
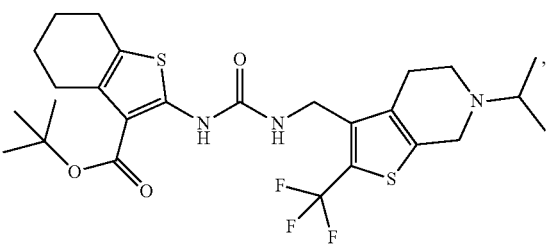
Formula 187
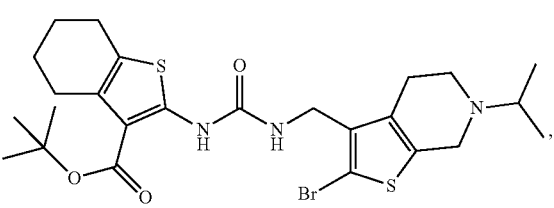

Formula 190
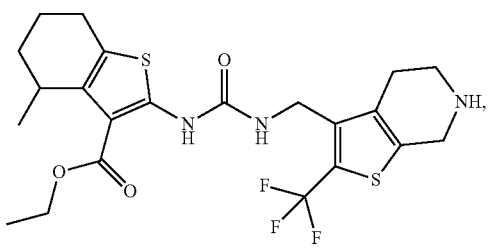
Formula 191
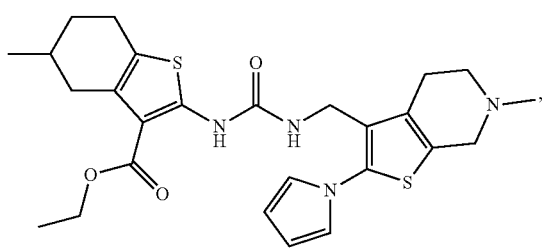
Formula 192
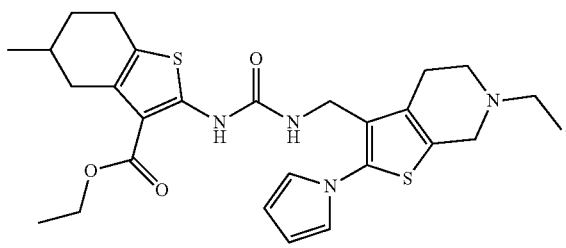
Formula 193
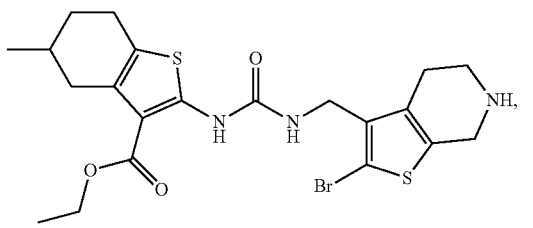
Formula 194
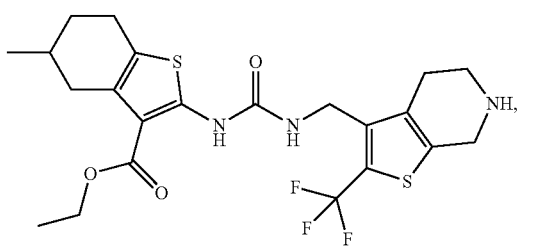
Formula 197
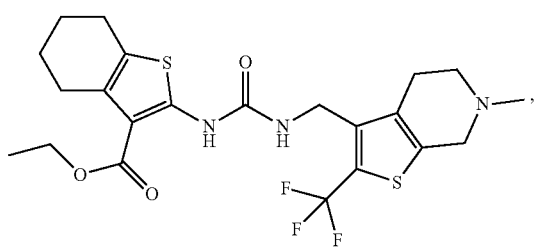
Formula 198
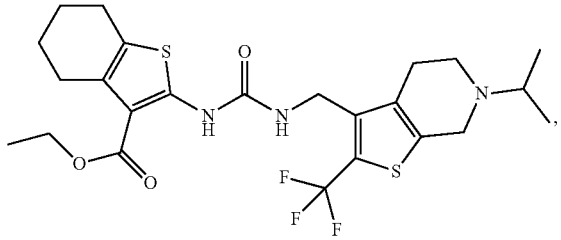
Formula 199
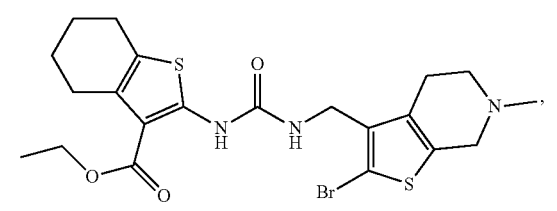
Formula 200
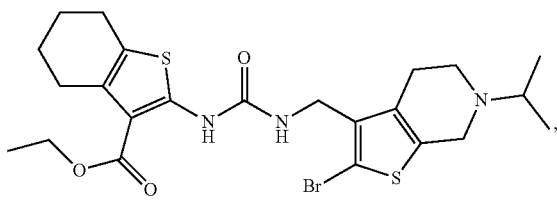
Formula 201
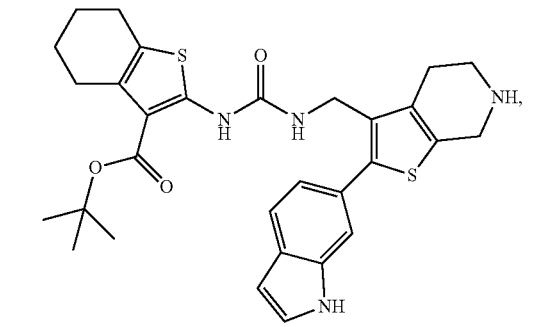
Formula 202
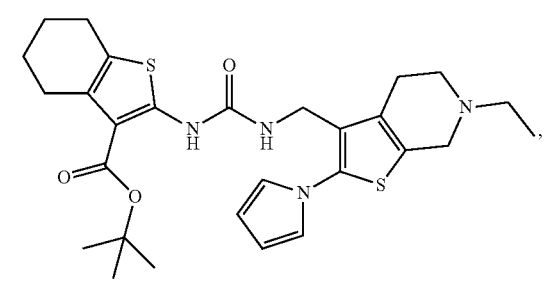
Formula 203
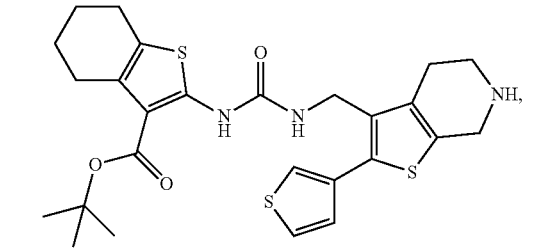

Formula 204
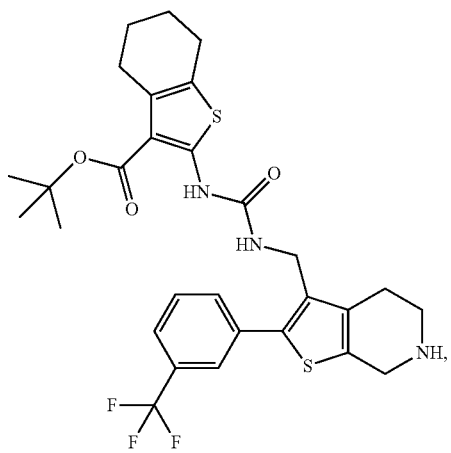
Formula 205
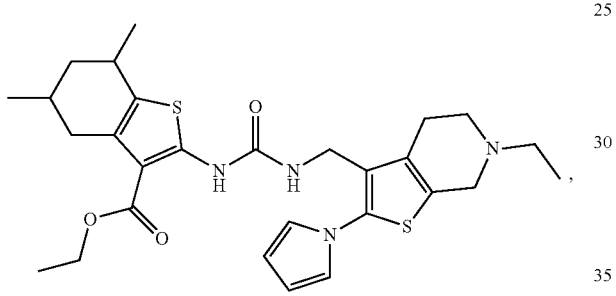
Formula 207
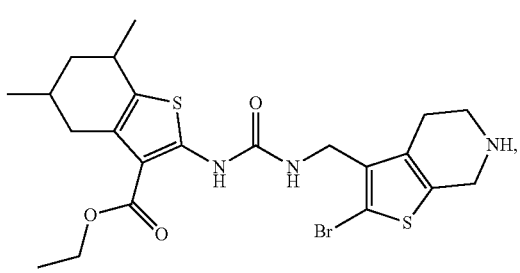
Formula 208
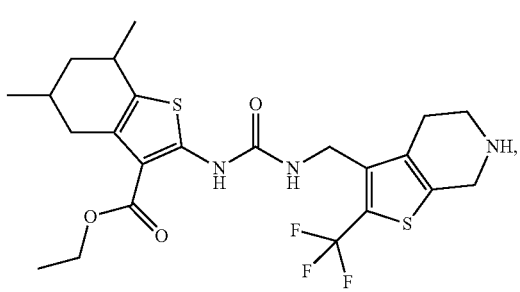
Formula 210
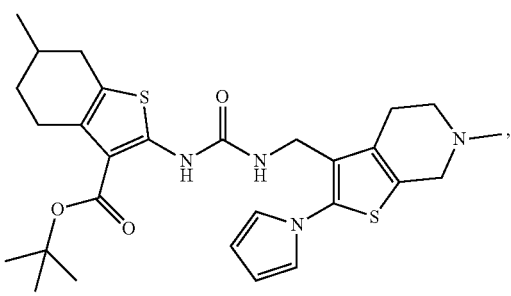
Formula 211
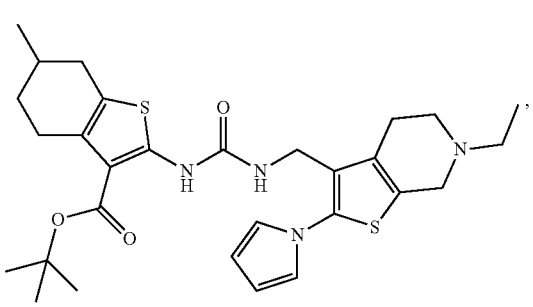
Formula 212
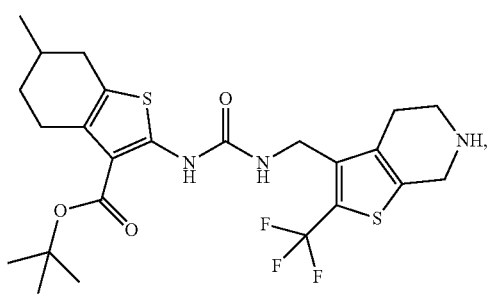
Formula 213
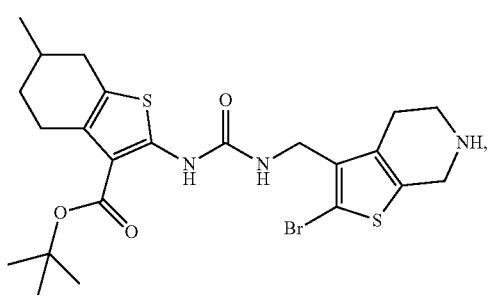
Formula 218
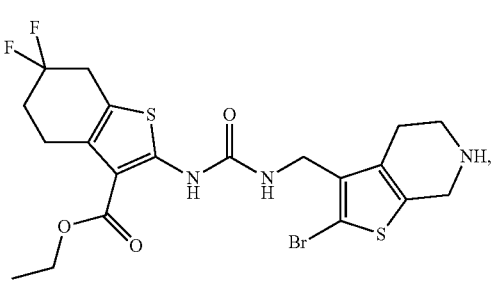

-continued
Formula 219
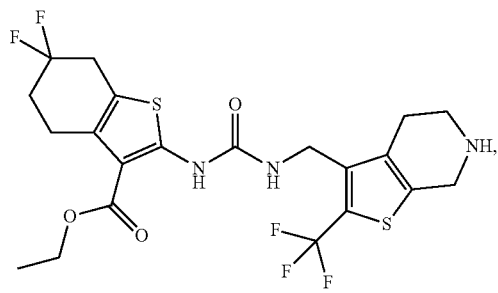
Formula 220
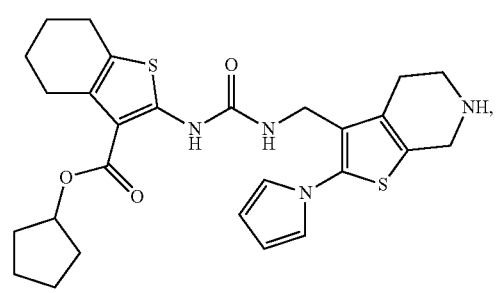
Formula 221
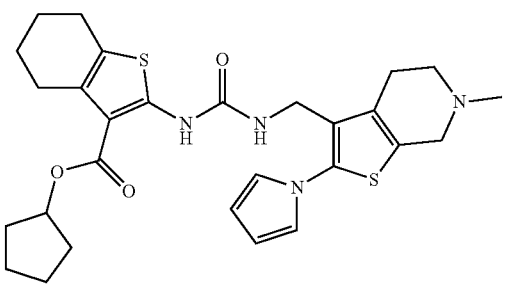
Formula 222
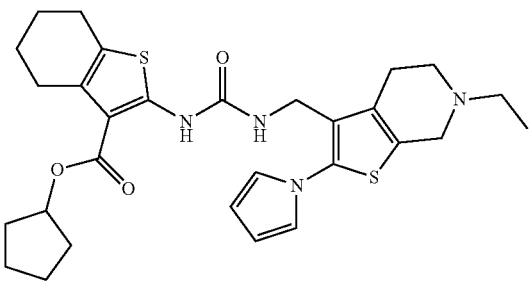
Formula 224
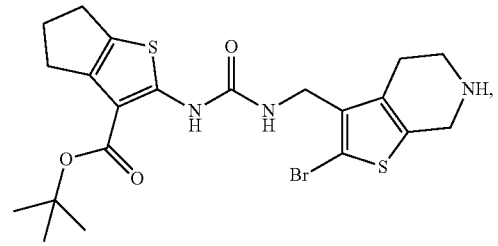
-continued
Formula 225
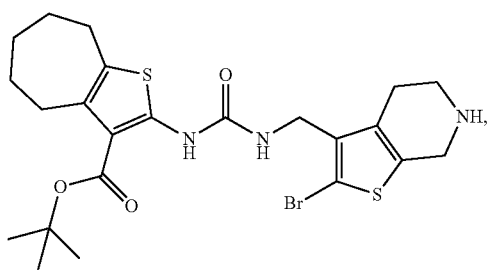
Formula 226
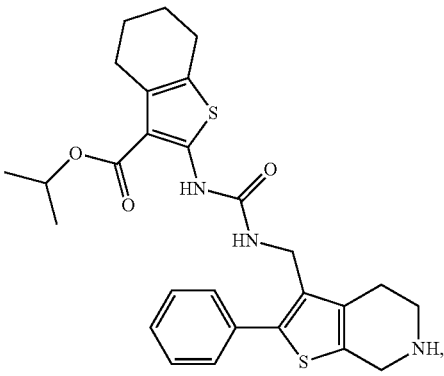
Formula 227
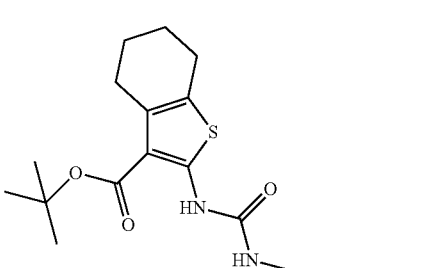
Formula 228
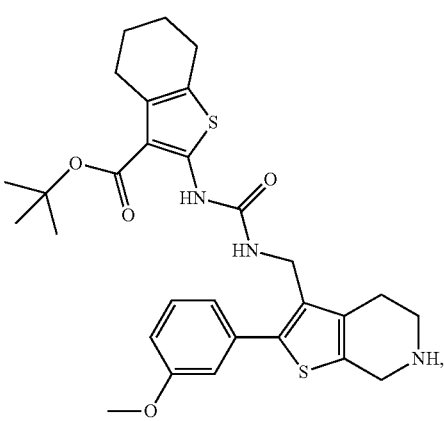

Formula 229
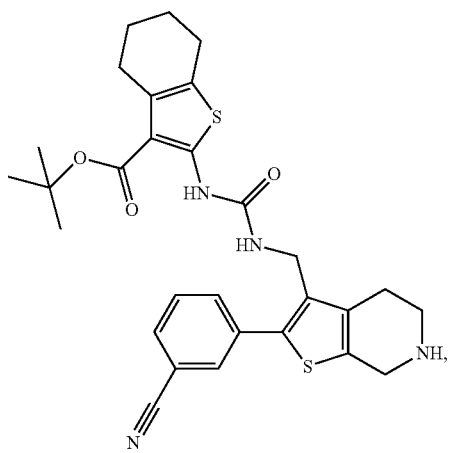
Formula 231
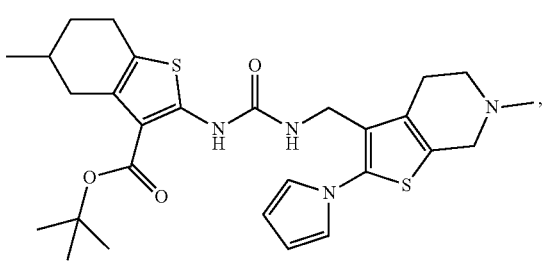
Formula 232
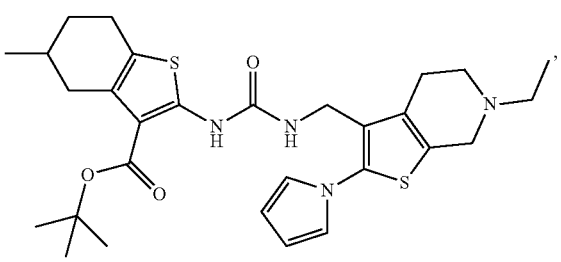
Formula 233
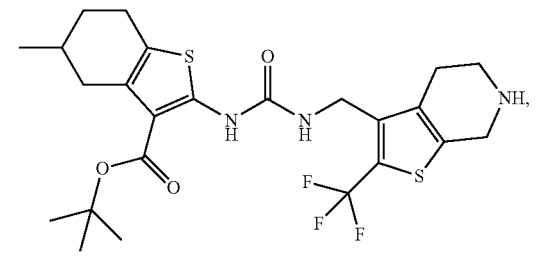
Formula 234
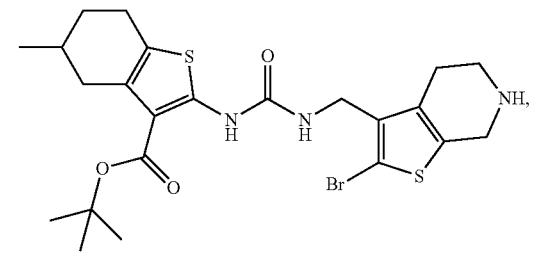
Formula 235
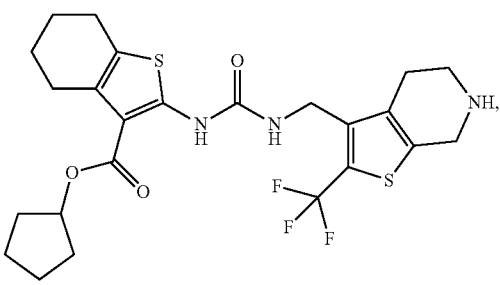
Formula 240
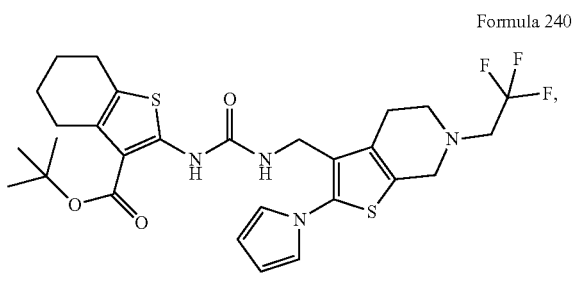
Formula 241
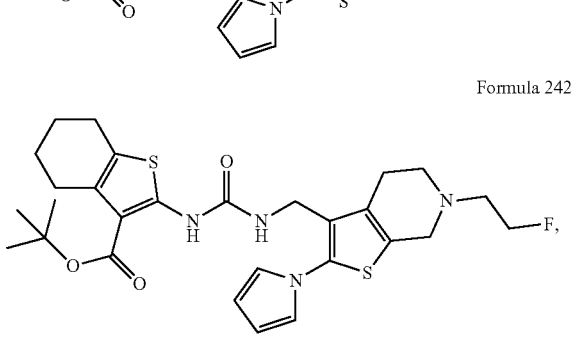
Formula 242
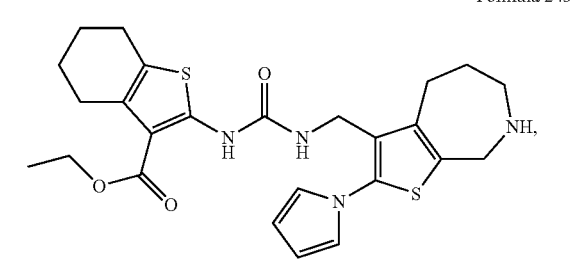
Formula 243
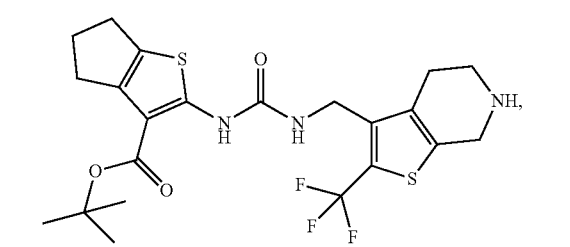
Formula 244

Formula 245
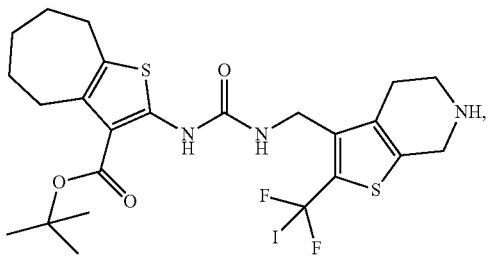
Formula 247
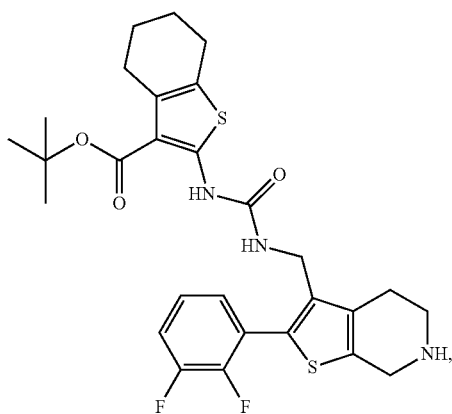
Formula 248
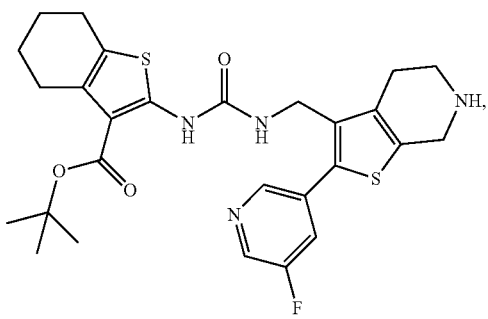
Formula 249
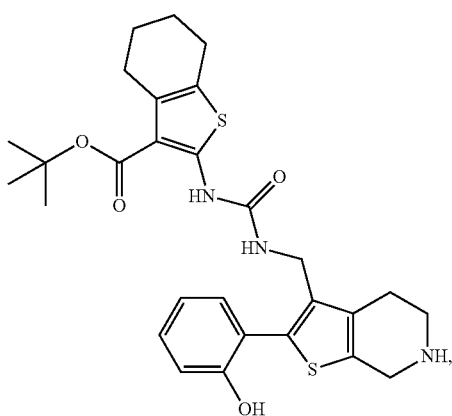
Formula 250
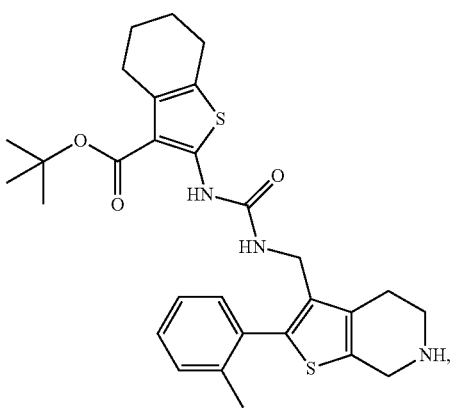
Formula 252
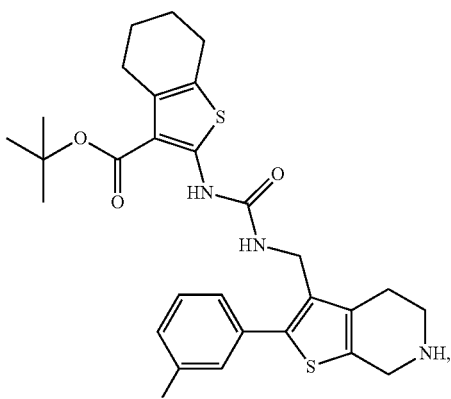
Formula 254
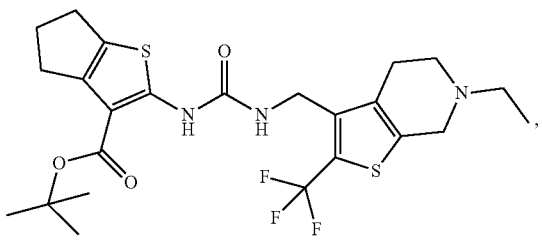
Formula 256
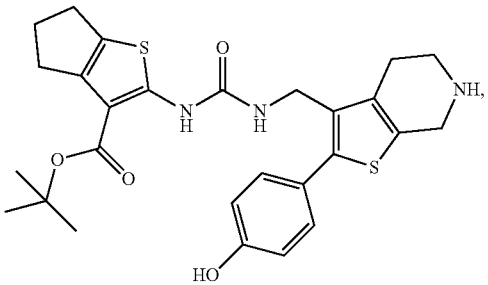

Formula 257
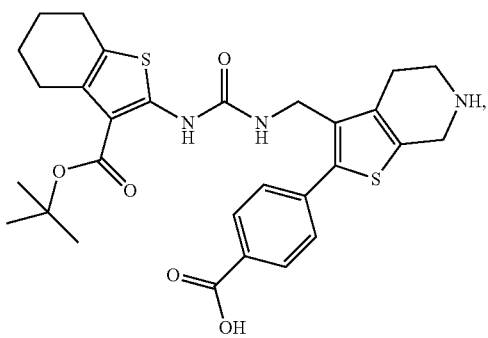
Formula 258
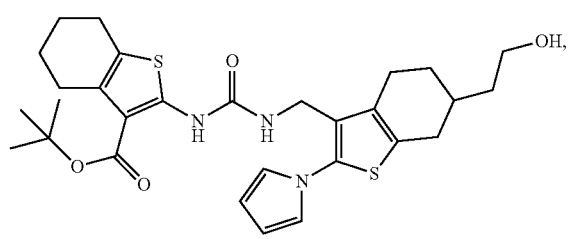
Formula 259
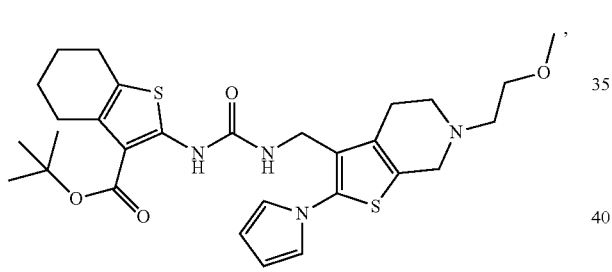
Formula 260
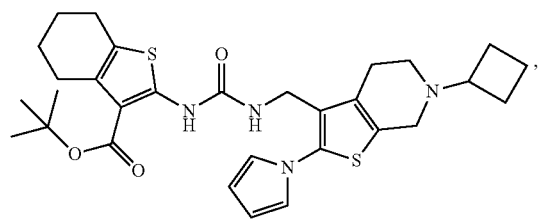
Formula 261
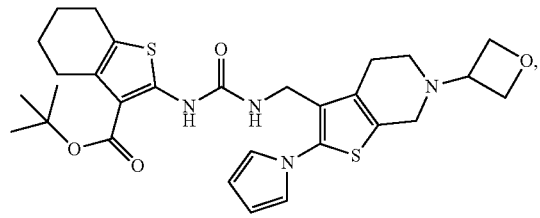
Formula 262
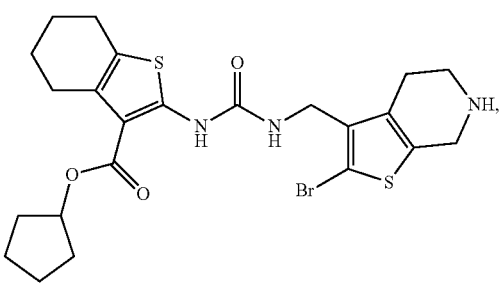
Formula 263
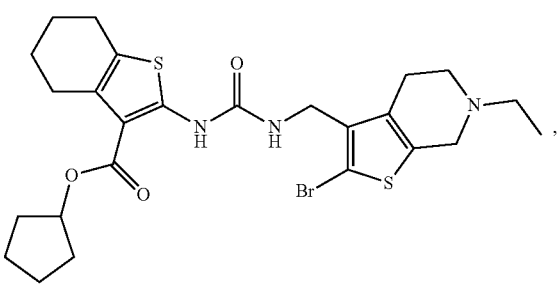
Formula 265
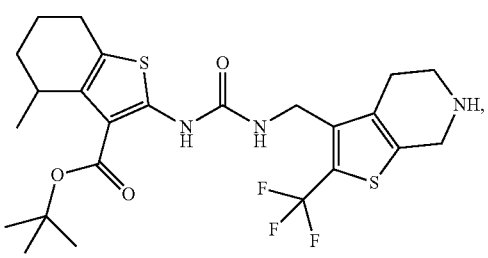
Formula 266
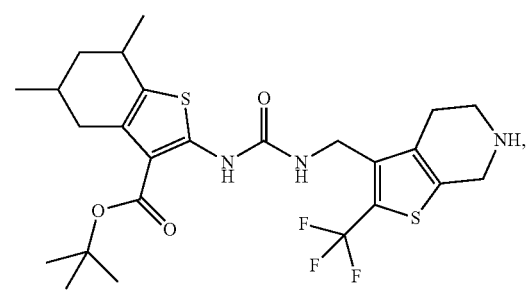
Formula 267
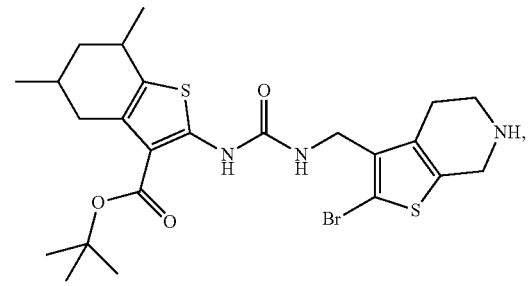

Formula 271
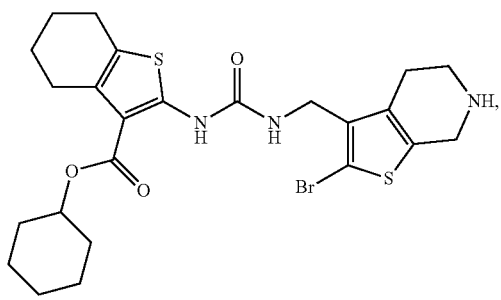
Formula 272
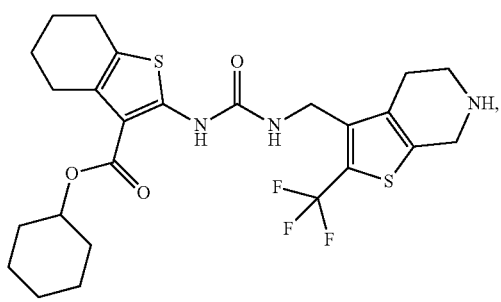
Formula 273
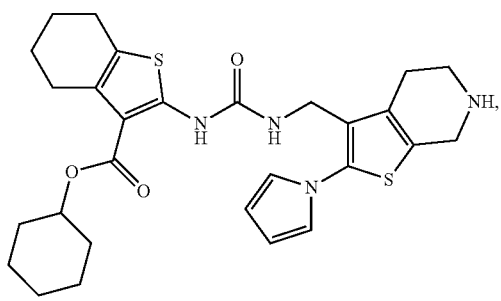
Formula 274
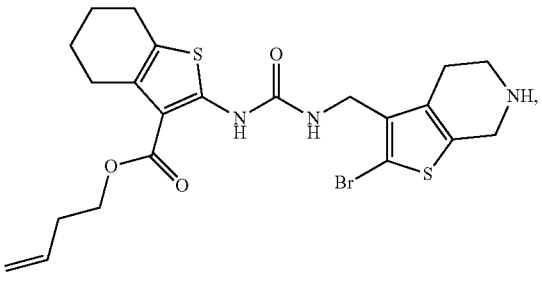
Formula 275
Formula 276
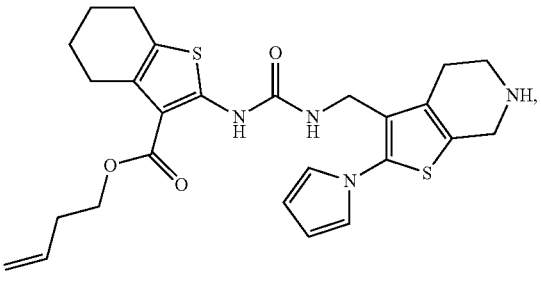
Formula 277
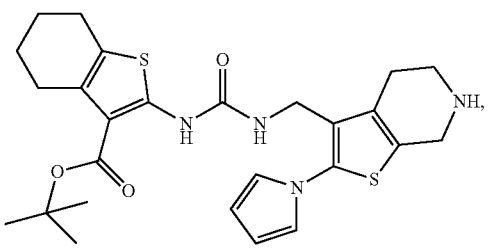
Formula 278
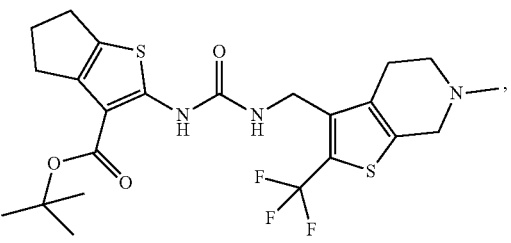
Formula 279
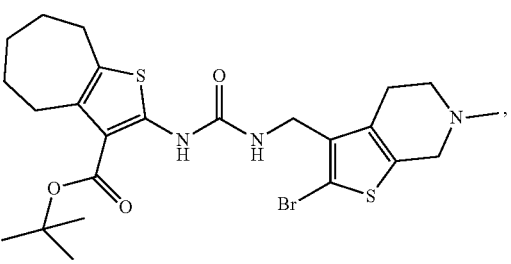
Formula 280
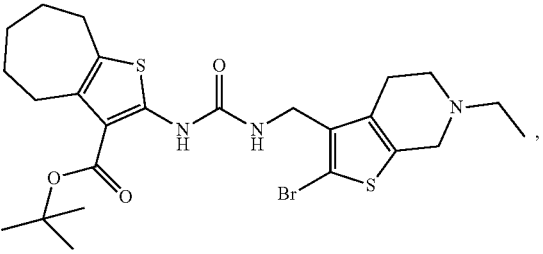

Formula 281
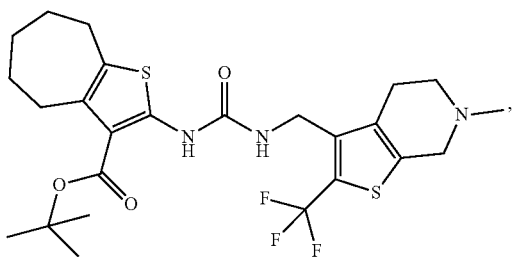
Formula 283
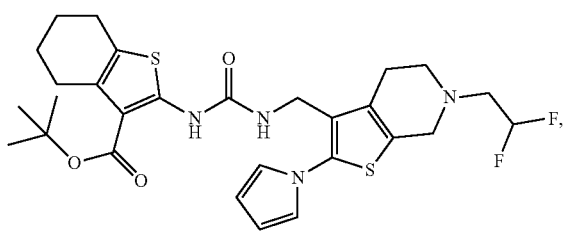
Formula 284
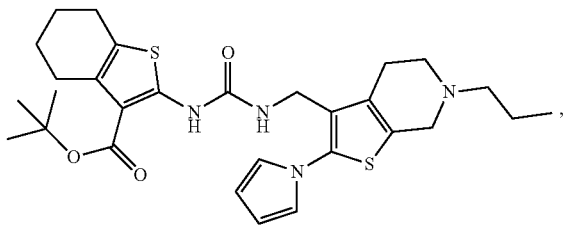
Formula 285
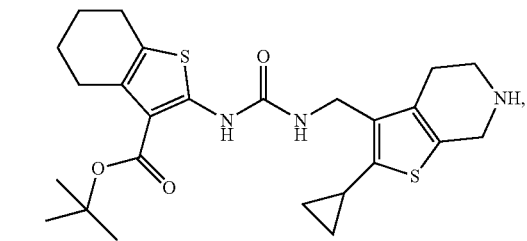
Formula 286
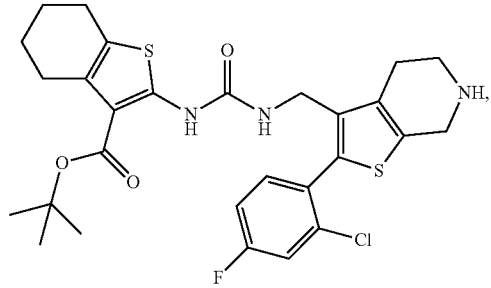
Formula 287
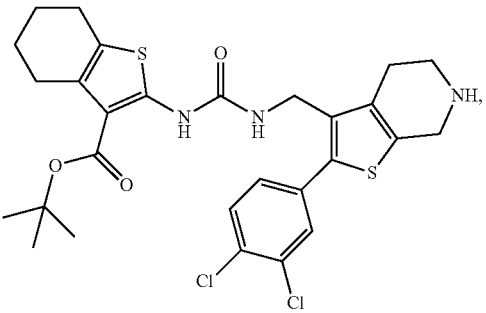
Formula 289
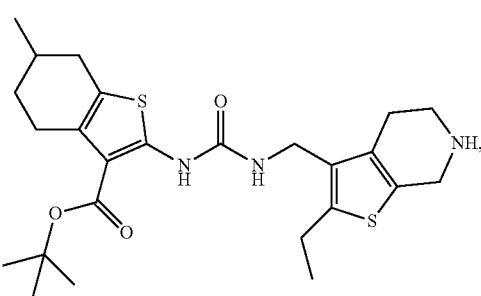
Formula 290
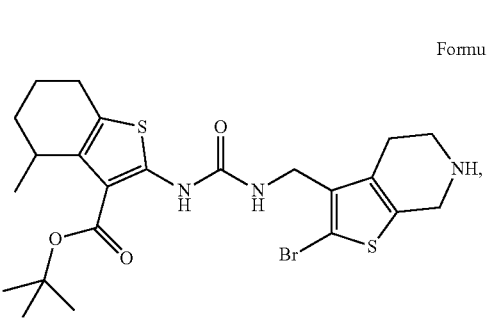
Formula 291
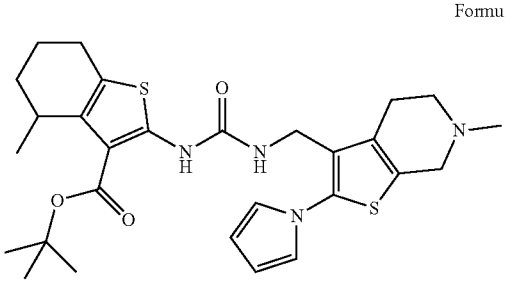
Formula 292
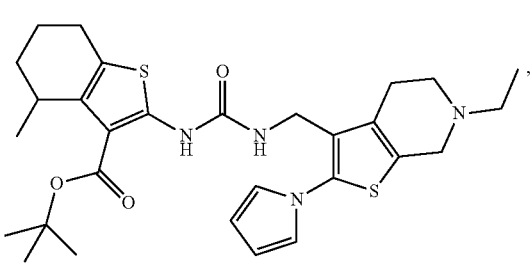

Formula 293
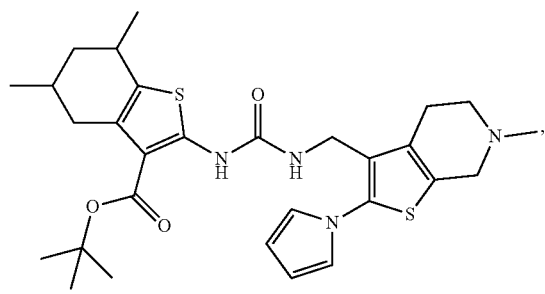
Formula 294
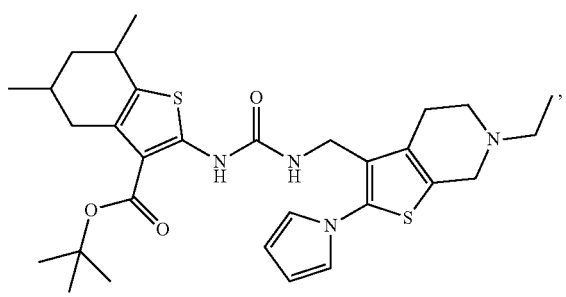
Formula 298
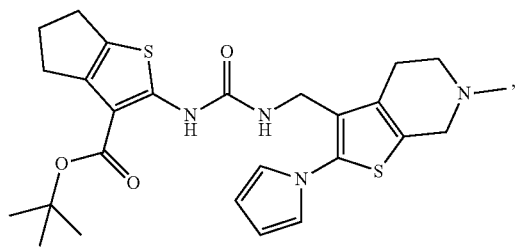
Formula 299
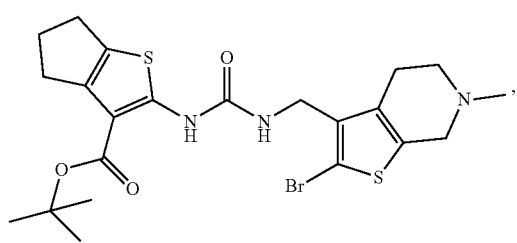
Formula 300
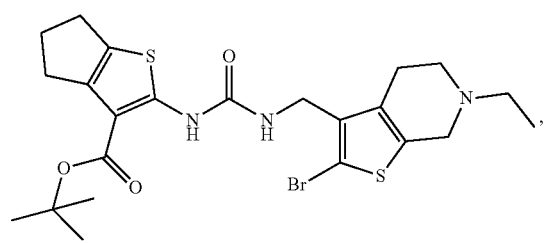
Formula 301
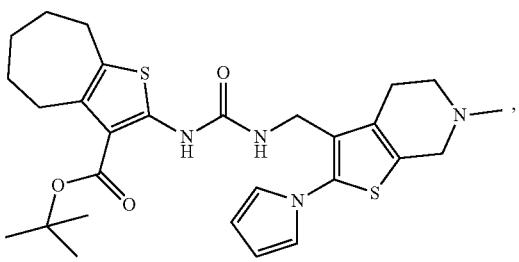
Formula 302
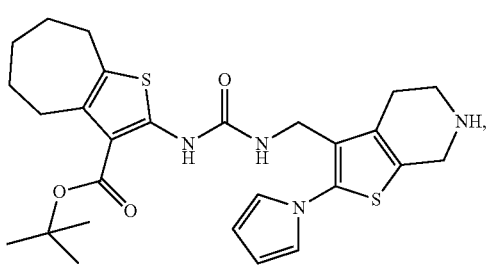
Formula 303
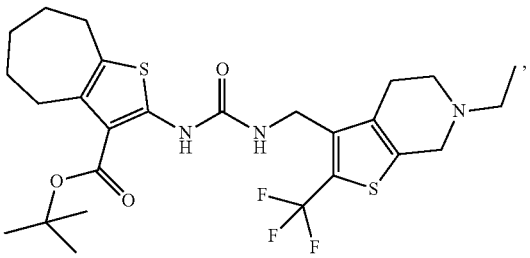
Formula 305
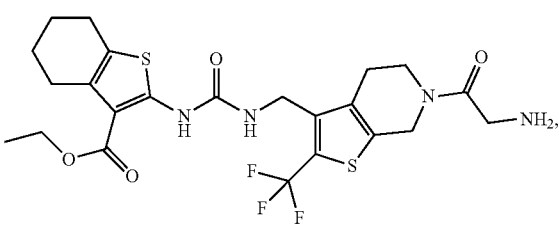
Formula 306
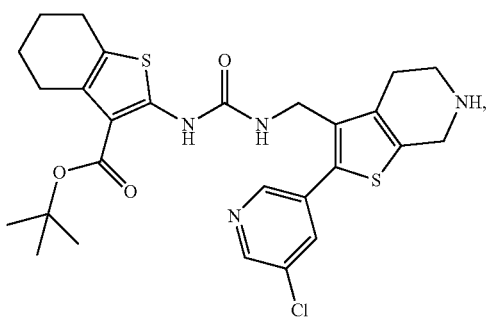

-continued
Formula 307
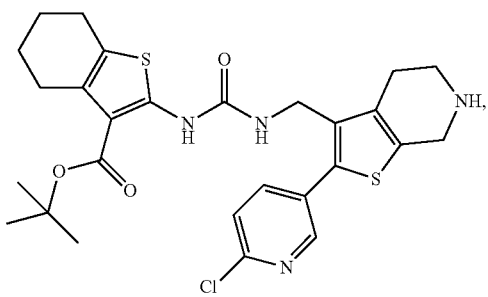
Formula 308
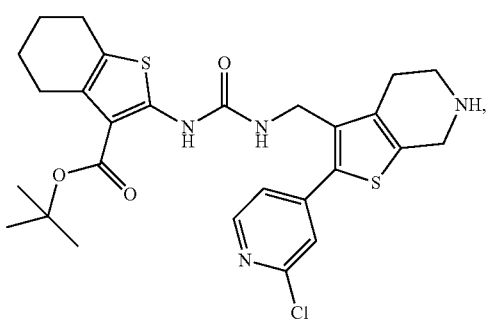
Formula 309
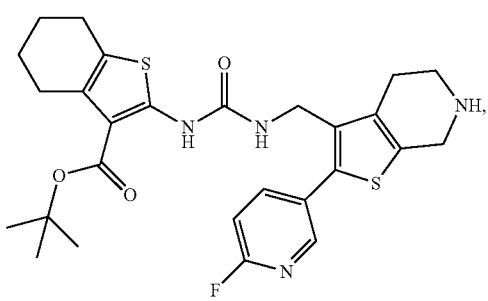
Formula 310
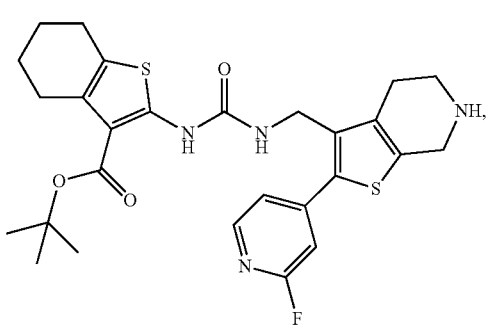
Formula 312
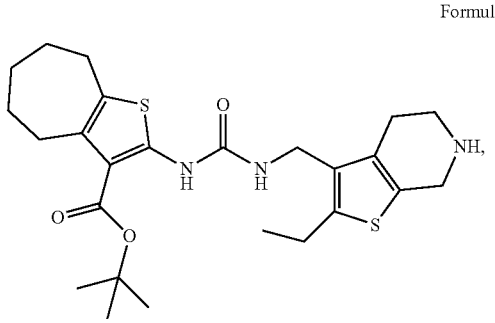
-continued
Formula 313
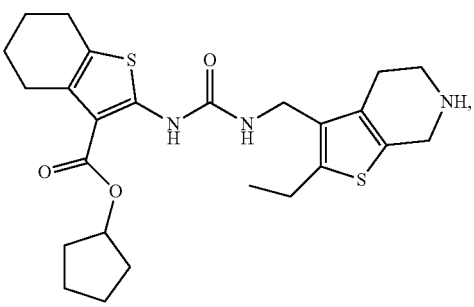
Formula 314
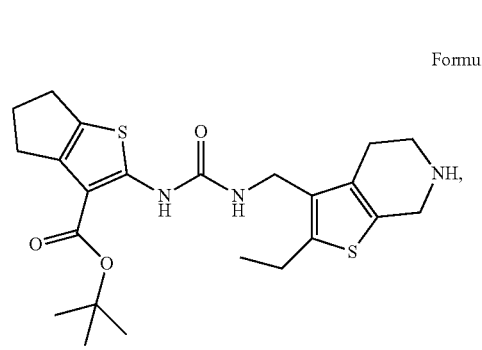
Formula 315
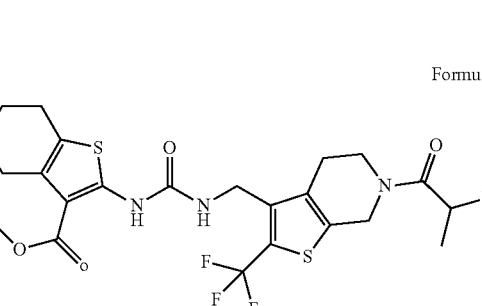
Formula 316
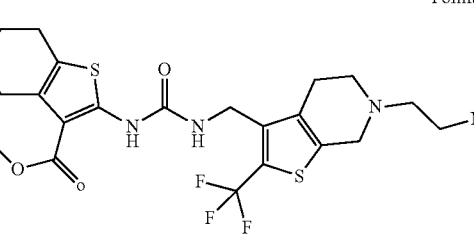
Formula 317
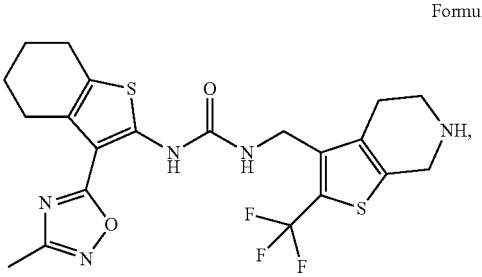

Formula 322
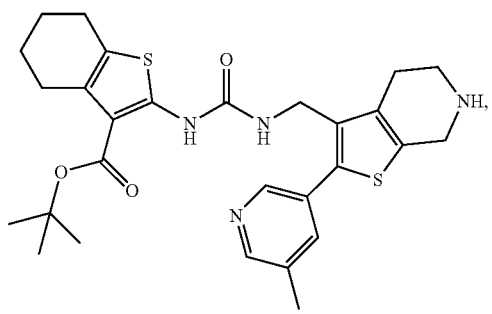
Formula 323
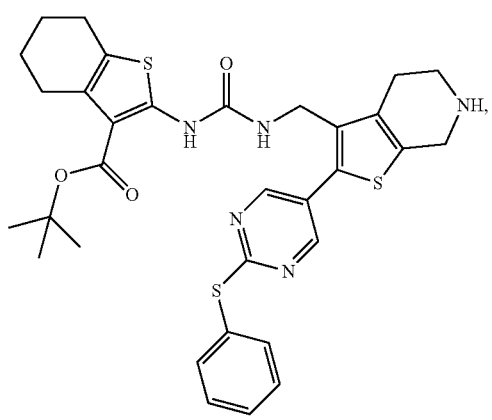
Formula 324
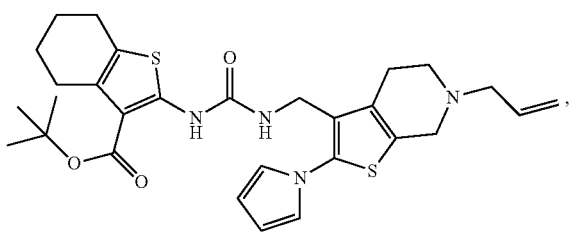
Formula 325
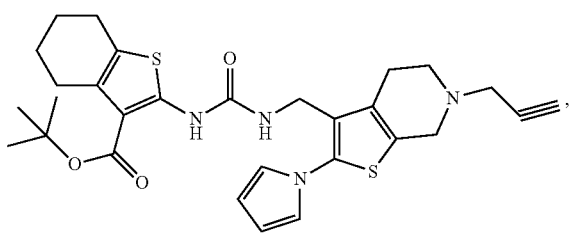
Formula 326
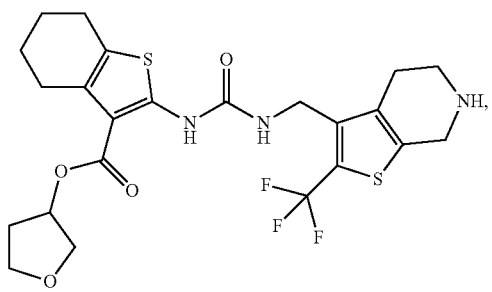
Formula 327
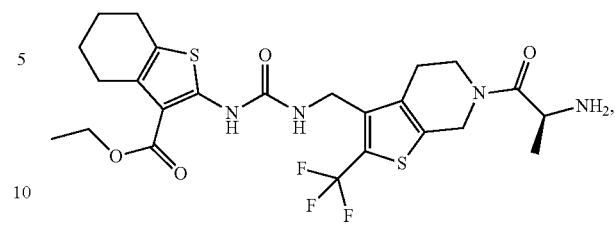
Formula 328
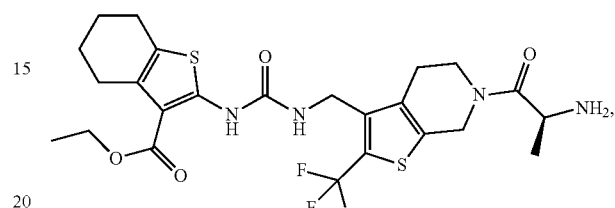
Formula 329
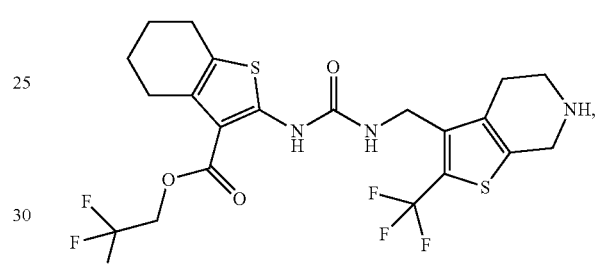
Formula 330
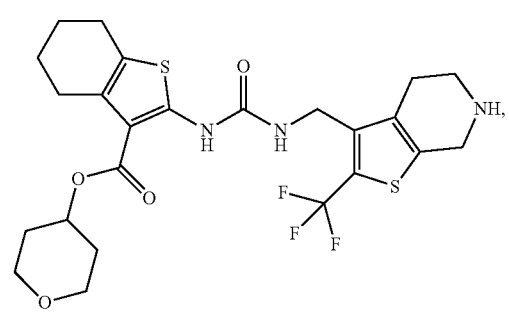
Formula 334
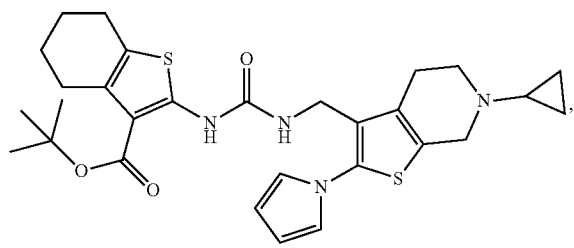
Formula 338
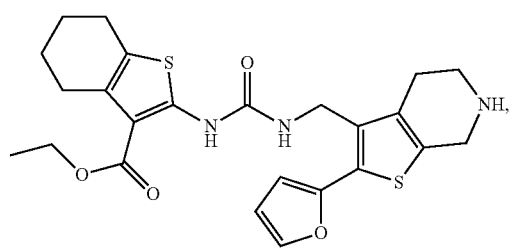

Formula 339
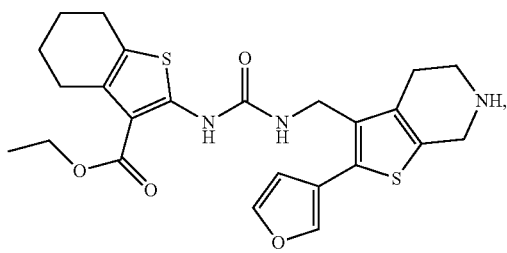
Formula 340
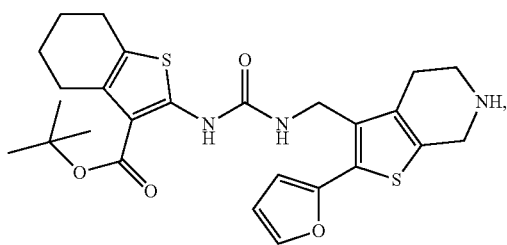
Formula 342
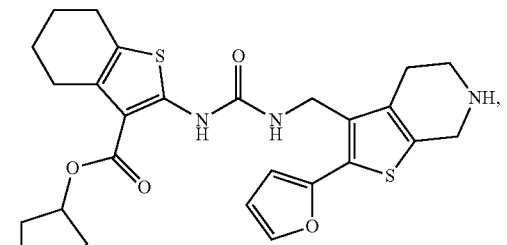
Formula 344
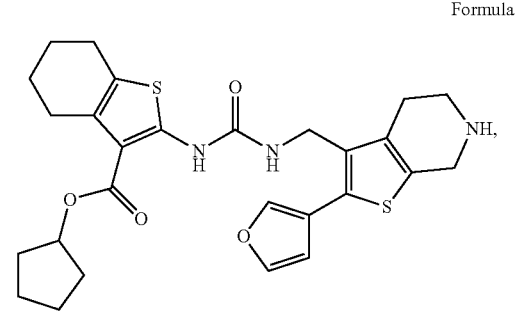
Formula 345
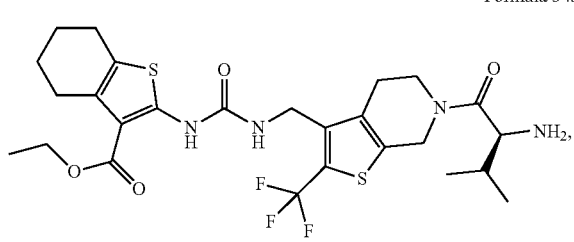
Formula 346
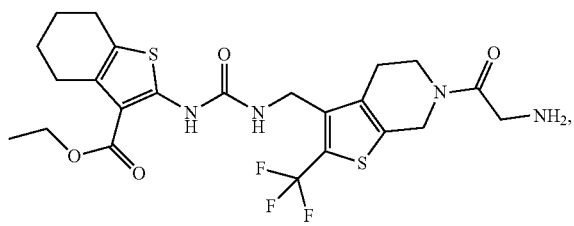
Formula 349
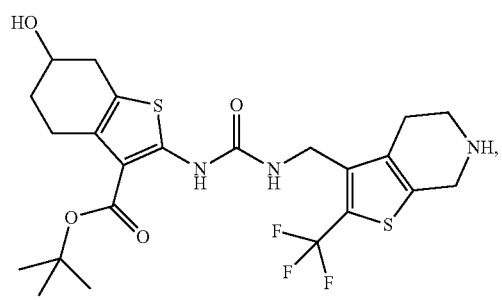
Formula 351
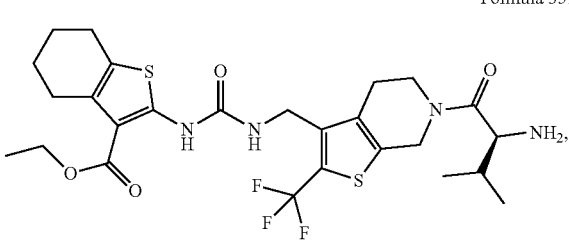
Formula 355
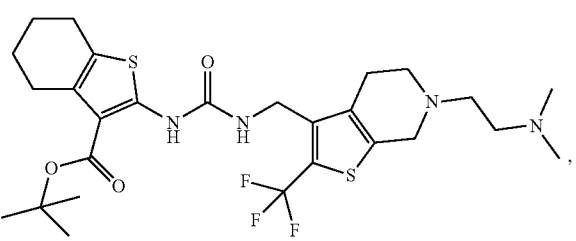
Formula 358
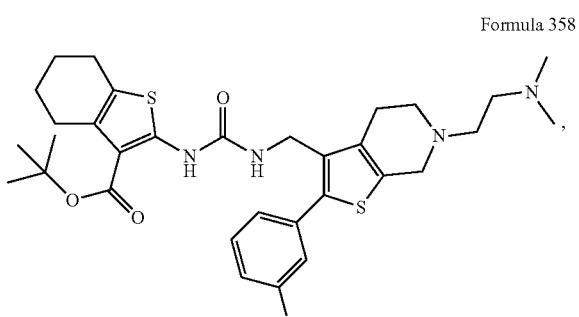
Formula 359
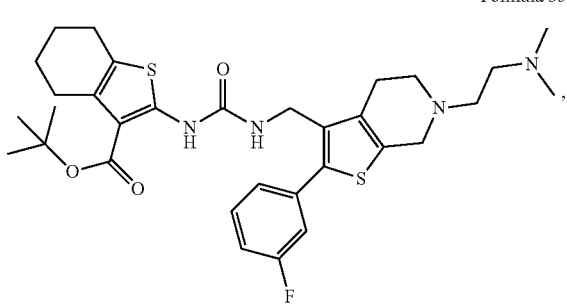

and a pharmaceutically acceptable salt thereof.
4. The compound according to claim 3, wherein the compound of Formula (If) is selected from the group consisting of:
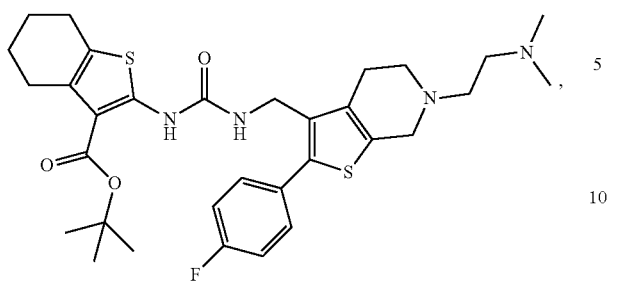

Formula 115
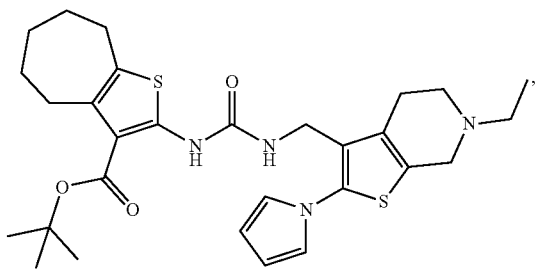

Formula 167
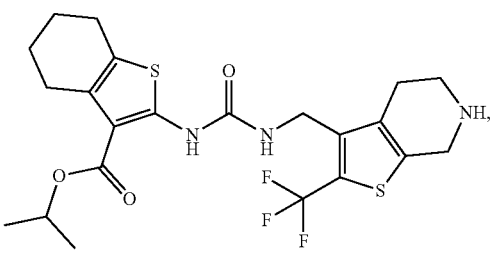

Formula 116
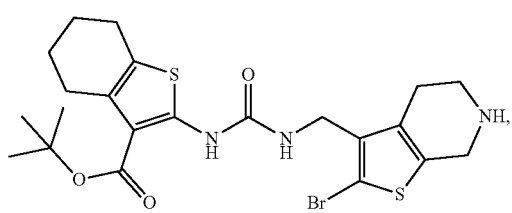

Formula 316
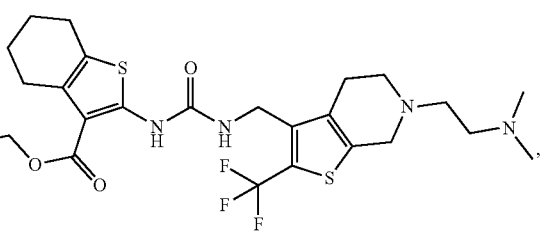

Formula 117
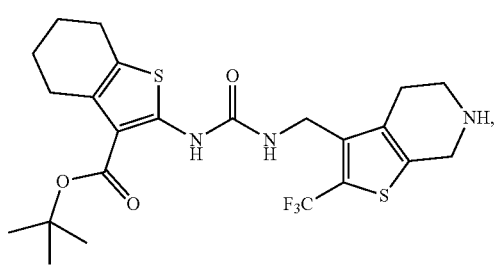

a pharmaceutically acceptable salt thereof.

5. The compound according to claim 1, having an inhibitory activity on viral infection at a concentration of said compound between 0.0001-50 uM.

6. A composition comprising a compound according to claim 1, and a pharmaceutically acceptable carrier, excipient or diluent.

7. The composition according to claim 6, further comprising at least one antiviral compound and, optionally, a pharmaceutically acceptable carrier, excipient or diluent.

8. A method of treatment of a viral disease, said method comprising the administration of a suitable amount of a compound according to claim or of a composition comprising a compound according to claim 1 to a patient in need thereof, suffering from a viral disease.

9. The method according to claim 8, wherein said viral disease is HCV.

10. The method according to claim 9, wherein said viral disease is HCV genotype 1, 2, 3, 4, 5, 6 or 7.

11. The method according to claim 8, wherein said suitable amount is an amount in the range of 0.01 mg/kg body weight to 1 g/kg body weight of said patient.

12. The method according to claim 8 for use in the treatment of a viral disease, wherein said compound is selected from the group consisting of:

Formula 118
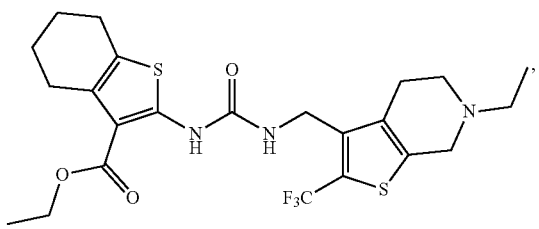

Formula 119
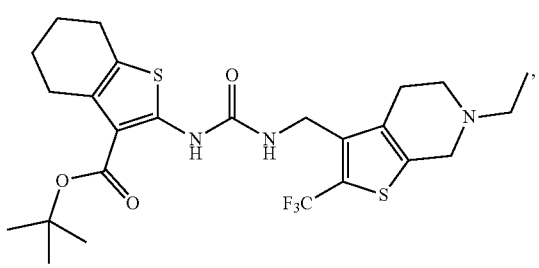

Formula 121
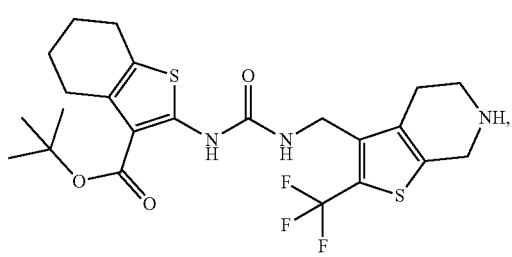

Formula 2
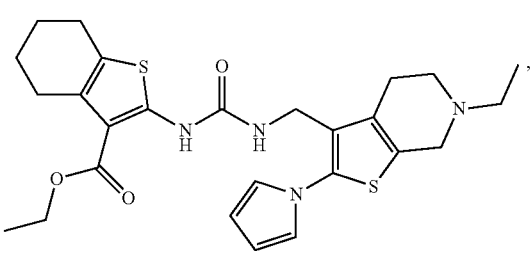

-continued
Formula 5
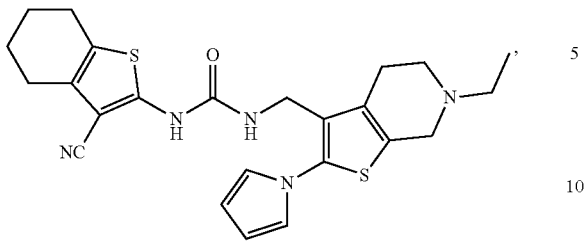
Formula 7
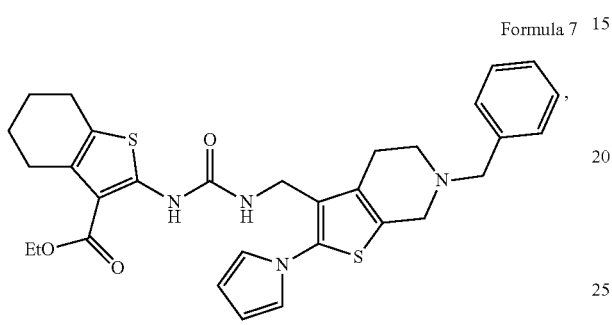
Formula 14
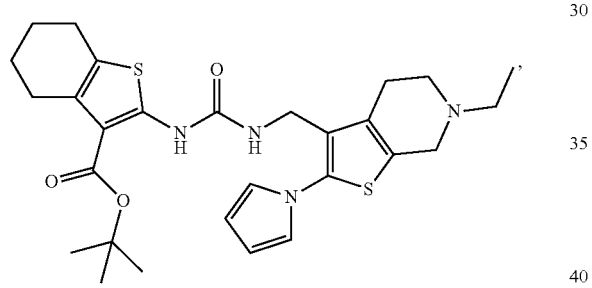
Formula 16
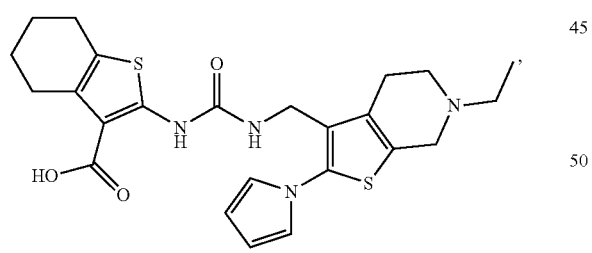
Formula 18
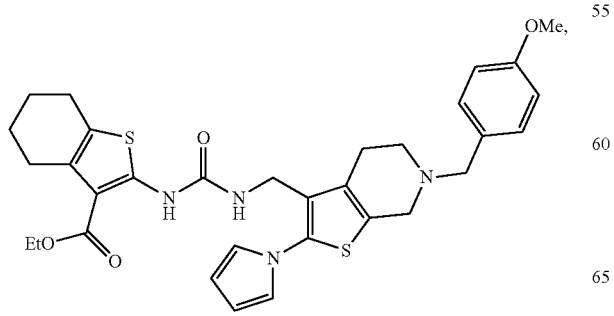
-continued
Formula 19
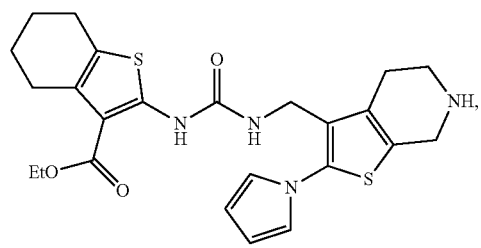
Formula 20
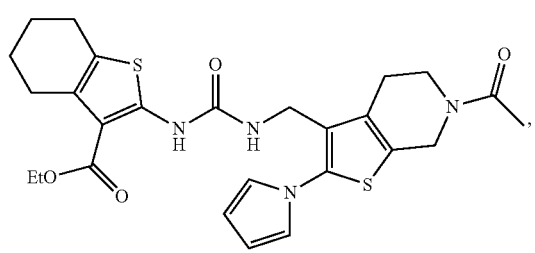
Formula 21
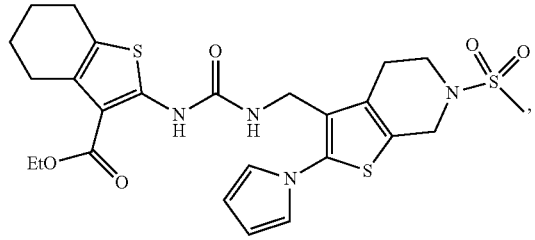
Formula 23
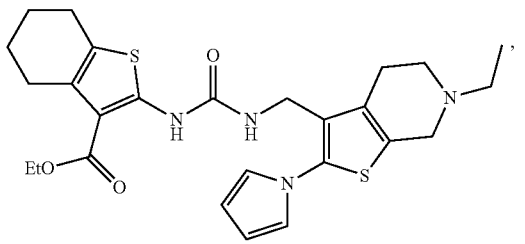
Formula 27
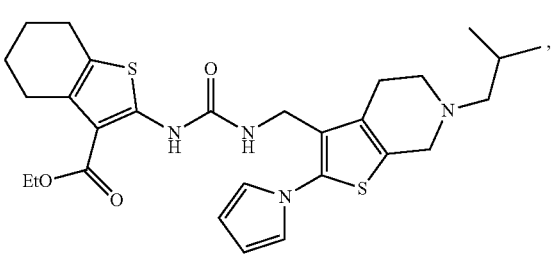
Formula 30
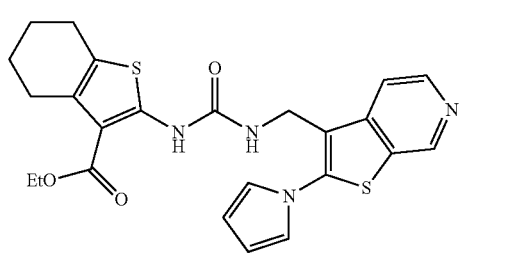

Formula 31
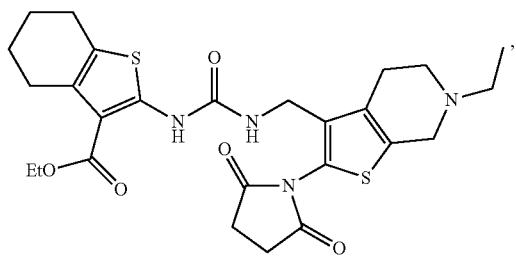
Formula 36
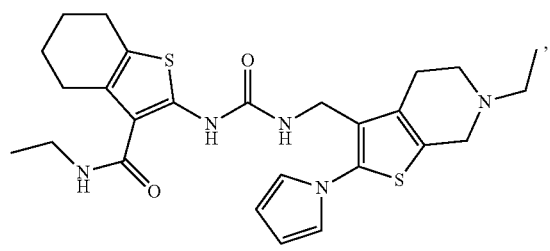
Formula 37
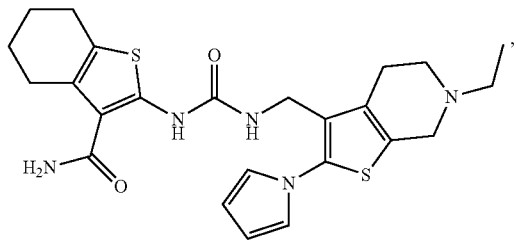
Formula 38
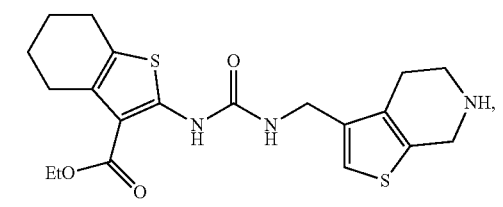
Formula 43
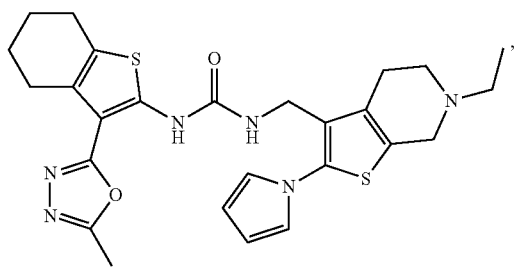
Formula 49
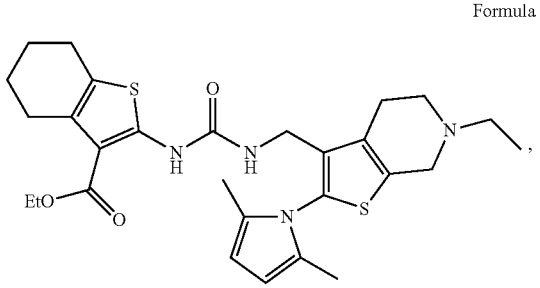
Formula 51
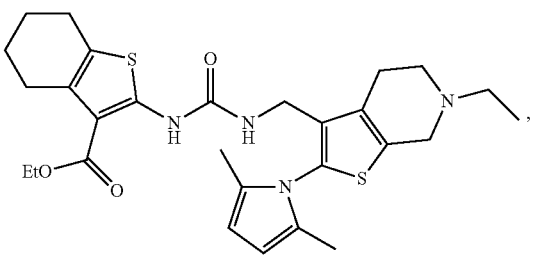
Formula 54
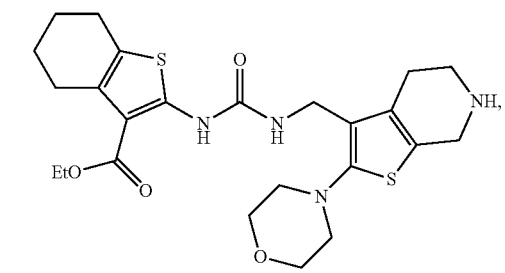
Formula 55
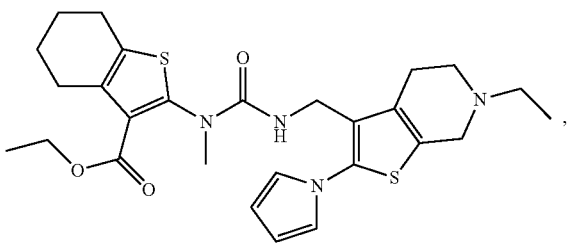
Formula 56
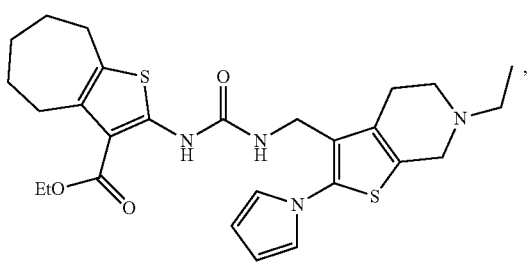
Formula 57
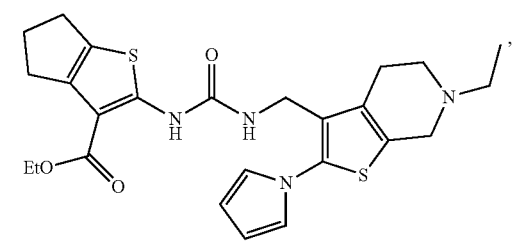

Formula 59
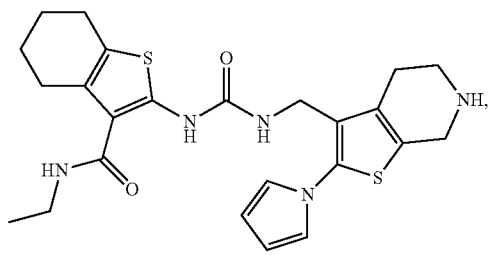
Formula 61
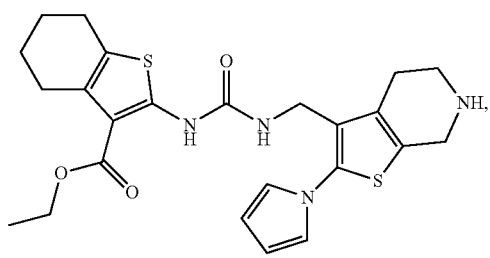
Formula 62
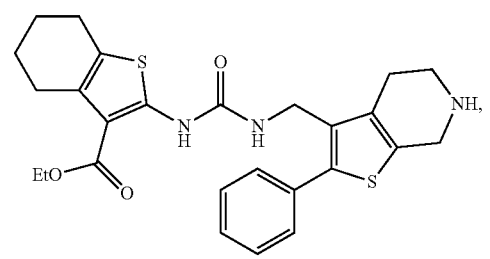
Formula 67
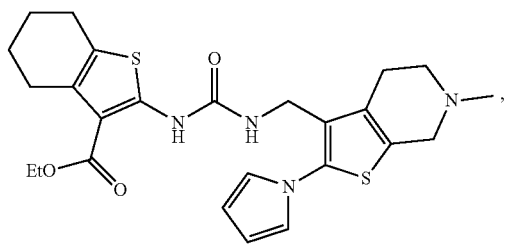
Formula 68
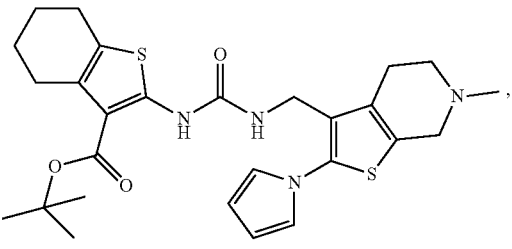
Formula 73
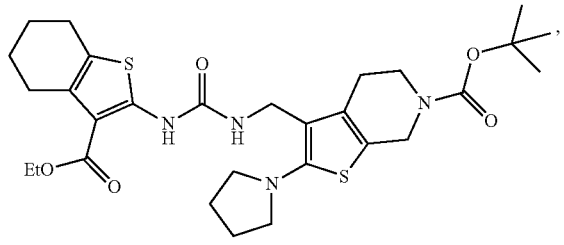
Formula 75
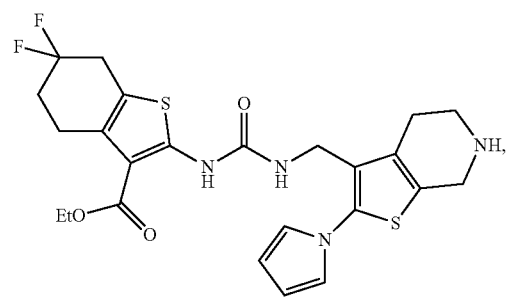
Formual 81
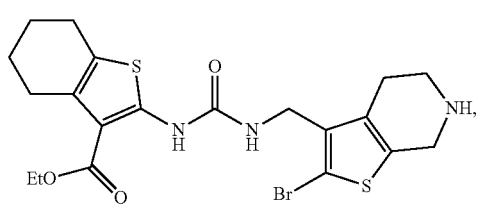
Formula 87
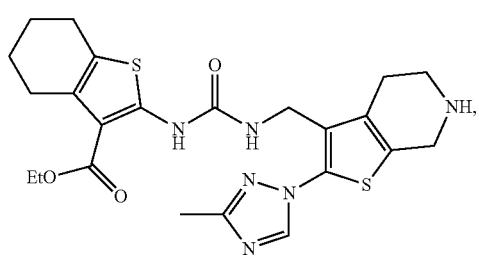
Formula 94
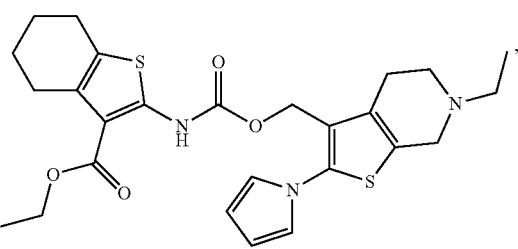
Formula 96
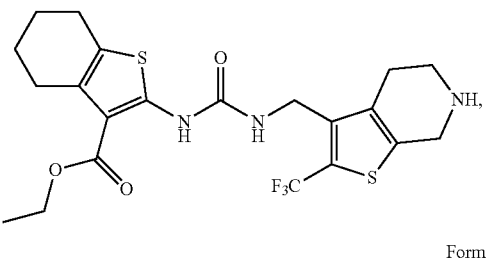
Formula 97
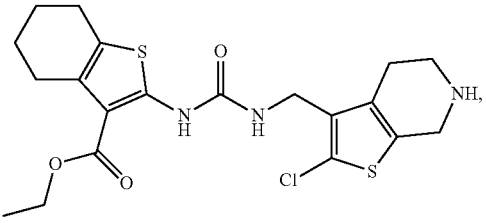

403
-continued
Formula 98
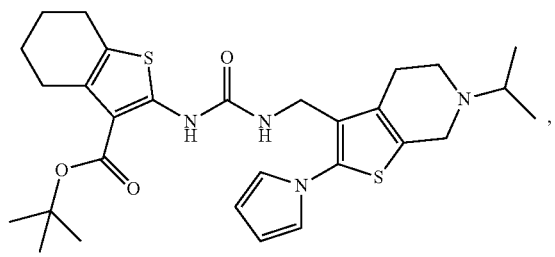
Formula 99
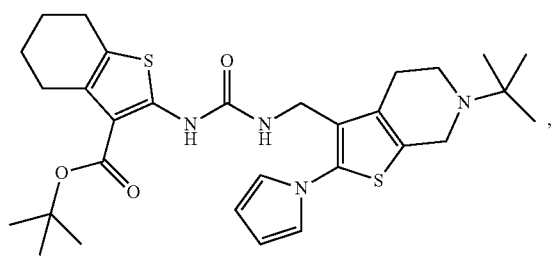
Formula 100
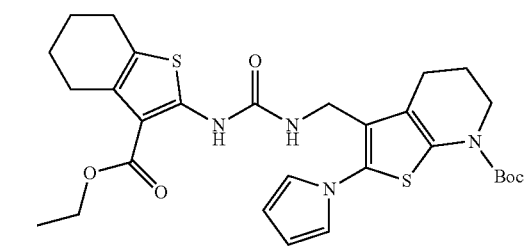
Formula 101
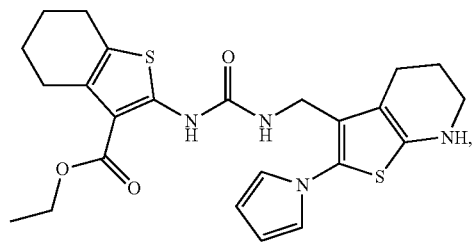
Formula 106
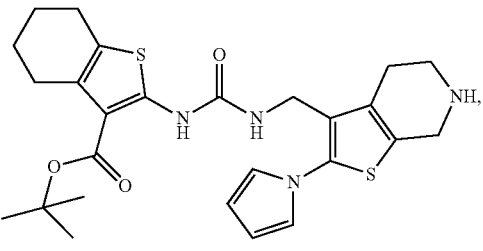
Formula 107
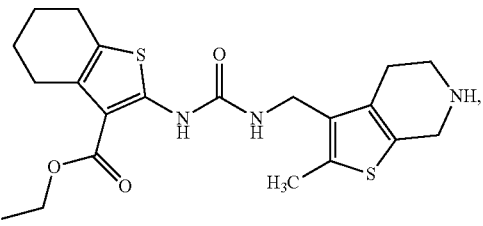
404
-continued
Formula 110
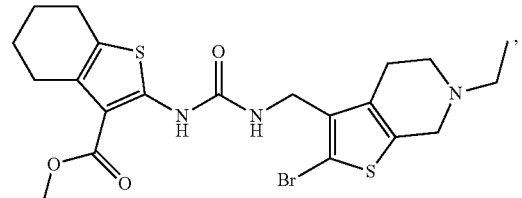
Formula 111
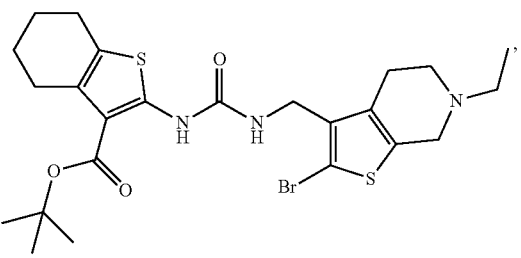
Formula 112
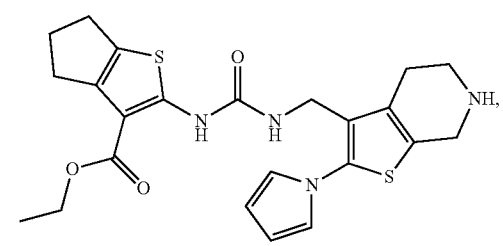
Formula 113
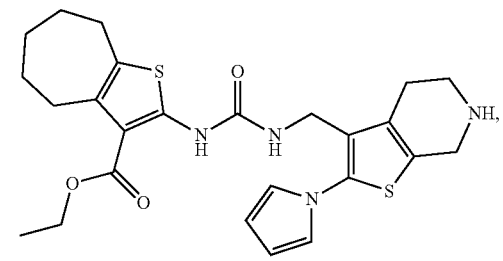
Formula 114
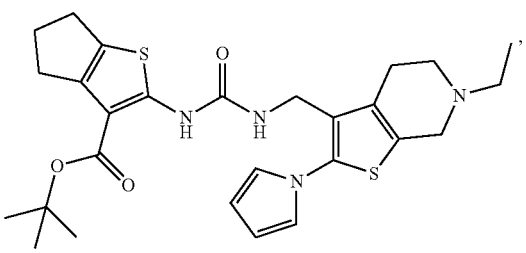
Formula 115
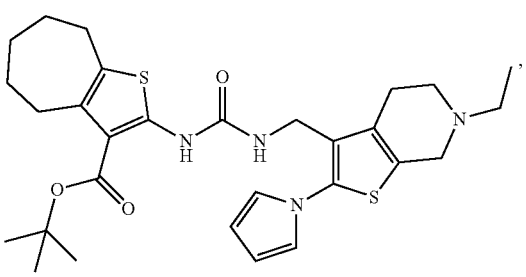

Formula 116
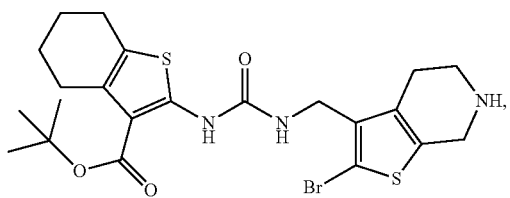
Formula 117
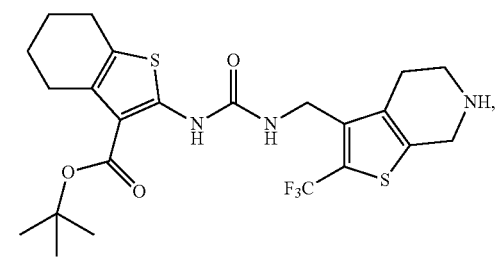
Formula 118
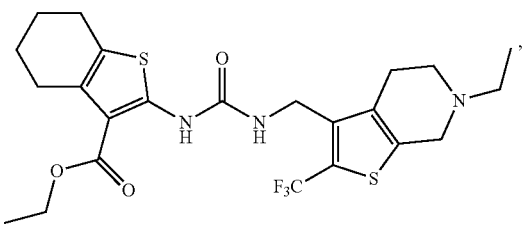
Formula 119
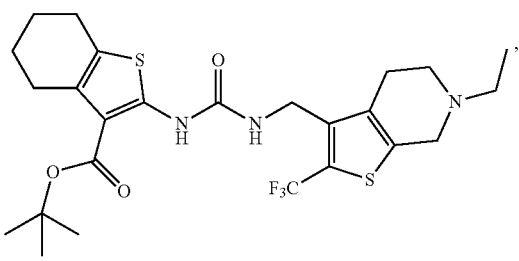
Formula 121
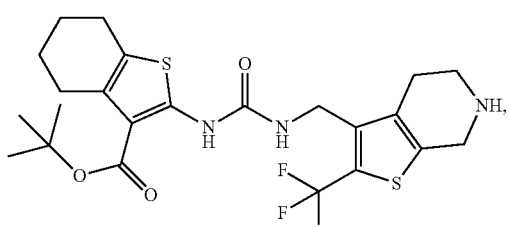
Formula 122
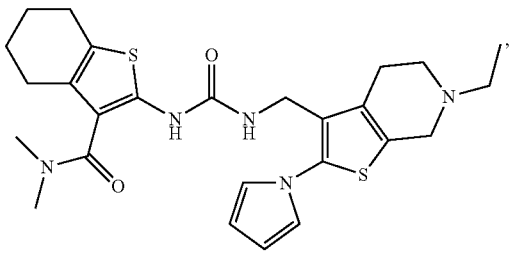
Formula 123
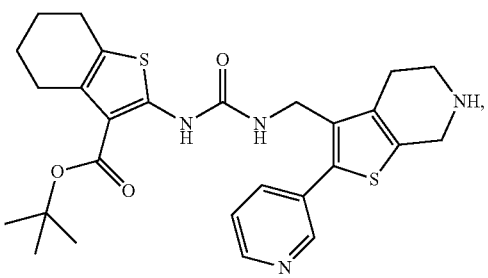
Formula 124
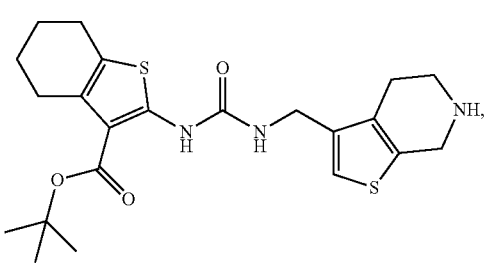
Formula 125
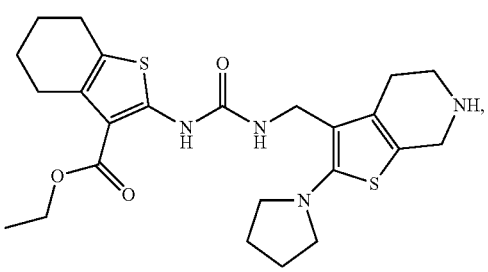
Formula 126
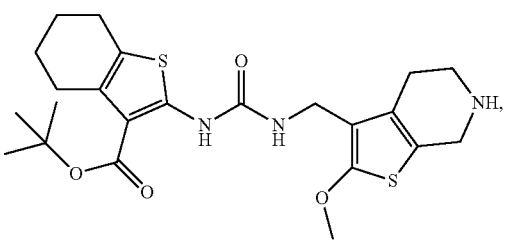
Formula 127
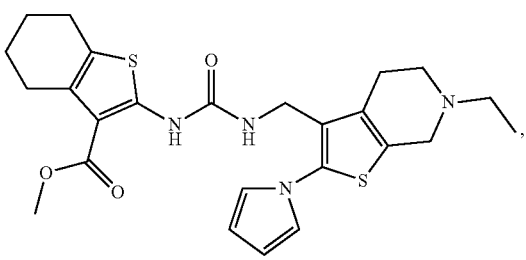
Formula 128
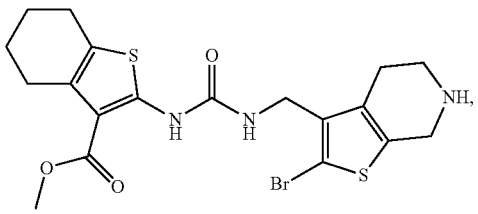

Formula 129
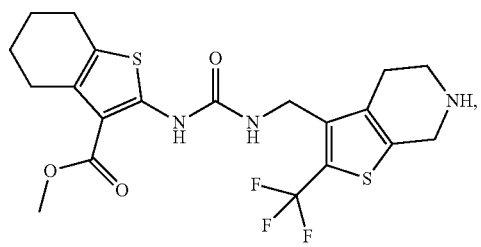
Formula 130
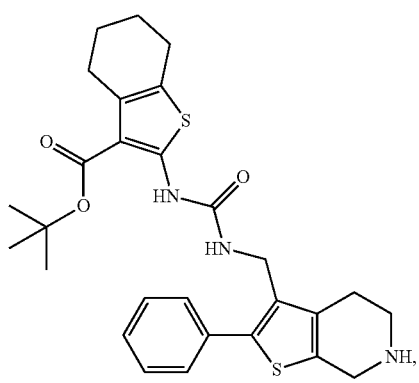
Formula 131
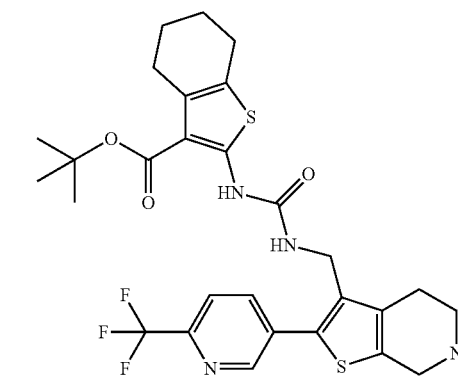
Formula 140
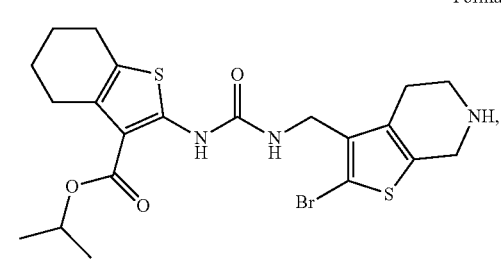
Formula 141
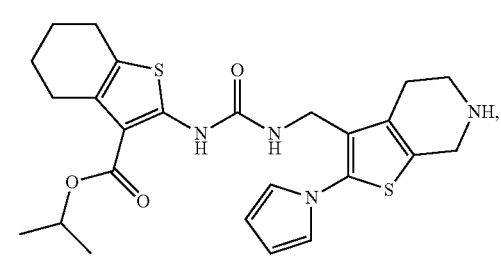
Formula 142
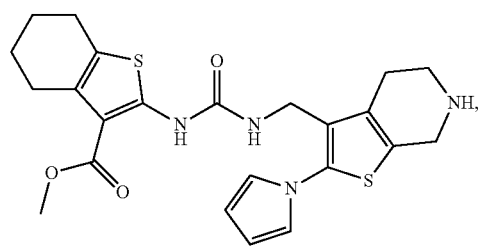
Formula 143
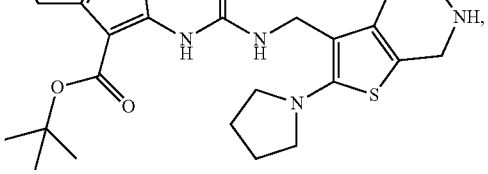
Formula 144
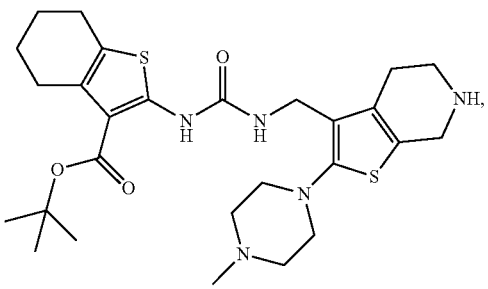
Formula 145
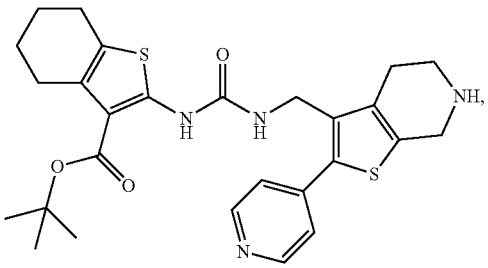
Formula 146
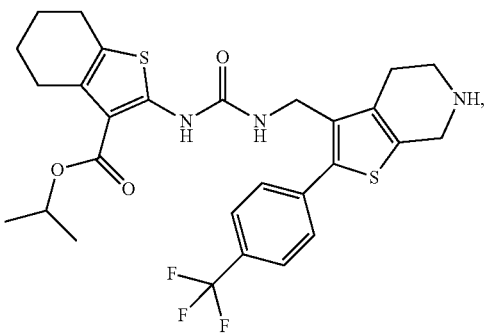

Formula 151
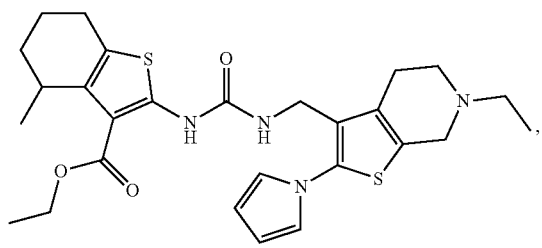
Formula 152
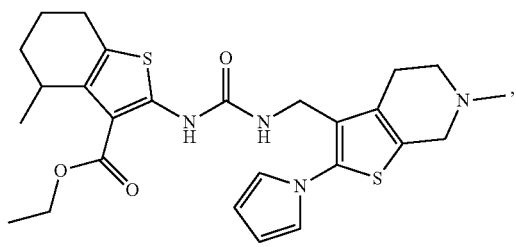
Formula 153
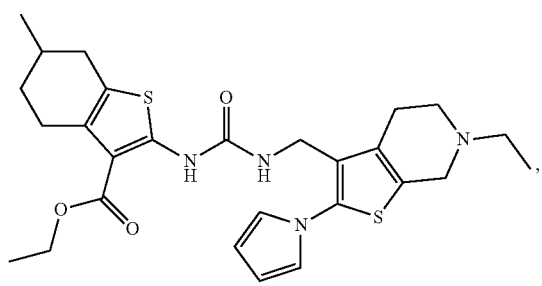
Formula 154
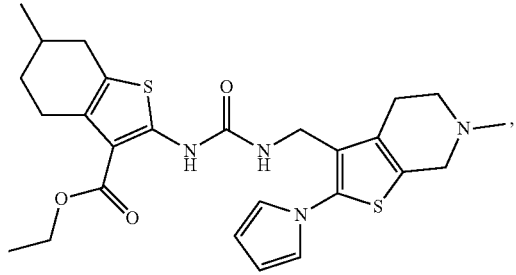
Formula 155
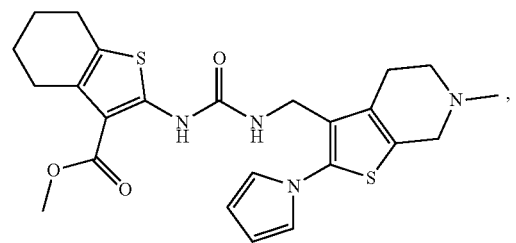
Formula 156
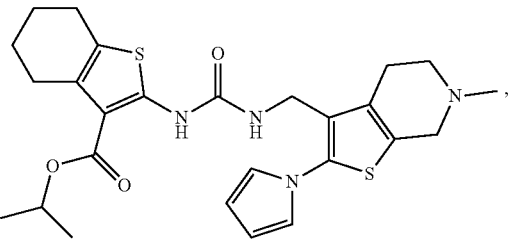
Formula 157
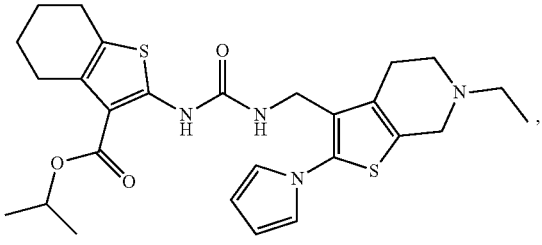
Formula 159
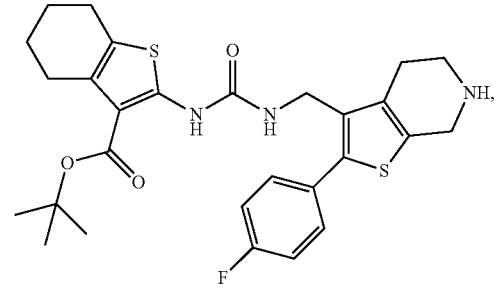
Formula 160
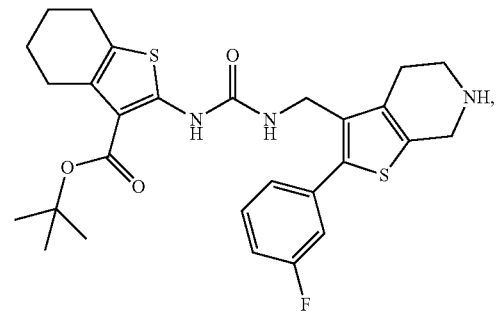
Formula 161
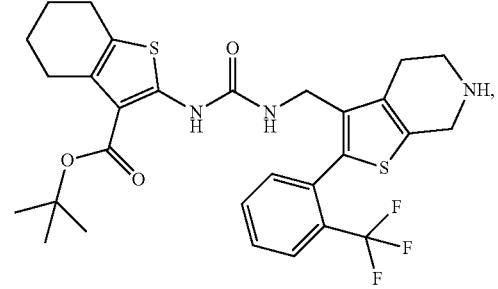

Formula 164
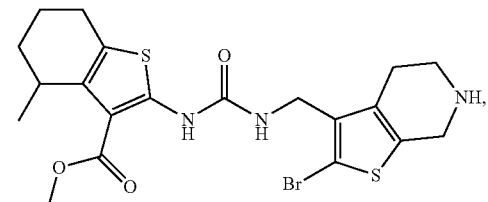
Formula 165
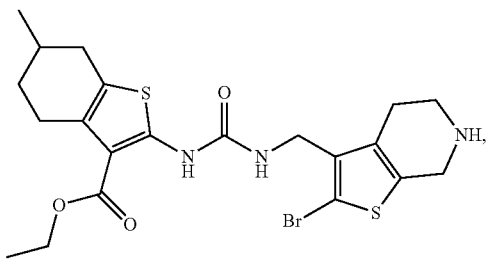
Formula 166
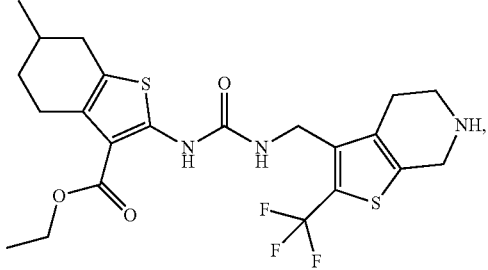
Formula 167
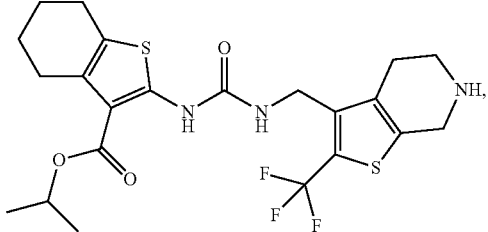
Formula 169
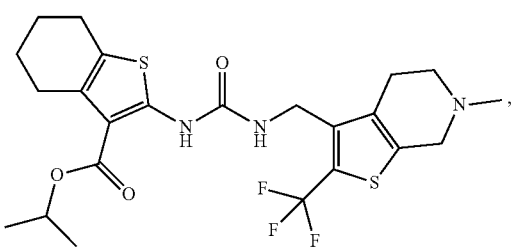
Formula 171
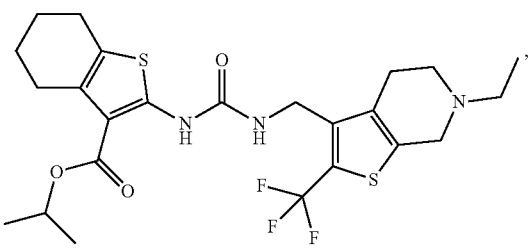
Formula 172
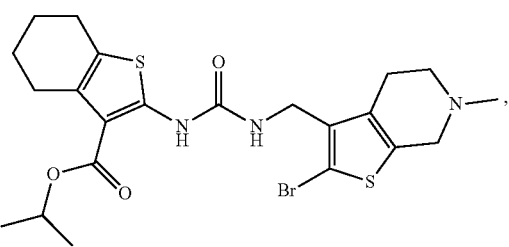
Formula 174
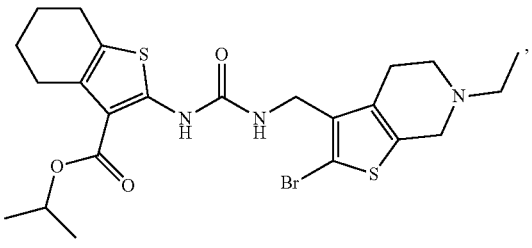
Formula 175
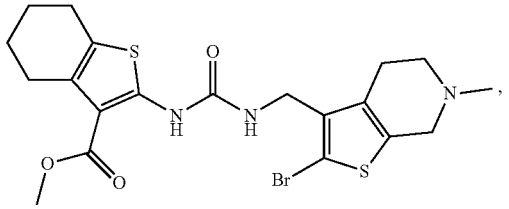
Formula 177
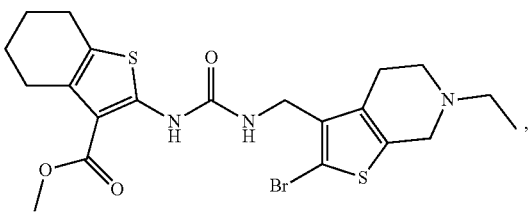
Formula 178
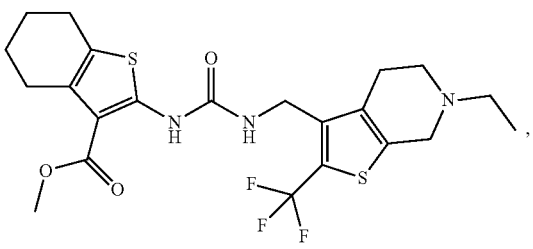
Formula 179
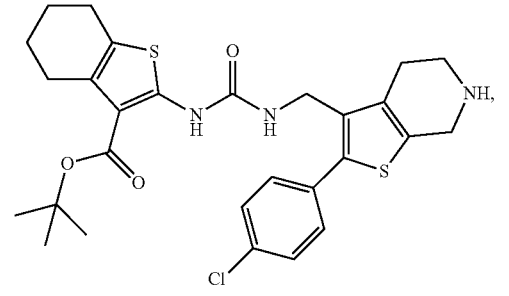

Formula 180
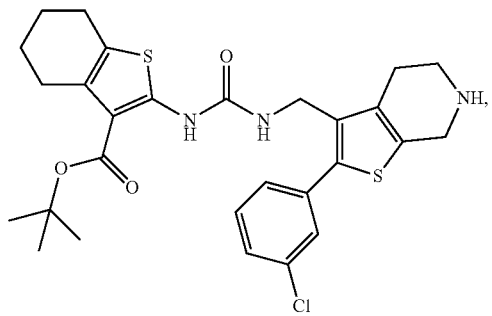
Formula 185
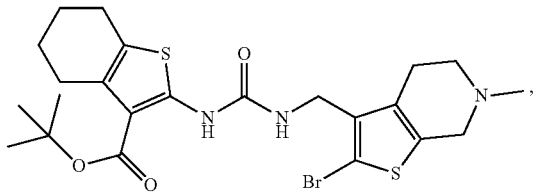
Formula 181
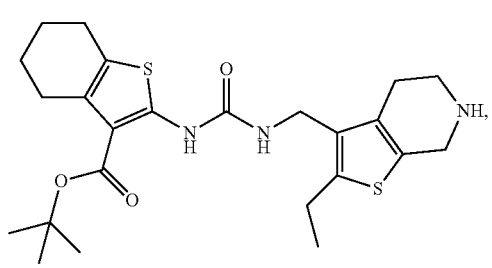
Formula 186
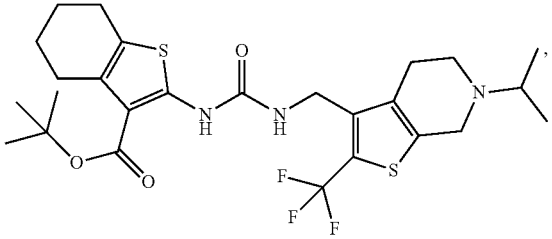
Formula 182
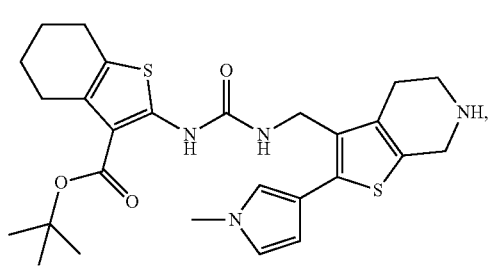
Formula 187
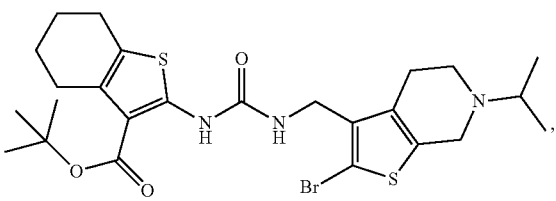
Formula 183
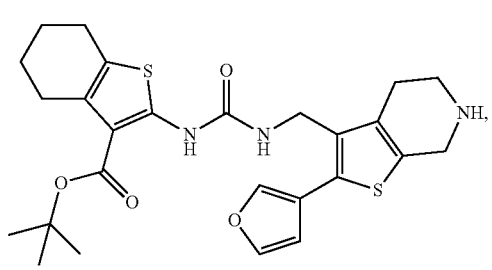
Formula 190
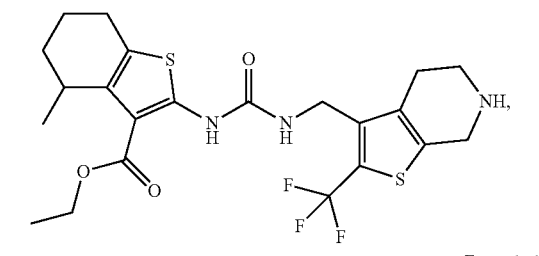
Formula 184
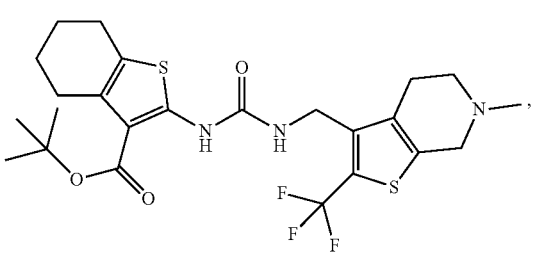
Formula 191
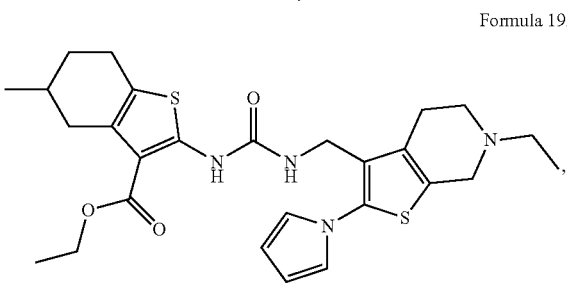
Formula 192

Formula 193
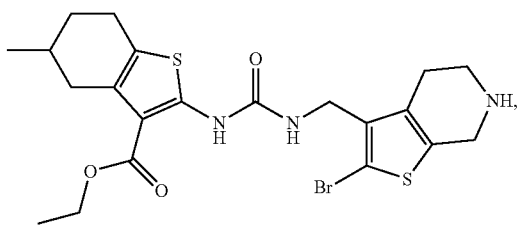
Formula 194
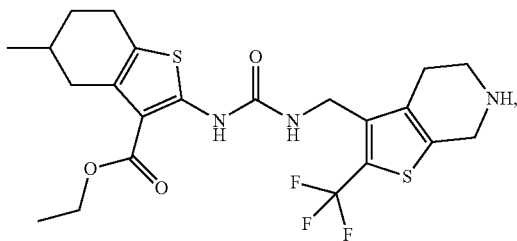
Formula 197
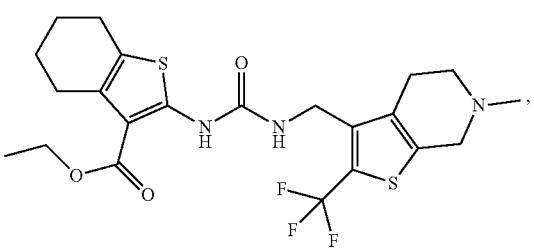
Formula 198
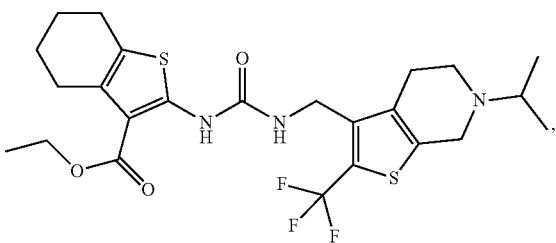
Formula 199
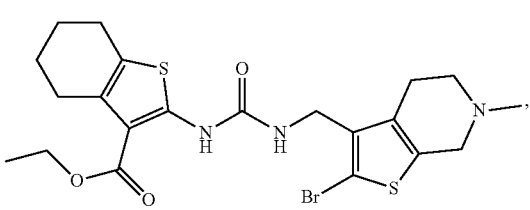
Formula 200
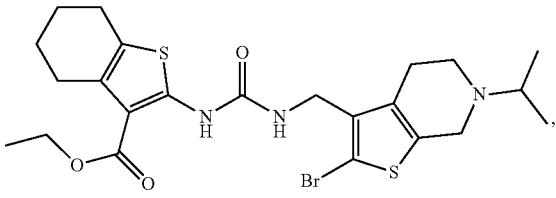
Formula 201
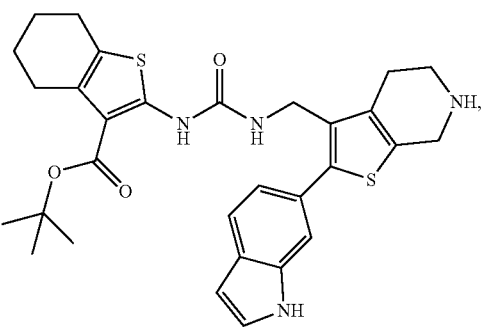
Formula 202
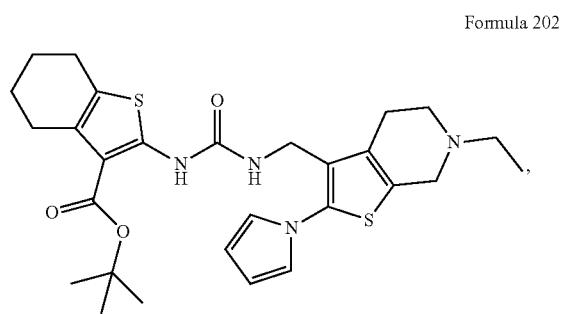
Formula 203
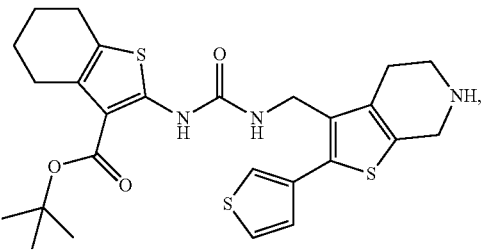
Formula 204
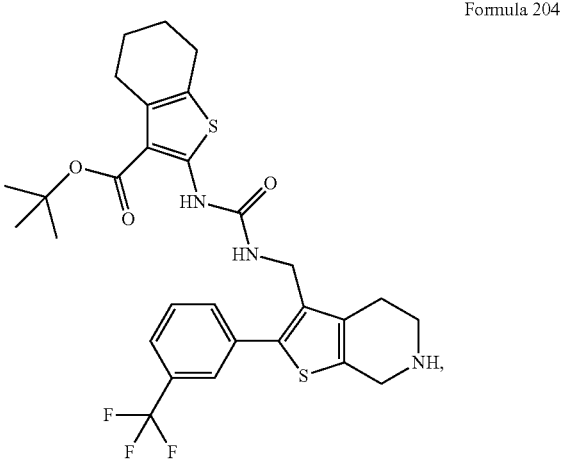

Formula 205

Formula 212

Formula 207

Formula 213

Formula 208

Formula 218

Formula 210

Formula 219

Formula 211

Formula 220

Formula 221
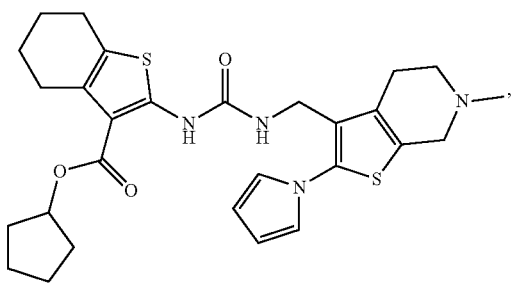
Formula 222
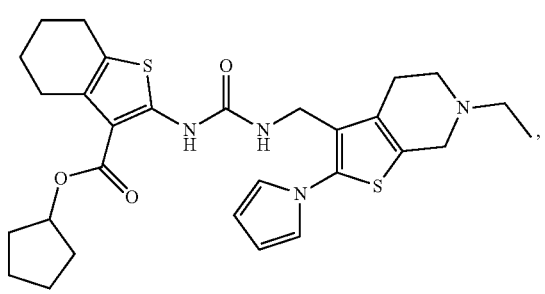
Formula 224
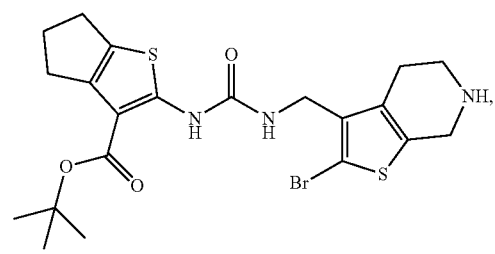
Formula 225
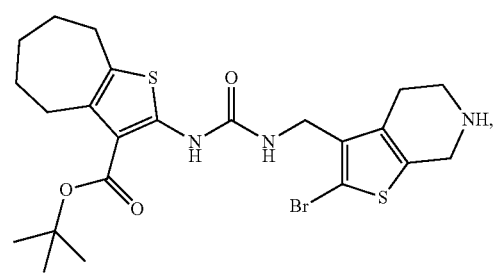
Formula 226
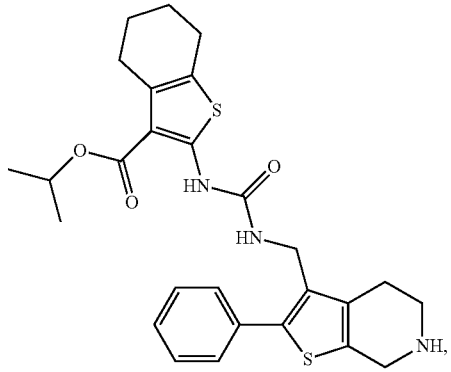
Formula 227
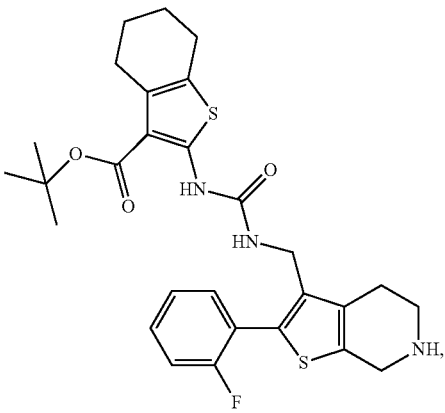
Formula 228
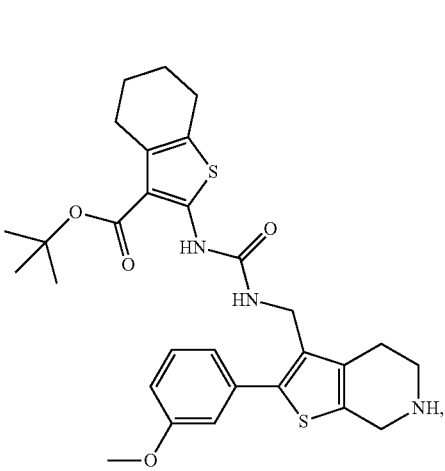
Formula 229
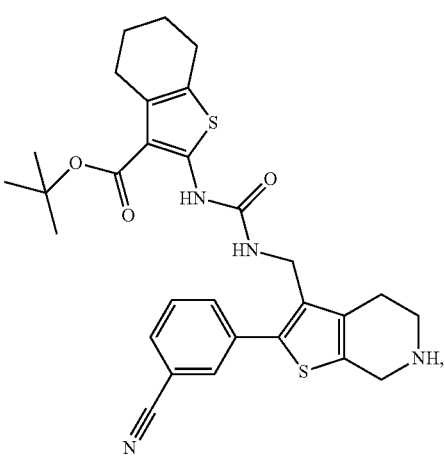

Formula 230
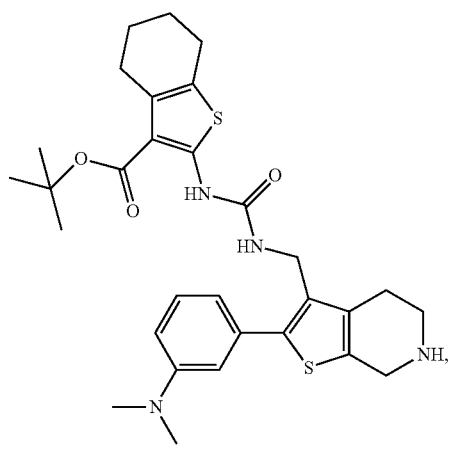
Formula 231
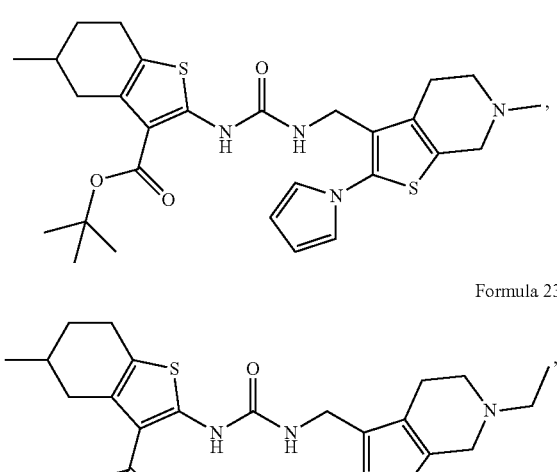
Formula 232
Formula 233
Formula 234
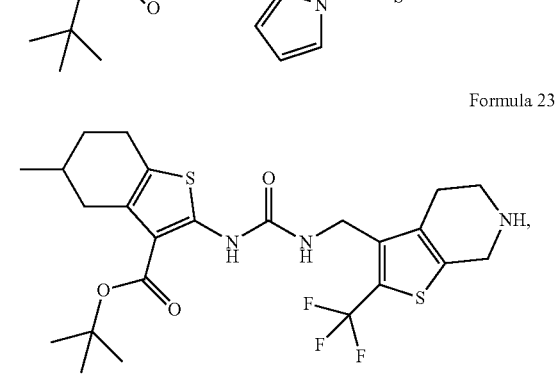
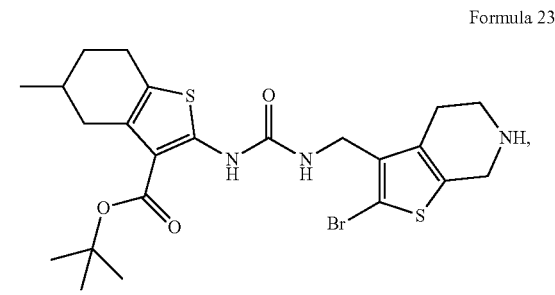
Formula 235
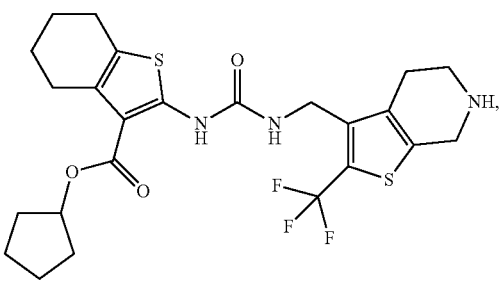
Formula 240
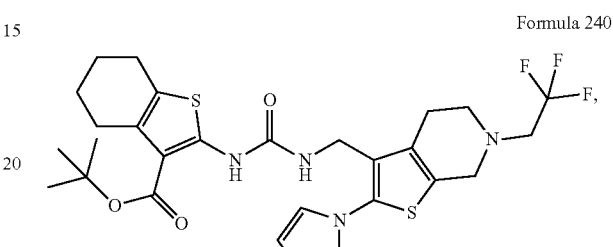
Formula 241
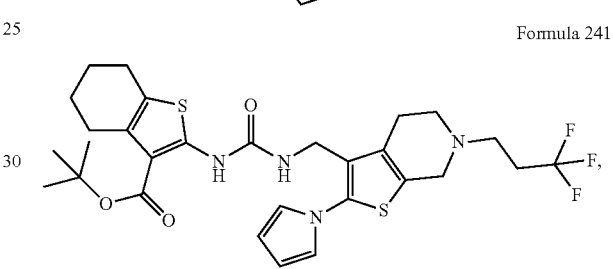
Formula 242
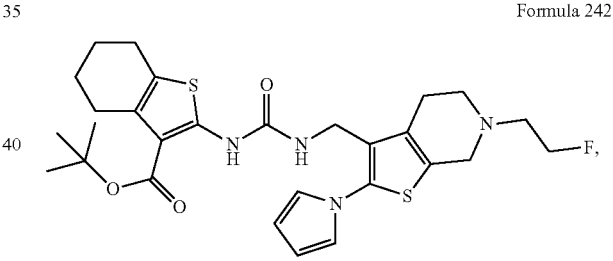
Formula 243
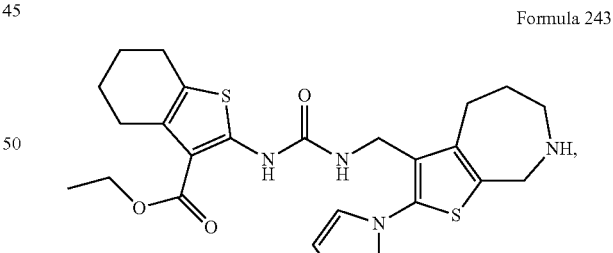
Formula 244
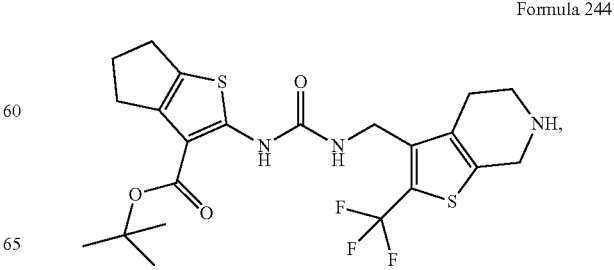

Formula 245
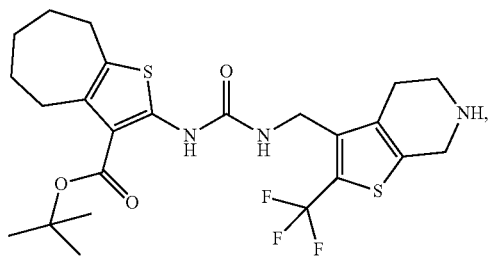
Formula 246
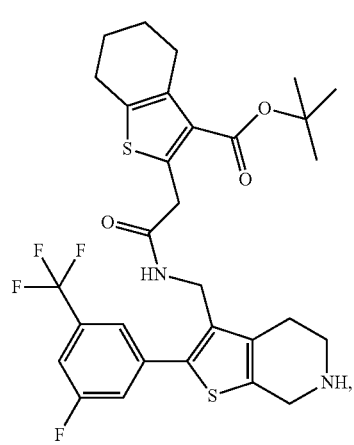
Formula 247
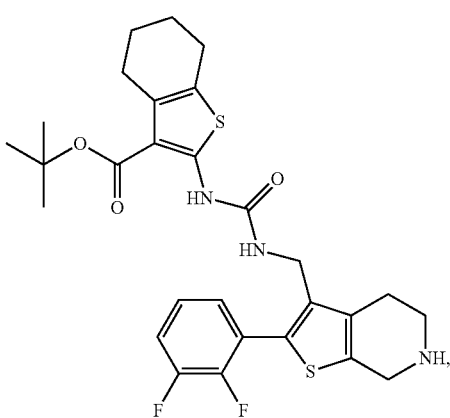
Formula 248
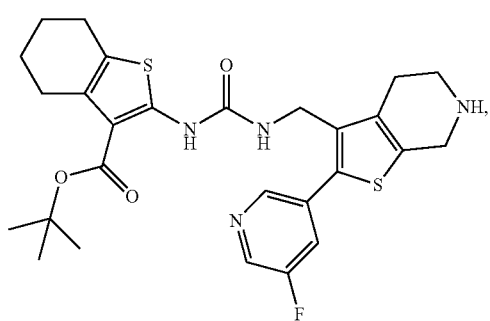
Formula 249
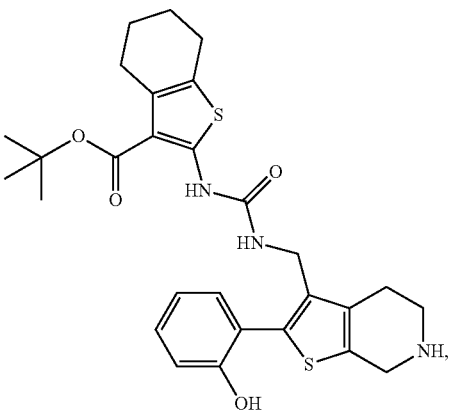
Formula 250
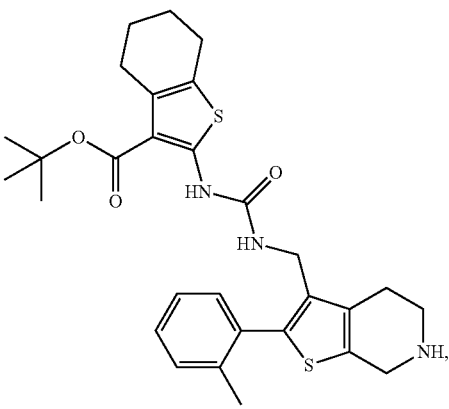
Formula 252
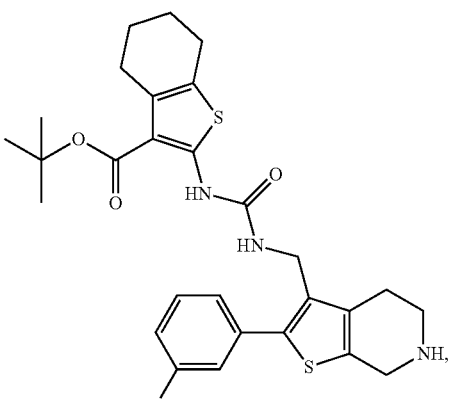
Formula 254
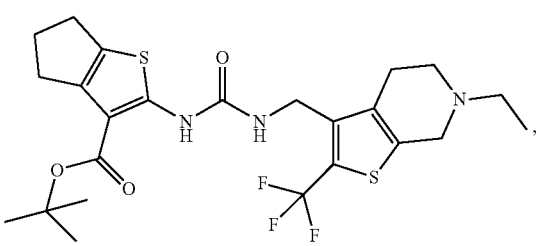

Formula 256
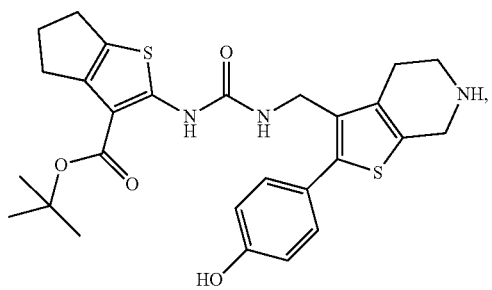
Formula 257
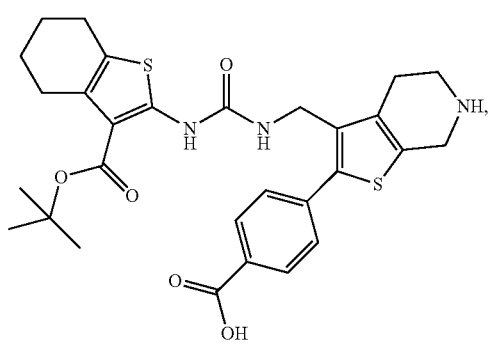
Formula 258
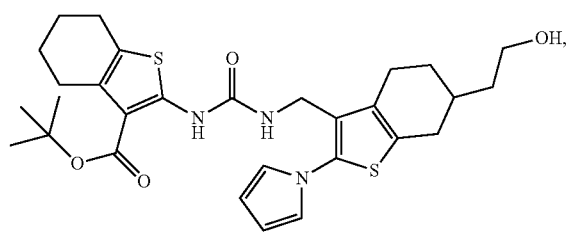
Formula 259
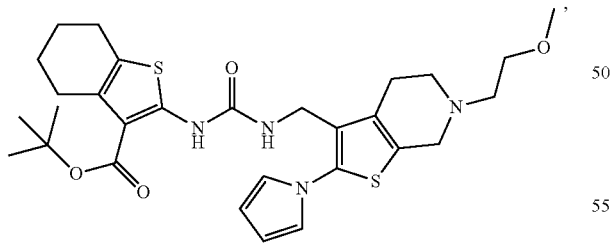
Formula 260
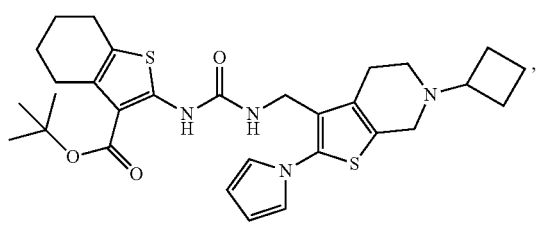
Formula 261
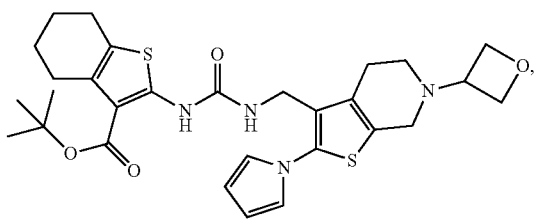
Formula 262
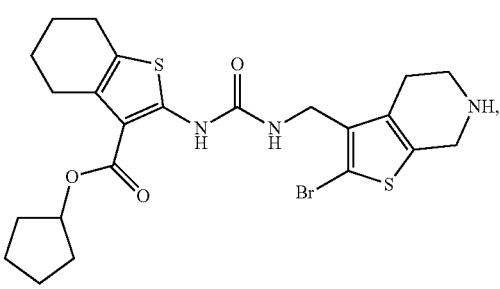
Formula 263
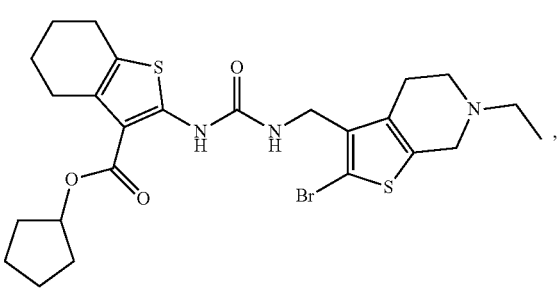
Formula 265
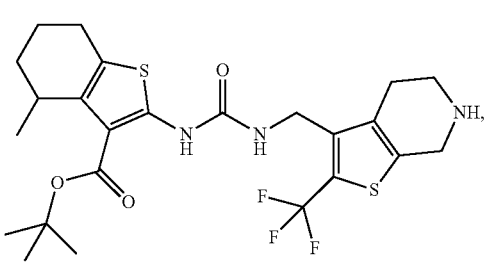
Formula 266
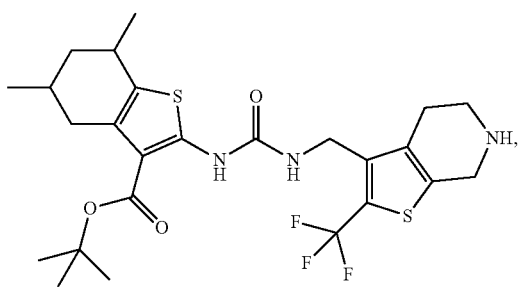

Formula 267
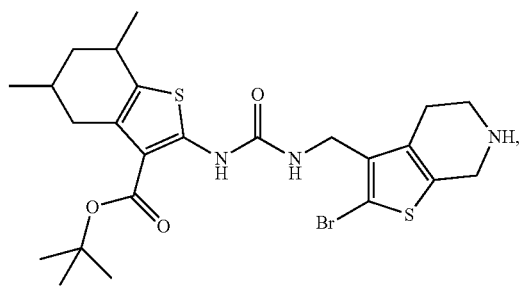
Formula 271
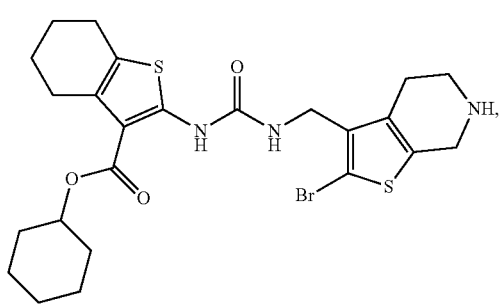
Formula 272
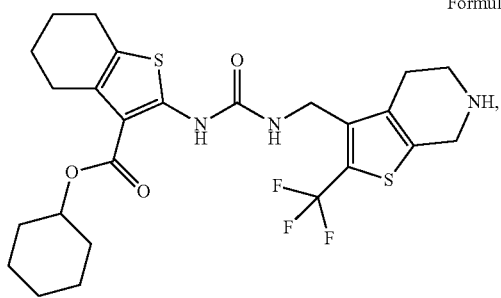
Formula 273
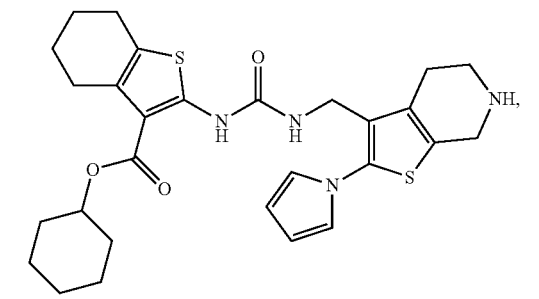
Formula 274
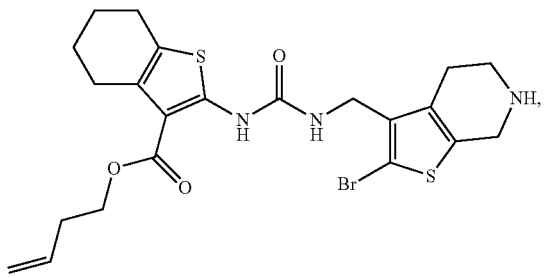
Formula 275
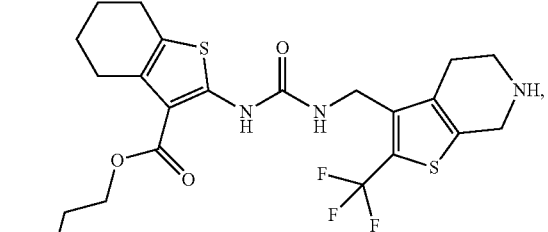
Formula 276
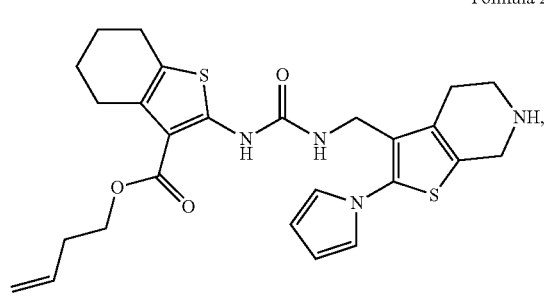
Formula 277
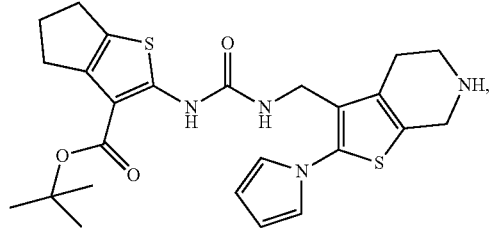
Formula 278
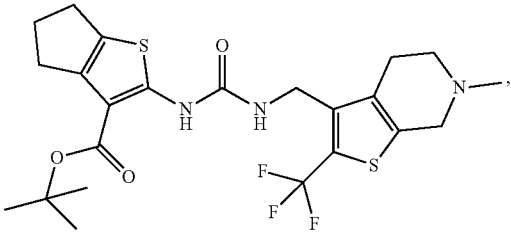
Formula 279
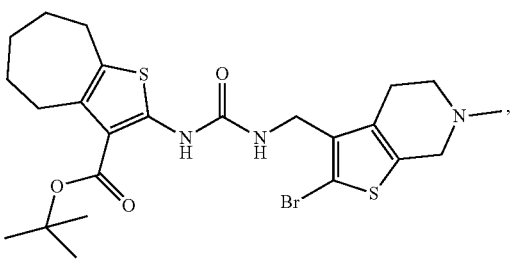

-continued
Formula 280
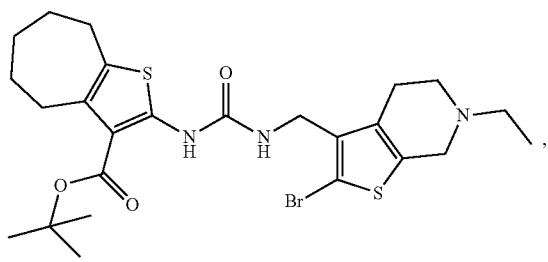
Formula 281
Formula 283
Formula 284
Formula 285
Formula 286
-continued
Formula 287
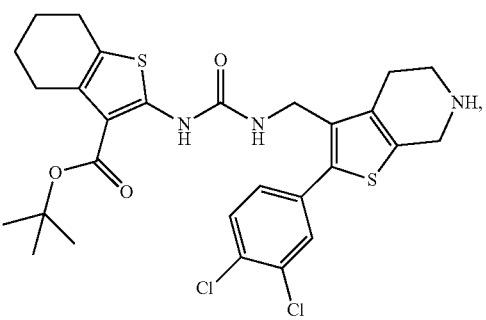
Formula 289
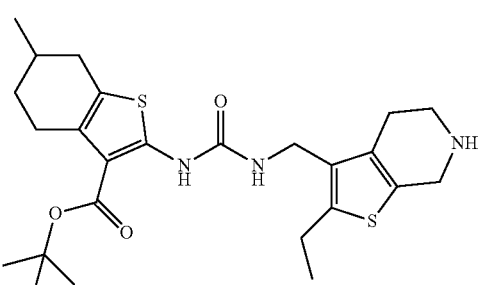
Formula 290
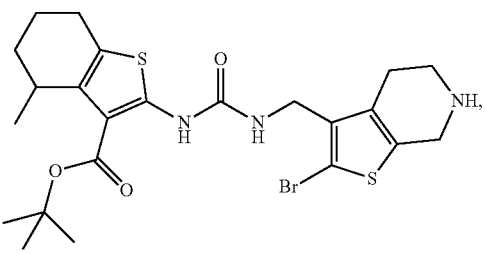
Formula 291
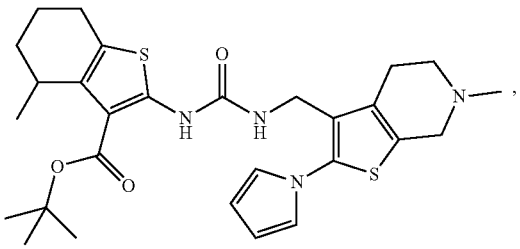
Formula 292
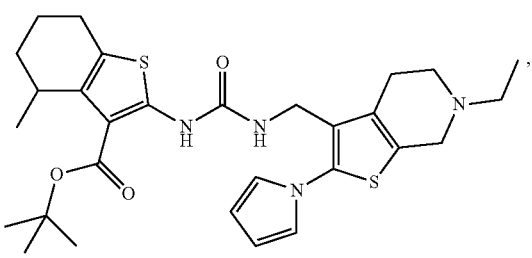

Formula 293
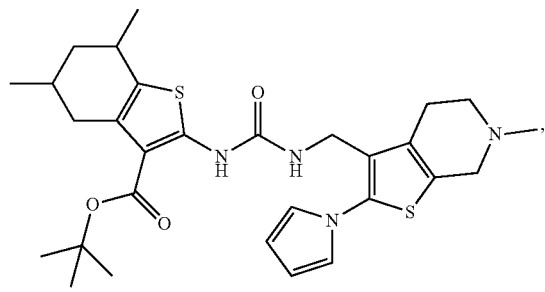
Formula 294
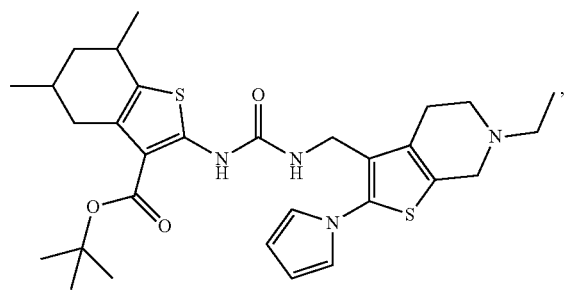
Formula 298
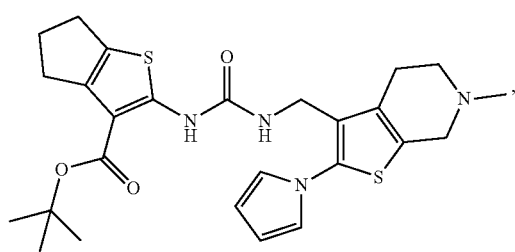
Formula 299
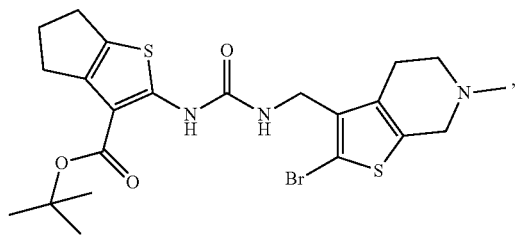
Formula 300
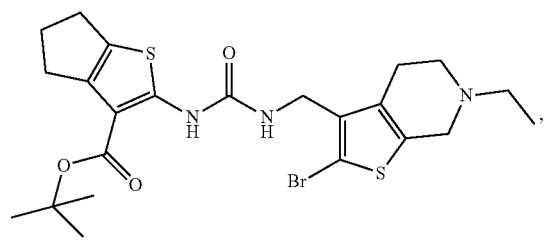
Formula 301
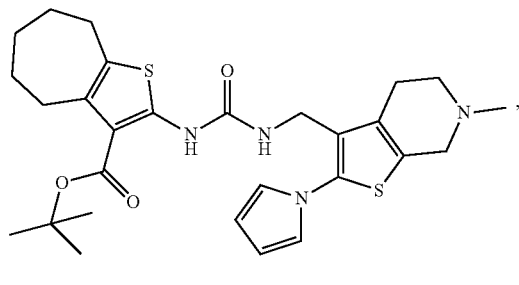
Formula 302
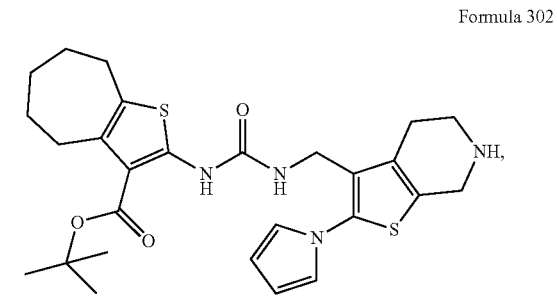
Formula 303
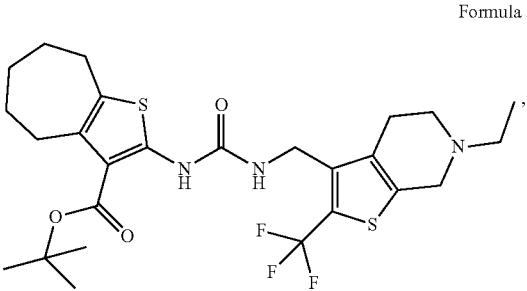
Formula 305
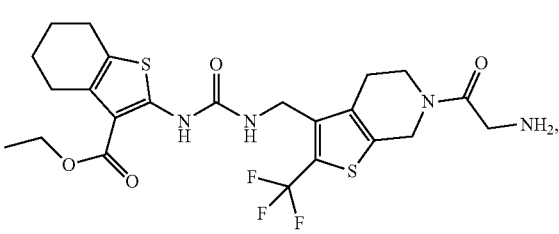
Formula 306
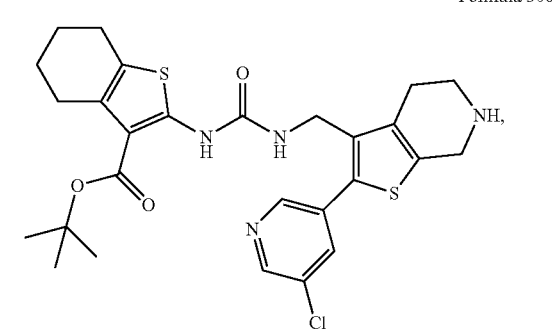

Formula 307
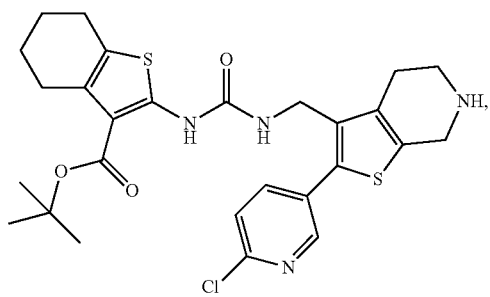
Formula 308
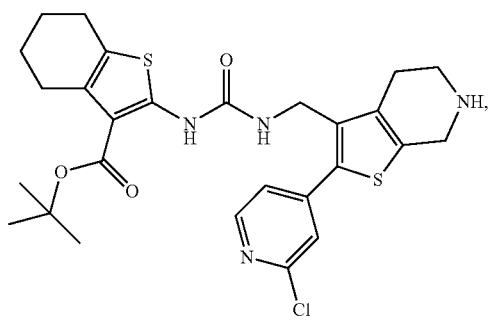
Formula 309
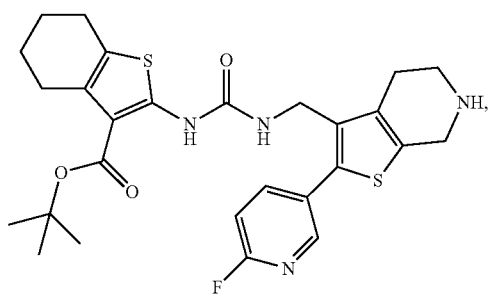
Formula 310
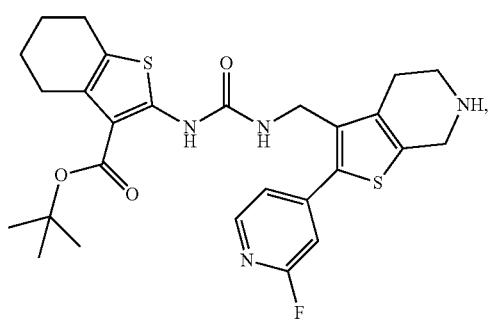
Formula 312
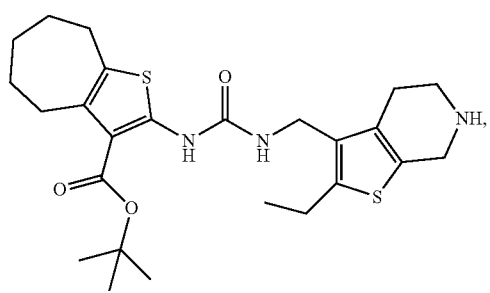
Formula 313
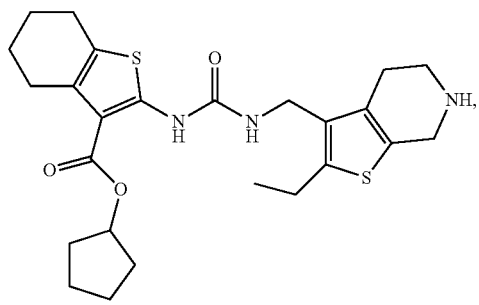
Formula 314
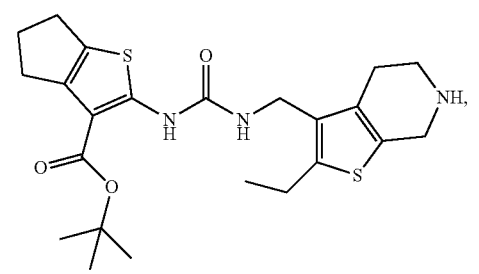
Formula 315
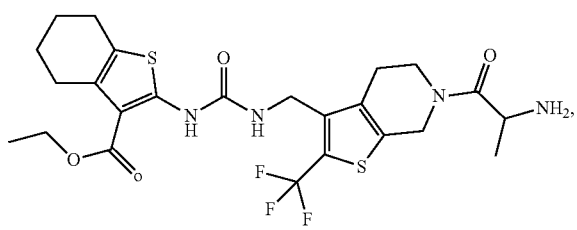
Formula 316
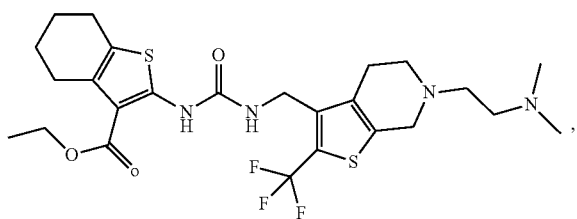
Formula 317
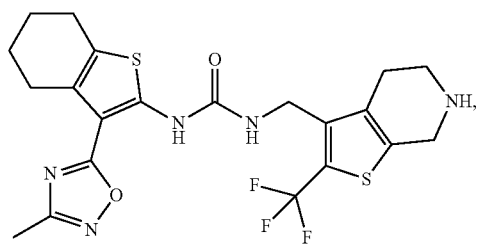

Formula 321
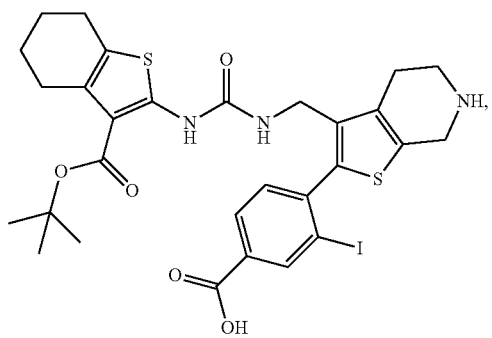
Formula 322
Formula 323
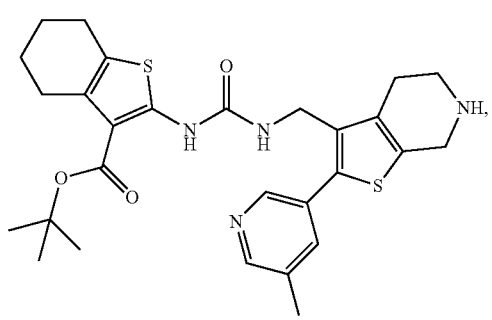
Formula 324
Formula 325
Formula 326
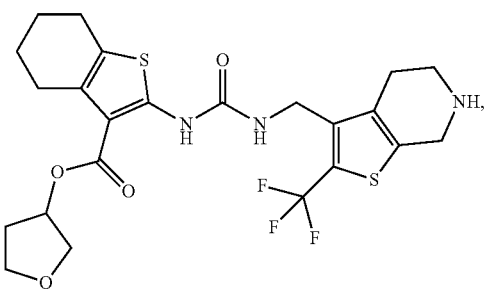
Formula 327
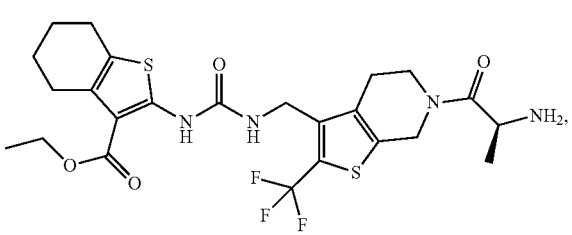
Formula 328
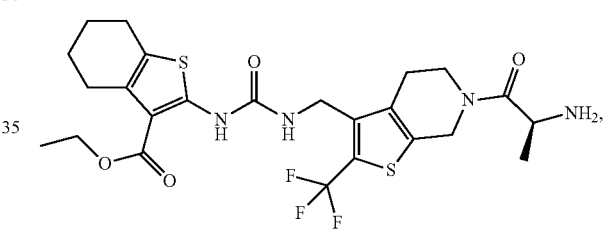
Formula 329
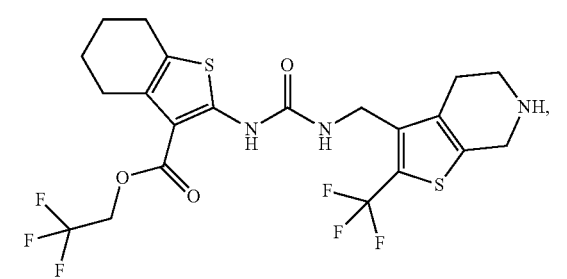
Formula 330
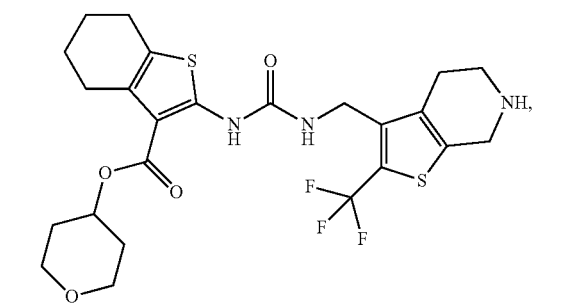

Formula 334
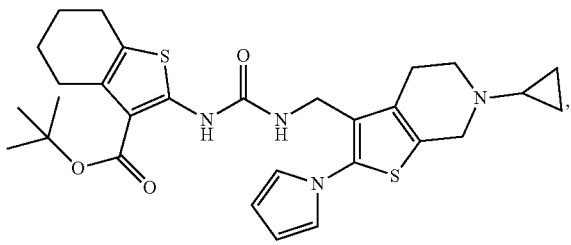
Formula 338
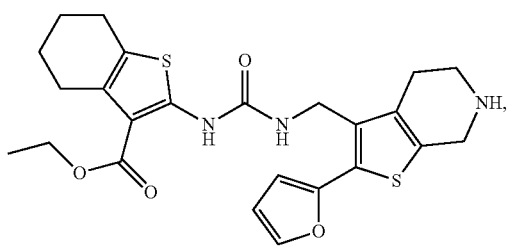
Formula 339
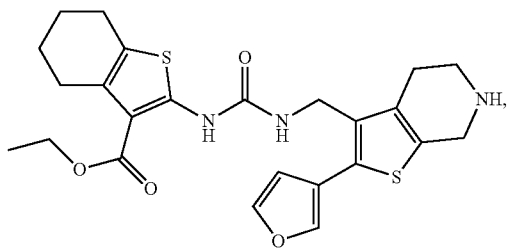
Formula 340
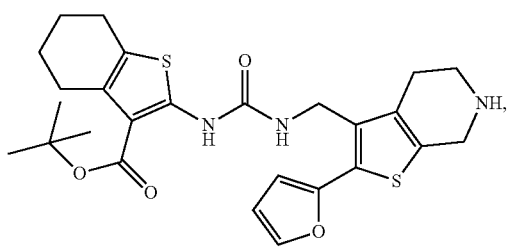
Formula 342
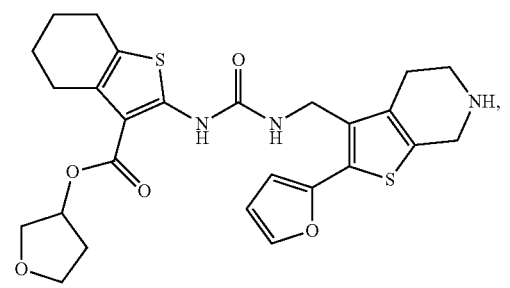
Formula 344
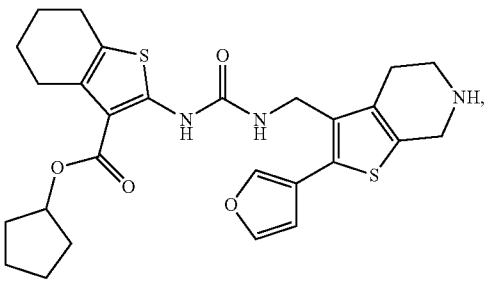
Formula 345
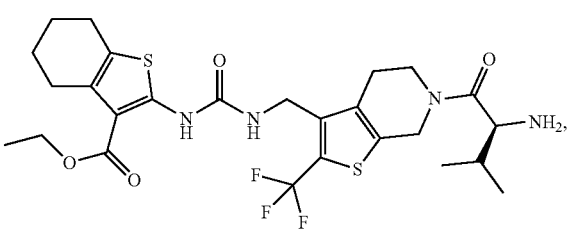
Formula 346
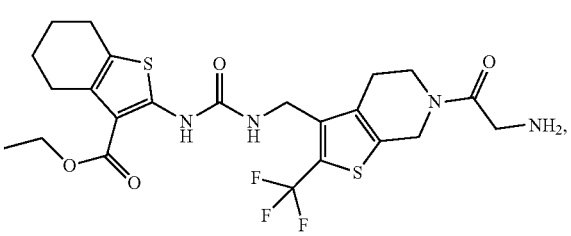
Formula 349
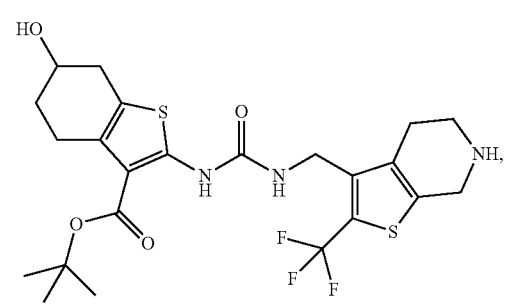
Formula 351
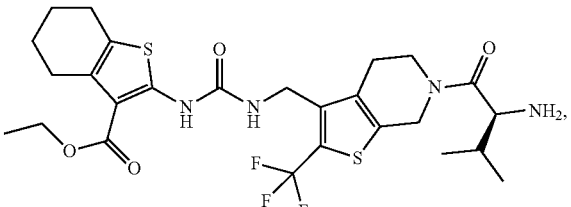
Formula 355
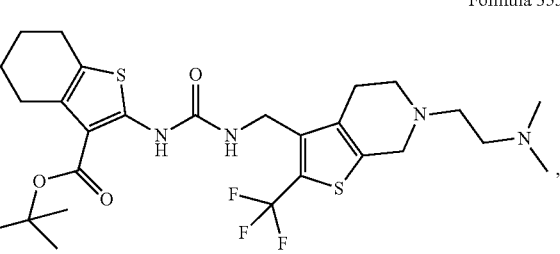

-continued
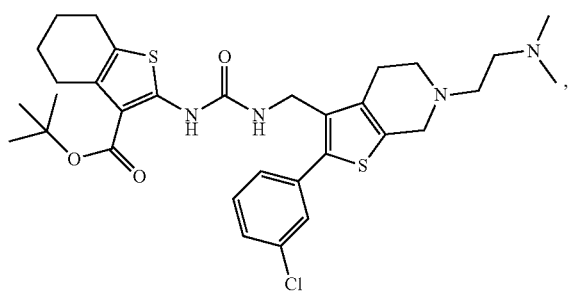
Formula 358
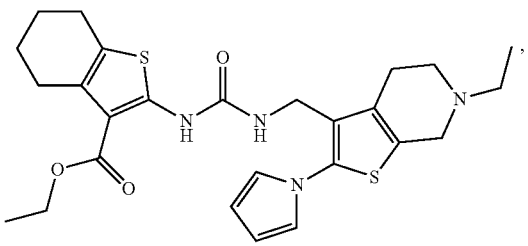
Formula 2
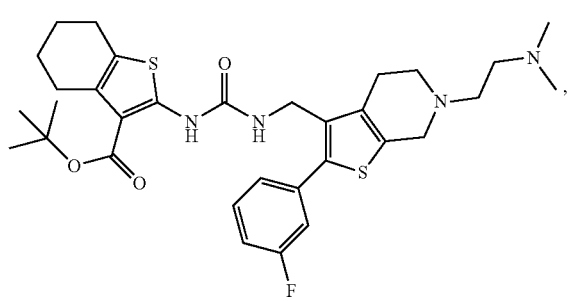
Formula 359
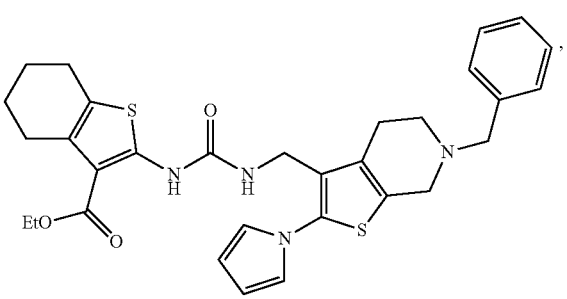
Formula 7
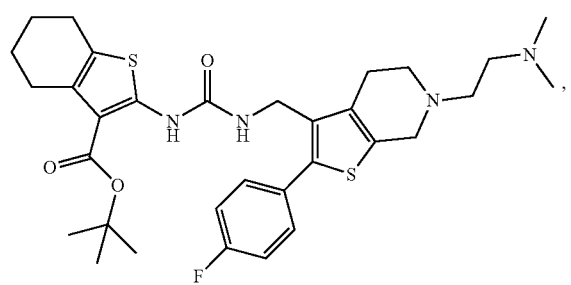
Formula 372
Formula 14
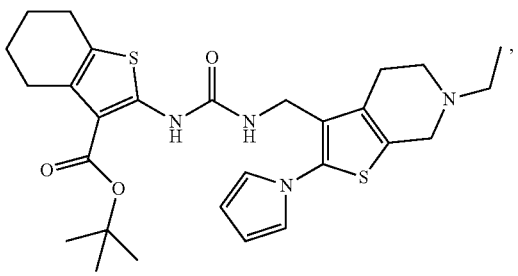
Formula 18
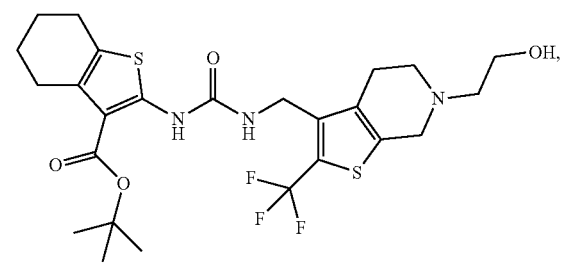
Formula 373
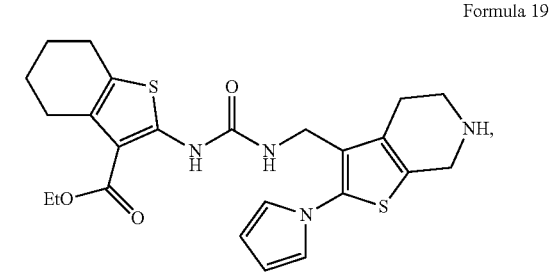
Formula 19
and a pharmaceutically acceptable salt thereof.
13. The method according to claim 12 for use in the treatment of a viral disease, wherein said compound is selected from the group consisting of:

Formula 20
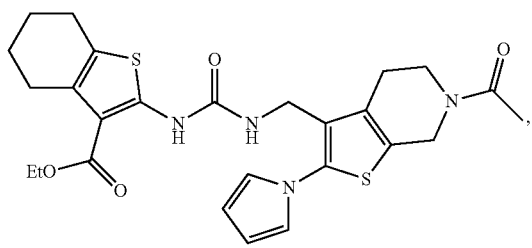
Formula 21
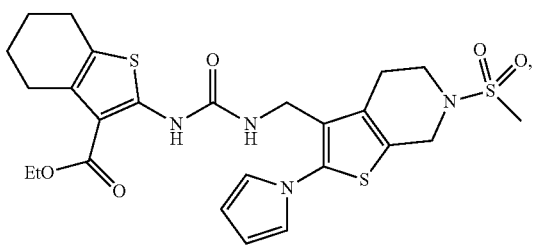
Formula 27
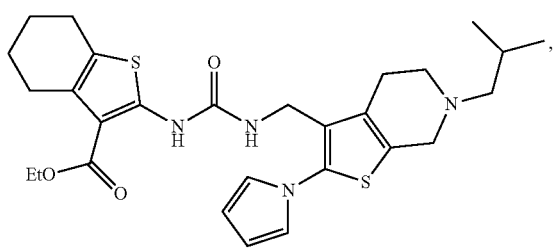
Formula 30
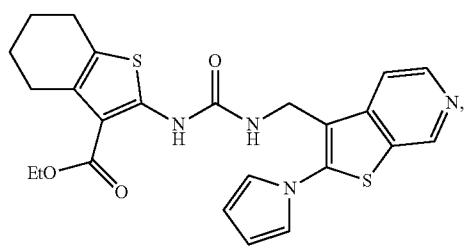
Formula 31
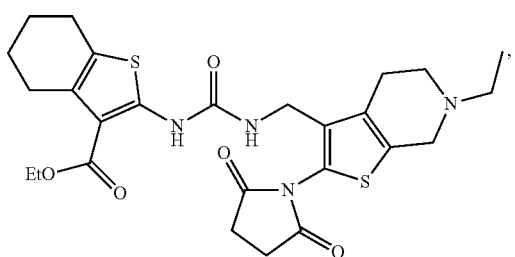
Formula 36
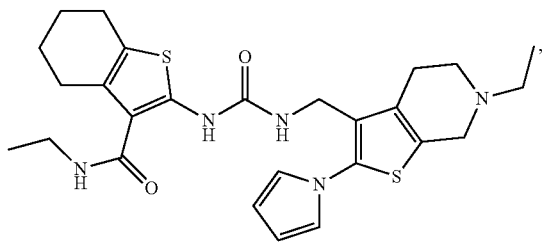
Formula 37
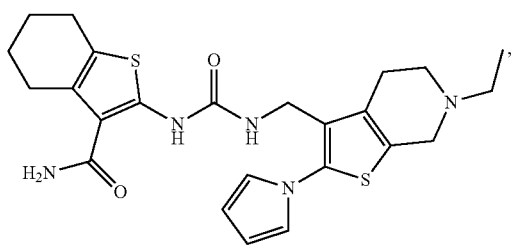
Formula 38
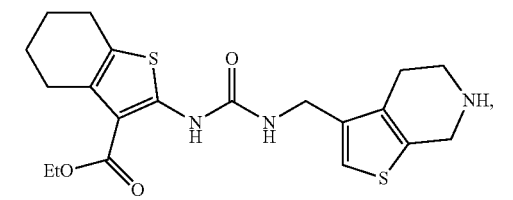
Formula 43
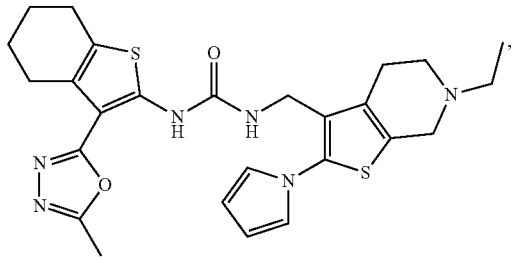
Formula 51
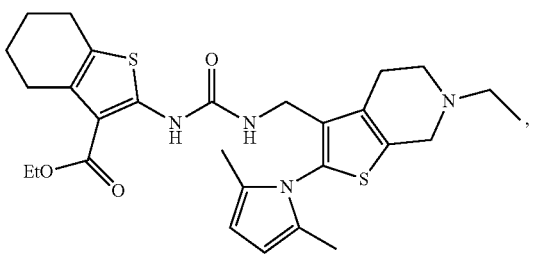
Formula 54
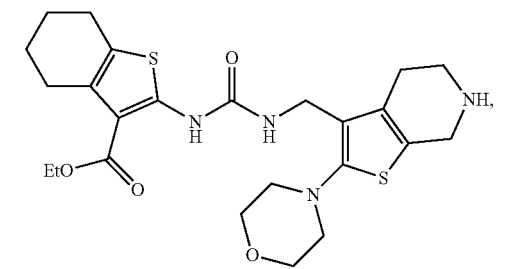
Formula 55

Formula 56
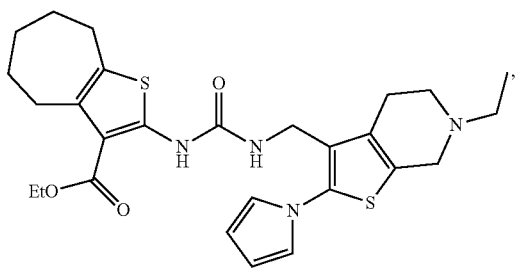
Formula 57
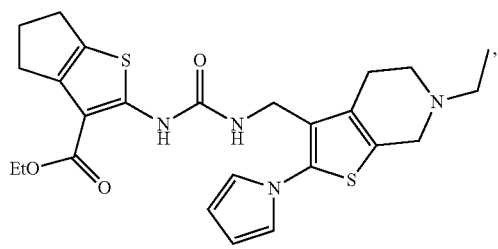
Formula 59
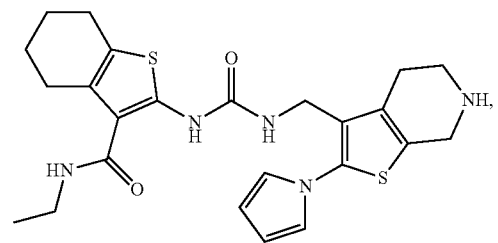
Formula 61
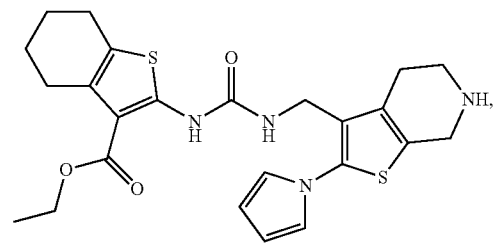
Formula 62
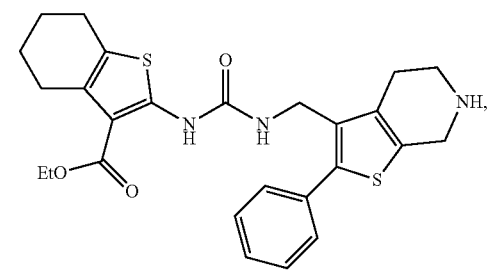
Formula 67
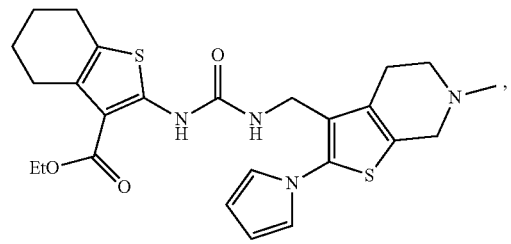
Formula 68
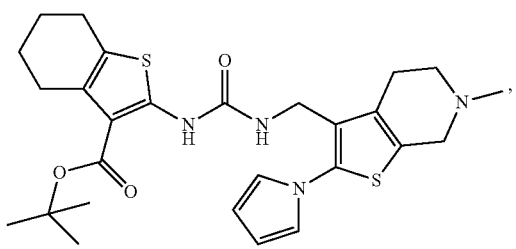
Formula 73
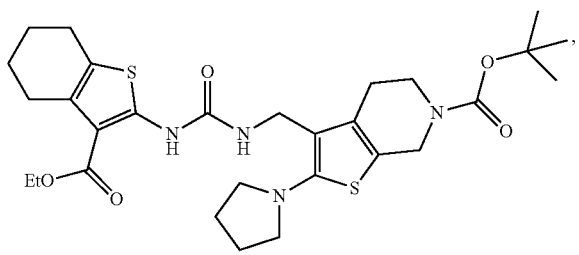
Formula 75
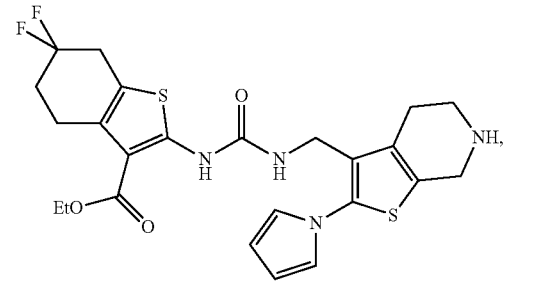
Formula 81
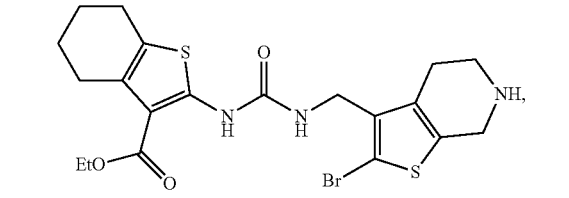
Formula 87
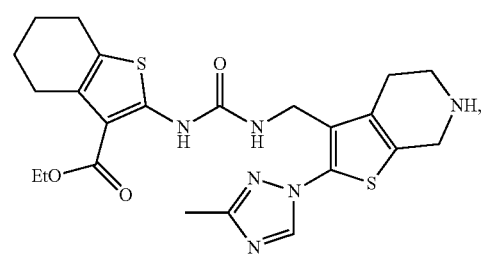

Formula 94
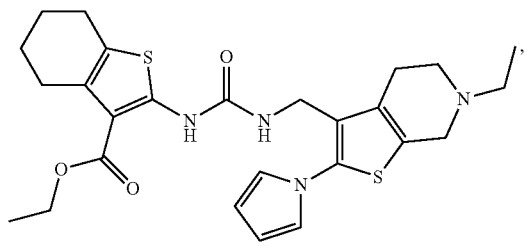
Formula 96
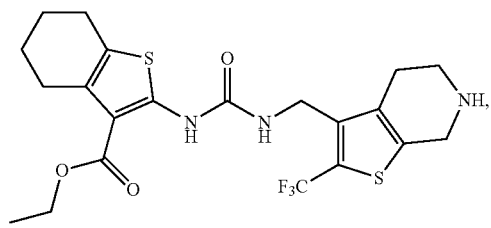
Formula 97
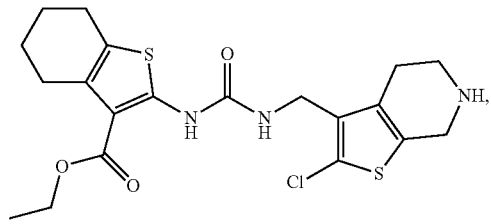
Formula 98
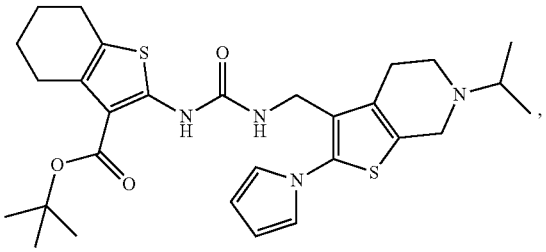
Formula 99
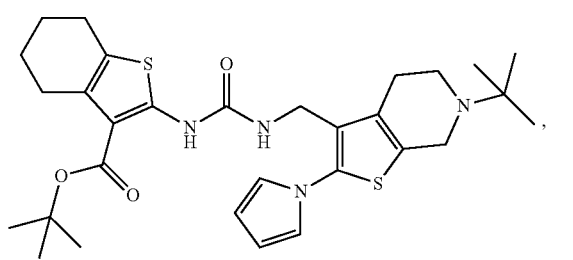
Formula 101
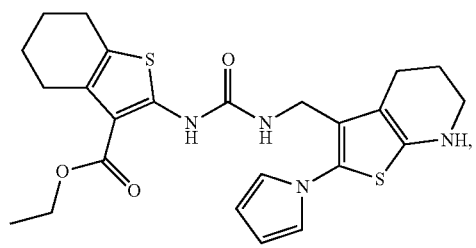
Formula 106
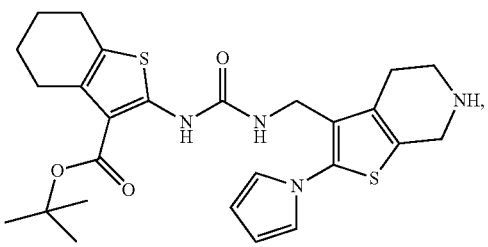
Formula 107
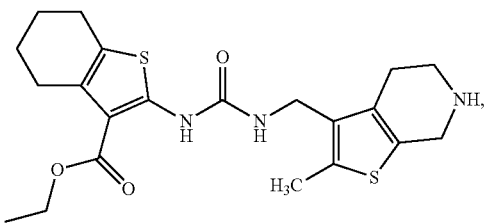
Formula 110
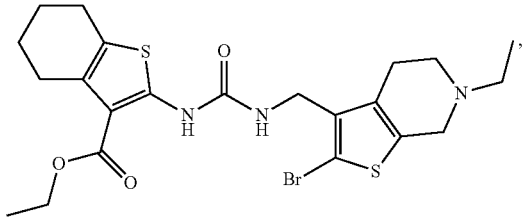
Formula 111
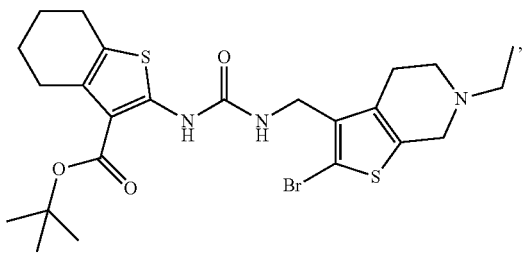
Formula 112
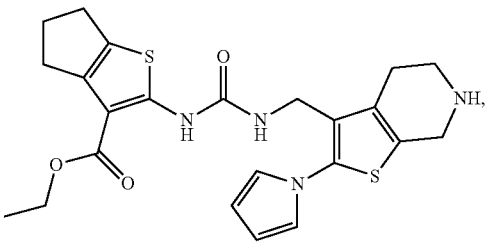
Formula 113
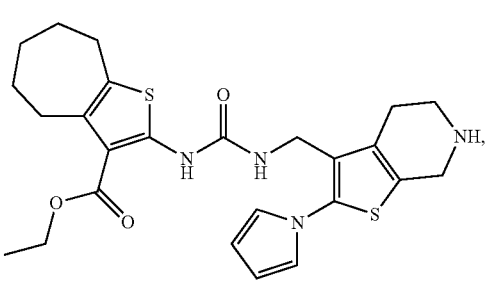

Formula 114
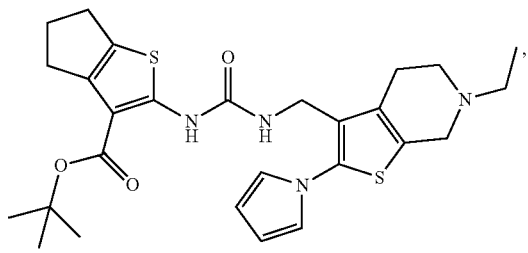
Formula 115
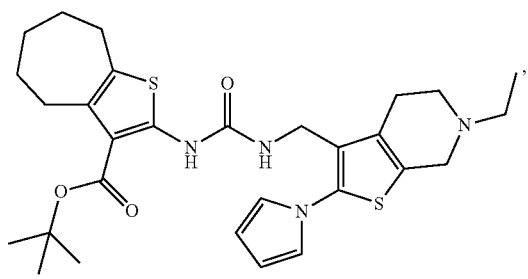
Formula 116
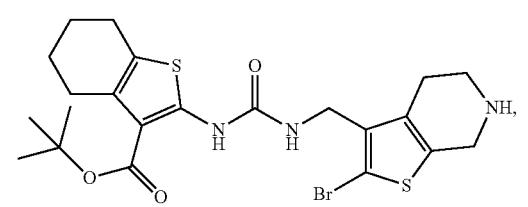
Formula 117
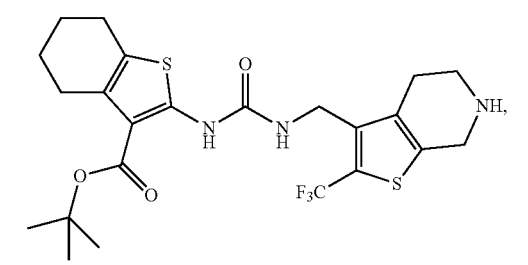
Formula 118
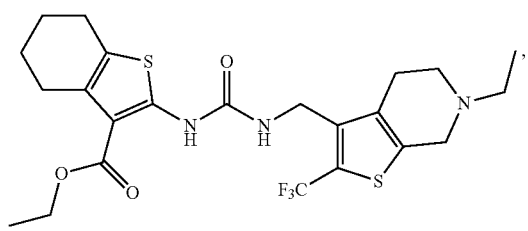
Formula 119
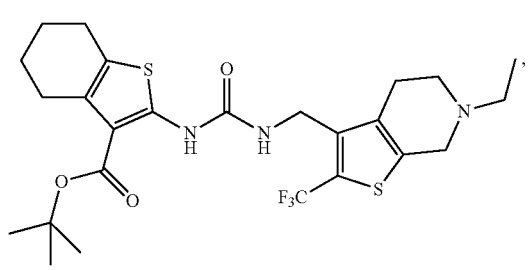
Formula 121
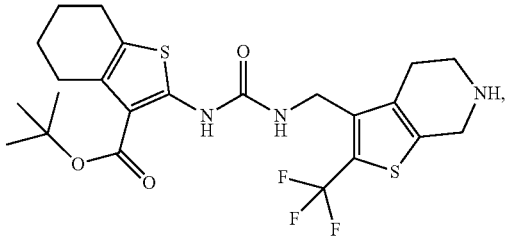
Formula 122
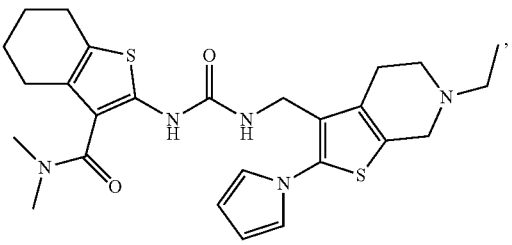
Formula 123
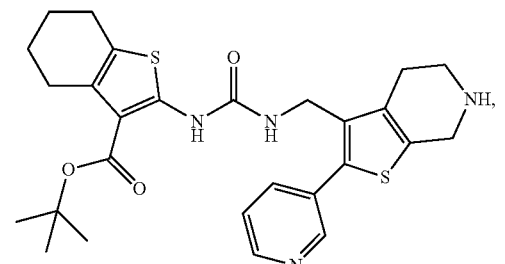
Formula 124
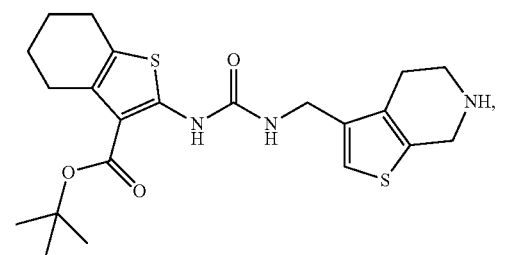
Formula 125
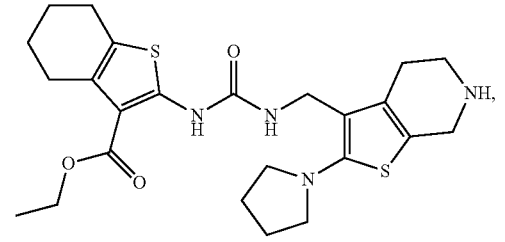
Formula 126
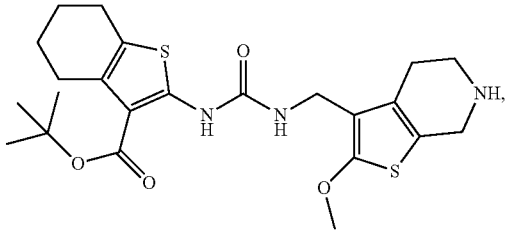

-continued
Formula 127
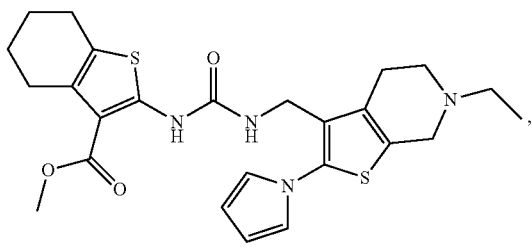
Formula 128
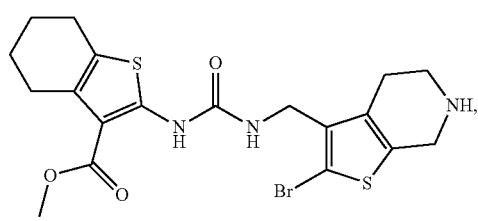
Formula 129
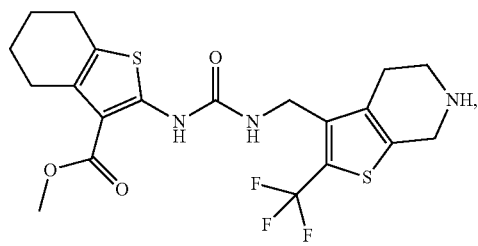
Formula 130
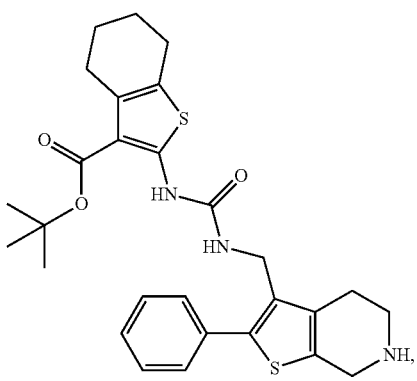
Formula 131
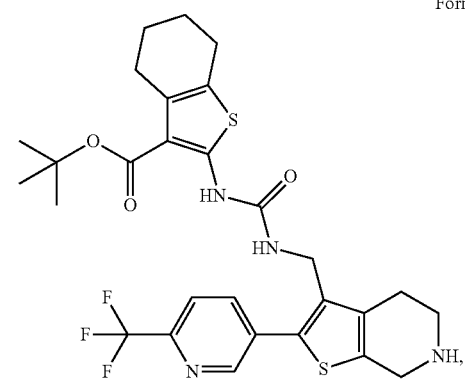
-continued
Formula 140
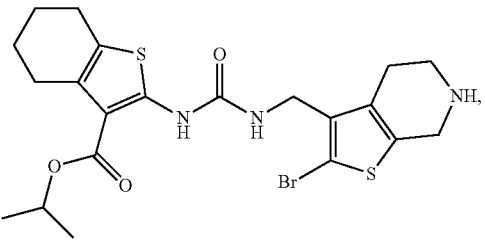
Formula 141
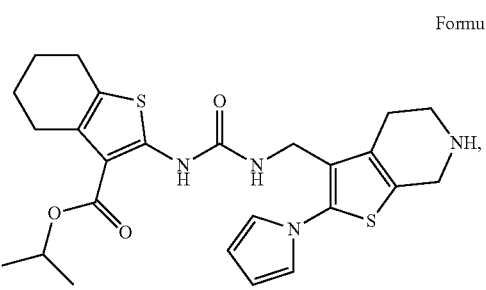
Formula 142
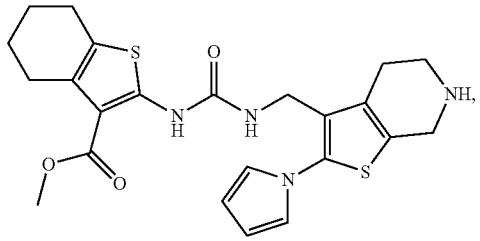
Formula 143
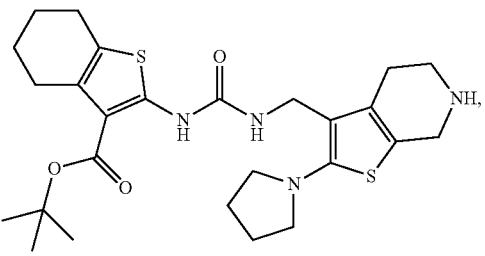
Formula 144
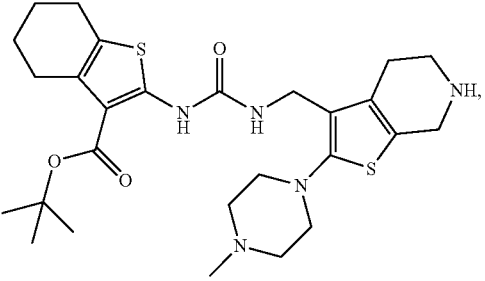

Formula 145

Formula 146

Formula 151

Formula 152

Formula 153

Formula 154

Formula 155

Formula 156

Formula 157

Formula 159

Formula 160
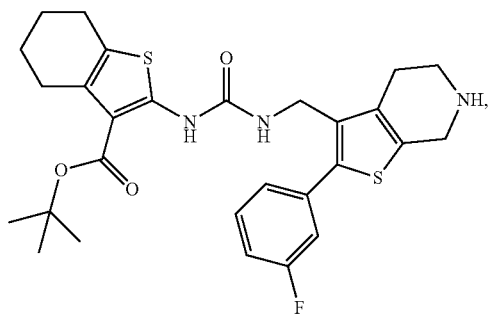
Formula 161
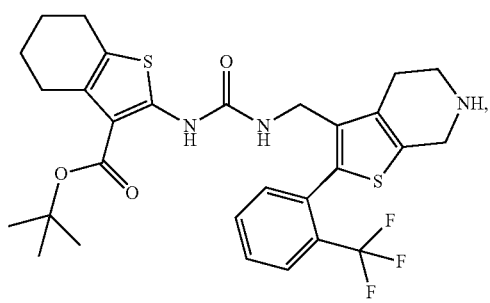
Formula 164
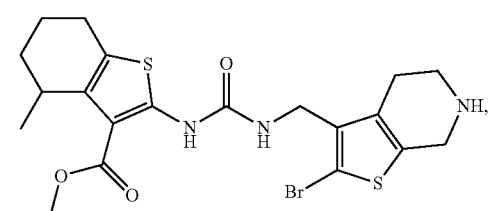
Formula 165
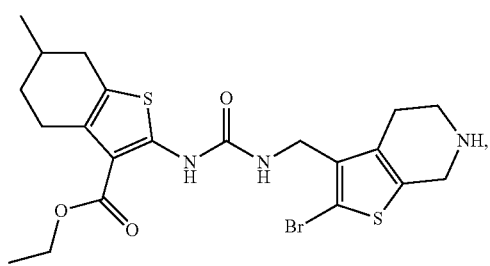
Formula 166
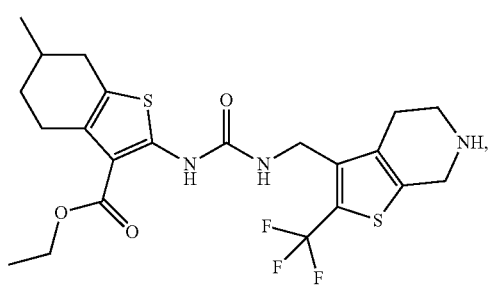
Formula 167
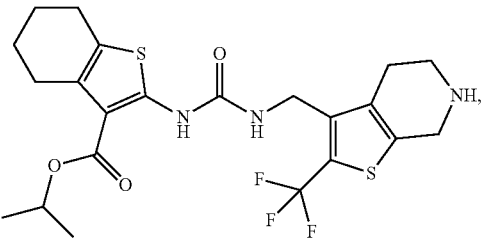
Formula 169
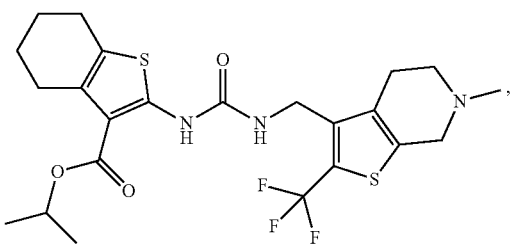
Formula 171
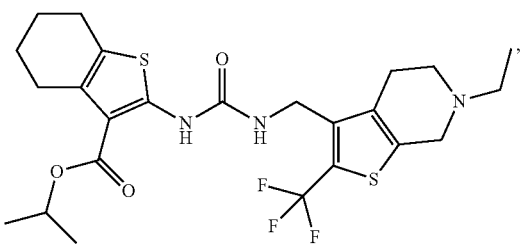
Formula 172
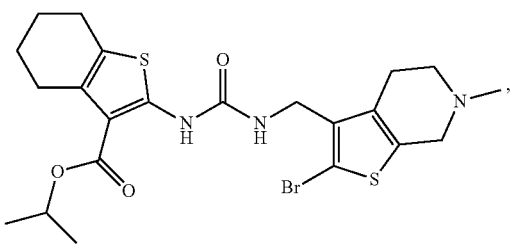
Formula 174
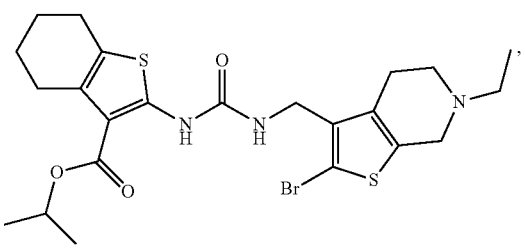
Formula 175
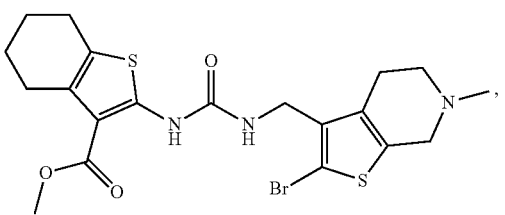

Formula 177
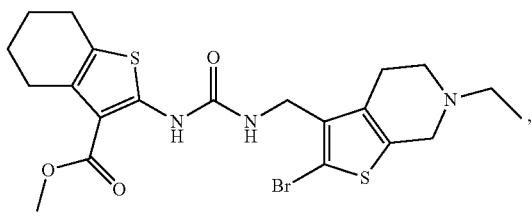
Formula 178
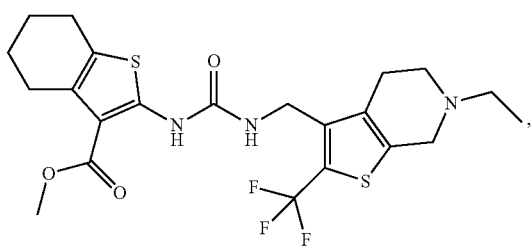
Formula 179
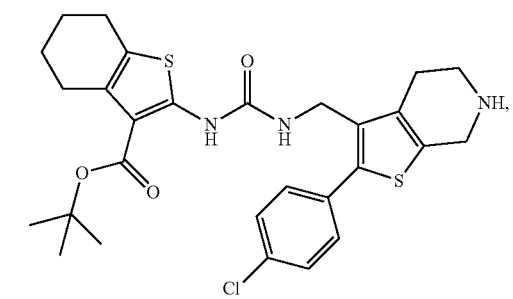
Formula 180
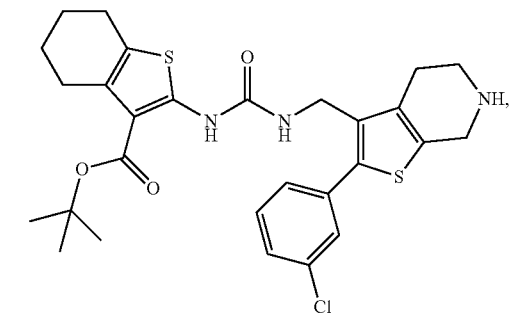
Formula 181
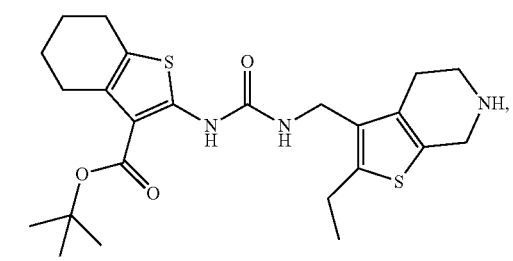
Formula 182
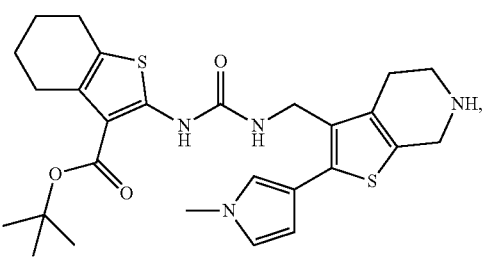
Formula 183
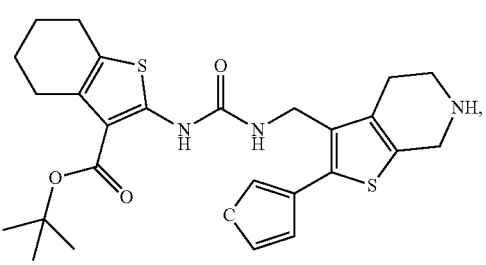
Formula 184
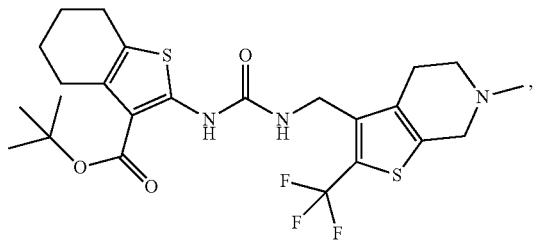
Formula 185
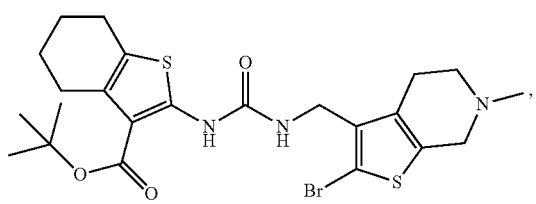
Formula 186
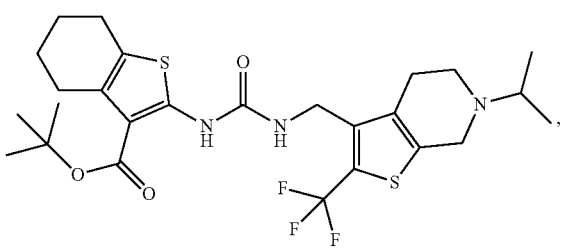
Formula 187
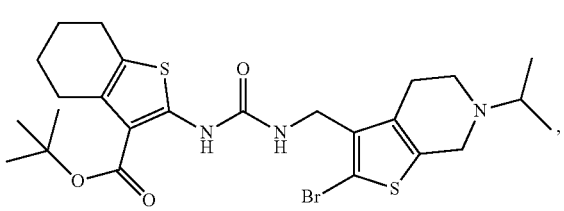

Formula 190
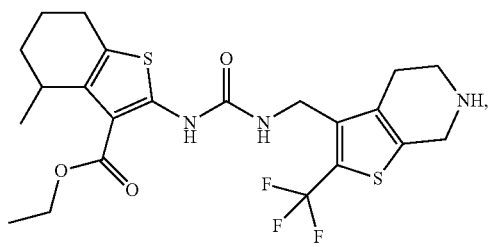
Formula 191
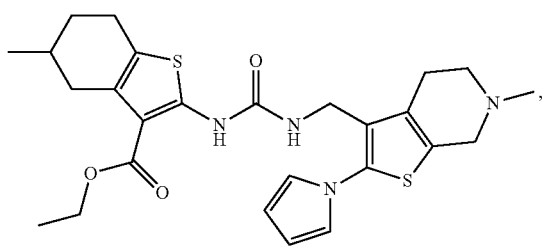
Formula 192
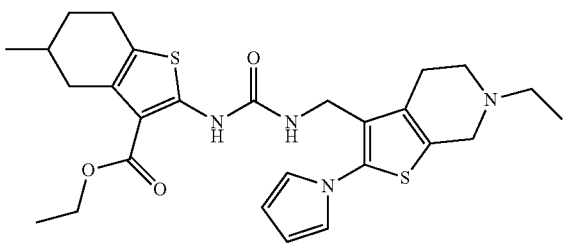
Formula 193
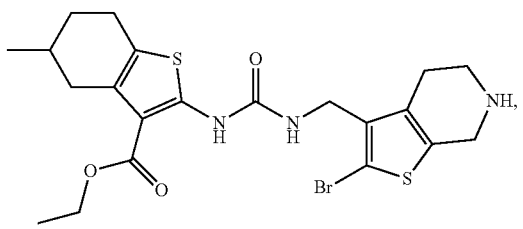
Formula 194
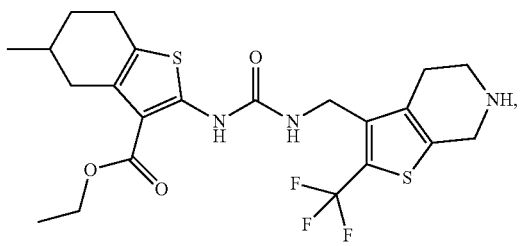
Formula 197
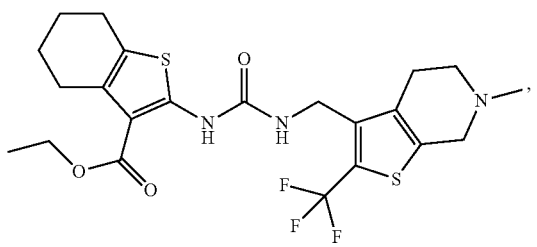
Formula 198
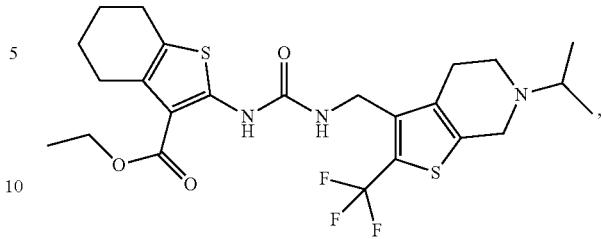
Formula 199
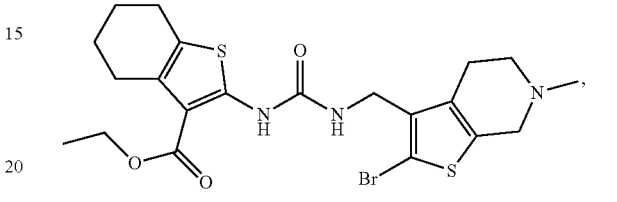
Formula 200
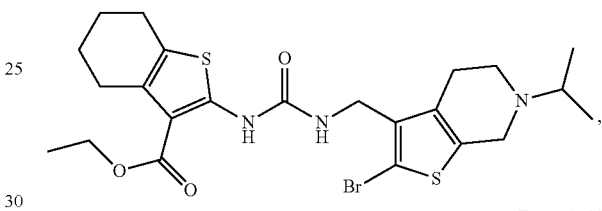
Formula 201
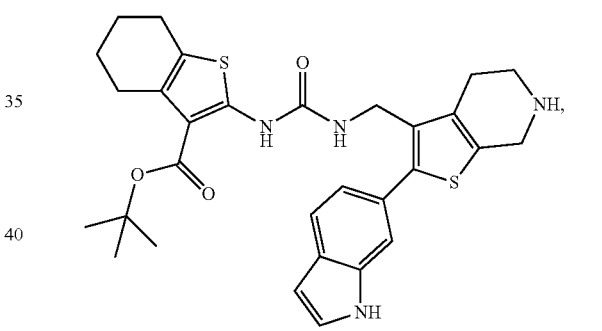
Formula 202
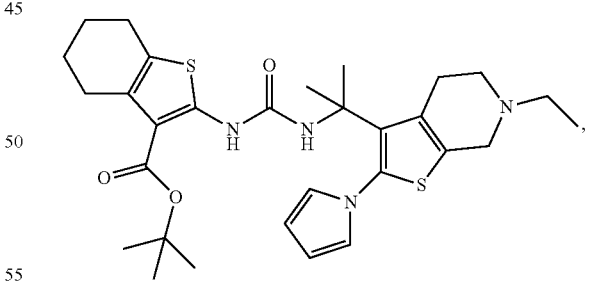
Formula 203
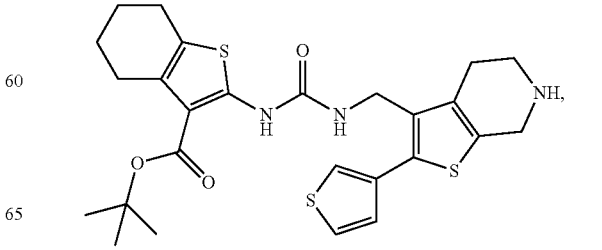

Formula 204
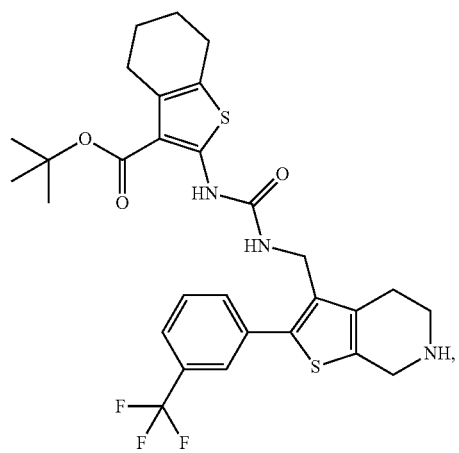
Formula 205
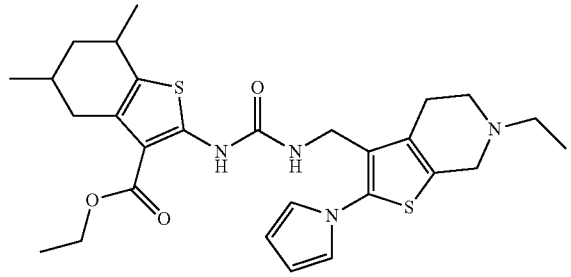
Formula 207
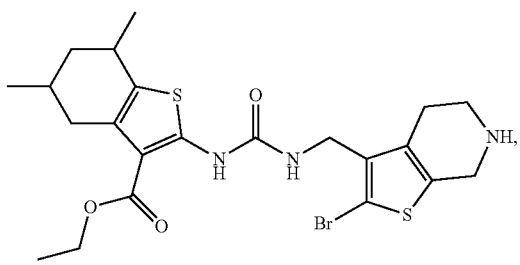
Formula 208
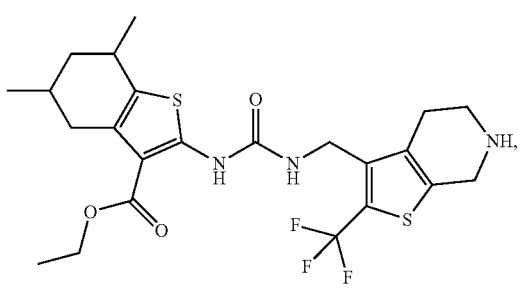
Formula 210
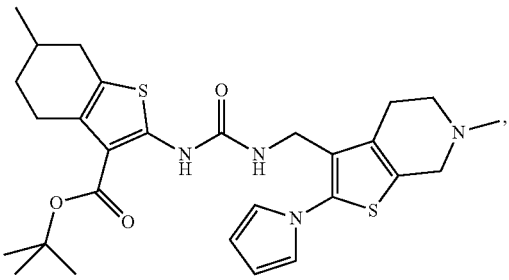
Formula 211
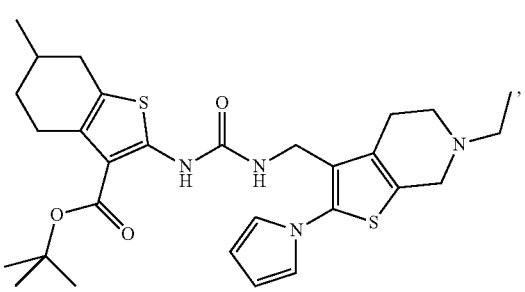
Formula 212
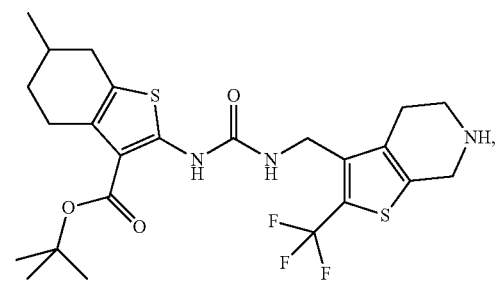
Formula 213
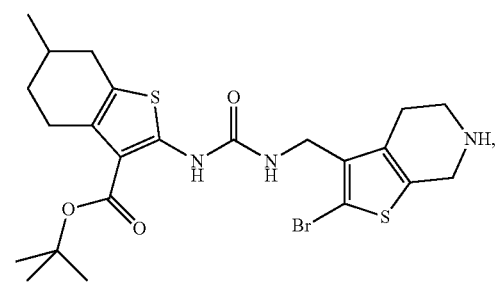
Formula 218
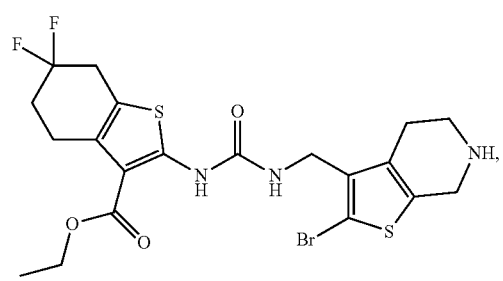

Formula 219
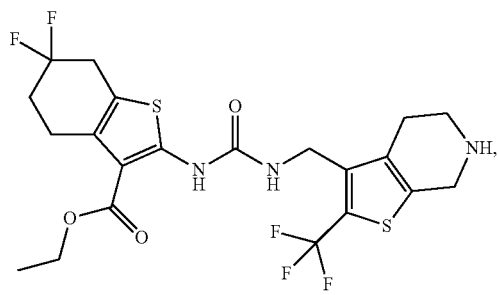
Formula 220
Formula 221
Formula 222
Formula 224
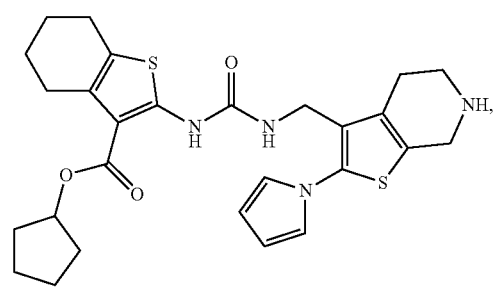
Formula 225
Formula 226
Formula 227
Formula 228
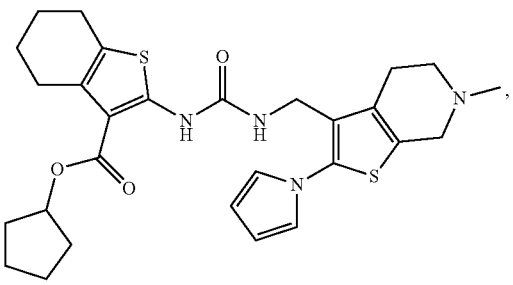
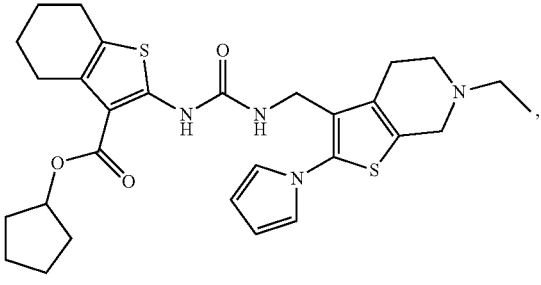

Formula 229
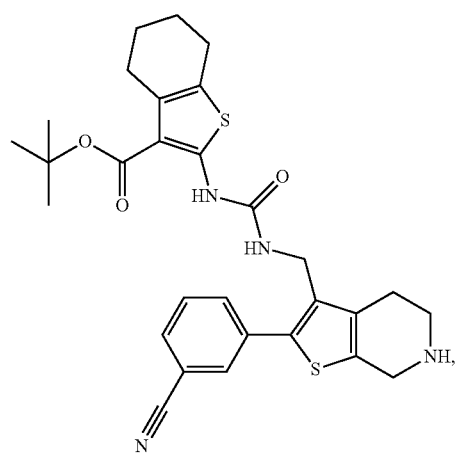
Formula 231
Formula 232
Formula 233
Formula 234
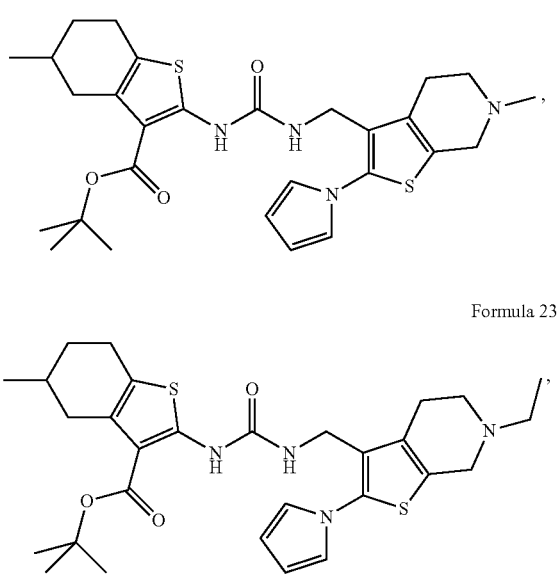
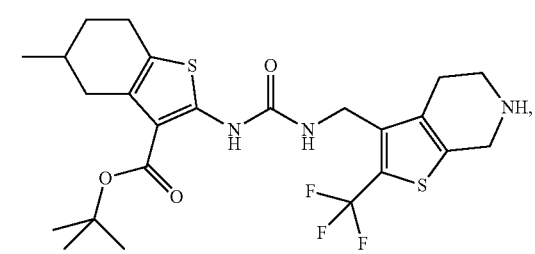
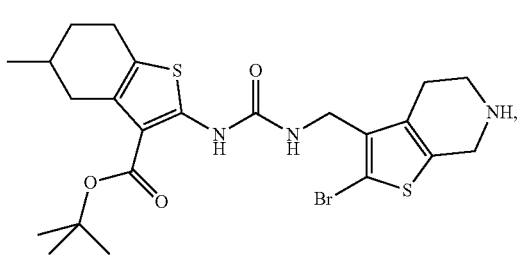
Formula 235
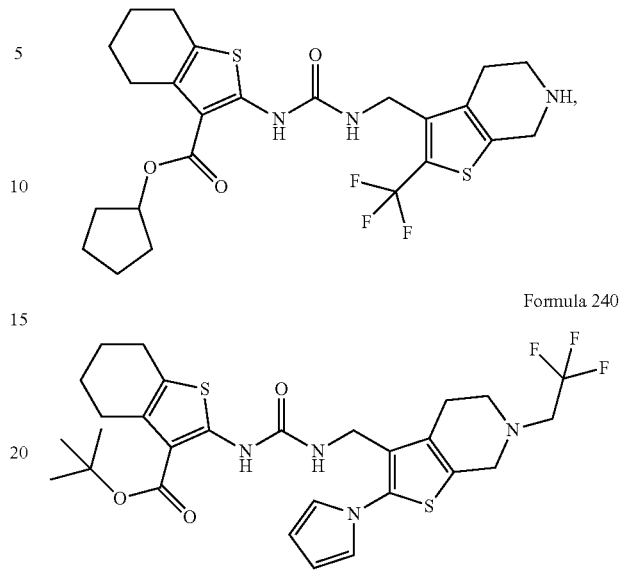
Formula 240
Formula 241
Formula 242
Formula 243
Formula 244

Formula 245
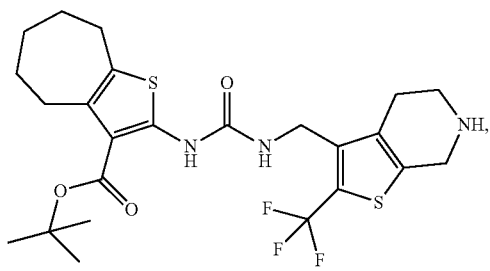
Formula 247
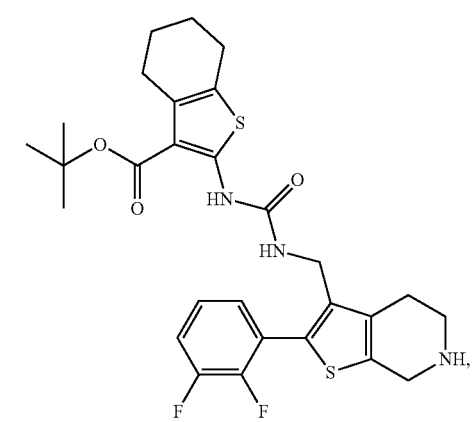
Formula 248
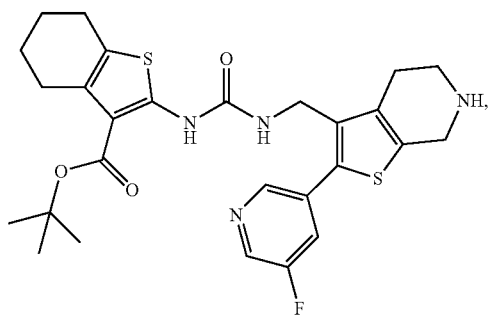
Formula 249
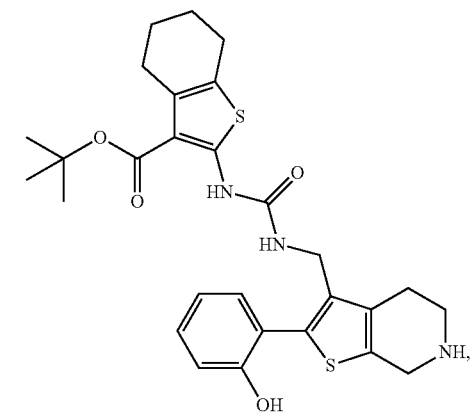
Formula 250
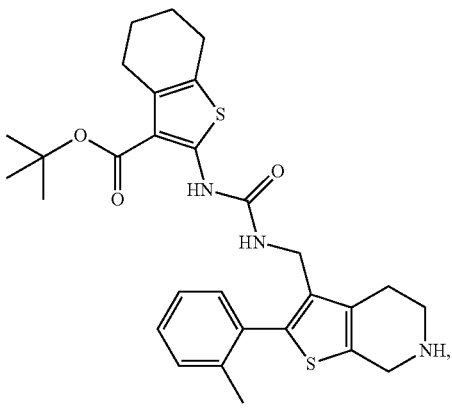
Formula 252
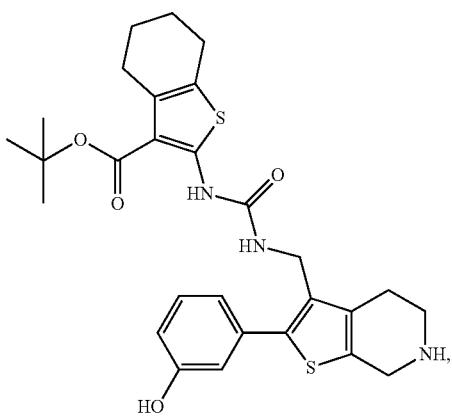
Formula 254
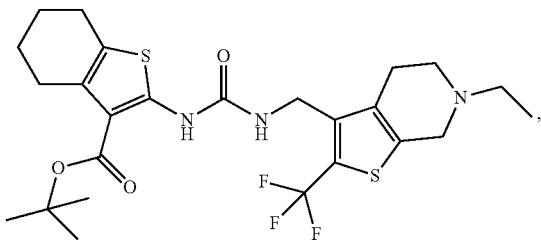
Formula 256
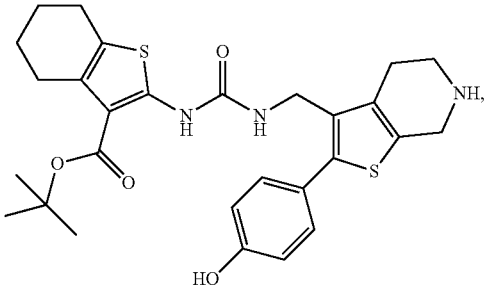

Formula 257
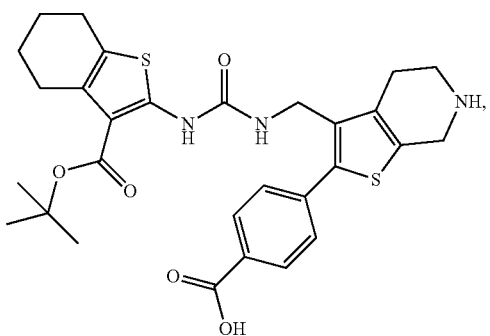
Formula 258
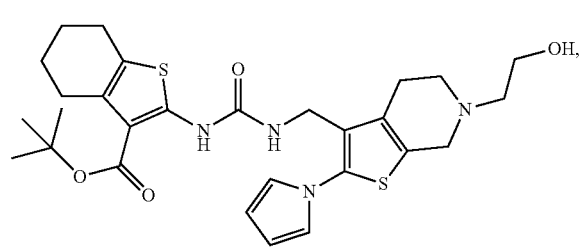
Formula 259
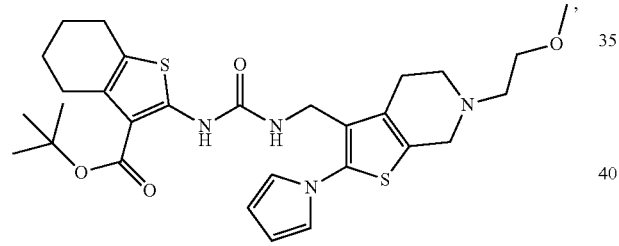
Formula 260
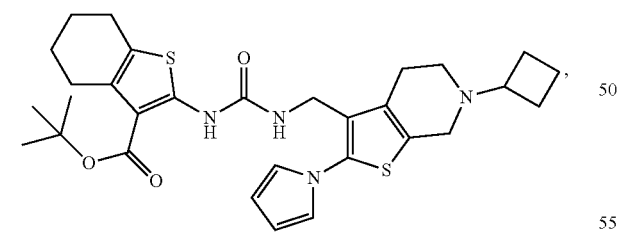
Formula 261
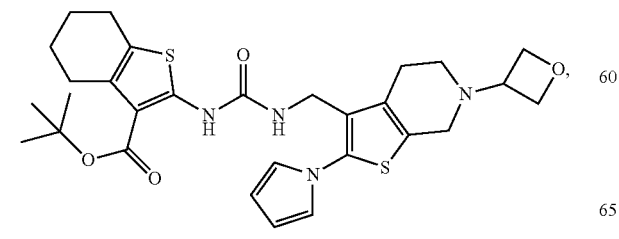
Formula 262
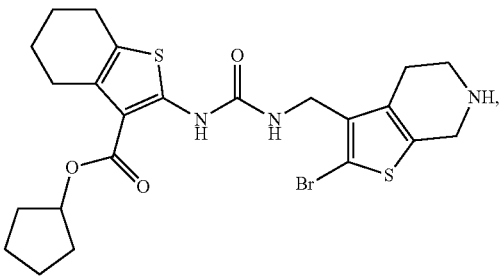
Formula 263
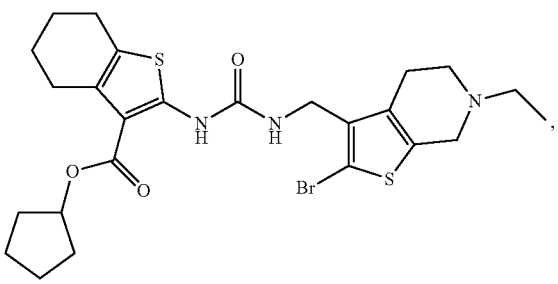
Formula 265
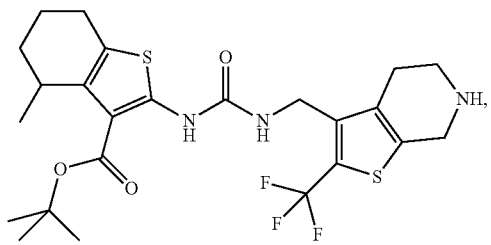
Formula 266
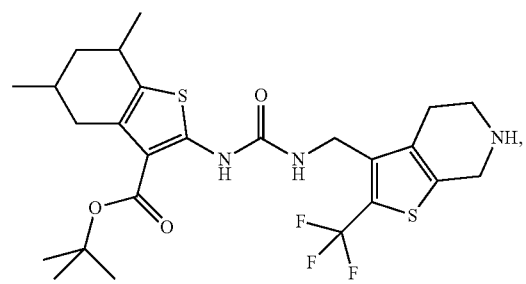
Formula 267
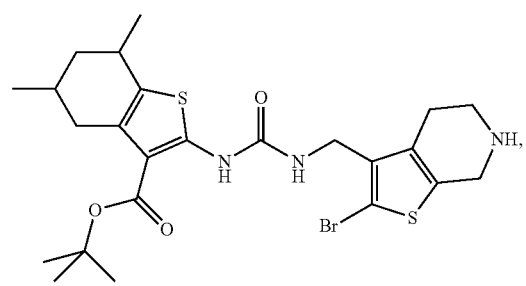

Formula 271
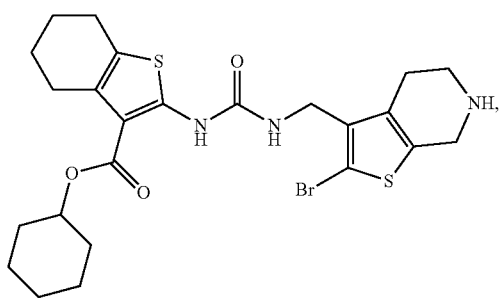
Formula 272
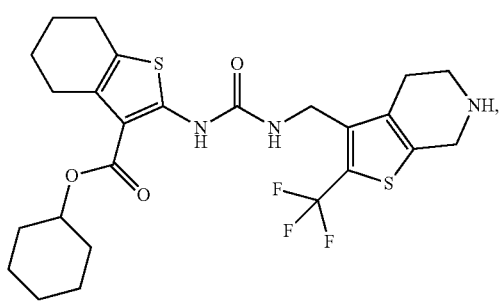
Formula 273
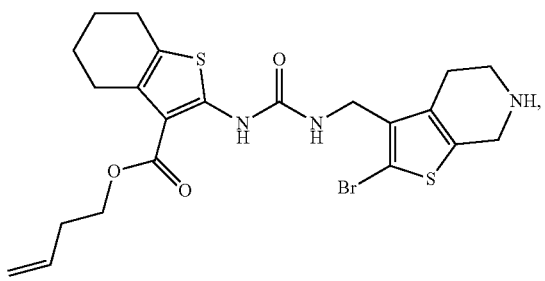
Formula 274
Formula 275
Formula 276
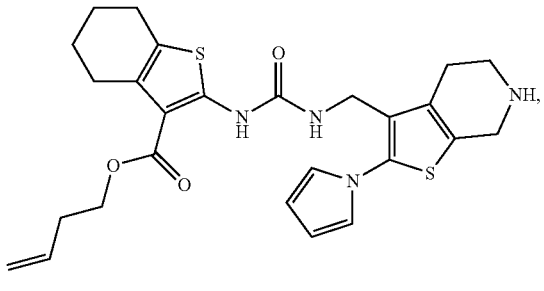
Formula 277
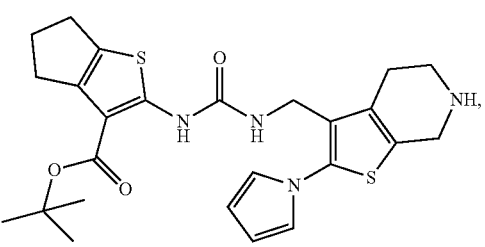
Formula 278
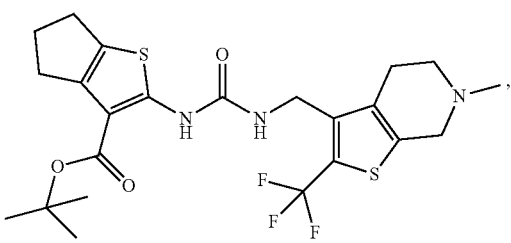
Formula 279
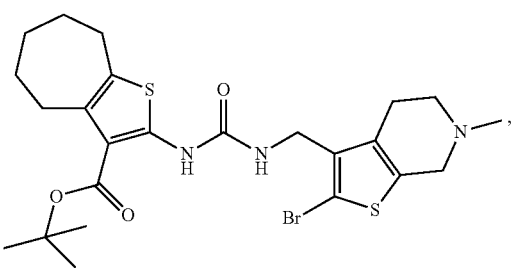
Formula 280
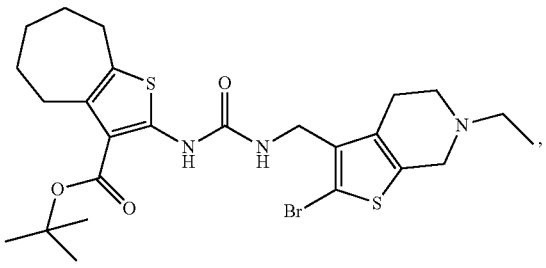

Formula 281
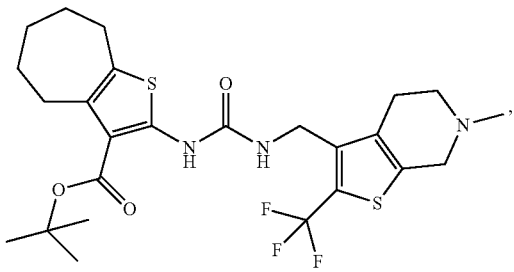
Formula 283
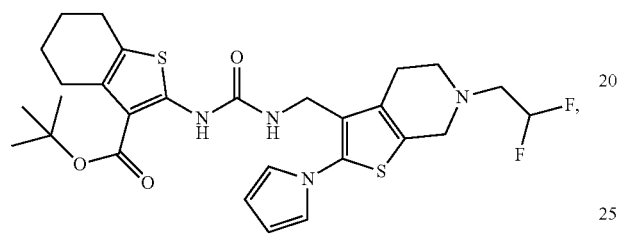
Formula 284
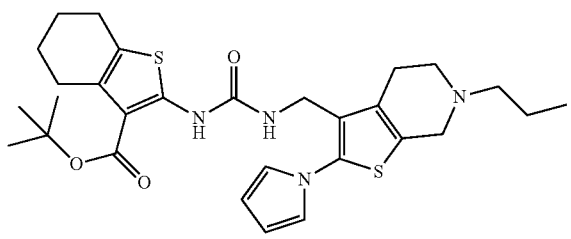
Formula 285
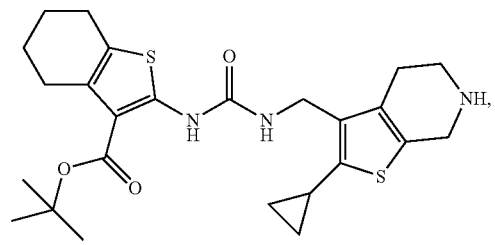
Formula 286
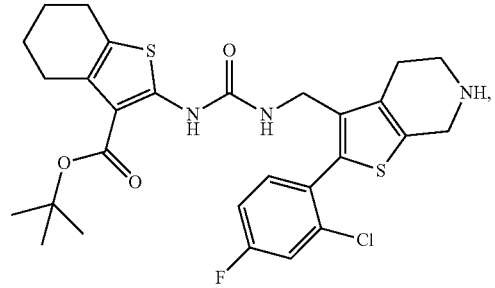
Formula 287
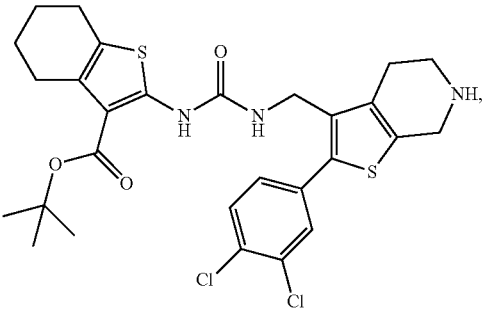
Formula 289
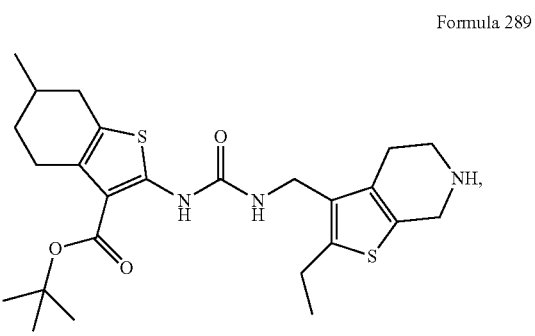
Formula 290
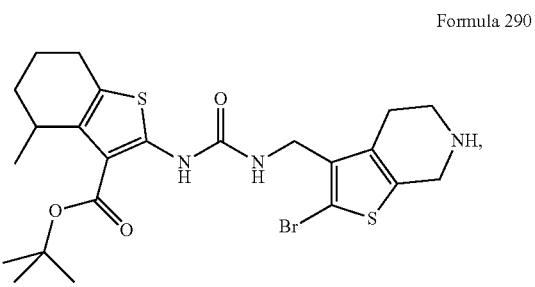
Formula 291
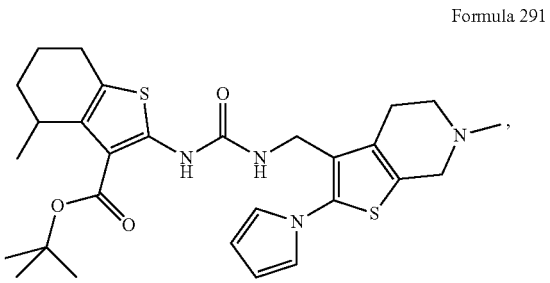
Formula 292
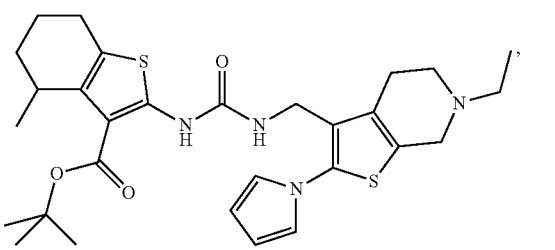

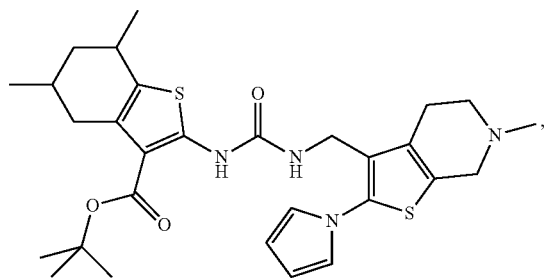

Formula 307
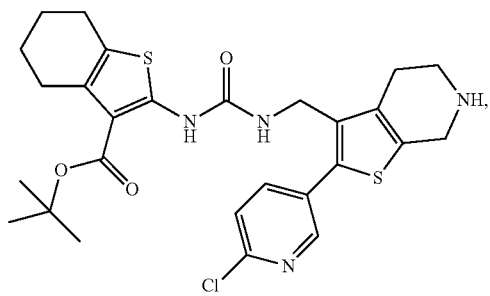
Formula 308
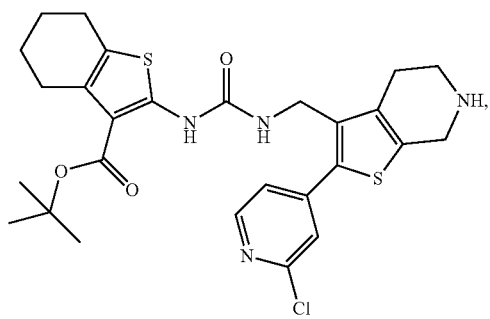
Formula 309
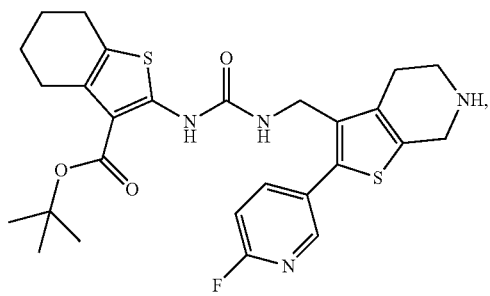
Formula 310
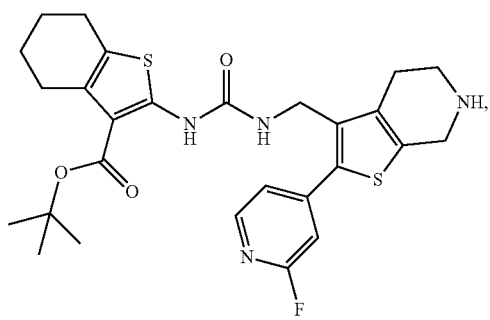
Formula 312
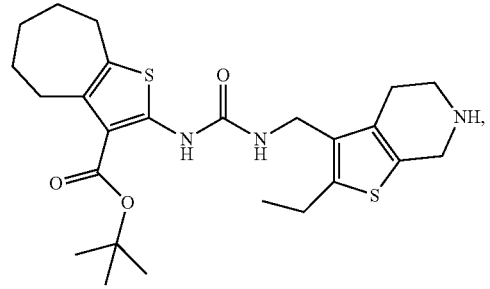
Formula 313
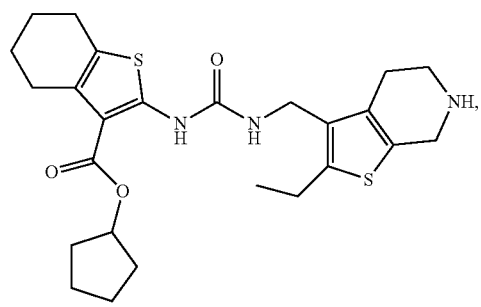
Formula 314
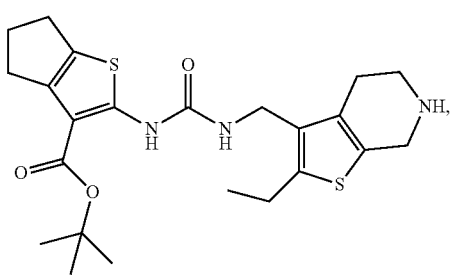
Formula 315
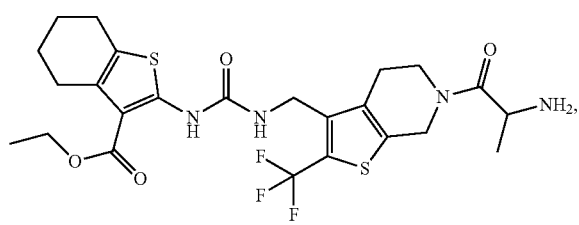
Formula 316
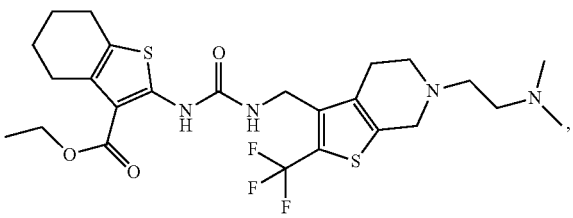
Formula 317
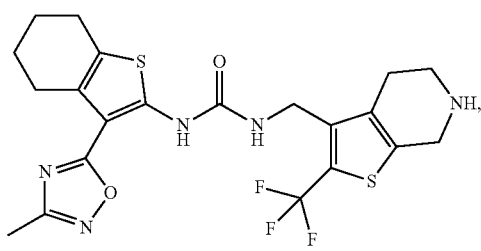

-continued
Formula 322
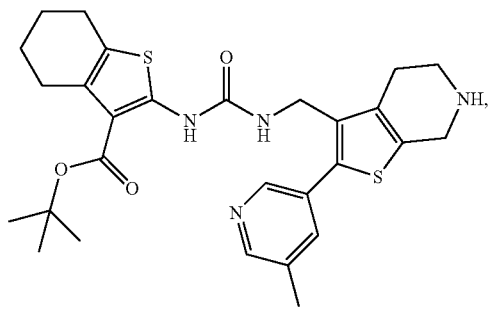
Formula 323
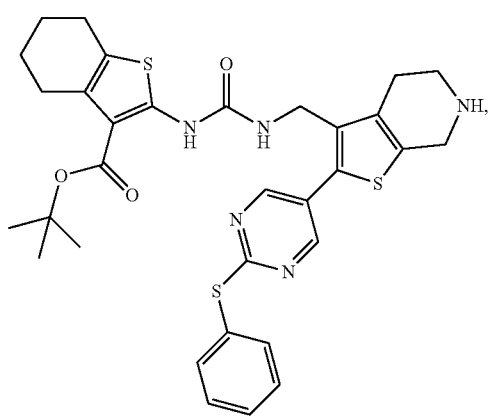
Formula 324
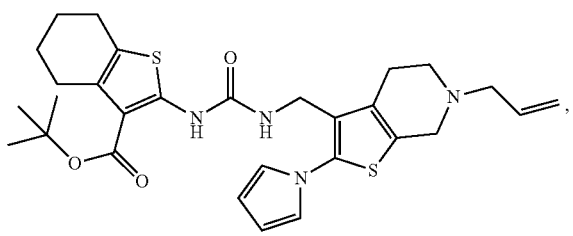
Formula 325
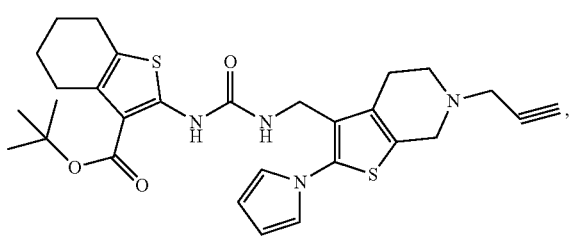
Formula 326
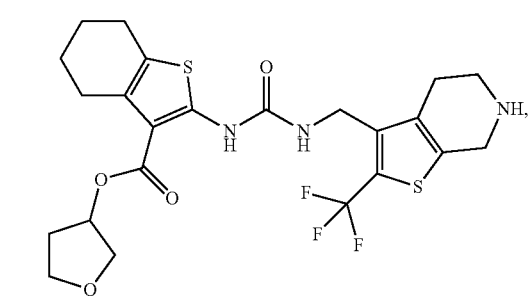
-continued
Formula 327
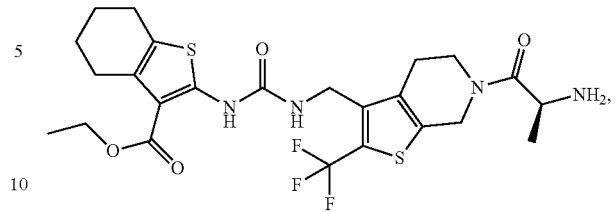
Formula 328
Formula 329
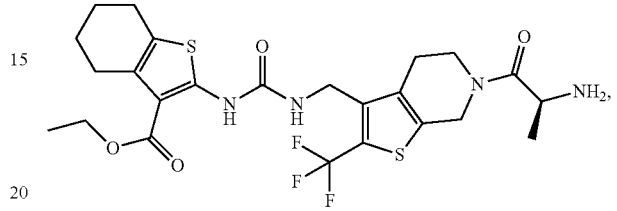
Formula 330
Formula 334
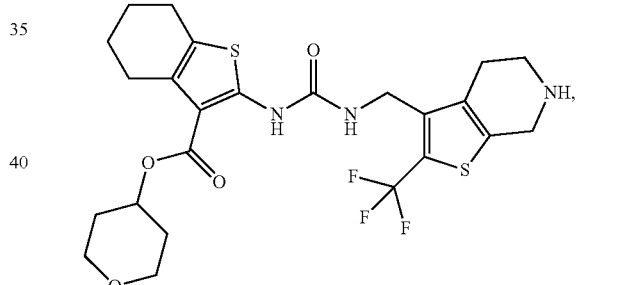
Formula 338
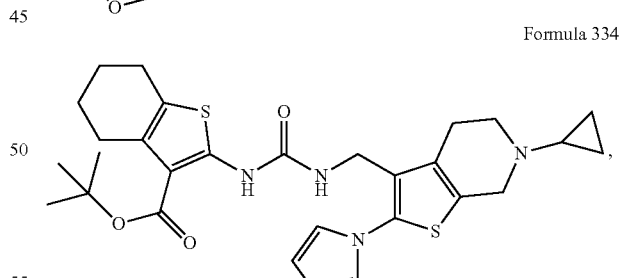
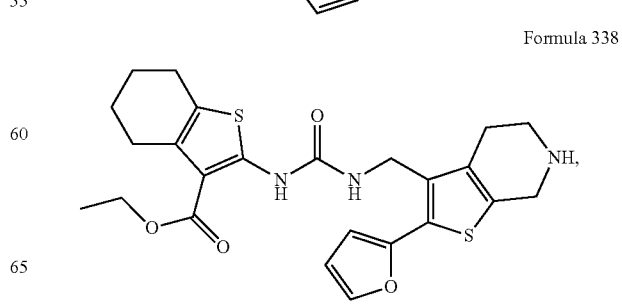

-continued
Formula 339
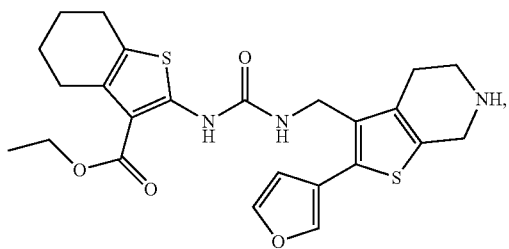
Formula 340
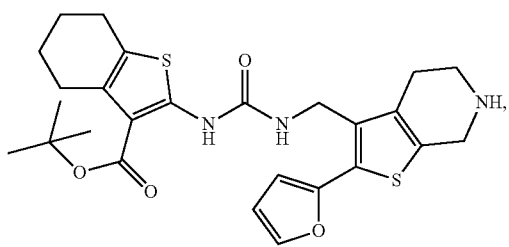
Formula 342
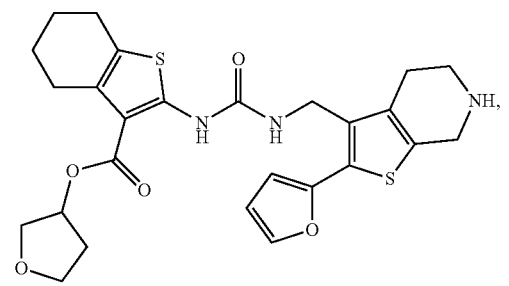
Formula 344
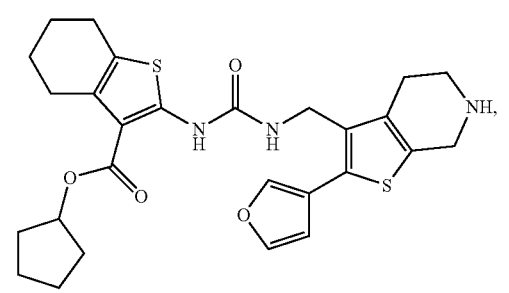
Formula 345
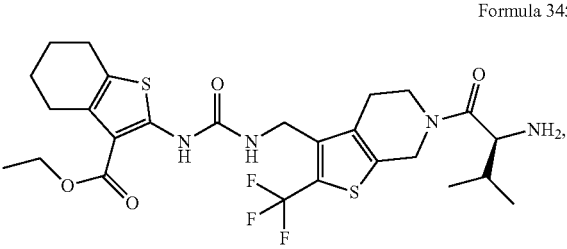
Formula 346
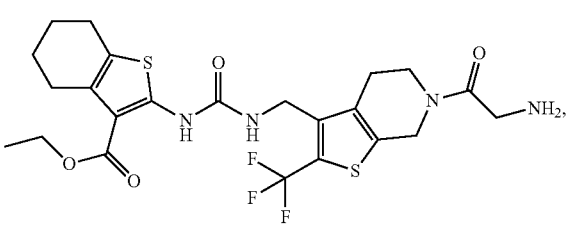
-continued
Formula 349
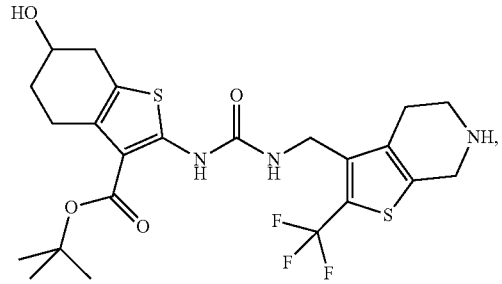
Formula 351
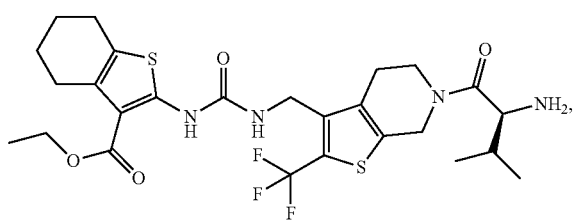
Formula 355
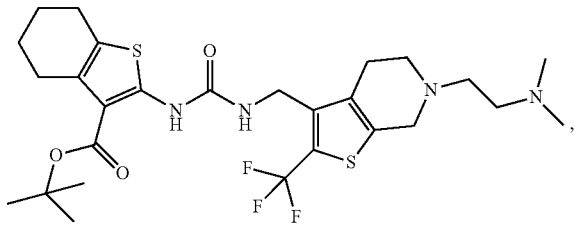
Formula 358
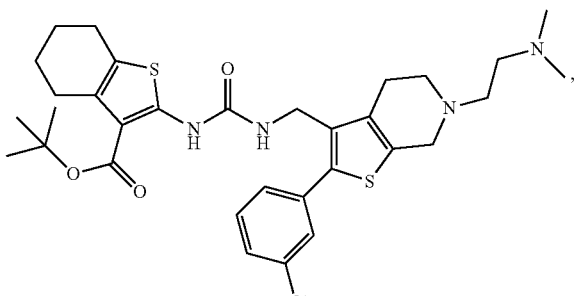
Formula 359
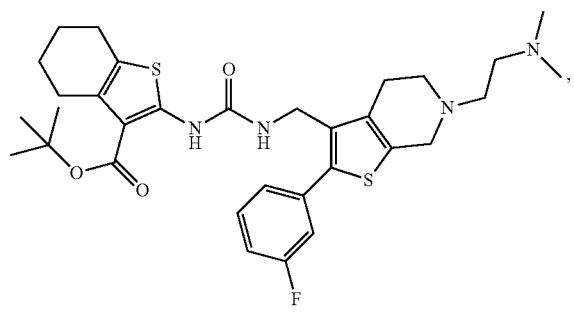

Formula 372
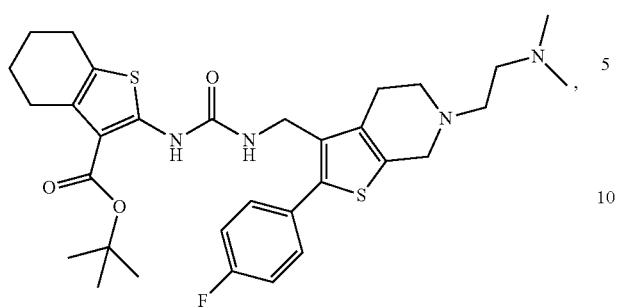
Formula 373
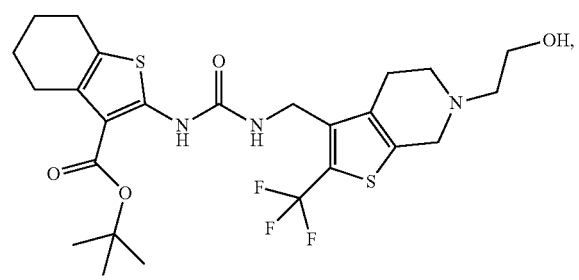
and a pharmaceutically acceptable salt thereof.
14. The method according to claim 13 for use in the treatment of a viral disease, wherein said compound is selected from the group consisting of:
Formula 14
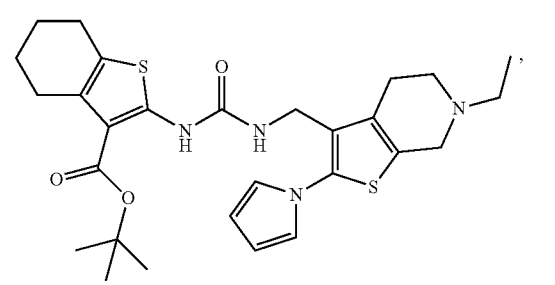
Formula 19
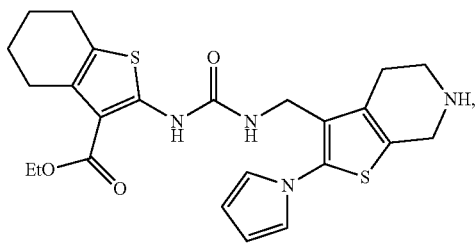
Formula 21
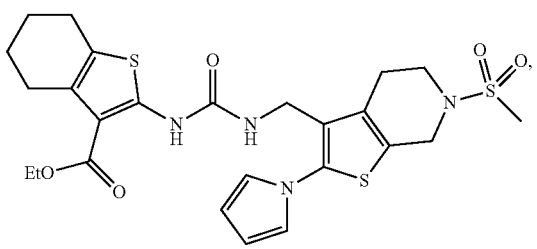
Formula 27
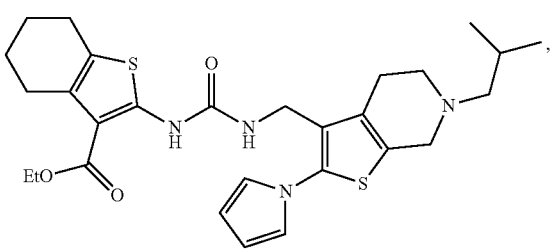
Formula 110
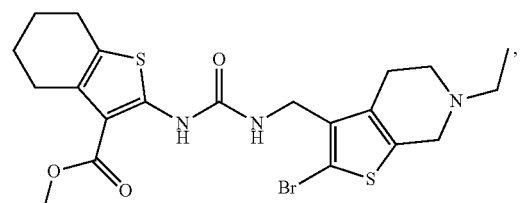
Formula 111
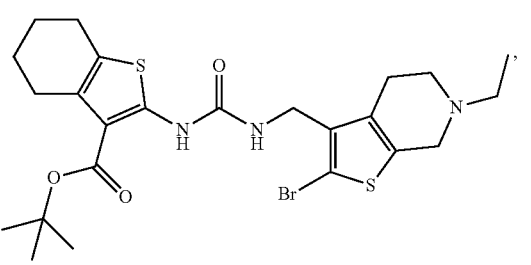
Formula 112
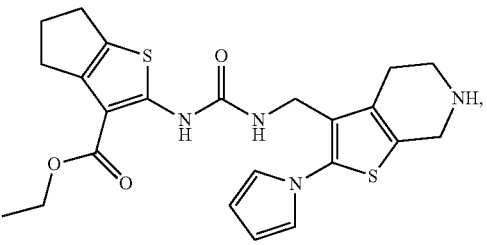
Formula 113
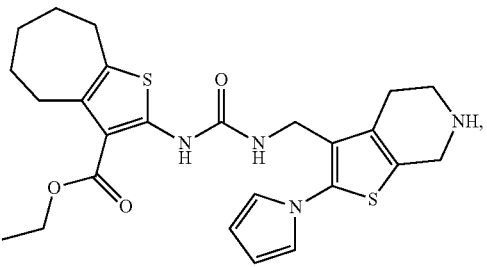
Formula 114
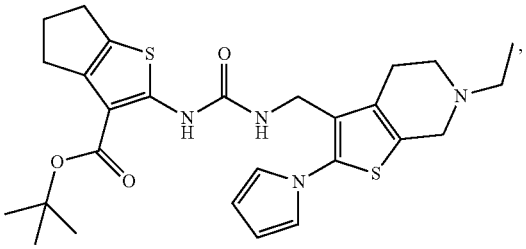

483
-continued

Formula 115
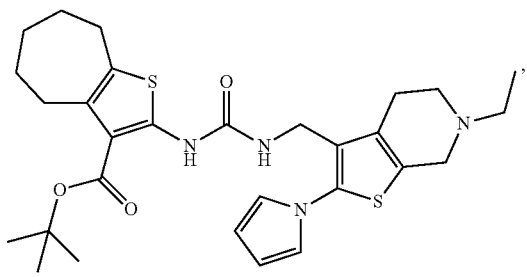

Formula 116
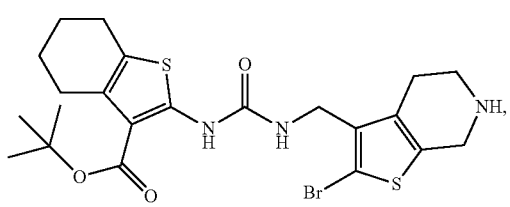

Formula 117
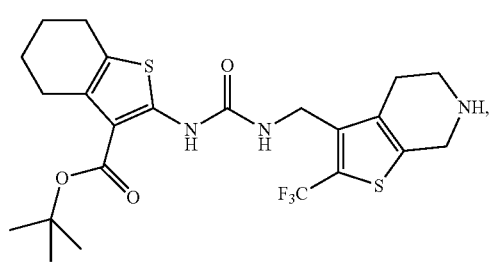

Formula 118
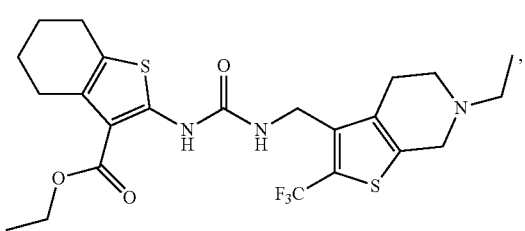

Formula 119
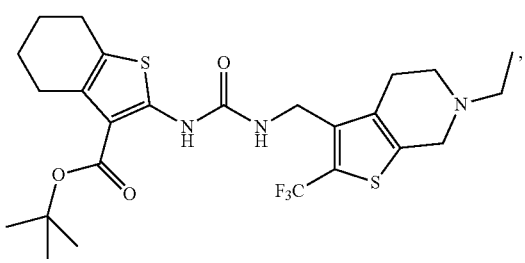

Formula 121
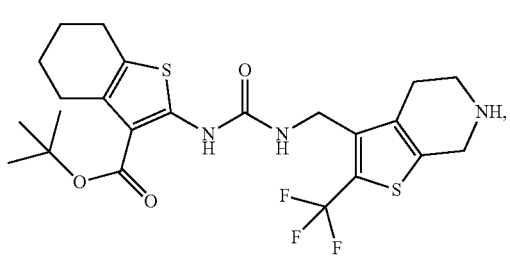

484
-continued

Formula 167
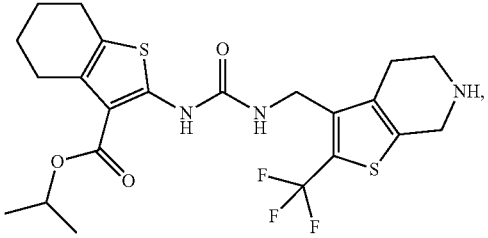

Formula 316
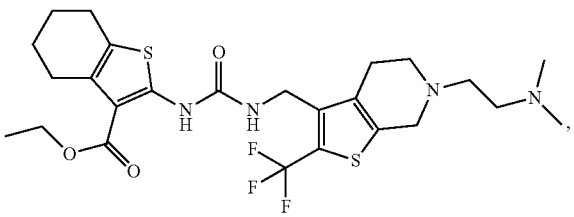

and a pharmaceutically acceptable salt thereof.

15. The method according to claim 8 for use in the treatment of a viral disease, said method further comprising the administration of at least one antiviral compound, to a patient in need thereof, suffering from a viral disease.

16. The method according to claim 15 for use in the treatment of a viral disease, wherein said viral disease is HCV.

17. A method of treatment of a viral disease, said method comprising the administration of a suitable amount of a compound selected from the group consisting of Formula 44, Formula 109, Formula 170, Formula 173, Formula 176, Formula 223, Formula 255, Formula 304, Formula 311, Formula 341, Formula 374, as shown below, and a pharmaceutically acceptable salt thereof, or of a composition comprising a compound selected from the group consisting of Formula 44, Formula 109, Formula 170, Formula 173, Formula 176, Formula 223, Formula 255, Formula 304, Formula 311, Formula 341, Formula 374, as shown below, Formula 44
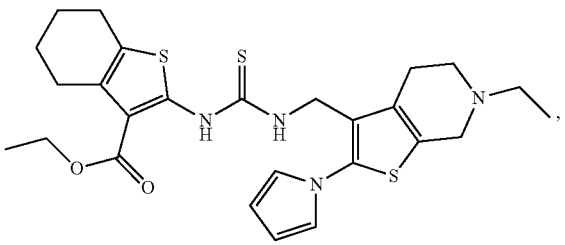

Formula 109
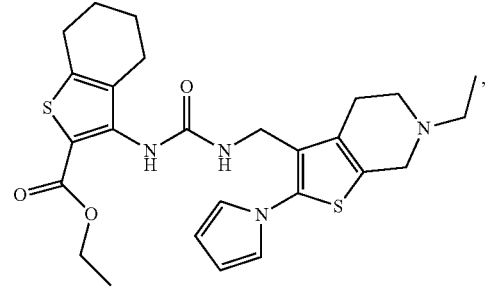

Formula 170
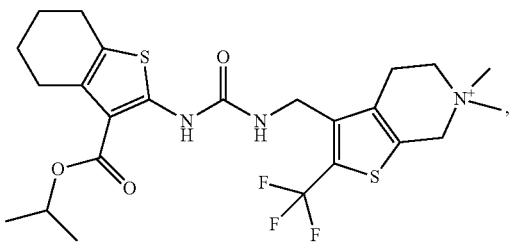
Formula 173
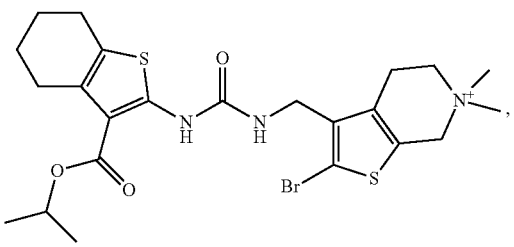
Formula 176
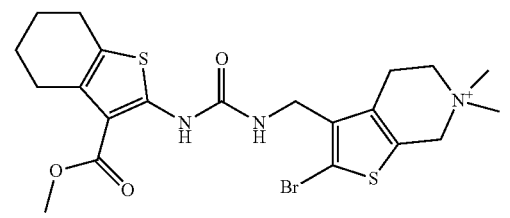
Formula 223
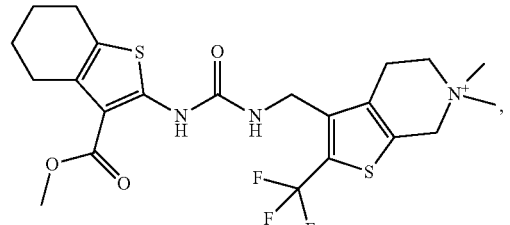
Formula 255
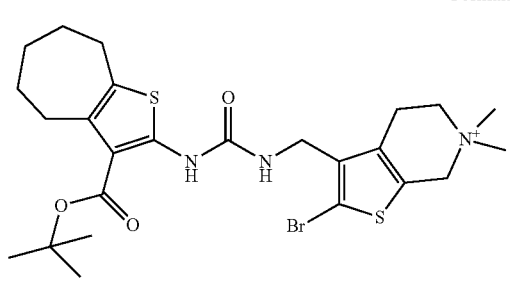
Formula 304
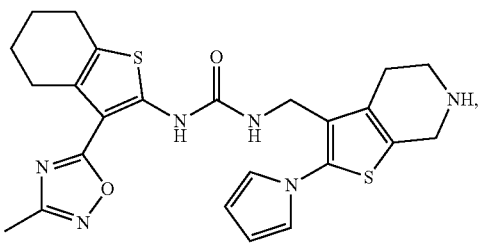
Formula 311
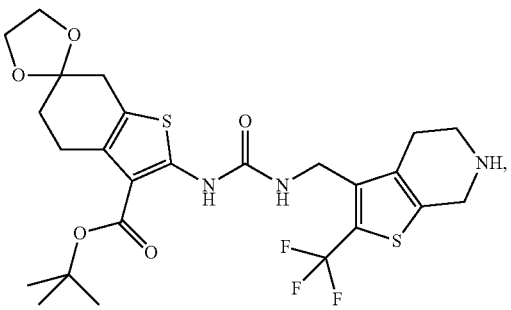
Formula 341
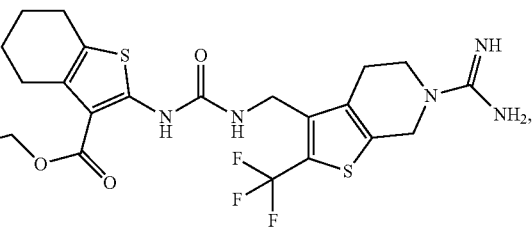
Formula 374
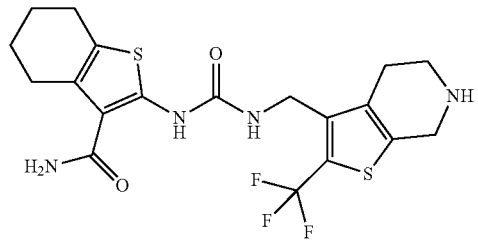
and a pharmaceutically acceptable salt thereof to a patient in need thereof, suffering from a viral disease.
* * * * *